United States Patent [19]

Corenman et al.

[11] Patent Number: 4,817,013
[45] Date of Patent: Mar. 28, 1989

[54] MULTICHANNEL GAS ANALYZER AND METHOD OF USE

[75] Inventors: James E. Corenman, Oakland; James R. Braig, Hayward; Daniel S. Goldberger, San Francisco; Emil P. Rojas, Los Gatos; James H. Stone, Saratoga, all of Calif.

[73] Assignee: Nellcor, Inc., Hayward, Calif.

[21] Appl. No.: 922,043

[22] Filed: Oct. 17, 1986

[51] Int. Cl.$^4$ .......................................... G01N 21/64
[52] U.S. Cl. .................................. 364/497; 250/343; 356/437; 422/83
[58] Field of Search ........................ 364/496-499; 250/341-347; 128/719; 422/83-84, 88; 73/23; 356/437

[56] References Cited

U.S. PATENT DOCUMENTS

| | | | |
|---|---|---|---|
| Re. 31,879 | 5/1985 | Lubbers et al. | 436/133 |
| 1,758,088 | 5/1930 | Schmick | 250/346 |
| 2,697,789 | 12/1954 | Skarstrom | 250/43.5 |
| 2,718,597 | 9/1955 | Heigl et al. | 250/43.5 |
| 2,720,594 | 10/1955 | Hutchins | 250/43.5 |
| 2,721,942 | 10/1955 | Friel et al. | 250/43.5 |
| 2,806,144 | 9/1957 | Berger et al. | 250/43.5 |
| 2,924,713 | 2/1960 | Liston | 250/43.5 |
| 2,951,939 | 9/1960 | Luft | 250/43.5 |
| 2,975,280 | 3/1961 | Waters | 250/43.5 |
| 3,004,664 | 10/1961 | Dreyfus | 209/111.5 |
| 3,016,195 | 10/1975 | Burch et al. | 250/345 |
| 3,162,761 | 12/1964 | Luft | 250/43.5 |
| 3,363,503 | 1/1968 | Shifrin | 88/14 |
| 3,539,804 | 11/1970 | Billetdeaux et al. | 250/43.5 |
| 3,562,522 | 2/1971 | Cederstrand et al. | 250/43.5 |
| 3,619,072 | 11/1971 | O'Hara et al. | 356/246 |
| 3,650,151 | 3/1972 | Drexel | 73/194 M |
| 3,678,262 | 7/1972 | Herrmann | 250/43.5 R |
| 3,696,247 | 10/1972 | McIntosh et al. | 250/83.3 H |
| 3,725,701 | 4/1973 | Link | 250/43.5 |
| 3,728,540 | 4/1973 | Todd et al. | 250/43.5 R |
| 3,745,349 | 7/1973 | Liston | 250/218 |
| 3,781,910 | 12/1978 | Herrmann | 250/341 |
| 3,790,797 | 2/1974 | Sternberg et al. | 250/345 |
| 3,799,149 | 3/1974 | Rummel et al. | 128/2.07 |
| 3,812,330 | 5/1974 | Bowman et al. | 235/92 CC |
| 3,832,548 | 8/1974 | Wallack | 250/343 |
| 3,860,344 | 1/1975 | Garfunkel | 356/51 |
| 3,860,818 | 1/1975 | Stalder et al. | 250/343 |
| 3,869,613 | 3/1975 | Link et al. | 250/343 |
| 3,877,812 | 4/1975 | Thompson | 356/97 |
| 3,887,473 | 6/1975 | Sternberg et al. | 250/345 |
| 3,893,770 | 7/1975 | Takami et al. | 356/96 |
| 3,895,630 | 7/1975 | Bachman | 128/2.07 |
| 3,898,462 | 8/1975 | Ishida et al. | 250/344 |
| 3,904,880 | 9/1975 | Benz et al. | 250/343 |
| 3,922,551 | 11/1975 | Williams | 250/343 |
| 3,926,527 | 12/1975 | Pembrook et al. | 356/246 |
| 3,932,754 | 1/1976 | Riedl et al. | 250/343 |

(List continued on next page.)

OTHER PUBLICATIONS

Allegheny International Medical Technology Brochure Entitled, "SARACAP: $CO_2$, $O_2$ and $N_2O$ Respiratory Monitor", 4/85.

(List continued on next page.)

Primary Examiner—Parshotam S. Lall
Assistant Examiner—Ellis B. Ramirez
Attorney, Agent, or Firm—Wayne M. Kennard

[57] ABSTRACT

An improved gas analyzer system (FIG. 1) and method of use for detecting and displaying the constituent gases of a respiratory gas stream, the system comprising an optical bench (109) through which a respiratory gas flows and in which measurements of the gas are taken; analog input circuits (122) for receiving signals output from the optical bench (109); analog processing circuits (124) for processing signals output from the analog input circuits (122); display processing circuits (128) for processing the signals output from the analog processing circuits (124) and other system circuitry; pixel logic circuits/analog outputs (130) for processing signals output from the display processing circuitry (128) and providing analog output ports; a five button panel (148), an alarm-knob board (144), and a speaker driver (152) for operator interface and activation of audible and visual alarms; a CRT driver for driving the CRT; and a power supply (158) for powering the system.

21 Claims, 23 Drawing Sheets

U.S. PATENT DOCUMENTS

| | | | |
|---|---|---|---|
| 3,938,506 | 2/1976 | Birnbaum et al. | 128/2.05 A |
| 3,939,348 | 2/1976 | Barrett | 250/339 |
| 3,953,734 | 4/1976 | Dimeff | 250/343 |
| 3,957,372 | 5/1976 | Jowett et al. | 250/345 |
| 3,968,367 | 7/1976 | Berg | 250/339 |
| 3,996,010 | 12/1976 | Fraser | 422/84 |
| 4,003,707 | 1/1977 | Lubbers et al. | 23/232 R |
| 4,008,394 | 2/1977 | Risgin et al. | 250/345 |
| 4,010,368 | 3/1977 | Pelta | 250/343 |
| 4,011,859 | 3/1977 | Frankenberger | 128/2 C |
| 4,013,260 | 3/1977 | McClatchie et al. | 250/343 |
| 4,027,972 | 6/1977 | Davies | 356/51 |
| 4,035,643 | 7/1977 | Barrett | 250/339 |
| 4,063,094 | 12/1977 | Schuman | 250/338 |
| 4,067,320 | 1/1978 | Olsson et al. | 128/2 C |
| 4,069,420 | 1/1978 | Ross | 250/341 |
| 4,075,481 | 2/1978 | Stoft et al. | 250/343 |
| 4,084,906 | 4/1978 | Bibbero | 356/96 |
| 4,110,619 | 8/1978 | Zorner | 250/344 |
| 4,136,959 | 1/1979 | Honkawa et al. | 356/418 |
| 4,153,837 | 5/1979 | Ross | 250/346 |
| 4,163,899 | 8/1979 | Burough | 250/343 |
| 4,177,381 | 12/1979 | McClatchie et al. | 250/343 |
| 4,178,919 | 12/1979 | Hall | 422/84 |
| 4,180,734 | 12/1979 | Gedeon | 250/345 |
| 4,205,913 | 6/1980 | Ehrfeld et al. | 356/72 |
| 4,221,130 | 9/1980 | Burrows | 73/421.5 R |
| 4,233,513 | 10/1980 | Elder et al. | 250/343 |
| 4,241,309 | 12/1980 | Elder | 328/115 |
| 4,266,131 | 5/1981 | Ahjopalo et al. | 250/341 |
| 4,281,248 | 7/1981 | Fabinski et al. | 250/345 |
| 4,295,471 | 10/1981 | Kaspari | 128/675 |
| 4,304,578 | 12/1981 | Hakala et al. | 55/189 |
| 4,306,152 | 12/1981 | Ross et al. | 250/343 |
| 4,320,297 | 3/1982 | Cederstrand et al. | 250/343 |
| 4,336,453 | 6/1982 | Imaki et al. | 250/344 |
| 4,346,296 | 8/1982 | Passaro et al. | 250/343 |
| 4,355,233 | 10/1982 | Warnke et al. | 250/343 |
| 4,356,834 | 11/1982 | LeMay | 137/89 |
| 4,370,553 | 1/1983 | Waycaster et al. | 250/343 |
| 4,398,091 | 8/1983 | Passaro | 250/343 |
| 4,399,686 | 8/1983 | Kindlund et al. | 73/23 |
| 4,423,739 | 1/1984 | Passaro et al. | 250/345 |
| 4,437,004 | 3/1984 | Passaro et al. | 250/343 |
| 4,446,869 | 5/1984 | Knodle | 128/716 |
| 4,456,014 | 6/1984 | Buck et al. | 128/719 |
| 4,480,190 | 10/1984 | Burough et al. | 250/343 |
| 4,485,305 | 11/1984 | Kuwano et al. | 250/338 |
| 4,509,359 | 4/1985 | Gedeon et al. | 73/23 |
| 4,522,204 | 6/1985 | Kurahashi et al. | 128/719 |
| 4,549,553 | 10/1985 | Hochberg | 128/719 |
| 4,578,762 | 3/1986 | Wong | 364/497 |
| 4,632,807 | 12/1986 | Marsoner | 422/83 |
| 4,692,621 | 9/1987 | Passaro et al. | 250/343 |
| 4,692,622 | 9/1987 | Tahiguchi et al. | 250/345 |

OTHER PUBLICATIONS

Andros Analyzers, Inc. Brochure Entitled, "Andros 400 Series End Tidal $CO_2$ Analyzer", Nov. 17, 1982.

Bergman et al., "The Collision Broadening Effect of Nitrous Oxide Upon Infrared Analysis of Carbon Dioxide During Anesthesia", Anesthesiology, Jan.-Feb. 1958, vol. 19, No. 1, pp. 19-26.

Cavitron Corp. Brochure Entitled, "Cavitron Introduces Patient Monitors for Respiratory Gas Analysis", 10/16/85.

Cavitron Corp. Hospital Price List Entitled, "$CO_2$ Patient Monitors & $N_2O$ Trace Gas Analyzers", 10/16/85.

Cavitron Corp. Brochure Entitled, "End Tidal $CO_2$ Monitor: PM-20R/NR", Cullen, Halothane Analyzer, Anesthesiology, May-Jun. 1962, vol. 23, No. 3, pp. 391-394.

Datascope Corp. Brochure Entitled, "Datascope Introduces the Most Advanced Monitoring System Available for Anesthesia", 10/16/85.

Engstrom AB Brochure Entitled, "Great Ideas Gros: Just Look at Engstrom Erica", 10/16/85.

Foxboro/Wilks, Inc. Application Report Entitled, "The Analysis of Anesthetic Gases with Miran Infrared Analyzers", (1977), pp. 1-21.

Glossop, "A Simple Method for the Estimation of Carbon Dioxide Concentration in the Presence of Nitrous Oxide", Brit. J. Anaesth., vol. 35, (1963), pp. 17-18.

Hill et al., "A Versatile Infra-Red Gas Analyzer Using Transistors", J. Sci. Instrum., vol. 41 (1964), pp. 732-735.

Hill et al., Non-Dispersive Infra-Red Gas Analysis in Science, Medicine and Industry (1968), pp. 43-48, 145-148.

"Infrared Gas Analysis", *Applications of Infrared Detectors,* Mullard Ltd., Mullard House, Torrington Place, London WC1E 7HD, Chap. 10 (1971), pp. 129-142.

Infrared Industries, Inc. Brochure Entitled, "Gas Analysis Instrumentation: IR-7251 $CO_2$ Analyzer Bench", 10/16/85.

Kawate et al., "Spectrophotometric Determinations of n-Propyl Alcohol and Other Alcohol Monohydric Alcohols", Tech. Reports of Kansai Univ., No. 18, (Mar. 1977), pp. 47-52.

OTHER PUBLICATIONS

Mapleson, "Physical Methods of Gas Analysis", Brit. J. Anaesth., vol. 34 (1962), pp. 631–636.

Perkin-Elmer Brochure Entitled, "Advantage: Confidence From Every Standpoint", 10/16/85.

Powell, "Infra-Red Spectroscopy and Its Application in Anesthesia and Respiratory Physiology", Wld. Med. Electron., vol. 3 (1965), pp. 8–17.

Puritan-Bennett Corp., Operating Manual Entitled, "AAM222 Operating Manual", 4/85.

Puritan-Bennett Corp. Brochure Entitled "Anesthesia and Brain Activity Monitor", 11/84.

Puritan-Bennett Corp. Brochure Entitled "$CO_2$ Monitoring Ssytem", 6/83.

Puritan-Bennett Corp. Brochure Entitled, "Puritan--Bennett 222 Anesthetic Agent Monitor", 3/84.

Puritan-Bennett Corp. Brochure Entitled, "You Can Depend on It!: Puritan Bennett $CO_2$ Monitor", 10/16/85.

Severinghaus et al., "Correction Factors for Infrared Carbon Dioxide Pressure Broadening by Nitrogen, Nitrous Oxide and Cyclopropane", Anesthesiology, May–Jun. 1961, vol. 22, pp. 429–432.

Severinghaus, "Methods of Measurement of Blood and Gas Carbon Dioxide During Anesthesia", Anesthesiology, Nov.–Dec. 1960, vol. 21, No. 6, pp. 717–726.

Solomon, "A Reliable, Accurate $CO_2$ Analyzer for Medical Use", Hewlett-Packard Journal, Sep. 1981, pp. 3–21.

Telfair et al., "A Micròcomputer-Controlled Infrared Analyzer for Multicomponent Analysis", American Laboratory, Nov. 1965, pp. 91–100.

Traverse Medical Monitors Brochure Entitled, "The TMM Capnometer: Analyze the Advantages", 7/84.

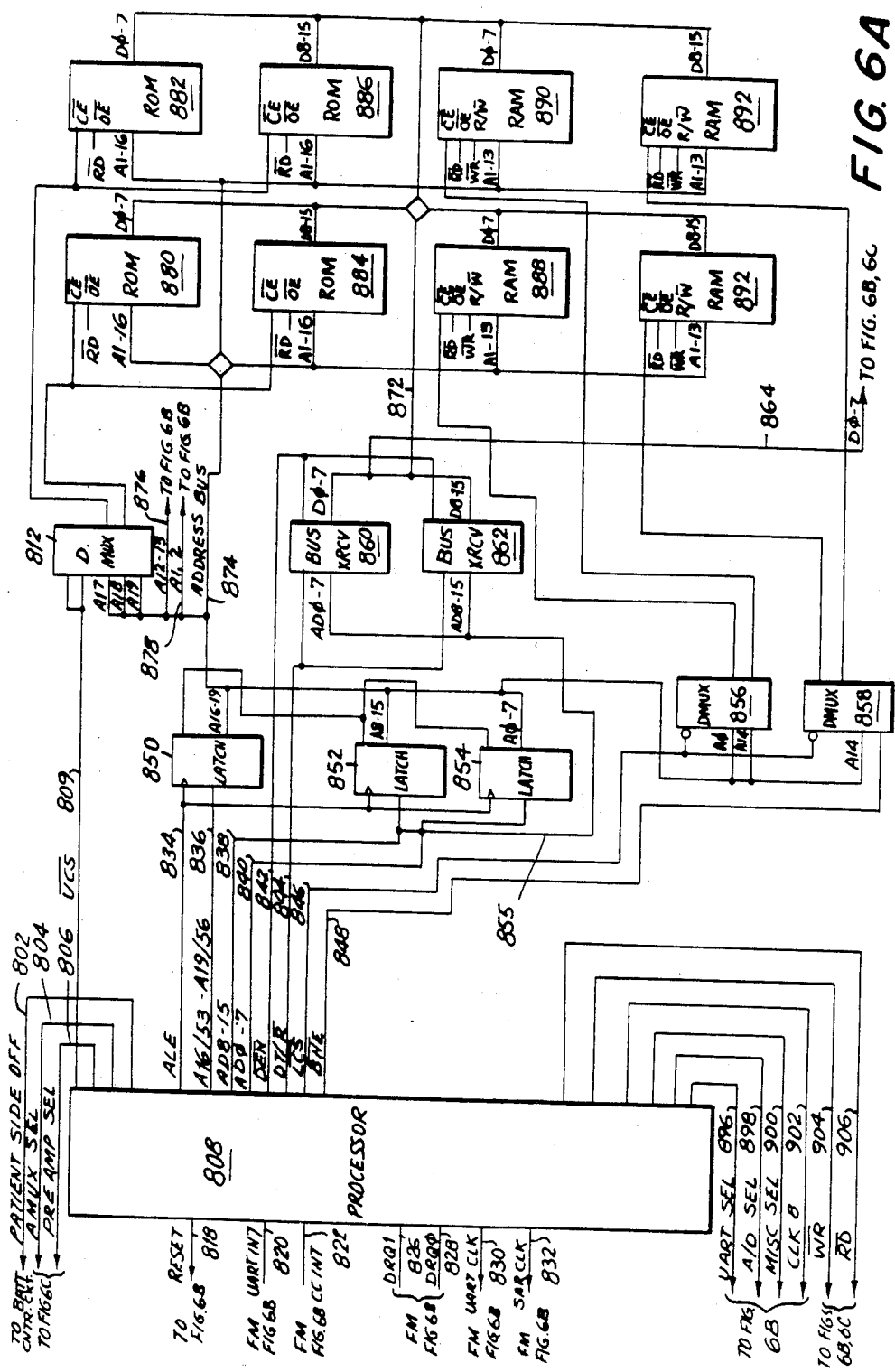

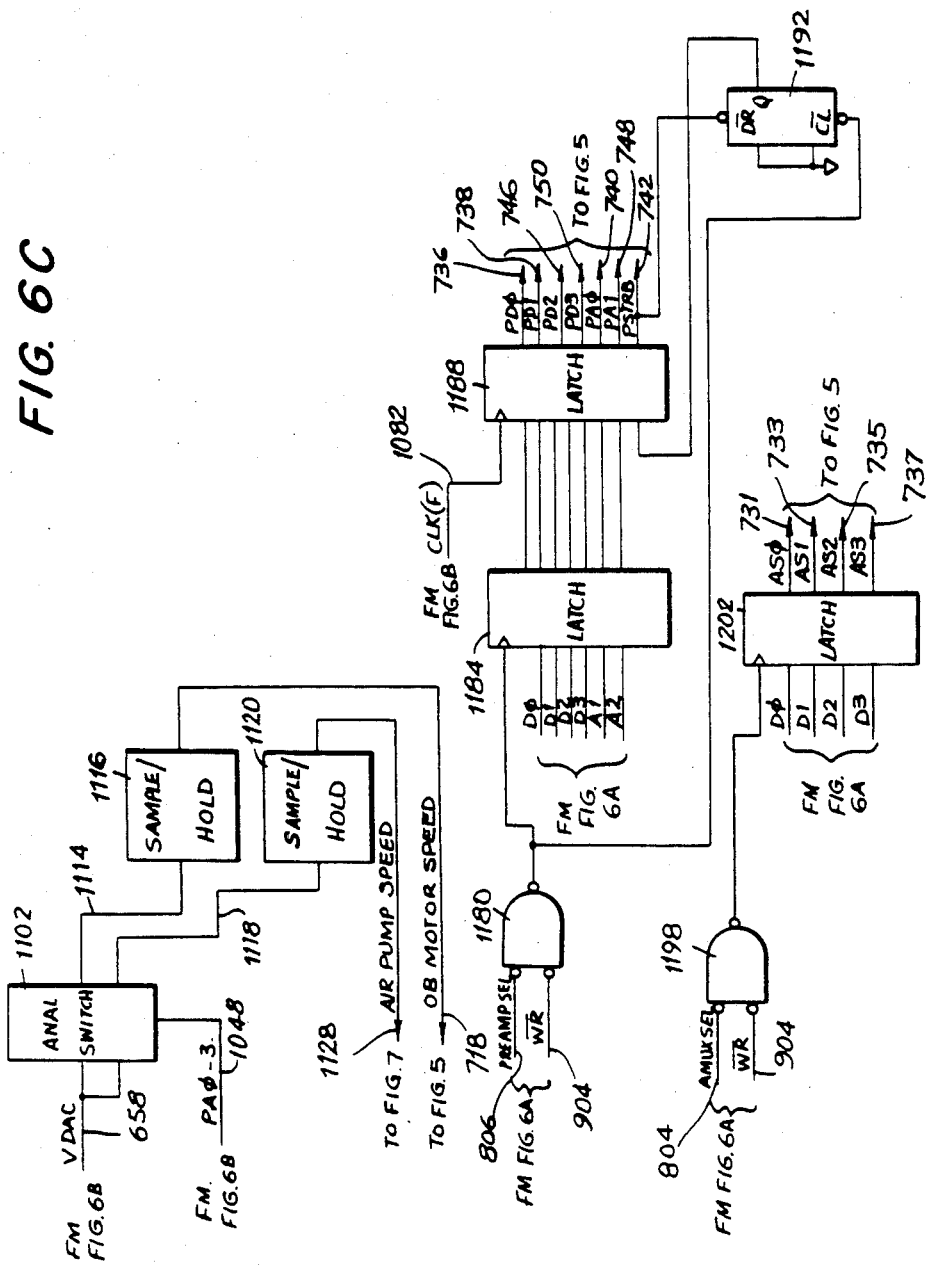

FIG. 7B

| Display Processor | Display Mother Board | Pixel Board |
|---|---|---|
| RD̄ | 1402 | RD̄ |
| W̄R̄ | 1404 | W̄R̄ |
| DRAM SEL | 1406 | DRAM SEL |
| VERT INTR | 1408 | VERT INTR |
| DARDY | 1410 | DARDY |
| A1-16 | 1412 | A1-16 |
| D0-15 | 1414 | D0-15 |
| C̄R̄T̄ S̄Ē L̄ | 1416 | C̄R̄T̄ S̄Ē L̄ |
| V̄ĪD̄ F̄C̄N̄ S̄Ē L̄ | 1418 | V̄ĪD̄ F̄C̄N̄ S̄Ē L̄ |
| S̄C̄R̄Ō L̄L̄ S̄Ē L̄ | 1420 | S̄C̄R̄Ō L̄L̄ S̄Ē L̄ |
| Ā N̄Ā L̄Ō Ḡ S̄Ē L̄ | 1422 | Ā N̄Ā L̄Ō Ḡ S̄Ē L̄ |
| Ā/D̄ S̄Ē L̄ | 1424 | Ā/D̄ S̄Ē L̄ |
| V.SYNC | 1344 | V.SYNC |
| DT/R̄ | 1428 | DT/R̄ |

| Display Processor | Display Mother Board | Digital Output Board |
|---|---|---|
| R̄D̄ | 1402 | R̄D̄ |
| W̄R̄ | 1404 | W̄R̄ |
| D0-D7 | 1414 | D0-D7 |
| DT/R̄ | 1428 | DT/R̄ |
| A1-3 | 1412 | A1-3 |
| SLAVE SEL | 1504 | SLAVE SEL |
| SLAVE INTR | 1506 | SLAVE INTR |
| CLKOUT | 1508 | CLKOUT |
| TxD | 1510 | TxD |
| RxD | 1512 | RxD |
| D̄T̄R̄ | 1514 | D̄T̄R̄ |
| D̄S̄R̄ | 1516 | D̄S̄R̄ |
| R̄T̄S̄ | 1518 | R̄T̄S̄ |
| C̄T̄S̄ | 1520 | C̄T̄S̄ |

| Display Processor | Display Mother Board | Knob Board |
|---|---|---|
| R̄D̄ | 1402 | R̄D̄ |
| W̄R̄ | 1404 | W̄R̄ |
| DISP SEL | 1602 | DISP SEL |
| D0-9 | 1414 | D0-9 |
| V.SYNC | 1344 | V.SYNC |

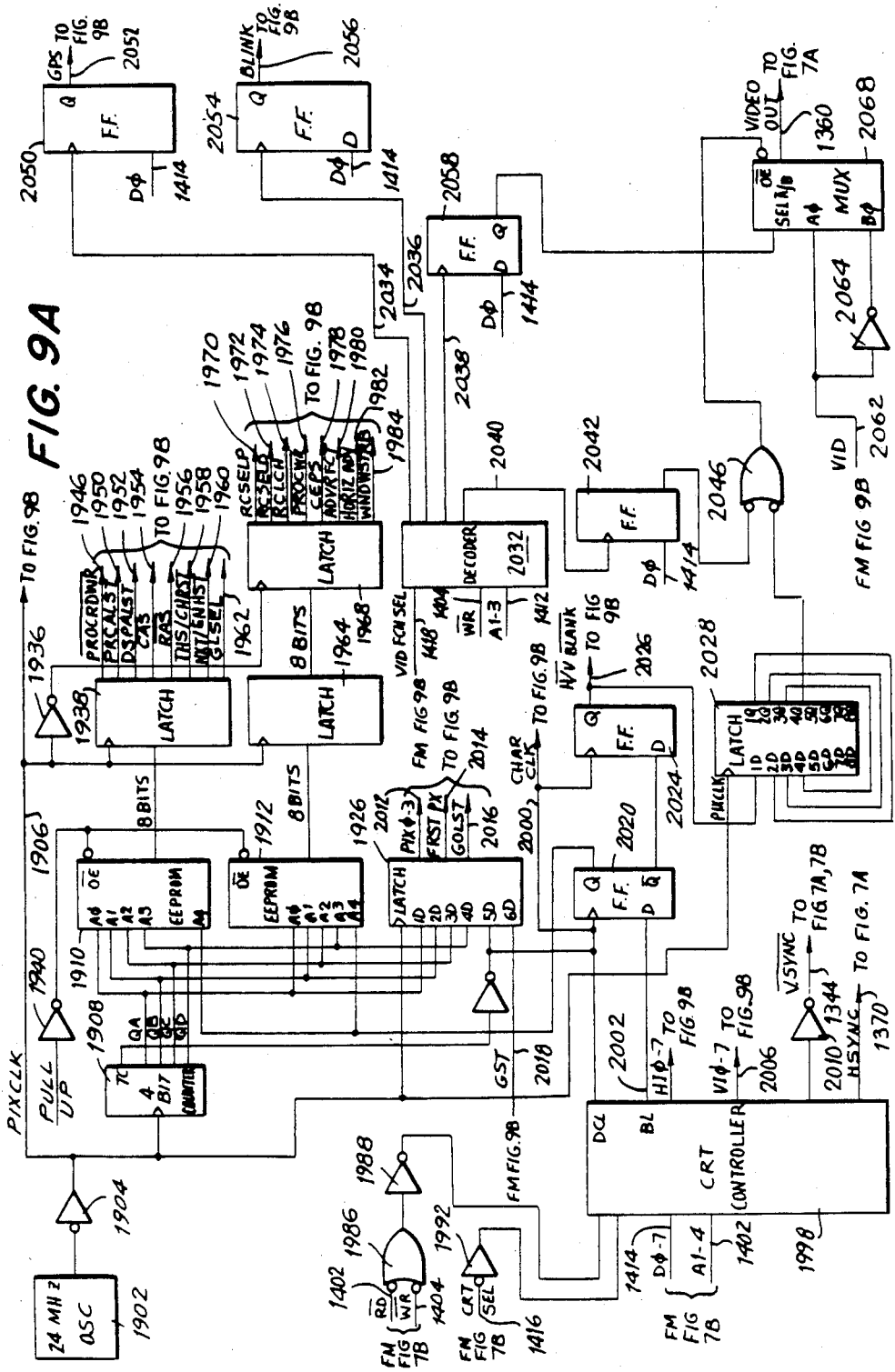

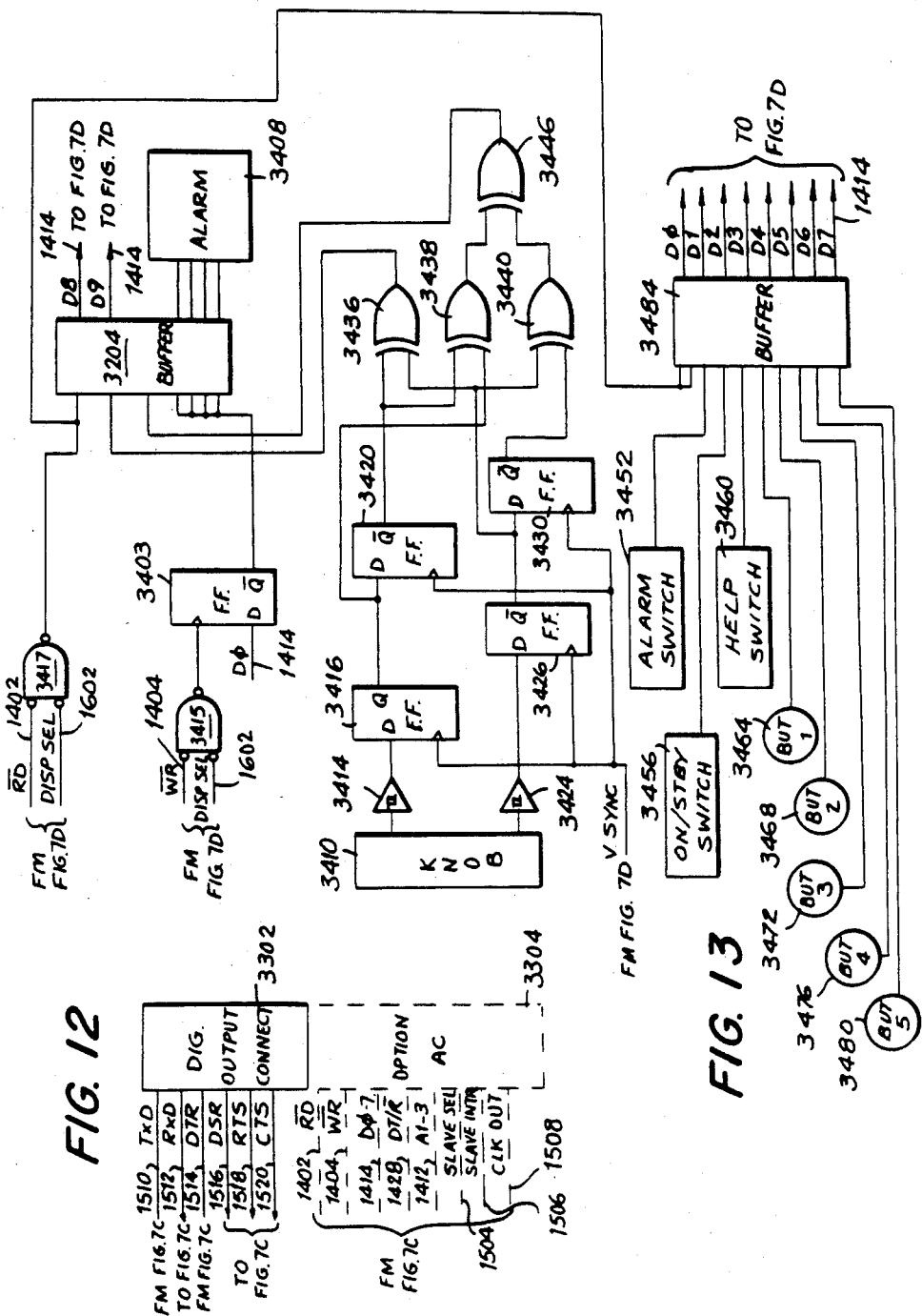

MULTICHANNEL GAS ANALYZER AND METHOD OF USE

TECHNICAL FIELD

The present invention relates to systems for measuring the partial pressures of constituent gases in a gas stream. More specifically, the invention relates to improved multichannel gas analyzer systems used to measure the partial pressures of constituent gases in respiratory gas streams and display representative gas data information on a CRT display.

BACKGROUND

During surgery, anesthetized patients are almost universally intubated. Measurement of respiratory gases is desirable when a patient is mechanically intubated through an endo-tracheal tube. An analysis of the inhaled and exhaled gas mixture provides information about the patient's ventilation. These observations can prevent the patient's receipt of excessive amounts of anesthetic.

Carbon dioxide ($CO_2$), nitrous oxide ($N_2O$) and the anesthetic agent are the constituent gases of most interest in measuring respiratory gas streams.

It is well known that $CO_2$ in the bloodstream equilibrates rapidly with $CO_2$ in the lungs. Hence, the partial pressure of the $CO_2$ in the lungs approaches the amount in the blood during each breath. Accordingly, the $CO_2$ content at breath's end, termed end-tidal $CO_2$, is a good indication of the blood $CO_2$ level.

Abnormally high end-tidal $CO_2$ values indicate that an insufficient amount of $CO_2$ is being transported away from the bloodstream through the lungs, i.e., inadequate ventilation. Conversely, abnormally low end-tidal $CO_2$ values indicate poor blood flow to the tissues, inadequate $CO_2$ transport through the lungs, or excessive ventilation.

Mass spectrometers are used for measuring the partial pressure of respiratory gases in, for example, operating room suites in which one spectrometer is shared by many rooms. Mass spectrometers have the advantage of measuring a multiplicity of gases; however, the disadvantages are their cost, maintenance and calibration requirements, slow response time, and noncontinuous measurement.

Gas analyzers using non-dispersive infrared spectrophotometry are also used for partial pressure gas measurement. While these analyzers are less expensive than mass spectrometers and continuously measure partial gas pressure, their disadvantages are poor response time and difficulty in calibration.

Prior art non-dispersive infrared gas analyzers include features for making $CO_2$ and $N_2O$ cross channel detection, temperature, and collision broadening corrections to their partial gas pressure measurements. Some of these corrections are made automatically by the analyzers while others are made manually by the operator.

Non-dispersive infrared gas analyzers generally have two configurations. The first, and most common, is the sampling or side-stream type. This type diverts a portion of the patient's respiratory gas flow through a sample tube to the infrared analyzer.

The second type mounts on the patient's airway and uses a portion of the airway as the sample chamber. This type is frequently occluded by the mucus and moisture in the patient's airway and its bulk on the airway can affect the patient's breathing.

Both infrared gas analyzer configurations are characterized by small absorption levels by the constituent gases which lead to small signals and stability problems.

Increasing the analyzer's sample chamber size improves the small signal and stability problems; however, it increases the response time. Increasing the gas flow rate through the analyzer improves the response time, but occlusions are more frequent and the patient's normal ventilation volume is impaired.

In this regard, neonates require sample flow rates equal to or less than 50 cc/minute. However, neonates also require the analyzer's response time to be compatible with breath rates well in excess of 60 breaths per minute. This condition equates to a response time of less than 100 milliseconds.

Another disadvantage of infrared gas analyzers is that they require frequent calibration for proper operation. Factors affecting calibration of the optical bench portion of a gas analyzer include manufacturing tolerances relating to the sample cell dimensions (particularly thickness); brightness of the infrared source and sensitivity of the photodetectors; temperature; barometric pressure; and the accumulation of dirt or moisture in the optical bench's gas pathways.

Changes in the optics and electronic circuitry over time require recalibration of infrared gas analyzers. Careful construction of the optics and electronic circuitry minimizes the number of calibration adjustments needed and the period between recalibration. Hence, interchangeability of the optical bench of an analyzer has not heretofore been practical because of the need for recalibration when the optical bench is connected to the analyzer.

Calibration of infrared gas analyzers is accomplished by various electronic circuit adjustments to correct for variations in sample chamber geometry as well as variations and drift of various sensing components.

Calibration usually requires taking the analyzer out of service and passing standard gases through it, in the presence of which the various adjustments are made. Another calibration method is to make a "zero gas" reading for the optical bench and adjust the analyzer's amplifier so that the analyzer's output actually reads zero. A still further method uses a reference cell filled with a non-absorbing gas or a reference filter having a wavelength at which no absorption takes place to stabilize the zero setting of the analyzer.

Prior art non-dispersive infrared gas analyzers also include some automatic calibration features. However, further operator controlled calibration procedures are required before the analyzers are ready for use.

The present invention overcomes these and other problems of prior infrared gas analyzers as will be set forth in the remainder of the specification.

SUMMARY OF THE INVENTION

The present invention is an improved non-dispersive infrared gas analyzer system for analyzing respiratory gas streams and displaying information about the detected constituent gases. The system has an optical bench with associated circuitry. The circuitry generates signals representative of the partial pressures of $CO_2$, $N_2O$ and the anesthetic agent present in a gas stream; the temperature within the optical bench; the flow rate of the gas stream through the optical bench; and the pressure within the optical bench's gas pathway. The system pump draws respiratory gases through the optical bench's gas pathway and backflushes this same pathway. Analog input circuitry is electrically connected to the optical bench and receives the optical bench's signal outputs indicative of certain measured values and characterization information. The analog input circuitry processes the input signals and outputs them to the analog processing circuitry. The analog processing circuitry, which includes a microprocessor, performs calculating functions on the received signals. The results are output signals indicative of the partial pressure of $CO_2$, $N_2O$ and the anesthetic agent corrected for temperature, barometric pressure, collision broadening, cross-correction and characterization. These signals along with those for the measured values of flow rate, temperature and pressure within the optical bench are output to the display section of the system.

The display section circuitry, according to its programming, processes the signals output from the analog processor circuitry. The output signals from the display section circuitry drive a CRT for display of graphics and characters representative of measured values from the optical bench.

The optical bench circuitry preliminarily processes the signals output from the gas and other detectors such as an absolute-reading pressure sensor for pressure measurement, a differential-reading pressure sensor for measuring flow rate, and a temperature sensing circuit.

The optical bench has three optical detection assemblies for simultaneously measuring $CO_2$, $N_2O$ and a volatile halogenated hydrocarbon anesthetic (or agent). The bench continuously measures these gases at a rate which allows separate analysis of the inspired and expired gas mixtures.

Preferably, the three optical detection assemblies and the connected detection circuitry are incorporated in a small optical bench that is placed next to the patient. The optical bench connects to a larger apparatus constituting the remainder of the gas analyzer system.

A small diameter sample tube, preferably one yard long or less, connects the optical bench to a side-stream type airway adaptor. A filter in the airway adaptor blocks liquids, such as water and mucus, from entering the sample tube and optical bench. The walls of the sample tube absorb water vapor condensing on them and evaporate it into the atmosphere. An optical bench entrance filter filters any remaining water vapor and dirt in the gas stream from entering the optical bench.

A system pump contained in a pump assembly draws a continuous stream of respiratory gas through the gas pathway of the optical bench. This pump also backflushes the gas pathway. A flow shaper at the entrance of the optical bench reshapes the gas flow cross-section from round to rectangular. The gas stream passes through the $CO_2$, $N_2O$ and agent detection channel assemblies in succession as it transits the gas pathway.

The $CO_2$ and $N_2O$ detection channel assemblies are disposed along the portion of the gas pathway having a rectangular cross-sectional shape. The agent detection channel assembly is located in another portion of the gas pathway having a cylindrical shape.

After leaving the portion of the gas pathway containing the agent channel, the gas stream enters the area in the gas pathway containing a pressure sensor and a flow rate sensor. The gas stream then leaves the optical bench, enters a scavenging tube and is exhausted from the system through the pump assembly.

The $CO_2$ and $N_2O$ detection channel assemblies each use a small section of the gas pathway with the rectangular cross-section. A sapphire window replaces a part of the gas pathway wall. An infrared source is located behind the window. A narrow-band infrared filter replaces a part of the gas pathway wall opposite the sapphire window. An infrared detector for each channel aligns with the respective optical paths behind the filter.

The agent detection channel assembly is in the portion of the gas pathway with a cylindrical shape. An infrared source is located at one end of the cylindrical section and a narrow-band filter closes the opposite end. The infrared detector aligns with the optical path behind the filter.

A chopper wheel, common to the three channels, rotates in a plane between the detectors and associated narrow-band filters. The chopper wheel chops the infrared light passing through the filters at a predetermined frequency.

The optical bench also includes an electrically erasable programmable read-only memory (EEPROM) which stores characterization information for the specific optical bench. The characterization information corrects the optical bench's measurements for system component performance that deviates from ideal theoretical performance. The characterization information obviates the need to calibrate the optical bench. Characterization information includes coefficients for temperature, collision broadening, cross correction, span, offset, and pressure. Characterization information also includes coefficients for detector sensitivity changes for changes in the detected DC voltage. The characterization information is used by the analog processor circuitry and the display circuitry in carrying out their signal processing functions.

The analog input circuitry and the analog processor circuitry process the analog signals generated by the optical bench circuitry. The processed signals, now digital, are output by the analog processor circuitry and transmitted to the display section. The display section processes the signals for display on a CRT.

The main display section circuits are the display processor circuitry and pixel circuitry.

The display processor circuitry bidirectionally communicates with the analog processor circuitry. The display processor circuitry controls the pixel circuitry. This control results in driving the CRT to display both the fixed characters and scrolled information, e.g., a capnogram.

Preferably, the CRT displays numerical and graphical data. The numerical data normally displayed are the inspired and expired values for $CO_2$, $N_2O$, and anesthetic agent, and respiration rate. The graphical data normally displayed are the waveforms for $CO_2$ and $N_2O$. These waveforms are an indication of the patient's respiratory cycle. Superimposed on, for example, the $CO_2$ waveform are the transition points between inspiration and expiration, and between expiration and inspiration. These points are marked with and "I" and an "E", respectively. The "I" and "E" markings provide the physician with the locations of selected transition points in both normal and abnormal capnograms.

An object of the present invention is to provide an apparatus and method for improved measurement of the partial pressure of respiratory gases.

Another object of the present invention is to provide an improved apparatus and method for measurement of the partial pressure of respiratory gases with a rapid repsonse time of less than 100 milliseconds and a sample flow rate less than or equal to 50 cc/min.

A further object of the present invention is to provide an apparatus capable of self characterization without calibration.

A still further object of the invention is to provide an improved apparatus which does not require the use of a reference channel for stabilized operations.

An even further object of the present invention is to provide an improved apparatus in which the optical bench portion of a gas analyzer can be interchanged without the need to recalibrate the system before use.

Another object of the present invention is to provide a system for displaying the gas concentrations of a patient's respiratory gas stream, scrolling waveforms across the display screen and marking inspired and expired transition points of a patient's breathing cycle.

These and other objects of the invention will be described more fully in the remaining portions of the specification.

BRIEF DESCRIPTION OF THE DRAWINGS

FIGS. 6A, 6B, and 6C comprise a schematic diagram of the analog processor circuitry of the multichannel gas analyzer system of the present invention.

FIGS. 7A thru 7D are a schematic diagram of the circuitry on the motherboard of the multichannel gas analyzer system of the present invention.

FIGS. 9A, 9B and 9C comprise a schematic diagram of the pixel circuitry of the multichannel gas analyzer system of the present invention.

FIG. 12 is a schematic diagram of the digital output section of the display section of the multichannel gas analyzer system of the present invention.

FIG. 13 is a schematic diagram of the system controls and alarms for the multichannel gas analyzer system of the present invention.

DETAILED DESCRIPTION OF THE PREFERRED EMBODIMENTS

The present invention is an improved multichannel gas analyzer system for measuring the partial pressure of constituent gases of a respiratory gas stream. The analyzer system also displays numerical and graphical information about the constituent gases detected.

The figures refer to electronic components or circuitry that consists of a group of components which carry out a known specific function. Those components or circuit elements that are well known by those skilled in the art will be referred to generally by their common names or functions and are not explained in detail.

Figure 1:
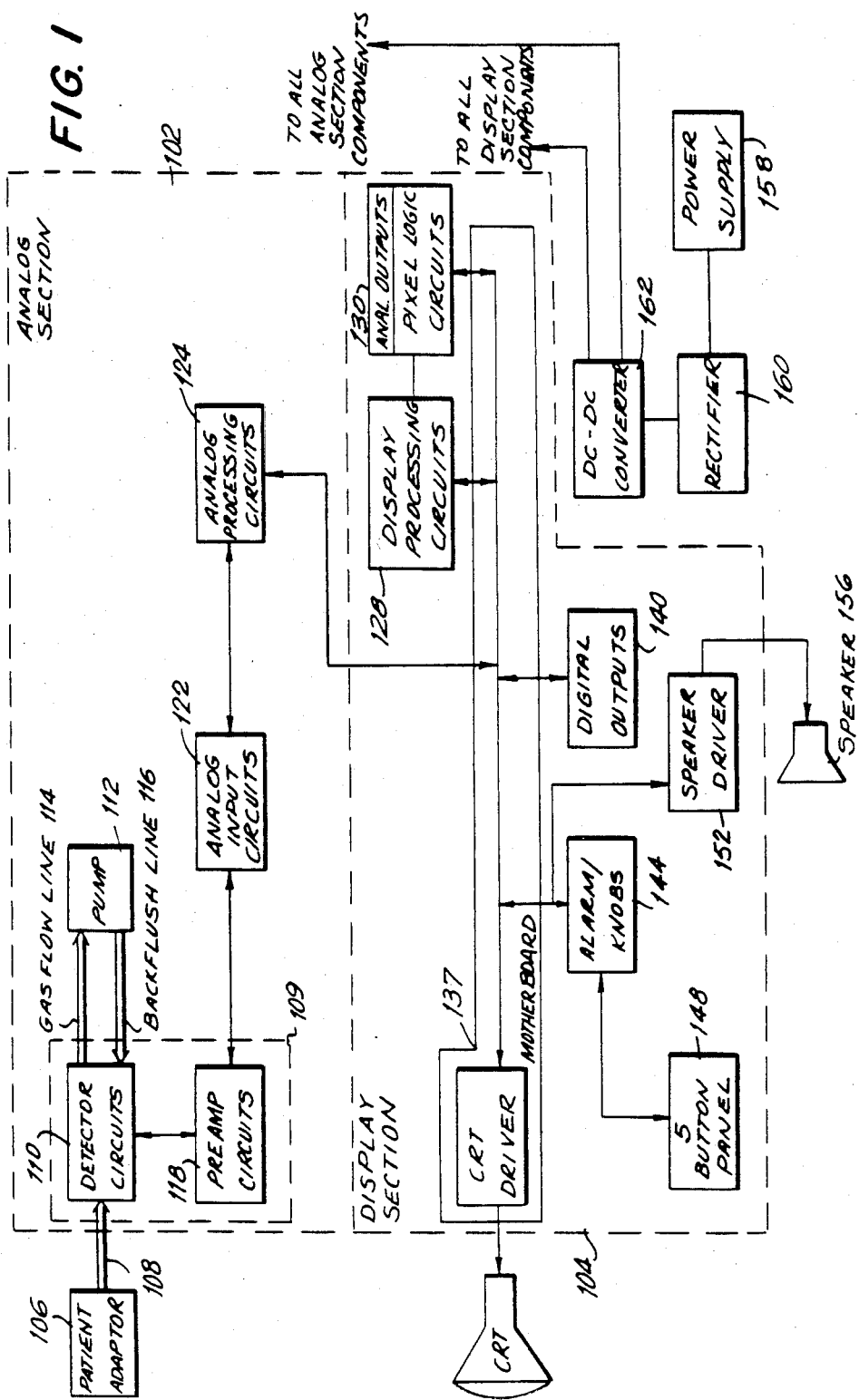
FIG. 1 is a block diagram of the multichannel gas analyzer system of the present invention.

FIG. 1 is a schematic diagram of the multichannel gas analyzer system of the present invention. The system comprises an analog section 102 and a display section 104. Analog section 102 detects and measures the constituent gases of a respiratory gas stream. This section also detects and measures other physical properties which affect the determination of the partial pressures of the constituent gases, i.e., $CO_2$, $N_2O$ and the agent. The measured values for $CO_2$, $N_2O$, the agent and the other physical properties are combined to calculate the "real" partial pressure of each constituent gas. The "real" partial pressures of the constituent gases are corrected for barometric pressure, temperature, collision broadening, channel cross-detection, sensitivity changes in the detection devices, and characterization of the detection circuitry and other detection components.

The calculated values for the partial pressure of $CO_2$, $N_2O$ and the agent are output from analog section 102 in digital form to display section 104. Analog section 102 also transmits measured values for flow rate, temperature, and pressure to the display section.

Display section 104 processes the analog section output signals. The $CO_2$, $N_2O$ and the agent output signals are processed for display on the CRT as numeric characters. The display section also processes at least the $CO_2$ signals for graphic display as, for example, a scrolling capnogram. The display section processes the temperature, pressure and flow rate signals for display and as historical data for later retrieval.

The display section has system controls for operator interface. These controls select system operation and choice of screen displays. The display section also has both digital and analog output ports for communicating with peripheral equipment. The display section includes visual and audible alarms to indicate alarm conditions or improper operation of the system.

Analog section 102 comprises optical bench 109 (whose electronics include detector circuitry 110 and preamp 118); pump assembly 112; analog input circuitry 122 and analog processing circuitry 124. Patient adaptor 106 and sample tube 108 are not part of analog section 102. Patient adaptor 106 is a conventional side-stream type and filters the gas stream drawn toward optical bench 109 by pump assembly 112.

Sample tube 108 connects patient adaptor 106 to optical bench 109. The walls of sample tube 108, preferably constructed of Nafion, absorb and then evaporate condensed water vapor within the tube. Nafion is commercially available from E. I. du Pont de Nemours and Company, Wilmington, Del. (Nafion is a trademark of E. I. du Pont de Nemours and Company, Wilmington, Del.)

Measurement accuracy increases the closer to the patient gas detection is made. For this reason, optical bench 109 is small and placed close through the intubated patient. The length of sample tube 108 is preferably one yard or less.

Display section 104 is described generally and in detail in discussing FIGS. 7 through 13.

FIGS. 2A-2D show optical bench 109. End cap 202 (FIG. 2A) forms the top of the optical bench. The hole through the center receives the end of stator shaft 216.

Detector block 204 is fixed to the inwardly directed surface of end cap 202. Detector block 204 has openings 205, 207 and 209. Infrared photodetectors 206, 208 and 210 are fixed in openings 205, 207 and 209, respectively. Detectors 206, 208 and 210 detect the amount of infrared light illuminating them from their optical paths. The trio of small holes, indicated generally at 211, having photodiodes fixed in them. Each photodiode is in an optical path with one of the LED's indicated generally at 246 mounted on lamp board 234. The three LED/photodiode pairs determine and maintain a constant chopping frequency. Detector block 204 also has an opening that receives stator shaft 216.

The chopper assembly 212 includes rotor 215, end shield 213, chopper wheel 214 fixed to the end of rotor 215 and a stator of which only stator shaft 216 is shown. The three LED/photodiode pairs accomplish motor speed control as will be discussed.

Block 218 contains gas inlet 228, first gas passageway 302 (FIG. 2B) and openings 220, 222 and 224 for receiving optical filters 308, 306 and 304 (FIG. 2B), respectively. Openings 222 and 224 do not extend through block 218. Another opening of a predetermined depth and aligned with each opening is formed in the opposite side of block 218 (not shown). These openings receive sapphire windows 238 and 244 (FIG. 2B) for the $N_2O$ and $CO_2$ detection channels, respectively.

Three bores, indicated generally at 226, extend through block 218. These bores are part of the optical paths for the three LED/photodiode pairs. Central opening 223 in block 218 receives motor 212.

Associated with block 218 are flow shaper 230, in-line filter 229 and lock nut 232. Flow shaper 230, in-line filter 229 and lock nut 232 connect sample tube 108 to optical bench 109.

Lamp board 234 has infrared lamps 240 and 242, and the three LEDs indicated at 246 mounted on one side. Agent channel 236 is shown disposed through lamp board 234. Agent channel 236, shown as a cylindrical tube, has a portion received by block 218 and a portion received by block 250, as is better shown in FIG. 2D.

Figure 2A:
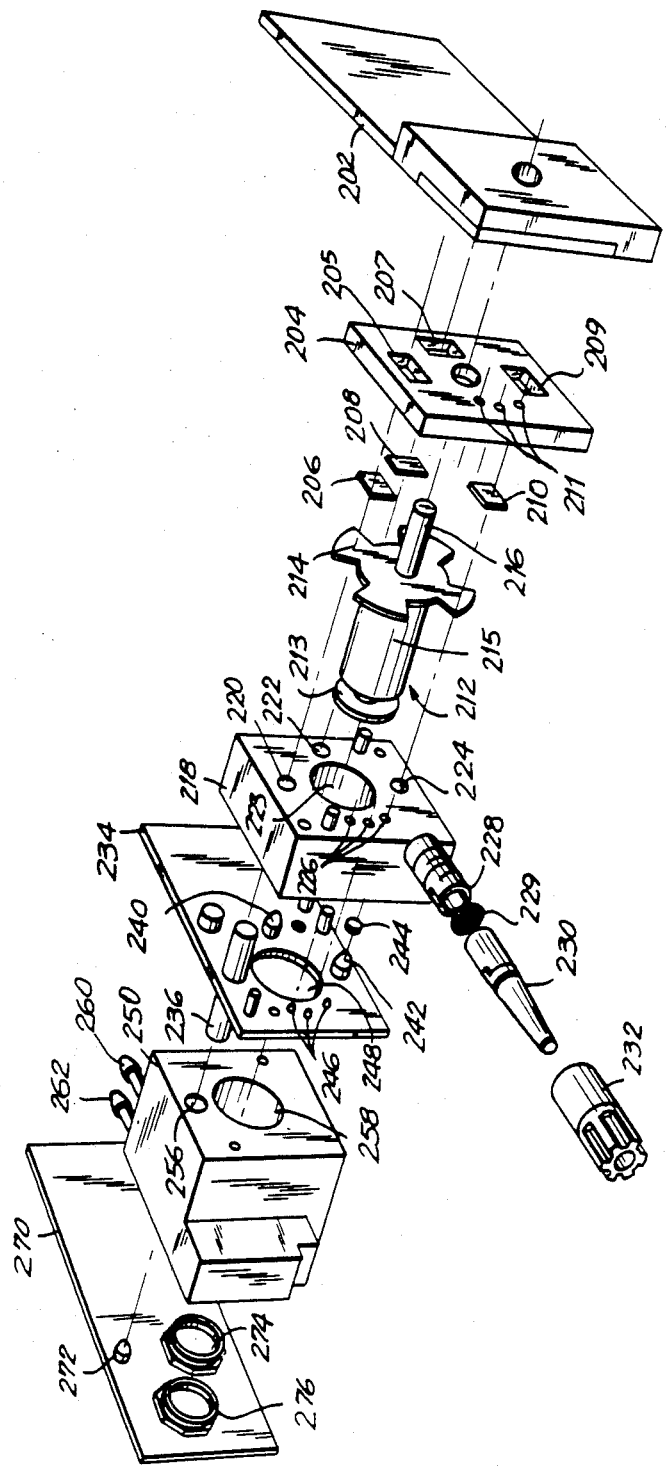
FIG. 2A is an exploded view of the optical bench portion of the multichannel gas analyzer of the system of the present invention.
Figure 2D:
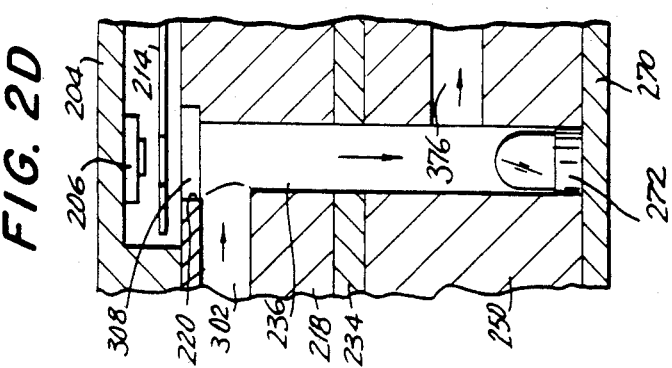
FIG. 2D shows the agent detection channel assembly of the optical bench shown in FIG. 2.
Figure 2C:
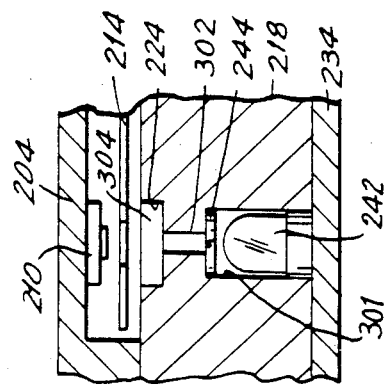
FIG. 2C shows the $CO_2/N_2O$ detection channel assembly of the optical bench shown in FIG. 2.

When the optical bench is assembled, lamps 240 and 242 fit in the openings aligned with openings 222 and 224 in the opposite side of block 218, as is best shown in FIG. 2C. The three LEDs fit in the bores indicated at 226 in block 218. Lamp board 234 has opening 248 that receives chopper motor 212.

Figure 4A:
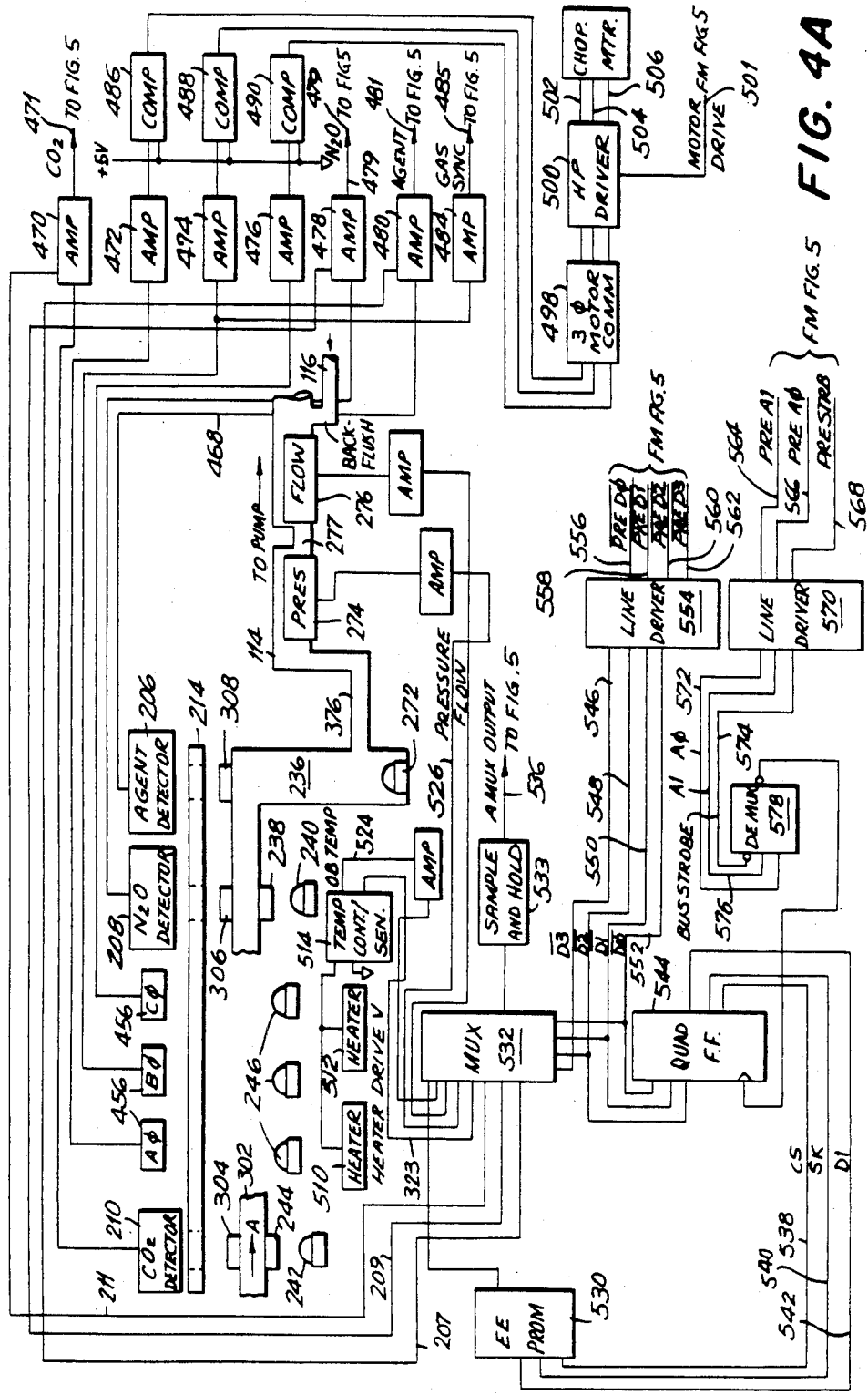
FIG. 4A is a schematic diagram of the circuitry of the optical bench of the multichannel gas analyzer system of the present invention.

Block 250 contains two cavities in its bottom surface. The first cavity receives pressure sensor 274 mounted on pressure sensor board 270; and the second cavity receives flow rate sensor 276 mounted on the same board. Gas passageway 376 connects the first cavity to agent channel 236. The first and second cavities are in fluid communication via the restriction at 277 (FIG. 4A). Block 250 has gas outlet fitting 260 and backflush inlet fitting 262. Both the gas outlet and backflush inlet fittings are in fluid communication with the second cavity in the bottom of block 250. Opening 258 receives chopper motor 212.

Pressure board 270 forms the bottom of the optical bench. Pressure sensors 274 and 276, and infrared lamp 272 are mounted on this board. Pressure sensor 274 is configured to measure pressure. Pressure sensor 276 is configured to measure flow rate as will be explained.

When assembled, infrared lamp 272 seats in the end of agent channel 236, as is best shown in FIG. 2D.

Figure 2B:
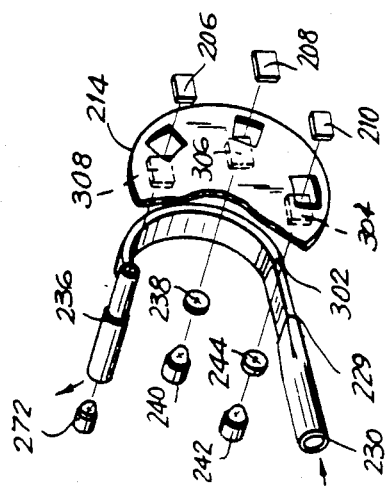
FIG. 2B shows the three optical detection channels, with the detection assembly equipment shown in an exploded view.

FIG. 2B shows the gas passageways that are used for the $CO_2$, $N_2O$ and agent detection channels. This Figure shows infrared lamps 242, 240 and 272; sapphire windows 244 and 238 ($CO_2$, $N_2O$ channels only), optical filters 304, 306 and 308; chopper wheel 214; and detectors 210, 208, and 206. These elements are combined to form the three detection channel assemblies as will be discussed in describing FIGS. 2C and 2D.

Preferably, infrared sources 240, 242 and 272 are subminiature lamps manufactured by Gilway Company, Woburn, Mass.

Optical filter 304 has a center wavelength of 4.265 microns and a bandwidth of 2.25%. This coincides with the absorption band of $CO_2$. Optical filter 306 has a center wavelength of 4.508 microns with a bandwidth of 2.35%. This coincides with the absorption band of $N_2O$. Optical filter 308 has a center wavelength of 3.310 microns with a bandwidth of 1%. This coincides with the absorption bands common to the three agent gases. These filters are commercially available from Optical Coating Laboratory, Inc., Santa Rosa, Calif.

Detectors 206, 208 and 210 are lead selenide infrared detectors. Preferably, the detectors have a 3 mm square active area and are manufactured by Optoelectronics, Inc., Petaluma, Calif.

Again referring to FIG. 2B, the respiratory gas stream enters the optical bench through flow shaper 230. In-line filter 229, preferably constructed of expanded PTFE with a .1 micron pore size, is disposed across the inlet passageway. The filter stops any foreign material from entering the optical bench. The entering gas flow has a circular cross-sectional shape. Flow shaper 230 and the inline filter reshape the flow to the rectangular cross-sectional shape of gas passageway 302 without forming eddies. However, other configurations for the inlet to accomplish flow shaping without a filter may be used.

The arced shape of gas passageway 302 accommodates using chopper wheel 214 for signal chopping. If other chopping methods are used, this passageway may have other shapes.

FIG. 2C depicts the $CO_2$ and $N_2O$ detection channel assemblies. The reference numbers in FIG. 2C are for the $CO_2$ detection channel. The $CO_2$ and $N_2O$ detection channel assemblies are identical. Hence, in describing FIG. 2C, the $N_2O$ detection channel component reference numbers will follow in parentheses those for the $CO_2$ detection channel.

$CO_2$ channel detector 210 (208) is fixed to one side of detector block 204. Optical filter 304 (306) for the $CO_2$ channel is fixed in opening 224 (222) of block 218. Optical filter 304 (306) forms part of the sidewall of gas passageway 302. Opening 301 is bored in the opposite side of block 218. Sapphire window 244 (238) is disposed in opening 301 and forms the side wall of gas passageway 302 opposite that formed by optical filter 304 (306). When lamp board 234 is fixed to block 218, infrared lamp 242 (240) is disposed in opening 301 behind sapphire window 244 (238).

Chopper wheel 214 rotates between detector 210 (208) and optical filter 304 (306). The openings in chopper wheel 214 are aligned with and common to the three optical paths. Chopping results in the generation of square wave signals indicative of the uncorrected partial pressures of $CO_2$, $N_2O$ and agent in the gas stream.

FIG. 2D shows the agent detection channel assembly.

Detector 206 is mounted on one side of detector block 204. Optical filter is fixed in opening 220 in block 218. Optical filter 308 forms one end of the agent optical channel 236. Infrared lamp 272 is mounted on pressure board 270. When the optical bench is assembled, lamp 272 ingresses and closes the other end of the agent optical channel. Gas passageway 376 in block 250 is the gas passageway to the cavities containing pressure and flow sensors 274 and 276, (FIG. 2A).

Preferably, the optical path length of passageway 302, as part of the $CO_2$ and $N_2O$ detector channels, is 0.1 inches; and the optical path length of agent detector channel 236 is 1 inch. The agent optical path length is longer because agents, such as halothane, ethrane and forane, are weaker absorbers than $CO_2$ and $N_2O$.

Figure 3:
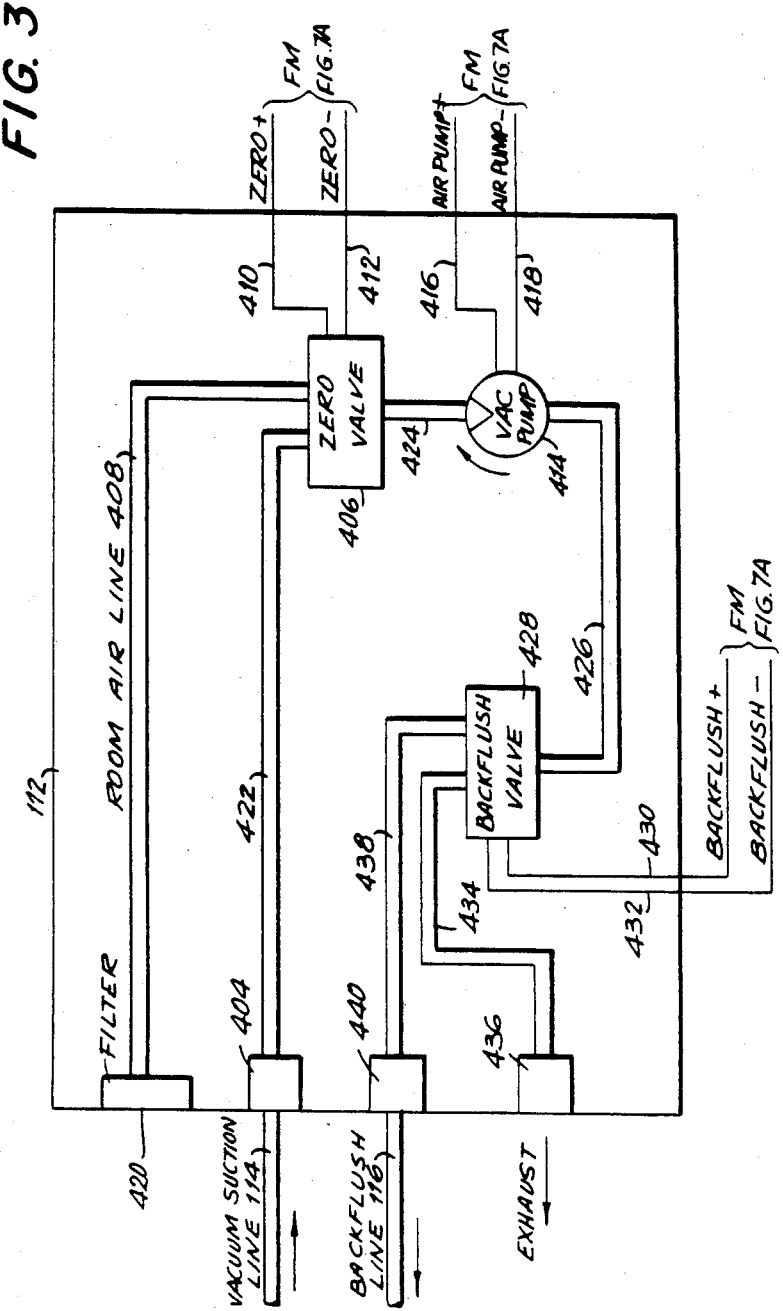
FIG. 3 is a block diagram of the pump assembly of the gas analyzer system of the present invention.

FIG. 3 discloses the pump assembly shown in FIG. 1 at 112. The pump assembly's purpose is to draw a respiratory gas stream through the gas pathway at the preferred rate of 50 cc/min. and backflush the system.

Vacuum suction line 114 is connected to inlet fitting 404. Internal passageway 422 connects inlet 404 to "zero" valve 406. Internal passageway 408 connects room air inlet filter 420 and "zero" valve 406. ZERO+ line 410 and ZERO— line 412 are the power lines for "zero" valve 406. The voltage across these lines determines which incoming passageway to "zero" valve 406 is selected.

Internal passageway 424 connects "zero" valve 406 to vacuum pump 414. The power lines to pump 414 are AIRPUMP+ line 416 and AIRPUMP— line 418. The voltage across these lines controls the speed of the pump.

Internal passage 426 connects vacuum pump 414 to backflush valve 428. The power lines to backflush valve 428 are BACKFLUSH+ line 430 and BACKFLUSH— line 432. The voltage across these lines determines which outlet passageway is selected by the valve.

The first outlet of backflush valve 428 is internal passageway 434. It connects backflush valve 428 to exhaust port 436. The other outlet is internal passageway 438. It connects backflush valve 428 to backflush line 116 to the optical bench via $CO_2$ scrubber 440. The $CO_2$ scrubber prevents, for example, any exhaled $CO_2$ from the operator from entering the optical bench during backflush. The timing of the selection of each output line will be discussed subsequently.

During normal operation, "zero" valve 406 is powered to select inlet passageway 422 containing the respiratory gas stream. Backflush valve 428 under these conditions is powered to select outlet passageway 434 that connects to exhaust port 436.

Periodically, the optical bench is backflushed to make a zero gas reading, determine the barometric pressure at the optical bench's location and clean filter 229 (FIG. 2B), as well as the patient adaptor filter (FIG. 1). To backflush, the voltage across the power lines to "zero" valve 406 and backflush valve 428 is changed. "Zero" valve 406 is powered to select internal passageway 408 containing room air. Backflush valve 428 is powered to select outlet passageway 438 that connects to backflush line 116 via $CO_2$ scrubber 440. The voltage across the power lines to vacuum pump 414 is changed as necessary to clean the filters.

FIG. 4A is a schematic diagram of the circuitry and selected components of optical bench 109. The gas stream enters passageway 302 in optical bench 109 traveling in direction A. The gas stream first travels past the $CO_2$ detection channel assembly comprising infrared light source 242, sapphire window 244, optical filter 304 and lead selenide detector 210. Second, it passes the $N_2O$ detection channel assembly comprising infrared light source 240, sapphire window 238, optical filter 306 and lead selenide detector 208. The gas stream leaves passageway 302 and enters agent detection channel 236. The agent detection channel assembly comprises infrared light source 272, optical filter 308 and lead selenide detector 206. Chopper wheel 214, common to all detection channel assemblies, has openings which allow simultaneous detection on all channels.

Broad band optical energy from each infrared source is passed through the gas stream. The filters only pass a narrow infrared band associated with the absorption characteristics of the specific gas. The energy streams exiting the filters are chopped and fall on the seperate detectors. Chopping forms a square wave output signal from each detector. The amplitude of the respective signals is indicative of the amount of energy within the filter's band transmitted through the gas stream.

Figure 4B:
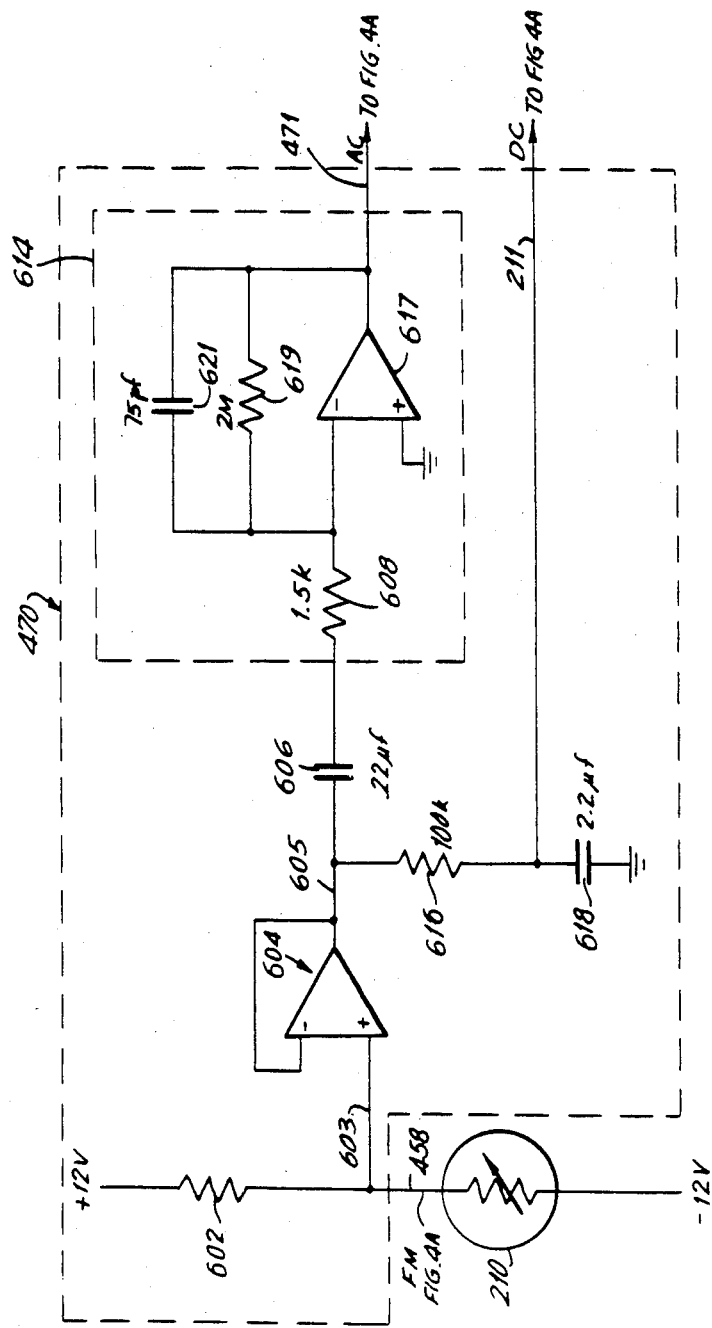
FIG. 4B is a schematic diagram of the AC/DC separation circuit in the amplifiers that receive the signals output from the three infrared detectors shown in FIG. 4A.

The output signal from $CO_2$ detector 210 is input to amplifier 470. The outputs of amplifier 470 are the AC component of the $CO_2$ signal on line 471 and the DC component of the $CO_2$ signal on line 211. The output signal from $N_2O$ detector 208 is input to amplifier 478. The outputs of amplifier 478 are the AC component of the $N_2O$ signal on line 479 and the DC component of the $N_2O$ signal on line 209. The signal output from agent detector 206 is input to amplifier 480. The outputs of amplifier 480 are the AC component of the agent signal on line 481 and the DC component of the agent signal on line 207. The circuit for separating the AC and DC components of the signals is shown in FIG. 4B.

The three LEDs, indicated generally at 246, and the three photodiodes, indicated generally at 456, detect the chopper motor φ position. One LED/photodiode pair is for the Aφ, a second pair is for the Bφ and a third pair is for the Cφ. These signals are used for insuring that the brushless motor is rotating chopper wheel 214 at the proper speed.

The three photodiodes detect the chopped light from the LEDs. The output of each photodiode is a "clean" square wave signal. The three photodiode output signals, when combined, approximate a standard three-phase signal.

The detected signals are output on lines 460, 462 and 464. The signal on line 460 is input to amplifier 472, the signal on line 462 is input to amplifier 474 and the signal on line 464 is input to amplifier 476. These amplified signals are input to comparators 486, 488, 490, respectively. The comparison signal for each comparator is a +5 V reference voltage.

The three comparator outputs are input to to 3$\phi$ brushless motor commutator 498. The outputs of commutator 498 are input to driver 500. The motor drive voltage on line 501 is also input to driver 500. The outputs of driver 500 are the $\phi$A signal on line 502, the $\phi$B signal on line 504 and the $\phi$C signal on line 506 which drive chopper motor 508 appropriately.

Prior to amplification of the detected $\phi$B signal from the center LED/photodiode pair, a branch line inputs the signal to amplifier 484. The amplifier output signal is the GAS SYNC signal on line 485. The GAS SYNC signal synchronously demodulates the $CO_2$, $N_2O$ and agent signals, as will be discussed.

After the gas stream leaves agent channel 236, it enters passageway 376. This passageway connects agent channel 236 to the first cavity in the bottom of block 250. This cavity contains pressure sensor 274. The first and second cavities are connected by the restriction at 277 (FIG. 4A). A passageway (not shown) connects the second cavity to the gas outlet and the backflush lines.

At this point, the only signals discussed which are ready for output from the optical bench are the detected $CO_2$, $N_2O$ and agent signals. The remainder of the signals output from the optical bench are multiplexed by multiplexer 532 and then output from the optical bench.

The first input to multiplexer 532 is the output of EEPROM 530. EEPROM 530 stores coefficients relating to characterization of the optical bench and the preferred bench temperature.

The characterization coefficients do not adjust or change the operation of any component of the optical bench or the bench as a whole. These coefficients correct the bench's measurements for system component deviation from ideal.

The inputs to EEPROM 530 are the data bus D1 signal on line 542, the SK (serial data clock) signal on line 540 and the CS (chip select) signal on line 538. The CS and SK signals control the EEPROM's output. The D1 signal is the data input to the EEPROM. All of these signals are output from quad. flip flop 544. The data inputs to quad. flip flip 544 are the D$\emptyset$-D3 signals on lines 552, 550, 548 and 546, respectively. The D$\emptyset$-D3 bar signals are outputs of line driver 554 whose inputs are the 4 bit parallel PRED$\emptyset$-PRED3 bar signals on lines 556, 558, 560 and 562. These signals are from the analog input circuitry. (The "bar" designation after a signal name indicates the inverted state of the signal without the bar designation, as is known by those skilled in the art).

Quad. flip flop 544 is clocked by the output of demultiplexer 578. The inputs to demultiplexer 578 are the A$\emptyset$ signal on line 572, the BUS STROBE signal on line 574 and the A1 signal on line 576. These signals are output from line driver 570. The inputs to line driver 570 are the PREA1 signal on line 564, PREA$\emptyset$ signal on line 566 and the PRESTRB signal on line 568. These signals are received from the analog input circuitry.

The output of demultiplexer 578 depends on the state of the BUS STROBE signal on line 574.

When properly instructed, the EEPROM outputs the characterization coefficients to multiplexer 532 as the first input.

The second input to multiplexer 532 is the amplified OB TEMP (optical bench temperature) signal on line 524. This signal is output from temperature sensing and control circuit 514. The fifth signal input to multiplexer 532 is the HEATER DRIVER V (heater driver voltage) signal on line 523 that is also output from temperature sensing and control circuit 514. The optical bench incorporates heating resistors 510 and 512.

The heating resistors are controlled by temperature control and sensing circuit 514. In operation, the optical bench temperature is sensed and its deviation from the preferred bench temperature is determined. Based on the temperature deviation, the temperature control and sensing circuit adjusts the voltage to the heating resistors via a voltage regulator. The sensed temperature is converted to a voltage and input to multiplexer 532 as the OB TEMP signal. The voltage to the heating resistors is input to multiplexer 532 as the HEATER DRIVER V signal.

The third input is the amplified flow rate signal on line 528. Flow rate through the optical bench is measured by differential pressure transducer 276. This transducer is commercially available from IC Sensors, Inc., Sunnyvale, Calif. For a 50 cc/min. flow rate, the restriction at 277 produces a pressure drop of approximately 0.5 psi. The reference side of the pressure transducer connects to one side of the restriction and the measurement side connects to the other. A change in flow rate causes a change in the pressure drop which is measured by the transducer which generates a representative voltage. This voltage is input to multiplexer 532.

The fourth signal input to multiplexer 532 is the amplified pressure signal on line 526. Pressure sensor 274 is an absolute pressure measuring type pressure sensor. The pressure sensor is commercially, available from IC Sensors, Inc., Sunnvdale, Calif. The pressure is continuously monitored during system operation. Rapid pressure changes may indicate various problems in the optical bench which need attention. The pressure within the optical bench must be considered in calculating gas concentrations, as more fully discussed subsequently.

The pressure sensor measures barometric pressure at system start up. This value is stored for later use. The stored value for barometric pressure is updated at every zero gas reading.

The sixth, seventh and eighth signals input to multiplexer 532 are DC coupled signals representing the bulk resistance of the detectors. The $CO_2$ signal output from amplifier 470 on line 211 is input as the sixth signal. The $N_2O$ signal output from amplifier 478 on line 209 is input as the seventh signal. The agent signal output from amplifier 480 on line 207 is input as the eighth signal.

The D$\emptyset$-D3 bar signals on the data bus are the control signals input to multiplexer 532. Based on their states, a multiplexed signal is output on line 536 after processing by sample and hold circuit 533.

FIG. 4B shows the AC/DC separation circuit associated with amplifier 470 for the $CO_2$ signal, amplifier 478 for the $N_2O$ signal and amplifier 480 for the agent signal. The circuit in FIG. 4B is identical in the three amplifiers. Accordingly, only the circuit for amplifier 470 is described.

The $CO_2$ signal output from detector 210 is input to amplifier 470. The input signal is biased by resistor 602. Resistor 602 preferably has approximately 16% of the resistance of detector 210 at normal operating temperatures. The signal on line 603 contains both the DC and AC components. This signal is buffered by amplifier 604.

Preferably, 0.22 $\mu$f capacitor 606 is disposed in line 605 to block the DC component of the signal and pass the AC component of the signal on to amplifier 614. Amplifier 614 preferably comprises op-amp 617, resistor 608 (preferably 1.5K ohms), and resistor 619 (preferably 2M ohms). The 75 pf capacitor 621 provides noise filtering. The amplifier output is the AC component of the signal online 471 (FIG. 4A).

The DC component is filtered by resistor 616 and capacitor 618. Preferably, the resistance value of resistor 616 is 100K ohms and the capacitance value of capacitor 618 is 2.2 $\mu f$. The DC component is output on line 211 for input to multiplexer 532 (FIG. 4A).

The significance of the DC signal component is that it represents the bulk resistance of the detector sensitivity changes with temperature. Hence, the DC component is a useful predictor of detector sensitivity changes when used wth the correlation coefficients stored in EEPROM 530. This avoids errors associated with using a separate temperature sensor for determining detector sensitivity changes.

Figure 5:
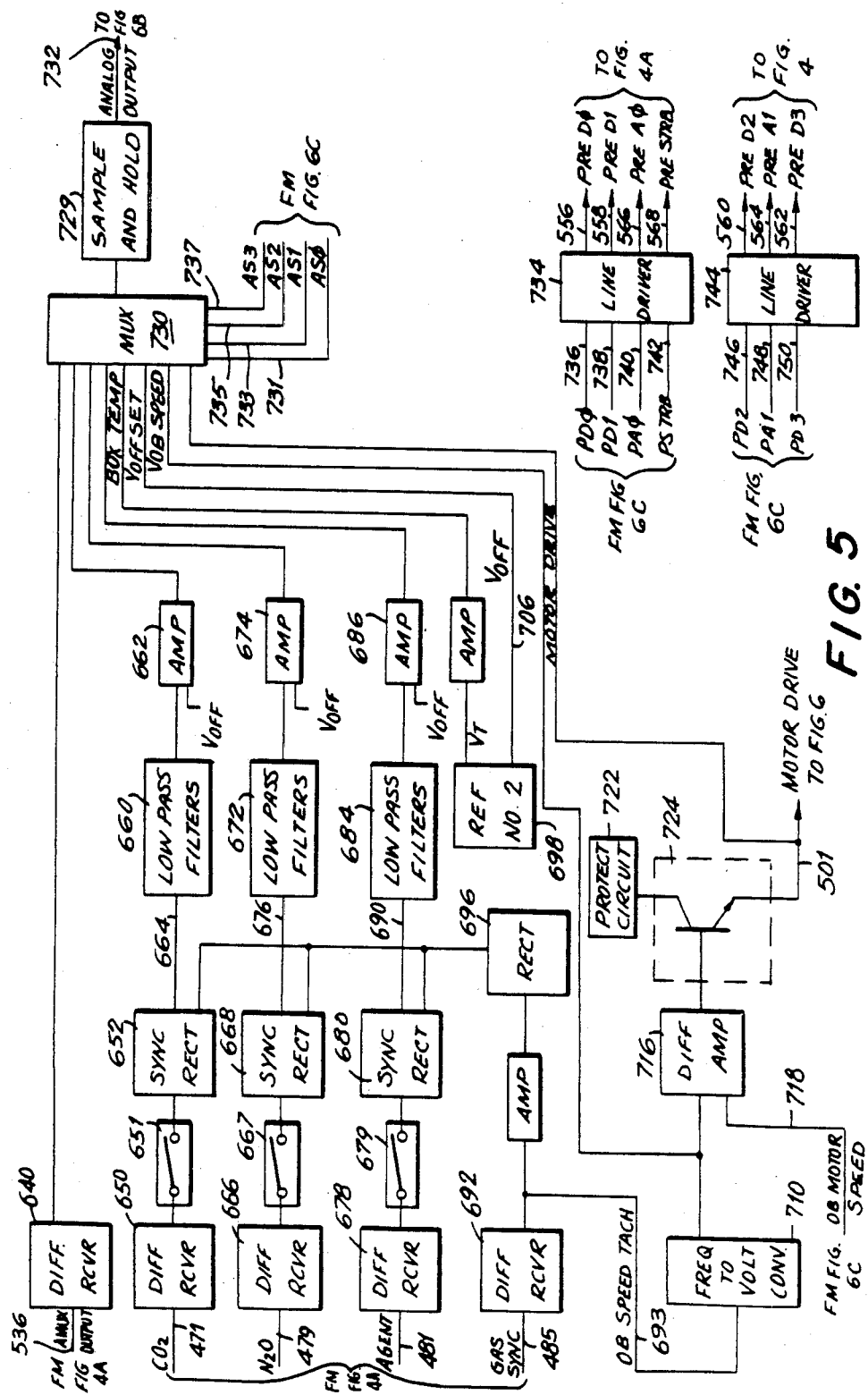
FIG. 5 is a schematic diagram of the analog input circuitry of the multichannel gas analyzer of the present invention.

FIG. 5 is a schematic diagram of analog input circuitry 122 (FIG. 1). A majority of the inputs to this circuitry are the analog outputs of optical bench 109.

The AMUX OUTPUT on line 536 from multiplexer 532 (FIG. 4A), is input to differential receiver 640. The output of differential receiver 640 is input to multiplexer 730.

The $CO_2$ signal on line 471, the $N_2O$ signal on line 479 and the agent signal on line 481 from the optical bench are identically demodulated before input to multiplexer 730. Accordingly, the $CO_2$ channel's demodulation path will be described and the reference numbers for the $N_2O$ and agent channels' demodulation paths will follow in parentheses.

The $CO_2$ signal on line 471 (479, 481) is input to differential amplifier 650 (666, 678). The output of differential amplifier 650 (666, 678) is input to synchronous rectifier 652 (668, 680) via switch 651 (667, 679).

The demodulating signal input to synchronous rectifier 652 (668, 680) is the GAS SYNC signal on line 485. The GAS SYNC signal is input to differential receiver 692, then amplified. The amplifier output is rectified by rectifier 696 and input to synchronous detector 652 (668, 680) to control demodulation of the $CO_2$ ($N_2O$, agent) signal.

After demodulation, the $CO_2$ ($N_2O$, agent) signal is input to a series of low pass filters 660 (672, 684). The $CO_2$ signal is amplified by amplifier 662 (674, 686) and then input to multiplexer 730.

The $V_{OFF}$ signal is input to amplifer 662 (674, 686) to insure that the output is never less than zero.

Electronic switch 651 (667, 679) is disposed in the line connecting differential amplifier 650 (666, 678) and synchronous rectifier 652 (668, 680). This switch is opened when it is desired to determine the system's offset voltage, as will be described subsequently.

The GAS SYNC signal output from differential receiver 692 is also the OB SPEED TACH signal (optical bench speed tachometer) on line 693. This signal is input to frequency to voltage converter 710. The output voltage, $V_{OBSPEED}$, is input to multiplexer 730 and to differential amplifier 716. The $V_{OBSPEED}$ signal is a voltage signal proportional to the chopper motor speed.

The second input to differential amplifier 716 is the OB MOTOR SPEED signal on line 718 from analog processor circuitry 124. This signal is the voltage set point for the chopper motor speed. The difference in the signals input to amplifier 716 is used to drive transistor 724, protected by protection circuit 722. The output of transistor 724 on line 501 is input to driver 500 (FIG. 4A) for use in powering the chopper motor and to multiplexer 730.

The temperature of the analog input circuitry is determined for use in making computations. REF-02, 698, commercially available from Precision Monolithics, Inc., Santa Clara, Calif. is used for this purpose. The $V_T$ output of REF-02 is amplified and input to multiplexer 730 as the BOX TEMP signal. Also output from REF-02 is the $V_{OFF}$ signal. This signal is input to multiplexer 730. This signal is also input to $CO_2$ amplifier 662, $N_2O$ amplifier 674 and agent amplifier 686 for insuring that their outputs are at least zero.

The control input to multiplexer 730 is the parallel 4 bit input AS$\emptyset$, AS1, AS2 and AS3 on lines 731, 733, 735 and 737, resectively. The AS$\emptyset$-AS3 signals are generated by analog processing circuitry 124, as will be explained subsequently.

Based on the states of control signals AS$\emptyset$-AS3, multiplexer 730 provides an output from the analog input circuitry on line 732 after processing by sample and hold circuit 729.

The multiplexed analog output signal on line 732 represents the detected partial pressures of $CO_2$, $N_2O$ and the agent; the flow rate of the gas through the optical bench; the pressure and temperature in the optical bench; the temperature of the apparatus containing the analog input circuitry; the speed of the chopper motor; the chopper motor driver voltage; and the voltage for maintaining a positive amplifier output values for selected amplifiers.

The parallel 4 bit input to line driver 734 from analog processing circuitry 124 comprises the PD$\emptyset$ signal on line 736, the PD1 signal on line 738, the PA$\emptyset$ on line 740 and the PSTRB signal on line 742. The parallel 4 bit output of this driver is the PRED$\emptyset$ on line 556, the PRED1 signal on line 558, the PREA$\emptyset$ signal on line 566 and the PRESTRB signal on line 568.

The parallel 3 bit input to line driver 744 comprises the PD2 signal on line 746, the PA1 signal on line 748 and the PD3 signal on line 750. The parallel 3 bit output of this driver is the PRED2 signal on line 560, the PREA1 signal on line 564 and the PRED3 signal on line 562.

PD$\emptyset$-PD3/PRED$\emptyset$-PRED3 are data lines to the optical bench's 4 bit data bus. PA$\emptyset$ and PA1/PREA$\emptyset$ and PREA1 are the 2 bit addresses to the optical bench circuitry. PSTRB/PRESTRB are the strobe signals for the optical bench address bits and data bus.

Figure 6B:
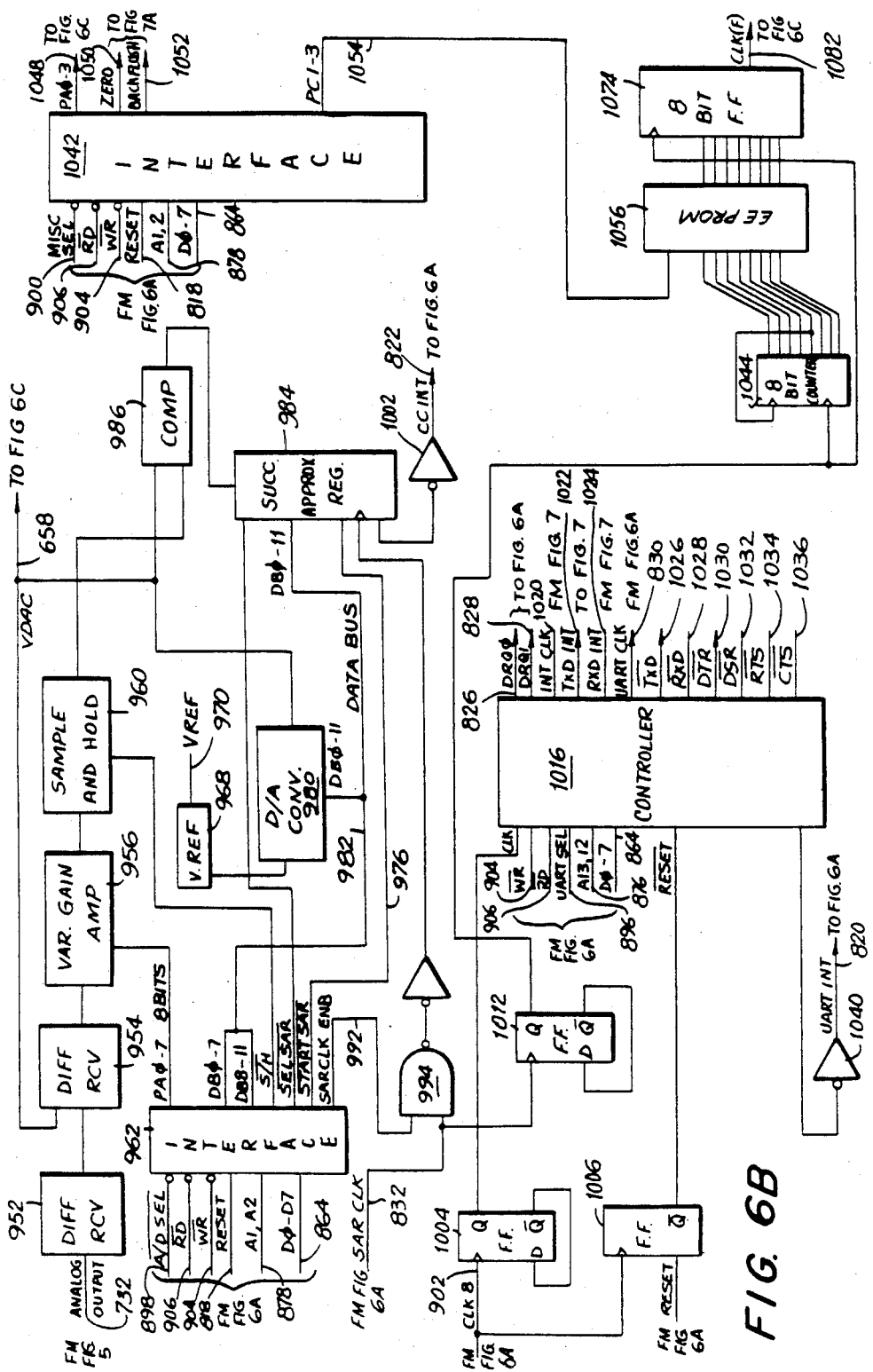

FIGS. 6A, 6B and 6C show analog processing circuitry 124 (FIG. 1). First the circuits in the three figures will be described, then their calculating functions will be described.

One component of analog processing circuitry 124 is microprocessor 808. Microprocessor 808 is a model 80186 CPU, commercially available from Intel Corp., Santa Clara, Calif.

The signals input to microprocessor 808 from the circuitry in FIG. 6B (to be discussed) are the UART INT signal on line 820, the CC INT signal on line 822, the DRQ$\emptyset$ signal on line 828, and the DRQ1 signal on line 826. The UART INT signal is an interrupt input from controller 1016 to microprocessor 808 to indicate the transmission or receipt of data. The CC INT signal is an interrupt input from successive approximation register 984 to indicate completion of the conversion of a predetermined analog signal input and that the coverted signals can be put on the data bus 966 (FIG. 6B).

The DRQ0 and DRQ1 signals are direct memory access request inputs indicating that a character is ready to be transmitted from memory or that a character has been received and must be transferred to memory.

The output signals of microprocessor 808 are the PATIENT SIDE OFF signal on line 802, the AMUX SEL signal on line 804, the PREAMP SEL signal on line 806, the RESET signal on line 818, the UART CLK signal on line 830, the SAR CLK signal on line 832, the UART SEL signal on line 896, the A/D SEL signal on line 898, the MISC SEL signal on line 900, the CLK8 signal on line 902, the WR bar signal on 904 and the RD bar signal on line 906.

The PATIENT SIDE OFF signal is input to the battery control circuit of power supply 158 (FIG. 1) which is conventional and is not shown in detail.

The AMUX SEL signal is one of the signals that controls the clocking of latch 1202 (FIG. 6C). The output of latch 1202 is the parallel 4 bit control signal AS0–AS3 input to multiplexer 730 (FIG. 5).

The PREAMP SEL signal is one of the signals controlling the clocking of latch 1184 and the clearing of flip flop 1192 (FIG. 6C). The clocking of the latch and the clearing of the flip flops result in the parallel 4 bit signal PD0–PD3 for the optical bench data bus; the 2 address bits, PA0 and PA1, for the optical bench; and the strobe signal PSTRB for the optical bench.

The RESET signal indicates that the microprocessor is in a reset condition.

The UART CLK signal is a timing signal to provide a baud rate clock for the asynchronous serial communications channel.

The SAR CLK signal is the successive approximation register clock used to control the analog to digital converter circuitry (FIG. 6B).

The A/D SEL signal is the chip selection input to interface 962 (FIG. 6B).

The MISC SEL signal is the chip selection signal input to interface 1042 (FIG. 6B).

The CLK8 signal is the 8 MHZ clock signal for clocking various circuit components of the processor circuitry.

The WR bar signal is the write timing signal indicating that the processor is writing data into memory or into an input/output device.

The RD bar signal is a read timing signal indicating that the processor is reading data.

The other signals associated with microprocessor 808 are for transmission to or retrieval from memory and will be discussed subsequently.

Memory in FIG. 6A consists of four read only memories (ROMs) 880, 882, 884 and 886; and four random access memories (RAMs) 888, 890, 892 and 894. All of these memories are conventionally connected to address bus 874 and data bus 872.

FIG. 6A shows three address latches, 850, 852 and 854. Each latch is enabled by the ALE (address latch enable) signal output from microprocessor 808 on line 834. Latch 850 receives a parallel 4 bit input for addresses A16/S3–A19/S6 on line 836. This four bit signal is shown as a single line. One skilled in the art would understand this is a four bit parallel input. The clocking of latch 850 will place the values of A16/S3–A19/S6 on address bus 874.

The parallel 8 bit information signal AD8-15, output from microprocessor 808 on line 838 is input to latch 852. The AD8-15 ports at microprocessor 808 are I/O ports handling both addresses and data information. When latch 852 is clocked, the latched address values are placed on address bus 874.

Similarly, the parallel 8 bit signal, AD0-7, output from microprocessor 808 on line 840 is input to latch 854. The AD0-7 ports at microprocessor 808 are I/O ports handling both address and data information. When clocked, the latched values are placed on address bus 874.

AD0-15 microprocessor I/O ports also connect to data bus 872 via bus 855 and bus transceivers 860 and 862. Bus transceiver 860 controls transfers between the AD0-7 I/O ports and the data bus. Bus transceiver 862 controls transfers between the AD8-15 I/O ports and the data bus.

Bus transceivers 860 and 862 are enabled by the DEN bar signal on line 842. The direction of the data transfer is controlled by the DT/R (R bar) signal on line 844.

Demultiplexers 856 and 858 are used to enable RAMs 888, 890, and 892, 894. The LCS bar signal on line 846 enables both demultiplexers.

The control signals input to demultiplexer 856 (the A0 and A14 signals from address bus 874) are decoded to provide the enabling input signals to RAMs 888 and 890. Whether reading or writing is the proper action is determined by the states of the RD bar and WR bar signals input to RAMs 888 and 890.

The control signals input to demultiplexer 858, A14 signal from the address bus and the BHE bar signal on line 848 from microprocessor 808, are decoded to enable RAMs 892 and 894. Similarly, whether reading or writing is accomplished depends on the states of the RD bar and WR bar signals input to RAMS 892 and 894.

Third demultiplexer 812 enables ROMs 880, 882, 884 and 886. The UCS bar signal output from microprocessor 808 on line 809 enables demultiplexer 812. The control inputs to demultiplexer 812 are the A17, A18 and A19 signals from address bus 874. The control inputs when demultiplexed are output to enable the ROMs. When an enabled ROM is read depends on the state of the RD bar signal input to each ROM.

Referring to FIG. 6B, the signals input to microprocessor interface 962 are the A/D SEL bar signal on line 898, the RD bar signal on line 906, the WR bar signal on line 904, the RESET signal on line 818, the parallel 2 bit address signal A1 and A2 on line 878, and the parallel 8 bit signal D0-7 on line 864. The outputs of interface 962 will be discussed subsequently in discussing the circuit.

The ANALOG OUTPUT signal on line 732 from multiplexer 730 (FIG. 5) is input to differential receiver 952. The output of differential receiver 952 is input to differential receiver 954. The other input to differential receiver 954 is the system offset which is output by digital to analog (D/A) converter 980.

The offset signal for each gas channel is generated by opening switches 651, 667 and 679 (FIG. 5). The voltage output by D/A converter 980 when each switch is open is that gas channel's voltage offset. The individual channel's voltage offset is the second input signal to differential receiver 954 when the corresponding gas signal in the multiplexed ANALOG OUTPUT signal is input to differential receiver 954.

The voltage difference output of differential receiver 954 is input to variable gain amplifier 956. The gain of the amplifier is controlled by the parallel 8 bit signal PA0–PA7 output from interface 962. These signals are from data bus 864 (FIG. 6A).

The amplified signal output from variable gain amplifier 956 is input to sample and hold circuit 960. The sample and hold circuit control signal is the S/H bar signal output from interface 962 on line 972. The duration of this signal is long enough for conversion of the current data in successive approximation register 984 and placement of that data on data bus 982.

The output of the sample and hold circuit is input to comparator 986. The second input to comparator 986 is the output of D/A converter 980 which is the VDAC signal on line 658. The output of comparator 986 is input to successive approximation register 984. The START SAR bar signal on line 976 is input to successive approximation register 984 to start the analog to digital converter process. The SELSAR bar signal on line 974 is input to successive approximation register 984. This is the output enable input to the successiive approximation register controlling placing the converted data on data bus 982.

Another output of successive approximation register 984 is the CC INT signal on line 822 which was discussed with respect to FIG. 6A. This signal after output is inverted by inverter 1002.

The SARCLK ENB signal output from interface 962 on line 992 is the first input to NAND gate 994. The other input to this gate is the SARCLK signal output from microprocessor 808 on line 832. The states of these signals control the output of NAND gate 994. The output of NAND gate 984 after inversion is used to turn the internal successive approximation register clock on and off.

The inputs to interface 1042 are the MISC SEL signal on line 900, the RD bar signal on line 906, the WR bar signal on line 904, the RESET signal on line 818, the parallel 2 bit input comprising signals A1 and A2 from the address bus on line 878 and the parallel 8 bit input comprising signals D∅-7 from data bus 864.

The outputs of interface 1042 are the parallel 4 bit output PA∅-3 on line 1048, the ZERO signal on line 1050, the BACKFLUSH signal on line 1052 and the parallel 3 bit output PC1-3 on line 1054.

The PA∅-3 output on line 1048 is input to analog switch 1102 (FIG. 6C). The ZERO signal output on line 1050 and the BACKFLUSH signal output on line 1052 are used for actuating the pump valves. The PC1-3 signals output on line 1054 are input to EEPROM 1056.

The other input to EEPROM 1056 is the parallel 8 bit output of 8 bit counter 1044. 8 bit counter 1044 is clocked by the output of flip flop 1012. The SARCLK signal clocks flip flop 1012. The data input and the Q bar output of this flip flop are tied. This causes the Q output to change state every two SARCLK clock pulses.

8 bit counter 1044 comprises two 4 bit counters. The terminal count of one 4 bit counter is tied to the clock input of the other 4 bit counter. Thus, the second 4 bit counter is clocked every sixteen clocks.

The parallel 8 bit output of EEPROM 1056 is input to 8 bit flip flop 1074. 8 bit flip flop 1074 is clocked by the same signal that clocks the first 4 bit counter of 8 bit counter 1044. The CLK(F) signal output on line 1082 clocks latch 1188 (FIG. 6C).

Controller 1016 will not be discussed. The Q output of flip flop 1004 clocks controller 1016. The CLK8 signal on line 902 clocks flip flop 1004. The Q bar output and data input of this flip flop are tied. Hence, the Q output will have a positive-going edge to clock controller 1016 every two CLK8 pulses.

The CLK8 signal also clocks flip flop 1006. The RESET signal on line 818 is input to this flip flop's data input. When the CLK8 signal clocks this flip flop, the state of the RESET signal is inverted and input to controller 1016. The controller resets one CLK8 pulse after microprocessor 808 experiences a reset condition.

The WR bar signal on line 904 and the RD bar signal on line 906 are input to controller 1016. These signals control whether data is transmitted from or received by controller 1016.

The UART SEL signal on line 896 is input to controller 1016 for chip selection and enabling reading from and writing into memory.

The parallel 2 bit address bus signals A12 and A13 are input to controller 1016 on line 876. These signals and are used for its control. The parallel 8 bit data bus signals D∅-7 are input to controller 1016 on line 864. This is the bus that is either read from or written onto.

The DRQ∅ signal on line 826 and the DRQ1 signal on line 828 are input to microprocessor 808 for notifying the microprocessor that data is ready to be transmitted from memory or that data is ready to be sent to memory.

The other signals that are output from or input to, or transmitted from, or received by controller 1016 are primarily associated with communicating with the display section or an external device.

The INT CLK signal on line 1020 is the baud rate clock for synchronous serial communications between the analog and display processors.

The TxD INT signal on line 1022 is the line on which data is transmitted from the analog processor to the display processor.

The RxD INT signal on line 1024 is the line on which data is received from the display processor.

The TxD bar signal on line 1026, the RxD bar signal on line 1028, the DTR bar signal on line 1030, the DSR bar signal on line 1032, the RTS bar signal on line 1034 and the CTS bar signal on line 1036 are for digitally communicating with external equipment.

The TxD bar signal is for transmitting data for synchronous communication. The RxD bar signal is for receiving data for synchronous communication. The DTR bar signal is a data terminal ready control signal. The DSR bar signal is a carrier detection signal. The RTS bar signal is the request to send signal. The CTS bar signal is the clear to send data signal.

The UART CLK signal output on line 830 from microprocessor 808 is the timing signal for providing a baud rate clock for synchronous serial communications with the display processor.

The UART INT signal output on line 820 is is inverted by inverter 1040. This signal is an interrupt signal to microprocessor 808 to indicate that data is ready to be sent or received.

Also shown on FIG. 6B is $V_{REF}$ voltage generator 968. The $V_{REF}$ voltage generator is conventional. This voltage is used throughout the analog processing circuitry.

Referring to FIG. 6C, the remaining portions of the analog circuitry will be described.

The VDAC signal from D/A converter 980 on line 658 is representative of the 12 bit converted data bus information. The VDAC signal is input to analog switch 1102. The output signal from analog switch 1102 on line 1114 is processed by sample and hold circuit 1116. The output of this circuit is the OB MOTOR SPEED signal on line 718.

The output signal of analog switch 1102 on line 1118 is processed by sample and hold circuit 1120. The output of this circuit is the AIR PUMP SPEED signal on line 1128.

The control signals for analog switch 1102 is the parallel 4 bit signal PA∅-3 output from interface 1042 on line 1048.

Again referring to FIG. 6C, the PREAMP SEL signal on line 806 is input to NAND gate 1180. The other input to this gate is the WR bar signal on line 904. The output of NAND gate 1180 clocks 8 bit latch 1184. The inputs to 8 bit latch 1184 are the D∅-D3 signals from data bus 864 and address bus bits A1 and A2. The signal that clocks latch 1188 is the CLK(F) signal on line 1082. The output of 8 bit latch 1184 is input to 8 bit latch 1188. Also input to 8 bit latch 1188 is the Q output of flip flop 1192. Flip flop 1192 is preset by the PsTRB signal on line 568 and cleared by the output of NAND gate 1180.

The outputs of 8 bit latch 1188 are the PD∅ signal on line 736, the PD1 signal on line 738, the PD2 signal on line 746, the PD3 signal on line 750, PA∅ on line 740, the PA1 signal on line 748 and the PSTRB signal on line 742. These signals are the data bus and address signals used by the optical bench (FIGS. 5, 6).

The AMUX SEL signal on line 804 is input to NAND gate 1198. The other input is the WR bar signal on line 904. The output of NAND gate 1198 clocks latch 1202. The inputs to latch 1202 are the D∅-D3 signals from the data bus (FIG. 5). The outputs of latch 1202 are the AS∅ signal on line 731, the AS1 signal on line 733, the AS2 signal on line 735 and the AS3 signal on line 737. These are the control input signals to multiplexer 730 (FIG. 5).

The primary function of microprocessor 808 of analog processing circuitry 124 is calculating the partial pressures and concentrations of the constituent gases. In calculating these, the microprocessor corrects for collision broadening, temperature, cross correction, barometric pressure, detector sensitivity changes and characterization.

Characterization allows for the interchangeability of optical benches without the need for calibration. Characterization coefficients of an optical bench are based on the fact that a manufacturer constructs each optical bench of a particular type with the same components. However, corresponding components in two different benches have different responses. The result is that two diferent benches making partial pressure measurements can derive two different values even though both are operating properly.

Accordingly, each bench has its own specific characterization coefficients. These coefficients are stored in EEPROM 530 (FIG. 4). Hence, the application of each bench's characterization coefficients to raw measurements of a known gas standard bring about the same result. This result is consistent with industry standards and made without any calibration to the bench's components.

Specific characterization coefficients for each gas channel are stored in EEPROM 530. The other values stored in the EEPROM are the preferred temperature for the bench; the collision broadening coefficients; the cross correction coefficients; the span factor for correcting flow measurements; the span factor and offset for correcting pressure measurements; and the span factor and offset for correcting temperature measurements.

The calculation of partial pressure and gas concentration will now be described.

The DC output voltages from $CO_2$ detector 210, $N_2O$ detector 208, and agent detector 206 are measured and stored every time a zero gas measurement or backflush is conducted. This is represented by the expression:

$$ZeroDC[X] = V[Xdc] \tag{1}$$

where,
- $X = CO_2$, $N_2O$ or agent.
- $V[Xdc]$ = the measured DC voltage output of the detector with zero gas.
- $ZeroDC[X]$ = the voltage value for the term $V[Vdc]$ that is stored in memory for $CO_2$, $N_2O$ or agent.

The demodulated voltages for $CO_2$ on line 664, for $N_2O$ on line 676 and for the agent on line 690 are also measured and stored every time a zero gas measurement or backflush is conducted. This is represented by the expression:

$$Zero[X] = V[X] \tag{2}$$

where,
- $X = CO_2$, $N_2O$ or agent.
- $V[X]$ = the measured demodulated voltage for $CO_2$, $N_2O$, or agent with zero gas.
- $Zero[X]$ = the voltage value for the term $V[X]$ that is stored in memory for $CO_2$, $N_2O$ or agent.

At predetermined intervals, the system calculates updates for temperature related values used in calculating the partial pressure of each gas. These values are calculated according to the following three expressions:

$$\Delta T = V[Tmp] - RefTmpVolts \tag{3}$$

where,
- $V[Tmp]$ = current measured voltage from the temperature sensor.
- $RefTmpVolts$ = the voltage for the preferred operating temperature of the optical bench stored in EEPROM 530.

$$tcB[X] = B_0[X] + ((B_1[X])(\Delta T)) + ((B_2[X])(\Delta T^2)) \tag{4}$$

where,
- $X = CO_2$, $N_2O$ or agent.
- $B_0[X]$, $B_1[X]$, $B_2[X]$ = the characterization coefficients for each gas stored in EEPROM 530.
- $tcB[X]$ = the B temperature correction for each gas.

$$tcC[N_2O] = C_0[N_2O] + ((C_1[N_2O])(\Delta T)) + ((C_2[N_2O])(\Delta T^2)) \tag{5}$$

where,
- $C_0[N_2O]$, $C_1[N_2O]$, $C_2[N_2O]$ = the C characterization coefficients for $N_2O$ stored in EEPROM 530.
- $tcC[N_2O]$ = the C temperature correction for $N_2O$.

The C temperature correction is only calculated for $N_2O$. The C temperature correction for $CO_2$ and the agent have negligible effect on the final partial pressure of the gases, so they are not used.

At predetermined intervals, collision broadening calculations are performed. These calculations are carried out according to the following three expressions:

$$\text{If } PP[N_2O] > 76 \text{ mmHg, then } CB[N_2/O_2] = 0 \tag{6}$$

where,

PP[N2O]=the average PP[N2O] over the update time interval.
CB[N2/O2]=the collision broadening factor for $N_2$ and $O_2$.

$$\text{Else, CB[N2/O2]}=(cbL)(1-(\%O_2/100)) \quad (7)$$

where,
CB[N2/O2]=the collision broadening factor for $N_2$ and $O_2$.
cbL=the collision broadening coefficient stored in EEPROM 530.
%O2=the measured %O2 from a peripheral device, or a manually set percentage, or 50% as a default value in the programming.

$$CB[N2O]=(cbM)(PP[N2O])/760 \quad (8)$$

where,
CB[N2O]=the collision broadening factor for $N_2O$.
cbM=the collision broadening coefficient for $N_2O$ stored in EEPROM 530.
PP[N2O]=the average PP[N2O] over the update time interval.

Collision broadening is only calculated for N2O on CO2 because that is the only collision broadening with any significant effect.

The sensitivity changes for an individual detector is determined by the expression:

$$CorrZero[X]=(T_oCorr[X])(V[Xdc]_{inst.}-ZeroDC[X]) \quad (9)$$

where,
X=$CO_2$, $N_2O$ or agent.
$T_oCorr[X]$=the constant for detector sensitivity changes for changes in DC voltage with respect to the $CO_2$, $N_2O$ or agent detector.
V[Xdc]$_{inst}$=instantaneous detector voltage for $CO_2$, $N_2O$ or agent.
ZeroDC[X]=the voltage value for the term V[Xdc] that is stored in memory for $CO_2$, $N_2O$ or agent.

The $T_oCorr[X]$ term is calculated during manufacturing characterization by measuring the detector sensitivity and the DC voltage at various temperatures. The $T_oCorr[X]$ term is calculated according to the following expression:

$$T_oCorr[X] = \frac{\left(\frac{\text{detector sensitivity }[X]}{\text{change in DC volts }[X]}\right)}{\text{Number of measurements}} \quad (10)$$

The absorption of light by each gas is continuously calculated according to the expression:

$$R[X] = -\ln \frac{V[X]_{inst}}{Zero[X] + CorrZero[X]} \quad (11)$$

where,
X=$CO_2$, $N_2O$ or agent.
CorrZero[X]=the correction for detector sensitivity changes.
V[X]$_{inst}$=the instantaneous demodulated gas voltage for $CO_2$, $N_2O$ or agent.
Zero[X]=the voltage value for the term V[X] that is stored in memory for $CO_2$, $N_2O$ or agent.
Having made the above calculations, microprocessor 808 calculates the partial pressure of each gas. In the expressions that follow for calculating the partial pressure for each gas, a partial pressure shown as PP[X] is a final partial pressure corrected for cross correction and collision broadening. A partial pressure shown as PP[X]' is a partial pressure corrected for collision broadening only. A partial pressure shown as PP[X]″ is corrected for neither.

The partial pressure of $CO_2$, $N_2O$ and agent are calculated according to expressions (12) to (20):

$$PP[N2O]'' = ((tcB[N2O])(R[N2O])) + ((tcC[N2O])(R[N2O]^2)) + ((D[N2O])(R[N2O]^3)) \quad (12)$$

where,
tcB[N2O]=the B temperature correction for $N_2O$.
R[N2O]=$N_2O$ absorption.
tcC[N2O]=the C temperature correction for $N_2O$.
D[N2O]=the D characterization coefficient for $N_2O$ stored in EEPROM 530.

The uncorrected $CO_2$ partial pressure is calculated according to the expression:

$$PP[CO2]''=((tcB[CO2])(R[CO2]))+((C_o[CO2])(R[CO2]^2)) \quad (13)$$

where,
tcB[CO2]=the B temperature correction for $CO_2$.
R[CO2]=$CO_2$ absorption.
$C_o$[CO2]=the C characterization coefficient for $CO_2$ stored in EEPROM 530.

The uncorrected $CO_2$ partial pressure is now corrected for collision broadening by the expression:

$$PP[CO2]'=((PP[CO2]'')(1+CB[N2O]+CB[N2/O2])) \quad (14)$$

where,
CB[N2O]=the collision broadening factor for $N_2O$.
CB[N2/O2]=the collision broadening factor for $N_2$ and $O_2$.

The final $CO_2$ partial pressure, corrected for cross correction, is calculated by the expression:

$$PP[CO2]=PP[CO2]'-((PP[N2O]'')(CCrsCorr[N2O])) \quad (15)$$

where, CCrsCorr[N2O]=the cross correction for $N_2O$ in the $CO_2$ channel stored in EEPROM 530.

The final partial pressure for $N_2O$ is calculated by the next expression:

$$PP[N2O]=PP[N2O]''-((PP[CO2])(NCrsCorr[CO2])) \quad (16)$$

where, NCrsCorr[CO2]=the cross correction for $CO_2$ in the $N_2O$ channel stored in EEPROM 530.

The remaining partial pressure to calculate is the agent's. Ethrane, Forane and Halothane are the agent considered in the present invention.

The initial partial pressure is calculated by the following expression:

$$PP[A]''=(tcB[A])(R[A]) \quad (17)$$

where, tcB[A] = the B temperature correction for the selected agent.
R[A] = agent absorption.

The final partial pressure of the agent is calculated by the expression:

$$PP[A] = PP[A]'' - ((PP[CO_2])(ACrsCorr[CO_2])) + ((PP[N_2O])(ACrsCorr[N_2O])) \quad (18)$$

where,
ACrsCorr[CO$_2$] = the cross correction for CO$_2$ in the agent channel stored in EEPROM 530.
ACrsCorr[N$_2$O] = the cross correction for N$_2$O in the agent channel stored in EEPROM 530.

Once the partial pressure for CO$_2$, N$_2$O and the agent are calculated, each is corrected to barometric pressure according to the following expression:

$$PPmmHg[X] = \left(\frac{PP[X]}{\text{Sample Cell Pressure}}\right)\left(\text{Barometric pressure}\right) \quad (19)$$

where,
X = CO$_2$, N$_2$O or agent.
Sample Cell Pressure = pressure measured in the sample cell when the gas voltages are measured.
Barometric Pressure = last measured barometric pressure stored in memory.

The above expression corrects the partial pressure for each gas to the barometric pressure where the optical bench is located.

If desired, each partial pressure of gas can be calculated and then displayed as a concentration:

$$\% \text{ Conc} = \frac{PPmmHg[X]}{\text{Barometric Pressure}} (100) \quad (20)$$

where,
% Conc = the concentration of the CO$_2$, N$_2$O or the agent.
X = CO$_2$, N$_2$O or agent.
PPmmHg[X] = the final partial pressure for CO$_2$, N$_2$O or agent corrected for barometric pressure.

As stated, the above calculations for partial pressure are made by the microprocessor 808. Once calculated, these are transmitted from the analog processor to the display section for display, as will be described subsequently.

The measured values for flow rate, pressure and temperature are corrected by microprocessor 808 and also sent to the display section.

It is desirable to maintain the flow rate at 50 cc/min. When the flow rate deviates from that targeted value, the pump is appropriately powered to return the system to that flow rate. The flow rate value is calculated by the following expression:

$$\text{Flow} = ((V[Flo])(FloSpan)) + FloOffset \quad (21)$$

where
V[Flo] = the instantaneous voltage from the differential pressure transducer 276.
FloSpan = the flow span function to characterize the pressure transducer. This coefficient is stored in EEPROM 530.
FloOffset = the offset for the flow measurement transducer. This is measured during backflush with the pump off.

The pressure within the optical bench passageways can vary between +4 psi and −4 psi. The pressure is −4 psi when the gas stream is drawn through the bench by the pump. It is as high as +4 psi during backflush. The expression for calculating pressure is:

$$\text{Press} = ((V[Prs])(PrsSpn)) + PrsOffset \quad (22)$$

where,
V[Prs] = the instantaneous voltage from pressure transducer 274.
PrsSpn = the pressure span factor to characterize the pressure transducer. This coefficient is stored in EEPROM 530.
PrsOffset = the offset from the pressure transducer. This coefficient is stored in EEPROM 530.

The final value calculated by microprocessor 808 for transmission to the display section is the optical bench temperature. The optical bench temperature is controlled by temperature sensor and control circuit 514. Circuit 514 controls the voltage applied to heating resistors 510 and 512. The expression for calculating temperature is as follows:

$$\text{Temp} = ((V[Tmp])(TmpSpan)) + TmpOffset \quad (23)$$

where,
V[Tmp] = the instantaneous voltage from temperature sensor and control circuit 514.
TmpSpan = the temperature span factor to characterize the temperature sensor. This coefficient is stored in EEPROM 530.
TmpOffset = the offset for temperature sensor. This coefficient is stored on EEPROM 530.

FIGS. 7A, 7B, 7C and 7D show the circuits contained on motherboard 137 (FIG. 1). The circuitry on motherboard 137 communicates between the analog processor 124 and display processor 128, between two or more elements in the display section circuitry and (not shown in FIG. 1) between the analog processor 124 and pump assembly 112.

Figure 7A:
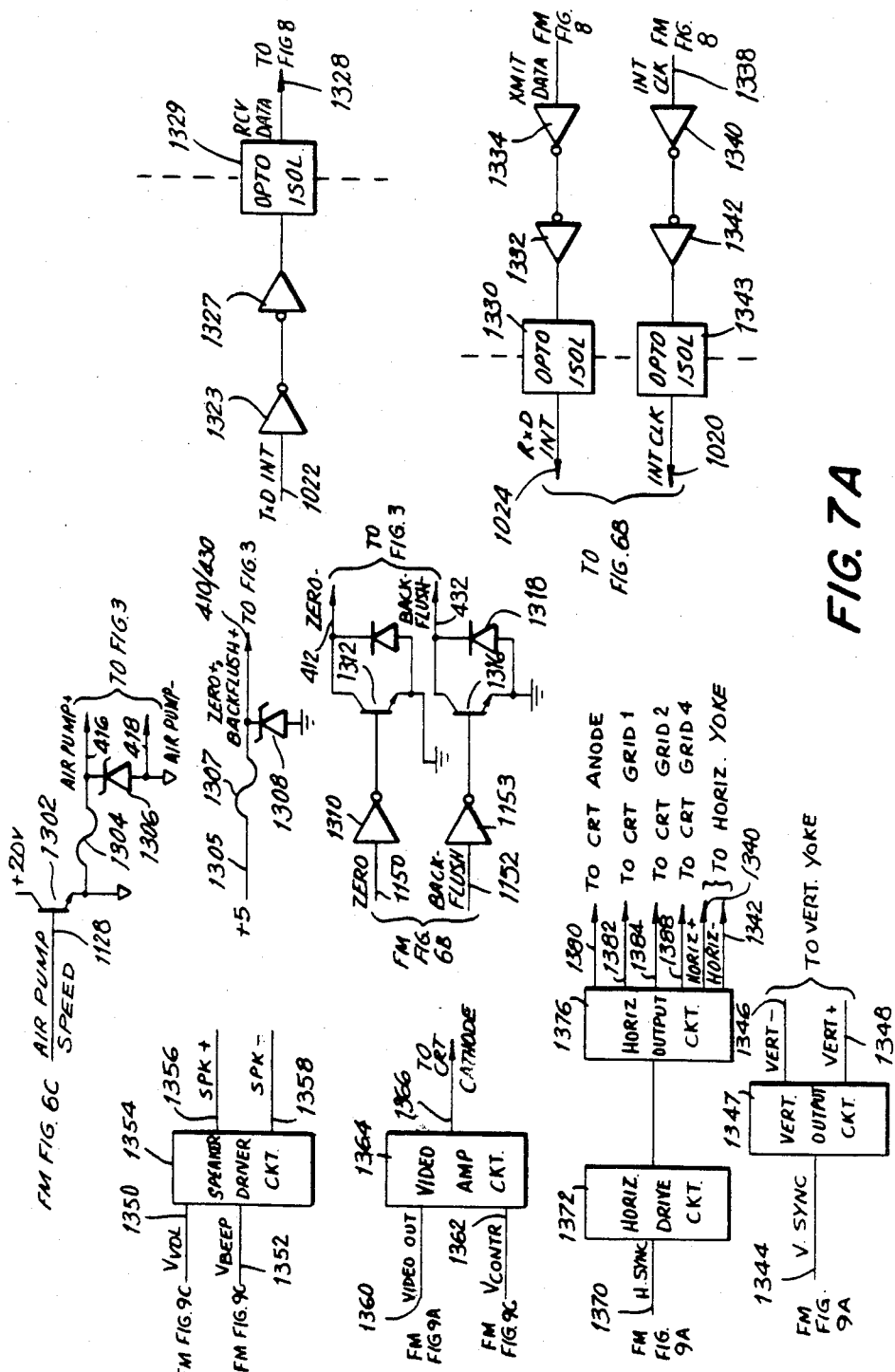

Referring to FIG. 7A, the signals input to speaker driver circuit 1354 are the V$_{VOL}$ signal on line 1350 and the V$_{BEEP}$ signal on line 1352. The V$_{BEEP}$ signal is the principal signal driving speaker driver circuit 1354. The V$_{VOL}$ signal adjusts the SPK+ voltage on line 1356. The SPK− output on line 1358 connects to ground. The SPK+ and SPK− lines connect to an external speaker.

The video amplifier circuit 1364 is for driving the CRT cathode. The signals input to the video amplifier circuit are the VIDEO OUT signal on line 1360 and the V$_{CONTR}$ signal on line 1362. The VIDEO OUT signal on line 1360 is the signal for driving the display screen. The V$_{CONTR}$ signal on line 1362 controls the voltage supplied to the cathode for the purpose of screen contrast. The output of this circuit to the cathode is on line 1366.

The H.SYNC (horizontal sync) signal on line 1370 from CRT controller 1998 of pixel circuitry 130 is input to horizontal drive circuit 1372. Following conventional processing by this circuit, the signal is input to horizontal output circuit 1376. The outputs of the horizontal output circuit are to the CRT anode on line 180, to CRT grids 1, 2, and 4 on lines 1382, 1384 and 1388, respectively, and the HORIZ+ and HORIZ− signals on lines 1340 and 1342 to the horizontal yoke.

The V.SYNC (vertical sync) signal on line 1344 is input to vertical output circuit 1347. Following conventional processing by this circuit, the output signals are the VERT− and VERT+ signals on lines 1346 and 1348, respectively. These signals are input to the vertical yoke.

The AIR PUMP SPEED signal on line 1128 is input to the base of transistor 1302. The output of transistor 1302 is the AIRPUMP+ voltage on line 416. The AIRPUMP− signal on line 418 is grounded. The circuit is protected by fuse 1304 on line 416 and by zener diode 1306.

The ZERO+ signal on line 410 and the BACKFLUSH+ on line 430 are output from fused line 1305. These signals are input to valves 406 and 428 (FIG.3). Fuse 1307 and zener diode 1308 protect the circuit.

The ZERO− signal on line 412 and BACKFLUSH− signal on line 432 are generated from the ZERO signal on line 1150 and the BACKFLUSH signal on line 1152. Each signal is processed by an identical circuit. So the description of the circuit for the ZERO signal also applies to the BACKFLUSH signal circuit (reference numbers in parentheses). The ZERO signal is input to inverter 1310 (1153). The inverted signal is input to the base of transistor 1312 (1316). The ZERO (BACKFLUSH) signal voltage determines whether the ZERO− (BACKFLUSH−) signal is grounded to establish a voltage difference between ZERO+ (BACKFLUSH+) and ZERO− (BACKFLUSH−) signals. Diode 1314 (1318) is in a feedback loop for the transistor.

The TxD INT signal on line 1022, the RxD INT signal on line 1024 and the INT CLK signal on line 1020 are signals communicated between analog processing circuitry 124 and display processing circuitry 128 via the motherboard. There is electrical isolation between the analog side and the display side.

Analog processing circuitry 124 transmits the TxD INT signal to display processing circuitry 128. The data in this signal is ultimately displayed on the CRT. The TxD INT signal is input to inverters 1323 and 1327 and then opto-isolator 1329. The TxD INT signal on the display side of opto-isolator 1329 is renamed the RCV DATA signal on line 1328.

The RxD INT signal on line 1024 contains data received from the display processing circuitry. The signal starts as the XMIT DATA signal on line 1366 on the display side. The signal is input to inverters 1334 and 1332, and then opto-isolator 1330. As the output of opto-isolator 1330, the signal is received on the analog side as the RxD INT signal on line 1024.

The INT CLK signal on line 1338 is used to synchronously control the transfer of data between the analog and display processing circuitry. The INT CLK signal on the display side is input to inverters 1340 and 1342, and then input to opto-isolator 1343. The signal is then output on line 1020 for input to the analog processing circuitry via the motherboard.

FIGS. 7B, 7C and 7D show signals which transit the motherboard without being processed by the circuitry. FIG. 7B shows signals communicated between display processing circuitry 128 and pixel circuitry 130. FIG. 7C shows signals communicated between display processing circuitry 128 and digital output board 140. FIG. 7D shows signals communicated between the display processing circuitry and knob board 144.

Figure 8:
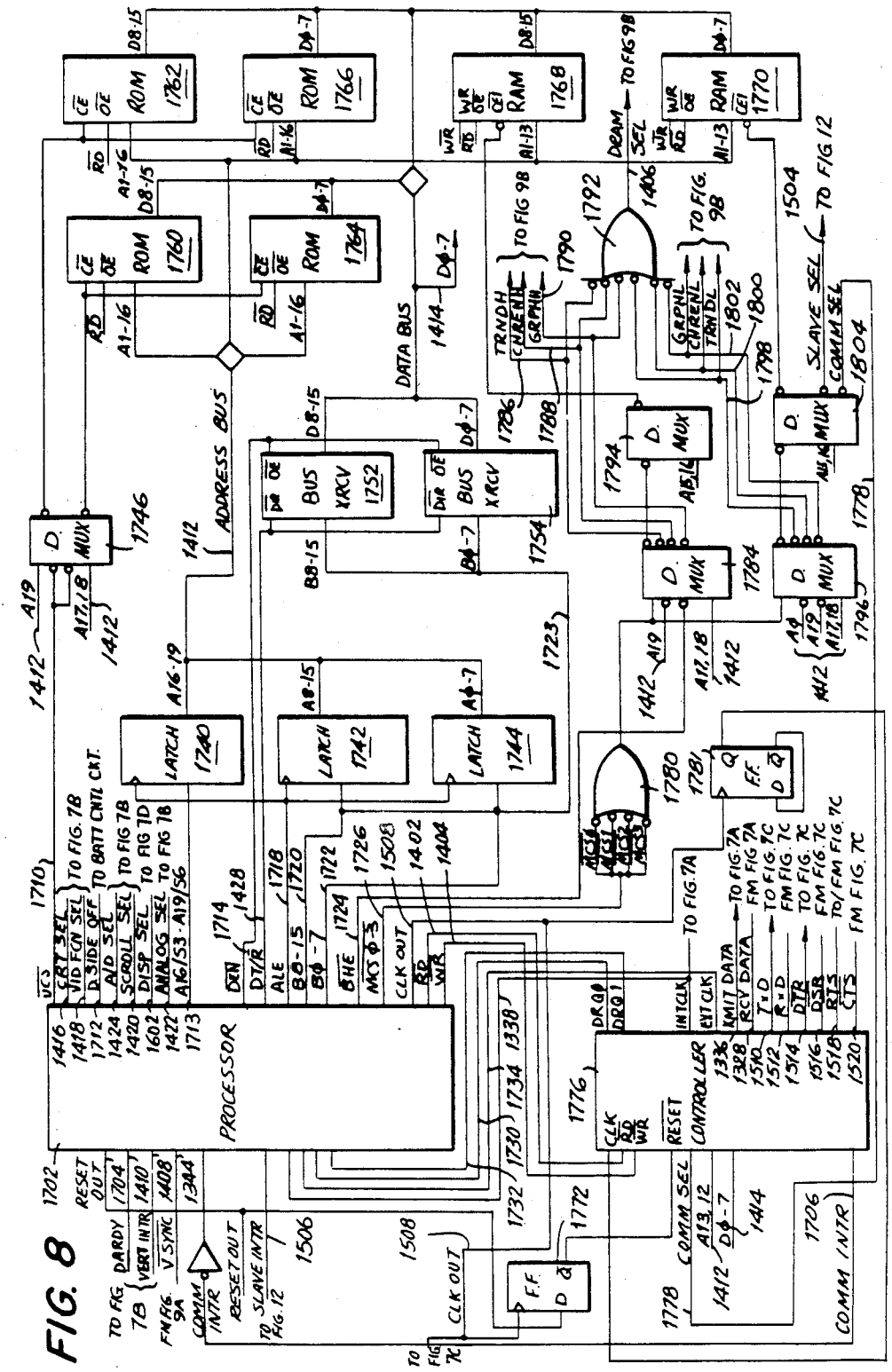
FIG. 8 is a schematic diagram of the display processor circuitry of the multichannel gas analyzer system of the present invention.

FIG. 8 is a schematic diagram of display processing circuitry 128. The principal functions of the display processing circuitry are processing the incoming data from analog processing circuitry 124, transmittal of the data back to the analog processing circuitry, and control of pixel circuitry 130.

The partial pressure of $CO_2$, $N_2O$ and the agent, the pressure and temperature within the optical bench, the gas flow rate through the optical bench and other information for display are received as RCV DATA on line 1328 by a controller 1776 of display processing circuitry 128. Data sent to the analog processing circuitry is the XMIT DATA output from controller 1776 on line 1336.

When the control signals input to controller 1776 have the proper states, data is transmitted to or received from the 8 bit data bus shown as D∅-7 on line 1414.

The INT CLK signal on line 1338 synchronizes the transmission of data between the analog and the display processing circuitry.

The DRQ∅ and DRQ1 signals output from the controller on lines 1730 and 1732, respectively, the 2 address bus signals A12 and A13 input to the controller, the COMM INTR signal output on line 1706, the COMM SEL signal input on line 1778, and the RD bar and WR bar signals on lines 1402 and 1404, respectively, operate conventionally in a manner known by those skilled in the art. The TxD signal on line 1510, the RxD signal on line 1512, the DTR bar signal on line 1514, the DSR bar signal on line 1516, the RTS bar signal on line 1518 and the CTS bar signal on line 1520 all connect to the digital output board 140. These signals are for communication with and control of an external device.

The EXT CLK signal on line 1734 is a clock signal for controlling synchronous communications between the controller and an external device.

Microprocessor 1702 is a model 80186 CPU, commercially available from INTEL Corporation, Santa Clara, Calif. The signals input to and output from microprocessor 1702 will now be discussed.

When microprocessor 1702 experiences a reset condition, the RESET OUT signal on line 1704 changes state. This state change resets controller 1776. The controller is reset one clock pulse after microprocessor 1702 experiences a reset condition because the signal is processed by flip flop 1772.

The VERT INTR interrupt signal on line 1408, the V.SYNC bar signal on line 1344, and the SLAVE INTR signal on line 1506 are all interrupt signals.

The VERT INTR signal is the interrupt signal to microprocessor 1702 to indicate when the end of the scrolled window is reached. The V.SYNC bar singal on line 1344 is used for driving the CRT. The SLAVE INTR signal on line 1506 is the interrupt signal from an external device.

The COMM INTR signal on line 1706 is the signal input into the microprocessor from the controller to indicate that data is being transferred from or received by the controller.

The DARDY signal on line 1410 is the asynchronous ready signal.

The UCS bar signal output on line 1710 selects the signal to be output from demultiplexer 1746. The output of this demultiplexer enables ROMs 1760, 1762, 1764 and 1766.

The D. SIDE OFF signal on line 1712 is output to the battery control circuit to indicate activation of the display side of the system.

The DISP SEL signal on line 1602 is output to the knob board for placing new instructions on the data bus and for the display and activation of the system's audible and visual alarms.

The VID FCN SEL signal on line 1418, the CRT SEL signal on line 1416, the A/D SEL signal on line 1424, the SCROLL EL signal on line 1420, and the ANALOG SEL signal on line 1422 are output to the motherboard for input to and control of pixel circuitry 130.

Figure 9B:
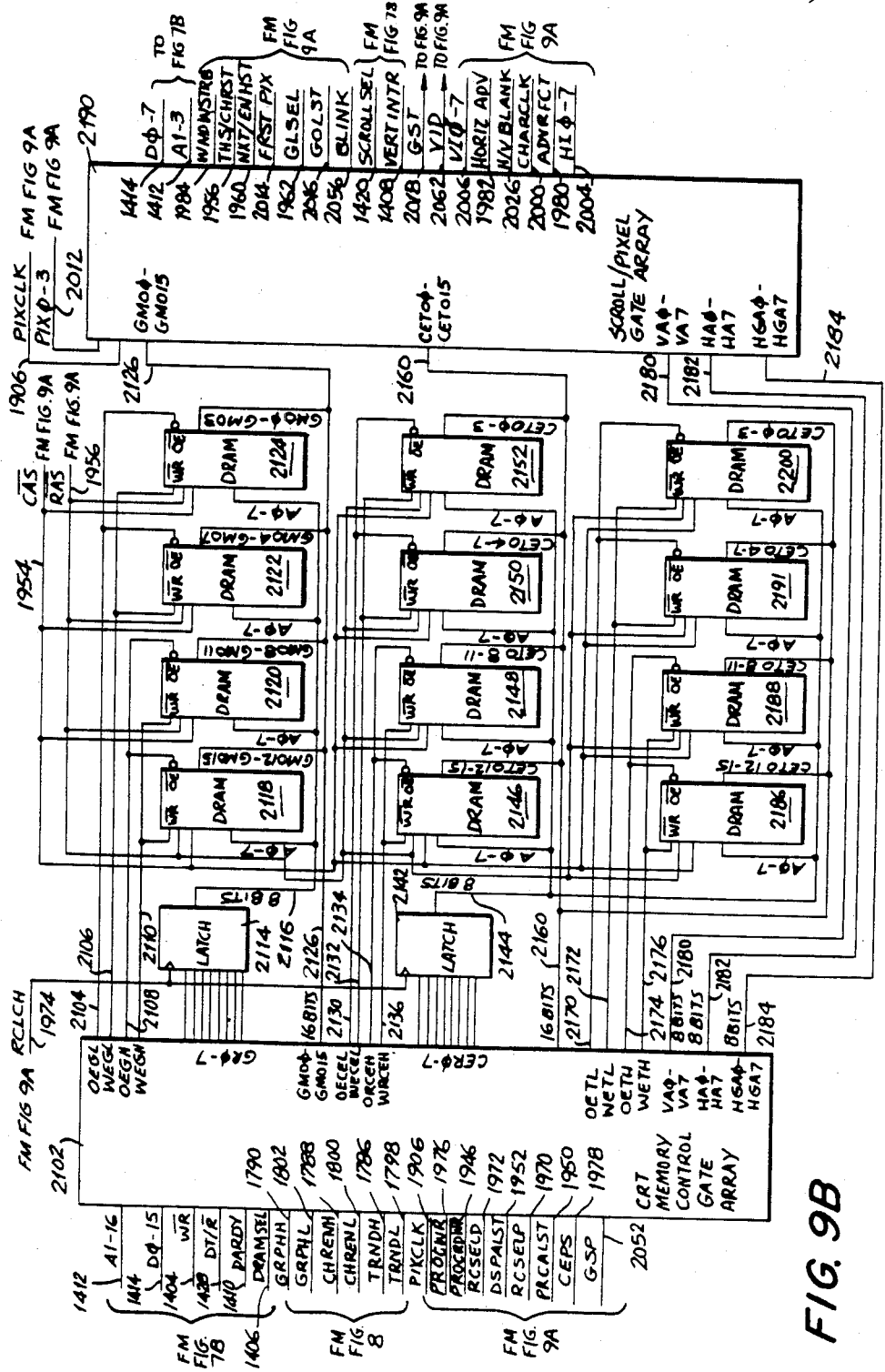

The CRT SEL and VID FCN SEL signals are input to the pixel circuitry 130. The CRT SEL signal on line 1416 is input to CRT controller 1998 (FIG. 9A) for output chip selection. The VID FCN SEL signal is input to decoder 2032 (FIG. 9A) to select a proper video diplay function for the CRT screen. The A/D SEL signal on line 1424 is used to put ECG information or battery comparison information on the data bus for transfer to memory (FIG. 9B). The ANALOG SEL signal on line 1422 is used to control selection among the analog output ports, the analog signals for driving an external speaker, the control analog signal for the video contrast input to the CRT driver, and the analog signal for an external ECG device.

The other signals associated with microprocessor 1702 yet to be described are signals for one of the busses or signals associated with accessing memory to read or write data The signals A16/S3–A19/S6, a parallel 4 bit output on line 1713, are the high order address bits. These bits are input to latch 1740. When this latch is clocked by the ALE (address latch enable) signal on line 1718, the address information is placed on the address bus.

The DEN bar (data enable) signal on line 1714 is the output enable signal for bus transceivers 1752 and 1754. The DT/R (R bar) (data transmit/receive) signal on line 1428 determines the direction of data flow in bus transceivers 1752 and 1754. Together, these two signals control the data transmitted to and received from memory on address/data busses 1720, 1722 and 1723.

When address/data busses 1722 and 1720 are used for address rather than data transfer, address bits ∅-7 are input into latch 1744 and address bits 8–15 are input to latch 1742. When these latches are loaded and then clocked by the ALE signal on line 1718, the latch values for these address bits are placed on the address bus.

RAM 1768 is enabled by the output of demultiplexer 1794. This demultiplexer is enabled by the output of demultiplexer 1784. Demultiplexer 1784 is enabled by the output of OR gate 1780, address bit A19 and the BHE bar (bus high enable) on line 1724.

RAM 1770 is enable by the output of demultiplexer 1804. This demultiplexer is enabled by the output of demultiplexer 1796. The signals that enable demultiplexer 1796 are the output of OR gate 1780, and the A∅ and A19 signals on line 1412 from the address bus.

The inputs to OR gate 1780 are the MCS∅–MCS3 bar signals output from microprocessor 1702 on line 1726. As stated, the output of OR gate 1780 output enables demultiplexers 1784 and 1796. The states of the outputs from these demultiplexers are controlled by high-order address bits A17 and A18 on line 1412.

The other output signals from demultiplexer 1784 are the TRNDH (trend high) signal on line 1786, the CHRENH (character/enhancement plane high) signal on line 1788 and the GRPHH (graphic plane high) signal on line 1790. These signals are also input to OR gate 1792. The word high in these signal names indicates the high-order address bits, 8–15, for a particular memory circuit in pixel circuitry 130.

The other output signals from demultiplexer 1796, are the GRPHL (graphic plane low) signal on line 1802, the CHRENL (character/enhancement plane low) signal on line 1800 and the TRNDL (trend low) signal on line 1798. These signals are also input to OR gate 1792. The word low is these signal names indicates the low-order address bits, 0–7, for a particular memory circuit in pixel circuitry 130.

The output of OR gate 1792 is the DRAM SEL (dynamic RAM select) signal on line 1406. The DRAM SEL signal is used in conjunction with other signals to select and write from a particular DRAM to the pixel memory circuits.

Demultiplexer 1804 has two other outputs. These are the COMM SEL signal on line 1778 and the SLAVE SEL signal on line 1504 previously discussed. These signals are output from the demultiplexer when it is not being used to enable RAM 1770.

The BHE bar (bus high enable) signal on line 1724 also assists in enabling RAM 1768 when the high order bits D8-15 are written onto or read.

The CLK OUT signal on line 1508 is the main clock signal for operating the display processor circuitry. The CLK OUT signal, through flip flop 1781, clocks controller 1776. However, because the data input and the Q bar output are tied, the controller is clocked every two CLK OUT pulses.

ROMs 1760, 1762, 1764 and 1766 and RAMs 1768 and 1770 are connected to data bus 1414 and address bus 1412 conventionally.

Figure 9C:
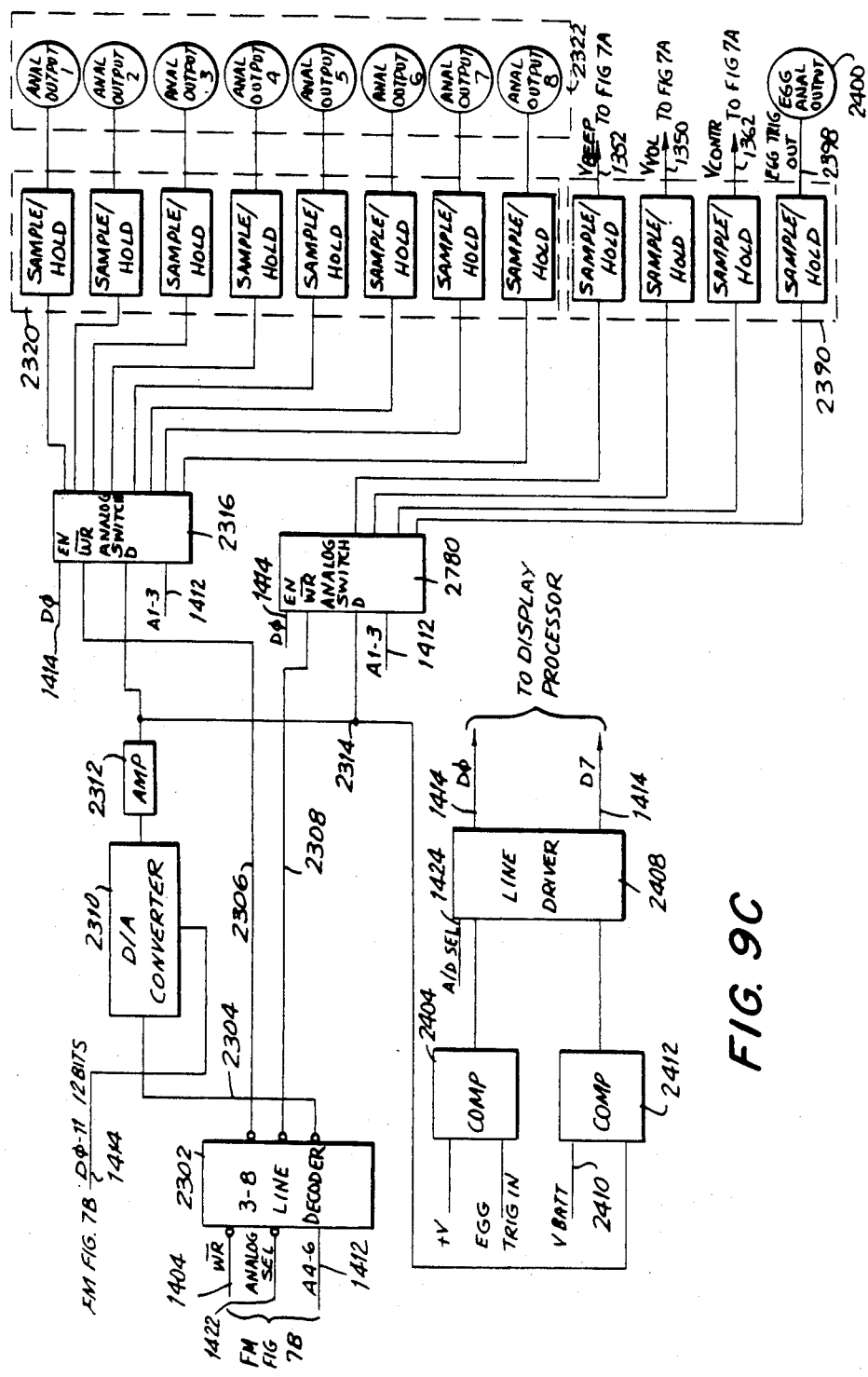

FIGS. 9A, 9B, and 9C show pixel circuitry 130. FIG. 9A shows the circuitry that generates a majority of the signals used by the circuitry shown in FIG. 9B.

The graphic plane refers to the scrolled information on the display screen. The character and enhancement planes refer to the fixed characters on the display screen.

Referring to FIG. 9A, the output of 24 MHz oscillator 1902, after being inverted by inverter 1904, is the PIX CLK signal on line 1906. This is the clock signal for clocking most of the pixel circuitry.

The PIX CLK signal clocks 4-bit counter 1908. The output signals from the 4-bit counter are input to EEPROMs 1910 and 1912, and latch 1926. EEPROMs 1910 and 1912 are enabled by a pull-up signal inverted by inverter 1940. The parallel 8-bit output of EEPROM 1910 is input to latch 1938. This latch is clocked by the PIX CLK signal. The following signals are output from this latch when clocked:

PROCRDWR bar (line 1946)—processor read/write. This provides a time window in which the processor can read from or write into memory.

PRCALST (line 1950)—processor address-latch strobe. It strobes the processor address latches.

DSPALST (line 1952)—display processor address-latch strobe. It strobes the display processor address latches.

CAS bar (line 1954)—column address latch strobe. It strobes the column address latches.

RAS bar (line 1956)—row address latch strobe. It strobes the row-address latches.

THS/CHRST (line 1958)—this/character strobe. It strobes different latches with data from the series memories for the graphic and character planes.

NXT/ENHST (line 1960)—next/enhancement strobe. It strobes to latch the next graphic plane and enhancement plane data.

GLSEL (line 1962)—a graphic latch select. It selects which graphic data latch is used for a 16-pixel area of the display screen.

The 8 bit output of EEPROM 1912 is input to latch 1964. This latch is clocked by the PIX CLK signal on the same clock pulse that latch 1938 is clocked. The 8 bit output of latch 1964 is input to latch 1968. This latch is clocked a half-clock pulse after latch 1964 because inverter 1963 is disposed in the clock line to latch 1968. The following signals are output by latch 1968:

RCSELP (line 1970)—row/column select for the processor memory.

RSCELD (line 1972)—row/column select for the display processor memory.

RCLCH (line 1974)—row/column select latch clock.

PROCWR bar (line 1976)—processor write. This signal is for writing data into the processor memory.

CEPS (line 1978)—character/enhancement plane select. This signal selects the proper character/enhancement plane.

ADVRFCT (line 1980)—the advanced refresh count. This signal is used by the DRAMs.

HORIZ ADV (line 1982)—horizontal advnce. This signal runs the graphic plane address counter.

WNDWSTRB (line 1984)—window strobe. This signal strobes the current graphic display addresses.

The inputs to CRT controller 1998 will now be discussed.

The RD bar and WR bar signals on lines 1402 and 1404, respectively, are input to OR gate 1986. The output of this gate is inverted by inverter 1988. The output of the inverter is input to the CRT controller 1998. This input strobes the horizontal address bits HI∅-7 on line 2004 and the vertical address bits VI∅-7 on line 2006. The contents of these signals are determined by the parallel 8 bit data bus signals D∅-7 on line 1414 and parallel 4 bit address A1-A4 on line 1412.

The CRT SEL signal on line 1416 is input to controller 1998 after inversion by inverter 1992. This signal selects the controller's output chip.

The CHAR CLK (character clock) signal on line 2000 is generated by the terminal count of 4 bit counter 1908. The CHAR CLK signal is used for clocking the character plane functions. After being inverted, the CHAR CLK signal is input to the character clock input of controller 1998. It is also input to a data input of latch 1926 and the clock inputs of flip flops 2020 and 2024.

The data input to flip flop 2020 is the BLANK signal from controller 1998 on line 2002. This signal indicates the non-active portion of the horizontal and vertical scans. The Q output of flip flop 2020 is input to EEPROMs 1910 and 1912. The Q bar output of flip flop 2020 is input to the data input of flip flop 2024. The Q output of flip flop 2024 is the H/V BLANK bar signal on line 2026. This signal indicates the blank portions of the horizontal and vertical scans.

There are two other outputs from CRT controller 1998. The first is the V.SYNC bar signal on line 1344 (after being inverted by inverter 2010). The second is the H.SYNC signal on line 1370. These signals are input to the CRT driver (FIG. 7A) for driving the screen display.

The H/V BLANK bar signal is also a data input to latch 2028. This latch is clocked by the PIX CLK signal. The output of the latch is delayed 4 clock pulses by a series of tied inputs and outputs of the latch. The output of this latch is input to OR gate 2046. The other input to OR gate 2046 is the Q bar output of flip flop 2042. This flip flop is clocked by the output of decoder 2032 on line 2040. This decoder selects the display video function.

The enabling input to decoder 2032 is the VID FCN SEL signal on line 1418. Depending on the state of address bits A1-3, one of the four functions is selected.

If line 2034 is selected, flip flop 2050 is clocked. The Q output of flip flop 2050 is the GPS (graphic plane select) signal on line 2052.

If line 2036 is selected, flip flop 2054 is clocked. The Q output of flip flop 2054 is the BLINK (display blink) signal on line 2056.

If line 2038 is selected, it will clock flip flop 2058. The Q bar output of flip flop 2058 is input to the SEL A/B (A bar) input of multiplexer 2068. The signals input to the data inputs of multiplexer 2068 are the VID signal on line 2062 (input to the A∅ input) and its complement (input to the B∅ input). The state of the selection input determines whether the A∅ or B∅ inputs is selected for outputs as the VIDEO OUT signal on line 1360.

If line 2040 is selected, flip flop 2042 is clocked. The Q bar output of flip flop 2042 is the second input to OR gate 2046.

The output of OR gate 2046 is the signal that strobes multiplexer 2068 for output of the VIDEO OUT signal on line 1360.

The signal input to the data inputs of flip flops 2050, 2054, 2058 and 2042 is the D∅ signal from the data bus.

The inputs to latch 1926 are the 4 bit output of 4 bit counter 1908, the CHAR CLK signal on line 2000 and the GST (graphic plane strobe) signal on line 2018. When clocked, the outputs of the latch are the pixel address PIX∅-3 signals on line 2012, the FRST PX signal on line 2014 and the GOLST signal on line 2016.

The FRST PX signal represents the first pixel word on the screen. The GOLST signal is the graphic plane output latch strobe signal. This strobes the current graphic plane output word.

FIG. 9B shows CRT memory control gate array 2102, scroll/pixel gate array 2190 and a series of DRAMs and latches used by both gate arrays. Many of the signals input to and output from both gate arrays have been described. Those signals will not be redescribed here.

Again referring to FIG. 9B, DRAMs 2118, 2120, 2122 and 2124 are used for graphic plane. DRAMs 2146, 2148, 2150, 2152, 2186, 2188, 2191, and 2200 are shared memory by character and enhancement planes, and by the trend section.

The parallel 8 bit GR-7 (graphic plane address) signal is input to latch 2114. When clocked, the latch places the latch address values on address bus 2116. The parallel 8 bit CER∅-7 (character/enhancement plane address) signal is input to latch 2142. When this latch is clocked, it places the latched address values on address bus 2144. Both latches are clocked by the RCLCH signal on line 1974.

The parallel 16 bit GMO∅-15 signal on line 2126 is the 16 bit data bus that connects conventionally to the graphic plane DRAMs. The parallel 16-bit CETO∅-15 signal on line 2160 is the 16-bit data bus that connects conventionally to the character/enhancement trend DRAMs. The CAS bar (column address strobe) signal on line 1954 and RAS bar (row address strobe) signal on line 1956 connected to each of the DRAMs and strobe them conventionally.

The high order data bits, D8-15, for the graphic plane DRAMs and the character/enhancement/trend DRAMs have separate output enable (OE bar) and write enable (WR bar) controls. This is also true for the low order bits, D0-7, for the graphic plane DRAMs and the character/enhancement/trend DRAMs. The following are the separate write enable and output enable signals for the DRMs.

OEGL (line 2104)—output enable graphic plane low (low means bits GMO0-7).

WEGL (line 2106)—write enable graphic plane low.

OEGH (line 2108)—output enable graphic plane high (high means bits GMO8-15).

WEGH (line 2110)—write enable graphic plane high.

OECEL (line 2130)—output enable character/enhancement plane low (low means bits CETO0-7).

WECEL (line 2132)—write enable character/enhancement plane low.

OECEH (line 2134)—output enable character/enhancement plane high (high means bits CETO8-15).

WECEH (line 2136)—write enable character/enhancement plane high.

OETL (line 2170)—output enable trend low (low means bits CETO0-7).

WETL (line 2172)—write enable trend low.

OETH (line 2174)—output enable trend high (high means bits CETO8-15).

WETH (line 2176)—write enable trend high.

The additional lines between CRT memory gate array 2102 and scroll/pixel gate array 2190 are the parallel 8 bit horizontal address bus HA0-7 on line 2182; the parallel 8 bit vertical address bus VA0-7 on line 2180; and the parallel 8 bit horizontal graphic address bus HGA0-7 on line 2184. These address busses are known by one skilled in the art without further explanation.

FIG. 9C is a schematic diagram of the analog output section of pixel circuitry 130.

The inputs to decoder 2302 are the WR bar signal on line 1404, the ANALOG SEL signal on line 1422 and the control inputs address bits A4-6 on line 1412.

The WR bar and ANALOG SEL signals enable the decoder. The address bits A4-6 select the output of the decoder.

The output of decoder 2302 on line 2306 is input to the WR bar input of analog switch 2316. This signal causes the analog inputs to the switch to be output. This output depends on the states of the control inputs. The control inputs are the the A1-3 signals from the address bus. The switch is enabled by the D0 signal on line 1414.

The decoder output on line 2308 is input to the WR bar input of analog switch 2780. Similarly, the analog inputs to the switch are output according to the states of the control inputs, the A1-3 signals from the address bus. The switch is enabled by the D0 signal on line 1414.

The decoder output on line 2304 is input to D/A convertor 2310. Data bits D0-11 from line 1414 control the output of the converter. The output of D/A convertor 2310 is amplified by amplifier 2312 and is input to the data inputs of analog switches 2316 and 2780.

When switch 2316 is enabled by the D0 signal and the WR bar input has the proper state, the latched values are output to the selected analog output lines. This energizes at least one of analog output ports shown generally at 2322 after processing by the appropriate sample and hold circuit shown generally at 2320.

Analog switch 2780 writes in the same manner, if line 2308 is selected by decoder 2302. Analog switch 2780 can select among four output lines. The first is the $V_{BEEP}$ signal on line 1352. The second is the $V_{VOL}$ signal on line 1350. The third is the $V_{CONTR}$ signal on line 1362. The fourth is the ECG TRIG OUT signal on line 2398 which connects to ECG OUT connector 2400.

Each of the four outputs is processed by the appropriate sample and hold circuit shown generally at 2390.

The amplified output of D/A convertor 2310 is also input to comparator 2412. The other input to the comparator is the $V_{BATT}$ signal from the battery. The comparator determines if the proper battery voltage is present. The output of the comparator 2412 is input to line driver 2408.

The other input to driver 2408 is the output of comparator 2404. The inputs to this comparator are the +V volts signal and the voltage value of the ECG TRIG IN signal received from an external device.

When the line driver is enabled by the A/D SEL signal on line 1424, the signals input to line driver are placed on the D0 and D7 bits of the data bus on line 1414.

Figure 10A:
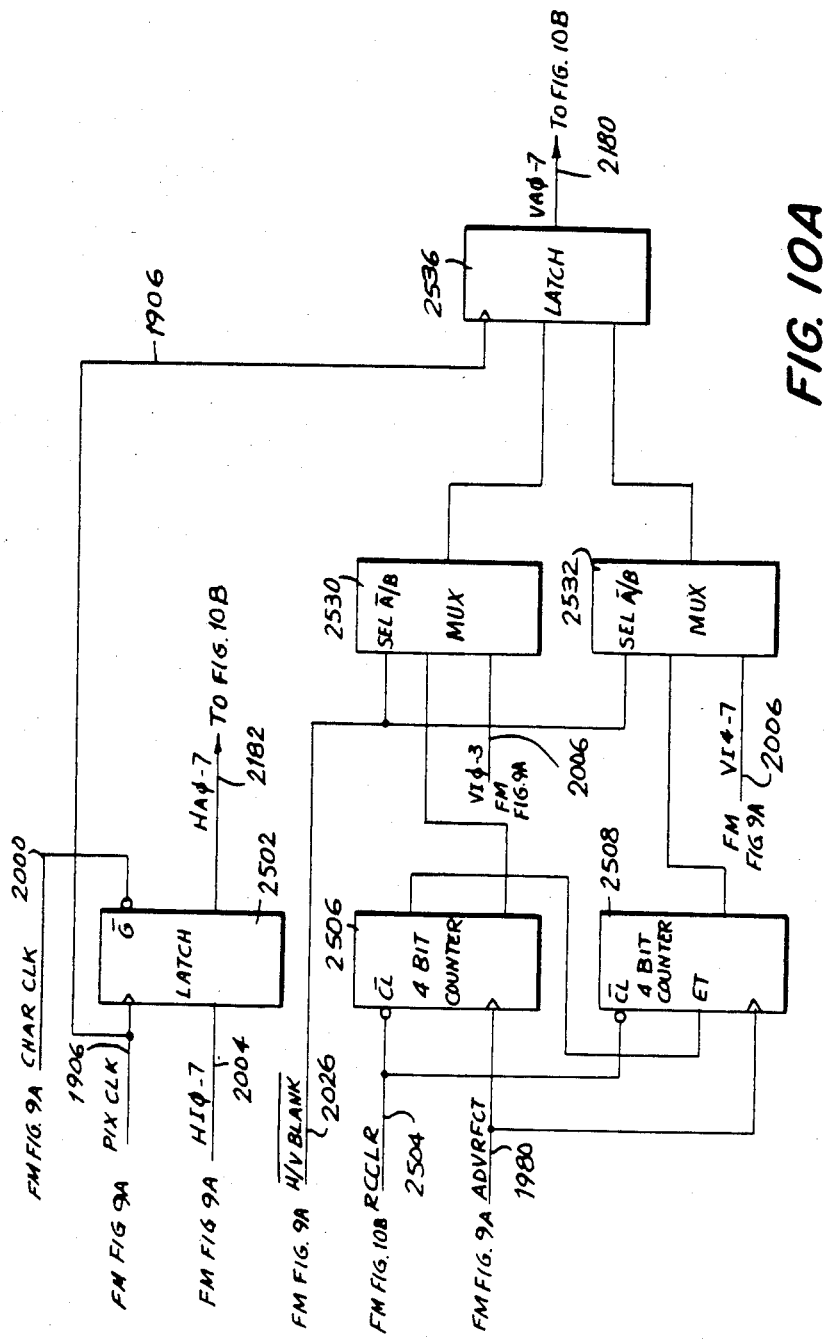
FIGS. 10A, 10B and 10C comprise a schematic diagram of the scroll/pixel gate array of the pixel circuitry shown in FIG. 9B.
Figure 10B:
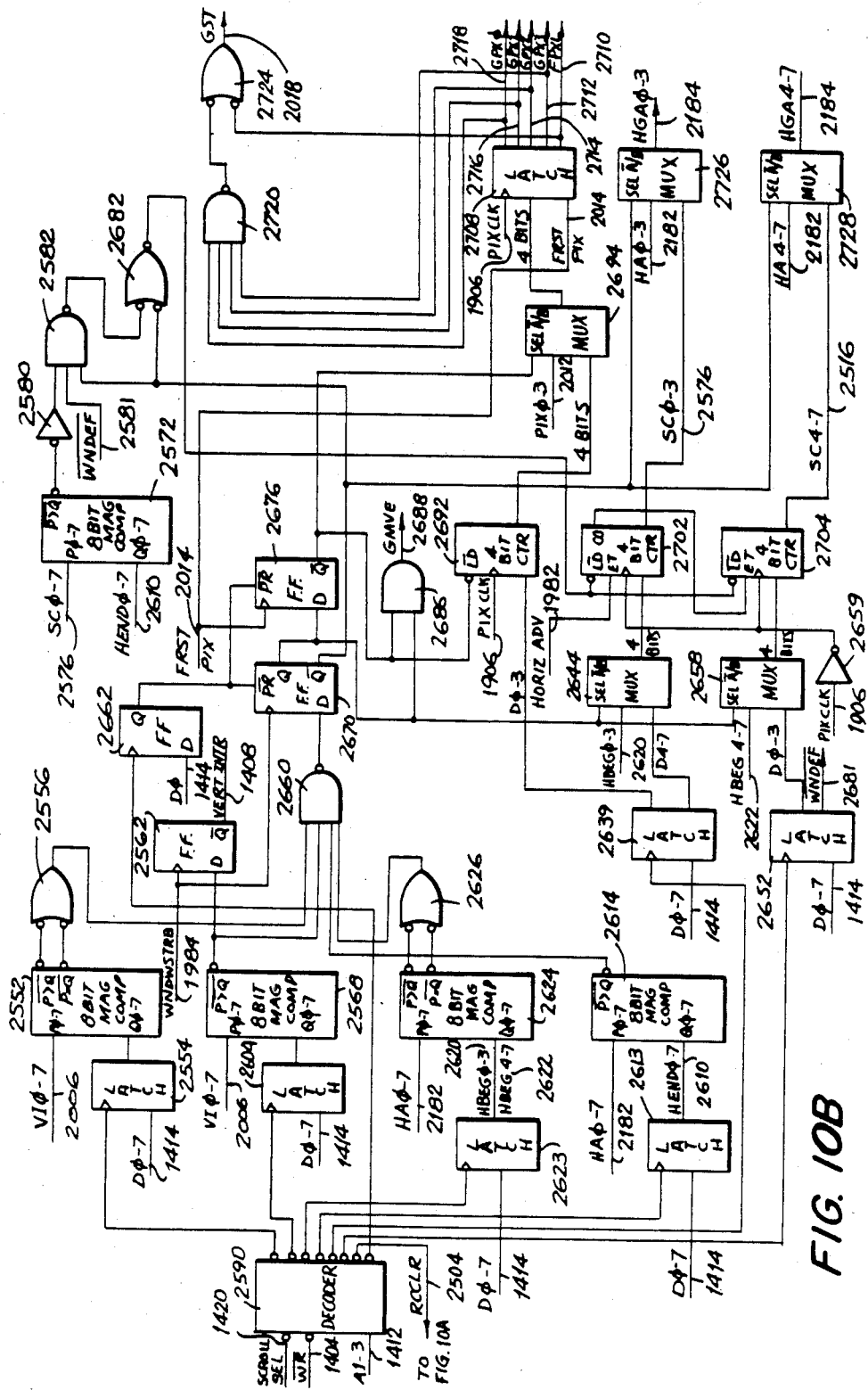
Figure 10C:
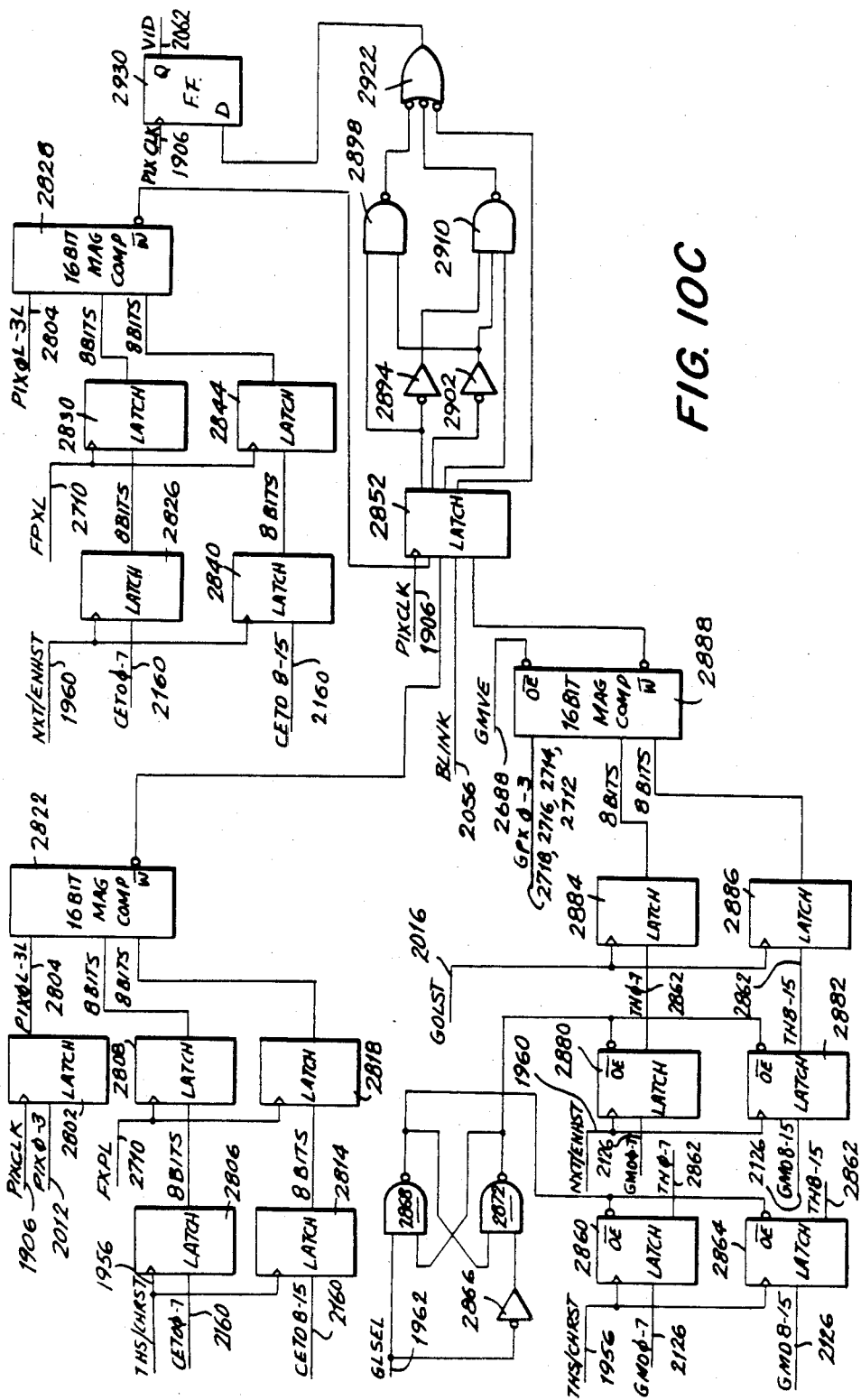

FIGS. 10A, 10B and 10C show scroll/pixel gate array 2190 shown in FIG. 9B.

Referring to FIG. 10A, generation of the horizontal and the vertical address bits is now described.

The parallel 8 bit signal HI0-7 on line 2004 is input to latch 2502. The latch is enabled by the CHAR CLK signal on line 2000. The latch is lcocked by the PIX CLK signal on line 1906. When the latch enabled and clocked, the output is the parallel 8 bit signal HA0-7 (horizontal address bits) on line 2182.

The ADVRFCT signal on line 1980 is input to the clock inputs of 4 bit counters 2506 and 2508. 4 bit counter 2506 will count out, then its terminal count will start 4 bit counter 2508.

The 4 bit output of counter 2506 is input to multiplexer 2530. Also input to this multiplexer are the parallel 4 bit vertical addresses VI0-3 on line 2006. Similarly, the 4 bit output of counter 2508 and the parallel 4 bit vertical addresses VI4-7 on line 2006 are input to multiplexer 2530.

The selection of the 4 bit counter input or the VI0-3 input as the output of multiplexer 2530 is determined by the state of the H/V BLANK bar signal on line 2026. In like manner, whether the 4 bit counter input or the VI4-7 input is selected as output of multiplexer 2532 is determined by the state of the H/V BLANK bar signal.

The RCCLR signal on line 2504 is input to counters 2506 and 2508. This signal clears the counters.

The outputs of multiplexers 2530 and 2532 are input to latch 2536. When this latch is clocked by the PIX CLK signal, the latched values are output as the VA0-7 (vertical address bits) signals on line 2180.

Referring to FIG. 10B, the generation of the HGA0-7, the GST and the VERT INTR signals will now be described.

The SCROLL SEL signal on line 1420 and the WR bar signal on line 1404 are the enabling inputs to decoder 2590. Address bits A1-3 input on line 1412 control the output from decoder 2590.

One output from decoder 2590 is the RCCLR signal on 2504. This is used in FIG. 10A to clear counters 2506 and 2508. Four other outputs of decoder 2590 determine the state of the inputs to NAND gate 2660.

The first input to NAND gate 2660 is the output of the OR gate 2556. The inputs to this gate are the outputs of 8 bit magnitude comparator 2552.

The first input to comparator 2552 is the parallel 8 bit signal VI0-7 on line 2006. This signal is input to the P data inputs of 8 bit magnitude comparator 2552. The parallel 8 bit signal D0-7 from the data bus on line 1414 is input to latch 2554. This latch is clocked by an output of decoder 2590. When clocked, the D0-7 signal are iput to the Q data inputs of 8 bit magnitude comparator 2552.

The output of the comparator is based on satisfying the conditions P>Q bar and P=Q bar. These outputs are input to OR gate 2556. The output of this OR gate is input to NAND gate 2660.

The second input to NAND gate 2660 is the output of 8 bit magnitude comparator 2568. The output of this comparator is determined as follows:

The parallel 8 bit signal D0-7 from the data bus on line 1414 is input to latch 2604. The second output of decoder 2590 clocks latch 2604. When clocked, the 8 bit output of latch 2604 is input to the Q data inputs of 8 bit magnitude comparator 2568.

The parallel 8 bit sgnal VI0-7 on line 2006 is input to the P data inputs of comparator 2568. The output of this comparator is conditioned on satisfaction of P>Q bar. When this condition is satisfied, the signal output from the comparator changes state and is input to NAND gate 2660.

The third input to NAND gate 2660 is the output of 8 bit magnitude comparator 2614. The output of this comparator is determined as follows:

The parallel 8 bit signal HA0-7 on line 2182 is input to the P data inputs of 8 bit magnitude comparator 2614. The parallel 8 bit signal D0-7 from the data bus on line 1414 is input to latch 2613. The latch is clocked by the fourth output of decoder 2590. When clocked, the parallel 8 bit output of latch 2613 is input to the Q data inputs of comparator 2614. The 8 bit output of latch 2613 on line 2610 is also termed HEND0-7 (horizontal end of the graphic plane window address).

The output of 8 bit magnitude comparator 2614 is determined by satisfaction of the condition P>Q bar. When this condition is satisfied, the state of the output changes. The output of comparator 2614 is input to NAND gate 2660.

The fourth input to NAND gate 2660 is the output of OR gate 2626. The inputs to the gate are the outputs of 8 bit magnitude comparator 2624. The states of the comparator's outputs are determined as follows:

The 8 bit parallel signal HA0-7 on line 2182 is input to the P data inputs of comparator 2624. The parallel 8 bit signal D0-7 from the data bus on line 1414 is input to latch 2623. This latch is clocked by a third output of decoder 2590. When the latch is clocked, the parallel 8 bit output is input to the Q data inputs of comparator 2624. The outputs of comparator 2624 are conditioned on satisfying P>Q bar and P=Q bar. Satisfaction of these conditions changes the state of the outputs. The comparator outputs are input to OR gate 2626. The output of OR gate 2626 is the fourth input to NAND gate 2660.

The output of latch 2623 is also termed HBEG0-7 (horizontal beginning of the graphic plane window address). The parallel 4 bit signal HBEG0-3 is on line 2620 and the parallel 4 bit signal HBEG4-7 ison line 2622.

The output of 8 bit magnitude comparator 2568 is also input to flip flop 2562. This flip flop is clocked by the WNDWSTRB signal of line 1984.

The Q bar output of flip flop 2562 is the VERT INTR signal on line 1408. The VERT INTR signal is input to display processor 1702 (FIG. 8).

The output of NAND gate 2660 is input to flip flop 2670. This flip flop is clocked by the WNDWSTRB signal on line 1984. The preset input to flip flop 2670 is controlled by the Q output of flip flop 2662. The data input to flip flop 2662 is the D0 signal on line 1414. The clock input is SSEL-7 from decoder 2590.

The Q output of flip flop 2670 is input to the selection inputs of multiplexers 2644 and 2658. The Q bar output is input to the selection inputs of multiplexers 2726 and 2728. The Q bar output is also input to NAND gate 2582.

The Q output of flip flop 2670 is input to the data input of flip flop 2676 and to AND gate 2686. Flip flop 2676 is clocked by the FRST PX signal on line 2014. The preset input to the flip flop is cnnected to the Q output of flip flop 2662.

When flip flop 2676 is clocked, its Q bar output is input to AND gate 2686. This signal also enables 4 bit counter 2692 and is input to the selection input of multiplexer 2694.

Having described each input to AND gate 2686, the output of this gate is the GMVE (graphic memory video enable) signal on line 2688. This signal causes blocking of the memory at the end of the graphic plane window.

The inputs to 4 bit counter 2692 will now be described.

The parallel 8 bit signal D0-7 on line 1414 is input to latch 2639. This latch is clocked by an output of decoder 2590. When clocked, the first 4 bits are input to 4 bit counter 2692. The remaining 4 bits are input to multiplexer 2644.

The PIX CLK signal on line 1906 is input to the clock input of 4 bit counter 2692. The parallel 4 bit output of counter 2692 is input to multiplexer 2694. The other input to multiplexer 2694 is the parallel 4 bit signal PIX0-3 on line 2012. Based on the control input to this multiplexer, either the 4 bit parallel PIX0-3 signal or the parallel 4 bit output of 4 bit counter 2692 is selected for output to latch 2708. The last input to latch 2708 is the FRST PX signal on line 2014.

When latch 2708 is clocked by the PIX CLK signal on line 1906, the output is the GPX0 signal on line 2718, the GPX1 signal on line 2716, the GPX2 signal on line 2714 and the GPX3 signal on line 2712. These signals are the graphic plane pixel select lines.

The final output of latch 2708 is the FPXL signal on line 2710. This signal is for latching the first pixel word. The GPX0-3 signals are input to NAND gate 2720. The output of NAND gate 2720 is input to OR gate 2724. The second input to that gate is the FPXL signal on line 2710. The output of OR gate 2724 is the GST (graphic plane strobe) signal on line 2018.

4 bits of the output of latch 2639 are input to multiplexer 2644. The other parallel 4 bit signal input to multiplexer 2644 is the HBEG0-3 signal on line 2620. The output selection input to multiplexer 2644 is the Q output of flip flop 2670.

The output of multiplexer 2644 is input to 4 bit counter 2702. This counter is enabled by the output of NOR gate 2682. The inputs to the NOR gate are as follows:

A first input is the Q bar output of flip flop 2670.

Now, the second input will be described.

The parallel 8 bit signal SC0-7 on line 2576 is input to the P data inputs of 8 bit magnitude comparator 2572. The parallel 8 bit signal HEND0-7 is input to the Q data inputs of the comparator. The output of the comparator is conditioned on the satisfaction of P>Q bar. The satisfaction of this condition changes the signal's state.

The output of 8 bit magnitude comparator 2572 is input to inverter 2580. The inverter's output is input to NAND gate 2582. The second input to this gate is the WNDEF bar signal on line 2581. The WNDEF bar signal determines if the current window available for scrolling is scrolled or not.

The third input to NAND gate 2582 is the Q bar output of the flip flop 2670. The output of NAND gate 2582 is the second input to NOR gate 2682.

Once enabled by the output of NOR gate 2682, the 4 bit counter 2702 is clocked by the PIX CLK signal on line 1906. This signal is inverted by inverter 2659. As such, counter 2702 is clocked one half clock pulse after other cmponents clocked by the PIX CLK signal.

The parallel 4 bit output of 4 bit counter 2702 is input to multiplexer 2726. The output is also the parallel 4 bit signal SC0-3 on line 2576. These are used as the graphic plane count bits for the scrolled areas.

The other input to multiplexer 2726 is the parallel 4 bit signal HA0-3 on line 2182. Based on the state of the Q bar output of flip flop 2670, one of the 4 bit inputs is output as the HGA0-3 signal. These are 4 bits of the 8 bits of the horizontal graphic plane address.

The parallel 8 bit signal D0-7 on line 1414 is input to latch 2652. The latch is clocked by an output of decoder 2590. When clocked, the first 4 bits are input to multiplexer 2658. The other 4 bit input to multiplexer 2658 is the parallel 4 bit signal HBEG4-7 on line 2622. According to the state of the Q output of flip flop 2670, one of the 4 bit inputs is selected and output from the multiplexer.

The output of multiplexer 2658 is input to 4 bit counter 2704. The terminal count of 4 bit counter 2702 starts counter 2704. The output of NOR gate 2682 enables 4 bit counter 2704.

The HORIZ ADV signal is input to the trigger input of counter 2702 for controlling the count.

The output of 4 bit counter 2704 is input to multiplexer 2728. This ouput is also the 4 bit SC4-7 signal (on line 2576). These are the remaining horizontal graphic plane count bits for the scroll areas.

The second input to multiplexer 2728 is the parallel 4 bit signal HA4-7 on line 2182. Based on the state of the Q bar output of flip flop 2670, one of the 4 bit inputs is output as the HGA4-7 signal on line 2184.

FIG. 10C shows generation of the VID signal on line 2062. The VID signal controls the information on the display screen.

With respect to the character plane, the parallel 4 bit signal PIX0-3 on line 2012 is input to latch 2802. This latch is clocked by the PIX CLK signal on line 1906. When clocked, the parallel 4 bit output is input to the control inputs of the 16 bit data selector 2822. The signals output by latch 2802 are also termed the PIX0L-3L signals on line 2804.

The data inputs to 16 bit data selector 2822 are the CETO0-15 signals on line 2160 after being latched twice.

The CETO0-7 signals on line 2160 are input to latch 2806 and the CETO8-15 signals on line 2160 are input to latch 2814. Both latches are clocked by the THS/CHRST signal on line 1956. The output of latch 2806 is input to latch 2808 and the output of latch 2814 is input to latch 2818. Latches 2808 and 2818 are clocked by the FPXL signal on line 2710. When clocked, the outputs of these latches are input to the sixteen data inputs of 16 bit data selector 2822. Based on the states of the PIX0L-3L signals, an output is selected. The selected output is input to latch 2852.

With respect to the enhancement plane, the CETO0-7 signals are input to 16 bit data selector 2848 after first being latched by latches 2826 and 2830. Similarly, the CETO8-15 signals input to 16 bit data selector 2848 are first latched by latch 2840 and then by latch 2844.

The first set of latches, 2826 and 2840, are clocked by the NXT/ENHST signal on line 1960. The second set of latches, 2830 and 2844, are clocked by the FPXL signal on line 2710.

The parallel 4 bit signal PIX0L-3L on line 2804 is input to the control inputs of data selector 2848. The output of 16 bit data selector 2848 is input to latch 2852.

A third input to latch 2852 is the BLINK signal discussed previously.

The fourth input to latch 2852 is associated with the graphic plane.

The control input to 16 bit data selector 2888 is the 4 bit GPX0-3 signal on lines 2718, 2716, 2714 and 2712.

The graphic plane data is double latched like the character and the enhancement plane data. The GMO0-7 signals on line 2126 are latched first by latch 2860 and then by latch 2884 before input to data selector 2888. The GMO8-15 signals on line 2126 are latched first by latch 2864 and then by latch 2886 before input to data selector 2888. The TH0-15 signals (on line 2862), shown at the outputs of latches 2860 and 2864, are signal designations to show the connection of the first set of latches to the input lines the latches 2884 and 2886 when this first set of latch is clocked by the THS/CHRST signal on line 1956.

The second set of latches, 2884 and 2886 are clocked by the GOLST signal on line 2016. When the second set of latches are clocked, their data is input to the 16 data inputs of 16 bit data selector 2888.

In a second instance, the GMO0-7 signal are latched first by latch 2880 and then latch 2884. The GMO8-15 signals are first latched by latch 2882 and then latch 2886.

In this case, the first sets of latches, 2880 and 2882, are clocked by the NXT/CHRST signal on line 1960. The second set of latches, 2884 and 2886, are clocked by the GOLST signal on line 2016.

The two first sets of latches, namely 2860 and 2864, and 2880 and 2882, are output enabled by an asynchronous flip flop consisting of NAND gates 2868 and 2872, and inverter 2866. One output of the flip flop connects to the output enable inputs of latches 2860 and 2864. The other output of the flip flop connects to the output enable inputs of latches 2880 and 2882. The GLSEL is input to the flip flop on line 1962. The state of the GLSEL signal determines which first set of latches is output enabled.

Once the data is input to 16 bit data selector 2888, the output of the data selector is enabled by the GMVE signal on line 2688. When enabled, thw selected output is input to latch 2852. The PIX CLK signal on line 1906 clocks latch 2852. The outputs of latch 2852 are input to a series of logic gates. These gates are inverters 2894 and 2902, NAND gates 2898 and 2910, and NOR gate 2922. Processing of the outputs of latch 2852 by these gates is known by one skilled in the art without further explanation.

The output of NOR gate 2922 is input to the data input of flip flop 2930. The PIX CLK signal on line 1906 clocks flip flop 2930. When clocked, the Q output is the VID signal on line 2062.

Figure 11:
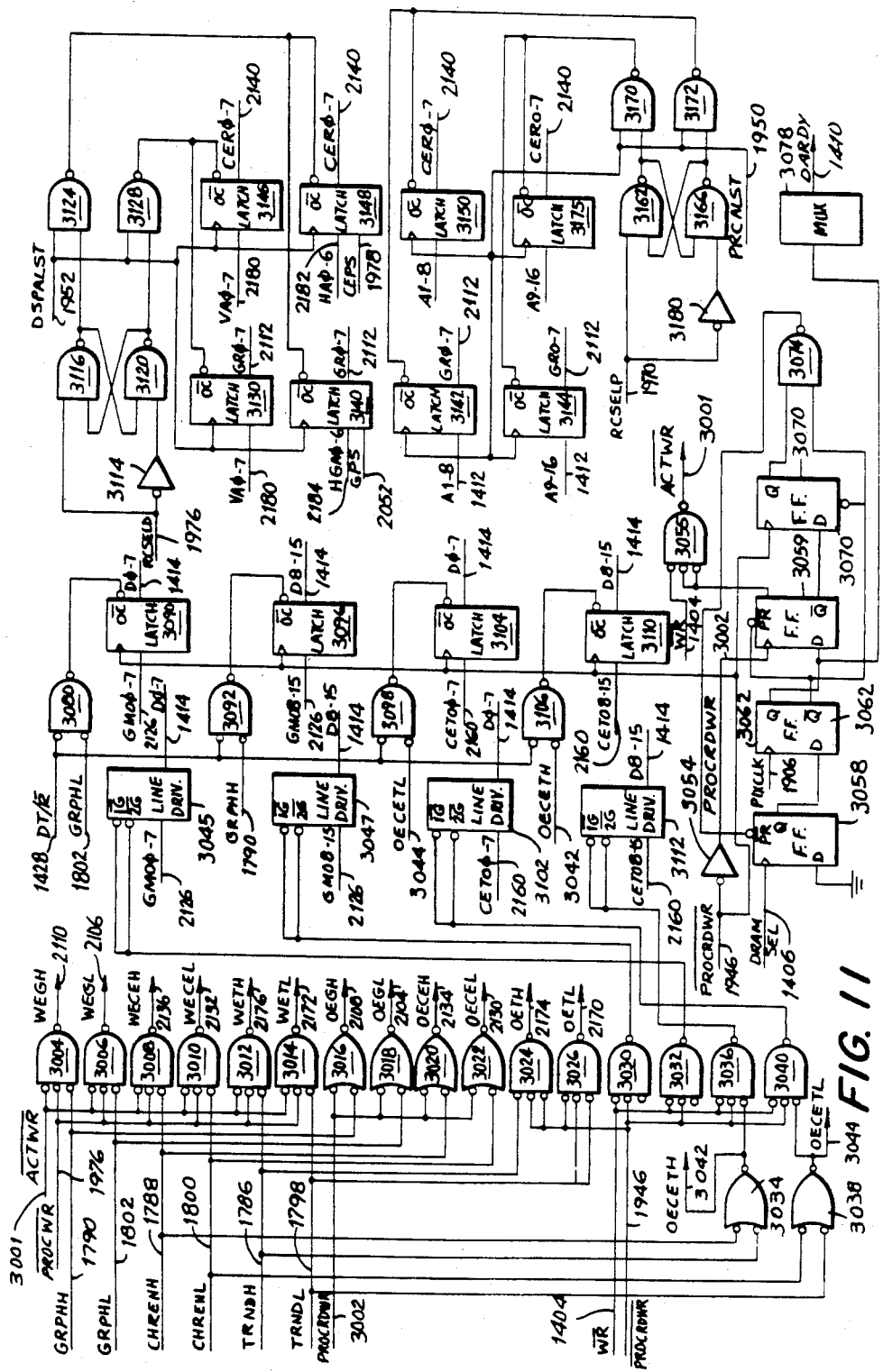
FIG. 11 is a schematic diagram of the CRT memory control gate array of the pixel circuitry shown in FIG. 9B.

FIG. 11 shows the CRT memory control gate array.

The DRAM SEL signal in line 1406 clocks flip flop 3058. The Q output of flip flop 3058 is the data input of flip flop 3062 which is clocked by the PIX CLK signal on line 1906.

The Q output of flip flop 3062 is input to the data input of flip flop 3059. This output is also input to the data input of multiplexer 3078. This multiplexer's output is the DARDY signal on line 1410.

The Q bar ouptut of flip flop 3062 is input to the preset input of flip flop 3059, to NAND gate 3074 and to the clear bar input of flip flop 3070. The clock input to flip flop 3059 is the PROCRDWR signal on line 3002.

The Q output of flip flop 3059 is tied to two inputs of NAND gate 3055. The other input to NAND gate 3055 is the WR bar signal on line 1404. The output of NAND gate 3055 is the ACTWR bar signal on line 3001. The ACTWR bar signal indicates that the microprocessor is actively writing into a DRAM.

The Q bar output of flip flop 3059 is input to the data input of flip flop 3070. The PROCRDWR bar signal on line 1946 clocks flip flop 3070. The Q output of flip flop 3070 is the second input to NAND gates 3074. The output of NAND gate 3074 is input to the preset input of the flip flop 3058.

Generation of the high and low output enable and write enable signals for the graphic plane, character/enhancement plane and trend section will be described.

Referring to FIG. 11, the write enable signals for the graphic plane, character/enhancement plane and trend section are determined by the outputs of NAND gates 3004, 3006, 3008, 3010, 3012 and 3014. Two inputs to each gate are the same. These inputs are the ACTWR bar signal on line 3001 and the PROCWR bar signal on line 1976. The third signal input to a particular NAND gate is one of the six signals generated by the display processor for use in determining the selection of the graphic plane high or low, character/enhancement plane high or low, and trend section high or low.

The GRPHH signal on line 1790 is the third input to NAND gate 3004, whose output is the signal WEGH on line 2110. The GRPHL signal on line 1802 is the third input to NAND gate 3006, whose output is the WEGL signal on line 2106. The CHRENH signal on line 1788 is the third input to NAND gate 3008, whose outputs is the WECEH signal on line 2136. The CHRENL signal on line 1800 is the third input to NAND gate 3010, whose output is the WECEL signal on line 2132. The TRNDH signal on line 1786 is the third input to NAND gate 3012, whose output is the WETH signal on line 2176. The TRNDL signal on line 1798 is the third input to NAND gate 3014, whose output is the WETL signal on line 2172.

The first input to NOR gates 3016, 3018, 3020 and 3022 is the PROCRDWR signal on line 3002. The second input to NOR gate 3016 is the GRPHH signal. The output of NOR gate 3016 is the OEGH signal on line 2108. The second input to NOR gate 3018 is the GRPHL signal. The output of NOR gate 3018 is the OEGL signal on line 2104. The second input to NOR gate 3020 is the CHRENH signal. The output of NOR gate 3020 is the OECEH signal on line 2134. The second input to NOR gate 3022 is the CHRENL signal. The output of NOR gate 3022 is the OECEL signal on line 2130.

The first two inputs to NAND gate 3024 are the PROCRDWR bar signal on line 1946 tied to two inputs. The third input is the TRNDH signal on line 1786. The first input to NAND gate 3026 is the PROCRDWR bar signal on line 1946. The second and third inputs are the TRNDL signal on line 1798 tied to two inputs.

The output of NAND gate 3024 is the OETH signal on line 2174. The output of NAND gate 3026 is the OETL signal on line 2170.

The inputs to NOR gate 3034 are the CHRENH signal on line 1788 and the TRNDH signal on line 1786. The output of NOR gate 3034 is the OECETH signal on line 3042.

The inputs to NOR gate 3038 are the CHRENL signal on line 1800 and the TRNDL signal on line 1798. The output of NOR gate 3038 is the OECETL signal on line 3044.

Bus buffers 3045 and 3047 are for transferring data from the data bus, D$\emptyset$-15, to the graphic plane memory outputs, GMO$\emptyset$-15. The low order bits are handled by bus buffer 3045 and the high order bits are handled by bus buffer 3047. In like manner, bus buffers 3102 and 3112 are for transferring data from the data bus, D$\emptyset$-15, to the character/enhancement/trend memory outputs, CETO$\emptyset$-15. The low order bits are handled by bus buffer 3102. The high order bits are handled by bus buffer 3112.

The signal enabling bus buffer 3045 is the output of NAND gate 3032. The inputs to NAND gate 3032 are the WR bar signal on line 1404, the PROCRDWR bar signal on line 1946 and the GRPHL signal on line 1802.

The signal enabling bus buffer 3047 is the output of NAND gate 3030. The inputs to this gate are the WR bar signal on line 1404, the PROCRDWR bar signal on line 1946, and the GRPHH signal on line 1790.

The signal enabling bus buffer 3102 is the output of NAND gate 3040. The inputs for the NAND gate 3040 are the WR bar signal on line 1404, the PROCRDWR bar signal on line 1946 and the OECETL signal on line 3044.

The signal enabling bus buffer 3112 is the output of NAND gate 3036. This gate's inputs are the WR bar signal on line 1404, PROCRDWR bar signal on line 1946 and the OECETH signal on line 3042.

Latches 3090 and 3096 are to transfer data from the graphic plane memory outputs to the data bus. Latches 3104 and 3110 are to transfer data from the character/enhancement/trend memory outputs to the data bus. All four latches are clocked by the PROCRDWR bar signal on line 1946. However, each of the four latches are output enabled by a different NAND gate. One input to the four NAND gates is the DT/R (R bar) signal on line 1428. The second signal input to each gate will now be described.

NAND gate 3080 output enables latch 3090. This latch transfers data from the low order bits of the graphic plane memory outputs, GMO$\emptyset$-7, to the low order bits of the data bus, D$\emptyset$-7. The second signal input to NAND gate 3090 is the GRPHL signal on line 1802.

NAND gate 3092 output enables latch 3096. The latch transfers data from the high order bits of the graphic plane memory outputs, GMO8-15, to the high order bits of the data bus, D8-15. The second signal input to NAND gate 3096 is the GRPHH signal on line 1790.

NAND gate 3098 output enables latch 3104. Latch 3104 transfers data from the low order bits of the character/enhancement/trend memory outputs, CETO0-7, to the low order bits of the data bus, D0-7. The second input to NAND gate 3098 is the OECETL signal on line 3044.

NAND gate 3106 output enables latch 3110. Latch 3110 transfers data from the high order bits of the character/enhancement/trend memory outputs, CETO8-15, to the high order bits of the data bus, D8-15. The second input to NAND gate 3106 is the OECETH signal on line 3042.

Latch 3130 transfers the vertical address information in the VA0-7 signals to the graphic plane addresses, GR0-7. Latch 3146 transfers the vertical address information in the VA0-7 signals to the character/enhancement plane addresses, CER0-7.

Latch 3140 transfers the horizontal address information in the HGA0-6 signals and the GPS signal to the graphic plane addresses, GR0-7. Latch 3148 transfers the horizontal address information in the HA0-6 signals and the CEPS signal to the character/enhancement plane addresses, CER0-7.

The signal that clocks latches 3130, 3140, 3146 and 3148 is the DSPALST signal on line 1952.

Enablement of these four latches is determined by an asynchronous flip flop comprising NAND gates 3116 and 3120, and inverter 3114. The output of NAND gate 3116 of the flip flop is input to NAND gate 3124. The output of NAND gate 3120 of the flop flop is input to NAND gate 3128. The second input to NAND gates 3124 and 3128 is the DSPALST signal on line 1952.

The ouput of NAND gate 3124 is input to the output enable inputs of latches 3140 and 3148 (for the horizontal addresses). The output of NAND gate 3128 is input to the output enable inputs of latches 3130 and 3146 (for the vertical addresses).

The RSCELD signal on line 1976 is input to the flip flop. When the DSPALST signal has the proper state, the state of the RSCELD signal determines the row or column address information transferred.

Latch 3142 transfers the row address information in the A1-8 signals to the graphic plane addresses, GR0-7. Latch 3150 transfers the row address information in the A1-8 signals to the character/enhancement plane addresses, CER0-7.

Latch 3144 transfers the column address information in the A9-16 signals to the graphic plane addresses, GR0-7. Latch 3175 transfers the column address information in the A9-16 signals to the character/enhancement plane addresses, CER0-7.

The signal that clocks latches 3142, 3144, 3150 and 3175 is the PRCALST signal on line 1950.

Enablement of the four latches is determined by an asynchronous flip flop comprising NAND gates 3162 and 3166, and inverter 3180. The output of NAND gate 3162 of the flip flop is input to NAND gate 3170. The output of NAND gate 3166 of the flop flop is input to NAND gate 3172. The second input to NAND gates 3170 and 3172 is the PRCALST signal on line 1950.

The output of NAND gate 3170 is input to the output enable inputs of latches 3144 and 3175 (for the column addresses). The output of NAND gate 3172 is input to the output enable inputs of latches 3142 and 3150 (for the row addresses).

The RCSELP signal is input to the flip flop on line 1970. When the PRCALST signal has the proper state, the state of the RCSELP signal determines the row or column address information transferred.

FIG. 12 shows the digital output board 140 (FIG. 1). The TxD signal on line 1510, the RxD signal on line 1512, the DRT signal on line 1514, the DSR signal on line 1516, the RTS signal on line 1518 and the CTS signal on line 1520 are for communications between controller 1776 (FIG. 8) and an external device connected to digital connector 3302.

The optional digital output connector 3304 is also shown in FIG. 12. The RD bar signal on line 1402, the WR bar signal on line 1404, the parallel 8 bit data bus signal D0-7 on line 1414, the DT/R (R bar) signal on line 1428, the parallel 3 bit address bus A1-3 on line 1412, the SLAVE SEL signal on line 1504, the SLAVE INTR signal on line 1506 and the CLK OUT signal on line 1508 are for communications with and control of an external device by the microprocessor 1702 (FIG. 8).

Referring to FIG. 13, the knob board 144 and five button panel 48 for control of the system of the present invention are shown.

Manual movement of knob 3410 changes the output to flip flops 3416 and 3426. The knob output to flip flop 3416 is processed by Schmitt trigger 3414 before input. The knob output to flip flop 3426 is processed by Schmitt trigger 3424 before input.

Flip flops 3416 and 3426 are clocked by the V.SYNC signal on line 1344. When flip flop 3416 is clocked, the Q output is input to the data input of flip flop 3420. The output of flip flop 3416 is also one of the inputs to exclusive OR gate 3438.

When flip flop 3426 is clocked, the Q bar output is input to the data input of flip flop 3430. The Q bar output is also input to exclusive OR gates 3436 and 3440.

Flip flops 3420 and 3430 are clocked by the V.SYNC signal on line 1344. When these flip flops are clocked, the Q bar output of flip flop 3430 is the second input to exclusive OR gate 3440 and the Q bar output of flip flop 3420 is the second input to exclusive OR gates 3436 and 3438.

The outputs of exclusive OR gates 3438 and 3440 are input to exclusive OR gate 3446.

The output of exclusive OR gate 3446 is input to buffer 3204. The output of exclusive OR gate 3436 is also input to buffer 3204. Another data input to buffer 3204 is the Q bar output of flip flop 3403. The Q bar output is tied to four inputs of buffer 3204. The D0 signal on line 1414 from the data bus is input to the data input of the flip flop.

Flip flop 3403 is clocked by the output of NAND gate 3415. The inputs to this NAND gate are the WR bar signal on line 1404 and the DISP SEL signal on line 1602.

The output of NAND gate 3417 enables buffer 3204. The inputs to NAND gate 3417 are the RD bar signal on line 1402 and the DISP SEL signal on line 1602.

When the buffer is enabled, the outputs from exclusive OR gates 3436 and 3446 are placed on the data bus, D8 and D9. The output from flip flop 3403 is input to alarm circuitry 3408 and used to drive selected alarms.

The output of NAND gate 3417 is also the output enable input to buffer 3484. The data inputs to buffer 3484 are the output of alarm switch 3452, the outputs of ON/STBY switch 3456, the output of HELP switch 3460 and the outputs of BUTTONS 1-5, shown at 3464, 3468, 3472, 3476 and 3480, respectively. The buttons and switches are the operator interface for system operation and control. When the buffer is enabled, the values of above-described inputs are placed on the data bus for transmission to microprocessor 1702.

The system powering the improved gas analyzer system is power supply 158, rectifier 160 and DC-DC converter 162. It is a split system with a first half powering the display section and the second half powering the analog section. Each half of the system has its own battery backup. This system is conventional and known to those skilled in the art.

Figure 14:
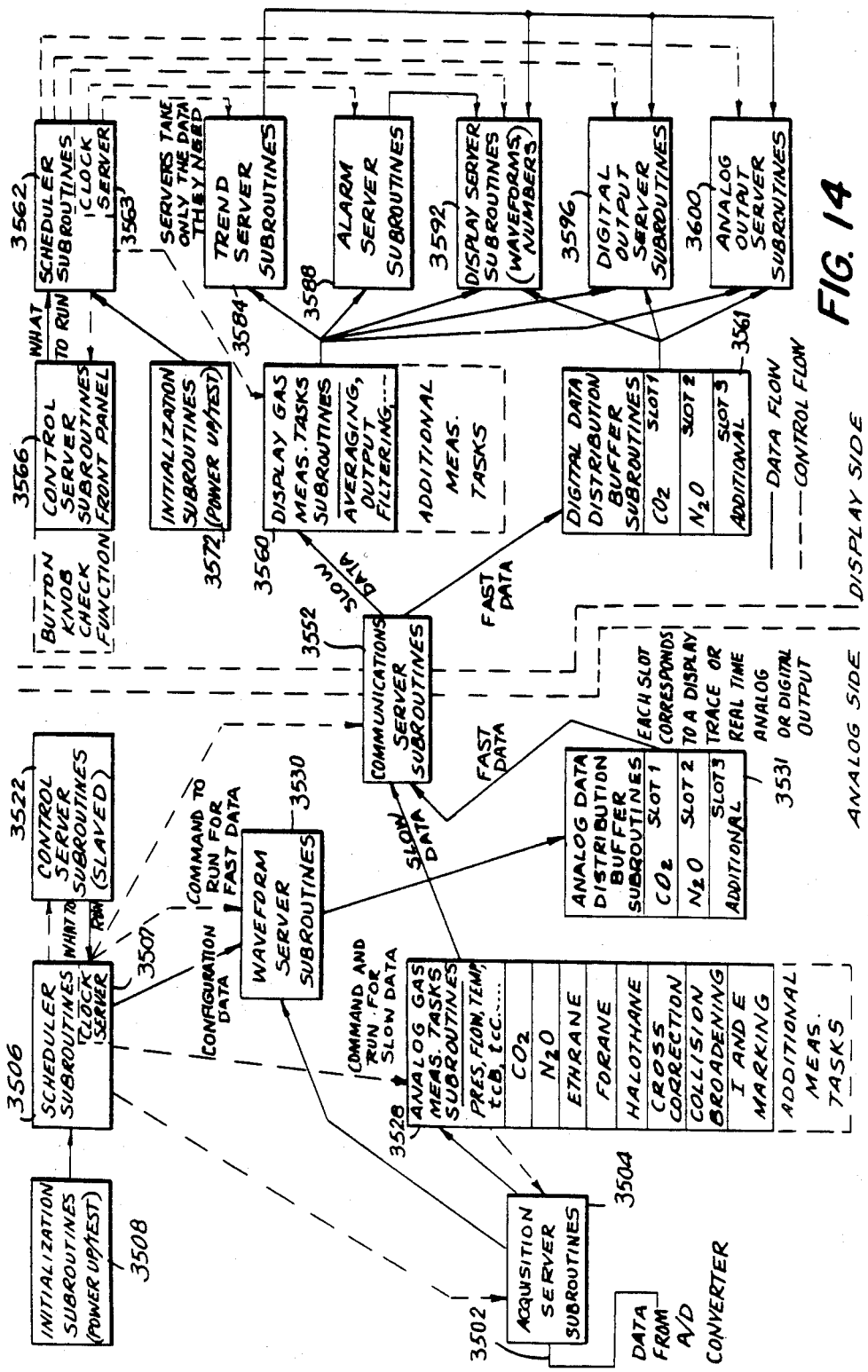
FIG. 14 is a block diagram of the software for controlling the multichannel gas analyzer system of the present invention.

FIG. 14 shows a block diagram of the software modules for the display and analog processors. For reference purposes, the software program listing, attached as Appendix 1, is divided into seven sections: MAIN, ACQ, GAS, SERVER, COMM, DISPLAY, and MENU. The modules will be described and the areas of the software program that correspond to a particular module will be indicated. An example of a code citation for identifying the location of a specific module is as follows: MAIN. In FIG. 14, the solid lines indicate data flow and the dashed lines indicate control flow.

The Initialization subroutines for both the display side and analog side power up the system and carry out initial start functions and tests. Analog Initialization subroutines 3508 are found at MAIN. Display Initialization subroutines 3572 are at MAIN.

The master Control Server is display Control Server 3566. Analog Control Server 3522 is slaved to master Control Server 3566. The Control Servers control overall system operations. The subroutines of display Control Server 3566 monitor the buttons, knobs and switches of the control panel and appropriately adjust system operations based on their positions. Both the analog and display Control Servers provide data to their respective Scheduler subroutines 3506 and 3562 on "what to run". Analog Control Server subroutines 3522 are found at MAIN. Display Control Server subroutines 3566 are found at MENU.

Analog Scheduler 3506 and display Scheduler 3562 manage the processes and events for their respective sides. The Schedulers insure the programmed functions for each side are carried out. Analog Scheduler subroutines 3506 are located in the code at MAIN. Display Scheduler subroutines 3562 are also located at MAIN.

The Scheduler subroutines for both the analog and display side also include Clock Server subroutines. The Clock Server subroutines manage system timing of all events. Analog Clock Server subroutines 3507 are found at MAIN. Display Clock Server subroutine 3563 are also found at MAIN.

Acquisition Server 3504 accesses the raw data from the A/D converter. It provides this data to Analog Measurement Tasks (AMT) subroutines 3528 to produce numerical output values. It also provides this data to Waveform Server subroutines 3530 to produce waveforms. Acquisition Server subroutines 3504 are found at ACQ.

Waveform Server 3530 is the programming for transforming raw data into waveform data. The Waveform Server subroutines acquire data from Acquisition Server subroutines 3504, process it and transfer the data to Communications Server subroutines 3552 that links the analog and display sides. Waveform Server subroutines 3530 are found at SERVER.

Analog Measurement Tasks (AMT) 3528 transform the raw data to usable information for display and output purposes. AMT subroutines 3528 are found at GAS.

Display Measurement Tasks (DMT) 3560 carry out data distribution to Trend Server subroutines 3584, Alarm Server subroutines 3588, Display Server subroutines 3592, Digital Output Server subroutines 3596, and Analog Output Server subroutines 3600. The DMT subroutines are found at GAS.

Analog Data Distribution Buffer (ADDB) 3531 and Display Data Distribution Buffer (DDDB) 3561 serve as common locations for access to fast data. ADDB structures 3531 are found at COMM. DDDB structures are also found at COMM.

Communications Server 3552 communicates data between the analog and the display sides. These subroutines are found out at COMM.

Display Server 3592 links to DMT subroutines 3560 and DDDB structures 3561. The Display Server subroutines receive the data from the DMT subroutines and the DDDB structures, and process the data for numerical and graphical display. The Display Server subroutines can be found at DISPLAY.

Trend server 3584 stores historical data from the DMT subroutines and provides it to Display Server subroutines 3592, Digital Output Server subroutines 3596 and Analog Output Server subroutines 3600 when ordered by Control Server subroutines 3562 via Scheduler subroutines 3566. Trend Server subroutines 3584 can be found in the code at MAIN.

Alarm Server 3588 links to the DMT subroutines and receives data from those subroutines. For output purposes, the Alarm Server subroutines provide data for both audible and visual alarms to the Display Server subroutines. Alarm Server subroutines 3588 are found at MAIN.

Digital Output Server 3596 processes the data from DMT subroutines 3560 and DDDB structures 3561 for digital output to external devices. This server's subroutines can be found at COMM.

Analog Output Server 3600 processes streams of output waveform and value data from the DMT subroutines and DDDB structures 3561 for output to external devices. The subroutines for this server are found SERVER.

The software operations will now be discussed.

At system start up, Initialization subroutines 3508 and 3572 initialize values for the system and conduct certain tests. In this procedure, data about the system is sent to Scheduler subroutines 3506 and 3562. Initialization subroutines 3508 and 3572 also start the Clock Servers subroutines 3567 and 3563, respectively.

The initialized Analog Scheduler subroutines 3506 query the analog Control Server subroutines 3522 for what processes to run. Analog Control Server subroutines 3522 are slaved to display Control Server subroutines 3566. The display Control Server runs a subroutine for a buttons and knobs check. As the result of the buttons and knobs check, analog Control Server subroutines 3522 determine the AMT subroutines to run and send data to the Analog Scheduler subroutines as to the AMT subroutines to run.

Analog Scheduler subroutines 3506 and AMT subroutines 3528, based on the data from analog Control Server subroutines 3522, provide control information to Acquisition Server subroutines 3504. The Acquisition Server subroutines, when commanded, access the A/D converter data on line 3502. Acquisition Server subroutine 3504 buffers the data until the Analog Scheduler subroutines direct that the data be sent to AMT subroutines 3528 and Waveform Server subroutines 3530. AMT subroutines 3528 and Waveform Server subroutines 3530 transform the data according to their respective programming.

The Analog Scheduler subroutines acknowledge that data is being sent to AMT subroutines 3528 and Waveform Server subroutines 3530. The Analog Scheduler subroutines command the AMT subroutines to run for slow data and command Waveform Server subroutines 3530 to run for fast data.

AMT subroutines 3528 calculate the common equations used by all of the gases, e.g., the flow rate, pressure in the optical bench and temperature in the optical bench. These subroutines also calculate the partial pressure for each gas. Further, these subroutines calculate the position for superimposing the "I" and "E" on the capnogram to indicate the transition points beteween inspiration/expiration and expiration/inspiration.

The AMT subroutines can have other subroutines which can be commanded to run other types of measurement calculations, e.g., $SaO_2$ measurement tasks.

Analog Scheduler subroutines 3506 continuously direct Waveform Server subroutines 3530 to run for fast data. Waveform Server subroutines 3530 send the transformed fast data to ADDB structures 3531. Analog Scehduler subroutines 3506 command Communications Server subroutines 3552 to acquire the fast data in the ADDB structures and transmit it to DDDB structures 3561.

Analog Clock Server subroutines 3507 time the events carried out by the AMT subroutines and the Waveform Server subroutines.

Analog Scheduler subroutines 3506, based on the subroutines of Clock Server subroutines 3507, instruct Communications Server subroutines 3552 to buffer data from Waveform Server subroutines 3530 and AMT subroutines 3528. Communications Server subroutines 3552 buffer data, and when time-out is reached, transfer the data to DMT subroutines 3560 and DDDB structures 3561 on the display side.

Now referring to the display side:

DMT subroutines 3560 receive data from the Communications Server subroutines as commanded by Display Scheduler subroutines 3562 and display Control Server subroutines 3566. The DMT subroutines carry out their required measurement tasks on the slow data.

The data output by DMT subroutines 3560 is input to the five output type servers. Scheduler subroutines 3562 command Trend Server subroutines 3584, Alarm Server subroutines 3588, Display Server subroutines 3592, Digital Output Server subroutines 3596, and Analog Output Server subroutines 3600 to receive specific data according to their programamming.

Once the data is received, the repsective server subroutines process the the data for output, or in the case of the Trend Server, process the data for historical purposes.

Display Scheduler subroutines 3562 command Display Server subroutines 3592, Digital Output Server subroutines 3596 and Analog Output Server subroutines 3600 to access the fast data in the DDDB structures 3561. After accessing the data, each processes it according to its programming.

Figure 15:
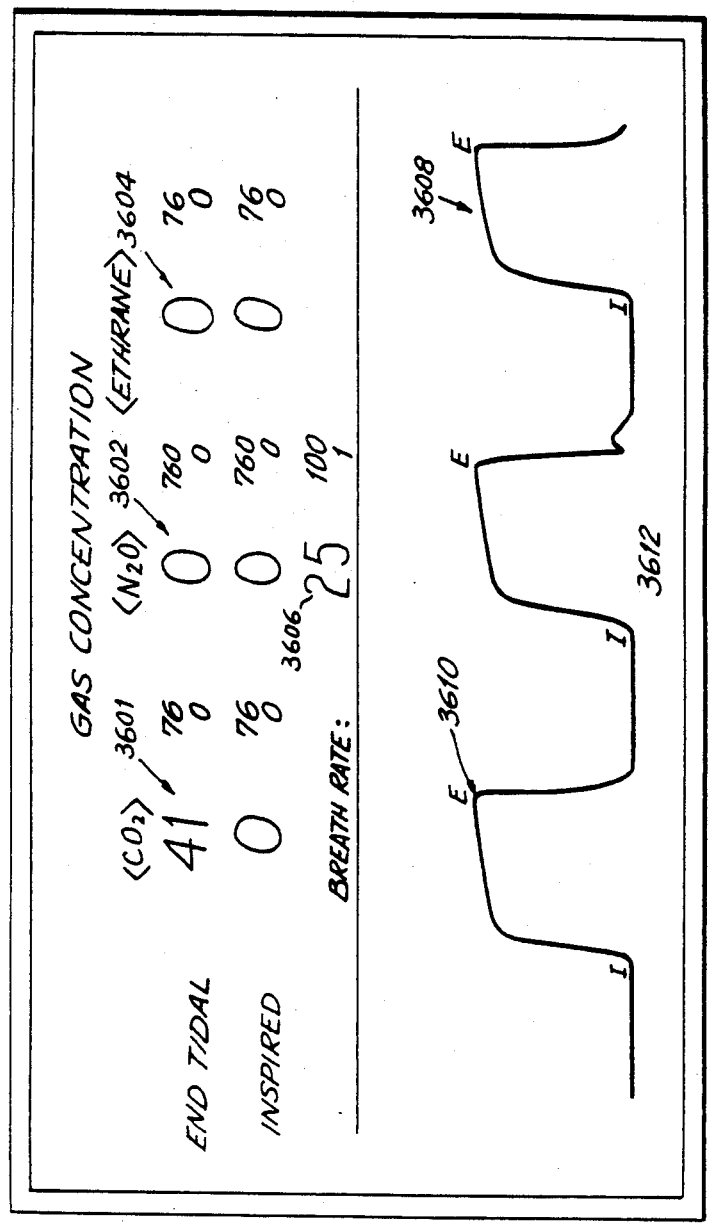
FIG. 15 shows a representative CRT screen display for the multichannel gas analyzer system of the present invention.

FIG. 15 shows a representative screen display of the multichannel gas analyzer system of the invention.

The end-tidal and inspired gas concentration for $CO_2$, $N_2O$ and ethrane are shown generally at 3601, 3602 and 3604, respectively. Also, the breath rate is shown generally at 3606.

A $CO_2$ capnogram is shown generally at 3608. Superimposed on the capnogram at the inspiration and expiration transition points are the "I" and "E" markings referred to previously.

The terms and expressions which are employed here are terms of description and not of limitation. There is no intention, in the use of such terms and expressions, to exclude the equivalents of the features shown and described, or portions thereof, it being recognized that various modifications are possible within the scope of the invention as claimed.

APPENDIX 1

TABLE OF CONTENTS

| Title | Section |
|---|---|
| MAIN | A |
| ACQ | B |
| GAS | C |
| SERVER | D |
| COMM | E |
| DISPLAY | F |
| MENU | G |

MAIN

SECTION A

```
1   .186
2   ROMCODE equ 1 ; take away comment to make ROMABLE Code!
3
4   ;***********************************************************
5   ; Module anlginit.s
6   ;
7   ; Purpose:
8   ;   This module does the initialization for the analog processor.
9       Name analoginit
10
11  ; Procedures:
12
13          Public   main, main
14          Public   XInterruptInit
15          Public   XRAMInit
16          Public   XHWInit
17
18  ; Public Data:
19          Public XStartUp
20
21  ;       This module is an original, unpublished work and is proprietary to
22  ;       NELLCOR INC., and may not be divulged or copied in any form
23  ;       whatsoever without the express written permission of NELLCOR INC.
24  ;       Copyright 1986.
25  ;***********************************************************
26  ; modification history:
27  ; 20 Aug 86 slc basic memory block is 64k, not 32k
28  ; 25 Aug 86 slc put 1 wait state in mmcs reg,clear timer before run
29  ;***********************************************************
30
31      include Xdef.i
32      include Xevent.i
33
34  CONST segment word public 'CONST'
35  CONSTFirstWord equ this word
36  Public CONSTFirstWord
37      org 0
38  CONST ends
39
40  DATA segment word public 'DATA'
41  DATAFirstWord equ this word
42  Public DATAFirstWord
43      org 0
44  DATA ends
45
46  BSS segment word public 'BSS'
47  BSSFirstWord equ this word
```

```
 51    Public _BSSFirstWord
 52    org 0
 53    _BSS ends
 54
 55    C_COMMON segment word public 'BSS'
 56    C_COMMONFirstWord equ this word
 57    Public _C_COMMONFirstWord
 58    org 0
 59    C_COMMON ENDS
 60
 61    LowMemEndSeg Segment byte public 'lastdata'
 62    ; Nothing can be in this segment except MemTop!!!
 63        extrn MemTop:byte
 64    LowMemEndSeg ends
 65
 66    _TEXT segment byte public 'code'
 67    _TEXTFirstWord equ this word
 68    Public _TEXTFirstWord
 69    org 0
 70    _TEXT ends
 71
 72    SAT_TEXT segment byte public 'code'
 73        extrn SatInit:far ; for test
 74    SAT_TEXT ends
 75
 76    ECG_TEXT segment byte public 'code'
 77    ECG_TEXT ends
 78
 79    BP1_TEXT segment byte public 'code'
 80    BP1_TEXT ends
 81
 82    BP2_TEXT segment byte public 'code'
 83    BP2_TEXT ends
 84
 85    TP1_TEXT segment byte public 'code'
 86    TP1_TEXT ends
 87
 88    TP2_TEXT segment byte public 'code'
 89    TP2_TEXT ends
 90
 91    ITP_TEXT segment byte public 'code'
 92    ITP_TEXT ends
 93
 94    ARS_TEXT segment byte public 'code'
 95    ARS_TEXT ends
 96
 97    MT_TEXT segment byte public 'code'
 98        extrn TCreateP:far ; for test
 99        extrn GCreateP:far ; for gas
100    MT_TEXT ends
101
102    SYS_TEXT segment byte public 'code'
103    SYS_TEXT ends
104
105    SYS_TEXT segment BYTE PUBLIC 'code'
106        extrn XCreateP:far
107        extrn XWait:far, XSchedProc:far, XSchedInit:near
108
```

```
109         extrn   XIllegalInstruction:far
110         extrn   AcqData:near, ainit:near
111         ;extrn  XReportMemErr:far
112         extrn   _End_SYS_TEXT:word
113         extrn   _cinit:far
114         extrn   _wfinit:far
115         SYS_TEXT ends
116
117         XINITCODE segment byte public 'xinitcode'
118         XINITCODEFirstWord equ this word
119         Public _XINITCODEFirstWord
120         org 0
121         XINITCODE ends
122
123
124         CONST   segment word public 'CONST'
125         ;   Hex2ROM interface
126         Hex2ROM equ this byte
127         Public Hex2ROM
128         dd      CONSTFirstWord          ; address of bottom of dgroup
129         dd      _BSSFirstWord           ; address of bottom of _BSS
130         dd      _MemTop                 ; end of memory
131         dd      _TEXTFirstWord          ; address of bottom of code class
132         dd      _End_SYS_TEXT           ; address of top of code class
133         dd      _XINITCODEFirstWord     ; address of bottom of reset code
134         CONST ends
135
136         _TEXT   segment byte public 'code'
137         Copyright equ this byte
138         db "This code is an original, unpublished work and is proprietary to"
139         db "NELLCOR INC., and may not be divulged or copied in any form"
140         db "whatsoever without the express written permission of NELLCOR INC."
141         db "Copyright 1986."
142         _TEXT ends
143
144
145         _DATA   segment word public 'DATA'
146
147         extrn   XInterruptProc:word
148         extrn   X_sp:word
149         extrn   XClockRate:word
150         extrn   _xMemTop:word, _xMemBeg:word, _xHeapTop:word
151         extrn   _End_DATA:word
152
153         org 0
154         actused dw ?
155         public  _actused
156
157         even
158         XInterruptTable dw (0ffffh)
159
160         XInterruptRate dw H2B00
161         Public XInterruptRate
162
163         XTimers dw 0
164         public XTimers
165
166
```

```
167         _DATA ends
168         _BSS segment word public 'BSS'
169         extrn _End__BSS:word
170
171         even
172
173         Public sysstackbeg, sysstackend
174         sysstackbeg dw 81 dup (?)
175         sysstackend dw ?
176
177         S0stackbeg dw 81 dup (?)
178         S0stackend dw ?
179
180         DeadTime dd ?
181         Public DeadTime
182
183         _BSS ends
184
185         MTCode segment byte public 'code'
186         MTCode ends
187
188         DGroup group LowMemEndSeg, c_common, _BSS, CONST, _DATA
189
190         SYS_TEXT segment byte public 'code'
191
192         ASSUME CS:SYS_TEXT, DS:DGROUP, SS:DGROUP, ES:DGROUP
193
194         main label far
195         _main label far
196                 mov     bp, offset XRAMInitRet
197                 jmp     XRAMInit
198         XRAMInitRet:
199         Public XRAMInitRet
200
201                 mov     ax, DGROUP
202                 mov     ds, ax
203                 mov     es, ax
204                 mov     ss, ax
205                 mov     sp, offset DGROUP:sysstackend
206                 and     sp, 0fffeh
207                 call    XInterruptInit
208                 call    XSchedInit
209
210                 mov     XInterruptProc, offset Acq_Data
211
212                 mov     ax, offset DGroup:_MemTop
213                 mov     _MemTop, ax
214                 mov     ax, offset DGroup:_End__BSS
215                 mov     _MemBeg, ax
216                 mov     _xHeapTop, ax
```

```
225         call    ainit
226
227    ;for test
228
229         xor     ax, ax          ;no terminate function
230         push    ax
231         push    ax
232         push    offset DGROUP:XTimers
233         push    offset DGROUP:S0stackend
234         push    SYS_TEXT
235         push    offset S0Proc
236         push    PID_CONTROL
237         call    far ptr XCreateP
238         add     sp, 14
239
240         push    'M'
241         call    _cInit
242         add     sp, 2
243
244         call    _wfInit
245
246    XStart:
247    Public XStart
248         IACK
249         mov     X=sp, sp
250         sub     X=sp, 6 ; add an interrupt (call)
251         sti     ; ********** Start things going!! *******************************
252
253    DeadLoop label near
254    ; Note that we don't use registers in this code, so we don't need
255    ; to restore regsiters (expecept ds, ss, sp, cs, ip) when we return here.
256         nop
257         cli                     ;********** Count some dead time ***************************
258         inc     word ptr DeadTime
259         jno     JmpDeadLoop
260         inc     word ptr DeadTime[2]
261    JmpDeadLoop:
262         sti                     ;********** Do some more ***********************************
263         jmp     DeadLoop
264
265
266
267    ;**********************************************************************************
268    ;
269    ; XRAMInit --- This code tests and initializes the system RAM
270    ;
271    ;**********************************************************************************
272
273    RAMInt0sError:
274    RAMIntAdrError:
275    RAMIntCntError:
276    RAMIntAsError:
277    RAMIntCsError:
278    RAMInitisError:
279         cli
280         hlt
281
```

```
282  XRAMInit proc near
283         xor     ax, ax          ; Start a Memory location 0:0
284         mov     ds, ax
285         mov     cx, (20 * 4) - 1 ; temporary limit during debug.
286         xor     bx, bx
287         mov     dx, -1
288         mov     si, 0aaaah
289         mov     di, 0cccch
290
291  RAMInitLoop:
292         mov     [bx], ax
293         cmp     [bx], ax
294         jne     RAMInt0sError
295         mov     [bx], bx
296         cmp     [bx], bx
297         jne     RAMIntAdrError
298         mov     [bx], cx
299         cmp     [bx], cx
300         jne     RAMIntCntError
301         mov     [bx], si
302         cmp     [bx], si
303         jne     RAMIntAsError
304         mov     [bx], di
305         cmp     [bx], di
306         jne     RAMIntCsError
307         mov     [bx], dx
308         cmp     [bx], dx
309         jne     RAMinit1sError
310         inc     bx              ; do this last so memory is left with 0ffffh
311         loop    RAMInitLoop     ; inc bx by one, testing both odd and even accesses.
312         mov     ax, _BSS
313         mov     es, ax
314         mov     di, offset _BSSFirstWord
315         mov     cx, offset _BSS:_MemTop
316         sub     cx, di
317         xor     ax, ax
318         rep     stosb
319  ifndef ROMCODE
320         jmp     bp
321  endif
322  XLoadDataSegment:
323  Public XLoadDataSegment
324         mov     ax, SYS_TEXT
325         mov     ds, ax
326         mov     bx, ax
327         mov     ax, offset End_SYS_TEXT
328         mov     si, ax
329         shr     ax, 4
330         add     ax, bx
331         and     si, 0ffh
332         jz      XLDSHaveROMDATASeg
333         inc     ax
334  XLDSHaveROMDATASeg:
335         xor     si, si
336         mov     ds, ax
337
338         mov     ax, CONST
339
```

```
340              mov      es, ax
341              mov      di, offset CONSTFirstWord
342              mov      cx, offset DGROUP:_End_DATA
343              sub      cx, di
344
345              rep movsb
346
347              jmp      bp
348
349   XRAMInit endp
350
351
352   XInterruptInit proc near
353              push     es
354              xor      ax, ax
355              mov      es, ax
356              mov      ax, offset XSchedProc
357              mov      di, 4 * (19) ; interrupt 19
358              stosw
359              mov      ax, SYS_TEXT
360              stosw
361              mov      ax, offset XIllegalInstruction
362              mov      di, 4 * (6) ; interrupt 19
363              stosw
364              mov      ax, SYS_TEXT
365              stosw
366              pop      es
367              ret
368   XInterruptInit endp
369
370   S0Proc proc near
371              nop
372              nop
373              call     SatInit
374              nop
375              nop
376              call     _Icreatep
377              nop
378              nop
379              call     _Gcreatep
380              nop
381              nop
382   S0ProcLoop:
383              mov      ax, 4000; XTIME_EV
384              mov      dx, 0; 2
385              call     XWait
386              jmp      S0ProcLoop
387   S0Proc endp
388
389   Public S0Proc
390
391
392
393
394
395   RRRase equ 0ff00h          ; relocation base.
396
```

```
397  RRReg    equ 01feh  ; relocation register location.
398  RRVal    equ 0d0ffh ;   rel reg val -- esc int, i/o space at 0ff00h offset.
399  UMCS     equ 0a0h   ;            = 0c038h
400  MPCS     equ 0a8h   ;            = 00b0bh
401  MMCS     equ 0a6h   ;            = 011f9h
402  LMCS     equ 0a2h   ;            = 007f8h
403  PCS      equ 0a4h   ;            = 00038h
404  UMCSVal  equ 0c038h ; 256k of ROM
405  MPCSVal  equ 00b0bh ; 16k each MCS for memory mapped I/O
406  MMCSVal  equ 011f9h ; memory mapped I/O starts at 80000h,1 wait state!!
407  LMCSVal  equ 007f8h ; Lower 32k RAM
408  PCSVal   equ 00038h ; Peripheral Chip Select register value (ask ed)
409  Timer0   equ 50h
410  Timer0Init equ 0
411  Timer0Mode equ 56h
412  Timer0ModeVal equ 0C001h     ; enabled for continous op./no int.
413  Timer0CntA equ 52h
414  Timer0CntAVal equ 0341h      ; 9604 baud
415  Timer1   equ 58h
416  Timer1Init equ 0
417  Timer1Mode equ 5eh
418  Timer1ModeVal equ 0C003h     ; enabled for continous alt op./no int
419  Timer1CntA equ 5ah
420  Timer1CntAVal equ 00003h     ; 3 * 500ns
421  Timer1CntB equ 5ch
422  Timer1CntBVal equ 00002h     ; 2 * 500ns
423  Timer2   equ 60h
424  Timer2Init equ 0
425  Timer2Mode equ 66h
426  Timer2ModeVal equ 0E001h     ; enabled for continuous op/with int
427  Timer2CntA equ 62h
428  Timer2CntAVal equ 07c4h      ; 800hz
429  TimerCtrlReg equ 32h
430  DMA0CtrlRegVal equ 34h
431  DMA0CtrlRegVal equ 0001h     ; priority 1 enabled.
432  DMA1CtrlReg equ 36h
433  DMA1CtrlRegVal equ 000fh     ; disabled
434  INT2CtrlReg equ 3ch
435  INT2CtrlRegVal equ 000fh     ; disabled
436  INT1CtrlReg equ 3ah
437  INT1CtrlRegVal equ 000fh     ; disabled -- enabled be comminit.
438  INT3CtrlReg equ 3eh
439  INT3CtrlRegVal equ 0000h     ; priority 0 enabled.
440  INT0CtrlReg equ 38h
441  INT0CtrlRegVal equ 0008h     ; priority 3 enabled.
442  INT0CtrlReg equ 38h
443  INT0CtrlRegVal equ 0000h     ; priority 3 enabled.
444
445  public HWInitConstants
446  HWInitConstants equ this Byte
447  db RRReg
448  dw RRVal
449  db UMCS
450  dw UMCSVal
451  db MPCS
452  dw MPCSVal
453  db MMCS
454  dw MMCSVal
```

```
455  db  LMC5
456  dw  LMC5Val
457  db  FCS
458  dw  FCSVal
459  db  Timer0              ;slc add
460  dw  Timer0Init
461  db  Timer0Mode
462  dw  Timer0Modeval
463  db  Timer0CntA
464  dw  Timer0CntAVal
465  db  Timer1              ;slc add
466  dw  Timer1Init
467  db  Timer1Mode
468  dw  Timer1ModeVal
469  db  Timer1CntA
470  dw  Timer1CntAVal
471  db  Timer1CntB          ;slc add
472  dw  Timer1CntBVal       ;slc add
473  db  Timer2
474  dw  Timer2Init
475  db  Timer2Mode
476  dw  Timer2ModeVal
477  db  Timer2CntA
478  dw  Timer2CntAVal
479  db  TimerCtrlReg
480  dw  TimerCtrlRegVal
481  db  DMA0CtrlReg
482  dw  DMA0CtrlRegVal
483  db  DMA1CtrlReg
484  dw  DMA1CtrlRegVal
485  db  INT2CtrlReg
486  dw  INT2CtrlRegVal
487  db  INT1CtrlReg
488  dw  INT1CtrlRegVal
489  db  INT3CtrlReg
490  dw  INT3CtrlRegVal
491  db  INT0CtrlReg
492  dw  INT0CtrlRegVal
493  db  0ffh
494
495  XHWInit label for
496          cli                         ;********** interrupts off! ***************************
497
498          cld
499          mov     ax, SYS_TEXT
500          mov     ds, ax
501          mov     dx, RRBase HWInitConstants
502          mov     si, offset XCtrlRegInitComplete
503
504  CtrlRegInitLoop:
505          mov     dl, [si]
506          cmp     dl, 0ffh
507          je      XCtrlRegInitComplete
508          inc     si
509          outsw
510          jmp     CtrlRegInitLoop
511
```

```
512         XCtrlRegInitComplete:
513         Public XCtrlRegInitComplete
514                 POLL
515                 or      ax, ax
516                 jz      XHWExit
517                 jACK
518                 jmp     XCtrlRegInitComplete
519   XHWExit:
520                 jmp     _main
521
522         SYS_TEXT ends
523
524         XINITCODE segment byte public 'xinitcode'
525
526         assume cs:XINITCODE
527
528         XStartUp label far
529                 cli
530                 mov     dx, RRBase + UMCS
531                 mov     ax, UMCSVal
532                 out     dx, ax
533                 jmp     XHWInit
534
535         XINITCODE ends
536
537         END XStartUp
538
Wed 10-15-86 12:10:22  07-24-86 15:07:54  BLAST.S
```

.186

```
1   ;****************************************************************
2   ;
3   ; Module blast.s
4   ;
5   ; Purpose:
6   ;       This module defines the end of all data segments.
7   ;
8   ; Procedures:
9   ;
10  ;       NAME XLAST
11  ;
12  ; Public Data:
13  ;
14  ;       This module is an original, unpublished work and is proprietary to
15  ;       NELLCOR INC., and may not be divulged or copied in any form
16  ;       whatsoever without the express written permission of NELLCOR INC.
17  ;       Copyright 1986.
18  ;
19  ; modification history:
20  ;       8-14-86 Creation
21  ;       8-26-86 corrected data segment ordering and class naming problems.
22  ;
23  ;****************************************************************
```

```
29  CodeSegEnd macro SegName
30  SegName segment byte public 'code'
31  End_&SegName equ this byte
32  Public End_&SegName
33  SegName ends
34  endm
35
36
37  DataSegEnd macro SegName,ClassName
38  SegName segment word public '&ClassName'
39  even
40  End_&SegName equ this byte
41  Public End_&SegName
42  SegName ends
43  endm
44
45  MTGroup group ITP_TEXT, TF2_TEXT, TF1_TEXT, ECG_TEXT, SAT_TEXT
46
47  DGroup group LowMemEndSeg, c_common, _BSS, CONST, _DATA
48
49  CodeSegEnd _TEXT
50
51  CodeSegEnd SAT_TEXT
52  CodeSegEnd ECG_TEXT
53  CodeSegEnd BF1_TEXT
54  CodeSegEnd BF2_TEXT
55  CodeSegEnd TF1_TEXT
56  CodeSegEnd TF2_TEXT
57  CodeSegEnd ITP_TEXT
58  CodeSegEnd MI_TEXT
59  CodeSegEnd SYS_TEXT
60
61  DataSegEnd CONST,const
62  DataSegEnd _BSS,bss
63  DataSegEnd c_common,bss
64  DataSegEnd _DATA,data
65
66  LowMemEndSeg Segment byte public 'lastdata'
67  MemTop equ this byte
68  Public _MemTop
69  LowMemEndSeg ends
70
71  End
```

```
Wed 09-24-86 15:09:58  DXALLOC.C        xALLOC
    10-15-86 12:10:22

1  /******************************************************************
 2   *
 3   *  MPO Ver 1.0
 4   *
 5   *  module: balloc.c
 6   *
 7   *  modification history :   reason(s)
 8   *        date       by
 9   *      08/14/86    jab    creation
10   *      08/19/86    jab    Removed indirection warnings.
11   *      08/26/86    jab    Fixed return without xUnLock.
12   *
13   *
14   *  This module is an original, unpublished work and is proprietary to
15   *  NELLCOR INC., and may not be divulged or copied in any form
16   *  whatsoever without the express written permission of NELLCOR INC.
17   *
18   *  purpose : Allocate a segment of memory within the data segment.
19   *
20   *  data descriptions : Argument is length of desired segment in bytes
21   *                      Returns near address of segment.
22   *
23   *  function descriptions :
24   *
25   ******************************************************************/
26
27  /* DXALLOC.C - Memory Allocator *****************************/
28  /* 08/19/86 */
29
30  /* xALLOC allocates a memory block in the data segment.
31     It returns a near pointer to the block in ax. If AX=0 upon
32     return, an error is indicated.
33     xFree frees a block for reallocation. If adjacent to the heap
34     it is merged with the heap. Otherwise it is linked to the free
35     list. AX=0 indicates a successful operation.
36  */
37  #include  "hserror.h"
38                                    /* public variables */
39  char      **xMemBeg = 0;          /* bottom of ram */
40  char      **xMemTop = 0;          /* top of ram */
41  char      **xHeapTop = 0;         /* top of heap */
42  char      **xHeapFree = 0;        /* root pointer */
43  void near  xLOCK ();
44  void near  xUNLOCK ();
45
46  /* xALLOC -------------------------------------------------------*/
47
48  char * far xALLOC (nBytes)
49    unsigned      nBytes;
50  {
51    unsigned      LGTH, RES, ENDf, FOUND;
52    char          **pCp;
53    char          **pCpLast;         /* ptrs to ptrs */
54
```

```
 55  ENDf = FOUND = 0;
 56  if (nBytes & 01)                                /* if length odd */
 57       nBytes++;                                  /*    then make it even */
 58  xLOCK();                                        /* lock out task switches */
 59  if (xHeapFree == 0)          /* if no freed space exists */
 60       ENDf = 1;               /*    set end flag */
 61  else
 62  {                            /* if freed space exists */
 63       pCp = (char **)xHeapFree;                  /* look for freed space */
 64       pCpLast = &xHeapFree;                      /* 'oot pointer */
 65       while (1)                                  /* loop through list */
 66       {    if (*pCp == 0)                        /* if end of list */
 67                 {ENDf = 1;
 68                  break;
 69                 }
 70            if (*(*(pCp+1) )>= (char *)nBytes)    /* if segment long enough */
 71                 {FOUND = 1;                      /* use if */
 72                  break;
 73                 }
 74            pCpLast = pCp;                        /* advance in list */
 75            pCp = (char *)*pCp;
 76       }
 77  }
 78  if (ENDf)                    /* allocate new space */
 79  {    if (xMemTop - xHeapTop < nBytes + 4)       /* can't allocate */
 80            goto EXIT;
 81       (pCp = 0;
 82       (char *)pCp = (char *)xHeapTop + 4;        /* points to alloc'd space */
 83       *(pCp-2) = (char *)pCp;                    /* write address to space */
 84       *(pCp-1) = (char *)nBytes;                 /* write length to space */
 85       xHeapTop = xHeapTop + nBytes + 4;          /* adjust heap top */
 86  }
 87  if (FOUND)                   /* allocate freed segment */
 88  {    *pCpLast = *pCp;                           /* unlink */
 89       *pCp = (char *)pCp;                        /* write address to space */
 90       *(pCp+1) = (char *)nBytes;                 /* write length to space */
 91       pCp = pCp + 2;                             /* points to alloc'd space */
 92  }
 93  EXIT:
 94  xUNLOCK();                                      /* allow task switches */
 95  return ((char *)pCp);
 96  }
 97
 98  /* xFREE ----------------            /* Returns freed block to heap if at edge of heap */
 99                                       /* Otherwise links freed block to free list ready */
100                                       /* for reallocation */
101  unsigned far xFREE (pFree)
102       unsigned      *pFree;                      /* pointer to freed segment */
103  {
104  unsigned    LGTH;
105
106  if (*(pFree-2) != (unsigned)pFree)   /* check for validity */
107       return (0 Free);
108  LGTH = *(pFree-1);                              /* pick out length */
109  xLOCK();                                        /* lock out task switches */
110  if ((char *)pFree+LGTH == xHeapTop)             /* is block at edge of heap */
```

```
113       xHeapTop = xHeapFree - LGTH - 4;
114     else {                                    /* otherwise link to free list */
115       *(pFree+1) = pFree - 2;                 /* to top of block */
116       *(pFree+1) = LGTH;                      /* write length to block */
117       *pFree = (unsigned)xHeapFree;           /* insert block into list */
118       xHeapFree = pFree;
119     }
120     UNLOCK ();                                /* allow task switches. */
121     return (0);
122   }

Wed 07-24-86 15:10:00   DXERROR.H
Wed 10-15-86 12:10:27

1   /* DXERROR.H : Error definitions for MF0 */
  2   /* 08/14/86 */
  3
  4   #define E_Alloc        1
  5   #define E_WfName       1
  6   #define E_ACB_Name     1
  7   #define E_Free         1

Wed 10-13-86 13:33:10   DISPINIT.S
Wed 10-15-86 12:10:22

1         186
  2   ; ROMCODE equ 1 ; take away comment to make ROMMABLE Code!
  3
  4   ;*******************************************************************
  5   ;
  6   ; Module dispinit.s
  7   ;
  8   ; Purpose:
  9   ;     This module does the initialization for the display processor.
 10   ;     Name dispinit
 11   ;
 12   ; Procedures:
 13   ;     Public    main, main
 14   ;     Public    XInterruptInit
 15   ;     Public    XRAMInit
 16   ;     Public    XHWInit
 17   ;     Public    XStartUp
 18   ;
 19   ; Public Data:
 20   ;     Public  DeadTime
 21   ;
 22   ; This module is an original, unpublished work and is proprietary to
 23   ; NELLCOR INC., and may not be divulged or copied in any form
 24   ; whatsoever without the express written permission of NELLCOR INC.
 25   ;     Copyright 1986.
 26   ;
 27   ;*******************************************************************
```

```
32    include xref.i
33    include xevent.i
34    include display\dhwdef.i
35
36    CONST segment word public 'CONST'
37    CONSTFirstWord equ this word
38    org 0
39    CONST ends
40
41    DATA segment word public 'DATA'
42    DATAFirstWord equ this word
43    org 0
44    DATA ends
45
46
47    C_COMMON segment word public 'BSS'
48    C_COMMONFirstWord equ this word
49    org 0
50    C_COMMON ends
51
52    BSS segment word public 'BSS'
53    BSSFirstWord equ this word
54    org 0
55    BSS ends
56
57    LowMemEndSeg Segment byte public 'lastdata'
58    ; Nothing can be in this segment except MemTop!!!
59    extrn MemTop:byte
60    LowMemEndSeg ends
61
62    Far_BSS segment word public 'Far_BSS'
63    Far_DataFirstWord equ this word
64    Far_BSS ends
65
66    DFont segment word public 'font'
67    DFont ends
68
69    _TEXT segment byte public 'code'
70    _TEXTFirstWord equ this word
71    org 0
72    Version equ this byte
73    Public Version
74    db "NELLCOR N1000 Ver. D-1.0 Oct. 1 1986 "
75    Copyright equ this byte
76    Public Copyright
77    db "This code is an original, unpublished work and is proprietary to "
78    db "NELLCOR INC., and may not be divulged or copied in any form "
79    db "whatsoever without the express written permission of NELLCOR INC. "
80    db "Copyright 1986."
81
82    _TEXT ends
83
84    ABS_TEXT segment byte public 'code'
85    ABS_TEXT ends
86
87    SAT_TEXT segment byte public 'code'
88    SAT_TEXT ends
89
```

```
 90  GAS_TEXT   segment byte public 'code'
 91  GAS_TEXT   ends
 92
 93  ECG_TEXT   segment byte public 'code'
 94  ECG_TEXT   ends
 95
 96  BP1_TEXT   segment byte public 'code'
 97  BP1_TEXT   ends
 98
 99  BP2_TEXT   segment byte public 'code'
100  BP2_TEXT   ends
101
102  TP1_TEXT   segment byte public 'code'
103  TP1_TEXT   ends
104
105  TF2_TEXT   segment byte public 'code'
106  TF2_TEXT   ends
107
108  SYS_TEXT   segment byte public 'code'
109  SYS_TEXT   ends
110
111  XINITCODE  segment word 'xinitcode'
112  XINITCODEFirstWord dw ?
113         org 0
114  XINITCODE  ends
115
116
117  SYS_TEXT   segment BYTE PUBLIC 'code'
118   extrn  XCreateP:far, XPost:far
119   extrn  XWait:far, XSchedProc:far, XSchedInit:near
120   extrn  _DispCreateP:near
121  ;extrn  XReportMemErr:far
122   extrn  XSetTime:near, XGetTime:near
123   extrn  End_SYS_TEXT:word
124   extrn  _mProcKnob:near
125   extrn  _mCreateP:far
126  SYS_TEXT   ends
127
128  CONST  segment word public 'CONST'
129  ; Hex2ROM interface
130  dd  CONSTFirstWord       ; address of bottom of dgroup
131  dd  _BSSFirstWord        ; address of bottom of _BSS
132  dd  _MemTop              ; end of memory
133  dd  _Far_DataFirstWord   ; address of bottom of ROMed stuff
134  dd  _End_SYS_TEXT        ; address of top of ROMed stuff
135  dd  _XINITCODEFirstWord  ; address of bottom of reset code
136  ABS_TEXT  segval dw ABS_TEXT
137  Public ABS_TEXT_segval
138  SAT_TEXT  segval dw SAT_TEXT
139  Public SAT_TEXT_segval
140  GAS_TEXT  segval dw GAS_TEXT
141  Public GAS_TEXT_segval
142  ECG_TEXT  segval dw ECG_TEXT
143  Public ECG_TEXT_segval
144  BP1_TEXT  segval dw BP1_TEXT
145  Public BP1_TEXT_segval
146  BP1_TEXT  segval dw BP1_TEXT
```

```
147         BP2_TEXT segval dw BP2_TEXT
148         Public BP2_TEXT_segval
149         TP1_TEXT segval dw TP1_TEXT
150         Public TP1_TEXT_segval
151         TP2_TEXT segval dw TP2_TEXT
152         Public TP2_TEXT_segval
153         SYS_TEXT segval dw SYS_TEXT
154         Public SYS_TEXT_segval
155         XINITCODE_segval dw XINITCODE
156         Public XINITCODE_segval
157         CONST ends
158
159         _BSS segment word public 'BSS'
160
161         extrn _End_BSS:word
162         extrn _XInterruptProc:word
163         extrn _x_sp:word
164
165         org 0
166         acrtused dw 0
167         public _acrtused
168
169
170
171         _BSS ends
172
173
174         _DATA segment word public 'data'
175
176         extrn _xMemTop:word, _xMemBeg:word, _xHeapTop:word
177         extrn _End__DATA:word
178
179         even
180         XInterruptRate dw Hz400
181         Public XInterruptRate
182
183         even
184         sysstackbeg dw 81 dup (?)
185         sysstackend dw ?
186
187         S0stackbeg dw 81 dup (?)
188         S0stackend dw ?
189
190         DeadTime dd ?
191
192         _DATA ends
193
194
195         MTCode segment byte public 'code'
196         MTCode ends
197
198         DGROUP Group _DATA, CONST, _BSS, C_COMMON
199
200         SYS_TEXT segment byte public 'code'
201
202         ASSUME CS:SYS_TEXT, DS:DGROUP, SS:DGROUP, ES:DGROUP
203
204         main label far
```

```
205         _main label far
206
207                 cli             ;********** interrupts off! ************************
208                 DISABLEVIDEO
209                 mov     bp, offset XRAMIRet
210                 jmp     XRAMInit
211     XRAMIRet:
212     Public XRAMIRet
213
214                 mov     ax, DGROUP
215                 mov     ds, ax
216                 mov     es, ax
217                 mov     ss, ax
218                 mov     sp, offset DGROUP:sysstackend
219                 and     sp, 0fffeh      ; insure even stack
220
221                 call    XInterruptInit
222                 call    XSchedInit
223
224                 mov     ax, offset DGroup:_MemTop
225                 mov     _xMemTop, ax
226                 mov     ax, offset DGroup:_End_BSS
227                 mov     _xMemBeg, ax
228                 mov     _xHeapTop, ax
229
230                 mov     XInterruptProc, offset _mProcKnob
231
232                 call    _mCreateP
233                 call    _DispCreatep
234
235     XStart:
236     Public XStart
237                 IACK
238                 mov     x_sp, sp
239                 sub     x_sp, 6 ; add an interrupt (call)
240                 sti             ;********** Start things going!! *****************
241
242     DeadLoop label near
243                 inc     word ptr DeadTime
244                 jne     DeadLoop
245                 inc     word ptr DeadTime[2]
246                 jmp     DeadLoop 251     ;***************************************************************
252     ;;  XRAMInit --- This code tests and initializes the system RAM
253     ;***************************************************************
254
255
256     RAMInt0sError:
257     RAMIntAdrError:
258     RAMIntCntError:
259     RAMIntAsError:
260     RAMIntCsError:
```

```
262  RAMinit1sError:
263         cli
264         hlt
265
266  XRAMinit proc near
267         xor     ax, ax
268         mov     ds, ax
269         mov     cx, (20 * 4) - 1
270         xor     bx, bx
271         mov     dx, -1
272         mov     si, @aaaah
273         mov     di, @cccch              ; temporary limit during debug.
274  RAMinitLoop:
275         mov     [bx], ax
276         cmp     [bx], ax
277         jne     RAMint@sError
278         mov     [bx], bx
279         cmp     [bx], bx
280         jne     RAMintAdrError
281         mov     [bx], cx
282         cmp     [bx], cx
283         jne     RAMintCntError
284         mov     [bx], si
285         cmp     [bx], si
286         jne     RAMintAsError
287         mov     [bx], di
288         cmp     [bx], di
289         jne     RAMintCsError
290         mov     [bx], dx
291         cmp     [bx], dx
292         jne     RAMinit1sError
293         inc     bx              ; inc bx by one, testing both odd and even acesses.
294         loop    RAMinitLoop     ; do this last so memory is left with 0ffffh
295         xor     ax, ax
296         mov     bx, 40000h
297         mov     es, bx
298         mov     cx, 8000h
299         rep     stosw
300         mov     bx, 50000h
301         mov     es, bx
302         mov     cx, 8000h
303         rep     stosw
304         mov     bx, 60000h
305         mov     es, bx
306         mov     cx, 8000h
307         rep     stosw
308         mov     bx, 70000h
309         mov     es, bx
310         mov     cx, 8000h
311         rep     stosw
312         mov     bx, BSS
313         mov     es, bx
314         mov     di, offset  BSSFirstWord
315         mov     cx, offset _End__BSS ; note: not DGROUP offset
316         sub     cx, di
317         rep     stosb
318  ifndef ROMCODE
319         jmp     bp
```

```
320         endif
321         XLoadDataSegment:
322         Public XLoadDataSegment
323                 mov     ax, SYS_TEXT
324                 mov     ds, ax
325                 mov     bx, ax
326                 mov     ax, offset _End_SYS_TEXT
327                 mov     si, ax
328                 mov     ax, 4
329                 shr     ax, bx
330                 add     si, 0fh
331                 and     si, 0fh
332                 jz      XLDSHaveROMDATASeg
333                 inc     ax
334         XLDSHaveROMDATASeg:
335                 mov     ds, ax
336
337                 mov     ax, CONST
338                 mov     es, ax
339                 mov     di, offset CONSTFirstWord
340                 mov     cx, offset DGROUP:_End_DATA
341                 sub     cx, di
342
343                 rep movsb
344         XRAMInit endp  jmp    bp
345
346
347         extrn  DVertSyncInt:far
348         extrn  DVertSyncInt:far
349         extrn  XIllegalInstruction:far
350         extrn  XBound:far
351
352         XInterruptVectors equ this word  ; int#  Name
353         dw  offset XIllegalInstruction   ; 0 --  div 0
354         dw  offset XIllegalInstruction   ; 1 --  Single Step
355         dw  offset XIllegalInstruction   ; 2 --  NMI
356         dw  offset XIllegalInstruction   ; 3 --  break point
357         dw  offset XIllegalInstruction   ; 4 --  Overflow
358         dw  offset XBound                ; 5 --  Array Bounds
359         dw  offset XIllegalInstruction   ; 6 --  Unsued Opcode
360         dw  offset XIllegalInstruction   ; 7 --  Esc Opcode
361         dw  offset XIllegalInstruction   ; 8 --  Timer 0
362         dw  offset XIllegalInstruction   ; 9 --  Reserved
363         dw  offset XIllegalInstruction   ; 10 -- DMA 0
364         dw  offset XIllegalInstruction   ; 11 -- DMA 1
365         dw  offset DVertWindowInt        ; 12 -- INT0
366         dw  offset DVertSyncInt          ; 13 -- INT1
367         dw  offset XIllegalInstruction   ; 14 -- INT2
368         dw  offset XIllegalInstruction   ; 15 -- INT3
369         dw  offset XIllegalInstruction   ; 16 -- Unused
370         dw  offset XIllegalInstruction   ; 17 -- Unused
371         dw  offset XIllegalInstruction   ; 18 -- Timer 1
372         dw  offset XSchedProc            ; 19 -- Timer 2
```

```
377  XInterruptInit proc near
378         push    ds
379         push    es
380         xor     ax, ax
381         mov     es, ax
382         mov     ax, Sys_Text
383         mov     ds, ax
384         mov     si, offset XInterruptVectors
385         xor     di, di
386         mov     cx, 20          ; fill the first 20 location
387  XIILoop:
388         lodsw
389         stosw
390         mov     ax, SYS_TEXT
391         stosw
392         loop    XIILoop
393         pop     es
394         pop     ds
395         ret
396  XInterruptInit endp
397
398  S0Proc proc near
399         mov     ax, XTIME_EV
400         mov     dx, 15
401         call    XWait
402         jmp     S0Proc
403  S0Proc endp
404
405  Public S0Proc
406
407
408
409  RRBase      equ 0ff00h      ; relocation base.
410  RRReg       equ 0feh        ; relocation register location.
411  RRVal       equ 0a0ffh      ; rel reg val -- esc int, i/o space at 0ff00h offset.
412  UMCS        equ 0a0h        ; = c038h
413  MFCS        equ 0a8h        ; = c0b8h
414  MMCS        equ 0a6h        ; = 01f8h
415  PCS         equ 0a4h        ; = 0038h
416  UMCSVal     equ 0c038h      ; 256k of ROM
417  MFCSVal     equ 0c0b8h      ; Lower 512k RAM
418  MMCSVal     equ 01f8h
419  PCSVal      equ 0038h       ; Peripheral Chip Select register value (ask ed)
420  Timer0Mode      equ 56h
421  Timer0Modeval   equ 0c001h  ; enabled for continous op./no int
422  Timer0CntA      equ 52h
423  Timer0CntAVal   equ 0341h   ; 9604 baud
424  Timer1Mode      equ 5eh
425  Timer1Modeval   equ 0c001h  ; enabled for continous op./no int
426  Timer1CntA      equ 5ah
427  Timer1CntAVal   equ 0004h   ; 0.5Mhz
428  Timer2Mode      equ 66h
429  Timer2Modeval   equ 0E001h  ; enabled for continous op/with int
430  Timer2CntA      equ 62h
431  Timer2CntAVal   equ 1388h   ; 400hz
432  TimerCtrlReg    equ 32h
433  TimerCtrlRegVal equ 0001h   ; priority 1 enabled.
434  DMA0CtrlReg     equ 34h
```

```
435         DMA0CtrlRegVal equ 000fh                    ; disabled.
436         DMA1CtrlRegVal equ 36h
437         INT0CtrlRegVal equ 38h                      ; disabled.
438         INT0CtrlRegVal equ 3ah
439         INT0CtrlRegVal equ 0000h
440         INT1CtrlRegVal equ 000fh                    ; priority 0 enabled.
441         INT1CtrlRegVal equ 3ch
442         INT2CtrlRegVal equ 000fh                    ; disabled.
443         INT2CtrlRegVal equ 3eh
444         INT3CtrlRegVal equ 000fh                    ; disabled.
445         INT3CtrlRegVal equ 3eh
446         INT3CtrlRegVal equ 000fh                    ; disabled.
447
448         public HWInitConstants
449         HWInitConstants equ this byte
450         db RRReg
451         dw RRVal
452         db UMCS
453         dw UMCSVal
454         db MPCS
455         dw MPCSVal
456         db MMCS
457         dw MMCSVal
458         db PCS
459         dw PCSVal
460         dw Timer0Mode
461         db Timer0ModeVal
462         dw Timer0CntA
463         db Timer0CntAVal
464         dw Timer1Mode
465         db Timer1ModeVal
466         dw Timer1CntA
467         db Timer1CntAVal
468         dw Timer2Mode
469         db Timer2ModeVal
470         dw Timer2CntA
471         db Timer2CntAVal
472         dw TimerCtrlReg
473         db TimerCtrlRegVal
474         dw DMA0CtrlReg
475         db DMA0CtrlRegVal
476         dw DMA1CtrlReg
477         db DMA1CtrlRegVal
478         dw INT0CtrlReg
479         db INT0CtrlRegVal
480         dw INT1CtrlReg
481         db INT1CtrlRegVal
482         dw INT2CtrlReg
483         db INT2CtrlRegVal
484         dw INT3CtrlReg
485         db INT3CtrlRegVal
486         db 0ffh
487
488         XHWInit label far
489                 cli
490                 cld
491                 mov     ax, SYS_TEXT
492
```

```
493                 mov      ds, ax
494                 mov      dx, RRBase
495                 mov      si, offset HWInitConstants
496         CtrlRegInitLoop:
497                 mov      dl, [si]
498                 cmp      dl, 0ffh
499                 je       XCtrlRegInitComplete
500                 inc      si
501                 outsw
502                 jmp      CtrlRegInitLoop
503
504         XCtrlRegInitComplete:
505         Public XCtrlRegInitComplete
506                 IPOLL
507                 or       ax, ax
508                 jz       XHWExit
509                 JACK
510                 jmp      XCtrlRegInitComplete
511
512         XHWExit:
513                 jmp      _main
514
515         SYS_TEXT ends
516
517         STACK segment stack 'stack'
518         ; dummy stack segment
519         STACK ends
520
521         XINITCODE segment word public 'xinitcode'
522
523         assume cs:XINITCODE
524
525         XStartUp label far
526                 cli
527                 mov      dx, RRBase + UMCS
528                 mov      ax, UMCSVal
529                 out      dx, ax
530                 jmp      XHWinit
531
532         XINITCODE ends
533
534         END XStartUp
535

Wed 09-21-86 09:55:58    XCLOCK.H                    DefineTimers
    10-15-86 12:10:22

1      /****************************************************************
 2       *
 3       * MF0 Ver 0.0
 4       *
 5       * module: XClock.h
 6       *
 7       * modification history :
 8       *       date         by      reason(s)
 9       *
10       *    5-5-86         epr       creation
11       *
```

```
12  *   9-18-86  kht       added date/time struct
13  *
14  *  This module is an original, unpublished work and is proprietary to
15  *  NELLCOR INC., and may not be divulged or copied in any form
16  *  whatsoever without the express written permission of NELLCOR INC.
17  *
18  *  Purpose :
19  *       C version of TIMER definitions
20  *
21  *  data descriptions :
22  *
23  *  function descriptions :
24  *
25  ***********************************************************************/
26
27  typedef struct ATIMER {
28          int timeremaining;
29          int defaulttime;
30          int (far *function) ();
31  } TIMER;
32
33  typedef struct {
34  int n;
35  struct ATIMER timers[1];
36  } TIMERS;
37
38  #define DefineTimers(Tname, n) \
39  struct { \
40  int size; \
41  struct ATIMER timers[n] \
42  } Tname = { n, {
43
44  #define EndTimers(it, rt, ft, Tname) \
45          {it, rt, ft} } \
46          } ;
47
48  #define DefineTimer(it, rt, ft) \
49          {it, rt, ft},
50
51  void far XLinkTimer();
52  void far XSetTimer();
53  void far XSetTimeDelay();
54  void far XTurnOffTIMER();
55  void far XTurnOnTIMER();
56  void far XTurnOFFTIMERS();
57  void far XTurnONTIMERS();
58
59  typedef struct time {
60          unsigned year;      /* starts at 1900 for 256 years */
61          unsigned month:8;
62          unsigned day:8;
63          unsigned hour:8;    /* 24 hours clock */
64          unsigned min:8;
65          unsigned sec:8;
66          unsigned csum:8;
67  } CURRENTTIME;
68
69
```

```
Wed 10-15-86 12:10:22                                    reason

1          .186
 2    ;****************************************************************
 3    ;
 4    ; MFO Ver 0.0
 5    ;
 6    ; Module: XClock.inc
 7    ;
 8    ; modification history :  reason(s)
 9    ;        date      by           Creation
10    ;       5-5-86     epr
11    ;
12    ;       This module is an original, unpublished work and is proprietary to
13    ;       NELLCOR INC., and may not be divulged or copied in any form
14    ;       whatsoever without the express written permission of NELLCOR INC.
15    ;       Copyright 1986.
16    ;
17    ; Purpose:
18    ;       XClock definitions.
19    ;
20    ; Procedures:
21    ;
22    ; Public Data:
23    ;
24    ;****************************************************************
25
26    NullFunction equ 0ffffh
27    ; The elements of the TIMER structure have the following meanings:
28    ;
29    ;       timeremaining is 15 bit timer. If its sign bit is set it is
30    ;          considered to be off.
31    ;
32    ;       resettime is value to reset the timer to when time remaining
33    ;          expires.
34    ;
35    ;       function is a long pointer to a function to be called when
36    ;          time remaining expires.
37
38    XTIMER struc
39    timeremaining dw -1
40    resettime dw -1
41    function dd NullFunction
42    XTIMER ends
43
44    XTIMERS struc
45    Tssize dw 0
46    oTimers dw 0
47    XTIMERS ends
48
49    XDefineTimers macro Tname, n
50    Tname dw n
51    endm
```

```
54      XDefineTimer macro tname, it, rt, func
55      tname dw it
56      dw rt
57      dd func
58      endm
59
60
61

Wed 10-15-86 12:10:22                                    reason

1      .186
 2  ;************************************************************
 3  ;*
 4  ;*  MFO Ver 0.0
 5  ;*
 6  ;*  Module: Xclock.s
 7  ;*       Name XCLOCK
 8  ;*
 9  ;*  modification history :
10  ;*       date        by      reason(s)
11  ;*
12  ;*  5-5-86          epr     creation
13  ;*  5 Aug 86        slc     add XTimerInit() to init CTloc
14  ;*
15  ;*
16  ;*  This module is an original, unpublished work and is proprietary to
17  ;*  NELLCOR INC., and may not be divulged or copied in any form
18  ;*  whatsoever without the express written permission of NELLCOR INC.
19  ;*       Copyright 1986.
20  ;*
21  ;*  Purpose:
22  ;*       To provide system clock functions
23  ;*
24  ;*  Procedures:
25  ;*       Public  XClock
26  ;*       Public  XLinkTimer,   XLinkTimer
27  ;*       Public  XSetTimer,    XSetTimeDelay
28  ;*       Public  -XTurnOffTIMER
29  ;*       Public  -XTurnOnTIMER
30  ;*       Public  -XTurnOFFTIMERS
31  ;*       Public  -XTurnONTIMERS
32  ;*       Public  XTimerInit      ;to Xsched.s
33  ;*
34  ;*  Public Data:
35  ;*       Public  XSysTime
36  ;*       Public  XTinterval
37  ;*       Public  CTLoc
38  ;*       Public  XClockTimers
39  ;*       Public  XClockRate
40  ;*
41  ;************************************************************
42
43
44      include XDef.i
45      include Xevent.i
46      include XClock.i
47
```

```
48   SYS_TEXT segment byte public 'code'
49   extrn XenQueProc:near
50   SYS_TEXT ends
51
52   CONST segment word public 'CONST'
53   CONST ends
54
55   _DATA segment word public 'DATA'
56
57   extrn XServerProcs:word
58   extrn MTProcs: word
59   extrn XServerQue:word
60   extrn MTQue: word
61   extrn XInterruptRate:word ; 800 on A.P and 400 on D.P
62
63   even
64
65   XTinterval dw XTimerDelay
66
67   CTLoc dw offset DGROUP:XClockTimers
68
69   _DATA ends
70
71   _BSS segment word public 'BSS'
72
73   even
74   XClockRate dw ?
75   XSysTime dd ? ; will be zeroed by XRAMInit
76
77   ; TIMERS far *XClockTimers[MaxTimers];
78   MaxTimers equ 32
79   XClockTimers dd MaxTimers dup (?)
80   ECT equ XClockTimers + MaxTimers*4
81
82   _BSS ends
83
84   DGROUP Group CONST, _DATA, _BSS
85
86   ASSUME CS:SYS_TEXT, DS:DGROUP, SS:DGROUP, ES:DGROUP
87
88   SYS_TEXT segment byte public 'Code'
89
90   ;*********************************************************
91   ;*********************************************************
92   ;
93   ; Function:     XClock -- system clock function.
94   ;
95   ;       This function keeps time for the schedular on by tick
96   ;       basis and time for other processes on a tick * tickfactor
97   ;       rate (50hz).
98   ;
99   ;*********************************************************
100  ;*********************************************************
```

```
105         XClockEarlyRet:
106             stc                                      ; indicate no tick
107             ret
108
109         XClock  proc near
110                 dec     XClockRate
111                 jg      XClockEarlyRet
112                 inc     word ptr XSysTime
113                 adc     word ptr XSysTime[2], 0
114                 mov     ax, XInterruptRate
115                 mov     XClockRate, ax
116                 mov     di, offset DGROUP:XServerProcs
117                 xor     bx, bx
118                 mov     cx, XProcTabSiz
119
120         XCSFLoop:
121                 mov     ax, [di][bx].delay
122                 or      ax, ax
123                 jz      XCNextSp
124                 dec     ax
125                 mov     [di][bx].delay, ax
126                 jnz     XCNextSP
127                 mov     ax, XTIME_EV
128                 mov     si, offset DGROUP:XServerQue
129                 call    XenQueProc
130
131         XCNextSP:
132                 add     bx, XPRWSize
133                 loop    XCSFLoop
134
135                 mov     di, offset DGROUP:MTProcs
136                 xor     bx, bx
137                 mov     cx, XProcTabSiz
138
139         XCMTLoop:
140                 mov     ax, [di][bx].delay
141                 or      ax, ax
142                 jz      XCNextMT
143                 dec     ax
144                 mov     [di][bx].delay, ax
145                 jnz     XCNextMT
146                 mov     ax, XTIME_EV
147                 mov     si, offset DGROUP:MTQue
148                 mov     [di][bx].wait, 8000h ; Indicate process is in run que.
149                 inc     [di][bx].dummy
150                 call    XenQueProc
151
152         XCNextMT:
153                 add     bx, XPRWSize
154                 loop    XCMTLoop
155
156                 dec     XTinterval
157                 jz      XCDoProcTimers
158
159         XCExit: clc                                    ; indicate tick
160                 ret
```

```
163     XCDoProcTimers:
164     Public XCDoProcTimers
165             mov     XTInterval, XTimerDelay
166             mov     si, offset DGROUP:XClockTimers - 4  ; back load it.
167
168     XCPTLoop:
169             add     si, 4           ; go to next TIMERS, or First!
170             cmp     si, CTLoc
171             jae     XCExit
172             les     bx, [si]
173             mov     cx, es:[bx]     ; get timer count!
174             jcxz    XCPTLoop
175             add     bx, 2           ; es:bx points to first timer
176
177     XCProcTsLoop:
178             mov     ax, es:[bx].timeremaining   ; get time remaining.
179             dec     ax
180             js      XCNextTimer                 ; timer is off get next timer.
181             jz      TimerExipired
182             mov     es:[bx], ax
183
184     XCNextTimer:
185             add     bx, 8           ; es:bx points to next timer.
186             loop    XCProcTsLoop    ; do next timer!
187             jmp     XCPTLoop
188
189     TimerExipired:
190             mov     ax, es:[bx].resettime       ; reinit timeremaining.
191             mov     es:[bx].timeremaining, ax
192             cmp     word ptr es:[bx].function, 0
193             je      XCNextTimer
194
195             push    bx              ; save used register.
196             push    cx
197             push    si
198             push    ds
199             push    es
200             mov     ax, es
201             mov     ds, ax
202             call    es:[bx].function
203             pop     es
204             pop     ds
205             pop     si
206             pop     cx
207             pop     bx
208
209             jmp     XCNextTimer
210
211     XClock  endp
212
213     ;****************************************************************
214     ;
215     ; Function:     XLinkTimer  -- system clock link function.
216     ;               _XLinkTimer -- system clock link function.
217     ;
218     ;       This function links a processes timers to the clock.
```

```
221  ;**************************************************************
222  ; Entry: dx:ax = pointer to timers, put in list ECT
223  ;
224  ;       ptimers equ 4  ; offset of timers in data segment.
225
226  ;**************************************************************
227
228
229  _XLinkTimer proc near
230          push    bp
231          mov     bp, sp
232
233          mov     dx, ds
234          mov     ax, [bp + ptimers]
235          call    XLinkTimer
236
237          pop     bp
238          ret
239  _XLinkTimer endp
240
241
242  XLinkTimer proc near
243          push    di
244          or      ax, ax
245          jz      LTExit
246          mov     di, CTLoc
247          cmp     di, offset DGROUP:ECT   ;end of clock table ?
248          jae     LTExit
249          add     di, 4
250
251          mov     [di - 4], ax
252          mov     [di - 2], dx
253          mov     CTLoc, di
254
255  LTExit: pop     di
256          ret
257  XLinkTimer endp
258
259
260  ;**************************************************************
261  ;
262  ; XSetTimer, XSetOffTIMER, XTurnOnTIMER, XTurnOFFTIMERS, XTurnONTIMERS
263  ; XSetTimeDelay
264  ;
265  ;**************************************************************
266
267
268  ; Parameters:
269  ;       tp equ 6        ; pointer to timer.
270  ;       it equ 8        ; integer time remaining
271  ;       tr equ 10       ; integer reset time.
272  ;       func equ 12     ; dword function pointer.
273
274
275  _XSetTimer proc far
276          push    bp
277          mov     bp, sp
278
```

```
279         mov     bx, [bp + tp]
280         mov     ax, [bp + it]
281         mov     [bx].timeremaining, ax
282         mov     ax, [bp + tr]
283         mov     [bx].resettime, ax
284         mov     ax, [bp + func]
285         mov     dx, [bp + func + 2]
286         mov     word ptr [bx].function, ax
287         mov     word ptr [bx + 2].function, dx
288         pop     bp
289         ret
290 _XSetTimer endp
291
292 _XSetTimeDelay proc far
293         push    bp
294         mov     bp, sp
295         mov     bx, [bp + tp]
296         mov     ax, [bp + it]
297         mov     [bx].timeremaining, ax
298         mov     ax, [bp + tr]
299         mov     [bx].resettime, ax
300         pop     bp
301         ret
302 _XSetTimeDelay endp
303
304 ;***********************************************************
305 ; Parameters:
306         tp equ 6                ; pointer to timer.
307 ;
308 ;***********************************************************
309 _XTurnOffTIMER proc far
310         push    bp
311         mov     bp, sp
312         cli     ;*********************************************
313         mov     bx, [bp + tp]
314         mov     ax, [bx].timeremaining
315         neg     ax
316         jns     TOffTExit
317         mov     [bx].timeremaining, ax
318 TOffTExit:
319         sti
320         pop     bp
321         ret     ;*********************************************
322 _XTurnOffTIMER endp
323
324 ;***********************************************************
325 ; Parameters:
326         tp equ 6                ; pointer to timer.
327 ;
328 ;***********************************************************
329 _XTurnOnTIMER proc far
330         push    bp
331         mov     bp, sp
332         cli     ;*********************************************
333         mov     bx, [bp + tp]
334         mov     ax, [bx].timeremaining
335         neg     ax
336         js      TOnTExit
```

```
337                 mov     [bx].timeremaining, ax
338 TOnTExit:
339         sti
340         pop     bp
341         ret
342 _XTurnOnTIMER endp
343
344 ; Parameters:
345         Tp equ 6        ; pointer to timer.
346 ;
347 ;
348 _XTurnOFFTIMERS proc far
349         push    bp
350         mov     bp, sp
351         mov     bx, [bp + tp]
352         mov     cx, [bx]
353         add     bx, 2
354 TOFFLoop:
355         mov     ax, [bx].timeremaining
356         neg     ax
357         jns     TOFFTLpEnd
358         mov     [bx].timeremaining, ax
359 TOFFTLpEnd:
360         add     bx, 8
361         loop    TOFFLoop
362         pop     bp
363         ret
364 _XTurnOFFTIMERS endp
365
366 ; Parameters:
367         Tp equ 6        ; pointer to timer.
368 ;
369 ;
370 _XTurnONTIMERS proc far
371         push    bp
372         mov     bp, sp
373         mov     bx, [bp + tp]
374         mov     cx, [bx]
375         add     bx, 2
376 TONLoop:
377         mov     ax, [bx].timeremaining
378         neg     ax
379         js      TONTLpEnd
380         mov     [bx].timeremaining, ax
381 TONTLpEnd:
382         add     bx, 8
383         loop    TONLoop
384         ret
385 _XTurnONTIMERS endp
386
387 XTimerInit      proc    near
388         mov     ETloc,offset DGroup: XClockTimers
389 XTimerInit      endp
390
391 SYS_TEXT ends
392
393 End
```

```
Wed 10-15-86 12:10:22                                      reason

1  ;************************************************************
  2  ;*
  3  ;* MFO Ver 0.0
  4  ;*
  5  ;* Module: Xdef.inc
  6  ;*
  7  ;* modification history :    reason(s)
  8  ;*      date     by
  9  ;*
 10  ;*      This module is an original, unpublished work and is proprietary to
 11  ;*      NELLCOR INC., and may not be divulged or copied in any form
 12  ;*      whatsoever without the express written permission of NELLCOR INC.
 13  ;*      Copyright 1986.
 14  ;*
 15  ;*
 16  ;* Purpose:
 17  ;*
 18  ;* Procedures:
 19  ;*
 20  ;* Public Data:
 21  ;*
 22  ;************************************************************
 23  ;
 24  ; System Error Definitions
 25  ; used in calls to _XReporterr
 26  XProcErr     equ 1
 27  XMemTestErr  equ 2
 28  Hz400        equ 1
 29  Hz800        equ 2
 30
 31  TrendSeg     equ 2000
 32  TrendEnd     equ 3fff
 33
 34
```

```
Wed 10-12-86 14:10:58  XEVENT.H
Wed 10-15-86 12:10:22

1  /************************************************************
  2  **
  3  ** MFO Ver 0.0
  4  **
  5  ** Module xevent.h
  6  **
  7  ** modification history :
  8  **      date     by        reason(s)
  9  **
 10  **
 11  **      This module is an original, unpublished work and is proprietary to
 12  **      NELLCOR INC., and may not be divulged or copied in any form
 13  **      whatsoever without the express written permission of NELLCOR INC.
 14  **
 15  **
 16  **      purpose :
```

```
17  *           Provide System Wide Definitions of System Events for
18  *           assemble files.
19  *
20  *                  data descriptions :
21  *
22  *
23  *                  function descriptions :
24  *
25  **********************************************************************/
26
27  /* Events for schedular */
28  typedef enum {
29  NO_EV = 0x0000,
30  ALWAYS_EV = 0x0001,
31  COMM_EV = 0x0002,
32  A_DATA_EV = 0x0004,
33  TIME_EV = 0x0008,
34  FP_INPUT_EV = 0x0010,
35  CONTROL_EV = 0x0020,
36  COMMISR_EV = 0x0040,
37  DISP_EV = 0x0080,
38  WININT_EV = 0x0100,
39  TIME_SLICE_EV = 0x8000
40  } SYSEVENTS;
41
42  #define tickspersecond 400
43  #define timerdelay tickspersecond/8 ; /* 50 hz */
44  #define TOCS tickspersecond
45
46  #define PID_WVF           1
47  #define PID_COMM          2
48  #define PID_DOUT          3
49  #define PID_AOUT          4
50  #define PID_ALARM         5
51  #define PID_DISPLAY       6
52  #define PID_CONTROL       7
53  #define PID_HISTORY_B     PID_HISTORY
54  #define PID_LASTSERVER    PID_HISTORY
55  #define PID_SAO2          1*256
56  #define PID_ECG           2*256
57  #define PID_GAS           3*256
58  #define PID_BP1           4*256
59  #define PID_BP2           5*256
60  #define PID_TEMP          6*256
61  #define PID_ITEST         7*256
62  #define PID_LASTMT        PID_ITEST
63
64  int far XWait();
65  void far XPost();
66  int far XCreateP();
67  void far XDeleteP();
68
69  int near XPID();
70  int near XLock();
71  int near XUnLock();
72
73
```

```
Wed 10-13-86 19:16:14   XEVENT.I         ;reason
    10-15-86 12:10:22

1  ;***************************************************************
 2  ;
 3  ;  MFO Ver 0.0
 4  ;
 5  ;  Module xEvent.i
 6  ;
 7  ;       modification history:
 8  ;         date      by      reason(s)
 9  ;       6-21-86    epr     creation
10  ;       8-1-86     slc     add process ids
11  ;       8-21-86    jab     added XCOMMISR_EV
12  ;
13  ;  Purpose:
14  ;       Provide System Wide Definitions of System Events for
15  ;       assemble files.
16  ;
17  ;  Procedures:
18  ;
19  ;  Public Data:
20  ;
21  ;       This module is an original, unpublished work and is proprietary to
22  ;       NELLCOR INC., and may not be divulged or copied in any form
23  ;       whatsoever without the express written permission of NELLCOR INC.
24  ;       Copyright 1986.
25  ;
26  ;***************************************************************
27
28  ;Events for schedular
29  XALWAYS_EV    equ  0001h
30  XCOMM_EV      equ  0002h
31  XA_DATA_EV    equ  0004h
32  XTIME_EV      equ  0008h
33  XFP_INPUT_EV  equ  0010h
34  XCONTROL_EV   equ  0020h
35  XCOMMISR_EV   equ  0040h
36  XDISP_EV      equ  0080h
37  WININT_EV     equ  0100h
38
39  XTIME_SLICE_EV  equ   8000h
40
41  ;process IDs
42
43  PID_WVF         equ  1
44  PID_COMM        equ  2
45  PID_DOUT        equ  3
46  PID_AOUT        equ  4
47  PID_ALARM       equ  5
48  PID_DISPLAY     equ  6
49  PID_CONTROL     equ  7
50
51  PID_HISTORY     equ  8
52  PID_LASTSERVER  equ  PID_HISTORY
53  PID_SAO2        equ  1*256
54  PID_ECG         equ  2*256
```

```
 55  PID_GAS        equ 3*256
 56  PID_BP1        equ 4*256
 57  PID_BP2        equ 5*256
 58  PID_TEMP       equ 6*256
 59  PID_ITEST      equ 7*256
 60  PID_LASTMT     equ PID_ITEST
 61
 62  XTicksPerSecond equ 400
 63  XTockFreq      equ 50      ; Xtickspersecond/Xtockfreq ; 50 hz
 64  XTimerDelay    equ 25
 65  MTSliceTime    equ
 66
 67  XPRShift       equ 4
 68  XPRWSize       equ 16
 69
 70  XProcTabSiz    equ 10
 71  XProcQueSiz    equ XProcTabSiz * 4
 72
 73  XProcRec struc
 74  post  dw 0    ; the sign bit of post indicates active process.
 75  wait  dw 0    ; post and wait store event codes.
 76                ;   sign bit on wait indicates in process run que.
 77  sptr  dw 0    ; the process sp while waiting for an event.
 78  sseg  dw 0    ; the process ss while waiting for an event.
 79  terminate dd 0 ; long pointer to this processes terminate function.
 80  delay dw 0    ; 16 bit delay, this delay has a 400hz resolution.
 81  dummy dw 0    ; used to count process invocations.
 82  XProcRec ends
 83
 84
 85  EOIReg    equ 0ff22h
 86  TimerEOI  equ 0000Bh
 87  DMA0EOI   equ 0000Ah
 88  DMA1EOI   equ 0000Bh
 89  INT0EOI   equ 0000Ch
 90  INT1EOI   equ 0000Dh
 91  INT2EOI   equ 0000Eh
 92  INT3EOI   equ 0000Fh
 93  NonspecificEOI equ 0B000h
 94  XEOI  equ TimerEOI       ; System int End of Int
 95  VSEOI equ INT1EOI        ; Video Sync int End of Int
 96  VWEOI equ INT0EOI        ; Video Window int End of Int
 97  CEOI  equ INT2EOI        ; Comm int End of Int
 98
 99  ; Video Sync interrupt acknowledge
100  VSIACK macro
101         mov   dx, EOIReg
102         mov   ax, VSEOI
103         out   dx, ax
104  endm
105
106  ; Video Window interrupt acknowledge
107  VWIACK macro
108         mov   dx, EOIReg
109         mov   ax, VWEOI
110         out   dx, ax
111  endm
112
```

```
113        ; System Timer interrupt acknowledge
114        XIACK   macro
115                mov     dx, EOIReg
116                mov     ax, XEOI
117                out     dx, ax
118                endm
119
120        ; Comm (8274) interrupt acknowledge
121        CIACK   macro
122                mov     dx, EOIReg
123                mov     ax, CEOI
124                out     dx, ax
125                endm
126
127        ; Highest priority interrupt acknowledge
128        IACK    macro
129                mov     dx, EOIReg
130                mov     ax, NonspecificEOI      ; general interrupt acknowledge
131                out     dx, ax
132                endm
133
134        XEOIReg      equ 0ff22h
135        XEOIRegVal   equ 8000h
136        PollStatusReg equ 0ff24h
137
138        IPOLL   macro
139                mov     dx, PollStatusReg
140                in      ax, dx
141                endm
142
143
Wed 10-14-86 22:23:54    XSCHED.S         XTimerInit
    10-15-86 12:10:22

.186
 1    ;**********************************************************************
 2    ;*
 3    ;* Module schedproc.s
 4    ;*
 5    ;**********************************************************************
 6    ; Purpose:
 7    ;     This module is the MGM schedular.  It is responsible for the
 8    ;     lowest level of process scheduling.
 9
10
11            NAME    XSCHED
12
13    ; Procedures:
14            Public  XSchedProc
15            Public  XWait, -XWait
16            Public  XPost, -XPost
17            Public  _XCreateP
18            Public  _XDeleteP
19            Public  XenQueProc
20            Public  XdeQueProc
21            Public  XPushProc
22            Public  _X_reset
23
```

```
24         Public XInitProcQues
25         Public XIllegalInstruction
26         Public _XCLI, _XSTI
27         Public _XLOCK, _XUNLOCK
28         Public _XPID
29         Public XBound
30         Public XSchedInit
31
32    ; Public Data:
33         Public XCP_ID, XCP_SP, XCP_SS, XLock_ID
34         Public XInterruptProc
35         Public X_sp, XSS_sp
36         Public XServerProcs
37         Public MTProcs
38         Public XSS_SB, XSS_spp
39
40    ; This module is an original, unpublished work and is proprietary to
41    ; NELLCOR INC., and may not be divulged or copied in any form
42    ; whatsoever without the express written permission of NELLCOR INC.
43    ; Copyright 1986.
44
45    ; modification history:          put NAME
46    ; 30 July 86 slc        Call XTimerInit() to init data base in Xclock.s
47    ; 5 Aug 86 slc
48
49    ;*************************************************************
50
51    include XDef.i
52    include Xevent.i
53
54    XServerState equ 0ffh
55    waitax equ 10
56
57    CONST segment word public 'CONST'
58    CONST ends
59
60    _DATA segment word public 'DATA'
61
62    XInterruptProc dw dumb; initialized to point to interrupt time function!
63
64    _DATA ends
65
66    _BSS segment word public 'BSS'
67
68    even
69
70    XInprocess dw ?; The in process flag -- controls reentry.
71    Public XInprocess
72
73
74    even
75    MTTimeSlice dw ?
76    Public MTTimeSlice
77
78    XCP_ID dw ? ; current process I.D.
79    XLock_ID dw ? ; current process Lock I.D.
80
81    even
```

```
 82         XCP_SP dw ? ; current process stack pointer
 83         XCP_SS dw ? ; current process stack segement
 84
 85         x_sp dw ? ; system stack pointer.
 86
 87         even
 88         XServerProcs XProcRec XProcTabSiz dup (<,,,,,>)
 89
 90         XProcTabLength equ XProcTabSiz * XPRWSize
 91
 92         even
 93         MTProcs XProcRec XProcTabSiz dup (<,,,,,>)
 94
 95
 96         Xpque struc
 97         pqget dw ?
 98         pqput dw ?
 99         pqend dw ?
100
101         pqstatus dw ?
102         pqcount dw ?
103         pqdata dw ?
104         Xpque ends
105
106         PQEMPTY equ 1
107         PQNotEMPTY equ 2
108
109         XPROCQUEUE macro qname, qsize
110         even
111         qname equ this word
112         public qname
113         dw ? ; pqget
114         dw ? ; pqput
115         dw ? ; pqend
116         dw ? ; pqstatus
117         dw ? ; pqcount of elemets
118         dw 2*qsize dup (?) ; 2 elements per entry.
119         endm
120
121         XPROCQUEUE XServerQue, XProcQueSiz
122
123         XPROCQUEUE MTQue, XProcQueSiz
124
125         even
126         XSS_SB equ this word
127         dw 99 dup (?)
128
129         XSS_sp dw ?
130
131         XSS_spp dw ?
132
133         _BSS ends
134
135         DGROUP Group _DATA, CONST, _BSS
136
137         SYS_TEXT segment byte public 'CODE'
138         ; in Xclock.s the clock server
139
```

```
140  extrn  XClock:near, XLinkTimer:near
141  extrn  XTimerInit:near  ;to init timer data base
142  extrn  _XReportErr:near
143
144
145  ASSUME CS:SYS_TEXT, DS:DGROUP, SS:DGROUP, FS:DGROUP
146
147  XSchedInit proc near
148          mov     MTTimeSlice, MTSliceTime
149          call    XInitProcQues
150          mov     ax, offset DGroup:XSS_sp
151          and     ax, 0fffeh
152          mov     XSS_spp, ax
153          ret
154  XSchedInit endp
155
156
157  ;***********************************************************
158  ; Function:    XSchedProc -- system schedular function.
159  ;
160  ;              This is the heart of the MFO schedular.
161  ;
162  ;
163  ;***********************************************************
164
165
166
167
168  IFOnly: call    XInterruptProc
169          jmp     XSHardExit
170
171
172  XSched label far
173  Public XSched
174  XSchedProc proc far
175          pusha
176          push    ds
177          push    es
178
179          XIACK
180
181          mov     ax, DGROUP
182          mov     ds, ax
183
184          cmp     XInprocess, 0
185          jne     IFOnly
186          mov     XInprocess, 1
187          mov     XCP_SP, sp
188          mov     XCP_SS, ss
189
190          mov     ss, ax
191          mov     sp, XSS_spp     ; get pointer to X Sched Stack Pointer
192
193          call    XInterruptProc
194
195          ;sti    ;************ allow the world back in ********************
196          call    XClock
197          inc     XCheckProcs
```

```
198                 jmp         XSExit
199
200     XCheckProcs:
201     public XCheckProcs
202             mov         bp, XCP_ID
203             test        bp, XServerState
204             jnz         XSExit   ; if Server is running don't do anything
205
206             ; if runable server preempt MT
207             mov         si, offset DGROUP:XServerQue
208             mov         di, offset DGROUP:XServerProcs
209             call        XdeQueProc   ; on ret cx = PID, ax = Event
210             jnc         XCheckMTTimeSlice
211
212             mov         si, bx
213             shr         si, XPRShift
214
215
216     XSPreemptMT:
217     public XSPreemptMT
218             mov         cx, [di][bx].sptr
219             mov         dx, [di][bx].sseg
220
221             xchg        cx, XCP_SP
222             xchg        dx, XCP_SS
223
224             xchg        si, XCP_ID
225
226             or          bp, bp
227             jz          XSPreemptExit
228             mov         di, si       ; save it as parameter to pushProc.
229             shr         di, 8 - XPRShift  ; get MT index.
230             jz          XSPreemptExit
231
232             xchg        word ptr MTProcs[di].sptr, cx
233             xchg        word ptr MTProcs[di].sseg, dx
234
235             push        ax
236
237             mov         ax, XTIME_SLICE_EV
238             mov         bx, di
239             mov         di, offset DGROUP:MTProcs
240             mov         si, offset DGROUP:MTQue
241             call        XPushProc    ; put this MT at head of the MTQue.
242
243             pop         ax
244
245
246     XSPreemptExit:
247             mov         sp, XCP_SP
248             mov         cx, XCP_SS
249             mov         ss, cx
250
251             mov         bp, sp + waitax
252             mov         [bp + waitax], ax
253
254
255             mov         XInprocess, 0
```

```
256             pop     es
257             pop     ds
258             popa
259             sti     ; ***************** Interrupts On *****************************
260             ret     ; Note: not an iret!
261
262     XSExit: mov     sp, XCP_SP
263             mov     ss, XCP_SS
264
265             mov     XInprocess, 0
266
267     XSHardExit:
268             pop     es
269             pop     ds
270             popa
271             iret
272
273     ;XSPreemptExit1:
274     ;               jmp     XSPreemptExit
275     ;XMTNotTimeOutEnQue:
276
277     XCheckMTTimeSlice:
278             or      bp, bp
279     Public XCheckMTTimeSlice
280             jnz     XDecMTSlice
281
282     XNoProcCheckForMT:
283             mov     si, offset DGROUP:MTQue
284             mov     di, offset DGROUP:MTProcs
285             call    XdeQueProc      ; on ret bx = Pindex, ax = Event
286             jnc     XSExit
287             mov     si, bx
288             shl     si, XPRShift            ; the PID to the high byte.
289             mov     cx, [di][bx].sptr
290             mov     dx, [di][bx].sseg
291
292             mov     XCP_SP, cx
293             mov     XCP_SS, dx
294
295             mov     XCP_ID, si
296
297             jmp     XSPreemptExit
298
299     XDecMTSlice:
300             dec     MTTimeSlice
301             jns     XSExit
302
303             mov     MTTimeSlice, MTSliceTime
304             mov     si, offset DGROUP:MTQue
305             mov     di, offset DGROUP:MTProcs
306             call    XdeQueProc      ; on ret bx = Pindex, ax = Event
307             jnc     XSExit
308             mov     si, bx
309             shl     si, XPRShift            ; the PID to the high byte.
310             mov     ax, XTIME_SLICE_EV
311             jmp     XSPreemptMT
```

```
314         XSchedProc endp
315
316 ;***********************************************************
317 ;
318 ; Function:    XWait  -- system wait function.
319 ;             _XWait  -- system C callable wait function.
320 ;
321 ;       This function cause the calling process to be suspended.
322 ;       until the a wait condition is satisfied.
323
324 ; Entry --  ax = wait for event(s)
325 ;           dx = delay if event set includes TIME_EV event
326
327 ;        C Call XWait(event, [delay])
328 XW_Event   equ 6
329 XW_Delay   equ 8
330
331 ;***********************************************************
332
333 _XWait    proc far
334           push   bp
335           mov    bp, sp
336           mov    ax, [bp + XW_Event]
337           test   ax, XTIME_EV
338           jz     XWCNotDelay
339           mov    dx, [bp + XW_Delay]
340 XWCNotDelay:
341           pop    bp
342           ; fall through to XWait
343 _XWait    endp
344
345 XWait     proc far
346           pusha                    ; ax contains wait for events
347           push   ds
348           push   es
349
350           mov    bx, DGROUP
351           mov    ds, bx
352
353           mov    bx, XCP_ID
354           xchg   bx, Ø ffffh
355           mov    bx, XServerState
356           test   di, offset DGROUP:XServerProcs
357           jnz    XWhaveProcTable
358
359           mov    bl, bh
360           xchg   di, offset DGROUP:MTprocs
361
362 XWhaveProcTable:
363           cmp    bx, 16
364           ja     XWErrorExit
365           shl    bx, XFRShift
```

```
3372            mov     [di][bx].sptr, sp
3373            mov     cx, ss
3374            mov     [di][bx].sseg, ss
3375            and     ax, 7fffh                ; can not wait for XTIME_SLICE_EV
3376            jz      XWErrorExit              ; if zero serious error
3377
3378            mov     [di][bx].wait, ax        ; and Not in Run Que.
3379
3380            test    ax, XTIME_EV
3381            jz      XWCheckAlways
3382            xor     ax, XTIME_EV
3383            mov     [di][bx].wait, ax        ; and Not in Run Que.
3384            mov     [di][bx].delay, dx
3385            jmp     short XWCheckAlways
3386
3387    XWErrorExit:
3388            cli
3389            hlt
3390
3391    XWCheckAlways:
3392            test    ax, XALWAYS_EV
3393            jz      XWCheckIfPosted
3394            mov     ax, XALWAYS_EV
3395            jmp     XWAlwaysPost
3396
3397    XWCheckIfPosted:
3398            mov     cx, ax
3399            and     cx, [di][bx].post
3400            jnz     XWEarlyPost
3401
3402    XWSGetNext:
3403    Public XWSGetNext
3404            mov     si, offset DGROUP:XServerQue
3405
3406            cli             ;*********** Critical Section ************************
3407            call    XdeQueProc
3408            sti             ;*********** End Critical Section ********************
3409
3410            jnc     XTryMTQue
3411
3412            mov     ss, word ptr XServerProcs[bx].sseg
3413            mov     sp, word ptr XServerProcs[bx].sptr
3414            mov     bp, sp
3415            mov     [bp + waitax], ax
3416
3417            shr     bx, XPRShift
3418            mov     XCP_ID, bx
3419
3420            pop     es
3421            pop     ds
3422            popa
3423            ret
3424
3425    XWEarlyPost:
3426            mov     dx, cx                   ; reduce cx to single event!
3427            neg     dx
3428            and     cx, dx
3429
3430            xor     ax, cx                   ; take event out of ax!
```

```
431                      xor      [di][bx].post, cx
432                      ;or      [di][bx].wait, ax
433                      mov      ax, cx
434        XWAlwaysPost:
435                      mov      si, offset DGROUP:XServerQue
436                      cmp      di, offset DGROUP:XServerProcs
437                      je       XWPostIt
438                      mov      si, offset DGROUP:MTQue
439
440
441        XWPostIt:
442        Public XWPostIt
443
444                      cli
445                      call     XenQueProc   ;************ Critical Section ***************************
446                      sti                   ;************ End Critical Section ***********************
447
448
449                      jmp      XWSGetNext
450
451        XTryMTQue:
452        Public XTryMTQue
453                      mov      si, offset DGROUP:MTQue
454
455                      cli                   ;************ Critical Section ***************************
456                      call     XdeQueProc
457                      sti                   ;************ End Critical Section ***********************
458
459                      jnc      XWGiveUp
460
461                      mov      MTTimeSlice, MTSliceTime
462                      mov      cx, word ptr MTProcs[bx].sseg
463                      mov      ss, cx
464                      mov      sp, word ptr MTProcs[bx].sptr
465                      mov      bp, sp
466
467                      shl      bx, 8 - XPRShift
468                      mov      XCP_ID, bx
469
470                      or       ax, ax
471                      js       TIME_SLICE_RET
472
473                      mov      [bp + waitax], ax
474
475                      pop      es
476                      pop      ds
477                      popa
478                      ret
479
480        XWGiveup:                           ; if jump here goes back to first level.
481        Public XWGiveup
482                      mov      XCP_ID, 0
483                      ;mov     MTTimeSlice, 0
484                      mov      ax, ds
485                      mov      ss, ax
486                      mov      sp, X_sp
487
488
```

```
489              iret
490   TIME_SLICE_RET:
491              pop       es
492              pop       ds
493              popa
494              iret      ; if time sliced out need an IRET
495
496   XWait endp
497
498   ;**********************************************************************
499   ;
500   ; Function:    XPost    -- system post function.
501   ;              _XPost   -- system C callable post function.
502   ;
503   ; Entry ---  ax = posted event
504   ;            bx = PID
505   ;
506   ;            C Call XPost(PID, Event)
507   ;            SP_PID equ 6
508   ;            SP_Event equ 8
509   ;
510   ;**********************************************************************
511
512   _XPost proc far
513          push    bp
514          mov     bp, sp
515          push    di
516          push    si
517          mov     bx, [bp + SP_PID]
518          mov     ax, [bp + SP_Event]
519          call    far ptr XPost
520          pop     si
521          pop     di
522          pop     bp
523          ret
524   _XPost endp
525
526   XPost proc far
527          mov     dx, ax
528          neg     dx
529          and     ax, dx    ; accept only one post event!
530          mov     dx, ax
531
532          mov     di, offset DGROUP:XServerProcs
533          mov     si, offset DGROUP:XServerQue
534          mov     bx, XServerState
535          test    bx, SPHaveTable
536          jnz     SPHaveTable
537          mov     di, offset DGROUP:MTProcs
538          mov     si, offset DGROUP:MTQue
539          xchg    bl, bh
540
541   SPHaveTable:
542          shl     bx, XPRShift
```

```
547             and     ax, [di][bx].wait
548             jz      SPNotReady
549
550             pushf           ; save interrupt flag state!
551             cli     ;******************* Critical *******************************
552             call    XenQueProc
553             popf    ;******************* End Critical ***************************
554             ret
555
556     SPNotReady:
557             or      [di][bx].post, dx
558             ret
559
560     XPost   endp
561
562     ;************************************************************************
563     ; Functions for process lock out.
564     ;   xLock, xUnlock, _XPID
565     ;   xCLI, xSTI
566     ;************************************************************************
567
568     ; Entry ---
569     ;************************************************************************
570
571     XLockWord equ 00ffffh
572
573     _XPID   proc    near
574             mov     ax, XCP_ID
575             cmp     ax, XLockWord
576             je      XPIDLocked
577             ret
578     XPIDLocked:
579             mov     ax, XLock_ID
580             ret
581     _XPID   endp
582
583     _XLOCK  proc    near
584             mov     ax, XCP_ID
585             xchg    ax, XLockWord
586             cmp     ax, XLockWord
587             je      XLockLocked
588             mov     XLock_ID, ax
589             ret
590     XLockLocked:
591             mov     ax, XLock_ID
592             ret
593     _XLOCK  endp
594
595     _XUNLOCK proc   near
596             cmp     XCP_ID, XLockWord
597             jne     xUNLexit
598             mov     ax, XLock_ID
599             mov     XCP_ID, ax
```

```
604        xUNLExit:
605               ret
606        _xUNLOCK endp
607
608        _xCLI proc far
609               cli
610               ret
611        _xCLI endp
612
613        _xSTI proc far
614               sti
615               ret
616        _xSTI endp
617
618
619
620   ;***************************************************************
621   ;
622   ; Function:    _XCreateP -- system process creation function.
623   ;
624   ;       This function initializes the process tables with to cause
625   ;       this process to run. This process is C callable.
626   ;
627   ; Entry --
628        XCP_Pid equ 6
629        XCP_Main equ 8
630        XCP_stackp equ 12
631        XCP_timers equ 14
632        XCP_terminate equ 16         ;process terminate function,long ptr
633
634   ;***************************************************************
635
636   _XCreateP proc far
637          push    bp
638          mov     bp, sp
639          push    di
640          push    si
641          push    ds
642
643          mov     ax, DGROUP
644          mov     ds, ax
645          mov     di, offset DGROUP:XServerProcs
646          mov     si, offset DGROUP:XServerQue
647          mov     bx, [bp + XCP_Pid]
648
649          test    bx, XServerState
650          jnz     XCPHaveProcs              ;server if nz
651          mov     di, offset DGROUP:MTProcs
652          mov     si, offset DGROUP:MTQue
653          xchg    bl, bh
654   XCPHaveProcs:
655
656          shl     bx, XPRShift
657          xor     [di][bx].post, XTIME_SLICE_EV
658          jns     XCPError
```

```
662                 mov     ax, XALWAYS_EV
663                 call    XenQueProc
664
665                 mov     ax, [bp + XCP_timers]
666                 mov     dx, [bp + XCP_data]
667                 mov     es, ds          ; was [bp + XCP_data]
668                 mov     dx
669                 call    XLinkTimer
670
671                 mov     ax, [bp + XCP_terminate]
672                 mov     dx, [bp + XCP_terminate + 2]
673                 mov     word ptr [di][bx].terminate, ax
674                 mov     word ptr [di][bx + 2].terminate, dx
675
676                 mov     ax, [bp + XCP_Main]
677                 mov     dx, [bp + XCP_Main + 2]
678
679                 mov     si, di
680                 mov     di, [bp + XCP_stackp]
681                 and     di, 0fffeh      ; insure even stack!
682
683                 std     ; ********************************
684
685                 mov     es:[di], dx
686                 sub     di, 2
687         stosw
688                 lea     ax, [di + 2]    ; store the sp for pusha
689                 mov     cx, 8           ; in all the registers.
690         rep stosw
691                 mov     ax,es           ; store the data segment and the
692         stosw
693                 cld     ; ******************* the extra segment.
694                 mov     es:[di], ax     ; the extra segment.
695                 mov     [si][bx].sptr, di
696                 mov     [si][bx].sseg, ax
697
698 XCFExit:
699                 mov     ax, [bp + XCP_Pid]
700                 pop     ds
701                 pop     si
702
703                 pop     di
704                 pop     bp
705                 ret
706
707 XCPError:
708                 xor     ax, ax
709                 jmp     short XCFExit
710
711 _XCreateP endp
712
713 ;*****************************************************************************
714 ;
715 ; Function:     _XDeleteP -- system delete process function.
716 ;
717 ; Entry --
718 ;       C callable XDeleteP(PID)
719 ;
```

```
;********************************************************************
;                SDF_Pid    equ   6
;********************************************************************

_XDeleteF  proc  far
           push  bp
           mov   bp, sp
           push  di
           push  si mov   bx, [bp + SDF_Pid]
           mov   di, offset DGROUP:XServerProcs
           mov   si, offset DGROUP:XServerQue
           test  bx, XServerState
           jnz   SDFHaveProcs mov   di, offset DGROUP:XServerProcs
           mov   si, offset DGROUP:XServerQue
           xchg  bl, bh
           or    bx, bx
           jz    SDFKillThisProc SDFHaveProcs:
           mov   ax, ds
           mov   es, ax
           shl   bx, XPRShift
           mov   cx, XPRWSize
           xor   ax, ax
           add   di, bx
           rep   stosw pop   si
           pop   di
           pop   bp
           ret SDFKillThisProc:
           mov   bx, XCP_ID      ; can only get here on an MT self kill.
           xchg  bl, bh
           mov   ax, cs
           mov   [bp + 8], ax
           mov   ax, offset XWSGetNext
           mov   [bp + 6], ax
           jmp   SDFHaveProcs _XDeleteF  endp ProcQue    struc
QuePID     dw    0
QueEvent   dw    0
ProcQue    ends ;********************************************************************
; Function:
```

```
;*****************************************************************
;               XenQueProc -- process queuing function
;
;       This function queues the PID and event as a runnable
;       process.
;
; Entry --
;       ax = event
;       bx = Process Table index
;       di = Process Table
;       si = Process Queue.
;*****************************************************************
XenQueProc proc near mov     [di][bx].wait, XTIME_SLICE_EV; Indicate process is in run que.
        mov     [di][bx].delay, 0; Stop timer
        inc     [di][bx].dummy
        push    cx
        push    di mov     di, [si].pqput
        cmp     di, [si].pqget
        je      enQPTestEmpty enQPDo:
        inc     [si].pqcount
        mov     [di].queevent, ax
        mov     [di].quePID, bx
        add     di, 4
        mov     [si].pqput, di
        cmp     di, [si].pqend
        jae     enQPWrap pop     di
        pop     cx
        ret enQPTestEmpty:
        cmp     [si].pqstatus, PQNotEMPTY
        je      enQPError
        mov     [si].pqstatus, PQNotEMPTY
        jmp     short enQPDo enQPError:
        cli                     ;************ Error halt *******************************
        hlt
        push    XProcErr
        call    _XReportErr
        add     sp, 2
        pop     di
        pop     cx
        ret enQPWrap:
        lea     ax, [si].pqdata
        mov     [si].pqput, ax
```

```
836            pop    di
837            pop    cx
838            ret
839
840    XenQueProc endp
841
842    ;************************************************************
843    ; Function:    XdeQueProc -- process de-queuing function
844    ;
845    ;     This function de-queues the PID and event of a runnable
846    ;     process.
847    ;
848    ; Entry --  si = Process Queue.
849    ;
850    ; Return --
851    ;     if not empty
852    ;              ax = event
853    ;              bx = Process Table index
854    ;              carry flag set
855    ;     else
856    ;              carry flag clear
857    ;
858    ;************************************************************
859    XdeQueProc proc near
860            push   cx
861            push   di
862
863            cmp    [si].pqstatus, PQNotEMPTY
864            jne    deQPEmpty
865
866            dec    [si].pqcount
867            mov    di, [si].Pqget
868            mov    ax, [di].QueEvent
869            mov    bx, [di].QuePID
870
871            add    di, 4
872            cmp    di, [si].pqend
873            jae    deQPWrap
874
875    deQPCheck:
876            mov    [si].pqget, di
877            cmp    di, [si].pqput
878            je     deQPEmptied
879
880    deQPEExit:
881            stc
882            pop    di
883            pop    cx
884            ret
```

```
894         deQFWrap:
895                 lea     di, [si].pqdata
896                 jmp     deQFCheck
897
898         deQFEmpty:
899                 clc
900                 pop     di
901                 pop     cx
902                 ret
903
904         deQFEmptied:
905                 mov     [si].pqstatus, PQEmpty
906                 jmp     short deQFEExit
907         XdeQueProc endp
908
909 ;********************************************************************
910 ;
911 ;       Function:       PushProc -- process de-queuing function
912 ;
913 ;       This function de-queues the PID and event of a runnable
914 ;       process.
915 ;
916 ;       Entry --
917 ;               ax = event
918 ;               bx = Process Table index
919 ;               si = Process Queue.
920 ;
921 ;********************************************************************
922
923         XPushProc proc near
924
925                 cmp     [si].pqstatus, 0
926                 jne     XPFenQue
927
928                 mov     [di][bx].wait, XTIME_SLICE_EV; Indicate process is in run que.
929
930                 push    di
931                 mov     di, [si].pqget
932                 sub     di, 4
933                 lea     cx, [si].pqdata
934                 cmp     di, cx
935                 jb      XPFWrap
936
937         XPFCheckFull:
938                 cmp     di, [si].pqput
939                 je      XPFError
940
941         XPFOK:
942                 mov     [di].queevent, ax
943                 mov     [di].quePID, bx
944                 mov     [si].pqget, di
945                 pop     di
946                 ret
947
948         XPFWrap:
```

```
951                mov     di, [si].pqend
952                sub     di, 4
953                jmp     XPFCheckFull
954
955     XPFPenQue:
956                jmp     XenQueProc
957
958     XPFError:
959                cli
960                hlt
961     XPushProc endp
962
963     ;****************************************************************
964     ;****************************************************************
965     ; Function:
966     ;       sys_reset() -- this function jumps to 0ffff:fff0, the 8086 reset
967     ;                      vector location.
968     ;
969     ;****************************************************************
970     ;****************************************************************
971
972     resetvector dd 0ffffff0h
973
974     _x_reset proc far
975              jmp     resetvector
976     _x_reset endp
977
978     dumb proc near
979          ret
980     dumb endp
981
982     XInitProcQues proc near
983              mov     bx, offset DGROUP:XServerQue
984              lea     ax, [bx].pqdata
985              mov     [bx].pqget, ax
986              mov     [bx].pqput, ax
987              lea     ax, [bx + (4 * XProcQueSiz) - 4]
988              mov     [bx].pqend, ax
989              mov     [bx].pqstatus, PQEMPTY
990              mov     [bx].pqcount, 0
991
992              mov     bx, offset DGROUP:MTQue
993              lea     ax, [bx].pqdata
994              mov     [bx].pqget, ax
995              mov     [bx].pqput, ax
996              lea     ax, [bx + (4 * XProcQueSiz) - 4]
997              mov     [bx].pqend, ax
998              mov     [bx].pqstatus, PQEMPTY
999              mov     [bx].pqcount, 0
1000
1001             call    XTimerInit      ;init timer data base
1002             ret
1003    XInitProcQues endp
1004    XIllegalInstruction proc far
1005             cli
1006             hlt     ; later this will be a system reset.
1007
```

```
1008        XIllegalInstruction endp
1009
1010        XBound proc far
1011                mov        ax, 0ffffh
1012                iret
1013        XBound endp
1014
1015        SYS_TEXT ends
1016
1017        END
1018
Wed  09-24-86 15:10:24    XWATCH.H
     10-15-86 12:10:22
```

```
 1  /*********************************************************************
 2  ** MFO Ver 0.0
 3  **
 4  ** module: xwatch.h
 5  **
 6  ** modification history :   reason(s)
 7  **         date    by           creation
 8  **       8-11-86  epr
 9  **
10  **
11  ** This module is an original, unpublished work and is proprietary to
12  ** NELLCOR INC., and may not be divulged or copied in any form
13  ** whatsoever without the express written permission of NELLCOR INC.
14  **
15  ** purpose :
16  **
17  ** data descriptions.:
18  **
19  ** function descriptions :
20  **
21  **********************************************************************/
22
23  typedef struct
24  {
25   unsigned int tensecs:4, seconds:4, tenths:4, hundredths:4;
26   unsigned int mode_24:1, mode_10_PM:2, hr:r, hour:4, tenmins:4, minutes:4;
27   unsigned int zero1:2, tendate:2, date:4, zero0:2, osc:1, reset:4, day:4;
28   unsigned int tenyear:4, year:4, tenmonth:4, month:4;
29  } TIME;
30
Wed  09-24-86 15:10:28    XWATCH.I
     10-15-86 12:10:22
```

```
1   .186
2
3   ;*********************************************************************
4                                        reason
```

```
      MFO Ver 0.0
      Module: xwatch.i modification history : reason(s)
          date       by        reason(s)
         8-11-86    epr        creation

COPYRIGHT (C) 1986 NELLCOR INCORPORATED

This module is an original, unpublished work and is proprietary to
         NELLCOR INC., and may not be divulged or copied in any form
         whatsoever without the express written permission of NELLCOR INC.

Purpose:

Procedures:

Public Data:
  ******************************************************************
Wed 09-24-86 15:10:30   XWATCH.S
    10-15-86 12:10:22             reason

******************************************************************
      .186
  ******************************************************************
      MFO Ver 0.0
      Module: XWatch.s
      Name xwatch modification history : reason(s)
          date       by        reason(s)

COPYRIGHT (C) 1986 NELLCOR INCORPORATED

This module is an original, unpublished work and is proprietary to
         NELLCOR INC., and may not be divulged or copied in any form
         whatsoever without the express written permission of NELLCOR INC.

Purpose:
         Code for taking to smart watch.

Procedures:
         Public    XWakeWatch      ;   -- writes the 'code' to wake the smart watch
         Public    XWriteWatch     ; [time] -- writes time to smart watch
         Public    XReadWatch      ; [] -- reads time from smart watch
         Public    XSetTime        ; (time) -- external call to set time.
         Public    XGetTime        ; (time) -- external call to set time.
  ;
```

```
31  ; Public Data:
32              Public TIMERet
33  ;***********************************************************
34
35  XWSEG   segment at 0
36      org 0
37  XDataLoc0 equ this word  ; for watch!
38      Public XDataLoc0
39  XWSEG   ends
40
41  CONST   segment word public 'CONST'
42  CONST   ends
43
44  _DATA   segment word public 'DATA'
45  _DATA   ends
46
47  _BSS    segment word public 'BSS'
48
49  TIMERet dw 4 dup (?)
50
51  _BSS    ends
52
53  DGROUP  Group CONST, _DATA, _BSS
54
55  SYS_TEXT segment byte public 'CODE'
56
57  assume cs:SYS_TEXT, ds:XWSEG, es:DGroup, ss:DGroup
58
59  ;***********************************************************
60  ; Procedure:
61  ;       XWriteWatch(time]  -- writes to the smart watch
62  ;       !Cannot use memory including stack!
63  ; Entry:
64  ;       ax = 10sec, sec, 1/10sec, 1/100sec in BCD nibbles
65  ;       dx = 12hrmode:1, 0:1, 10hr/pm:1, hr:1, 10min:4, min:4
66  ;       si = 10date:4, date:4, 0:2, osc:1, reset:1, day:4
67  ;       di = 10year:4, year:4, 10month:4, month:4
68  ;       bp = return address
69  ; Exit:
70  ;***********************************************************
71
72  XWriteWatch proc near
73  XWW_SecLoop:
74          mov     cx, 16
75          mov     word ptr XDataLoc0, ax
76          shr     ax, 1
77          loop    XWW_SecLoop
78  XWW_HrLoop:
79          mov     cl, 16
80          mov     word ptr XDataLoc0, dx
81          shr     dx, 1
```

```
 89              loop    XWW_HrLoop
 90              mov     cl, 16
 91      XWW_DateLoop:
 92              mov     word ptr XDataLoc0, si
 93              shr     si, 1
 94              loop    XWW_DateLoop
 95              mov     cl, 16
 96      XWW_YearLoop:
 97              mov     word ptr XDataLoc0, di
 98              shr     di, 1
 99              loop    XWW_YearLoop
100              jmp     bp
101
102      XWriteWatch    endp
103
104      ;****************************************************************
105      ;
106      ; Procedure:
107      ;   XReadWatch[time] -- Reads to the smart watch
108      ;   !Cannot use memory including stack!
109      ;
110      ; Entry:
111      ;   bp = return address
112      ;
113      ; Exit:
114      ;   ax = 10sec, sec, 1/10sec, 1/100sec in BCD nibbles
115      ;   dx = 12hrmode:1, 10hr/pm:1, hr:1, hour:4, 10min:4, min:4
116      ;   si = 10date:4, date:4, 0:2, osc:1, reset:1, day:4
117      ;   di = 10year:4, year:4, 10month:4, month:4
118      ;
119      ;****************************************************************
120
121      XReadWatch     proc near
122              mov     cx, 16
123              xor     ax, ax
124      XRW_SecLoop:
125              mov     bx, word ptr XDataLoc0
126              and     bx, 1
127              or      ax, bx
128              shl     ax, 1
129              loop    XRW_SecLoop
130
131              mov     cl, 16
132              xor     dx, dx
133      XRW_HrLoop:
134              mov     bx, word ptr XDataLoc0
135              and     bx, 1
136              or      dx, bx
137              shl     dx, 1
138              loop    XRW_HrLoop
```

```
147            mov      cl, 16
148            xor      si, si
149   XRW_DateLoop:
150            mov      bx, word ptr XDataLoc0
151            and      bx, 1
152            or       si, bx
153            shl      si, 1
154            loop     XRW_DateLoop
155
156            mov      cl, 16
157            xor      di, di
158   XRW_YearLoop:
159            mov      bx, word ptr XDataLoc0
160            and      bx, 1
161            or       di, bx
162            shl      di, 1
163            loop     XRW_YearLoop
164
165            jmp      bp
166
167   XReadWatch  endp
168
169   ;************************************************************
170   ;
171   ; Procedure:
172   ;   XWakeWatch(time) -- writes to the smart watch
173   ;   !Cannot use memory including stack!
174   ;
175   ; Entry: ax = 10sec, sec, 1/10sec, 1/100sec in BCD nibbles
176   ;        dx = 12hrmode:1, 0:1, 10hr/pm:1, hr:1, 10min:4, min:4
177   ;        si = 10date:4, date:4, 0:2, osc:1, reset:1, day:4
178   ;        di = 10year:4, year:4, 10month:4, month:4
179   ;        bx = return address
180   ; Exit:
181   ;
182   ;************************************************************
183
184   XWakeWatch  proc near
185            mov      ax, 3ac5h
186            mov      ch, 2
187
188   XWW_BigLoop:
189            mov      cl, 16
190   XWW_FirstLoop:
191            mov      word ptr XDataLoc0, ax
192            ror      ax, 1
193            dec      cl
194            jnz      XWW_FirstLoop
195
196            mov      cl, 15
197            rol      ax, 1
198            mov      word ptr XDataLoc0, ax
199   XWW_SecondLoop:
```

```
204              mov     word ptr XDataLoc0, ax
205              rol     ax, 1
206              dec     cl
207              jz      XWW_SecondLoop
208
209              dec     ch
210              jnz     XWW_BigLoop
211
212              jmp     bx
213
214    XWakeWatch endp
215
216    ;*************************************************************
217    ; Function:
218    ;    Void XSetTime(time) TIME time;
219    ;
220    ; Entry: time equ 4    ; time is 4 words long
221    ;
222    ; Exit:
223    ;*************************************************************
224    XSetTime proc near
225              enter   0, 0
226              push    ds
227              push    es
228              mov     ax, XWSEG
229              mov     ds, ax
230              mov     ax, DGroup
231              mov     es, ax
232              push    bp          ; save bp again
233              push    si
234              push    di
235              push    word ptr XDataLoc0
236
237              mov     bp, [bp + time]
238              mov     dx, [bp + time + 2]
239              mov     si, [bp + time + 4]
240              mov     di, [bp + time + 6]
241
242              mov     bx, offset XST_XWakeW_Ret
243              cli     ;************** Critical ***************************
244                      jmp     XWakeWatch
245    XST_XWakeW_Ret:
246              mov     ax, bp
247
248              mov     bp, offset XST_XWriteW_Ret
249                      jmp     XWriteWatch
250    XST_XWriteW_Ret:
251              pop     word ptr XDataLoc0
252              sti     ;************** Critical ***************************
```

```
2262              pop       di
2263              pop       si
2264              pop       bp
2265              pop       es
2266              pop       ds
2267              leave
2268              ret
2269
2270     XSetTime endp
2271
2272     ;*********************************************************************
2273     ;
2274     ; Function:  Time XGetTime(time) TIME time;
2275     ;
2276     ; Entry:
2277     ;
2278     ; Exit:      TIMERet = time
2279     ;            ax = &TIMERet
2280     ;
2281     ;*********************************************************************
2282
2283     XGetTime proc near
2284              enter     0, 0
2285              push      ds
2286              push      es
2287              mov       ax, XWSEG
2288              mov       ds, ax
2289              mov       ax, DGroup
2290              mov       es, ax
2291              push      bp        ; save bp again
2292              push      si
2293              push      di
2294              push      word ptr XDataLoc0
2295
2296              mov       bx, offset XGT_XWakeW_Ret
2297
2298              cli ;************ Critical *********************************
2299              jmp       XWakeWatch
2300     XGT_XWakeW_Ret:
2301
2302              mov       ax, bp
2303
2304              mov       bp, offset XGT_XReadW_Ret
2305              jmp       XReadWatch
2306     XGT_XReadW_Ret:
2307
2308              pop       word ptr XDataLoc0
2309              sti ;************ Critical *********************************
2310
2311              mov       bx, offset DGroup:TIMERet
2312              mov       [bx], ax
2313              mov       [bx + 2], dx
2314              mov       [bx + 4], si
```

```
320            mov          [bx + 6], di
321            mov          ax, bx
322
323            pop          di
324            pop          si
325            pop          bp
326            pop          es
327            pop          ds
328            leave
329            ret
330
331     XGetTime endp
332
333     SYS_TEXT ends
334            end
335
336
337
Wed 10-14-86 20:11:20  LARMSVR.C            LarmLink
Wed 10-15-86 12:10:22
```

```
1      /***********************************************************
2       *
3       *  MFO Ver 0.0
4       *
5       *  module: LARMSVR.C
6       *
7       *  modification history :
8       *       date      by      reason(s)
9       *     7-20-86    kht     creation
10      *
11      *     9-22-86    kht     Revised for system integration
12      *
13      *  This module is an original, unpublished work and is proprietary to
14      *  NELLCOR INC., and may not be divulged or copied in any form
15      *  whatsoever without the express written permission of NELLCOR INC.
16      *
17      *  Purpose : This is the source file of the alarm sever.
18      *
19      *  data descriptions :
20      *
21      *  function descriptions :
22      *
23      ***********************************************************/
24
25     #include "nsid.h"
26     #include "xclock.h"
27     #include "xevent.h"
28     #include "\nfo\display\daudio.h"
29     #include "\nfo\display\dalarm.h"
30
31     #define INITLARMSVR
32     #include "larmsvr.h"
33
34
35
```

```
36  /* This function is used to enable an alarm type in the alarm table so that
37  ** the alarm server can check it whenever the server is awaked.
38  **
39  ** invoked by: measurement tasks
40  **
41  */
42  void far
43  LarmLink(alid,alfunptr,alarmtime)
44  int alid;                  /* alarm type identifier */
45  int (*alfunptr)();         /* pointer to the alarm function */
46  int alarmtime;             /* alarm time interval */
47  {
48
49  larm[alid].actionflag = TRUE;  /* enable the alarm */
50  larm[alid].al_time = alarmtime;  /* set alarm server wait time */
51  larm[alid].funptr = alfunptr;    /* set pointer to a function */
52  larm[alid].al_count = 0;         /* reset the current alarm counter */
53  /* larm[alid].al_event_ct = 0;      /* reset the alarm event counter */
54  /* larm[alid].delay_ct = 0;         /* alarm delay counter */
55  larm[alid].audiolevel = NONE;
56  larm[alid].alarmtype = OK;
57  larm[alid].silent = FALSE;
58
59  /* assume measurement task will bring up all the info on the screen. */
60  return;
61  }
62
63
64  /* This function is used to disable an alarm type in the alarm table so that
65  ** the alarm server can skip checking it if the server is awaked.
66  **
67  ** invoked by: measurement tasks
68  **
69  ** subroutine involved: LUpdateAudio();
70  */
71  void far
72  LarmTerminate(alid)     /* long pointer for XCreatP */
73  int alid;               /* alarm id to unlink.  If alid = 0, use current PID */
74  { int i, temppid;
75
76
77
78  if (alid)  /* use alarmid ( specify ET or Ins ) */
79  { larm[alid].actionflag = FALSE;  /* change alarm table flag */
80      larm[alid].al_time = 0;         /* disable wait time */
81      larm[alid].al_count = 0;        /* reset the current alarm counter */
82  /*  larm[alid].al_event_ct = 0;        /* reset the alarm event counter */
83  /*  larm[alid].delay_ct = 0;           /* alarm delay counter */
84      larm[alid].audiolevel = NONE;
85      larm[alid].alarmtype = OK;
86      larm[alid].silent = FALSE;
87
88     /* assume other functions responsible to turn off video alarm. */
89
90  }
91  else
92  { temppid = (xpid() >> 8);
93      for (i=1; i<=pid2lid[temppid][0]; ++i)  /* use global PID to determine alid */
94          { larm[pid2lid[temppid][i]].actionflag = FALSE;  /* change alarm table flag */
```

```
 94        larm[pid2][idt1emppid[i]].al_time = 0;        /*disable wait time */
 95        larm[pid2][idt1emppid[i]].al_count = 0;       /* reset the current alarm counter */
 96             larm[pid2][idt1emppid[i]].al_event_ct = 0;    /* reset the alarm event counter */
 97             larm[pid2][idt1emppid[i]].delay_ct = 0;       /* alarm delay counter */
 98         larm[pid2][idt1emppid[i]].audiolevel = NONE;
 99         larm[pid2][idt1emppid[i]].alarmtype = OK;
100         larm[pid2][idt1emppid[i]].silent = FALSE;
101     }
102     /*assume other functions responsible to turn off video alarm. */
103
104     LUpdateAudio(ALL);
105     /* XFree(alarmstack);    /* only when all process ids are unlinked */
106     return;
107 }
108
109
110 char *alarmstack =0;         /* alarm server stack pointer */
111 /* This external function is used to create the alarm process
112 **
113 ** invoked by: DispInit.s
114 **
115 ** external functions involved:  Xalloc();
116 **                               XCreateP();
117 **/
118 void far
119 LarmCreateP()
120 {
121     alarmstack = Xalloc(ALARMSTACKSIZE);   /* assume 200 bytes stack size */
122     XCreateP(PID_ALARM, LarmServer, (alarmstack+ALARMSTACKSIZE-2), 0, LarmTerminate );
123     return;
124 }
125
126 /* This external function is used to store the key event and limit set number
127 ** for ALS.
128 **
129 ** invoked by: control server whenever an alarm related key is pressed.
130 **
131 ** external function involved: XPost();
132 */
133 void near
134 LKeyInput(key_event, alid, lmtsetnum)
135 int key_event;            /* key-event type i.e. PRESET_LIMIT, SAVE_LIMIT, */
136                           /*                     SILENT_KEY */
137 int lmtsetnum;            /* limit set number or alarm id */
138 int alid;
139 {
140     fp_event = key_event;
141     /* if (fp_event == PRESET_LIMIT || fp_event == SAVE_LIMIT) */
142     setnum = lmtsetnum;   /* selected limit set or alarm id for silent key */
143     larmsilentid = alid;
144     XPost(PID_ALARM, (int)FP_INPUT_EV);
145     return;
146 }
147
148 /* This external function is used to store the key event, knob value for ALS.
149 **
150 ** invoked by: control server when the knob is moved to change the alarm
```

```
151    **       status.
152    **
153    **       external function involved:   XPost();
154    */
155    void near
156    LKnobInput(key_event, alid, limit_type, knob_value)
157    int key_event;   /* key-event type i.e. CHNG_SILENT_PERIOD, */
158                     /*  UPDATE_LIMIT_VALUE, CHNG_PULSE_VOL or CHNG_ALARM_VOL */
159
160    int alid;          /* alarm ID */
161    int limit_type;    /* low or high limit of the alarm ID */
162    int knob_value;    /* the changed value in base unit */
163    {
164    knob_event = key_event;
165    switch(knob_event)
166     { case CHNG_SILENT_PERIOD:
167            asilentperiod += knob_value;
168            break;
169      case UPDATE_LIMIT_VALUE:
170            knobval = knob_value;
171            limitid = alid;
172            limittype = limit_type;
173            break;
174      case CHNG_PULSE_VOL:
175            pulsevol += knob_value;
176            if (pulsevol >MAXVOLUME)
177                 pulsevol = MAXVOLUME;
178            else if (pulsevol < OFFVOLUME)
179                 pulsevol = OFFVOLUME;
180            break;
181      case CHNG_ALARM_VOL:
182            alarmvol += knob_value;
183            if (alarmvol >MAXVOLUME)
184                 alarmvol = MAXVOLUME;
185            else if (alarmvol < OFFVOLUME)
186                 alarmvol = OFFVOLUME;
187            break;
188     }
189    XPost(FID_ALARM, (int)FP_INPUT_EV);
190    return;
191    }
192
193    /* This external function is used to determine and update the audio alarm.
194    ** The interface parameters are:
195    **    button click sound - (CLICK_LEVEL, THIRDPR, 0, BUTTON_CLICK_ID);
196    **    pulse beep - (PULSE_BEEP_LEVEL, THIRDPR, Pulse Pitch, mPULSE);
197    */
198    void far
199    LOutputAudio(olevel, opr, freq, oid)
200    int olevel;
201    int opr;
202    int freq;
203    int oid;
204    { int outputtime;
205
206        outputtime = 1;
207        while (doainuse)
208            outputtime = AFTERALARM;
```

```
209     lvlfromlarm = olevel;
210     prfromlarm = opr;
211     idfromlarm = oid;
212
213     if (opr ( THIRDPR)      /* alarm audio */
214        volfromlarm = alarmvol;
215     else if (oid == (int)mPULSE)
216        { volfromlarm = pulsevol;
217          pulsefreq = freq;
218        }
219     else /* button click */
220        volfromlarm = CLICK_VOLUME;
221
222     if (outputtime >1)
223        XSetTimeDelay( &DAudioTimers.timers[5], outputtime, TDISABLE );
224     else
225        { /* XSetTimeDelay( &DAudioTimers.timers[5], TDISABLE, TDISABLE ); */
226          DOutputAudio();
227        }
228     return;
229  }
230  /* This subroutine is used to determine the output audio alarm level.
231  *** note: alarm type must be reset to OK when alarm id is linked
232  *** It always output the highest alarm and the new alarm and send alarm
233  *** level even in silent period.
234  ***
235  *** invoked by: LarmCond(); LarmCheck(); LarmSetLimit(); Larmserver();
236  ***             LarmTerminate();
237  ***
238  *** external function involved: XSetTimeDelay();
239  */
240  void near
241  LUpdateAudio(alid)
242  int alid;   /* alarm id */
243  { int opr, oid, olevel, i;
244
245     if (alid != ALL && larm[alid].audiolevel == LEVEL1)   /* new alarm */
246        { opr = SECONDPR;
247          for (i=0; i<LASTFPALARM; ++i)       /* check if it is first priority alarm */
248             { if (alid == fpaa[i][0] && larm[alid].alarmtype == fpaa[i][1])
249                  { oid = -fpaa[i][0];
250                    opr = FIRSTPR;
251                    i = LASTFPALARM;
252                  }
253             }
254          if (opr == SECONDPR)
255             { for (i=0; i<LASTSPALARM; ++i)    /* find second priority alarm */
256                  { if (alid == spaa[i][0] && larm[alid].alarmtype == spaa[i][1])
257                       { oid = spaa[i][0];
258                         i = LASTSPALARM;
259                       }
260                  }
261             }
262
263          olevel = (asilentflag)? LEVEL0: LEVEL1; /* ASSUME display function inc audiolevel if
                                                      >=LEVEL1*/
264        }
265     else if (audiodisable == TRUE) /* no audio level update because LALUpdate() will not be
```

```
266    called */
267    else return;
268    {  opr = SECONDPR;
269       oid = olevel = NONE;
270       for (i=0; i(LASTFFALARM; ++i) /*pick the highest first priority alarm */
271       { if (larm[fpaa[i]].actionflag == TRUE && \
272                larm[fpaa[i]].alarmtype == fpaa[i][1] && \
273                olevel < larm[fpaa[i][0]].audiolevel && \
274                larm[fpaa[i]].silent == FALSE)
275          { olevel = larm[fpaa[i][0]].audiolevel;
276            opr = FIRSTPR;
277            oid = fpaa[i][0];
278          }
279       }
280       if (opr == SECONDPR) /* second priority alarm */
281       { for (i=0; i(LASTSPALARM; ++i) /*pick the highest second priority alarm */
282          { if (larm[spaa[i][0]].actionflag == TRUE && \
283                 larm[spaa[i][0]].alarmtype == spaa[i][1] && \
284                 olevel < larm[spaa[i][0]].audiolevel && \
285                 larm[spaa[i][0]].silent == FALSE)
286            { oid = spaa[i][0];
287              olevel = larm[spaa[i][0]].audiolevel;
288            }
289          }
290       }
291    LOutputAudio(olevel, opr, 0, oid);
292    return;
293    }
294
295    void near
296    LVideoAlarm(id)
297    int id;
298    { if (larm[id].alarmtype == ABVLIMIT)
299         DVideoAlarm(id, larm[id].alarmtype, larm[id].limit_val[HIGH]);
300      else if (larm[id].alarmtype == BLOLIMIT)
301         DVideoAlarm(id, larm[id].alarmtype, larm[id].limit_val[LOW]);
302      else
303         DVideoAlarm(id, larm[id].alarmtype, 0);
304      return;
305    }
306
307    /* This subroutine is used to echo the current alarm conditions by checking
308    ** their alarm condition flags in priority order. It also determine the
309    ** output audio level and priority.
310    **
311    ** invoked by: Larmserver();
312    **
313    ** external function involved: LVideoAlarm();
314    **
315    ** subroutine involved: LUpdateAudio();
316    */
317    void near
318    LarmCond()
319    { int i;
```

```
323     for (i=1; i<=MAXALARMID; ++i)
324     { if (larm[i].actionflag ==TRUE)
325         LVideoAlarm(i);
326     }
327     LUpdateAudio(ALL);   /* output audio alarm level */
328     return;
329   }
330
331   void far
332   LALUpdate()
333   { int i;
334
335     for (i=0; i<LASTFPALARM; ++i)
336     { if (larm[fpaa[i][0]].actionflag ==TRUE &&  \
337         larm[fpaa[i][0]].alarmtype == fpaa[i][1])
338       { if (larm[fpaa[i][0]].audiolevel ==LEVEL1) ;
339         larm[fpaa[i][0]].alct )= LUDFACTOR)
340         { larm[fpaa[i][0]].audiolevel=(larm[fpaa[i][0]].audiolevel(FPMAXLVL)
341           ?++larm[fpaa[i][0]].audiolevel:FPMAXLVL;
342           larm[fpaa[i][0]].alct =0;
343         }
344         larm[fpaa[i][0]].alct =(larm[fpaa[i][0]].alct <LUDFACTOR
345                 && larm[fpaa[i][0]].audiolevel >LEVEL1)
346                 ?++larm[fpaa[i][0]].alct:1;
347     }
348     for (i=0; i<LASTSPALARM;++i) /* check for second priority alarm */
349     { if (larm[spaa[i][0]].actionflag ==TRUE && \
350         larm[spaa[i][0]].alarmtype == spaa[i][1])
351       { if (larm[spaa[i][0]].audiolevel == LEVEL1) ;
352         larm[spaa[i][0]].alct )= LUDFACTOR)
353         { larm[spaa[i][0]].audiolevel=(larm[spaa[i][0]].audiolevel(SPMAXLVL)
354           ?++larm[spaa[i][0]].audiolevel:SPMAXLVL;
355           larm[spaa[i][0]].alct =0;
356         }
357         larm[spaa[i][0]].alct =(larm[spaa[i][0]].alct <LUDFACTOR
358                 && larm[spaa[i][0]].audiolevel )=LEVEL1)
359                 ?++larm[spaa[i][0]].alct:1;
360     }
361     return;
362   }
363
364   /* This function is used to check the alarm condition of the specified alarm
365   ** ID. It assumes that the alarm type must be active for changing the limit
366   **
367   ** invoked by: Larmserver();
368   **
369   ** external function involved: LVideoAlarm();
370   **
371   ** subroutine involved: LUpdateAudio();
372   */
373   void near
374   LarmCheck(alid)
```

```
3381    int alid;         /* alarm ID */
3382    int (*function)();
3383    int lastalarmtype, lastaudiolevel, tempalarmtype;
3384
3385    lastalarmtype = larm[alid].alarmtype;
3386    lastaudiolevel = larm[alid].audiolevel;
3387    function = larm[alid].funptr;    /*call MTO function */
3388    tempalarmtype = (*function)(larm[alid].limit_val[LOW],
3389                                 larm[alid].limit_val[HIGH]);
3390
3391    if (tempalarmtype != WAIT)
3392        larm[alid].alarmtype = tempalarmtype;
3393    if (lastalarmtype != larm[alid].alarmtype )
3394    { /*LVideoAlarm(alid);
3395        if (larm[alid].alarmtype) /*current alarm type is not OK */
3396        { /* larm[alid].al_event_ct = 0;    /* reset event counter */
3397            larm[alid].audiolevel = LEVEL1;  /* reset audio level */
3398            larm[alid].alct = 0;             /* reset audiolevel counter */
3399            /* larm[alid].delay_ct = 0;     /* reset delay counter */
3400        }
3401        else
3402            larm[alid].audiolevel = NONE;    /* NO audio alarm */
3403
3404        LUpdateAudio(alid);
3405    }
3406    /* else if (larm[alid].alarmtype) /* also increment for WAITing condition */
3407    /* { if ((++larm[alid].delay_ct) >= larm[alid].delay_time)
3408        { if (larm[alid].silent == FALSE)
3409            larm[alid].audiolevel = (larm[alid].audiolevel < 4)
3410                                     ?++larm[alid].audiolevel:4;
3411            if (audiodisable == FALSE &&
3412                lastaudiolevel != larm[alid].audiolevel)
3413                LUpdateAudio(alid);
3414        }
3415        /* larm[alid].al_event_ct = 0; */
3416        /* larm[alid].delay_ct = larm[alid].delay_time; */
3417    }
3418    */
3419    larm[alid].al_count = (larm[alid].alarmtype)?
3420                          ACTIVE_ALARM_TIME:larm[alid].al_time;
3421    return;
3422 }
3423
3424 /*  The following are the internal functions used in the alarm server.
3425 **  This function is used to change the limit values for different alarm types
3426 **
3427 **  invoked by: Larmserver();
3428 **
3429 **  external function involved: DWarningAlarm();
3430 **
3431 **  NOTE: all gas limit values are scaled by 10 so that the measurement task
3432 **        can convert them into scale (floating point) values for alarm check
3433 **        and display on the screen.
3434 */
3435 void near
3436 LarmSetLimit(alid,lmttype)
3437 int alid;
```

```
439    int lmttype;      /* to determine low limit or high limit */
440
441    /* knob value, larm[alid].limit_val[lmttype], is updated in LInput() */
442
443    if (larm[alid].limit_val[LOW] >= larm[alid].limit_val[HIGH])
444    {  if (lmttype == LOW)    /* active low limit */
445       {  if (larm[alid].limit_val[LOW] )>=larm[alid].limit_val[HIGH])
446          {  larm[alid].actionflag = FALSE;  /* disable alarm */
447             larm[alid].limit_val[LOW] = larm[alid].max_val[LOW];
448             larm[alid].limit_val[HIGH] = larm[alid].max_val[HIGH];
449             DWarningCond(REACHMIN);
450          }
451          else if (larm[alid].limit_val[LOW] <= larm[alid].max_val[LOW])
452          /*modify high limit */
453             larm[alid].limit_val[HIGH] = larm[alid].limit_val[LOW] +1;
454             DWarningCond(TOOBIG);
455          }
456          else
457          {  larm[alid].limit_val[LOW] = larm[alid].max_val[LOW];
458             DWarningCond(REACHMAX);
459             /* default to use the min. value*/
460          }
461       }
462       else if    /* active high limit */
463       {  (larm[alid].limit_val[HIGH] <= larm[alid].min_val[LOW])
464          {  larm[alid].actionflag = FALSE;  /*disable alarm */
465             larm[alid].limit_val[LOW] = larm[alid].min_val[LOW];
466             larm[alid].limit_val[HIGH] = larm[alid].min_val[HIGH];
467             DWarningCond(REACHMAX);
468          }
469          else if (larm[alid].limit_val[HIGH] >= larm[alid].min_val[HIGH])
470          /* modify low limit*/
471             larm[alid].limit_val[LOW] = larm[alid].limit_val[HIGH] -1;
472             DWarningCond(TOOBIG);
473          }
474          else
475          {  larm[alid].limit_val[HIGH] = larm[alid].min_val[HIGH];
476             DWarningCond(REACHMIN);
477             /* default to use the max. value*/
478          }
479       }
480    }
481    else if (larm[alid].limit_val[lmttype] < larm[alid].min_val[lmttype])
482    {  larm[alid].limit_val[lmttype] = larm[alid].min_val[lmttype];
483       DWarningCond(REACHMIN);
484       /* default to use the min. value*/
485    }
486    else if (larm[alid].limit_val[lmttype] > larm[alid].max_val[lmttype])
487    {  larm[alid].limit_val[lmttype] = larm[alid].max_val[lmttype];
488       DWarningCond(REACHMAX);
489       /* max_val is one count greater than the actual used max. value */
490    }
491    return;
492 }
493
494 void near
495 limitinit()
496
```

```
497   { /* default to use N100 adult limit */
498
499     larm[(int)mSAO2].limit_val[LOW] = 85;
500     larm[(int)mSAO2].limit_val[HIGH] = 100;
501     larm[(int)mSAO2].min_val[LOW] = 50;
502     larm[(int)mSAO2].min_val[HIGH] = 50;
503     larm[(int)mSAO2].max_val[LOW] = 100;
504     larm[(int)mSAO2].max_val[HIGH] = 100;
505
506     larm[(int)mPULSE].limit_val[LOW] = 55;
507     larm[(int)mPULSE].limit_val[HIGH] = 140;
508     larm[(int)mPULSE].min_val[LOW] = 35;
509     larm[(int)mPULSE].min_val[HIGH] = 35;
510     larm[(int)mPULSE].max_val[LOW] = 250;
511     larm[(int)mPULSE].max_val[HIGH] = 250;
512
513   /* ALL gas limit values are scaled by 10 (e.g. 39 = 3.9) */
514     larm[(int)mCO2ET].limit_val[LOW] = 39;
515     larm[(int)mCO2ET].limit_val[HIGH] = 66;
516     larm[(int)mCO2ET].min_val[LOW] = 13;
517     larm[(int)mCO2ET].min_val[HIGH] = 26;
518     larm[(int)mCO2ET].max_val[LOW] = 66;
519     larm[(int)mCO2ET].max_val[HIGH] = 100;
520
521   /* ALL gas limit values are scaled by 10 (e.g. 200 = 20.0) */
522     larm[(int)mCO2INS].limit_val[LOW] = 0;
523     larm[(int)mCO2INS].limit_val[HIGH] = 26;
524     larm[(int)mCO2INS].min_val[LOW] = 0;
525     larm[(int)mCO2INS].min_val[HIGH] = 0;
526     larm[(int)mCO2INS].max_val[LOW] = 66;
527     larm[(int)mCO2INS].max_val[HIGH] = 79;
528
529   /* ALL gas limit values are scaled by 10 (e.g. 6000 = 600.0) */
530     larm[(int)mN2OET].limit_val[LOW] = 0;
531     larm[(int)mN2OET].limit_val[HIGH] = 789;
532     larm[(int)mN2OET].min_val[LOW] = 0;
533     larm[(int)mN2OET].min_val[HIGH] = 0;
534     larm[(int)mN2OET].max_val[LOW] = 1000;
535     larm[(int)mN2OET].max_val[HIGH] = 1000;
536
537   /* ALL gas limit values are scaled by 10 (e.g. 6000 = 600.0) */
538     larm[(int)mN2OINS].limit_val[LOW] = 0;
539     larm[(int)mN2OINS].limit_val[HIGH] = 789;
540     larm[(int)mN2OINS].min_val[LOW] = 0;
541     larm[(int)mN2OINS].min_val[HIGH] = 0;
542     larm[(int)mN2OINS].max_val[LOW] = 1000;
543     larm[(int)mN2OINS].max_val[HIGH] = 1000;
544
545   /* ALL gas limit values are scaled by 10 (e.g. 15 = 1.5) */
546     larm[(int)mAGAET].limit_val[LOW] = 0;    /* halothane */
547     larm[(int)mAGAET].limit_val[HIGH] = 15;
548     larm[(int)mAGAET].min_val[LOW] = 0;
549     larm[(int)mAGAET].min_val[HIGH] = 10;
550     larm[(int)mAGAET].max_val[LOW] = 60;
551     larm[(int)mAGAET].max_val[HIGH] = 60;
```

```
555    /* ALL gas limit values are scaled by 10 (e.g. 15 = 1.5) */
556    larm[(int)mAGAINS].limit_val[LOW] = 0;
557    larm[(int)mAGAINS].limit_val[HIGH] = 15;    /* halothane */
558    larm[(int)mAGAINS].min_val[LOW] = 0;
559    larm[(int)mAGAINS].min_val[HIGH] = 10;
560    larm[(int)mAGAINS].max_val[LOW] = 60;
561    larm[(int)mAGAINS].max_val[HIGH] = 60;
562
563    /* No set up for other agents in this version. */
564
565
566    larm[(int)mBR].limit_val[LOW] = 2;
567    larm[(int)mBR].limit_val[HIGH] = 40;
568    larm[(int)mBR].min_val[LOW] = 0;
569    larm[(int)mBR].min_val[HIGH] = 10;
570    larm[(int)mBR].max_val[LOW] = 150;
571    larm[(int)mBR].max_val[HIGH] = 150;
572
573    return;
574    }
575
576    void near
577    lcheckkeytype()
578    {int i;
579
580
581    switch (fp_event)  /* key is stored in Linput() */
582    { case SILENT_KEY:
583        asilentflag = (asilentflag)?FALSE:TRUE;
584        /* toggle silent condition. This flag is reset by display function */
585
586
587        if (asilentflag)
588          { larm[setnum].audiolevel = LEVEL1; /*reset audio level to level 1 */
589            larm[larmsilentid].alct = 0;      /* reset audio level */
590            larm[setnum].silent = TRUE;
591            DSilentAlarm();
592          }
593        else
594          { for (i=1; i(=MAXALARMID; ++i)
595              larm[i].silent = FALSE;
596            LarmCond();
597          }
598        break;
599
600    case PRESET_LIMIT:
601        /* when 'preset' key is pressed. */
602
603        for (i=1; i(=MAXALARMID; ++i)
604          { larm[i].limit_val[LOW] = larmlmtset[i].limit_val[LOW][setnum];
605            larm[i].limit_val[HIGH] = larmlmtset[i].limit_val[HIGH][setnum];
606            DEchoLimit(i, larm[i].limit_val[LOW], larm[i].limit_val[HIGH] );
607            LarmCheck();  /* check all alarm conditions for the new limit values */
608          }
609        break;
610
611    case SAVE_LIMIT:
612        /* when 'save' key is pressed. */
```

```
613              for (i=1; i<=MAXALARMID; ++i)
614              { larmlmtset[i].limit_val[LOW][setnum] = larm[i].limit_val[LOW];
615                larmlmtset[i].limit_val[HIGH][setnum] = larm[i].limit_val[HIGH];
616              }
617              break;
618         }
619      fp_event = FALSE;
620      return;
621  }
622
623  void near
624  lcheckknobtype()
625  { switch (knob_event)
626    { case UPDATE_LIMIT_VALUE:
627        /* when knob is rotated. */
628        larm[limitid].limit_val[limittype] += knobval;
629        LarmSetLimit(limitid.limittype);  /* limitid & limittype stored in LInput() */
630
631        LVideoAlarm(limitid);
632        LarmCheck(limitid);
633        break;
634
635      case CHNG_SILENT_PERIOD:
636        /* turn the knob while holding down the 'silent' key to change*/
637        /* silent period. It disables all audio alarm if silent period*/
638        /* is above or below the limit. */
639
640        /* asilentperiod (+=) is updated in LarmKeyInput() */
641        if (asilentperiod < MIN_ASILENT_PERIOD)
642        { asilentperiod = MIN_ASILENT_PERIOD;
643
644           audiodisable = FALSE; /* turn on audio alarm */
645           LUpdateAudio(ALL);
646           break;
647        }
648        else if (asilentperiod <= MAX_ASILENT_PERIOD)
649        { audiodisable = FALSE; /*turn on audio alarm */
650           LUpdateAudio(ALL);
651           break;
652        }
653        else /* above the max. audio volume */
654        { asilentperiod = MAX_ASILENT_PERIOD +1;
655           DSilentAlarm();
656
657           audiodisable = TRUE; /*turn off audio alarm */
658           /* assume the function keeps track the silent period and */
659           /* reactivate the audio alarm automatically. */
660
661           break;
662        }
663    }
664    knob_event = FALSE;
665    return;
666  }
```

```
671  /* The entry of the alarm server.
672  **
673  ** invoked by: schedular (TIME_EVENT and FP_KEY_EVENT driven)
674  **
675  ** external function involved:
676  **
677  ** subroutine involved: LarmCond(); LarmSetLimit();
678  **                     LarmCheck();
679  */
680  void far
681  LarmServer()      /* long address for XCreateP */
682  { int event, i;
683    int alid;
684
685  /* initialization */
686  for(alid = 1; alid <= MAXALARMID; ++alid)
687    { larm[alid].actionflag = FALSE;
688      larm[alid].al_time = 0;
689      larm[alid].al_count = 0;        /* reset the current alarm counter */
690      /* larm[alid].al_event_ct = 0;     /* reset the alarm event counter */
691      * larm[alid].delay_ct = 0;         /* alarm delay counter */
692      larm[alid].audiolevel = NONE;
693      larm[alid].alarmtype = OK;
694      larm[alid].silent = FALSE;
695    }
696
697  limitinit();  /* initialize the current limit values to N100 adult range */
698              /* note: control server or MT will do the initialization after the show*/
699
700  audiodisable = FALSE;
701  event = (int)TIME_EV;  /* default to time event at the beginning */
702  /* setnum is battery-back up */
703
704  for(;;)  /* infinite loop */
705    { if (event == (int)FP_INPUT_EV)  /* alarm associated key is pressed. */
706      { if (fp_event)
707          !checkkeytype();
708        if (knob_event)
709          !checkknobtype();
710      }
711
712      for (alid = 1; alid <= MAXALARMID; ++alid)
713      { if (larm[alid].actionflag)
714          { if (larm[alid].al_count > 0)        /*not ready for checking*/
715              --larm[alid].al_count;
716            else if (larm[alid].al_count == 0)  /* check alarm condition */
717              LarmCheck(alid);
718          }
719      }
720
721      event = XWait(((int)FP_INPUT_EV ! (int)TIME_EV), ALARMCKTIME);
722    }
723  }
```

```
/*****************************************************************
** MFO Ver 0.0
** module: HS.C
**
** This module is an original, unpublished work and is proprietary to
** NELLCOR INC., and may not be divulged or copied in any form
** whatsoever without the express written permission of NELLCOR INC.
**
** purpose : The history sever source file.
**
** data descriptions :
**
** function descriptions :
**
** modification history :
**         date     by    reason(s)
**       8-12-86   kht    creation
**
**       8-17-86   kht    include "hs.h"
**
**       7-18-86   kht    changed trend sever scheme to fit the new interface scheme
**                        of the display server and the control server.
**                        - 1. Trend Server never call display functions to
**                             put up anything.
**                        - 2. Trend Server provides functions for the display
**                             server to extract the data points for display.
**                        - 3. Trend Server keeps track the window size and
**                             averages the real time data for the display server.
******************************************************************/ include "nsid.h"
include "xevent.h"
#include "xclock.h"
#define INITHS
#include "hs.h"

/* This external function is used to changed the agent stamp which is used */
/* to identify the type of trend data in the agent buffer. It will be      */
/* called whenever a new agent is selected.                                */
/* invoked by:  control server                                             */
void near
HNewAgent(type)
int type; /* selected agent type */
{ switch (type)
  { case AGENT_A:
      agentStamp = AGENT_A;
```

```
 53            break;
 54        case AGENT_B:
 55            agentstamp = AGENT_B;
 56            break;
 57        case AGENT_C:
 58            agentstamp = AGENT_C;
 59            break;
 60        }
 61    return;
 62    }
 63
 64
 65  /* This external function is called to restore the static trend data for   */
 66  /** all parameters before saving any new trend data.                         */
 67  /*  invoked by: control server                                               */
 68
 69  /*** may need to zero the entire buffer first. ******/
 70  void near HStatic()
 71  {int i, hid;
 72
 73  for (hid=1; hid<=LASTHISID; ++i)
 74      {
 75      for (i=0; i(=sramsize; ++i)   /* restore the static data to the dynamic buffer */
 76          histhid].dbuffer[i] = hstatic[hid].sbuffer[i];
 77          histhid].dyptr = hstatic[hid].styptr;
 78          histhid].zerotimeptr = histhid].dyptr;
 79
 80      HPtrUpdate(hid);      /* zero the gap */
 81      }
 82  return;
 83  }
 84
 85
 86
 87  /* This external function is called whenever the 'clear' key is pressed in  */
 88  /** trend menu mode.                                                          */
 89  /*  invoked by: control server                                                */
 90  /*                                                                            */
 91  /* external functions involved:                                               */
 92  /*      - XTime();    ***return current time and date in a struct pointer**/
 93  void near HClear(hid)
 94  int hid;
 95  { unsigned int i;
 96
 97  if (hid == (int)mAGAET || hid == (int)mAGAINS)    /* special case for agent parameter */
 98      { for (i=0; i(dramsize; ++i)   /* only clear corresponding agent */
 99          { if ((histhid].dbuffer[i] & 0x0f) != agentstamp)
100              histhid].dbuffer[i] = 0;
101          }
102      for (i=0; i(sramsize; ++i)
103          { if ((hstatic[hid].sbuffer[i] & 0x03) != agentstamp)
104              hstatic[hid].sbuffer[i] = 0;
105          }
106      }
```

```
111      else    /* regular parameters */
112      {  for (i=0; i<dramsize; ++i)
113              hstatic[hid].dbuffer[i] = 0;
114         for (i=0; i<sramsize; ++i)
115              hstatic[hid].sbuffer[i] = 0;
116      }
117      ctime = XTime();                        /* update the time */
118      hstatic[hid].lrtime->hour = ctime->hour;
119      hstatic[hid].lrtime->min  = ctime->min;
120      hstatic[hid].lrtime->sec  = ctime->sec;
121      hstatic[hid].lrtime->year = ctime->year;
122      hstatic[hid].lrtime->month= ctime->month;
123      hstatic[hid].lrtime->day  = ctime->day;
124      return;
125   }
126
127
128
129   /* This subroutine is used to synchronize the pointer with the real time by */
130   /** filling the buffer with zero within the gap (turn off period).         **/
131   /*** invoked by: HLink() and HStatic()                                     ***/
132   /****                                                                     ****/
133   /***** external functions involved:                                      *****/
134   /****   XTime();    **return current time and date in a struct pointer   ****/
135   /***    XTimeDiff(time struct pointer);                                    ***/
136   /**         ** find the time difference (sec) **                           **/
137   /*                                                                          */
138   void near
139   HPtrUpdate(hid)
140   int hid;
141   {  unsigned int bytediff,i;
142
143      bytediff = ((double)XTimeDiff(hstatic[hid].lrtime))/hstatic[hid].recordrate;
144      if (bytediff >= dramsize)   /* determine the buffer size to be zero */
145      {  bytediff = dramsize;
146         for (i=1; i<bytediff; ++i)       /* both pointers move forward */
147         {  if (hstatic[hid].stptr < sramsize) /*determine the static buffer pointer */
148              ++hstatic[hid].stptr;
149         }
150         else
151              hstatic[hid].stptr = 0;
152         if (hstatic[hid].dyptr < dramsize) /*determine the dynamic buffer pointer */
153              ++hstatic[hid].dyptr;
154         else
155              hstatic[hid].dyptr = 0;
156         hstatic[hid].dbuffer[hstatic[hid].dyptr] =  /* zero the buffers */
157         hstatic[hid].sbuffer[hstatic[hid].stptr] = 0;
158         if (hid == (int)mAGAET || hid == (int)mAGAINS)   /* update agent stamp*/
159              hstatic[hid].dbuffer[hstatic[hid].dyptr] =
160                 (hstatic[hid].dbuffer[hstatic[hid].dyptr] & 0xfc) | agentstamp;
161              hstatic[hid].sbuffer[hstatic[hid].stptr] =
162                 (hstatic[hid].sbuffer[hstatic[hid].stptr] & 0xfc) | agentstamp);
163         /* stamp the agent buffer */
164      }
165      hstatic[hid].zerotimeptr = hstatic[hid].dyptr; /* update the zero time pointer */
166      ctime = XTime();     /* update the time */
167      hstatic[hid].lrtime->hour = ctime->hour;
168      hstatic[hid].lrtime->min  = ctime->min;
```

```
169     hstatic[hid].lrtime->sec = ctime->sec;
170     hstatic[hid].lrtime->year = ctime->year;
171     hstatic[hid].lrtime->month = ctime->month;
172     hstatic[hid].lrtime->day = ctime->day;
173
174     return;
175 }
176
177 /*                                                                    */
178 /* This external function is used to add a measurement ID to the history */
179 /* table.                                                              */
180 /* invoked by: MTO                                                     */
181 /*                                                                    */
182 /* subroutine involved:                                                */
183 /*     - HPtrUpdate(hid);   ** to synchronize the pointer to the real time*/
184 /*                                                                    */
185 void near
186 HLink(hid, funptr, his_time)
187 int hid;                    /* history identifier */
188 int (*funptr)();            /* MTO function pointer which returns measured data */
189 int his_time;               /* trend wait time */
190 {
191
192     his[hid].action_flag = TRUE;   /* enable the MID for trend display */
193     his[hid].his_time = his_time;  /* set individual trend data wait time */
194     his[hid].funptr = funptr;      /* set pointer to MTO function */
195     his[hid].his_count = 0;        /* set record time to record a new data immediately */
196
197     HPtrUpdate(hid);               /* synchronize the pointer by filling zero */
198                                    /* in the buffer gap */
199     return;
200 }
201
202 /*                                                                    */
203 /* This external function is used to disable a MID in the history table so */
204 /* that the history server can skip checking it if the server is awakened. */
205 /* invoked by: MTO                                                     */
206 /*                                                                    */
207 void near HTerminate(hid)
208 int hid;
209 {
210     his[hid].action_flag = FALSE;  /*change history table flag*/
211     his[hid].his_time = -1;        /*disable individual trend update time */
212     return;
213 }
214
215 /* Create trend server process */
216 void far HCreateP()
217 {
218     trendstack = Xalloc(TRENDSTACKSIZE);  /* assume 100 bytes stack size */
219     XCreateP(PID_HISTORY, HSave, (trendstack+TRENDSTACKSIZE-2), 0, HTerminate);
220     return;
221 }
```

```
227  /* This subroutine is used to find the pointer in the dynamic buffer   */
228  /* invoked by:   HDisplayData()                                          */
229  /*                                                                       */
230  /* returns:  - a pointer to the dynamic buffer                           */
231  int near
232  HFindPtr(current_ptr, direction, npoints)
233  int current_ptr;
234  int npoints;
235  int direction;
236  int i;
237  {
238    for (i=1; i<=npoints; ++i)
239      { if (direction == RIGHT )  /* pointer moves forward */
240          current_ptr = (current_ptr < (dramsize)?++current_ptr:0;
241        else                      /* Pointer moves backward */
242          current_ptr = (current_ptr > 0)?--current_ptr:dramsize;
243      }
244    return(current_ptr);
245  }
246
247
248
249
250  /* This external function is used to output a set of data point for display.*/
251  /* invoked by:  Display Server                                              */
252  /*                                                                          */
253  void near
254  HDisplayData(hid, starttime, endtime, numpoint, bufftype )
255  int hid;
256  unsigned int starttime;  /* how many sec before '+' current time */
257  unsigned int endtime;    /* how many sec after ,-, or before '+' the start time */
258  unsigned int numpoint;   /* number of points between the start and end time */
259  int bufftype;
260  { int direction;         /* direction flag */
261    unsigned int timediff, bytediff, average;
262    unsigned int tempvalue; /* make sure tempvalue size is big enough for the sum*/
263    char *databuff;
264    unsigned i, j, startptr, buffptr;
265
266    direction = LEFT;      /* default to move pointer to backward */
267    timediff = starttime - endtime;  /* assume timediff (= dramsize */
268    startbytediff = starttime/hstatic[hid].recordrate;
269    timebytediff = timediff/hstatic[hid].recordrate;
270    if ((timebytediff + startbytediff) <=dramsize)  /* o.k. */
271
272    else if (endtime > 0)  /* end time before the start time */
273      dispbuff.numpoint = numpoint = (dramsize - startbytediff)*numpoint/timebytediff;
274    else
275      dispbuff.numpoint = numpoint = numpoint - startbytediff * numpoint/timebytediff;
276
277    if (timediff < 0)
278      { timediff = -timediff;  /* make it positive */
279        direction = RIGHT;     /* pointer moves forward */
280      }
281    bytediff = timediff/hstatic[hid].recordrate; /* calculate how may data points available*/
282    average = (bytediff > numpoint)?bytediff/numpoint:1;
283    databuff = (bufftype)?dispbuff->fdisdata: dispbuff->sdisdata;
```

```
285         buffptr = startptr = HFindPtr(his[hid].zerotimeptr, LEFT, ((starttime/hstatic[hid].
286             recordrate)-1));
287         for (i=0; i<(numpoint; ++i )
288         { if ((startbyteptr ) his[hid].startbytect)   /* zero the unmeasured data*/
289             tempvalue = 0;
290             else
291             { tempvalue = his[hid].dbuffer[startptr];
292                 for (j=1; j <average; ++j)
293                 { buffptr = HFindPtr(buffptr, direction, 1);
294                     tempvalue += his[hid].dbuffer[buffptr];
295                     if (buffptr ==his[hid].starttimeptr || buffptr == his[hid].zerotimeptr)
296                         average = ++j;
297                 }
298                 tempvalue /= average;
299             }
300             *databuff = tempvalue;
301             *databuff++; /* increment the buffer pointer */
302             buffptr = startptr = HFindPtr(startptr, direction, 1);
303         }
304         return;
305     }
306
307 /* This external function is used to generate a set of data for displaying*/
308 /* a single trend parameter. The data will be averaged and saved in a data*/
309 /* struct (i.e. dispbuff->fdisdata[ptr]). A struct pointer will be returned.*/
310 TDDATAS * far
311 HSDData(hid, starttime, endtime, numpoint )
312 int hid;
313 unsigned int starttime;    /* how many sec after "-" or before "+" current time */
314 unsigned int endtime;      /* how many sec after "-" or before "+" start time */
315 unsigned int numpoint;     /* number of points between the start and end time */
316 {
317     HDisplayData(hid, starttime, endtime, numpoint, 1);
318     return(dispbuff);
319 }
320
321 /* This external function is used to generate two sets of data for displaying*/
322 /* a pair of trend parameters. The data will be averaged and saved in a data*/
323 /* struct (i.e. dispbuff->fdisdata[ptr] for the first trend parameter, hid1  */
324 /*              dispbuff->sdisdata[ptr] for the second trend parameter, hid2). */
325 /* A struct pointer will be returned.*/
326 TDDATAS * far
327 HDDData(hid1, hid2, starttime, endtime, numpoint )
328 int hid1;                  /* first hid */
329 int hid2;                  /* second hid */
330 unsigned int starttime;    /* how many sec before current time */
331 unsigned int endtime;      /* how many sec after/before the start time */
332 unsigned int numpoint;     /* number of points between the start and end time */
333 {
334     HDisplayData(hid1, starttime, endtime, numpoint, 1);
335     HDisplayData(hid2, starttime, endtime, numpoint, 0);
336
337     return(dispbuff);
338 }
```

```
342  /* The entry of the history server. It returns the buffer error if exists. */
343  /* invoked by: scheduler (time event driven)                                 */
344  //
345  // external functions involved:
346  //    XTime();           return current time and date in a struct pointer
347  //    XWait(TIME_EV, HISTIME); ** wait for next time event **
348  //    XFalloc(buffer_size); ** allocate a far pointer to an array ***
349  //
350  //    Xalloc(buffer_size);   ** allocate a pointer to an static array**
351  //    XFfree(buffer_ptr);    ** free a far buffer **
352  //    Xfree(buffer_ptr);     ** free a static buffer **
353  //
354  /* returns: BUFFER_ERROR if buffer array cannot be allocated or set free */
355
356  int near HSave()
357  { int (*function)();
358    int i,hid;
359
360   /* initialization */
361   /* partition the memory (static and dynamic RAM) for the trending parameters. */
362   dramsize = DYNAMICRAM/numparam;
363   sramsize = STATICRAM/numparam;
364
365   for (i=1; i(LASTHISID; ++i)
366   {  his[i].dbuffer = XFalloc(dramsize);
367      hstatic[i].sbuffer = XSalloc(sramsize);  /* xalloc for static RAM */
368   }
369
370   for (i=1; i<=LASTHISID; ++i)
371   {  his[i].dyptr = hstatic[i].stptr = -1;  /* initialize buffer pointer */
372      his[i].action_flag = FALSE;
373   }
374
375   for (;;)  /* infinite loop */
376   {  for (hid = 1; hid <= LASTHISID; ++hid)
377      {  if (his[hid].action_flag)
378         {  if (his[hid].his_count > 0)    /*data not ready for saving*/
379            --his[hid].his_count;
380            else if (his[hid].his_count == 0)  /* save data */
381            {  his[hid].his_count = his[hid].his_time;  /* reset record counter */
382               if (hstatic[hid].stptr < sramsize)/* determine static buffer ptr */
383                  ++hstatic[hid].stptr;            /* pointer moves forward */
384            else
385               hstatic[hid].stptr = 0;
386            if (his[hid].dyptr < dramsize)  /* determine dynamic buffer ptr */
387               ++his[hid].dyptr;
388            else
389               his[hid].dyptr = 0;
390            function = his[hid].funptr;      /* save new data in both buffers */
391            his[hid].dbuffer[his[hid].dyptr] =
392            hstatic[hid].sbuffer[hstatic[hid].stptr] = (*function)();
393            if (hid == (int)mAGAET :: hid == (int)mAGAINS) /* update agent stamp*/
394            {  his[hid].dbuffer[his[hid].dyptr] =
395               (his[hid].dbuffer[his[hid].dyptr]
396               & 0xfc) ;agentstamp);
397               hstatic[hid].sbuffer[hstatic[hid].stptr] =
398               ((hstatic[hid].sbuffer[hstatic[hid].stptr]
```

```
400            } & 0xfc) ! agents\.mp);
401            }  /* stamp the agent buffer */
402            hisChid].zerotimeptr=hisChid].dyptr;  /* update the last record time */
403            ctime = xtime();  /* update the current time ptr */
404            hstatic[chid].lrtime->hour  = ctime->hour;
405            hstatic[chid].lrtime->min   = ctime->min;
406            hstatic[chid].lrtime->sec   = ctime->sec;
407            hstatic[chid].lrtime->year  = ctime->year;
408            hstatic[chid].lrtime->month = ctime->month;
409            hstatic[chid].lrtime->day   = ctime->day;
410
411        }
412    }
413
414    xWait((int)TIME_EV, HISTIME);
415
416 }
417
418
419
420
421
```

Wed 10-09-86 11:11:58    MSID.H
Wed 10-15-86 12:10:22

```
 1  /****************************************************************************
 2  *
 3  *   MFO Ver 0.0   kht  7/16/86   2:00pm
 4  *
 5  *   module: MSID.H
 6  *
 7  *   This module is an original, unpublished work and is proprietary to
 8  *   NELLCOR INC., and may not be divulged or copied in any form
 9  *   whatsoever without the express written permission of NELLCOR INC.
10  *
11  *   purpose: This header file defines all the measurement IDs used in the MFO
12  *            modules. It should be included in all the C modules for
13  *            consistency and future maintenance.
14  *
15  *   change log:
16  *         date       by       reason(s)
17  *       8/8/86       kht      deleted ET/Ins Agent B and C
18  *                             added mPLETH for pulse waveform
19  *
20  *       10-7086      kht      moved mPULSE after mBR (breath rate)
21  *
22  ****************************************************************************/
23
24  /* All measurement IDs start with 'm' */
25  typedef enum measurementid {
26      mSAO2 = 1,    /* oxygen saturation */
27      mCO2ET,       /* ET CO2 */
28      mCO2INS,      /* Ins CO2 */
29      mN2OET,       /* ET N2O */
30      mN2OINS,      /* Ins N2O */
31      mAGAET,       /* ET agent A */
32      mAGAINS,      /* Ins agent A */
```

```
33      mBR,            /* breath rate */
34      mPULSE,         /* heart rate from saturation measurement */
35      mECG,           /* ECG */
36      mBP1SYS,        /* blood pressure 1 (systolic) */
37      mBP1DIA,        /* blood pressure 1 (diastolic) */
38      mBP2SYS,        /* blood pressure 2 (systolic) */
39      mBP2DIA,        /* blood pressure 2 (diastolic) */
40      mT1,            /* temperature 1 */
41      mT2,            /* temperature 2 */
42      mLAST,          /* last measurement ID */
43      mPLETH,         /* pulse waveform */
44      mAPNEA,
45      mPulseTimeOut
46      } MSID;
```

ACQ

SECTION B

```
Wed 09-04-86 11:35:48  ALEFTOVE.S
    10-15-86 14:07:36

1      .186
 2      ACQ_MAIN    NAME    Aleftover
 3      include amacro.i      equ    1      ;for amacro.i
 4      include aprolog.i
 5
 6      page+
 7
 8      extrn   _A_BUFNum:word
 9      extrn   _A_Util:far
10
11      extrn   XWait:far
12      ;;;;public _xreporter
13
14      public  COMMLINK,WFLINK,temp0      ;XPOSTA
15
16      BSS     SEGMENT word PUBLIC 'BSS'
17      extrn XCF_ID:word ;ASLV3.OBJ(ASLV3).ASLEDCTRL.OBJ(
18      Lwvf_ptr dw 2 dup(?)        ;assume only if uses
19
20      ;wvf table :
21      dest_b0  dw ?    ;length
22               dw ?    ;length
23      src_b0   dw ?    ;length
24               dw ?
25
26      dest_b1  dw ?    ;length
27               dw ?    ;length
28      src_b1   dw ?    ;length
29               dw ?
30
31      dest_b2  dw ?
```

```
34      src_b2  dw  ?   ;length
35              dw  ?   ;length
36              dw  ?   ;length
37
38      ;temp dest. data buffers (for icomm)
39      temp0   dw  10 dup(?)
40      temp1   dw  10 dup(?)
41      temp2   dw  10 dup(?)
42
43      _BSS    ENDS
44
45      SYS_TEXT  SEGMENT byte PUBLIC 'CODE'
46
47      XPOSTA  proc    far     ;fm. AACQ.OBJ(AACQ)
48              ;gen. wvf. ptr. addr. based on acq. buffer number=0,1 or 2)
49              mov     bx,offset DGroup: dest_b0
50
51              mov     ax,A_BUFNum
52              mov     dx,8            ;8 bytes a wvf table
53              mul     dx
54              add     bx,ax
55              push    bx
56              call    dword ptr Lwvf_ptr
57              pop     bx
58              ret
59      xposta  endp
60
61      ;_xreporter     proc    far
62      ;_xreporter     ret
63                      endp
64
65      COMMLINK proc   far     ;fm. ASLV3.OBJ(ASLV3)...
66      commlink        ret
67                      endp
68
69      WFLINK  proc    far     ;fm. ASWVF.OBJ(ASWVF)
70              ; wvflink ( wf_function, dest_id, number_of_sources,
71              ;            src1_id, src2_id,... )
72              ;wvf server table :
73              ;input: pointer in stack to entry of waveform address table :
74              ;          00 word  pointer to iconn (dest.) buffer
75              ;          02 word  length of dest. buffer
76              ;          04 word  pointer to source (acq.) # 1 buffer
77              ;          06 word  length of source #1buffer
78              ;          buffer structure: (both in acq. server or in comm server')
79              ;          00 word  task id  ;assume the same in src or dest.
80              ;          02 word  data id
81              ;          04 word  count in bytes
82              ;          06....   data
83              c_push
84              mw      Lwvf_ptr,arg1[bp]    ;ofgfset
85              mw      Lwvf_ptr+2,arg2[bp]  ;cs:
86              mov     ax,arg5[bp]          ;src_id
87              GetFacb ax                   ;get token
88              mov     bx,ax
89              mov     ax,offset DGroup: temp0
90              mov     dest_b0,ax
91              mov     ax,offset DGroup: temp1
```

```
 92              mov      dest_b1,ax
 93              mov      ax,offset DGroup: temp2
 94              mov      dest_b2,ax
 95
 96              mw       src_b0,[bx].A_BUFFER0
 97              mw       src_b1,[bx].A_BUFFER1
 98              mw       src_b2,[bx].A_BUFFER2
 99              xor      ax,ax     ;good return
100              c_ret
101
102     wflink  endp
103
104     SYS_TEXT         ENDS
105
106              END
107
108
Wed 10-15-86 14:09:36      AANOUT.S 1      ;SEE if need to wait 50 us bet ADC set & S/H
  2      ;AAnoutInit() called by AInit()
  3      ;need SetAnal()
  4      ;Sndanout() is in s_dlv3.s
  5      ;SEchopulse() is in s_wvf.s
  6      ;arrange is EXTRN; naddip
  7
  8                       page 52,132
  9      .LIST
 10      ;TESTSAT         equ      1            ;take out comment to allow SAT to use
 11                                              ;motor & pump control for test
 12                       title "Analog output"
 13              NAME     AANOUT
 14      ;**********************************************************************
 15
 16      ; MFO Ver 0.0
 17      ;
 18      ; COPYRIGHT (C) 1986 NELLCOR INCORPORATED
 19      ;
 20      ; THIS IS AN ORIGINAL, UNPUBLISHED WORK AND IS PROPRIETARY TO NELLCOR, INC.,
 21      ; AND MAY NOT BE DIVULGED OR COPIED IN ANY FORM WHATSOEVER WITHOUT
 22      ; EXPRESS PERMISSION FROM NELLCOR, INC.
 23      ;
 24      ; Module: a_adcvt.s
 25      ;
 26      ; modification history :
 27      ;
 28      ; 8th July 85 rak   Separate module
 29      ; 6th June 86 slc   revised for MFO, putback sndanout();
 30      ;                    echopulse() moved to s_wvf.s
 31      ;  1 July 86 slc    A_SetAnal() in aacq.s
 32      ;  5 Sept 86 slc    modif. anon(), delete allsample() & jamall()
 33      ; 10 Sept 86 slc    add raw drivers for both aeep,r.n.c & gas modules
 34
 35      ;External & Public modules
```

```
38  ;
39  PUBLIC  AAnout        ;refresh an on board analog level, called by acq_data()
40                        ;A_SetAnal ;not available yet
41  PUBLIC  AAnoutInit    ;called by AInit() in aacq.s
42  PUBLIC  anon          ;set analog demux
43  PUBLIC  anat@         ;turn all analog channels to 0
44          EXTRN         Aputadv:NEAR
45  public  anopbf        ;to aacq.s for ASetAnal()
46  public  AVLEDir       ;ir sensor LED level
47  public  AVLEDred      ;red sensor LED level
48  public  _AVmotor      ;voltage rel. to motor speed
49  public  _AVpump       ;voltage rel. to pump speed
50
51  ; for eeprom.c
52  public  _A_OUTEEP     ;write eeprom port
53
54  ; raw drivers for gas module
55
56  public  _AMotorPower
57  public  _APumpPower
58  public  _AZeroSig
59  public  _ABackFlushsig
60
61          extrn  svdvpa:byte    ;save the device port a
62          extrn  Asetict:word   ;settling const.
63
64  ;*******************************************************************
65
66  include amacro.i        ;ald.1 & acb.1 included
67  ;INCLUDE DEFS.a88
68  ;INCLUDE IO MACRO.a88
69  ;INCLUDE RAM.EXT
70
71  include aprolog.i
72
73
74  _BSS    SEGMENT word PUBLIC 'BSS'
75
76          SUBTTL "Analog OUTPUT STUFF..."
77
78  ;!The sequence of this table must match the sequence
79  ;of the table in the AANOUT routine!!
80
81  ;???    EXTRN    anrange:byte
82
83  EEPWRPORT equ   0       ;eeprom write port in AMux
84  anopbf    LABEL WORD    ;beginning marker for the buffers
85  AVLEDir   DW    ?       ;ir sensor LED level
86  AVLEDred  DW    ?       ;red sensor LED level
87  _AVmotor  DW    ?       ;voltage rel. to motor speed
88  _AVpump   DW    ?       ;voltage rel. to pump speed
89  ANOFMX    EQU   ($-anopbf)/2   ;no. of anout channels
90  anopix    dw    ?       ;anout index:0,1,2,3,0...
91  public  anopix
92  Vvolsv    DW    ?       ;SAVED VOLUME (FOR END OF COUNT)
93  tempx     DB    ?
94  DLEN      equ   $ - anopbf
95
```

```
  96          _BSS    ENDS
  97
  98
  99                  SUBTTL  "Output to next analog line"
 100
 101          ;Controls analog O/P voltages for AVLEDs, AVmotor, AVpump
 102          ;Routine sets voltage and O/P device select in turn
 103          ;Elapsed time (approx.):810 us (was ~250 microsec)
 104
 105          SYS_TEXT        SEGMENT BYTE PUBLIC 'CODE'
 106
 107          anidx   equ     this byte
 108
 109          ; analog output channel select patterns on 8255 device port a
 110
 111                  DB      1110B           ;ir analog out channel on dvpa
 112                  DB      1101B           ;red analog out channel on dvpa
 113                  DB      1011B           ;motor speed analog out channel on dvpa
 114                  DB      0111B           ;pump speed analog out channel on dvpa
 115
 116          AANOUT:                         ; PUBLIC
 117          ;Aputadv (ax=anopbf[anopix]); (no settling)
 118          ;if (++ anopix == ANOPMX ) anopix = 0;
 119          ;call anon();
 120
 121                  MOV     bx,anopix       ;cycle to next O/P voltage
 122                  shl     bx,1            ;get current value of index
 123                  MOV     ax,offset DGroup ;into word
 124                  call    Aputadv         anopbf[BX]  ;get voltage in 12 bits
 125                  shr     bx,1            ;anout ch.#
 126                  call    anon            ;gate to the channel indexed by bx
 127                  RET
 128
 129
 130          ;init routine; called by AInit()
 131
 132          AAnoutInit      proc    near
 133                  clrram  anopbf,DLEN
 134                  call    anat0           ;zero all analog output
 135                  ret
 136          AAnoutInit      endp
 137
 138          ;ANON - Turn on the analog O/P selected by anopix. Pulse the
 139          ;switch for the following sample/hold. The assumption is made
 140          ;that only one analog O/P channel is operating at one time, so
 141          ;this routine leaves only the selected channels on.
 142          ; ~ 10 us, was 147 states = 48 microsec
 143
 144
 145          ANON:                           ; PUBLIC
 146                  mov     al,svdvpa
 147                  and     al,0F0h
 148                  or      al,CS:anidx[bx]
 149                  mov     di,ANVPORT       ;to analog demux index
 150                  mov     es,di
 151                  xor     di,di
 152                  mov     es:[di],al       ;es:di = device port a
```

```
153                    ;step the index while charging the S/H capacitor
154            INC     bx
155            CMP     bx,ANOFMX       ;same as max num O/P voltages ?
156            JNZ     L_15            ;no
157            xor     bx,bx           ;clr anopix
158     L_15:  MOV     anopix,bx       ;update index
159                    ;disable analog demux and stop charging the capacitor
160            or      al,0fh
161            mov     es:[di],al
162            ret
163            get_pb
164            OR      AL,SH_EN        ;enable the s/h demux
165            put_pb
166            XOR     BX,BX
167            MOV     BL,anopix
168            MOV     offset DGroup: sh_sel[BX],AL    ;trigger the s/h demux
169            ret
170
171
172
173     ;ANAT0 - Set all analog O/P to 0 volts
174
175     anat0: xor     ax,ax
176            mov     anopix,ax
177            mov     bx,ax
178            mov     cx,ANOFMX
179            mov     offset dgroup:anopbf[bx],ax    ;clr all output buffers
180     a0loop: inc    bx
181            inc     bx
182            loop    a0loop
183            call    aanout
184            call    aanout                          ;clr all 4 outputs
185            call    aanout
186            call    aanout
187            RET
188
189     _OutEep proc    near            ;write eeprom port
190            push    bp
191            mov     bp,sp
192            push    dx
193            mov     ax,4[bp]
194            mov     dx,EEPWPORT     ;eeprom write port
195            out     dx,al
196            pop     dx
197            pop     bp
198            ret
199     _OutEep endp
200
201     ;***********************************************************
202     ; raw drivers for gas module
203
204     _AMotorPower proc   far
205     IFNDEF TESTSAT push  bp
206            mov     bp,sp
207            mov     ax,6[bp]
208            mov     _AVMotor,ax
209
```

```
210        ENDIF
211               pop     bp
212               ret
213        _AMotorPower  endp
214
215        _APumpPower   proc    far
216        IFNDEF TESTBAT
217               push    bp
218               mov     bp,sp
219               mov     ax,6[bp]
220               mov     _APump,ax
221        ENDIF
222               pop     bp
223               ret
224        _APumpPower   endp
225
226        ; Zero and Back flush signals be sent by anon() every 5 ms
227        _AZeroSig     proc    far
228               push    bp
229               mov     bp,sp
230               cmp     word ptr 6[bp],0
231               jne     setoff
232               or      svdvpa,ZEROSIG
233               pop     bp
234               ret
235        setoff: and   svdvpa,not ZEROSIG
236               pop     bp
237               ret
238        _AZeroSig     endp
239
240        _ABackFlushsig proc   far
241               push    bp
242               mov     bp,sp
243               cmp     word ptr 6[bp],0
244               jne     Fsetoff
245               or      svdvpa,BACKFLUSH
246               pop     bp
247               ret
248        Fsetoff: and  svdvpa,not BACKFLUSH
249               pop     bp
250               ret
251        _ABackFlushsig endp
252
253        SYS_TEXT      ENDS
254               END
255
256        ACCMAIN.S
257
Wed 10-14-86 10:30:14
    10-15-86 14:02:36

1 ; design notes:
2 ;ADD _APGOFFCHG(FACB,PGAIN,OFFSET) FOR LUCICLLE
3 ;
4 ; pid, did, DID is built into buffer0,1,2 every time linked
5 ; smux() remote/local
6 ; Ainit() is the 1st one to be called, chk if iniclk()
```

```
 7      .186    NAME    ACQMAIN
 8              title "*** AACQMAIN - The Analog Acquisition Process ***"
 9
10              page 52,132
11
12     page+
13     ****************************************************************************
14     ****************************************************************************
15
16
17     MFO Ver 0.0
18
19     Module: acq_proc.s
20
21     COPYRIGHT (C) 1986 NELLCOR INCORPORATED
22
23     THIS IS AN ORIGINAL, UNPUBLISHED WORK AND IS PROPRIETARY TO NELLCOR, INC.,
24     AND MAY NOT BE DIVULGED OR COPIED IN ANY FORM WHATSOEVER WITHOUT
25     EXPRESS PERMISSION FROM NELLCOR, INC.
26
27     recent modification history :
28
29      1 May 86  slc   start MGM project, start this module from INTS.a86 of N100
30      2 May 86  slc   start AcqData(), build ACB tables
31      3 May 86  slc   move in lag_init(), led_init() measpoff() into Ainit()
32      5 May 86  slc   A_Putlist() is done
33      6 May 86  slc   A_Util() is done
34      7 May 86  slc   second round acq_proc spec done, _A_Linkc(), _A_Linkc() done
35      9 May 86  slc   3rd round spec, readjust all functions, merge _A_Link() into _A_Util()
36     12 May 86  slc   tri-buffer init done, SysConst segm not used
37     13 May 86  slc   split defs file "acq.inc", hdwr init is in talch_init()
38     14 May 86  slc   split _A_Link() from _A_Util(), renewed spec.,macros in acq.inc
39     15 May 86  slc   split _AJData() from _A_Util, A_COND & A_LENGTH redefined
40     19 May 86  slc   acq_data doesn't bother offset any more
41     28 May 86  slc   remote ADC supported
42     30 May 86  slc   Xpost to every MT with block mode
43     13 June 86 slc   split include files aname.inc,amacro.inc,acb.inc
44     18 June 86 slc   remote channel setup in the begining of sampling interval
45     20 June 86 slc   change ASCII name into A_ID, add A_PID
46     21 July 86 slc   add A_SetAnal(); 2 local channels per slot max.
47      2 July 86 slc   sat sampling limit = 3 ir or led, calls ARmux() for remote
48
49      1 Aug 86  slc   inamp/led/softrail flags are checked in every entry
50      6 Aug 86  slc   Ainit() called by anlginit(), near
51     15 Aug 86  slc   A_PutList() doesn't pass in stack, no xpost() call
52     22 Aug 86  slc   add eeprom ACB & init call
53     24 Sept 86 slc   suspend acq. if _Acq_Disable is set (for aeeprom.c)
54     29 Sept 86 slc   buffer switching in acq_data() is interruptable
55                      calls xpost to awaken wave form server
56
57     Purpose:
58
59     Acq_Data is the main body of this process, which gets in analog
60     samples @ main system interrupt, assumed every 1.25 milliseconds.
61
62     Procedures:
```

```
65  --  call AADcvt() (explicitly or implicitly) to do Analog to Digital
66        conversions based on ACB tables pointed to by A_ArryPtr,
67        see ACB structure for detail.
68  --  if slow data, use A_LIST to pass sample to linked MTs.
69  --  if waveform data, put data in one of the 3 linear buffers.
70  --  call AAnout() to refresh analog levels
71  --  check if end of time slice, post to WVF server and MTs and
72        switch to next linear buffer if so.
73
74  ; Public Data:
75  ; to wvf_proc()
76
77      PUBLIC    _A_BufNum   ;0,1,2 = linear buffer 0,1 or 2 is just full
78      PUBLIC    _A_BufTbl   ;array of 3 offset addr.s of linear buffer 0,1,2
79      PUBLIC    _A_ArrayPtr ;array ptrs to successive ACBs, init'd by AInit()
80      public    _Acq_Disable ;for eeprom.c
81  ;for test
82      public    AcqCnt       ;interrupt counter
83      extrn     anopbf:word  ;from aanout.s; beginning marker for
84                             ;the analog refresh buffers
85      extrn     svdvpa:byte
86
87  ; Public procedures:
88
89      PUBLIC    Acq_Data   ;the system process
90
91      PUBLIC    AInit      ; called during system init by anlginit.s
92                           ; init data base & analog hdwr
93
94      PUBLIC    _A_Link    ; for MTs to build linked data transfer function pointers
95                           ; to ACB (Acquisition Control Block)
96
97      PUBLIC    _A_Data    ; for MTs to pass acquisition procedure pointer to ACB
98                           ; (Acquisition Control Block)
99
100     PUBLIC    _A_Util    ; C level utility call,
101                          ; some ACB items can be read or modified thru it.
102     PUBLIC    _A_SetAnal ;to pass an analog refresh level
103
104 ; local procedures:
105
106 --  A_PutList   ; make a slow data sample or a waveform data block known
107               ; to all linked MTs functions
108
109 ;*******************************************************************************
110 ;page+
111
112     EXTERNAL Declaration, all in sys_text
113
114 ;in sched.s
115     EXTRN   _XReportErr:far   ;post error
116     extrn   _xpid:near        ;to get process id
117     extrn   _post:far
118     ;A                        ;acq. error code
119 ACQ_ERR equ
```

```
123  ;in aeeprom.c
124         extrn    _AEEPInit:near
125         extrn    _aeread:far
126         extrn    _aewrite:far
127  ;in AAdcvt.s
128         EXTRN    AAdcvt:far      ;A to D conversion
129         EXTRN    AAdcInit:near   ;init Aadcvt.s data base
130         EXTRN    ASRmux:near     ;select remote channel mux
131  ;in Aanout()
132         EXTRN    AAnout:near     ;on board analog level refreshing
133         EXTRN    AAnoutinit:near ;analog output routine init
134         EXTRN    calch_init:far  ;0X_calch
135  ;;;
136  ; System Definition
137
138         BUF_CYCLE  equ  40       ;every 40 * 1.25 milliseconds to switch buffer
139         A_BUF_LEN  equ  200      ;max. tri-buffer size is 200 word each
140         LINK_MAX   equ  100      ;max. linked functions = 100
141         CALRFQ     equ  7*30     ;ox. sensor calibration frq, about twice a second
142         ANOUTFQ    equ  4        ;do anout() every 4*1.25=5 ms
143
144  ACQ_MAIN  equ  1       ; to avoid external decls in amacro.inc
145  include  amacro.i
146  include  ..\xevent.i
147  include  ..\xclock.i
148  include  acbdefs.i   ; ACB channel definitions
149  include  aprolog.i
150
151  SYS_TEXT  SEGMENT byte PUBLIC 'CODE'
152  include  acbtable.i
153  SYS_TEXT  ENDS
154
155  _BSS      SEGMENT word PUBLIC 'BSS'
156
157  AcqDataStart   LABEL  word           ; start mark
158  StartDelayCnt  dw  ?    ;wait 500 ms till disp. side ready
159  AcqCnt         dw  ?    ;interrupt counter
160  _Acq_Disable   dw  ?    ;for eeprom.c
161  _A_BufNum      DW  ?    ;tri-buffer index 0,1 or 2, is public (to WvfProc());
162                          ;to be updated if the buffer pt. to by A_BufINum is full
163  A_BufINum      DW  ?    ;as above, but local
164  A_BufIINum     DW  ?    ;as above, but used during buffer switching processing
165  A_CycleCnt     DW  ?    ;no. of cycles since last buffer switch
166  public _A_CycleCnt
167  RemotePtr      DW  ?    ;set if time to do remote A/D
168  anoutct        DW  ?    ;timer for anout refresh
169
170         ; 3 tri-buffers for wave form data
171  ; Structure :
172  ; Process ID       DW  ?   ;A_IDs
173  ; Data (Channel) ID DW  ?   ;total sampled data (no. of words) of that channel
174  ; Data Length      DW  ?   ;defined in ACB.A_BUFLNGTH0,the max.length in words
175  ; data            next channel
176  ;........
177
178
179  _A_BufTbl  DW  3 dup(?)  ; public offset addr. of the tri-buffers 0,1 & 2
180            DW  0         ; end mark
```

```
181     A_Buf0         DW      A_BUF_LEN dup(?)    ; 3 buffers, actual lengths build by a_ACBInit()
182     A_Buf1         DW      A_BUF_LEN dup(?)
183     A_Buf2         DW      A_BUF_LEN dup(?)
184
185     _A_ArrayPtr  LABEL   WORD                  ;array ptrs to successive ACBs, init'd by AInit()
186                    DW      ACB_CNT dup (?)
187                    DW      ?                   ;end mark, 0
188
189     A_AcbBlk       ACB     ACB_CNT dup (<>)    ;ACB s
190
191     ;      MT function links data structure
192
193     LinkList       struc
194            AT_LIST    DW   ?                   ;code offset
195            AT_PROC    DW   ?                   ;code segment
196                       DW   ?
197     Linklist       ends
198
199     ; function pointers control block, linked list of MT function entries
200     ; check A_FutList() & _A_Util() for explanation
201
202     A_LinkBlk  label      word
203                    DW  ?                       ;the free space pointer,start from 0
204                    LinkList   LINK_MAX dup (<>) ;temporarily assume not more than 100 funcs
205
206     aeep_blk dw 64 dup (?)                     ;space for EEPROM test
207     public aeep_blk
208
209     D_LENGTH       equ     $ - AcqDataStart    ;data size
210     _BSS     ENDS
211     Page+
212
213     SYS_TEXT       SEGMENT byte PUBLIC 'CODE'
214
215            SUBTTL  "Acq_Data Main "
216
217     ;********************************************************************
218     ;
219     ; MFO sampling rate specification :
220     ;CH #   DATA      LOCAL    SAMPLING               CH #   DATA        LOCAL    SAMPLING
221     ;                          RATE (HZ)                                          RATE (HZ)
222     ;  1    ECG  GAS                200                11    GAS PRESS             50
223     ;  3    CO2  GAS                100                12    GAS TEMP              1
224     ;  4    N2O  GAS                100                13    GAS FLOW              1
225     ;  5    BP1           X         100                14    BODY T1               1
226     ;  6    BP2           X         100                15    BODY T2               1
227     ;  7    RESPIRATION              57.1              16    SaO2 CAL              1
228     ;  8    SaO2 IR       X          57.1
229     ;  9    SaO2 RED      X          50
230     ; 10    AGENT                    50
231     page+
232     ;********************************************************************
233     ;
234     ;
235     ;********************************************************************
236     ; Function:     Acq_Data
237     ;
```

```
238  purpose:     1) Do analog to digital conversion and pass to MTs
239               2) Refresh on board analog voltage
240
241  procedure :
242
243  Called by SchdProc every 1.25 milliosec., to get analog samples , is
244  table driven, with ACB table entry pointers in _A_ArrayPtr
245
246  I) if (Acq_Disable=true) goto Acq_Ret;
247      /* do ad measure if remote channel is waiting */
248  if (RemotePtr != 0) { RemotePtr.A_COND.A_WAIT = RemotePtr =0;
249                         AdcProc(bx=RemotePtr); } /* RemotePtr = remote ACB ptr */
250
251  II)  /* pick next REMOTE channel */
252  for (n=0; n ( RemoteCnt; n++;)
253  { p = A_ArrayPtr [n];
254    if (bx.A_COND.Active)   /*if channel not disabled */
255      { if (-- bx.A_TIMERCOUNT==0)
256        { bx.A_TIMERCOUNT=bx.A_TIMERSET;
257          bx.A_COND.A_WAIT = true; }
258          if  { bx.A_COND.A_WAIT && RemotePtr==0)
259          { bx.A_COND.A_WAIT = 0;
260            RemotePtr=bx;
261            ASRmux(bx);    /* select remote channel mux */ }
262       }
263    }
264
265  III)  /* process all timed out LOCAL ACBs */
266  for ( ; p = A_ArrayPtr [n] !=0 ; n++)
267  { if (bx.A_COND.Active)   /* if channel not disabled */
268      { if (-- bx.A_TIMERCOUNT==0 )  /*if time is up */
269        { bx.A_TIMERCOUNT=bx.A_TIMERSET;
270          AdcProc(bx);  /* do local a to d */ }
271      }
272  }
273
274  IV)  /* refresh analog level */
275  if ( -- anoutct==0 ) { anicct=ANOUTFQ; AAnout();}
276
277  V) if ( -- A_CycleCnt != 0 ) return;
278      /*switch buffer & post Wvf Proc., MTs */
279  A_CycleCnt = BUF_CYCLE;   A_BufINum =:A_BufINum;
280  if ( ++ A_BufINum == 3 ) A_BufINum = 0;
281      /* if wvf data, then init data count to 0 */
282  for ( n = 0 ; p = A_ArrayPtr[n] != 0; n++ )
283  { if( bx.COND.F_DATA = bx.COND.Active== 1 )
284        bx.[A_BufferCA_BufINum].A_PUTIDX] = 0;
285  }
286  STI;  /* enable interrupt */
287      /* if wvf data, then send data pt. to MTs linked after A_LIST */
288  for ( n = 0 ; bx= A_ArrayPtr[n] != 0; n++)
289  { if( [bx].COND.F_DATA = [bx].COND.Active == 1 )
290        A_PutList (ax = [bx].A_BUFFER0[_A_BufINum]); }
291  }
292  VI)
```

```
295     ;   _A_BufNum = A_BufINum;      /* for wvf server */
296     ;   _xpost (PID_WVF,XA_DATA_EV);  /* awaken wvf server */
297     ;Acq_Ret:
298     ;****************************************************************
299     ;****************************************************************
300     page+
301     Acq_Data proc   near
302             ;wait a while until display side ready
303             cmp     StartDelayCnt,0
304             jz      AcqStart
305             dec     StartDelayCnt
306             jmp     Acq_ret
307     AcqStart:
308             mov     al,svdvPa               ;test accuracy
309             or      al,TEST_FIN1
310             mov     di,ADVPORT
311             mov     es,di
312             mov     es:[di],al              ;es:di = device port a
313             xor     ax,ax
314             mov     ax,AcqCnt
315             inc     ax                      ;interrupt counter
316             jz      acq_start
317             mov     AcqCnt,ax
318     acq_start:
319     ; I)    /* do ad measure if remote channel is waiting */
320             cmp     Acq_Disable,0           ;suspend acq if eeprom R/W
321             je      Acq_sti
322             jmp     Acq_Ret
323     Acq_st1:
324             mov     bx,RemotePtr
325             or      bx,bx
326             jz      Acq_II
327             mov     RemotePtr,0             ;clr the flag
328             and     [bx].A_COND,not A_WAIT
329             call    AdcProc                 ;assume already settled, do it
330     ; II)   /* setup REMOTE channel */
331     Acq_II: xor     si,si
332     Acq_II0: mov    bx,_A_ArrayPtr[si]      ;get an ACB entry ptr
333     Acq_II1: test   [bx].A_COND.Active      ;channel is active ?
334             jz      Acq_II20                ;n, next one
335             dec     [bx].A_TIMERCOUNT
336             jnz     Acq_II0
337             mov     [bx].A_TIMERCOUNT,[bx].A_TIMERSET ;reset timer
338             or      [bx].A_COND,A_WAIT      ;yes, set wait flag
339     Acq_II10: ;set RemotePtr if highest priority
340             test    [bx].A_COND,A_WAIT
341             jz      Acq_II20
342     Acq_II15:
```

```
3351            cmp     RemotePtr,0
3352            jnz     Acq_II20
3353            mov     RemotePtr,bx        ;set remote mux
3354            call    ASRmux
3355   Acq_II20:
3356            inc     si
3357            inc     si
3358            cmp     si,RemoteCnt * 2    ;finished all remote channels ?
3359            jne     Acq_II0             ;not yet
3360
3361   ; III)           /* process all timed out LOCAL ACBs */
3362
3363   Acq_III:
3364            mov     bx,A_ArrayPtr[si]
3365            or      bx,bx                       ;end of array ?
3366            jz      Acq_IV                      ;y, go to chk buffer switch
3367            test    [bx].A_COND,Active          ;channel is active ?
3368            jz      Acq_III5
3369            dec     [bx].A_TIMERCOUNT
3370            jnz     Acq_III5
3371            mov     [bx].A_TIMERCOUNT,[bx].A_TIMERSET  ;reset timer
3372            call    AdcProc                     ;yes, do it
3373
3374   Acq_III5:
3375            inc     si
3376            inc     si
3377            jmp     Acq_III
3378
3379   ;IV)            /* refresh analog level */
3380   Acq_IV:
3381            dec     anoutct
3382            jnz     Acq_V
3383            mov     anoutct,ANOUTFQ
3384            call    AAnout  ; refresh analog level
3385
3386   ; V)            /* switch buffer & post Wvf_Proc , MTs */
3387
3388   Acq_V:          ;chk if to switch tri-buffer
3389            mov     al,svdvpa                   ;test accuracy
3390            mov     di,ADVPORT
3391            mov     es,di
3392            xor     di,di                       ;es:di = device port a
3393            mov     es:[di],al
3394            dec     A_CycleCnt
3395            jz      Acq_VI
3396            jmp     Acq_ret                     ;not yet
3397
3398   Acq_VI:
3399            mov     A_CycleCnt,BUF_CYCLE
3400            mov     A_BufINum,A_BufINum         ;don't use A_Buf_Num
```

```
401                    ;incr A_BufINum for next time slot
402             mov     ax,A_BufINum
403             inc     ax
404             cmp     ax,3
405             jne     Acq_V2
406             xor     ax,ax
407     Acq_V2: mov     A_BufINum,ax
408             mov     di,ax
409             shl     di,1
410             mov     si,-2
411     Acq_V25: ;      /* if wvf data, then init data count to 0 in the new buffer */
412             add     si,2
413             mov     bx,A_ArrayPtr[si]
414             mov     bx,5x
415             or      Acq_V3          ;if end
416             jz      ax,[bx].A_COND
417             mov     ax,Active+F_DATA   ;channel is active & wave form ?
418             and     ax,Active+F_DATA
419             cmp     Acq_V25            ;no
420             jne     bx,[bx].A_BUFFER@[di] ;get block addr.
421             mov     [bx].FUTIDX,0      ;zero A_BUFFERx.LENGTH
422             mov     Acq_V25
423             jmp
424     Acq_V3: ; start interruptable part
425             STI
426     ;..     nop
427             mov     si,-2
428     ;to post if waveform data
429     Acq_V35: add    si,2
430             mov     bx,A_ArrayPtr[si]
431             mov     bx,5x
432             or      Acq_VI          ;if end
433             jz      ax,[bx].A_COND
434             mov     ax,Active+F_DATA   ;channel is active & wave form ?
435             and     ax,Active+F_DATA
436             cmp     Acq_V35            ;no
437             jne
438             ; post to MTs if wave form data
439             ; pass ax = buffer pointer
440             mov     di,A_BufINum
441             shl     di,1
442             mov     ax,[bx].A_BUFFER@[di]
443             push    si
444             call    A_FutList
445             pop     si
446             mov     Acq_V35
447             jmp     ; awaken wvf server
448
449     Acq_VI: mov     A_BufNum,A_BufIINum  ; for wvf server
450             mov     bx,PID_WVF
451             mov     ax,XA_DATA_EV
452             call    xpost
453
454     public Acq_Ret
455     Acq_Ret: mov    al,svdvpa       ;test accuracy
456
457
```

```
458         mov     di,ADVPORT
459         mov     es,di
460         xor     di,di           ;es:di = device port a
461         mov     es:[di],al
462         ret
463 Acq_Data endp
464 page+
465 ;*****************************************************************************
466 ; Function:     AdcProc
467 ;
468 ; purpose:      1) Do analog to digital conversion directly or indirectly
469 ;               2) Error Post if error exist
470 ;               3) send sampled data to linear buffer (if wave form data)
471 ;               4) or post data to linked measurement task procedures
472 ;                  (if slow data)
473 ;
474 ; input   :     only called by acq_data()
475 ;               bx = ACB offset pointer = p; ax=1/0 = remote/local channel
476 ;
477 ; procedure :
478 ;
479 ; { if (bx.A_PROC != 0) DX = bx.A_PROC();  /* assembly level */
480 ;   else ax = AAdcvt ();                   /* dx = data */
481 ;   if ( bx.A_COND.F_DATA == 1 )  /* if wave form data, put in tri-buffer */
482 ;               /* struc: PID_, DID, FUTIDX, data */
483 ;       m = bx.A_BUFFER [A_BufINum]
484 ;       ++ FUTIDX;  m.[FUTIDX] = ax;
485 ;   }
486 ;   else A_PutList (ax);  /* make slow data known to all concerned */
487 ;
488 ;*****************************************************************************
489
490 AdcProc proc    near
491         push    si                      ;saves
492         push    bx
493         cmp     word ptr 2[bx].A_PROC,0 ;want to do it yourselves?(if ptr linked)
494         jnz     Acq_Sd                  ;y, n, I do it
495         call    AAdcvt
496         call    Acq_chkerr              ;see if error ?
497         jmp     Acq_ok
498 ;
499 Acq_U10: call   dword ptr [bx].A_PROC
500 Acq_ok: pop    bx                       ; you do it
501         test    [bx].A_COND.F_DATA
502         jz      Acq_Sd                  ;to post slow data
503 ;wave form data, put in tri-buffer
504 ;get present tri-buffer address
505         mov     di,A_BufINum
506         shl     di,1
507         mov     si,[bx+di].A_BUFFER     ;get a tri-buf. ptr in si
508         add     si,FUTIDX               ;update FUTIDX
509         mov     cx,[si]
510         add     cx,2
511         mov     [si],cx
```

```
516             acq_10: add     si,cx           ;pt. to data
517                     mov     [si],ax         ;save a wvf sample
518                     pop     si
519                     ret
520
521             Acq_Sd: ;post slow data
522                     call    A_PutList
523             Acq_Sdret:
524                     pop     si
525                     ret
526
527             AdcProc endp
528
529 ;*********************************************************************
530 ;
531 ;       Function        A_PutList       ;local
532 ;
533 ;       -- call & pass a slow data sample or a block of data to linked
534 ;          MT functions (C level), the root of the link is the A_LIST of ACB.
535 ;          bx saved
536 ;
537 ;       entry
538 ;       -- bx   : ACB token
539 ;       -- ax   : data to be passed to all linked functions ( for slow data )
540 ;       -- cx   : data block offset address ( for wave form data)
541 ;
542 ;*********************************************************************
543
544             A_PutList proc   near
545
546                     push    bx              ;list addr.
547                     mov     bx,[bx].A_LIST
548             PutList1:
549                     or      bx,bx
550                     jnz     PutList2
551                     pop     bx
552                     ret                     ;quit if A_LIST = 0 or its last link
553             PutList2:
554                     push    bx
555                     push    ax              ;save sampled data
556                     call    dword ptr [bx].AT_PROC
557                     pop     ax
558                     pop     bx
559                     mov     bx,[bx].AT_LIST ;to next link
560                     jmp     PutList1
561
562             A_PutList endp
563             page+
564 ;*********************************************************************
565 ;
566 ;       Function        A_Link
567 ;
568 ;       purpose:
569 ;       -- to pass a data transfer function pointer from MT into linked list
570 ;
571 ;       -- entry
572
```

```
          arg1        arg2         arg3
       A_ID      AT_PROC offset   AT_PROC seg
     while AT_PROC = function pointer that a sample (if slow data) or
                     data block (if wave form data) to be posted
;*************************************************************
;*************************************************************

_A_Link proc    far
         c_push
         mov    si,arg1[bp]     ;get A_ID, arg1
         mov    bx,offset DGroup: A_ArrayPtr - 2
L_f1_1:  inc    bx              ;next ACB table
         inc    bx
         mov    di,[bx]
         or     di,di
         jz     U_err           ;error if end of table
         cmp    si,[di]
         jne    L_f1_1          ;same ?
         mov    si,di           ;y, get ACB offset (FACB)
; to extend the linked list
; si = FACB arg2,3 = AT_PROC offset,AT_PROC
; ret: ax=status.. 0 ok; -1 space ovfl;
         mov    di,offset DGroup: A_LinkBlk ;get free space pointer
         mov    ax,[di]
         or     ax,ax           ;init A_LinkBlk
         jnz    L_f2_1
         mov    ax,di           ;free space starts after A_LinkBlk
         add    ax,2
         mov    [di],ax
L_f2_J:  ; update free sp.ptr by + 1 link size for next round
         add    ax,type LinkList
         ;error if over the space limit
         cmp    ax,offset DGroup: A_LinkBlk + LINK_MAX*type LinkList
         jb     L_f2_1
         mov    ax,-1
         jmp    short U_ret1
L_f2_1:  xchg   [di],ax
         mov    bx,[si].A_LIST  ;no link yet ?
         or     bx,bx
         jnz    L_f2_4
         mov    [si].A_LIST,ax  ;not yet, to set it
         mov    bx,ax
         jmp    short L_f2_7    ;bx=link root ptr
;di=free sp.ptr, bx=link root ptr
;search till the end of the link
L_f2_4:  cmp    word ptr [bx],0 ;end ?
         jz     L_f2_6
         mov    bx,[bx]         ;follow the stream
         jmp    L_f2_4
```

```
631  l_f2_6: ;end of link
632          mov    [bx],ax                      ;next link pointer
633          mov    bx,ax                        ;at the free space
634  l_f2_7:
635          mov    cx,arg2 [bp]
636          mov    [bx].AT_PROC,cx              ;put fct_offset
637          mov    cx,arg3[bp]
638          mov    [bx+2].AT_PROC,cx            ;put fct_seg
639          jmp    short U_ret
640  U_Err:
641          mov    ax,ACQ_ERR
642          call   _XReportErr                  ;post error
643  c_ret
644  A_Link endp
645  page+
646
647  ;************************************************************
648  ;
649  ;        Function   A_Data
650  ;
651  ;  purpose: -- to pass an acquisition function pointer from MT into ACB
652  ;
653  ;  -- entry
654  ;          arg1         arg2        arg3
655  ;          A_ID     A_PROC offset  A_PROC seg
656  ;
657  ;   while A_PROC == an ACB field, is a function pointer of a wave form data
658  ;                                  acquisition server
659  ;
660  ;************************************************************
661
662  A_Data proc    far
663          c_push
664          mov    si,arg1 [bp]    ;get A_ID, arg1
665          mov    bx,offset DGroup: A_ArrayPtr - 2
666  A_f1_1: inc    bx
667          inc    bx                              ;next ACB table
668          mov    di,[bx]
669          or     di,di
670          jz     U_Err                           ;if end of table
671          cmp    si,[di]
672          jne    A_f1_1                          ;same ?
673          ;get ACB offset (PACB)
674          ;to setup the func ptr of acquisition procedrue
675          ; si = PACB arg3 = A_PROC offset
676          ; ret: ax=status.. 0 ok; -1 if already set up
677          mov    ax,arg2 [bp]     ;put fct_offset
678          xchg   ax,[di].A_PROC
679          or     ax,ax            ;already setup ?
680          jz     l_f1_1           ;v
```

```
688              mov     [di].A_PROC,ax  ;n,put back
689              jmp     short U_reti
690     l_d_1:   mov     [di+2].A_PROC,arg3[bp] ;error ret, ax <> 0
691              jmp     short U_ret                    ;put fct_seg
692
693     _A_Data  endp
694              page+
695     ;********************************************************************
696                     Function   _A_Util
697     ;********************************************************************
698     ; purpose:
699     ;
700     ; -- it support  A_Link() & _A_Data to setup acquisition or data transfer
701     ;         function pointers. (by function code 2 & 3)
702     ; -- pass PGAIN or modify A_COND as MTs' need
703     ;
704     ; -- entry   status = _A_Util ( fctn code, arg2, arg3, arg4 )
705     ;            status returned in AX = 0 .... ok
706     ;
707     ; fctn code    arg2       arg3      arg4     returns
708     ;
709     ;    1         A_ID    ;get TOKEN ( ACB pointer ),error if return=0
710     ;    2         PACB    ACB offset      data    ;to write an ACB field
711     ;    3         PACB    ACB offset      data    ;to read an ACB field
712     ;    4         PACB                  status    ;activate an acq. channel
713     ;    5         PACB                            ;deactivate an acq. channel
714     ;
715     ; while PACB = offset address of acquisition control block, 0 is an error
716     ;       AT_PROC = function pointer that a sample (if slow data) or
717     ;                 data block (if wave form data) to be posted
718     ;        A_PROC = function pointer of a wave form data acquisition server
719     ;********************************************************************
720              page+
721     ;********************************************************************
722
723     _A_Util  proc    far
724
725              c_push
726              mov     bx,arg1 [bp]       ;get fctn code
727              shl     bx,1               ;into jmp addr.
728              mov     si,arg2 [bp]       ;get 2nd argu.
729              add     bx,offset u_jmp_tbl
730              jmp     cs:[bx]
731
732     U_ret:   xor     ax,ax              ;good ststus
733     U_reti:  c_ret
734     ;******************* ; to return token (ACB offset)
735     U_fctn1:         ;si = A_ID  ret:  ax=PACB
736     U_f1_1:  mov     bx,offset DGroup: _A_ArrayPtr - 2
737              inc     bx                  ;next _ACB id
```

```
745         inr     bx
746         mov     di,[bx]
747         or      di,di
748         jz      U_ret           ;error (ax=0) if end of table
749         cmp     di,[di]         ;cmp with A_ID
750         jnz     U_f1_1          ;same ?
751 ;init pids in all 3 buffers if waveform data
752         test    [di].A_COND,F_DATA
753         jz      U_f1_2
754 ;set process_id
755         push    si
756         call    xpid
757         pop     di
758         pop     si
759         mov     [di].A_PID,ax   ;set process id
760         mov     si,[di].a_buffer0
761         mov     [si].[di].a_buffer0,ax
762         mov     si,[di].a_buffer1
763         mov     [si].[di].a_buffer1,ax
764         mov     si,[di].a_buffer2
765         mov     [si].[di].a_buffer2,ax
766         mov     [si].PID_BUF,ax
767
768 U_f1_2: mov     ax,di           ;y;get ACB offset (PACB)
769         jmp     U_ret1          ;ret, with ax=PACB
770
771 ;*********************************************************
772 ;*********************************************************
773
774 U_fctn2: ;si = PACB (to write an ACB field)
775
776         mov     bx,arg3[bp]     ;get field offset
777         mov     [si+bx],arg4[bp] ;get data to be written
778         jmp     U_ret
779
780 U_fctn3: ;si = PACB (to read an ACB field)
781
782         mov     bx,arg3[bp]     ;get field offset
783         mov     ax,[si+bx]      ;read it
784         jmp     U_ret
785
786 U_fctn4: ;si = PPACB (activate a acq. channel)
787
788         or      [si].A_COND,Active
789         jmp     U_ret
790
791 U_fctn5: ;si = PPACB (deactivate a acq. channel)
792
793         and     [si].A_COND,NOT Active
794         jmp     U_ret
795
796 u_jmp_tbl:
797         DW      offset Acq_chkerr  ;fctn code=0 is error
798         DW      offset U_fctn1
799         DW      offset U_fctn2
800         DW      offset U_fctn3
```

```
B001            DW  offset U_fctn4
B002            DW  offset U_fctn5
B003
B004    Acq_chkerr:        ; returns AX,DX = status & data
B005            mov     ah,'A'     ;error code
B006            call    _XReportErr  ;post error code = 'A',al
B007            hlt
B008
B009    _A_Util endp
B010    page+
B011
B012    ;*************************************************************
B013    ; Function: _A_SetAnal
B014    ;
B015    ; Purpose: to pass an analog refresh level to aanout()
B016    ;
B017    ; Input: (index, value)
B018    ;    while index = 1,2,3,4 = ir sensor drive, red sensor drive, motor, flush etc
B019    ;          value = the 12 bit analog drive level
B020    ;    no error checking built in, all registers saved
B021    ;
B022    ;*************************************************************
B023
B024    _A_SetAnal  proc    far
B025            c_push
B026            mov     si,arg1[bp]
B027            dec     si
B028            shl     si,1
B029            mov     di,arg2[bp]     ;get index
B030            mov     offset DGroup:  ;pass the level
B031                    anopbf[si],di
B032            c_ret
B033
B034    _A_SetAnal  endp
B035
B036    ;*************************************************************
B037    ; Function: AInit   ;public
B038    ;
B039    ; Purpose: to init both data base & analog frontend
B040    ; Procedure:
B041    ;    - call A_ACBInit() to init data base
B042    ;    - init input amplifier, Sa02 LED driver and pattern generator
B043    ;    - Calibrate post gain amplifier and IR, RED mux channels
B044    ;
B045    ;*************************************************************
B046
B047    AInit   proc    near
B048
B049    ; a_acbinit(); anoutct=ANOUTFQ; aanoutinit();
B050            mov     StartDelayCnt,400   ;500 ms acq wait until disp. side ready
B051            CALL    A_ACBInit           ;init data base
B052            CALL    AadcInit            ;init Aadcvt.s data base & 8255, pattern gen.
B053            CALL    AAnoutInit          ;init analog out routine
B054            mov     anoutct,ANOUTFQ     ;analog refresh fq.
B055            call    _AEEPINIT           ;init read EEPROM task
```

```
859              call    eeptest
860              nop
861              nop
862              RET
863  ;
864  eeptest: push    offset DGroup: aeep_blk
865           call    _aewrite          ;don't do that until you have EEPROM
866
867  testp:   push    offset DGroup: aeep_blk
868           call    _aeread
869           jmp     testp
870
871
872  AInit    endp
873  page+
874
875  ;****************************************************************
876  ;
877  ; Function: A_ACBinit
878  ;
879  ; Purpose:    to init data base
880  ; Procedure:
881  ;    - called by AInit() to init data base
882  ;    - it moves ACBs to data segment A_AcbBlk; init A_ArrayPtr;
883  ;    - init A_Buf0,1,2 & A_BufTbl; init all TIMESETs;
884  ;    - init ACB A_IDs & A_BUFFER0,1,2
885  ;
886  ;****************************************************************
887
888  A_ACBinit    proc    near
889
890          ; clear all local data area
891          clr/an  AcqDataStart,D_LENGTH
892          ; init ACB block
893          mov     si,offset AcbTblinit
894          mov     di,offset DGroup: A_AcbBlk
895          mov     cx,ACB_CNT * TYPE ACB
896  Init_1: mb      [di],CS:[SI]
897          inc     si
898          inc     di
899          LOOP    Init_1
900          ; init A_ArrayPtr
901          mov     di, offset DGroup: A_ArrayPtr
902          mov     ax, offset DGroup: A_AcbBlk
903          mov     cx,ACB_CNT
904  Init_2: mov     [di],ax
905          add     ax,type ACB
906          inc     di
907          inc     di
908          loop    Init_2
909  page4   mov     word ptr [di],0        ;put end mark
910
911  Init_3:                        ;init all A_TIMERCOUNT,( all channel timers )
912          mov     di, offset DGroup: _A_ArrayPtr
```

```
917         mov    si,[di]
918         mov    ax,[si].A_TIMERINIT
919         mov    [si].A_TIMERCOUNT,ax
920         inc    di
921         inc    di
922         cmp    word ptr [di],0
923         jnz    Init_3
924         mov    A_CycleCnt,BUF_CYCLE   ;init buffer switch counter
925
926  ;init A_BufTbl
927         mov    si, offset DGroup: A_Buf0
928         mov    A_BufTbl,si
929         add    si,2 * A_BUF_LEN
930         mov    A_BufTbl+2,si
931         add    si,2 * A_BUF_LEN
932         mov    A_BufTbl+4,si
933         mov    A_BufTbl+6,0           ;end mark
934
935  ;init A_BUF0's ID & all ACBs' A_BUFFER0,1,2
936         mov    di, offset DGroup: A_Buf0
937         mov    si, offset DGroup: A_ArrayPtr
938  Init_9: mov   bx,[si]
939         mov    bx,bx                  ;get an ACB ptr.
940         jz     Init_15                ;end of ACBs
941  ;set buffer ptr in ACBs
942         test   [bx].A_COND,F_DATA     ;skip if not waveform data
943         jz     Init_10
944         mov    [bx].A_BUFFER0,di      ;A_BUFFER0,1,2= di,di+2*A_BUF_LEN,DI+4*A_BUF_LEN
945         mov    [di].AID_BUF,[bx].A_ID ;set ID in tri-buffers
946         add    di,2 * A_BUF_LEN
947         mov    [bx].A_BUFFER1,di      ;set buf. ptr
948         mov    [di].AID_BUF,ax        ;set ID in tri-buffers
949         add    di,2 * A_BUF_LEN
950         mov    [bx].A_BUFFER2,di      ;set buf. ptr
951  ;get next channel offset within A_BUF0 ;incl. 2 words of ID & putindex
952         mov    [di].AID_BUF,ax        ;set ID in tri-buffers
953         add    di,[bx].A_LENGTH
954         sub    di,4 * A_BUF_LEN
955  Init_10: add  si,2
956         jmp    Init_9                 ;next ACB
957
958  Init_15: ret
959
960
961  A_ACHInit  endp
962  SYS_TEXT   ENDS
963            END
964
```

```
Wed 10-15-86 14:00:36    AADCVT.S

1  ;temp fix for gas switches: aco2dc()....
 2  ;change icnar of all functions
 3  ;SAinit (adreset) should be called at last moment
 4  ;use settling time in Aadmeas
 5  ;calc. aadcvt()elapsed time
 6  ;see if to move spffv() in aadcvt()
 7  .186
 8        NAME    AADCVT
 9
10        title "A:D Operations"
11
12        page 52,132
13
14  include aprolog.i
15
16  ;************************************************************
17
18  ;MFO Ver 0.0
19
20  ;COPYRIGHT (C) 1986 NELLCOR INCORPORATED
21
22  ;THIS IS AN ORIGINAL, UNPUBLISHED WORK AND IS PROPRIETARY TO NELLCOR, INC.,
23  ;AND MAY NOT BE DIVULGED OR COPIED IN ANY FORM WHATSOEVER WITHOUT
24  ;EXPRESS PERMISSION FROM NELLCOR, INC.
25
26  ;Module: Aadcvt.s
27
28  ;modification history :
29  ;---------------------------------
30  ;RECENT EDIT HISTORY:
31  ;18th July 85   rak  Separate module
32  ;18th July 85   rak  cleanup of 17th
33  ;17th Sept 85   rak  Interrupts off correctly around Aadmeasure
34  ;10th Nov  85   slc  8088 mode
35  ;16th Dec  85   slc  for NIM prototype
36  ; 4th Feb  86   slc  seperate spffv() & adcvt(), no arith call
37  ;27th Feb  86   slc  add SAR interrupt, modified Aadmeas() for that
38  ; 5th Mar  86   slc  SAR comparator's gain changed from 256 to 32
39  ;               slc  spgain() & adcvt() are modified for that
40  ;13 May    86   slc  start MGM proj.; incl. defs file "acq.i"
41  ;15 May    86   slc  modified AAdcvt(), with incoff(), decoff() moved
42  ;                    in from a cx.s, makel6() is local only
43  ;17 May    86   slc  AADCVT() does't adjust offset, back to N100 status
44  ;20 May    86   slc  "noise" reset moved to rstdelta() in tweak.s
45  ;23 May    86   slc  Smakel6 mov'd out to asacq.s
46  ;16 May    86   slc  settling wait moved from smux() to aadcvt()
47  ; 1 July   86   slc  adapted to MFO analog processor,add AdcRemote()
48  ; 2 July   86   slc  no AdcRemote() but ARmux(), Aadcvt() knows remote or not
49  ;15 Aug    86   slc  add eeprom write routine
```

```
;22     Aug 86    slc  add aadcvt(), ASRMUX() for aeeprom.c
;25     Aug 86    slc  fixed 8255 mode change problem (drops output pins);
;26     Aug 86    slc  noise stuffs in lv3_init() & Spistmo(), not adreset()
;10     Sept 86   slc  S/H & SARCLK_EN lines moved to device 8255
;                     moved back again since S/H def. changed
;                     temp. fix for gas switches for the show
;
; Purpose:   do analog to digital conversion
;
; Public & External Data:
;
          PUBLIC  Acalpat,Aledpat
          public  Aselict  ; to aanout.s; A:D settling time, after S/H triggered,init as 16
;
; Public Functions:
;
          PUBLIC  AAdcvt
          public    aadcvt                    ; for aeeprom.c
          PUBLIC  ASRMUX                      ;set remote channel mux, called by acq_data()
          public    ASRMUX                   ; for aeeprom.c
          PUBLIC  AAdmeas
          PUBLIC  Aspagain
          PUBLIC  Aspatrn
          PUBLIC  Aputadv                    ;put data to a;d converter
          PUBLIC  AadcInit                   ;called by ainit() in acqmain.s
;temp. fix for gas switches, called only during _nit
          PUBLIC  ACo20C
          PUBLIC  AN20DC
          PUBLIC  AASTDC
;
;               EXTERNAL FUNCTIONS CALLED
;
;???
;*************************************************************
include amacro.i
;INCLUDE IOEFS.i
;       IO port address :
;
AR_MUX   equ    02H     ;remote channel multiplxer addr.,use data bits as mux code
AL_MUX   equ    80H     ;local channel multiplexer addr.
AGASSWPORT equ  06H     ;port for 3 gas switches
;
;a to d Port C high
;
START_SAR   equ    10000000B      ;BITS/6 low to select/start SAR,bit 4/5=0/1 to
SELECT_SAR  equ    11000000B      ;hold the sample/enable SAR clock
SAR_DIS     equ    01110000B      ;BIT5 low to select SAR(already started)
                                  ;disable SAR
OUT_MODE  equ  80H ;for adcvt control device 8255 mode setup
IN_MODE   equ  83H    ; port b and low port c in output mode
                      ; port b and low port c in input mode
.list
```

```
108  page+
109
110        _BSS    SEGMENT WORD PUBLIC 'BSS'
111
112  ;;Most pattern defs are found n the SPATRN routine
113  ;;ptmask        EQU     bit3 + bit2 + bit1    ;ptadd0 + ptadd1 + ptadd2
114  ;Pattern Selectors & pgain defs., see adefs.i
115
116  Asetlct    DW    ?        ; A:D settling time, after S/H triggered,init as 16
117  ;The patterns:
118  Aledpat    DB    ?        ;pattern for IR and red sensors ;init as PTFAST=0
119  Acalpat    DB    ?        ;pattern for calibrating channels ;init as PTCALCH=5
120  curpat     DB    ?        ;the current pattern
121  svdypa     DB    ?        ;save the port a on device 8255
122  public     svdypa
123  public     curpat
124  AGasSW     DW    ?        ;gas switch on/off status
125
126  .list
127  _BSS   ENDS
128
129
130        SUBTTL  "MFO A:D conversion"
131
132
133  Sys_Text  SEGMENT byte PUBLIC 'Code'
134  ;****************************************************************
135  ; Function:
136  ;    AAdcvt
137  ;
138  ; purpose:  to do Analog to Digital Conversion
139  ;
140  ; entry:  bx=token= ACB table entry
141  ;
142  ;****************************************************************
143  AAdcvt  proc    far
144
145  ; smux ( bx );
146  ; soffv (ax=bx.A_OFFSET); /* set offset voltage */
147  ; pgain_sel = bx.A_PGAIN * 8;
148  ; 30 us wait; ret (ax=Aadmeas());
149
150  ;Elapsed time (approximate): ~ 214 us (was 470us)
151
152  ;for test
153  testp:  mov   ax,[BX].A_OFFSET  ;get 12 bits of value
154          CALL  soffv             ;set offset
155          CALL  SMUX              ;set anlog mux
156          mov   ax,[BX].A_PGAIN   ;collect gain requested
```

```
165             SHL      ax,3            ;* 8 is the real gain needed
166             mov      es:[di],al      ;send p-gain to port a
167             mov      CX,Asetict      ;setict;settling count = 16*1.9 ~ 30 us
168                                      ;see inilst for initial value
169             loop     $               ;1.9 microsec
170             call     AAdmeas         ;get data in ax
171             jmp      testp
172             nop
173             nop
174             ret
175     AAdcvt  endp
176
177     ;
178     _AAdcvt proc    far             ;used by aeeprom.c only during init
179             c_push
180             mov      bx,6tbpJ
181             call     aadcvt          ;get token
182             c_ret
183     _AAdcvt endp
184
185     ;
186     AAdmeas proc    near            ;AADMEASure - Measure a voltage using the SAR
187                                      ;input:  es:di=AADFA
188                                      ;output: ax=sample 12 bits
189             mov      byte ptr es:PCTRL[di],IN_MODE ; port b and low port c in input mode
190             mov      byte ptr es:PORTC[di],START_SAR ;to select/start SAR,sar clock en.
191             nop                      ;allow 2.5 us before set START_SAR high
192             nop
193             mov      byte ptr es:PORTC[di],SELECT_SAR ;select SAR,start SAR bit high
194             ;WAIT    30 US           ;= 32 US = 16*2 us
195             mov      CX,Asetict
196             LOOP     $
197             ;read the voltages, lsb is in port b, msb nibble in port c
198             mov      al,es:PORTB[di] ;read port b and port c
199             mov      ah,es:PORTC[di]
200             AND      ah,0FH          ;returns 12 bits in ax
201             mov      byte ptr es:PCTRL[di],OUT_MODE ; port b and low port c in output mode
202             mov      byte ptr es:PORTC[di],SAR_DIS ;de-select SAR, sar clk, all-pass sample
203             ret
204     AAdmeas endp
205
206     SOFTV:                           ;set a offset voltage in ax
207     AFUTADV proc    near             ;PUBLIC; to send a analog out to S/H.
208             mov      di,AADPORT      ;set es:di for all adc routines
209             mov      es,di
210             xor      di,di           ;AADFA
211             mov      es:PORTB[di],al ;out to DAC, port b & port c
212             or       ah,SAR_DIS      ;disable bits in PC high
213             mov      es:PORTC[di],ah
214             RET
```

```
2222        AFUTADV endp
2223
2224        ;SMUX - Select the mux channel
2225        ;On entry, BX point to mux channel to set (OFFSET xxxtbl)
2226        ;A:D device control is permanently ready to accept mux
2227        ;BX are preserved.
2228
2229        smux:   ;trigger the mux decoder, ax used
2230        public  smux
2231                mov     dx,AL_MUX       ;get mux io port addr.
2232                test    [BX].A_COND,A_REMOTE   ;remote channel ?
2233                jnz     mux_r
2234                mov     ax,[BX].A_MUX   ;get mux channel code
2235                out     dx,al           ;open the local channel
2236                ret
2237        mux_r:  xor     ax,ax           ;remote is 0 in the local mux
2238                out     dx,al           ;open the remote channel
2239                RET
2240
2241        ASRmux  proc    near            ;set remote channel mux, called by acq_data()
2242        public  ASRmux
2243                mov     ax,[BX].A_MUX   ;get mux channel code
2244                mov     dx,AR_MUX       ;open the local channel
2245                out     dx,al
2246                ret
2247
2248        ASRmux  endp
2249
2250        _ASRmux proc    near            ;set remote channel mux, called by aeeprom.c
2251                c_push
2252                mov     bx,4[bp]
2253                mov     ax,[BX].A_MUX   ;get mux channel code
2254                mov     dx,AR_MUX       ;open the local channel
2255                out     dx,al
2256                c_ret
2257
2258        _ASRmux endp
2259
2260        ;***************************************************
2261        ;temp. fix for gas switches, called only during init
2262        ;***************************************************
2263        _ACo2OC proc    far
2264                mov     al,BIT0         ;bit0,1,2 for co2,n2o,agt
2265        asetsw:
2266                c_push
2267                cmp     word ptr 6[bp],0   ;0/1 to open/close the switch
2268                je      OpenSW
2269                not     ax
2270                and     AGasSW,ax
2271                jmp     setsw
2272        OpenSW:
2273                or      AGasSW,ax       ;gas on off bits
2274        setsw:  mov     ax,AGasSW
2275                mov     dx,AGASSWPORT   ;open the local channel
```

```
200              out     dx,al
281  sswwait:    mov     ax,255          ;have to wait 320 us
282              dec     ax
283              jnz     sswwait
284              c.ret
285  _ACo2DC     endp
286
287  _AN2ODC     proc    far
288              mov     ax,BIT1         ;bit0,1,2 for co2,n2o,agt
289              jmp     asetsw
290  _AN2ODC     endp
291
292
293  _AAGTDC     proc    far
294              mov     al,BIT2         ;bit0,1,2 for co2,n2o,agt
295              jmp     asetsw
296  _AAGTDC     endp
297
298  ;SPGAIN - set the gain for programmable input amplifier.
299  ;input: By point to gain: RX is preserved. Pgain_sel ((B.P.[BX]
300  ;Programmable gain is restricted to five values: 1, 2, 4, 8 and 16.
301  ;This simplifies voltage computation.          ~11 us
302
303  Aspagain:           ;PUBLIC, not called by aadcvt() to save time
304  ;pgain_sel (in aadpa) = 8 * B.P.[BX]
305              mov     ax,AADPORT
306              mov     es,ax
307              xor     di,di           ;to port a
308              mov     ax,[BX].A_PGAIN ;collect gain requested
309              shl     AX,3            ;*8
310              mov     es:[di],al      ;bung it out
311              RET
312
313  Aadcinit    proc    near            ;called by Ainit( in aacq.s
314
315          ;init both 8255 io chips
316              mov     ax,AADPORT
317              mov     es,ax
318              xor     di,di
319              mov     byte ptr es:PCTRL[di].OUT_MODE
320              mov     ax,ADVPORT
321              mov     es,ax
322              mov     byte ptr es:PCTRL[di].88h ;port c high input, else output
323              mov     al,0fh                    ;init device port a image
324              mov     svdvpa,al                 ;& all aanout select pins off
325              mov     es:[di],al
326              mov     Asetict,16   ; A:D settling time after S/H triggered
327          ;The patterns:
328              mov     Aledpat,PIFAST     :=0,pattern for.IR and red mid speed sensors
329              mov     Acalpat,FTCALCH    :=5,Pattern for calibrating channels
330              MOV     AL,acalpat                ;use IR/RED pattern
331              CALL    far ptr Aspatrn
332  ;init gas switches
333              push    1           ;closes all
334              call    far ptr ACO2DC
```

```
337                 call    far ptr _AN2ODC
338                 call    far ptr _AA6TDC
339                 pop     ax
340                 ret
341     AadcInit    endp
342
343     ;SFATRN - PUBLIC
344     ;translates pattern ordinal into 8255 Port B bit 4,3,2
345
346     ;Table of 8255 Port C pattern-selection bits
347
348     PTMASK      EQU     00000111.0B
349     ;patrns  DB      00, 0B, 04, 0CH, 02, 0aH, 06, 0eH  ;MF0, same as n100's
350
351     ;patrn0,patrn1,patrn2,patrn3,patrn4,patrn5,patrn6,patrn7
352
353     ASFATRN     proc    far
354
355     ;input : AL = requet pattern (0 - 7).
356     ;if (AL=curpat) return;
357     ;curpat = dsvpat = AL;
358     ;port_b &= PTMASK; port_b != CS:patrns [AL];
359
360                 CMP     AL,L_32         ;comp. with current pattern
361                 JNZ     L_32            ;different from requested?
362                 RET                     ;no change, exit
363     L_32:
364                 MOV     curpat,AL       ;save the new pattern number
365     ;MF0        MOV     dsvpat,AL       ;for diagnostics
366     ;...        CMP     AL,5            ;!!!patch *** Pattern 0 & 5 only
367     ;...        JZ      L_33
368                 XOR     AC,AL
369                 shl     al,1
370                 mov     di,ADVPORT
371                 mov     es,di
372                 mov     di,PORTC
373                 mov     es:[di],al
374                 RET
375     ASFATRN     endp
376
377     Sys_Text    ENDS
378                 END Wed 89-04-06 11:27:26  AFROLOG.I
    10-15-06 14:09:36

1      CONST   segment word public 'const'
 2              CONST ends
 3
 4      _DATA   segment word public 'data'
 5              _DATA ends
 6
 7      _BSS    segment word public 'bss'
 8              _BSS ends
 9
10      c_common segment word public 'bss'
11              c_common ends
```

```
   12        SYS_TEXT  segment byte public 'code'
   13        SYS_TEXT  ends
   14
   15        SAT_TEXT  segment byte public 'code'
   16        SAT_TEXT  ends
   17
   18        ECG_TEXT  segment byte public 'code'
   19        ECG_TEXT  ends
   20
   21        DGroup    group    c_common, _BSS, CONST, _DATA
   22
   23        ASSUME CS:SYS_TEXT, DS:DGROUP, SS:DGROUP, ES:DGROUP
   24
   25
   26

Wed 09-10-86  17:16:32   ADEFS.I
    10-15-86  14:09:36

1    .xlist
    2    ;************************************************************************
    3    ;
    4    ;   MFO Ver 0.0
    5    ;
    6    ;   Module:  iom.inc
    7    ;        ** this file is included in amacro.inc
    8    ;
    9    ;   COPYRIGHT (C) 1986 NELLCOR INCORPORATED
   10    ;
   11    ;   THIS IS AN ORIGINAL, UNPUBLISHED WORK AND IS PROPRIETARY TO NELLCOR, INC.,
   12    ;   AND MAY NOT BE DIVULGED OR COPIED IN ANY FORM WHATSOEVER WITHOUT
   13    ;   EXPRESS PERMISSION FROM NELLCOR, INC.
   14    ;
   15    ;   modification history :
   16    ;
   17    ;    3 July  slc   use equ defs for all i/o locations
   18    ;    7 July  slc   included in amacro.inc
   19    ;   20 Aug   slc   all io are EQU defined
   20    ;   24 Aug   slc   8255 use a1,a2 not a0,a1 address lines
   21    ;
   22    ;************************************************************************
   23
   24    bit0    equ    1
   25    bit1    equ    2
   26    bit2    equ    4
   27    bit3    equ    8
   28    bit4    equ    10H
   29    bit5    equ    20H
   30    bit6    equ    40H
   31    bit7    equ    80H
   32    bit8    equ    100H
   33    bit9    equ    200H
   34    bit10   equ    400H
   35    bit11   equ    800H
   36    bit12   equ    1000H
   37    bit13   equ    2000H
```

```
38  bit14       equ    40000H
39  bit15       equ.   80000H
40
41  ;;Most pattern defs are found in the SPATRN routine
42  ;;ptmask      EQU    bit3 + bit2 + bit1       ;ptadd0 + ptadd1 + ptadd2
43  ;Pattern Selectors
44  PTFAST      EQU    0              ;pattern for fast-response sensors
45  PTMID       EQU    1              ;pattern for middling-response sensors
46  PTSLOW      EQU    2              ;pattern for slow-response sensors
47  PTCALCH     EQU                   ;(or 6) pattern used to calibrate the channels
48
49  mingain     EQU    1              ;minimum gain *p-gain*|
50  maxgain     EQU    16             ;maximum *p-gain*
51  mxpg        EQU    4              ;this value comes from the table below:
52
53  ;Calibrate channels flag values.  The word 'calibrate' is all this
54  ;has in common with the calibration resistor. This is for control
55  ;of channel calibration.
56
57  CALCHI      EQU    1              ;initial state
58  CALCHW      EQU    2              ;waiting for the filters to settle
59  CALCHR      EQU    3              ;calibration requested, do it at the
60                                    ;right moment
61
62  ;Inhibit periods for filter settling, expressed in terms of data-sample
63  ;     decr. by SIRacq() every 17.5 ms in asacq.s
64  intervals
65  FILSETTLE   EQU    6              ;regular wait (100 ms) on inamp change
66  CALSETTLE   EQU    20             ;200 /* 350 */ ms wait for exact channel offset
67  calxsettle  EQU    14             ;from calibration back to regular, otherwise
68  ;inaccurate first sat after initial calibration will overly influence
69  ;following sat readings, since the sat filters are turned way down then
70
71  ;For offset and other computations:
72  ONEV12      EQU    4096/10        ;one volt in 12-bit representation
73  ONEVNZ      EQU    1999H          ;= 4096*maxgain/10 - one volt in 16 bits
74
75          title  "Device Addresses and Parameters"
76
77  ;Device definitions appear in ascending order of address
78
79  ;  memory mapped address :
80  8274 comm chip = 8000H
81
82          title  "MFO 8255 ADCVT Controllers"
83
84  ; Port A - post gain (DAC10/20), always * 8 before output
85  ;   to chip (ADC6012
86  ; Port B ; to read SAR output/write offset , low byte
87  ; Port C low - to read SAR output/write offset , high nibble
88
89          ORG    014000H
90  AADPORT  equ    014000H  ; adsel line = MCS1
91  PORTA    equ    0        ;segment ES
92  PORTB    equ    2        ;offsets from port a
93  PORTC    equ    4
94  PCTRL    equ    6
95
```

```
 96    FCLOW    EQU   0FH
 97    FCHIGH   EQU   0F0H
 98
 99
100             title "MFO 8255 Device Controllers"
101    ;
102    ; Port A - low nibble ; to DG 201 analog demultiplexer
103    ; bit0,1,2,3 low to send Avledir, Avmotor, Avpump
104    ; Port A - high nibble :
105    ;
106
107    TEST_PIN1    equ   bit4    ;test acq. server freq.
108    ZEROSIG      equ   bit6
109    BACKFLUSH    equ   bit7
110
111    FALOW    EQU   0FH
112    FAHIGH   EQU   0F0H
113
114    ; Port B : to set input amplifier gain
115    ; Port C low - BIT1,2,3 ;to select pattern generator prom code
116    ; Port C high - BIT4,5 ;test jumpers input
117    ;            - BIT6 ;  sensor LED overdrived if set (detected in pre-amp stage)
118    ;            - BIT7 ;  input amplifier hits the high rail if set
119    ;
120    PREAMP_FLAG    equ    BIT6
121    INAMP_FLAG     equ    BIT7
122
123    ;           ORG    18000H   ;adsel line = MCS2
124    ADVPORT     equ    01B00H   ;segment ES
125
126    ; CP0 *** Port B high - input: LEDLO, SWITCH, RESET, LEADSOK
127    ; CP0 *** Port C - output :PSEN, S/HEN, PAT_SEL0,1,2, GATE2, ECG_NVRT, NC
128    ; Port C high
129    ; ** SH_EN           equ    BIT4    ;low to update sample to comparator,
130                                         ;turned high after SAR compl'd
131    ; ** SAR_SEL         equ    BIT5    ; low to select SAR
132    ; ** START_SAR       equ    BIT6    ; low to start SAR
133    ; ** SARCLK_EN       equ    BIT7    ; high to enable SAR clock
134    .list
```

Wed 10-01-86 16:14:56    AMACRO.I
Wed 10-15-86 14:07:36

```
  1    .xlist
  2    ;*********************************************************************
  3    ; MFO Ver 0.0
  4    ;
  5    ; Module: amacro.i
  6    ;
  7    ; modification history :
  8    ;
 10    ; 19 May 86 slc redef. ACB,A_COND, add A_Util related macros
 11    ; 30 May 86 slc add macros acq_ptr & a link_ptr & external declarations
 12    ; 20 June 86 slc change ASCII names into id word
```

```
13  ;  1  July 86 slc add a_set macro
14  ;
15  ;  COPYRIGHT (C) 1986 NELLCOR INCORPORATED
16  ;
17  ;  THIS IS AN ORIGINAL, UNPUBLISHED WORK AND IS PROPRIETARY TO NELLCOR, INC.,
18  ;  AND MAY NOT BE DIVULGED OR COPIED IN ANY FORM WHATSOEVER WITHOUT
19  ;  EXPRESS PERMISSION FROM NELLCOR, INC.
20  ;
21  ;       This file is to be included in following modules:
22  ;       all acquisition server modules and all saturation process modules
23  ;       and any module that need access acquisition on raw data or change
24  ;       the acq. channel status.
25  ;
26     include  \nfo\acq\ADEFS.i
27     include  \nfo\acq\aid.i
28     include  \nfo\acq\acb.i
29     .xlist
30
31  IFNDEF ACQ_MAIN              ;ACQ_MAIN is defined only in aacq.s
32
33     EXTRN    A_Data:far
34     EXTRN    A_Link:far
35     EXTRN    A_Util:far
36     EXTRN    CSendSlow:far, CommLink:far    ;in comm.s
37     EXTRN    A_SetAnal:far
38     extrn    _wflink:far
39
40  ENDIF
41
42  MACRO defs:
43  GetPacb   AID                        ;ret PACB in ax
44  W_ACB     PACB,offset,data           ;W. ACB
45  R_ACB     PACB,offset                ;R. ACB
46  Act_Ch    PACB                       ;activate a channel
47  DeAct_Ch  PACB                       ;deactivate a channel
48  acq_ptr   AID,proc                   ;pass data acquisition procedure pointer to acq_data()
49  alink_ptr AID,proc                   ;pass data transfer pointer to acq_data()
50  send_w    id,ptr                     ;to pass a word to thru intercomm
51  ;  mw, mb : mem to mem movement
52
53            arg1   equ   6
54            arg2   equ   8
55            arg3   equ   10
56            arg4   equ   12
57            arg5   equ   14
58            arg6   equ   16
59
60  c_push    macro
61            push   bp
62            mov    bp,sp
63            push   di
64            push   si
65            endm
66
67  c_ret     macro
68            pop    si
69            pop    di
70            pop    bp
71            ret
72            endm
```

```
71  ;*********************************************************************
72  ;
73  ;            status = A_Util ( fctn code, arg2, arg3, arg4 )
74  ;            status returned in AX = 0 .... ok
75  ;
76  ;fctn code     arg2      arg3        arg4      returns
77  ;
78  ;   1         A_ID                             ;get TOKEN ( ACB pointer),error if return=0
79  ;   2         FACB      ACB offset  data       ;to write an ACB field
80  ;   3         FACB      ACB offset    "        ;to read an ACB field
81  ;   4         FACB                             ;activate an acq. channel
82  ;   5         FACB                             ;deactivate an acq. channel
83  ;
84  ;
85  ; while FACB = offset address of acquisition control block, 0 is an error
86  ;       AT_PROC = function pointer that a sample (if slow data) or
87  ;                 data block (if wave form data) to be posted
88  ;       A_PROC  = function pointer of a wave form data acquisition server
89  ;
90  ;*********************************************************************
91  ;
92  ;           ; A_Util() function code defs
93  ;
94  GetFacb_code    equ     1                  ;get ACB pointer
95  WACB_code       equ     2                  ;to write an ACB field
96  RACB_code       equ     3                  ;to read an ACB field
97  Act_code        equ     4                  ;make a channel active
98  DeAct_code      equ     5                  ;make a channel non active
99  ;
100 ;
101 ;macro to get FACB, it returns pacb in ax, error if ax=0
102 ;
103 GetFACB macro   A_ID
104         push    A_ID       ;acq. id
105         push    GetFacb_code
106         call    A_Util
107         add     sp,4       ;clear up stack
108         endm
109 ;
110 ;macro to write an item in ACB
111 W_ACB macro     FACB,offset,data
112         push    data
113         push    offset
114         push    FACB
115         push    WACB_code
116         call    A_Util
117         add     sp,8       ;clear up stack
118         endm
119 ;
120 ;macro to reset offset & pgain in ACB
121 Rst_Ch  macro   FACB
122         W_acb   FACB,A_PGAIN,1      ;pgain=1
123         W_acb   FACB,A_OFFSET,0     ;offset=0
124         endm
125 ;
126 ;macro to read an item in ACB
127
128
```

```
129  R_ACB    macro   FACB,offset
130           push    offset
131           push    FACB
132           push    RACB_code
133           call    A_Util
134           add     sp,6        ;clear up stack ;data in ax
135           endm
136
137  ;macro to enable a channel
138  Act_Ch   macro   FACB
139           push    FACB
140           push    Act_code
141           push    A_Util
142           call    A_Util
143           add     sp,4        ;clear up stack , data in ax
144           endm
145
146
147  DeAct_Ch macro   FACB
148           push    FACB
149           push    DeAct_code
150           call    A_Util
151           add     sp,4        ;clear up stack , data in ax
152           endm
153
154
155  ;macro to pass data acquisition procedure pointer to acq_data()
156  acq_ptr  macro   A_ID, proc_offset
157           push    cs
158           push    offset proc_offset
159           push    A_ID
160           call    A_Data
161           add     sp,6        ;clear up stack ,status in ax
162           endm
163
164
165  ;macro to pass data transfer pointer to acq_data()
166  a_link_ptr macro A_ID, proc_offset
167           push    cs
168           push    offset proc_offset
169           push    A_ID
170           call    A_Link
171           add     sp,6        ;clear up stack ,status in ax
172           endm
173
174  ; macro to pass function ptr to comm proc
175  c_link   macro   proc_offset
176           push    cs
177           push    offset proc_offset
178           call    CommLink
179           add     sp,4
180           endm
```

```
187  ; macro to pass LENG bytes thru intercomm
188  SendIt macro  id_,var,LENG
189         mov    ax,id_
190         mov    bx,offset DGroup: var
191         mov    cx,LENG
192         call   CSendSlow
193         endm
194
195  ;macro to pass wave form procedure pointer to waveform server
196  ;assume 1 data source buffer & 1 data dest. buffer with 4 bytes src/dest. name
197
198  wvf_ptr macro   sid_,did_, proc_offset
199
200         push   sid_              ; 1 src. buffer
201         push   1                 ; 1 data sources
202         push   did_              ; 1 dest. id
203         push   1
204         push   cs
205         push   offset proc_offset ;fct ptr
206         call   far ptr _wfrlink
207         add    sp,10
208         or     ax,ax             ;ret = 0 = ok
209         endm
210
211  a_set  macro   id,val            ;set an 12 bit val into analog channel # id
212                                   ;id=1,2,3,4 = lr,red,motor,flush
213         push   val
214         push   id
215         call   A_SetAnal
216         add    sp,4              ;clear up stack
217         endm
218
219  ;INIT_D macro - for documentation - shows how many bytes (nbytes) to
220  ;initialize starting at addr.  The nbyte-long list of values must
221  ;follow the macro call.
222  ;ADDRESS FOLLOWED BY A BYTE OF DATA, ZERO TERMINATES...
223
224  init_d MACRO  var,nbytes
225         DW    OFFSET DGroup : var
226         DB    nbytes
227         ENDM
228
229  ;macro to clear local data area
230
231  clrram macro  addr, LENG         ;length in byte
232         local  L
233         mov    bx,offset DGroup: addr
234         mov    cx,LENG
235         xor    ax,ax
236  L:     mov    [bx],al
237         inc    bx
238         loop   L
239         endm
240
241  mv     macro  var1,var2
242         mov    ax,var2
243         mov    var1,ax
244         endm
```

```
245         mb      macro   var1,var2
246                 mov     al,var2
247                 mov     var1,al
248                 endm
249         .list
250
251
252

Wed 10-07-86 13:05:50  AID.I
    10-15-86 14:09:36

1   ;.xlist
2   ;**********************************************************************
3   ;*
4   ;       MFO Ver 0.0
5   ;       Module: aid.inc
6   ;
7   ;       modification history :
8   ;
9   ;
10  ;       20 June 86      slc     change from ASCII name to id code in acq. server
11  ;        8 Sept 86      slc     big change via schematic
12  ;       19 Sept 86      slc     add DC channels for gases
13  ;
14  ;       COPYRIGHT (C) 1986 NELLCOR INCORPORATED
15  ;
16  ;       THIS IS AN ORIGINAL, UNPUBLISHED WORK AND IS PROPRIETARY TO NELLCOR, INC.,
17  ;       AND MAY NOT BE DIVULGED OR COPIED IN ANY FORM WHATSOEVER WITHOUT
18  ;       EXPRESS PERMISSION FROM NELLCOR, INC.
19  ;
20  ;       This file is to be included in following modules:
21  ;               amacro.inc
22  ;
23  ;**********************************************************************
24  ;
25  ;Primary data id for acquisition channel, the high byte of the ID code
26  ;****************************************
27                                  17 * 256
28  DID_ACQ         equ
29
30          AID_Eep         equ     DID_ACQ + 0      ;eeprom data out
31          AID_Ecg         equ     DID_ACQ + 1
32          AID_OBTemp      equ     DID_ACQ + 2      ;Optical Bench temp.
33          AID_SampFre     equ     DID_ACQ + 50h    ;sample pressure,fast
34          AID_Co2DC       equ     DID_ACQ + 51h    ;DCs for gases
35          AID_N2oDC       equ     DID_ACQ + 52h
36          AID_AgentDC     equ     DID_ACQ + 53h
37          AID_FloPres     equ     DID_ACQ + 3      ;gas flow pressure,slow
38          AID_SSampPre    equ     DID_ACQ + 4      ;sample cell pressure
39          AID_HtrDrv      equ     DID_ACQ + 5      ;heater drive voltage
40
41          AID_Bp1         equ     DID_ACQ + 6
42          AID_Bp2         equ     DID_ACQ + 7
43          AID_Resp        equ     DID_ACQ + 8
```

```
 44         AID_Body1       equ     DID_ACQ + 9
 45         AID_Body2       equ     DID_ACQ + 0ah
 46
 47         AID_Vcal        equ     DID_ACQ + 10h   ;oxi. sensor resistance
 48         AID_Vref        equ     DID_ACQ + 11h   ;5 volts reference
 49
 50         ; Local channels
 51         AID_Poff        equ     DID_ACQ + 20h   ;post gain offset error
 52         AID_Cir         equ     DID_ACQ + 21h   ;ir chan. calib.
 53         AID_Cred        equ     DID_ACQ + 22h   ;red ch:n calib.
 54         AID_Ir          equ     DID_ACQ + 23h   ;ir ser s r in.
 55         AID_Red         equ     DID_ACQ + 24h   ;red sensor in.
 56
 57         AID_Co2         equ     DID_ACQ + 30h
 58         AID_N2o         equ     DID_ACQ + 31h
 59         AID_Agent       equ     DID_ACQ + 32h
 60         AID_Co2S        equ     DID_ACQ + 33h   ;co2    slow
 61         AID_N2oS        equ     DID_ACQ + 34h   ;n2o    slow
 62         AID_AgentS      equ     DID_ACQ + 35h   ;agent  slow
 63
 64         AID_MotDrv      equ     DID_ACQ + 40h   ;motor drive level
 65         AID_ORSpeed     equ     DID_ACQ + 41h   ;optical bench speed
 66         AID_Bat         equ     DID_ACQ + 42h   ;battery input
 67
 68         ;waveform ids
 69         WID_IR          equ     101h
 70         WID_RED         equ     201h
 71         WID_PLETH       equ     /* pulse waveform */
 72
 73         ;slow data ids, ACCORDING TO bxid.h
 74         ;*****************************************************
 75         DID_SAT         equ     300h
 76
 77         SID_UNFIL       equ     DID_SAT+02
 78         SID_FIL         equ     DID_SAT+03
 79         SID_OXSTA       equ     DID_SAT+27h
 80         ;*****************************************************
 81         DID_RATE        equ     400h
 82
 83
 84         RID_UNFIL       equ     DID_RATE+02
 85         RID_FIL         equ     DID_RATE+03
 86
 87         .list Wed 10-13-86 20:22:16 ACB.I
    10-15-86 14:09:36

1  .xlist
  2  ;*********************************************************************
  3
  4  MFO Ver 0.0
  5  Module: acb.inc
  6
  7
```

```
08  ; modification history :
09  ;
10  ;   10 May 86 slc split from acq.s
11  ;   20 June 86 slc change ASCII names into id word
12  ;   26 June 86 slc add A_PID in ACB
13
14  ; COPYRIGHT (C) 1986 NELLCOR INCORPORATED
15
16  ; THIS IS AN ORIGINAL, UNPUBLISHED WORK AND IS PROPRIETARY TO NELLCOR, INC.,
17  ; AND MAY NOT BE DIVULGED OR COPIED IN ANY FORM WHATSOEVER WITHOUT
18  ; EXPRESS PERMISSION FROM NELLCOR, INC.
19
20  ;       This file is to be included in following modules:
21  ;           acq.inc amacro.inc
22
23
24          ;bit defs for A_COND
25  F_DATA      equ     BIT7        ;data type,1=waveform or 0=slow data
26  A_WAIT      equ     BIT8        ;a remote channel is waiting
27                                  ;this bit is maintained by system only
28  A_REMOTE    equ     BIT9        ;set if remote channel
29  ACTIVE      equ     BIT15       ;a zero deactivate the source
30
31  ACB     struc
32  A_ID        DW  ?       ;acq. channel id
33  A_NAME      DB  4 dup(?) ;name of data source, 4 characters
34  A_TIMERINIT DW  ?       ;timer init
35  A_TIMERSET  DW  ?       ;timer set value
36  A_TIMERCOUNT DW ?       ;timer count
37
38  A_COND      DW  ?       ;channel condition flags, see bit defs below
39  A_MUX       DW  ?       ;multiplexer address (preamp head mux included)
40  A_FGAIN     DW  ?       ;ADC post amplifier gain setting
41  A_OFFSET    DW  ?       ;ADC amplifier offset
42  A_LIST      DW  ?       ;pointer to linked list of data transfer MT functions in C
43  A_PROC      DW  2 dup(?) ;of acquisition procedure in Assembly codes
44  A_PID       DW  ?       ;process id
45
46          /* put in tri-buffer, wave form data only, not used by slow data */
47  A_LENGTH    DW  ?       ;max data length (incl. pid,aid & index words)
48  A_BUFFER0   DW  ?       ;offset addr. to data block in buffer0
49  A_BUFFER1   DW  ?       ;offset addr. to data block in buffer1
50  A_BUFFER2   DW  ?       ;offset addr. to data block in buffer2
51
52  ACB     ends
53
54  ;acqsition source data buffer (tri-linear buffer) data structure
55
56  ACQ_BUF struc
57  PID_BUF     DW  ?       ;task id
58  AID_BUF     DW  ?       ;data id
59  FUTIDX      DW  ?       ;data length
60  FUTDATA     DW  ?       ;data starts from here
61  ACQ_BUF ends
62
63  .list
```

```
Wed 09-25-86 14:14:30  ACBDEFS.I
 1      .xlist
 2      ;******************************************************************
 3      ;
 4      ;       MFO Ver 0.0
 5      ;
 6      ;       Module: acq.inc
 7      ;
 8      ;       modification history :
 9      ;
10      ;       13 May  86 slc  split from aacq.s
11      ;       18 May  86 slc  remote channels on top of ACB
12      ;       20 June 86 slc  change ASCII names into id word
13      ;       10 July 86 slc  split from acq.inc
14      ;       19 Sept 86 slc  add DC channels for gases
15      ;
16      ;       COPYRIGHT (C) 1986 NELLCOR INCORPORATED
17      ;
18      ;       THIS IS AN ORIGINAL, UNPUBLISHED WORK AND IS PROPRIETARY TO NELLCOR, INC.,
19      ;       AND MAY NOT BE DIVULGED OR COPIED IN ANY FORM WHATSOEVER WITHOUT
20      ;       EXPRESS PERMISSION FROM NELLCOR, INC.
21      ;
22      ;       This file is to be included in following modules:
23      ;               aacq.s only
24      ;
25      ;       page+
26      ;
27      ;******************************************************************
28      ;
29      ;       Channel ACB Definition
30      ;
31      ONE_HZ              equ    800         ;1 hz rate
32      ;***** REMOTE CHANNELS                 should never set as 1
33      ; remote channel ::_Tset should never set as 1
34
35      Eep_Tinit           equ    2
36      Eep_Tset            equ    2
37      EepCond             equ    A_REMOTE
38      EepMux              equ    0
39
40      Ecg_Tinit           equ    3
41      Ecg_Tset            equ    4
42      EcgCond             equ    F_DATA + A_REMOTE
43      EcgMux              equ    16          ;?
44      EcgLen              equ    20          ; (50 ms / 4*1.25 ms)*2 = 20
45
46                                 ;Optical Bench temp.
47      OBT_Tinit           equ    3
48      OBT_Tset            equ    ONE_HZ
49      OBTCond             equ    A_REMOTE
50      OBTMux              equ    1
51
52      Vcal_Tinit          equ    3           ;after Cir/Cred, before IR/RED
53      Vcal_Tset           equ    2           ;to enabled by asclock() or SIRacq()
54      VcalCond            equ    A_REMOTE
```

```
 55  VcalMux      equ          2
 56
 57               ;gas flow pressure
 58  FP_Tinit     equ          2
 59  FP_Tset      equ          ONE_HZ
 60  FPCond       equ          A_REMOTE
 61  FPMux        equ          3
 62
 63               ;sample cell pressure
 64  SF_Tinit     equ          4
 65  SF_Tset      equ          16
 66  SFCond       equ          F_DATA + A_REMOTE
 67  SFMux        equ          4
 68  SFLen        equ          6
 69
 70               ;sample cell pressure, slow
 71  SPS_Tset     equ          ONE_HZ
 72  SPSCond      equ          A_REMOTE
 73
 74               ;5 volts reference
 75  Vref_Tinit   equ          5
 76  Vref_Tset    equ          5
 77  VrefCond     equ          A_REMOTE
 78  VrefMux      equ          5
 79
 80               ;heater drive voltage
 81  HtrDrv_Tinit equ          2
 82  HtrDrv_Tset  equ          3
 83  HtrDrvCond   equ          A_REMOTE
 84  HtrDrvMux    equ          6
 85
 86  Bp1_Tinit    equ          2
 87  Bp1_Tset     equ          8
 88  Bp1Cond      equ          F_DATA + A_REMOTE
 89  Bp1Mux       equ          16
 90  Bp1Len       equ          12
 91  Bp2_Tinit    equ          3
 92  Bp2_Tset     equ          8
 93  Bp2Cond      equ          F_DATA + A_REMOTE
 94  Bp2Mux       equ          16
 95  Bp2Len       equ          12
 96
 97  Resp_Tinit   equ          7
 98  Resp_Tset    equ          8
 99  RespCond     equ          F_DATA + A_REMOTE
100  RespMux      equ          16
101  RespLen      equ          12
102
103  Body1_Tinit  equ          5
104  Body1_Tset   equ          ONE_HZ
105  Bt1Cond      equ          A_REMOTE
106  Bt1Mux       equ          16  ;?
107
108  Body2_Tinit  equ          6
109  Body2_Tset   equ          ONE_HZ
110  Bt2Cond      equ          A_REMOTE
111  Bt2Mux       equ          16  ;?
112
```

```
113  Co2DCMux       equ   15
114  Co2DCCond      equ   A_REMOTE    ;DCs for gases
115  N2oDCMux       equ   14
116  N2oDCCond      equ   A_REMOTE
117  AgentDCMux     equ   13
118  AgentDCCond    equ   A_REMOTE
119
120  ;*** LOCAL CHANNELS
121
122  Poff_Tinit     equ   1
123  Poff_Tset      equ   1
124  PoffCond       equ   0
125
126  ; Cir/Cred same as Poff's
127
128  Ir_Tinit       equ   1
129  Ir_Tset        equ   14
130  IrCond         equ   F_DATA
131  IrMux          equ   6
132  IrLen          equ   6
133
134  RedMux         equ   5           ;else the same as IR
135
136  N2o_Tinit      equ   2
137  N2o_Tset       equ   8
138  N2OCOND        equ   F_DATA
139  N2oMux         equ   3
140  NO2Len         equ   12
141
142  Agent_Tinit    equ   3
143  Agent_Tset     equ   8
144  AgentCond      equ   F_DATA
145  AgentMux       equ   4
146  AgentLen       equ   12
147
148  Co2_Finit      equ   4
149  Co2_Tset       equ   8
150  CO2COND        equ   F_DATA
151  CO2Mux         equ   2
152  CO2Len         equ   12
153
154  Co2S_Tinit     equ   1
155  Co2S_Tset      equ   ONE_HZ
156  CO2SCOND       equ   0
157
158  N2oS_Tinit     equ   2
159  N2oS_Tset      equ   ONE_HZ
160  N2OSCOND       equ   0
161
162  AgentS_Tinit   equ   3
163  AgentS_Tset    equ   ONE_HZ
164  AgentSCond     equ   0
165
166
167  Bat_Tinit      equ   1
168  Bat_Tset       equ   ONE_HZ
169  BatCond        equ   0
170  BatMux         equ   1
```

```
171           MDrv_Tinit    ;motor drive level
172           MDrv_Tset     equ     1
173           MDrvCond      equ     1
174           MDrvMux       equ     0
175                         equ     10
176
177           OBS_Tinit     ;optical bench speed
178           OBS_Tset      equ     1
179           OBSCond       equ     1
180           OBSMux        equ     0
181                         equ     11
182           .list
183

Wed 09-25-86 10:17:08  ACBTABLE.I
    10-15-86 14:09:36

1   ;.xlist
2   ;****************************************************************
3   ;
4   ;       MFO Ver 0.0
5   ;
6   ;       Module: acq.inc
7   ;
8   ;       modification history :
9   ;
10  ;       13 May  86  slc  split from aacq.s
11  ;       18 May  86  slc  remote channels on top of ACB
12  ;       20 June 86  slc  change ASCII names into id word
13  ;       10 July 86  slc  split defs into acddefs.inc
14  ;        8 Sept 86  slc  big change via schematic
15  ;       19 Sept 86  slc  add DC channels for gases
16  ;
17  ;       COPYRIGHT (C) 1986 NELLCOR INCORPORATED
18  ;
19  ;       THIS IS AN ORIGINAL, UNPUBLISHED WORK AND IS PROPRIETARY TO NELLCOR, INC.,
20  ;       AND MAY NOT BE DIVULGED OR COPIED IN ANY FORM WHATSOEVER WITHOUT
21  ;       EXPRESS PERMISSION FROM NELLCOR, INC.
22  ;
23  ;       This file is to be included in following modules:
24  ;               acqmain.s  only
25  ;
26  ;       page+
27  ;
28  ;****************************************************************
29  ;
30  ;    ACB initialization, 13 ITEMS for each ACB
31  ;    You have to init A_NAME,A_TIMERSET,A_TIMERINIT,A_COND,A_MUX,A_PGAIN,A_OFFSET
32  ;    A_LENGTH here, total 8 items
33  ;    Note : A_LENGTH = 2 * No. of Samples + 2
34  ;    Item Sequence IN ACB :
35  ;    A_ID,         A_TIMERINIT, A_TIMERSET, A_TIMERCOUNT, A_TIMERINIT,
36  ;    A_MUX,        A_PGAIN,     A_OFFSET,   A_LIST,       A_PROC
37  ;    A_PID,        A_LENGTH,    A_BUFFER0,  A_BUFFER1,    A_BUFFER2
38
39  AcbTblInit      LABEL   word    ;ACB (A:D tables) init beginning
40
```

```
41      ;********** REMOTE CHANNELS START HERE **********
42      ;with highest priority channel on the top
43  LO_     equ     6       ;length overhead (incl. pid,aid,length words)
44
45  ACB_Eep     ACB (AID_Eep,Eep_Tinit,Eep_Tset,,EepCond,EepMux,1,0)      ;Eeprom channel
46  ACB_Ecg     ACB (AID_Ecg,Ecg_Tinit,Ecg_Tset,,EcgCond,EcgMux,1,0,,,EcgLen + LO_) ;ECG channel
47  ACB_OBTemp  ACB (AID_OBTemp,OBT_Tinit,OBT_Tset,,OBTCond,OBTMux,1,0)   ;Optical Bench temp.
48  ACB_FloPres ACB (AID_FloPres,FP_Tinit,FP_Tset,,FPCond,FPMux,1,0)      ;gas flow pressure
49  ACB_SSPres  ACB (AID_SSampPre,SP_Tinit,SPS_Tset,,SPSCond,SPMux,1,0)   ;sample pressure,fast sample
50  ACB_SampPre ACB (AID_SampPre,SP_Tinit,SP_Tset,,SPCond,SPMux,1,0,,,SPLen + LO_) ;sample
        cell pressure
51  ACB_HtrDrv  ACB (AID_HtrDrv,HtrDrv_Tinit,HtrDrv_Tset,,HtrDrvCond,HtrDrvMux,1,0) ;heater
        drive voltage
52  ACB_Bp1     ACB (AID_Bp1,Bp1_Tinit,Bp1_Tset,,Bp1Co..1, Bp1Mux, 1,0,,,BpiLen + LO_) ;BP1 channel
53  ACB_Bp2     ACB (AID_Bp2,Bp2_Tinit,Bp2_Tset,,Bp2Ccnn, Bp2Mux, 1,0,,,BpiLen + LO_) ;BP2 channel
54  ACB_Resp    ACB (AID_Resp,Resp_Tinit,Resp_Tset,,RespCond,RespMux,1,0,,,RespLen + LO_) ;RESP
        channel
55  
56  ACB_Body1   ACB (AID_Body1,Body1_Tinit,Body1_Tset,,Bt1Cond, Bt1Mux, 1,0) ;BODY TEMP 1
        channel ;slow data
57  ACB_Body2   ACB (AID_Body2,Body2_Tinit,Body2_Tset,,Bt2Cond, Bt2Mux, 1,0) ;BODY TEMP 2
        channel ;slow data
58  ACB_Vcal    ACB (AID_Vcal,Vcal_Tinit,Vcal_Tset,,VcalCond,VCalMux,1,0) ;vcal channel ;slow
        data
59  ACB_Vref    ACB (AID_Vref,Vref_Tinit,Vref_Tset,,VrefCond,VrefMux,1,0) ;5 volts reference
60  ACB_N2oDC   ACB (AID_N2oDC, 2,ONE_HZ,,N2oDCCOND,N2oDCMux,1,0 )
61  ACB_AgentDC ACB (AID_AgentDC, 3,ONE_HZ,,AgentDCCOND,AgentDCMux,1,0 )
62  ACB_CO2DC   ACB (AID_co2DC, 4,ONE_HZ,,co2DCCOND,co2DCMux,1,0 ) ;DCs for gases
63
64
65  ;note : PROC is calrck()
66
67
68  RemoteCnt       equ     ($ - AcbTblInit) / TYPE ACB ;no. of remote channels
69
70      ;********** LOCAL CHANNELS START HERE **********
71
72  ; NOTE: sequence: ACB_Poff, ACB_Cir, ACB _Cred then ACB_ir, ACB_red
73
74  ACB_Poff    ACB (AID_Poff,Poff_Tinit,Poff_Tset,,PoffCond,PoffMux,1,0) ;p-gain offset channel ;
        slow data
75
76  ACB_Cir     ACB (AID_Cir,Poff_Tinit,Poff_Tset,,PoffCond,IrMux,1,0) ;calibrating channel 1 ;
        slow data
77
78  ACB_Cred    ACB (AID_Cred,Poff_Tinit,Poff_Tset,,PoffCond,RedMux,1,0) ;calibrating channel 2 ;
        slow data
79
80  ACB_Ir      ACB (AID_Ir,Ir_Tinit,Ir_Tset,,IrCond,IrMux,1,0,,,IrLen+LO_) ;IR channel
81
82  ACB_Red     ACB (AID_Red,Ir_Tinit,Ir_Tset,,IrCond,RedMux,1,0,,,IrLen+LO_) ;red channel
83
84  ACB_N2o     ACB (AID_N2o,N2o_Tinit,N2o_Tset,,N2OCOND,N2OMux,1,0,,,CO2Len+LO_)
85
86  ACB_Agent   ACB (AID_Agent,Agent_Tinit,Agent_Tset,,AgentCOND,AgentMux,1,0,,,AgentLen+LO_) ;
        AGENT channel
87
```

SECTION C

GAS

```
 88      ACB_N2oS    ACB   (AID_N2oS,N2oS_Tinit,N2oS_Tset,,N2oSCOND,N2oMux,1,0 )
 89      ACB_AgentS  ACB   (AID_AgentS,AgentS_Tinit,AgentS_Tset,,AgentSCOND,AgentMux,1,0 )  ;AgentS
 90                          channel
 91      ACB_Co2S    ACB   (AID_co2S,co2S_Tinit,co2S_Tset,,co2SCOND,co2Mux,1,0 )
 92      ACB_Co2     ACB   (AID_Co2,Co2_Tinit,Co2_Tset,CO2COND,CO2Mux,1,0,,,CO2Len+LO_)
 93
 94
 95      ACB_MotDrv  ACB   (AID_MotDrv,MDrv_Tinit,MDrv_Tset,,MDrvCond,MDrvMux,1,0) ;motor drive level
 96      ACB_OBSpeed ACB   (AID_OBSpeed,OBS_Tinit,OBS_Tset,,OBSCond,OBSMux,1,0) ;optical bench speed
 97      ACB_Bat     ACB   (AID_Bat,Bat_Tinit,Bat_Tset,,BatCond,BatMux,1,0) ;battery
 98
 99      ;AcbTbLen   equ    $ - offset AcbTblInit
100
101      ACB_CNT     equ    ($ - offset AcbTblInit) / type ACB
102      .list
103
```

```
Wed 10-07-86 12:07:16   DGHIST.H                      CO2VAL2HIST
    10-15-86 13:02:30

1    /*********************************************************************
  2    **      info:       project
  3    **
  4    **      module:     dghist.h
  5    **
  6    **      modification history :   reason(s)
  7    **          date        by        creation
  8    **      10-07-86       laf        creation
  9    **
 10    **      Copyright (C) 1985, NELLCOR INCORPORATED
 11    **
 12    **      This module is an original, unpublished work and is proprietary to
 13    **      NELLCOR INC., and may not be divulged or copied in any form
 14    **      whatsoever without the express written permission of NELLCOR INC.
 15    **
 16    **      purpose :
 17    **
 18    **      data descriptions :
 19    **
 20    **
 21    *********************************************************************/
 22
 23
 24    #define MAXCO2VALUE     10        /* 10 % */
 25    #define MAXCO2HIST      255       /* 1 byte for now later to be expanded to 2 bytes */
 26    /* conversion factor from measured value to trend value */
 27    #define CO2VAL2HIST     (MAXCO2HIST/MAXCO2VALUE)
```

```
28  #define MAXN2OVALUE     100     /* 100 % */
29  #define MAXN2OHIST      255
30  /* conversion factor from measured value to trend value */
31  #define N2OVAL2HIST     (MAXN2OHIST/MAXN2OVALUE)
32  #define MAXAGTVALUE     100     /* 1 byte for now later to be expanded to 2 bytes */
33  #define MAXAGTHIST      255
34  /* conversion factor from measured value to trend value */
35  #define AGTVAL2HIST     (MAXAGTHIST/MAXAGTVALUE)
36  #define MAXBRVALUE      255     /* 255 % */
37  #define MAXBRHIST       255     /* 1 byte for now later to be expanded to 2 bytes */
38  /* conversion factor from measured value to trend value */
39  #define BRVAL2HIST      (MAXBRHIST/MAXBRVALUE)
40
41  typedef struct
42  {   SCALED  etCO2, etN2O, etAgent;
43      SCALED  insCO2, insN2O, insAgent;
44      SCALED  brate;
45  } Histsum;
46
47  typedef struct
48  {   short   etCO2, etN2O, etAgent;
49      short   insCO2, insN2O, insAgent;
50      short   brate;
51  } Histcnt;
52
53
54  /* function */
55  void near GrstHist();
56  void near GCO2ETHist();
57  void near GN2OETHist();
58  void near GAGTETHist();
59  void near GCO2INSHist();
60  void near GN2OINSHist();
61  void near GAGTINSHist();
62  void near GBRHist();
63  char far GCO2ETHistavg();
64  char far GN2OETHistavg();
65  char far GAGTETHistavg();
66  char far GCO2INSHistavg();
67  char far GN2OINSHistavg();
68  char far GAGTINSHistavg();
69  char far GBRHistavg();
70
71  #ifdef INITDGHIST
72  Histsum ghistsum = { 50m, 50m, 50m, 50m, 50m, 50m, 50m };
73  Histcnt ghistcnt = {  0,  0,  0,  0,  0,  0,  0 };
74
75  #else
76  extern Histsum ghistsum;
77  extern Histcnt ghistcnt;
78
79  #endif
```

```
Wed 10-02-86 18:40:10   AGGLOBAL.H
     10-15-86 13:02:30

1  /*******************************************************************
 2  **
 3  **  mfo project
 4  **
 5  **  module = agglobal.h
 6  **
 7  **  modification history :     reason(s)
 8  **        date          by
 9  **      09-03-86        laf    created
10  **
11  **  Copyright (C) 1985, NELLCOR INCORPORATED
12  **
13  **  This module is an original, unpublished work and is proprietary to
14  **  NELLCOR INC., and may not be divulged or copied in any form
15  **  whatsoever without the express written permission of NELLCOR INC.
16  **
17  **  purpose :
18  **
19  **  function descriptions :
20  **
21  *******************************************************************/
22  /* functions */
23  void far Azerosig();
24  void far Abackflushsig();
25  void far Apumppower();
26  void far Amotorpower();
27
28
29  void far xcli();
30  void far xsti();
31  void far xSetTimeDelay();
32
33  char far WFLink();
34
35  void far cSendSlow();
```

```
Wed 10-10-86 12:53:30   AGSTART.C
     10-15-86 13:02:30

1  /*******************************************************************
 2  **
 3  **       mfo    project
 4  **
 5  **       module: agstart.c
 6  **
 7  **       modification history :     reason(s)
 8  **            date         by
 9  **          12-22-85       epr     creation.
10  **          01-08-86       bpb     modifications to initializing system.
11  **          07-09-86       laf     additional zero offsets and valve sequence to init.
12  **          07-01-86       laf     converted from alpha's gas.c
13  **
```

```
                /***********************************************************
        *       Copyright (C) 1985, NELLCOR INCORPORATED
        *
        *       This module is an original, unpublished work and is proprietary to
        *       NELLCOR INC., and may not be divulged or copied in any form
        *       whatsoever without the express written permission of NELLCOR INC.
        *
        *       purpose :
        *
        *       data descriptions :
        *
        ************************************************************/
#include         "..\bxid.h"
#include         "..\xclock.h"
#include         "..\xevent.h"
#include         "..\itest\aiglue.h"
#include         "..\itest\aiglobal.h"
#include         "..\itest\aistart.h"
#include         "..\itest\bique.h"
#include         "..\itest\aleep.h"
#include         "agacq.h"
#define          INITAGSTART
#include         "agstart.h"
#include         "agbscan.h"
#include         "agbuffer.h"
#include         "agctrans.h"
#include         "agevent.h"
#include         "agfindie.h"
#include         "agglobal.h"
#include         "agpres.h"
#include         "agtemp.h"
#include         "agtrans.h"
#include         "agzcalib.h"
#include         "agtimers.h"

char *gstackp = NULL;

void far
GCreateP()
{
        gstackp = xALLOC(GSTACKSIZE);
        xCreateP(PID_GAS, Gmain, (gstackp + GSTACKSIZE - 2), >hingstodo, Gterm);
} void far
Gmain()
{
        long    eventmask = 0;
/*      not sure about these things
        getautocaltime(++cp);
        getagentdelay(++cp);
        getagentbrate(++cp);
*/
initsystem:
/*      Do all system initilization here. */
/*      Greadeep(); */
/***********************************************************/
```

```
 72  /*    done forget to add the eeprom read */
 73  /*******************************************/
 74        GenableH20Corr();
 75        gcorrection = gtakedata = TRUE;
 76        Gbufinit();   /* initialize buffers before reset */
 77        Gstbrth();
 78        gcorrection = gtakedata = FALSE;
 79  /* before taking real data */
 80        Amotorpower(NORMMOTORPWR);  /* get initial values for breath events */
 81        Gacqinit();                  /* get control block pointers */
 82        Ginitpacb();                 /* get acq server */
 83        GinitALink();                /* link to acq server */
 84        GinitWFLink();               /* link to waveform server */
 85        Azerosig(FALSE);             /* normal pump valve mode */
 86        (backflushsig(FALSE);
 87        Gactivate();                 /* activate acq channels */
 88        Greadbaropressure();         /* pump gets jump started in this routine */
 89        Grstautocaltimer();
 90        Gautocalibration();
 91        Gflowset(PUMPNORMAL);        /* should already be in this mode */
 92        /* Call to sched is an infinite loop except for a termination event. */
 93        eventmask = eventmask ; (short)A_DATA_EV;
 94        while(1)
 95          {    ;Wait(eventmask, 0);
 96               Gtevent();    /* in event.c */
 97          }
 98  }
 99
100
101  void near
102  Ginitpacb()
103  {    register short i;
104
105        for (i = 0; i < NCHNL; i++)
106               gchnlinfo[i].pacb = A_Util( GetPacb_acq, gchnlinfo[i].id);
107  }
108
109  void near
110  GinitALink()
111  {    register short i;
112        for (i = 0; i < NCHNL; i++)
113          {    if(gchnlinfo[i].funct != NULL)
114                    A_Link(gchnlinfo[i].id, gchnlinfo[i].funct);
115          }
116  }
117
118  void near
119  Gactivate()
120  {    register short i;
121        /**********************************************/
122        /* need to add test for what is attached */
123        /* for now turn all of them on */
124        /**********************************************/
125        for (i = 0; i < NCHNL; i++)
126               A_Util(Act_acq, gchnlinfo[i].pacb);
127  }
128
129
```

```
130   void near
131   GinitWFLink()
132   {
133       WFLink(GwfCO2, wID_CO2, 1, AID_CO2);
134   }
135
136   void near
137   Greadeep()
138   {
139       char (*eeptr)[3];          /* special char point will inc by three bytes */
140       short i;
141
142       Irsteepbuf();               /* reset ieepbuf[] to all zeros */
143       Aeread(ieepbuf);            /* read the eeprom into the buffer in special format */
144                                   /*************************************************
145       eeptr = ieepbuf;            *   /* warning : 'i=?' : different levels of
146                                    *   indirection */
147                                   /*************************************************/
148                   /* short eeprom list, all othest are SCALED S0 */
149   /* *3* getabszero */ for( i = 0; i < 3; i++) /* CO2, N20, Agent */
150       gcalref[i] = SptoS(eeptr++);
151
152       gcalref[3] = gcalref[0];
153   /* *7* getTemperatureConstants */    gcalref[4] = gcalref[5] = gcalref[6] = gcalref[0];
154       gRefTmprtr = SptoS(eeptr++);
155       for( i = 0; i < 2; i++) /* CO2, N20 */
156           gtctfb0[i] = SptoS(eeptr++);
157       for( i = 0; i < 2; i++) /* CO2, N20 */
158           gtctfc0[i] = SptoS(eeptr++);
159       for( i = 0; i < 2; i++) /* CO2, N20 */
160           gtctfd0[i] = SptoS(eeptr++);
161   /* *1* getZeroCorr */
162       gdTfor0 = SptoS(eeptr++);
163   }
164
165   void far
166   Gterm()
167   {
168       *FREE(gstackp);
169   }
170
```

```
Wed 10-01-86 11:48:36  AGSTART.H
Wed 10-15-86 13:02:30

1  /********************************************************************
2  **
3  **   mfo project
4  **
5  **   module = agstart.h
6  **
7  **   modification history :
8  **       date          by          reason(s)
```

```
  9  **    07-03-86    laf    created
 10  **
 11  **    Copyright (C) 1985, NELLCOR INCORPORATED
 12  **
 13  **    This module is an original, unpublished work and is proprietary to
 14  **    NELLCOR INC., and may not be divulged or copied in any form
 15  **    whatsoever without the express written permission of NELLCOR INC.
 16  **
 17  **    purpose :
 18  **
 19  **    function descriptions :
 20  **
 21  ****************************************************************************/
 22
 23  #define GSTACKSIZE 220
 24
 25  #define XWAITSEC      400       /* 400Hz = 0.0025 sec */
 26  #define TIMERSEC       50       /*  50  = 0.0200 sec */
 27
 28  #define NCHNL          6
 29  #define DID_ACQ       17 * 256  /* all fast data */
 30
 31  #define AID_CO2   DID_ACQ+0x30    DID_ACQ+0x03
 32  #define AID_N2O   DID_ACQ+0x31    DID_ACQ+0x02
 33  #define AID_Agt   DID_ACQ+0x32    AID_FloPres
 34  #define AID_Pre   DID_ACQ+0x50    AID_OBTemp
 35
 36  #define AID_FloPres               DID_ACQ+0x03
 37  #define AID_OBTemp                DID_ACQ+0x02
 38  #define AID_FloS                  AID_FloPres
 39  #define AID_TmpS                  AID_OBTemp
 40
 41  struct Gidtble
 42  {   short    id;            /* global data identifier */
 43      short    pacb;          /* pointer to acq control block returned from A_Util */
 44      void    (far *(funct))();
 45  };
 46
 47  /* functions */
 48  void far  GCreateP();
 49  void far  Gmain();
 50  void near Ginitpacb();
 51  void near GinitALink();
 52  void near Gactivate();
 53  void near GinitWFLink();
 54  void near Greadeep();
 55  void far  Gterm();
 56
 57  #ifdef INITAGSTART
 58  struct Gidtble gchnlinfo[NCHNL] =
 59  {   {AID_CO2,  0, Gacqco2},
 60      {AID_N2O,  0, Gacqn2o},
 61      {AID_Agt,  0, Gacqagt},
 62      {AID_TmpS, 0, Gacqtmp},
 63      {AID_Pre,  0, Gacqpre},
 64      {AID_FloS, 0, Gacqflo}
 65  };
 66
```

```
67   #else
68   extern struct GIdtble gchnlinfo[];
69   #endif
70
71

Wed 10-10-86 17:11:12   AGEVENT.C
Wed 10-15-86 13:02:30

1   /*****************************************************************************
 2   **
 3   **     project:         mfg
 4   **
 5   **     module:          agevent.c
 6   **
 7   **     modification history :
 8   **        date       by     reason(s)
 9   **        12/11/85   epr    creation
10   **        01/20/86   epr    changed from error and normal events to just Events
11   **        02/13/86   epr    moved postevents to pevents
12   **        05/29/85   epr    modified buffer sceem to allow agent delay.
13   **        07/14/86   laf    change temperature check timer from 10 sec to 1 sec
14   **        07/17/86   laf    added haloselbut and halothane select
15   **                          cntrl H haloset temptime!
16   **        07-19-86   epr    added resettemptime.
17   **        07-04-86   laf    convert from alpha's event.c
18   **        09-16-86   laf    split gsched() into gbevent() for breath related events
19   **                          and gtevent() for time related events. removed
20   **   Gpostevents()
21   **
22   **   Copyright (C) 1985, NELLCOR INCORPORATED
23   **
24   **   This module is an original, unpublished work and is proprietary to
25   **   NELLCOR INC., and may not be divulged or copied in any form
26   **   whatsoever without the express written permission of NELLCOR INC.
27   **
28   **   purpose :
29   **     to post and schedule events.
30   **
31   **   data descriptions :
32   **     event data types
33   **     event queue      -- is a queue of to be scheduled events.
34   **     timers           -- this is union of timed down timers for time based
35   **        event.
36   **        systime       -- is a count of all ticks.
37   **        timedowntime  -- the time remaining before a timedown event.
38   **        lastetbtime   -- used to save time of last etb for brate calc.
39   **        waittimer     -- timer used by the wait function.
40   **        apneaalarmon  -- boolean indicator of apnea condition.
41   **        disptorr      -- boolean indicator of pressure display mode.
42   **        tracefreeze   -- boolean indicator of tracefreeze mode.
43   **        keyevents     -- contains button/event pairs, used to create event
44   **                         associated with button.
45   **        timers        -- contains time remaining/time interval/event triples
46   **                         that are used by the timer function to generate event at selected
47   **                         intervals.
```

```
 48   *   function descriptions :
 49   *
 50   *     sched() takes events out of the event queue and runs the appropiate
 51   *             function for that event.
 52   *
 53   *     timer() is scheduled every one second, and it in turn schedules
 54   *             all functions that operate on a time base.
 55   *
 56   *     havekeyevent() is scheduled by the keypad interrupt routine. It
 57   *             looks at the recived keys and schedules events associated with
 58   *             those events.
 59   *
 60   *     putevent(event) puts an event number in the evnet queue.
 61   *
 62   *     postdelayevents(delay, event) -- after a delay it causes
 63   *             event to be posted.
 64   *
 65   ************************************************************************/
 66   #include     "../xclock.h"
 67   #include     "../itest/aiglue.h"
 68   #include     "../itest/aiglobal.h"
 69   #include     "../itest/bique.h"
 70   #include     "../xevent.h"
 71   #include     "agevent.h"
 72   #define INITAGEVENT
 73   #include     "agacq.h"
 74   #include     "agbscan.h"
 75   #include     "agbuffer.h"
 76   #include     "agtrans.h"
 77   #include     "agfindle.h"
 78   #include     "agglobal.h"
 79   #include     "agpres.h"
 80   #include     "agstart.h"
 81   #include     "agtemp.h"
 82   #include     "agtrans.h"
 83   #include     "agcalib.h"
 84   #include     "agtimers.h"
 85   #include     "agcomm.h"
 86
 87   void   near
 88   GsWait(smpcnt)
 89   short    smpcnt;  mintick;
 90   {
 91   /*
 92        if waiting for a number of data points, time should be in 100 msec
 93        intervals since that is when data transfer occurs. There should also be
 94        a 200 msec off set added
 95   */
 96
 97        mintick = smpcnt/CO2DSETCNT + 2;
 98        mintick = mintick * WTICKSPERDSET;
 99        GtWait(mintick);
100   }
101
102   void   near
103   GtWait(ticks)
104   short    ticks;
105
```

```
106       short eventmask = (short)NO_EV;
107       if(ticks == 0)
108          return;
109       /* allows the data collection to continue to run */
110       eventmask = eventmask | (short)A_DATA_EV;
111       eventmask = eventmask | (short)TIME_EV;
112       while(1)
113       {
114          if(xWait(eventmask, ticks) == (short)TIME_EV)
115             ticks = 0xffff; /* just for debug */
116             return;
117          }
118          else
119          {
120             Gtevent();           /* in event.c */
121             ticks = ticks - WTICKSPERDSET;
122             if(ticks ( 1)
123                return;
124          }
125       }
126    }
127
128    void near
129    Gtevent()
130    {
131       register Event event;
132       register short i;
133       short s;
134       while ((short) (event = (Event)Igetfromque(>eventQ)) != NOQUEDATA)
135          switch (event)
136          {
137          case ACQDSETFULL:
138             for(i = 0; i ( CO2DSETCNT; i++)
139                if(Gfilladarray() == ERROR)
140                   Ipushinque(&gbeventQ, BBREATH); /* big
                                                     problems */
141                   break;
142             }
143             Gbscan();
144             Gbevent();
145             break;
146          case MINMAXTIME:
147    /* reset this timer when buffers are cleared or not full */
148             Gfindminmax();
149             break;
150          case AUTOCALTIME:
151             Grstautocaltimer();
152          case MANZEROEVENT:
153             Gautocalibration();
154             Gresettemptimer();          */
155             break;
156          case APNEATIME:
157             gapneaalarmon = TRUE;
158             Gcommapnea();
159             gcorrection = TRUE;
160             Grstbrth();
161             gcorrection = FALSE;
162             break;
```

```
163                    case FLOWCHECKTIME:
164                            Gpresupdate();        /*                              */
165                            break;
166                    case TEMPCHECKTIME:
167                            Gtempupdate();
168                            break;
169    /*                 gnancalibration();                                   */
170                    case MANSPANEVENT:
171                            break;
172                    case AGNTSELEVENT:
173                            Gagentselect();
174                            break;
175    /*          }
176
177             }
178     }
179     void near
180     Gbevent()
181     {
182             register Event event;
183             register short i;
184
185             while ((short) (event = (Event)Igetfromque(&gbeventQ)) != NOQUEDATA)
186             switch (event)
187             { case ETBREATH:
188                            gfirstbreath = TRUE;      /* find exp before look for ins */
189                            i = (short) (getbtime - glastetbtime);
190                            Gexpclinbreath(i);
191                            Grstapneatimer();         /* also starts it going the first
192                                                         time */
193                            if(gapneaalarmon == TRUE)
194                            {
195                                    gapneaalarmon = FALSE;
196                                    Gcommapnea();
197                            }
198                            Gsetminmaxtimer((i*TIMERSEC)/CO2PERSEC);
199                            glastetbtime = getbtime;
200                            break;
201                    case INSBREATH:
202                            /* haven't found an expired since last reset */
203                            if(gfirstbreath ==FALSE)
204                                    break;
205                            i = (short) (ginstime - glastinstime);
206                            Ginsclinbreath(i);
207                            Grstapneatimer();         /* also starts it going the first
208                                                         time */
209                            if(gapneaalarmon == TRUE)
210                            {
211                                    gapneaalarmon = FALSE;
212                                    Gcommapnea();
213                            }
214                            Gsetminmaxtimer((i*TIMERSEC)/CO2PERSEC);
215                            glastinstime = ginstime;
216                            break;
217                    case BBREATH:  /* buffer filled without finding a breath */
                               /* not sure we need this case at all anymore */
                               /* both findminmax and apnea are now timer functions */
                               Gfindminmax();
```

```
218              if (gendt == -1)
219                  gendt = TRUE; /* fix non-understood bug! */
220              break;
221
222          default:
223              break;
224      }
225  }
```

```
Wed 10-01-86 16:35:48  AGEVENT.H
    10-15-86 13:02:30

1  /****************************************************************
 2  *
 3  *        pcopp - endtidal co2 project
 4  *
 5  *        module = agevent.h
 6  *
 7  *        modification history :
 8  *        date      by    reason(s)
 9  *        12/11/85  epr   creation
10  *        07-17-86  laf   added haloselevent to enum Event
11  *        09-02-86  laf   converted from alpha's event.h
12  *        09-16-86  laf   add ACQSETFULL to enum normalevent
13  *
14  *        Copyright (C) 1985, NELLCOR INCORPORATED
15  *
16  *        This module is an original, unpublished work and is proprietary to
17  *        NELLCOR INC., and may not be divulged or copied in any form
18  *        whatsoever without the express written permission of NELLCOR INC.
19  *
20  *        purpose :
21  *
22  *        data descriptions :
23  *            normal and error event definitons.
24  *
25  *        function descriptions:
26  *            putevent(event) is pseudo function that calls
27  *            putinque(enventque, event)
28  *
29  *            getevent() is a pseudo function that calls
30  *            getfromque(eventque)
31  *
32  ****************************************************************/
33
34  typedef enum normalevent {
35      NBUFFULL = -4,
36      ETBREATH = 1,
37      INSBREATH = 2,
38      DBREATH = 3,
39      MINMAXTIME,
40      AFNEATIME,
41      ACQSETFULL,
42      FLOWCHECKTIME,
43      TEMPCHECKTIME,
```

```
            AUTOCALTIME,
            MANZEROEVENT,
            MANSFANEVENT,
            AGNTSELEVENT,
            TERMEVENT = 100
         } Event;

/* functions */
   void    near    GsWait();
   void    near    GtWait();
   void    near    Gtevent();
   void    near    Gbevent();

#ifdef INITAGEVENT
boolean gdisp_torr = TRUE;
boolean gtracefreeze = TRUE;
SCALED  gtickspermin = (0x7700, 12, POS, NOTZERO, 0); /* 60*100 = 6000.0 */
IQUEUE(gbeventQ,32)
IQUEUE(gteventQ,32)
boolean gapneaalarmon = FALSE;
boolean gfirstbreath = FALSE;
short   gbbcount = 0;

unsigned gwaittimer = 0;
long     gsystime = 0;
long     getbtime = 0;
long     ginstime = 0;
long     glastebtime = 0;
long     glastinstime = 0;
short    geventcntr = 0;  /* if this counter exceeds 300 pevents stops breath
                             detection operation. */
#else
extern boolean  gdisp_torr;
extern boolean  gtracefreeze;
extern SCALED   gtickspermin;
IEXTQUEUE(gbeventQ, 32)
IEXTQUEUE(gteventQ, 32)
extern boolean  gapneaalarmon;
extern boolean  gfirstbreath;
extern short    gbbcount;
extern unsigned gwaittimer;
extern long     gsystime;
extern long     getbtime;
extern long     ginstime;
extern long     glastebtime;
extern long     glastinstime;
extern short    geventcntr;
#endif
```

Wed 10-02-86 14:57:38  AGBSCAN.C                                           Gbscan
    10-15-86 13:02:30

```
 1  /**********************************************************************
 2   *
```

```
 3    *                project:    mfo
 4    *                module:     agbscan.c
 5    *
 6    *                modification history :
 7    *                    date            by          reason(s)
 8    *                                                reason(s)
 9    *                    09-07-86        laf         converted from alpha's pevent.s
10    *                    09-16-86        laf         changed from agacquire.c
11    *
12    *
13    *                Copyright (C) 1985, NELLCOR INCORPORATED
14    *
15    *    This module is an original, unpublished work and is proprietary to
16    *    NELLCOR INC.; and may not be divulged or copied in any form
17    *    whatsoever without the express written permission of NELLCOR INC.
18    *
19    *    purpose :
20    *
21    *    function descriptions :
22    *
23    ***********************************************************************/
24
25    #include     "..\itest\aiglue.h"
26    #include     "..\itest\aiglobal.h"
27    #include     "..\itest\bique.h"
28    #define      INITAGBSCAN
29    #include     "agbscan.h"
30    #include     "agacq.h"
31    #include     "agbuffer.h"
32    #include     "agctrans.h"
33    #include     "agevent.h"
34    #include     "agfindie.h"
35    #include     "agglobal.h"
36    #include     "agpres.h"
37    #include     "agstart.h"
38    #include     "agtemp.h"
39    #include     "agtrans.h"
40    #include     "agzcalib.h"
41
42    void near
43    Gbscah()
44    {
45      gsystime++;
46    doconvert:
47      grawtemperature = gad_array[ADTMP];
48      !putinque (>emp0, grawtemperature );
49      grawflow = gad_array[ADFLO];
50      if(gcorrection==TRUE) /* don't do breath detection */
51
52    dodatastorage:      Gbufput( gco2buf, gad_array[ADCO2]);
53                        Gbufput( gn2obuf, gad_array[ADN2O]);
54                        Gbufput( gagentbuf, gad_array[ADAGT]);
55                        grawpressure = gad_array[ADPRE];
56                        Gbufput( gprebuf, grawpressure);
57                        return;
58                      }
59    dobreathstorage:
```

```
 60         if(Gbufput(gagentbuf, gad_array[ADAGT]) == ERROR)
 61             !forceinque(&gbevent@,BBREATH);
 62     Abuffer:
 63         if(gendt != -1)          /* not waiting for agent */
 64         {
 65             gticksthisbuf++;
 66             Gbufput(gco2buf, gad_array[ADCO2]);
 67             Gbufput( gn2obuf, gad_array[ADN2O]);
 68             grawpressure = gad_array[ADPRE];
 69             Gbufput( gprebuf, grawpressure);
 70     dobreathdetection:
 71         if(( gticksthisbuf )>= MINTICKFOREVENT) &&
 72             (gad_array[ADCO2] ( gcurr_min) &&
 73             (gendt == FALSE))
 74         {
 75             gcurr_min = gad_array[ADCO2];
 76             if(gcurr_min <= gthins)
 77             {
 78                 gendt = -1;
 79                 gbufferticks += gticksthisbuf;
 80                 gticksthisbuf = 0;
 81                 ginstime = gsystime;
 82                 !pushinque(&gbevent@, INSBREATH);
 83                 gcurr_max = gcurr_min = gthresh;
 84             }
 85         }
 86         else if(( gticksthisbuf )>= MINTICKFOREVENT) &&
 87             (gad_array[ADCO2] )>= gcurr_max) &&
 88             (gendt == TRUE))
 89         {
 90             gcurr_max = gad_array[ADCO2];
 91             if(gcurr_max )>= gthexp)
 92             {
 93                 gendt = -1;
 94                 gbufferticks += gticksthisbuf;
 95                 gticksthisbuf =0;
 96                 getbtime = gsystime;
 97                 !pushinque(&gbevent@, ETBREATH);
 98                 gcurr_min = gcurr_max = gthresh;
 99             }
100         }
101     }
102     void near
103     Gacqinit()
104     {
105         register short izero;
106
107         izero = StoI
108                 (      , addS( gcalzeros[ICO2GAS], gcalref[ICO2GAS])
109                 );
110         gthresh = izero - 100; /* midpoint of exp/ins thresholds */
111         gcurr_min = gthresh;
112         gcurr_max = gthresh;
113         gthexp = izero - 50;  /* inspired event threshold */
114         gthins = izero - 150; /* expired event threshold */
115     }
```

```
Wed 09-23-86 18:04:12  AGBSCAN.H
    10-15-86 13:02:30

1  /****************************************************************
 2  **
 3  **       project:       mfo
 4  **
 5  **       module: agbscan.h
 6  **
 7  **       modification history :
 8  **            date               by              reason(s)
 9  **            date               by              reason(s)
10  **            09-07-86           laf             converted from alpha's pevent.s
11  **
12  **       Copyright (C) 1985, NELLCOR INCORPORATED
13  **
14  **       This module is an original, unpublished work and is proprietary to
15  **       NELLCOR INC., and may not be divulged or copied in any form
16  **       whatsoever without the express written permission of NELLCOR INC.
17  **
18  **       purpose :
19  **
20  **       data descriptions :
21  **
22  **       function descriptions :
23  **
24  ****************************************************************/
25
26  #define RVOLTOFFSET     21
27  #define MINTICKFOREVENT 10
28  #define ADCO2           0
29  #define ADN2O           1
30  #define ADAGT           2
31  #define ADTMP           3
32  #define ADPRE           4
33  #define ADFLO           5
34
35  /* function */
36  void near Gbscan();
37  void near Gacqinit();
38
39  #ifdef INITAGBSCAN
40  short   gticksthisbuf = 0;
41  /* The following are variables used for breath detection */
42  short   gthresh = 0;    /* midpoint of exp/ins threshholds */
43  short   gthexp  = 0;    /* inspired event threshold */
44  short   gthins  = 0;    /* expired event threshold */
45  short   gcurr_max = 0;
46  short   gcurr_min = 0;
47
48  #else
49  extern short    gticksthisbuf;
50  extern short    gthresh;
51  extern short    gthexp;
52  extern short    gthins;
53  extern short    gcurr_max;
```

```
54    extern short  gcurr_min;
55    #endif
56

Wed 10-10-86 08:49:16 AGZCALIB.C
    10-15-86 13:02:30

1   /*****************************************************************
 2    **
 3    **   project:        mfo
 4    **
 5    **   module:         agzcalib.c
 6    **
 7    **   modification history :
 8    **     date         by      reason(s)
 9    **     12-18-85     epr     creation.
10    **     07-09-86     laf     incorporated additional zero offset (zeroOff[]).
11    **                          added 8 step valve sequence.
12    **     08-28-86     laf     converted from alpha cal.c
13    **
14    **   Copyright (C) 1985, NELLCOR INCORPORATED
15    **
16    **   This module is an original, unpublished work and is proprietary to
17    **   NELLCOR INC.; and may not be divulged or copied in any form
18    **   whatsoever without the express written permission of NELLCOR INC.
19    **
20    **   purpose : This object is responsible for the calibration functions which
21    **             generate the calibration values in calzeros[] and calspan[].
22    **             It also needs to generate a user interface that is a simple
23    **             steep by step procedure for obtaining the calibration values.
24    **
25    **   data descriptions :
26    **     calzeros[] is an array of calibration constants that are indexed
27    **                by GAS type values. These are produced by auto or manual zero operation.
28    **
29    **     calspan[] is an array of calibration constants taht are indexed
30    **               by GAS type values. These are produced by the Manual Calibration
31    **               operation.
32    **
33    **   function descriptions :
34    **     autocalibration() -- responsible for all air calibration
35    **                          factors. It is called by event every fifteen minutes or
36    **                          when manual zero is pressed.
37    **     mancalibration() -- responsible for all gas calibration
38    **                         factors. It is called when manual span is pressed.
39    **
40    *****************************************************************/
41
42
43   #include   "..\xevent.h"
44   #include   "agglobal.h"
45   #include   "..\itest\aiglue.h"
46   #include   "..\itest\aiglobal.h"
47   #include   "..\itest\bique.h"
48   #define    INITAGZCALIB
49   #include   "agzcalib.h"
50   #include   "agacq.h"
```

```
 51   #include    "agbscan.h"
 52   #include    "agbuffer.h"
 53   #include    "agtrans.h"
 54   #include    "agevent.h"
 55   #include    "agfindle.h"
 56   #include    "agpres.h"
 57   #include    "agstart.h"
 58   #include    "agtemp.h"
 59   #include    "agtrans.h"
 60
 61   void near
 62   Gautocalibration()
 63   {
 64       register int *ip;
 65       register int i;
 66       long sum;
 67
 68       Gflowset(PUMPFULL);
 69       gcorrection = TRUE;
 70       for(i = 0; i < 8; i++)   /* don't look for breaths */
 71           Gvalvcmd(gvalvseq[i].valvmode, gvalvseq[i].valvtime);
 72                                /* run the valve sequence */
 73       /* seq leave it in backflush mode */
 74       Grstbrth();
 75       Gflushtemp();
 76       GsWait(AVGCALNUM);
 77       for (sum = i = 0, ip = &(gco2buf->data[1]); i < AVGCALNUM; i++, ip++)
 78           sum += *ip;
 79       gcalzerosref[ICO2GAS] = subS
 80                               (  subS
 81                                  ( divS( LtoS(sum), ItoS(i) ),
 82                                    gcalref[ICO2GAS]
 83                                  ),
 84                                  gzeroOff[ICO2GAS]
 85                               );
 86       xcli();
 87       gcalzerosref[ICO2GAS] = gcalzerosref[ICO2GAS];
 88       xsti();
 89       for (sum = i = 0, ip = &(gn2obuf->data[1]); i < AVGCALNUM; i++, ip++)
 90           sum += *ip;
 91       gcalzerosref[IN2OGAS] =
 92           gcalzerosref[IN2OGAS]= subS
 93                               (  subS
 94                                  ( divS( LtoS(sum), ItoS(i) ),
 95                                    gcalref[IN2OGAS]
 96                                  ),
 97                                  gzeroOff[IN2OGAS]
 98                               );
 99       for (sum = i = 0, ip = &(gagentbuf->data[1]); i < AVGCALNUM; i++, ip++)
100           sum += *ip;
101       gcalzeros[IAGAS] =
102           gcalzerosref[IAGAS] =            subS
103                               (  subS
104                                  ( divS( LtoS(sum), ItoS(i) ),
105                                    gcalref[IAGAS]
106                                  ),
107                                  gzeroOff[IAGAS]
108                               );
                                  gcalzeros[(short) FORANEGAS]
```

```
109                = gcalzeros[(short) HALOTHANEGAS]
110                = gcalzeros[(short) ETHRANEGAS]
111                = gcalzeros[(short) PRESSUREGAS]
112                = gcalzeros[IAGAS];
113     gcalzerosref[(short) FORANEGAS]
114                = gcalzerosref[(short) HALOTHANEGAS]
115                = gcalzerosref[(short) ETHRANEGAS]
116                = gcalzerosref[(short) PRESSUREGAS]
117                = gcalzerosref[IAGAS];
118
119     Gflowset(PUMPNORMAL);
120     GtWait(2 * XWAITSEC);
121     GlastTemp();       /* does not flush the que */
122     Gtempupdate();
123     Grstbrth();
124     Abackflushsig(FALSE);     /* finally return things to normal */
125     Azerosig(FALSE);
126     GtWait(5 * XWAITSEC);
127     GZeroOut();
128     gcorrection = FALSE;
129 }
130 /* when ready for mancalibration get from alpha/cal.c */
131
132 void near
133 Gvalvcmd(mode, msectime)
134 char    mode;
135 short   msectime;
136 {
137     long longtime;
138     switch(mode){
139     case NORMALVALV:
140             Azerosig(FALSE);
141             Abackflushsig(FALSE);
142             break;
143     case BLWFMFVALV:
144             Azerosig(TRUE);
145             Abackflushsig(FALSE);
146             break;
147     case CLRVACVALV:
148             Azerosig(FALSE);
149             Abackflushsig(TRUE );
150             break;
151     case BKFLSHVALV:
152             Azerosig(TRUE);
153             Abackflushsig(TRUE);
154             break;
155     default:
156             return;
157             break;
158     }
159     longtime = msectime;       /* short to long for math */
160     longtime = (longtime * XWAITSEC)/1000;
161     msectime = longtime;       /* long to short fro parameter passing */
162     if(msectime > 0)
163             GtWait(msectime);
164     return;
165 }
```

```
Wed 10-02-86 11:59:14  AGZCALIB.H
    10-15-86 13:02:30

1  /*****************************************************************
 2   **
 3   **    pcopp - endtidal co2 project
 4   **
 5   **    module = agzcalib.h
 6   **
 7   **    modification history :
 8   **       date         by         reason(s)
 9   **    12-18-85        epr        creation
10   **    07-09-86        laf        add additional zeroOff[] variable
11   **                               define 4 possible Zero/Backflush valve modes
12   **    08-28-86        laf        converted from alpha cal.h
13   **
14   **    Copyright (C) 1985, NELLCOR INCORPORATED
15   **
16   **    This module is an original, unpublished work and is proprietary to
17   **    NELLCOR INC.; and may not be divulged or copied in any form
18   **    whatsoever without the express written permission of NELLCOR INC.
19   **
20   **    purpose :
21   **           To provide the gobal data for the
22   **           object that is responsible for the calibration functions which
23   **           generate the calibration values in calzeros[] and calspan[].
24   **           It also needs to generate a user interface that is a simple
25   **           step by step procedure for obtaining the calibration values.
26   **
27   **    data descriptions :
28   **           calzeros[] is an array of calibration constants that are indexed
29   **           by GAS type values. These are produced by auto or manual zero operation.
30   **
31   **           calspan[] is an array of calibration constants taht are indexed
32   **           by GAS type values. These are produced by the Manual Calibration
33   **           operation.
34   **
35   ******************************************************************/
36
37
38  #define N2OSPAN      S100m
39  #define CO2SPAN      S100m
40  #define AGENTSPAN    S100m
41
42  #define CO2ZEROREF    {0x3334, -1, NEG, NOTZERO, 0}
43  #define N2OZEROREF    {0x3334, -1, NEG, NOTZERO, 0}
44  #define AGENTZEROREF  {0x3334, -1, NEG, NOTZERO, 0}
45
46  #define CO2ZERO       {0xf120, 11, POS, NOTZERO, 0} /* 3977.000000 */
47  #define N2OZERO       {0x8c00,  8, POS, NOTZERO, 0} /*  396.000000 */
48  #define AGENTZERO     {0x9a0,  14, POS, NOTZERO, 0} /* 17000.000000 */
49
50  #define CO2ZEROOFF    S0m
51  #define N2OZEROOFF    S0m
52  #define AGENTZEROOFF  S0m
53
```

```
54   #define ZEROCALSECONDS 6
55   #define AVGCALNUM 100
56   #define MINMANCALNUM 90
57
58
59   #define ICO2GAS (short) CO2GAS
60   #define IN2OGAS (short) N2OGAS
61   #define IAGAS   (short) AGENTGAS
62
63   #define NORMALVALV  0
64   #define BLWPMPVALV  1
65   #define CLRVACVAL   2
66   #define BKFLSHVALV  3
67
68   #define SUMN 10
69   #define AVGN 5
70
71   struct valvparam
72        short valvmode;  /*    Backflush    Zero   valvmode Process
73                                                    Off  Off    0   NORMALVALV
74                                                    Off  On     1   BLWPMPVALV
75                                                    On   Off    2   CLRVACVAL
76                                                    On   On     3   BKFLSHVALV
77                                               */
78       short valvtime;
79   };
80   /* functions */
81   void  near  Gautocalibration();
82   void  near  Greadbaropressure();
83   void  near  Gvalvcmd();
84
85   #ifdef INITAGZCALIB
86
87
88   short gautocaldelay = ZEROCALSECONDS;
89
90   /* from eep: needs to be subtracted from raw value in calc of modulation */
91   SCALED gcalref[7] = {CO2ZEROREF, /* CO2Gas */ N2OZEROREF, /* N2OGas */
92                                                AGENTZEROREF, /* ForaneGas */
93                                                AGENTZEROREF, /* HalothaneGas */
94                                                AGENTZEROREF, /* EthraneGas */
95                                                AGENTZEROREF, /* AgentGas */
96                                                AGENTZEROREF}; /* PressureGas */
97
98
99   SCALED gcalspan[7] = {CO2SPAN, /* */    N2OSPAN, /* */
100                                          AGENTSPAN, /* */
101                                          AGENTSPAN, /* */
102                                          AGENTSPAN, /* */
103                                          AGENTSPAN, /* */
104                                          AGENTSPAN}; /* */
105
106  /* calzeroref compensated for temp */
107  SCALED gcalzeros[7] = {CO2ZERO, /* CO2Gas */  N2OZERO, /* N2OGas */
108                                                AGENTZERO, /* ForaneGas */
109
110
```

```
111                                              AGENTZERO,  /* HalothaneGas */
112                                              AGENTZERO,  /* EthraneGas */
113                                              AGENTZERO,  /* AgentGas */
114                                              AGENTZERO}; /* PressureGas */
115
116  /* room air value - zerooff */
117  SCALED gcalzerosref[7] = {CO2ZERO,  /* CO2Gas */
118                            AGENTZERO, /* N2OGas */
119                            AGENTZERO, /* ForaneGas */
120                            AGENTZERO, /* HalothaneGas */
121                            AGENTZERO, /* EthraneGas */
122                            AGENTZERO, /* AgentGas */
123                            AGENTZERO}; /* PressureGas */
124
125  /* from eep: subtracted from room air value to calc calzeroref[]s */
126  SCALED gzerooff[7] = {CO2ZEROOFF, /* CO2Gas */
127                       N2OZEROOFF, /* N2OGas */
128                       AGENTZEROOFF, /* ForaneGas */
129                       AGENTZEROOFF, /* HalothaneGas */
130                       AGENTZEROOFF, /* EthraneGas */
131                       AGENTZEROOFF, /* AgentGas */
132                       AGENTZEROOFF}; /* PressureGas */
133
134  short gcorrection = FALSE;
135  short gtakedata = TRUE;
136
137  /* These are emperical constants used the collision broadening equation. */
138  SCALED gcbL = {0x322e, -14, NEG, NOTZERO, 0}; /* -0.000073 */
139  SCALED gcbM = {0x4f8a, -19, NEG, NOTZERO, 0}; /* -0.000002 */
140  /* This is an emperical constant used in the co2 modulation correction. */
141  SCALED gCO2NmodPFCorr = {0, 0, POS, ISZERO, 0}; /* 0.000000 */
142  SCALED gSpareCorr = {0, 0, POS, ISZERO, 0}; /* 0.000000 */
143  /* These are emperical constants used in the agent modulation correction. */
144  SCALED gCO2AmodPFCorr = {0x8734, -9, NEG, NOTZERO, 0}; /* -0.002985 */
145  SCALED gN2OAmodPFCorr = {0x556b, -12, NEG, NOTZERO, 0}; /* -0.000326 */
146  SCALED gSpanCO2Target = {0x1999, 2, POS, NOTZERO, 0}; /* 4.399963 */
147  SCALED gSpanAgentTarget = {0x51e, 2, POS, NOTZERO, 0}; /* 4.079956 */
148  SCALED gSpanN2OTarget = {0x6ecc, 6, POS, NOTZERO, 0}; /* 91.699219 */
149
150  struct valvparam gvalvseq[8] = {         /* 8 step valve seq from eep file */
151                                  {BLWPMPVALV, 500},
152                                  {CLRVACVALV, 200},
153                                  {BLWPMPVALV, 500},
154                                  {BKFLSHVALV, 1800},
155                                  {BKFLSHVALV, 0},
156                                  {BKFLSHVALV, 0},
157                                  {BKFLSHVALV, 0},
158                                  {BKFLSHVALV, 0}
159                                };
160
161  SCALED glaststep = 50m;
162  short *gipn = NULL;
163  short *gplateaustart = NULL, *gplateauend = NULL;
164  SCALED gminmmHg = {0x7000, 4, POS, NOTZERO, 0}; /* = 25 mmHg */
165  short gthis = 0, glast = 0, gpastend = 0;
166
167
```

```
168     #else
169     extern  short   gautocaldelay;
170     extern  SCALED  gcalzeros[7];
171     extern  SCALED  gcalzerosref[7];
172     extern  SCALED  gcalspan[7];
173     extern  SCALED  gcalref[7];
174     extern  SCALED  gzerooff[7];
175     extern  short   gcorrection;
176     extern  short   gtakedata;
177     extern  SCALED  gcbL, gcbM;
178     extern  SCALED  gCO2NmodPPCorr, gSpareCorr, gCO2AmodPPCorr, gN2OAmodPPCorr;
179     extern  SCALED  gSpanCO2Target;
180     extern  SCALED  gSpanAgentTarget;
181     extern  SCALED  gSpanN2OTarget;
182     extern  struct  Valvparam gvalvseq[];
183     extern  SCALED  glaststep;
184     extern  short   *gipn;
185     extern  short   *gplateaustart, *gplateauend;
186     extern  SCALED  gminmmHg;
187     extern  short   gthis, glast, gpastend;
188     #endif
189
```

Wed 09-29-86 07:23:18 AGBUFFER.C
Wed 10-15-86 13:02:30

```
 1   /*******************************************************
 2    *
 3    *   project:    mfo
 4    *
 5    *   module:     agbuffer.c
 6    *
 7    *   modification history :
 8    *       date            by      reason(s)
 9    *       2-09-85         BFB     creation
10    *       02-10-85        epr     moved the bufput operation to buffer.s
11    *       08-28-86        laf     converted from alpha's buffer.c
12    *
13    *   This module is an original, unpublished work and is proprietary to
14    *   NELLCOR INC., and may not be divulged or copied in any form
15    *   whatsoever without the express written permission of NELLCOR INC.
16    *
17    *   purpose :
18    *       to create and maintain buffers of [rawdata].
19    *
20    *   data descriptions :
21    *       buffers of [rawdata]:
22    *           format:
23    *                   0     1        2              BUFSIZ + 1
24    *           -- | putpntr | rawdata | rawdata | ... | rawdata |
25    *
26    *   input to functions :
27    *           pointers to specific buffers created by bufcreate.
28    *           single items of [rawdata].
29    *   output from functions :
30    *           pointers to buffers and positions within specific buffers.
```

```
    *       "download" entire buffers of [rawdata].
    *
    *    function descriptions :
    *       bufinit()
    *          type : medium.
    *          data : pointers.
    *          output: sets up all buffers and initializes pointers.
    *          **** returns 0.
    *
    *       bufcreate()
    *          type : primitive.
    *          data : pointers.
    *          output: none.
    *          **** returns pointer to specific buffer created.
    *          (end of epr comments )
    *
    *    void near Gbufinit(); creates and initializes data buffers for co2, n2o,
    *    agent and pressure
    *
    *    BB * near Gbufcreate(); returns pointer to next available buffer
    *
    *    void near Gzerobuf(bufp);    zero's data[] of buffer "bufp.data[]"
    *
    *    void near Grstbufs();        sets buf.ptr = &(buf.data[0])
    *
    *    short near Gbufput(buf , x);    places value "x" int buffer "buf"
    **********************************************************************/
#include       "../itest/aiglue.h"
#include       "../itest/aiglobal.h"
#include       "../itest/bique.h"
#define INITAGBUFFER
#include       "agbuffer.h"
#include       "agacq.h"
#include       "agbscan.h"
#include       "agctrans.h"
#include       "agevent.h"
#include       "agfindie.h"
#include       "agglobal.h"
#include       "agpres.h"
#include       "agstart.h"
#include       "agtemp.h"
#include       "agtrans.h"
#include       "agzcalib.h"

void near
Gbufinit()
{
    gco2buf = Gbufcreate();
    gn2obuf = Gbufcreate();
    gagentbuf = Gbufcreate();
    gprebuf = Gbufcreate();
    Gzerobuf(gco2buf);                          /* fill data array with 0 */
    Gzerobuf(gn2obuf);
    Gzerobuf(gagentbuf);
    Gzerobuf(gprebuf);
```

```
 88            Grstbufs();                    /* reset all ptr to data[0] */
 89    }
 90
 91    BB * near
 92    Gbufcreate()
 93    {       return (gbufnext++);
 94    }
 95
 96
 97    void near
 98    Gzerobuf(bufp)
 99    BB * bufp;
100    {       register short  * ptr ;
101            register short  i;
102            ptr = bufp->data;
103            for(i = 0; i < BUFSIZ; i++,ptr++)
104                    *ptr = 0;
105    }
106
107
108    void near
109    Grstbufs()
110    {       gco2buf->ptr = gco2buf->data;
111            gn2obuf->ptr = gn2obuf->data;
112            gagentbuf->ptr = gagentbuf->data;
113            gprebuf->ptr = gprebuf->data;
114            /* for waveform marking */
115            gbufroll = 0;
116            grolltime = gsystime;
117    }
118
119
120    short near
121    Gbufput(buf, x)
122    BB    *buf;
123    short x;
124    {       if ((buf->ptr - buf->data) < EXTRASIZ)
125    bpextra:        /* in the first EXTRASIZ locations */
126                    *(buf->ptr + BUFSIZ -1) = x;
127                    *buf->ptr++ = x;
128                    return(OK);
129            }
130            else if ( (buf->ptr - buf->data) >= BUFSIZ)
131            {       buf->ptr = buf->data;
132                    *buf->ptr++ = x;
133                    gbufroll = TRUE;
134                    grolltime = gsystime;
135                    return(ERROR);
136            }
137            else
138                    *buf->ptr++ = x;
139    }
```

```
Wed 09-25-86 16:29:42 AGBUFFER.H
    10-15-86 13:02:30

1  /****************************************************************
2   *    project: mfo
3   *
4   *    module:  agbuffer.h
5   *
6   *    modifications:
7   *         date        by     reason(s)
8   *         12-02-85    BFB    creation
9   *         08-28-86    laf    changed from alpha' buffer.h to agbuffer.h
10  *
11  *    Copyright (C) 1985, NELLCOR INCORPORATED
12  *
13  *    This module is an original, unpublished work and is proprietary to
14  *    NELLCOR INC., and may not be divulged or copied in any form
15  *    whatsoever without the express written permission of NELLCOR INC.
16  *
17  *    purpose:
18  *         To define # of buffers and size of buffers utilized by buffer.c
19  *
20  *    data descriptions:
21  *         Constants relating to buffers of [rawdata] created and maintained
22  *         by (buffer.c).
23  *         (end of epr comments)
24  *
25  *         BB gbufspace[BUFCNT] generic declaration of all breath buffers for
26  *         gathering data including pointer, data array and extra data array
27  *
28  *         BB *gbufnext; counts through beginning of each gbufspace[] pointing to
29  *         next available breath buffer
30  *
31  ****************************************************************/
32
33
34  #define BUFCNT      4    /* (co2, n2o, agent, pressure) */
35  /* changes in BUFSIZ and EXTRASIZ must be reflected in agfindle.s */
36  #define BUFSIZ      500  /* 4 * buffersize corresponds to apnea event */
37  #define EXTRASIZ    10   /* extra data buffer size */
38
39  typedef struct breathbuffer
40  {
41      short *ptr;
42      short data[BUFSIZ];   /* any change must be reflected in bufput.s */
43      short extradata[EXTRASIZ];
44  } BB;
45
46  #define BBSIZE sizeof(BB);
47
48  /* macros if no one uses it, get rid of it
49  #define Ginitbufptr(bufpntr) bufpntr->ptr = bufpntr->data
50  */
51  /* functions */
52  void   near   Gbufinit();
53  BB *   near   Gbufcreate();
54  void   near   Gzerobuf();
```

```
55    void    near    Grstbufs();
56    short   near    Gbufput();
57
58    #ifdef           INITAGBUFFER
59    BB *gco2buf = NULL, *gn2obuf = NULL, *gagentbuf = NULL, *gprebuf = NULL;
60    BB gbufspace[BUFCNT] = {0};
61    BB *gbufnext = gbufspace;
62
63    short gbufroll  = 0;
64    long  grolltime = 0;
65
66    #else
67    extern  BB  *gco2buf, *gn2obuf, *gagentbuf, *gprebuf;
68    extern  BB  gbufspace[BUFCNT];
69    extern  BB  *gbufnext;
70
71    extern short gbufroll;
72    extern long  grolltime;
73
74    #endif
```

```
Wed 10-02-86 13:34:12 AGTEMP.C
    10-15-86 13:02:30

1    /**********************************************************************
 2    *
 3    *   pcopp - endtidal co2 project
 4    *
 5    *   module  = agtemp.c
 6    *
 7    *   modification history :    reason(s)
 8    *   date            by        creation
 9    *   12-20-85        epr       convert from alpha's temprtr.c
10    *   09-02-86        laf
11    *
12    *   Copyright (C) 1985, NELLCOR INCORPORATED
13    *
14    *   This module is an original, unpublished work and is proprietary to
15    *   NELLCOR INC., and may not be divulged or copied in any form
16    *   whatsoever without the express written permission of NELLCOR INC.
17    *
18    *   purpose :
19    *       To determine temperature and temperature correction coeficients.
20    *
21    *   data descriptions :
22    *       gtctfA, gtctcB, TctfC the partial pressure correction coeficients
23    *       gtctfa0, gtctfa1, gtctfa2 the coeficients for calculating gtctfA
24    *       gtctfb0, gtctfb1, gtctfb2 the coeficients for calculating gtctfB
25    *       gtctfc0, gtctfc1, gtctfc2 the coeficients for calculating gtctfC
26    *       currenttemperature is the temperature translated form
27    *       rawtemperature.
28    *
29    *   function descriptions :
30    *       temperatureupdate() -- function scheduled by event that updates
31    *           the current temperature.
32    *       tmpcrtrnfnc() -- calculates the temperature coeficients needed
```

```
 * *       RtoKT(t)      for partial pressure calculation.
 * *       RtoVolts(t)   -- converts raw temperature to Kelvin (macro).
 * *       KelvinToCelcius(k) -- converts raw temperature to volts (macro).
 *                              -- converts kelvin to celcius.
 **********************************************************************/
#include    "..\itest\aiglue.h"
#include    "..\itest\aiglobal.h"
#include    "..\itest\bique.h"
#include    "agevent.h"
#define INITAGTEMP
#include    "agtemp.h"
#include    "agacq.h"
#include    "agbscan.h"
#include    "agbuffer.h"
#include    "agtrans.h"
#include    "agfindie.h"
#include    "agglobal.h"
#include    "agpres.h"
#include    "agstart.h"
#include    "agtrans.h"
#include    "agzcalib.h"

void near
Gtempupdate()
{
    register short gasi;
    SCALED tsqr;
    gCT = ImeanQue(>empQ);
    if (equS(gCT, S0)) /* test if the que was empty */
        return;
    gCT = GRTtoC(gCT);
    GflushtempQ();
    if (gtS( absS( subS(gCT, glastCdeg) ), gdTfor0))
    {   Ipushinque(>eventQ, AUTOCALTIME);
    } gtdelta = subS(gCT, gRefTmprtr);
    tsqr = mulS(gtdelta, gtdelta);

for (gasi = (short) FIRSTGAS; gasi (= (short) LASTGAS; gasi++)
    {   /* B = b0 + (b1 * T) + (b2 * T * T) */
        gtctfB[gasi] = addS  (                    gtctfb0[gasi],
                             addS
                             ( mulS(gtctfb1[gasi], gtdelta),
                               mulS(gtctfb2[gasi], tsqr) )
                             );

/* C = c0 + (c1 * T) + (c2 * T * T) */
        gtctfC[gasi] = addS  (                    gtctfc0[gasi],
                             addS
                             ( mulS(gtctfc1[gasi], gtdelta),
                               mulS(gtctfc2[gasi], tsqr) )
                             );
```

```
 90                                  /* D = d0 + (d1 * T) + (d2 * T * T) */
 91                     gtctfD[gas1] = addS
 92                                         (
 93                                          ( gtctfd0[gas1],
 94                                            addS
 95                                               ( muls(gtctfd1[gas1], gtdelta),
 96                                                 muls(gtctfd2[gas1], tsqr)
 97                                               )
 98                                         );
 99                                  /* Z = rZ * (1 + ((Tnew - Told) * f)) */
100                     gcalzeros[gas1] = mulS
101                                             (
102                                               gcalzerosref[gas1],
103                                               addS
104                                                 (
105                                                   S1,
106                                                   mulS
107                                                      ( subS(gCT, glastCdeg),
108                                                        gT0Corr[gas1]
109                                                      )
110                                                 )
111                                             );
112              }
113              gtctfA[AGENTGAS] = gtctfA[(short) gAagent];
114              gtctfB[AGENTGAS] = gtctfB[(short) gAagent];
115              gtctfC[AGENTGAS] = gtctfC[(short) gAagent];
116              gtctfD[AGENTGAS] = gtctfD[(short) gAagent];
117       }
118       void near
119       GlastTemp()
120       {   SCALED TC;
121           TC = ImeanQue(>empQ);
122           if(equS(TC, S0))                          /* test if the que was empty */
123             return;
124           glastCdeg = GRTtoC(TC);
125       }
126       void near
127       GflushtempQ()
128       {   IflushQue(>empQ);
129       }
130       SCALED near
131       GRTtoC(t)
132       SCALED t;
133       {   return
134                  mulS
135                      (
136                        subS
137                            (
138                              mulS(t, ADCSCALE),   /* A/D counts to volts */
139                              gKELVINOFF           /* 273 oK = 0 oC */
140                            ),
141                        S100                /* 10 mv/ oK */
                          );
          }
```

```
Wed 10-02-86 16:08:44  AGTEMP.H
    10-15-86 13:02:30

/*******************************************************************
**
**      pcopp - endtidal co2 project
**
**      module = agtemp.h
**
**      modification history :
**        date       by      reason(s)
**        02-20-85   epr     creation
**        07-02-86   laf     converted form alpha's temprtr.h
**
**      Copyright (C) 1985, NELLCOR INCORPORATED
**
**      This module is an original, unpublished work and is proprietary to
**      NELLCOR INC., and may not be divulged or copied in any form
**      whatsoever without the express written permission of NELLCOR INC.
**
**      purpose :
**           To determine temperature and temperature correction coeficients.
**
**      data descriptions :
**           tctfA[7] array of constants for partial pressure calculation.
**           tctfB[7] array of constants for partial pressure calculation.
**           tctfC[7] array of constants for partial pressure calculation.
**           tempvolts --
**           tempdeg --
**
**      needs ../itest/bique.h
*******************************************************************/ define KELVINOFF        {0x5d71, 1, POS, NOTZERO, 0}    /* 2.73 */ define AGENTTCTFB0      {0x0000, 0, POS, ISZERO, 0}/*  1.000000 */
define AGENTTCTFB1      {0x0000, 0, POS, ISZERO, 0}/*  0.000000 */
#define AGENTTCTFB2      {0x0000, 0, POS, ISZERO, 0}/*  0.000000 */
#define AGENTTCTFC0      {0x0000, 0, POS, NOTZERO, 0}/* 1.000000 */
#define AGENTTCTFC1      {0x0000, 0, POS, ISZERO, 0}/*  0.000000 */
#define AGENTTCTFC2      {0x0000, 0, POS, ISZERO, 0}/*  0.000000 */
#define AGENTTCTFD0      {0x0000, 0, POS, NOTZERO, 0}/* 1.000000 */
#define AGENTTCTFD1      {0x0000, 0, POS, ISZERO, 0}/*  0.000000 */
define AGENTTCTFD2      {0x0000, 0, POS, ISZERO, 0}/*  0.000000 */ define CO2TCTFA         50m
define CO2TCTFB         {0xe347, -1, POS, NOTZERO, 0}  /* 51m */
#define CO2TCTFB0        {0xe347, -1, POS, NOTZERO, 0}  /* 50m */
#define CO2TCTFB1        50m
#define CO2TCTFB2        50m
#define CO2TCTFC         {0x60cc, -6, POS, NOTZERO, 0}  /* 50m */
#define CO2TCTFC0        {0x60cc, -6, POS, NOTZERO, 0}  /* 50m */
#define CO2TCTFC1        50m
#define CO2TCTFC2        50m
#define CO2TCTFD         {0x76a6, -11, POS, NOTZERO, 0} /* 50m */
#define CO2TCTFD0        {0x76a6, -11, POS, NOTZERO, 0} /* 50m */
#define CO2TCTFD1        50m
```

```
55
56  #define CO2TCTFD2  50m
57
58  #define N2OTCTFA           50m
59  #define N2OTCTFB          {0x0c6c,  3, POS, NOTZERO,  0}  /* 61m */
60  #define N2OTCTFB0         {0x0c6c,  3, POS, NOTZERO,  0}  /* 50m */
61  #define N2OTCTFB1          50m
62  #define N2OTCTFB2          50m
63  #define N2OTCTFC          { 0x77Bb, -2, NEG, NOTZERO,  0}  /* 50m */
64  #define N2OTCTFC0         { 0x77Bb, -2, NEG, NOTZERO,  0}  /* 50m */
65  #define N2OTCTFC1          50m
66  #define N2OTCTFC2          50m
67  #define N2OTCTFD          { 0xae68, -8, POS, NOTZERO,  0}  /* 50m */
68  #define N2OTCTFD0         { 0xae68, -8, POS, NOTZERO,  0}  /* 50m */
69  #define N2OTCTFD1          50m
70  #define N2OTCTFD2          50m
71
72  #define FORTCTFA   50m
73  #define FORTCTFB   50m
74  #define FORTCTFB0  50m
75  #define FORTCTFB1  50m
76  #define FORTCTFB2  50m
77  #define FORTCTFC   50m
78  #define FORTCTFC0  50m
79  #define FORTCTFC1  50m
80  #define FORTCTFC2  50m
81  #define FORTCTFD   50m
82  #define FORTCTFD0  50m
83  #define FORTCTFD1  50m
84  #define FORTCTFD2  50m
85
86  #define ETHTCTFA   50m
87  #define ETHTCTFB   50m
88  #define ETHTCTFB0  50m
89  #define ETHTCTFB1  50m
90  #define ETHTCTFB2  50m
91  #define ETHTCTFC   50m
92  #define ETHTCTFC0  50m
93  #define ETHTCTFC1  50m
94  #define ETHTCTFC2  50m
95  #define ETHTCTFD   50m
96  #define ETHTCTFD0  50m
97  #define ETHTCTFD1  50m
98  #define ETHTCTFD2  50m
99
100 #define HALTCTFA   50m
101 #define HALTCTFB   50m
102 #define HALTCTFB0  50m
103 #define HALTCTFB1  50m
104 #define HALTCTFB2  50m
105 #define HALTCTFC   50m
106 #define HALTCTFC0  50m
107 #define HALTCTFC1  50m
108 #define HALTCTFC2  50m
109 #define HALTCTFD   50m
110 #define HALTCTFD0  50m
111 #define HALTCTFD1  50m
    #define HALTCTFD2  50m
```

```
112     #define CO2T@CORR  50m
113     #define N2OT@CORR  50m
114     #define AGENTT@CORR  50m
115
116     #define TQSIZE 50
117
118     /* functions */
119     void    near    gtempupdate();
120     void    near    GlastTemp();
121     void    near    Gflushtemp();
122     SCALED  near    GRTtoC();
123
124     #ifdef INITAGTEMP
125     /* These are indexed by the GAS type. */
126     SCALED gKELVINOFF = KELVINOFF;
127     SCALED gtctfA[] = {
128             CO2TCTFA,/* CO2 gas */
129             N2OTCTFA,/* N2O gas */
130             SZEROm, /* Agent gas */
131             FORTCTFA,/* Forane gas */
132             HALTCTFA,/* Halothane gas */
133             ETHTCTFA,/* Ethrane gas */
134             SZEROm}; /* Pressure Gas */
135
136     SCALED gtctfB[] = {
137             CO2TCTFB, /* CO2 gas */
138             N2OTCTFB, /* N2O gas */
139             S1m, /* Agent gas */
140             FORTCTFB, /* Forane gas */
141             HALTCTFB, /* Halothane gas */
142             ETHTCTFB, /* Ethrane gas */
143             S1m}; /* Pressure gas */
144
145     SCALED gtctfC[] = {
146             CO2TCTFC, /* CO2 gas */
147             N2OTCTFC, /* N2O gas */
148             SZEROm, /* Agent gas */
149             FORTCTFC, /* Forane gas */
150             HALTCTFC, /* Halothane gas */
151             ETHTCTFC, /* Ethrane gas */
152             SZEROm}; /* Pressure gas */
153
154     SCALED gtctfD[] = {
155             CO2TCTFD, /* CO2 Gas */
156             N2OTCTFD, /* N2O Gas */
157             SZEROm, /* Agent Gas */
158             FORTCTFD, /* Forane Gas */
159             HALTCTFD, /* Halothane Gas */
160             ETHTCTFD, /* Ethrane Gas */
161             SZEROm}; /* pressure gas */
162
163     SCALED gtempvolts = S0m, gtempdeg = S0m;
164     short grawtemperature = 0;
165     SCALED gRefTmprtr = {0x86fd, 5, POS, NOTZERO, 0}; /* 48.8734 */
166     SCALED glastCdeg = S0m;
```

```
SCALED  gCT = 50in, gtdelta = 50m;
SCALED  gdTfor0 = {0x999a, -3, POS, NOTZERO, 0}; /* 0.2 */
SCALED  gtctfb0[] = {CO2TCTFB0,        N2OTCTFB0,
                                       FORTCTFB0, HALTCTFB0, ETHTCTFB0,
                                       AGENTTCTFB0;
                                       AGENTTCTFB0};

SCALED  gtctfb1[] = {CO2TCTFB1,        N2OTCTFB1,
                                       FORTCTFB1, HALTCTFB1, ETHTCTFB1,
                                       AGENTTCTFB1;
                                       AGENTTCTFB1};

SCALED  gtctfb2[] = {CO2TCTFB2,        N2OTCTFB2, HALTCTFB2, ETHTCTFB2,
                                       FORTCTFB2, HALTCTFB2, ETHTCTFB2,
                                       AGENTTCTFB2;
                                       AGENTTCTFB2};

SCALED  gtctfc0[] = {CO2TCTFC0,        N2OTCTFC0,
                                       FORTCTFC0, HALTCTFC0, ETHTCTFC0,
                                       AGENTTCTFC0;
                                       AGENTTCTFC0};

SCALED  gtctfc1[] = {CO2TCTFC1,        N2OTCTFC1,
                                       FORTCTFC1, HALTCTFC1, ETHTCTFC1,
                                       AGENTTCTFC1;
                                       AGENTTCTFC1};

SCALED  gtctfc2[] = {CO2TCTFC2,        N2OTCTFC2,
                                       FORTCTFC2, HALTCTFC2, ETHTCTFC2,
                                       AGENTTCTFC2;
                                       AGENTTCTFC2};

SCALED  gtctfd0[] = {CO2TCTFD0,        N2OTCTFD0,
                                       FORTCTFD0, HALTCTFD0, ETHTCTFD0,
                                       AGENTTCTFD0;
                                       AGENTTCTFD0};

SCALED  gtctfd1[] = {CO2TCTFD1,        N2OTCTFD1,
                                       FORTCTFD1, HALTCTFD1, ETHTCTFD1,
                                       AGENTTCTFD1;
                                       AGENTTCTFD1};

SCALED  gtctfd2[] = {CO2TCTFD2,        N2OTCTFD2,
                                       FORTCTFD2, HALTCTFD2, ETHTCTFD2,
                                       AGENTTCTFD2;
                                       AGENTTCTFD2};
```

```
226       SCALED gtØCorr[] = { /* Correction Constants for calZero */
227                            CO2TØCORR,
228                            N2OTØCORR,
229                            AGENTTØCORR,
230                            AGENTTØCORR,
231                            AGENTTØCORR,
232                            AGENTTØCORR,
233                            AGENTTØCORR
234                          };
235
236       IQUEUE(gtempQ, TQSIZE);
237
238       #else
239
240       extern  SCALED  gKELVINOFF;
241       extern  SCALED  gtctfA[], gtctfB[], gtctfC[], gtctfD[];
242
243       extern  SCALED  gtempvolts, gtempdeg, glastCdeg;
244       extern  SCALED  grefTmprtr;
245       extern  short   grawtemperature;
246       extern  SCALED  gCT, gtdelta;
247
248       extern  SCALED  gdTforØ;
249
250       extern  SCALED  gtctfbØ[];
251       extern  SCALED  gtctfb1[];
252       extern  SCALED  gtctfb2[];
253       extern  SCALED  gtctfcØ[];
254       extern  SCALED  gtctfc1[];
255       extern  SCALED  gtctfc2[];
256       extern  SCALED  gtctfdØ[];
257       extern  SCALED  gtctfd1[];
258       extern  SCALED  gtctfd2[];
259       extern  SCALED  gtØCorr[];
260
261       IEXTQUEUE(gtempQ, 24)
262       #endif Wed 10-02-86 12:54:06   AGACQ.C         Gacqdum
    10-15-86 13:02:30

1   /****************************************************************
  2    **
  3    **   projects:        mfo
  4    **
  5    **   module:          agacq.c
  6    **
  7    **   modification history :         reason(s)
  8    **   date             by            creation
  9    **   09-16-86         laf
 10    **
 11    **   Copyright (C) 1985, NELLCOR INCORPORATED
 12    **
 13    **   This module is an original, unpublished work and is proprietary to
 14    **   NELLCOR INC., and may not be divulged or copied in any form
 15    **   whatsoever without the express written permission of NELLCOR INC.
 16    **
```

```
17  **
18  **       purpose :
19  **       functions:
20  ***************************************************************/
21
22  #include      "../xevent.h"
23  #include      "../itest/aiglue.h"
24  #include      "../itest/aiglobal.h"
25  #include      "../itest/bique.h"
26  #define       INITAGACQ
27  #include     "agacq.h"
28  #include     "agbscan.h"
29  #include     "agbuffer.h"
30  #include     "agctrans.h"
31  #include     "agevent.h"
32  #include     "agfindie.h"
33  #include     "agglobal.h"
34  #include     "agpres.h"
35  #include     "agstart.h"
36  #include     "agtemp.h"
37  #include     "agtrans.h"
38  #include     "agzcalib.h"
39
40
41  void far
42  Gacqdum(fptr)      *fptr;
43  Acqwfbuf
44  { return;
45  }
46
47  void far
48  Gacqco2(fptr)      *fptr;
49  Acqwfbuf
50  {       short       *rd, i;
51          for(rd = fptr->data, i = fptr->length/2; i > 0; i --)
52              Iputinque(&gco2setQ, *rd++);     /* do the transfer */
53          Gtstsetfull();   /* check if you have filled it up */
54  }
55
56  void far
57  Gacqn2o(fptr)      *fptr;
58  Acqwfbuf
59  {       short       *rd, i;
60          for(rd = fptr->data, i = fptr->length/2; i > 0; i --)
61              Iputinque(&gn2osetQ, *rd++);     /* do the transfer */
62  }
63
64
65  void far
66  Gacqagt(fptr)      *fptr;
67  Acqwfbuf
68  {       short       *rd, i;
69          for(rd = fptr->data, i = fptr->length/2; i > 0; i --)
70              Iputinque(&gagtsetQ, *rd++);
71  }
72
73
```

```
 74   void far
 75   Gacqpre(fptr)
 76   Acqwfbuf   *fptr;
 77   {   short   *rd, i;
 78       for(rd = fptr->data, i = fptr->length/2; i > 0; i --)
 79           Iputinque(&gpresetQ, *rd++);
 80   }
 81
 82   void far
 83   Gacqtmp(data)
 84   short   data;
 85   {   gad_array[ADTMP] = data;
 86       Iputinque(>empQ, data);
 87   }
 88
 89
 90
 91   void far
 92   Gacqflo(data)
 93   short   data;
 94   {   gad_array[ADFLO] = data;
 95   }
 96
 97
 98   void near
 99   Gtstsetfull()
100   {
101       switch(gsetfull)
102       {   case SETEMPTY:   /* had none and now has one as a */
103                   gsetfull = SETPART1;
104                   break;
105           case SETPART1:
106                   gsetfull = SETPART2;
107                   break;
108           case SETPART2:
109                   gsetfull = DSETFULL;
110                   break;
111           case DSETFULL:
112                   gsetfull = SETPART2;
113                   Iputinque(>eventQ, ACQDSETFULL);
114                   xPost(PID_GAS, A_DATA_EV);
115                   break;
116           default:    xcli();
117                       Ginitacqset();
118                       xsti();
119                       break;
120       }
121   }
122
123   /* #define HALFDEF
124   if the sample rate of Agent is reduce from 100z to its minimum of 50 Hz */
125
126   short near
127   Gfilladarray()
128   {   short localagt, localpre, local;
129       if((local = Igetfromque(&gco2setQ)) == NOQUEDATA)
130           return(ERROR);
131
```

```
132         else gad_array[ADCO2] = local;
133         if((local = Igetfromque(&gco2setQ)) == NOQUEDATA)
134             return(ERROR);
135         else gad_array[ADN2O] = local;
136         if((local = Igetfromque(&gagtsetQ)) == NOQUEDATA)
137             return(ERROR);
138         else gad_array[ADAGT] = local;
139         /* odd value but not the last value then interpolate */
140         if(gevenodd = gevenodd+1)%2)  /* because only sampled at 50 Hz */
141         {   if((local = Igetfromque(&gpresetQ)) == NOQUEDATA)
142                 return(ERROR);
143             else gad_array[ADPRE] = glastpre = local;
144         }
145         else   /* because only sampled at 50 Hz */
146         {   if((local = Igetfromque(&gpresetQ)) == NOQUEDATA)
147                 return(ERROR);
148             else
149             {   Ipushinque(&gpresetQ, local);  /* put it back where you got it */
150                 gad_array[ADPRE] = (glastpre + local + 1)/2;
151             }
152         }
153     }
154     return(OK);
155 }
156 void near
157 Ginitacqset()
158 {   Iflushque(&gco2setQ);
159     Iflushque(&gn2osetQ);
160     Iflushque(&gagtsetQ);
161     Iflushque(&gpresetQ);
162     gsetfull = SETEMPTY;
163     gevenodd = 0;
164 }

Wed 10-01-86 16:47:48    AGACQ.H              MSECPERDSET
    10-15-86 13:02:30

1  /*****************************************************************
 2   *  mfo project
 3   *
 4   *  module = agacq.h
 5   *
 6   *  modification history :          reason(s)
 7   *       date        by        creation
 8   *     09-16-86      laf
 9   *
10   *  Copyright (C) 1985, NELLCOR INCORPORATED
11   *
12   *  This module is an original, unpublished work and is proprietary to
13   *  NELLCOR INC., and may not be divulged or copied in any form
14   *  whatsoever without the express written permission of NELLCOR INC.
15   *
16   *  purpose :
17   *
18   *  functions:
19   *
```

```
20  /*****************************************************************/
21  /*****************************************************************/
22
23  #define MSECPERSET    50           /* a set is sent every 50 msec */
24  #define MSECPERDSET   (2*MSECPERSET) /* but process double sets at a time */
25  #define CO2PERSEC     100          /* 100 Hz */
26  #define N2OPERSEC     100          /* 100 Hz */
27  /*#define AGTPERSEC   50                     50 Hz */
28  #define AGTPERSEC     100          /* 100 Hz */
29  #define PREPERSEC     50           /* 50 Hz */
30
31  #define CO2DSETCNT    10           /* (CO2PERSEC*MSECPERDSET/1000) */
32  #define N2ODSETCNT    10           /* (N2OPERSEC*MSECPERDSET/1000) */
33  #define AGTDSETCNT    10           /* (AGTPERSEC*MSECPERDSET/1000) */
34  #define PREDSETCNT    5            /* (PREPERSEC*MSECPERDSET/1000) */
35  #define WTICKSPERDSET 40           /* (MSECPERDSET*XWAITSEC/1000) */
36
37  typedef struct
38  {       short    taskid;
39          short    dataid;
40          short    length;
41          short    data[1];
42  } Acqwfbuf;
43
44  typedef enum
45  {       SETEMPTY = 0,
46          SETPART1,
47          SETPART2,
48          DSETFULL,
49          Setstat;
50  }
51  /* functions */
52  void far Gacqdum();
53  void far Gacqco2();
54  void far Gacqn2o();
55  void far Gacqagt();
56  void far Gacqpre();
57  void far Gacqtmp();
58  void far Gacqflo();
59  void near Gtstsetfull();
60  short near Gfilladarray();
61  void near Ginitacqset();
62
63  #ifdef INITAGACQ
64  IQUEUE( gco2setQ, 4*(CO2DSETCNT+2));
65  IQUEUE( gn2osetQ, 4*(N2ODSETCNT+2));
66  IQUEUE( gagtsetQ, 4*(AGTDSETCNT+2));
67  IQUEUE( gpresetQ, 4*(PREDSETCNT+2));
68  Setstat gsetfull = SETEMPTY;
69  short   gevenodd = 0;
70  short   glastagt = 0, glastpre = 0;
71  short   gad_array[6] = {0, 0, 0, 0, 0, 0 };
72
73  #else
74  IEXTQUEUE( gco2setQ, 3*(CO2DSETCNT+2));
75  IEXTQUEUE( gn2osetQ, 3*(N2ODSETCNT+2));
76  IEXTQUEUE( gagtsetQ, 3*(AGTDSETCNT+2));
77  IEXTQUEUE( gpresetQ, 3*(PREDSETCNT+2));
```

```
78    extern  Setstat gsetfull;
79    extern  short   gevenodd;
80    extern  short   glastgt, glastpre;
81    extern  short   gad_array[];
82
83    #endif Wed 10-09-86 10:14:24  10-15-86 13:02:30   AGPRES.C 1     /**********************************************************************
2     **
3     **    project:        mfo
4     **
5     **    module  = agpres.c
6     **
7     **    modification history :  reason(s)
8     **    date        by      creation
9     **    12-20-85    epr     creation
10    **    01-30-86    epr     moved pressure related gas correction functions to gtrans.c
11    **    08-29-86    laf     converted from alpha's pressure.c
12    **    09-17-86    laf     moved readbaropressure() from alpha's cal.c
13    **
14    **    Copyright (C) 1985, NELLCOR INCORPORATED
15    **
16    **    This module is an original, unpublished work and is proprietary to
17    **    NELLCOR INC., and may not be divulged or copied in any form
18    **    whatsoever without the express written permission of NELLCOR INC.
19    **
20    **    purpose :   This object is responsible for all things directly related to
21    **                pressure.  This includes controling the flow, backflushing, and
22    **                pressure conpensation and correction.
23    **
24    **    data descriptions :
25    **
26    **    function descriptions :
27    **        pressureupdate() -- function that checks the pressure and flow
28    **                            and assures proper ranges for pressure time event.
29    **                            is scheduled via the pressure time event.
30    **        backflush()  -- preforms backflush operation.
31    **        flowset(direction, level) -- sets up flow and direction.
32    **
33    **
34    **********************************************************************/
35    #include     "..\xevent.h"
36    #include     "..\itest\aiglue.h"
37    #include     "..\itest\aiglobal.h"
38    #include     "..\itest\bique.h"
39    #include     "agglobal.h"
40    #define      INITAGPRES
41    #include     "agpres.h"
42    #include     "agacq.h"
43    #include     "agscan.h"
44    #include     "agbuffer.h"
45    #include     "agctrans.h"
46
```

```
 47     #include         "agevent.h"
 48     #include         "agfindie.h"
 49     #include         "agstart.h"
 50     #include         "agtemp.h"
 51     #include         "agtrans.h"
 52     #include         "agzcalib.h"
 53     #include         "agcomm.h"
 54
 55     SCALED near
 56     GRFtoCC(flow, press, tmpr, mmHgN2O)
 57     SCALED flow;
 58     SCALED press;
 59     SCALED tmpr, mmHgN2O;
 60     {
 61             muls(
 62                     addS(
 63                             subs(muls(flow, gFlowfactor), gFlowterm),
 64                                  muls(subs(tmpr, gFlowTterm), gFlowTfactor)),
 65                             addS(
 66                                  muls(mmHgN2O, gFlowN2Ofactor),
 67                                  divS(gSTDmmHg, press)),
 68     }
 69
 70     short near
 71     GCCtoRF(press, tmpr, mmHgN2O)
 72     SCALED press, tmpr, mmHgN2O;
 73     {
 74             StoI(muls(
 75                     addS(gRFterm,
 76                             addS(muls(gRFTfactor, tmpr),
 77                                  muls(gRFN2Ofactor, mmHgN2O))),
 78                     divS(press, gSTDmmHg)));
 79     }
 80
 81     /* raw pressure conversion */
 82     SCALED near
 83     GRPtoHg(press)
 84     SCALED press;
 85     {
 86             return
 87             (
 88                     divS
 89                     (
 90                             muls(press, ADCSCALE),   /* A/D counts to volts */
 91                             gpressfactor             /* volts to mmHg */
 92                     )
 93             );
 94     }
 95
 96     void near
 97     Gpresupdate()     /* called from agevent.c but not yet */
 98     {
 99     /*      return;       I guess really not yet */
100
101             gNominalFlow = GCCtoRF( GRPtoHg( ItoS(grawpressure) ), glastCdeg, gFmmN2O );
102             gMinimalFlow = gNominalFlow - (gNominalFlow * 2)/10;
```

```
104       if (gflowalarmon)
105           if (grawflow > gMinimalFlow)
106               gflowalarmon = FALSE;
107
108   /* check for serious conditions first */
109       if (grawflow < (gNominalFlow - gFlowMargin))
110       {
111           gflowcorrection = TRUE;
112           if (grawflow < gMinimalFlow)
113           {
114               if (gflowlevelout >= (PUMPNORMALMAX))
115               {
116                   gflowalarmon = TRUE;
117                   /* can't do anything, so return ASP to check again */
118                   !pushinque(>eventQ, FLOWCHECKTIME);
119                   return;
120               }
121               if (gflowlevelout <= (PUMPNORMALMAX - LOWFLOWDELTA))
122               {   Gflowset(gflowlevelout + LOWFLOWDELTA);
123                   return;
124               }
125               else if (gflowlevelout <= (PUMPNORMALMAX - FLOWDELTA))
126               {   Gflowset(gflowlevelout + FLOWDELTA);
127                   return;
128               }
129               else if (gflowlevelout <= (PUMPFULL - 2))
130               {   Gflowset(gflowlevelout + 1);
131                   return;
132               }
133           }
134           if (gflowlevelout < (PUMPNORMALMIN + FLOWDELTA))
135               Gflowset(gflowlevelout + FLOWDELTA);
136           return;
137       }
138       else if (grawflow > (gNominalFlow + gFlowMargin))
139       {   gflowcorrection = TRUE;
140           if (gflowlevelout > (PUMPNORMALMIN + FLOWDELTA))
141           {   Gflowset(gflowlevelout - FLOWDELTA);
142               return;
143           }
144       }
145       if (gflowcorrection)
146       {/* Arrive here if we had a previous error condition */
147           if (grawflow < (gNominalFlow - gCorrMargin))
148           {   if (gflowlevelout <= (PUMPFULL - 2))
149               {   Gflowset(gflowlevelout + 1);
150                   return;
151               }
152           }
153           else
154               gflowcorrection = FALSE;
155       }
156       else
157       {   if (grawflow > (gNominalFlow + gCorrMargin))
158           {   if (gflowlevelout > (PUMPNORMALMIN + 2))
159               {   Gflowset(gflowlevelout - 1);
160                   return;
```

```
161            }
162            else     gflowcorrection = FALSE;
163        }
164        return;
165    }
166
167
168   void near
169   Gflowset(level)
170   short level;
171   {   switch(level)
172       {
173       case PUMPOFF:
174       case PUMPFULL:
175           /* special case values; should not be used except for off/full op. */
176           gpumpvolts = GRtoVolts(ItoS(level));
177           Apumppower(level);
178           return;
179       case PUMPNORMAL:
180           /* Restores pump to last setting after off/full operation. */
181           level = gflowlevelout;
182       default:
183           gpumpvolts = GRtoVolts(ItoS(level));
184           gflowlevelout = level;
185           Gpostdelayevents(FLOWDELAY, FLOWCHECKTIME);    */
186           Apumppower(level);
187           return;
188       }
189   }
190
191   void near
192   GUpdateFN20(new)
193   SCALED new;
194   {   gFmmN20 = pow25(addS(new, gFmmN20), -1);
195       return;
196   }
197
198
199   void near
200   Greadbaropressure()
201   {   long sum;
202       register short i;
203       short *ip;
204
205       gcorrection = TRUE;
206       Gflowset(PUMPOFF);
207       GtWait(2 * XWAITSEC);
208       Grstbrth();
209       GsWait(AVGPRESNUM);
210       for (sum = i = 0, ip = &(gprebuf->data[1]); i < AVGPRESNUM; i++)
211           sum += *(ip++);
212       gbaropressure = GRtoHg(divS(ItoS(sum), ItoS(i)));
213       Gcommbaro();   /* send baropressure to display side */
214       /* once pump is turned off need min of 6v or PUMPFULL to restart */
215       Gflowset(PUMPFULL);
216       Grstbrth();
217       Gflowset(PUMPNORMAL);
218       gcorrection = FALSE;
219   }
```

```
Wed 10-10-86 11:56:42    A6PRES.H         FLOWDELAY
    10-15-86 13:02:30

1  /*********************************************************************
 2   *
 3   *    pco2pp - endtidal co2 project
 4   *
 5   *    module = agpres.h
 6   *
 7   *    modification history:
 8   *    date       by     reason(s)
 9   *    12-8-85    BFB    creation
10   *
11   *    Copyright (C) 1985, NELLCOR INCORPORATED
12   *
13   *    This module is an original, unpublished work and is proprietary to
14   *    NELLCOR INC., and may not be divulged or copied in any form
15   *    whatsoever without the express written permission of NELLCOR INC.
16   *
17   *    purpose :
18   *        To define various constants related to pressure components/factors
19   *        in the system.
20   *
21   *    data descriptions :
22   *    Values for pump dac location (0,1), activation (0..4095).
23   *    function descriptions:
24   *
25   *********************************************************************/
26
27  /* Pump values */
28  #define PUMPDAC    0   /* dac to which pump is connected */
29  #define PUMPINIT   2949 /* 7.2v initial normal running voltage */
30  #define PUMPFOWFACTOR 50pl
31
32  #define IFLOWTERM  1589  /* 3.88 volts */
33  #define FLOWDELTA  2
34  #define LOWFLOWDELTA 3 * FLOWDELTA
35  #define FLOWDELAY  (2 * SECOND)
36
37  #define PUMPOFF    0   /* can be use as both a direction and a mode */
38  #define PUMPFULL   2949 /* reduce pump full to 7.2 v from 4095 */
39  #define PUMPNORMAL -1  /* out of range value to restore last value */
40  #define PUMPNORMALMAX PUMPFULL - 1
41  #define PUMPNORMALMIN PUMPOFF + 1
42
43  #define AVGFRESNUM 100
44
45  /* functions */
46  SCALED  near   GRFtoCC();
47  short   near   GCCtoRF();
48  SCALED  near   GRFtoHg();
49  void    near   Gpresupdate();
50  short   near   Gbackflush();
51  void    near   Gflowset();
52  void    near   GUpdateFN2O();
53
54  #ifdef INITAGPRES
```

```
55    short       gNominalFlow = IFLOWTERM + 459;  /* 409 = 1volt */
56    short       gMinimalFlow = IFLOWTERM + 367;
57    short       gFlowMargin = 23;  /* 5% of Nominal */
58    short       gCorrMargin = 9;   /* 2% of Nominal */
59    boolean     gflowalarmon = FALSE;
60    boolean     gflowcorrection = FALSE;
61
62    SCALED      gFlowterm   = {0xa66, 7, POS, NOTZERO, 0};   /* 133.199219 */
63    SCALED      gFlowfactor = {0x6e00, -4, POS, NOTZERO, 0}; /* 0.089355 */
64    SCALED      gFlowTterm  = {0x4266, 5, POS, NOTZERO, 0};  /* 40.299805 */
65    SCALED      gFlowTfactor = {0x69eb, 3, POS, NOTZERO, 0}; /* 11.309937 */
66    SCALED      gFlowN2Ofactor = {0x6872, -4, POS, NOTZERO, 0}; /* 0.087999 */
67
68    SCALED      gRFN2Ofactor = {0xfB51, -1, NEG, NOTZERO, 0};  /* 0.984973 */
69    SCALED      gRFTfactor   = {0xfa66, 6, NEG, NOTZERO, 0};   /* 126.599609 */
70    SCALED      gRFterm      = {0xbef0, 12, POS, NOTZERO, 0};  /* 7151.000000 */
71
72    SCALED      gFmmN2O = 50m;
73
74    /* raw flow conversion is based on the following equation
75           flow(CC) = [(volts*36.6)-133.2] + [(T-40.3)*11.31] + [mmHgN2O*0.088]
76           and Nominal Flow is 50 cc/min
77    */
78    SCALED      gpressfactor = {0xfc8e, -9, POS, NOTZERO, 0}; /* 0.00388 volts/mmHg */
79
80    SCALED      gpumpvolts = 50m, gflowvolts = 50m, gflowccmin = 50m;
81    short       grawflow = 0, grawpressure = 0, grco2 = 0, grn2o = 0, gragent = 0;
82    boolean     gbackflushon = FALSE;
83
84    SCALED      gSTDmmHg = {0x7c00, 7, POS, NOTZERO, 0}; /* 760.000000 */
85    short       gflowlevelout = PUMPINIT;
86
87    #else
88
89    extern SCALED  gpumpvolts, gflowvolts, gflowccmin;
90    extern short   grawflow, grawpressure, grco2, grn2o, gragent;
91    extern boolean gbackflushon;
92    extern SCALED  gSTDmmHg, gpressfactor;
93    extern short   gflowlevelout;
94    extern SCALED  gNominalFlow;
95    extern short   gMinimalFlow;
96    extern short   gFlowMargin;
97    extern short   gCorrMargin;
98    extern boolean gflowalarmon;
99    extern boolean gflowcorrection;
100   extern SCALED  gFlowterm;
101   extern SCALED  gFlowfactor;
102   extern SCALED  gFlowTterm;
103   extern SCALED  gFlowTfactor;
104   extern SCALED  gFlowN2Ofactor;
105
106   extern SCALED  gRFN2Ofactor;
107   extern SCALED  gRFTfactor;
108   extern SCALED  gRFterm;
109
110   extern SCALED  gFmmN2O;
111
112   #endif
```

```
1  /***********************************************************
2   *
3   *    project:         mfo
4   *
5   *    module:          agctrans.c
6   *
7   *    modification history :
8   *       date       by      reason(s)
9   *       02-24-86   epr     moved findminmax, FindET, and FindIns to bufput.s
10  *       05-30-86   epr     changed buffer concept, and added agent delay.
11  *       07-03-86   laf     converted from alpha's ctrans.c
12  *
13  *    This module is an original, unpublished work and is proprietary to
14  *    NELLCOR INC., and may not be divulged or copied in any form
15  *    whatsoever without the express written permission of NELLCOR INC.
16  *
17  *    purpose :
18  *       Responsible for implementing w/gtrans the clincal transform
19  *       for the mfo protype.
20  *
21  *    data descriptions :
22  *       tfdiv -- constat for time filter.
23  *       tfmultsizetfdivj -- array of constants for time filter.
24  *
25  *    function descriptions :
26  *       clinbreath(deltaT) -- this function is responsible for maintining
27  *          the clinical numbers when in clincal mode.
28  *       timefilter(ptr) -- does local filtering on the raw data, it returns
29  *          a SCALED value for further processing.
30  *       expagentupdate() -- this function called after a delay at the end
31  *          of clinbreath
32  *       insagentupdate() -- this function called after a delay at the end
33  *          of clinbreath
34  *
35  ***********************************************************/
36  #include    "../xevent.h"
37  #include    "../itest/aiglue.h"
38  #include    "../itest/aiglobal.h"
39  #include    "../itest/bique.h"
40  #include    "agglobal.h"
41  #include    "agacq.h"
42  #define INITAGCTRANS
43  #include    "agtrans.h"
44  #include    "agbscan.h"
45  #include    "agbuffer.h"
46  #include    "agevent.h"
47  #include    "agfindie.h"
48  #include    "agpres.h"
49  #include    "agstart.h"
50
51  #include    "agtemp.h"
52  #include    "agtrans.h"
53  #include    "agzcalib.h"
54  #include    "agcomm.h"
55
56  SCALED near
57  Gtimefilter(ptr) /* This could be in assembly. */
```

```
58  register int *ptr;
59  {
60      register int i;
61      /*  register int *ip; */
62      long tf;
63
64      /* commented out from epr
65      for (i = 0, ip = ptr - 2, tf = 0; i < 5; i++)
66          tf += *ip;
67      return divS(LtoS(tf), ItoS(i));
68      */
69      tf = *ptr * gtfmul[0];
70      for (i = 1; i < ((SIZETFDIV + 1) / 2); i++)
71          tf += (*(ptr - i) + *(ptr + i)) * gtfmul[i];
72      return mulS(LtoS(tf), gtfdiv);
73  }
74
75  void near
76  Grstbrth()   /* resets buffers, local vars for restart. */
77  /* no breaths are being detected (gcorrection==TRUE) when Grstbrth is called */
78  {
79      xcli();
80      Grstbufs();
81      GZeroOut();
82      Ginitacqset();
83      gendt = FALSE;
84      gticksthisbuf = 0;
85      gfirstbreath = FALSE;     /* for the start with an expiration */
86      xsti();
87      /* after clearing buffers need to collect some data before enabling
88         breath detection again
89      */
90      GtWait(1 * XWAITSEC);
91  }
92
93  void near
94  GZeroOut()
95  {
96      gOut.CO2 = gOut.N2O = gOut.Agent = gOut.Baro =
97      gETout.CO2 = gETout.N2O = gETout.Agent = gETout.br = gOut.br =
98      ginsOut.CO2 = ginsOut.N2O = ginsOut.Agent = S0;
99      GZeroOutvalues();
100 }
101
102 void near
103 GZeroOutvalues()
104 {
105     gOutvalues.etCO2 =
106     gOutvalues.etN2O =
107     gOutvalues.etAgent =
108     gOutvalues.insCO2 =
109     gOutvalues.insN2O =
110     gOutvalues.insAgent = S0;
111     gOutvalues.brate = S10;
112 }
113 void far
114 Gexpclinbreath(deltatime)
```

```
115  short deltatime;
116  {
117      register short breathoffset;
118      register short adelay;
119      SCALED n2oaccum, co2accum, agentaccum, n2oHg, co2Hg;
120      short *rawn2o, *rawco2, *rawagent, *rawbaro;
121
122  /* test values based on CO2 sample rate of 100 Hz */
123      if ((gbufferticks ( 20) ); (deltatime ( 10))
124      {   /* Too fast to handle wait for an other */
125          gendt = FALSE;
126          return;
127      }
128      gbufferticks = 0;              /* shouldn't this be after the (breathoffset ( 5) ??? */
129      rawco2 = GFindET();
130      breathoffset = rawco2 - gco2buf->data;
131  /* test values based on CO2 sample rate of 100 Hz */
132      if (breathoffset ( 5)
133      {
134          gendt = FALSE;
135          return;
136      }
137  #ifdef LATER
138      rawn2o = gn2obuf->data + breathoffset;
139  #endif
140      rawbaro = gprebuf->data + breathoffset;
141  /* test values based on CO2 sample rate of 100 Hz */
142      if (deltatime ( 20)
143      { /* if instantanious breath rate is ( 150/min */
144  #ifdef LATER
145          if (deltatime ( gagentswticks)
146              rawagent = gagentbuf->data + breathoffset;
147          else
148          {   breathoffset = (breathoffset + gagentdelay + 5) % BUFSIZ;
149  /* test values based on CO2 sample rate of 100 Hz */
150              if (breathoffset ( 10)
151                  breathoffset += BUFSIZ;
152              rawagent = gagentbuf->data + breathoffset - 5;
153              adelay = rawagent - (gagentbuf->ptr);
154              if (adelay > (gagentdelay + 6))
155              {   gendt = FALSE;
156                  return;
157              }
158              if (adelay > 0) /* wait for a given number of samples */
159                  /* guarantee that adelay points have been processed */
160                  GsWait(adelay);
161      }
162  #endif
163      co2accum = Gtimefilter(rawco2);
164  #ifdef LATER
165      n2oaccum = Gtimefilter(rawn2o);
166      agentaccum = Gtimefilter(rawagent);
167  #endif
168      gOut.Baro = GRPtoHg( Gtimefilter(rawbaro));
169      }
170      else
171  #ifdef LATER  (
```

```
172              rawagent = gagentbuf->data + breathoffset;
173   #endif
174              co2accum = ItoS(*rawco2);
175   #ifdef LATER
176              n2oaccum = ItoS(*rawn2o);
177              agentaccum = ItoS(*rawagent);
178   #endif
179              gOut.Baro = GRPtoHg( ItoS( *rawbaro));
180           }
181           Grstbufs();
182           gendt = FALSE;
183           gcurr_et = StoI(co2accum);
184   #ifdef LATER
185           n2oaccum = Ggasmod(N2OGAS, n2oaccum);
186   #endif
187           co2accum = Ggasmod(CO2GAS, co2accum);
188   #ifdef LATER
189           agentaccum = Ggasmod(AGENTGAS, agentaccum);
190   #endif
191   CalcFreN2O:
192           n2oHg = Gppgas(N2OGAS, n2oaccum);
193   #endif
194   Correct_CO2:
195           co2accum = Gppgas(CO2GAS, co2accum);
196   #ifdef LATER
197           co2accum = Gpbcor(co2accum);
198           /* This is CO2 so do collision broadening also. */
199           co2accum = Gcbcor(co2accum, n2oHg);
200   #endif
201           co2accum = GPFmmHg(co2accum, gOut.Baro, TRUE);
202           if (ltS(co2accum, gCO2LL))
203                co2accum = S0;
204           if (gtS(co2accum, S1000))
205                return;
206   #ifdef LATER
207   Correct_N2O:
208           n2oaccum = GNmodCO2Corr(n2oaccum, co2Hg);
209           n2oaccum = Gppgas(N2OGAS, n2oaccum);
210           n2oaccum = Gpbcor(n2oaccum);
211           n2oHg = n2oaccum = GPFmmHg(n2oaccum, gOut.Baro, TRUE);
212           if (ltS(n2oaccum, gN2OLL))
213                n2oaccum = S0;
214           GUpdateFN2O(n2oHg);
215           if (gtS(n2oaccum, S1000))
216                return;
217   Correct_Agent:
218           if (ltS(agentaccum, S0))
219           {    if (ltS(agentaccum, gmodmin))
220                     Ipushinque(>eventQ, AUTOCALTIME);
221                agentaccum = S0;
222           }
223           agentaccum = GAmodPPCorr(agentaccum, co2Hg, n2oHg);
224           agentaccum = Gppgas(AGENTGAS, agentaccum);
225           agentaccum = Gpbcor(agentaccum);
226           agentaccum = GPFmmHg(agentaccum, gOut.Baro, TRUE);
227
228
```

```
229         if (lts(agentaccum, gAgentLL))
230             agentaccum = S0;
231         if (gts(agentaccum, S1000))
232             return;
233 #endif
234 Breath_Output:
235     gbreathrate = divS(gtickspermin, ItoS(deltatime));
236     /* output averaging is 3/4 new value plus 1/4 old value. */
237     if (equS(gOut.br, S0))
238     {   gETOut.br = gbreathrate;
239         gETOut.CO2 = co2accum;
240         gETOut.N20 = S0;
241         gETOut.Agent = S0;
242     }
243 #ifdef LATER
244         gETOut.N20 = n2oaccum;
245         gETOut.Agent = agentaccum;
246 #endif
247     }
248     gOut.br = gETOut.br  /* = 1/4*(old + 3*new) */
249         = pow2S ( /* 1/4 of sum */
250                 ( /* old + new + 2*new = old + 3*new */
251                     addS
252                     (   addS(gETOut.br, gbreathrate),
253                         pow2S(gbreathrate, 1)
254                     ),
255                     -2
256                 );
257     gOut.CO2 = gETOut.CO2
258         = pow2S
259             (   addS
260                 (   addS(gETOut.CO2, co2accum),
261                     pow2S(co2accum, 1)
262                 ),
263                 -2
264             );
265 #ifdef LATER
266     /* reduce the noise in N2O */
267     n2oaccum = pow2S( ItoS( Stol( pow2S( n2oaccum, -2)), 2);
268     gOut.N20 = gETOut.N20
269         = pow2S
270             (   addS
271                 (   addS( gETOut.N20, n2oaccum),
272                     pow2S( n2oaccum, 1)
273                 ),
274                 -2
275             );
276     if (gAagent != PRESSUREGAS)
277     { /* agent output averaging: 1/5 new + 4/5 old */
278         gOut.Agent = gETOut.Agent
279             = divS
280                 (   addS
281                     (       agentaccum,
282                             pow2S( gETOut.Agent, 2)
283                     ),
284                     ItoS(5)
285                 );
```

```
286             if (gAAMsg || (deltatime ( gagentswticks))
287             { /* have or just had fast breaths */
288                 if (deltatime > gagentok)
289                 { /* if hysterisess overcome; here if fast brths then slow brths */
290                     gAAMsg = FALSE;
291                 }
292                 else
293                 { /* any time fast breaths enter here */
294                     gAAMsg = TRUE;
295                     /* average 1/2 ETOut.Agent and 1/2 InsOut.Agent */
296                     gOut.Agent = pow25( adds( gOut.Agent, gInsOut.Agent), -1);
297                 }
298             }
299             else gOut.Agent = 50
300         }
301 #endif
302             gOut.Agent = 50;
303             gOut.N20 = 50;
304 Display:
305 #ifdef LATER
306             gOut.N20 = GPFpercent(gOut.N20);
307             gOut.Agent = GPFpercent(gOut.Agent);
308 #endif
309             gOut.CO2 = GPFpercent(gOut.CO2);
310             GupdateEtvalues();
311 }
312
313 void near
314 Ginsclinbreath(deltatime)
315 register short deltatime;
316 {
317     register short breathoffset;
318     register short adelay;
319     SCALED n2oaccum, co2accum, agentaccum, n2oHg, co2Hg;
320     short *rawn2o, *rawco2, *rawagent, *rawbaro;
321
322     if ((gbufferticks ( 20) || (deltatime ( 10))
323     { /* Too fast to handle wait for an other */
324         gendt = TRUE;
325         return;
326     }
327     gbufferticks = 0;
328     rawco2 = GFindIns();
329     breathoffset = rawco2 - gco2buf->data;
330     if (breathoffset ( 5)
331     { gendt = TRUE;
332         return;
333     }
334 #ifdef LATER
335     rawn2o = gn2obuf->data + breathoffset;
336 #endif
337     rawbaro = gprebuf->data + breathoffset;
338     if (deltatime > 20)
339     { /* if instantanious breath rate is ( 150/min */
340 #ifdef LATER
341         if (deltatime ( gagentswticks))
```

```
342                    rawagent = gagentbuf->data + breathoffset;
343            else
344            {
345                    breathoffset = (breathoffset + gagentdelay + 5) % BUFSIZ;
346                    if (breathoffset ( 10)
347                            breathoffset += BUFSIZ;
348                            breathoffset -= 5;
349                    rawagent = gagentbuf->data + breathoffset;
350                    adelay = rawagent - (gagentbuf->(gagentdelay + 6))->ptr);
351                    if (adelay > (gagentdelay + 6))->ptr);
352                            gendt = TRUE;
353                    return;
354            }
355            if (adelay > 0) /* wait for a given number of samples */
356                        /* guarantee that adelay points have been processed */
357                        GsWait(adelay);
358   #endif
359   #ifdef LATER
360            co2accum = Gtimefilter(rawco2);
361            n2oaccum = Gtimefilter(rawn2o);
362            agentaccum = Gtimefilter(rawagent);
363   #endif
364            gOut.Baro = GRFtoHg( Gtimefilter(rawbaro));
365            }
366            else
367            {
368   #ifdef LATER
369            rawagent = gagentbuf->data + breathoffset;
370            co2accum = ItoS(*rawco2);
371   #endif
372   #ifdef LATER
373            n2oaccum = ItoS(*rawn2o);
374            agentaccum = ItoS(*rawagent);
375   #endif
376            gOut.Baro = GRFtoHg(ItoS(*rawbaro));
377            }
378            gcurr_ins = StoI(co2accum);
379            adelay = gcurr_ins - gcurr_et;
380            if (adelay > 200)
381                    gfinddelta = (adelay / 200);
382            else
383                    gfinddelta = 1;
384            /* pick a point 1/2 up so that smaller breath can be detected.*/
385            gtthins = gcurr_et + (adelay >> 1);
386            /* pick a point 1/8 down so that short drops are ignored. */
387            gtthexp = gcurr_ins - (adelay >> 3);
388            gtthresh = gtthins + ((gtthexp - gtthins) >> 1); /* mid theshholds */
389            if
390            (   ((gcurr_ins - gcurr_et) > 103) &&
391                (gtthresh > 100) &&
392                (gtthresh < 4000) &&
393                (abs(gtthresh - gthresh) > 26) &&
394                TRUE
395            )
396            {
397                    gthresh = gtthresh;
398                    gthexp = gtthexp;
399                    gthins = gtthins;
```

```
399            }
400         Grstbufs();
401         gendt = TRUE;
402  #ifdef LATER
403         n2oaccum = Ggasmod(N20GAS, n2oaccum);
404  #endif
405         co2accum = Ggasmod(CO2GAS, co2accum);
406  #ifdef LATER
407         agentaccum = Ggasmod(AGENTGAS, agentaccum);
408  CalcFreN20:
409         n2oHg = Gppgas(N20GAS, n2oaccum);
410  #endif
411  Correct_CO2:
412         if (ltS(co2accum, S0))
413                 if (ltS(co2accum, gmodmin))
414                         Ipushinque(>eventQ, AUTOCALTIME);
415                 co2accum = S0;
416         }
417         co2accum = Gppgas(CO2GAS, co2accum);
418  #ifdef LATER
419         co2accum = Gpbcor(co2accum);
420  /* This is CO2 so do collision broadening also. */
421         co2Hg = co2accum = Gcbcor(co2accum, n.of g);
422  #endif
423         co2accum = GPFmmHg(co2accum, gOut.Baro, FALSE);
424         if (ltS(co2accum, gCO2LL)) co2accum = S0;
425         if (gtS(co2accum, S1000)) return;
426  #ifdef LATER
427  Correct_N20:
428         if (ltS(n2oaccum, S0))
429                 if (ltS(n2oaccum, gmodmin))
430                         Ipushinque(>eventQ, AUTOCALTIME);
431                 n2oaccum = S0;
432         }
433         n2oaccum = GNmodCO2Corr(n2oaccum, co2Hg);
434         n2oaccum = GPpgas(N20GAS, n2oaccum);
435         n2oaccum = Gpbcor(n2oaccum);
436         n2oHg = n2oaccum = GPFmmHg(n2oaccum, gOut.Baro, FALSE);
437         if (ltS(n2oaccum, gN20LL)) n2oaccum = S0;
438         GUpdateFN20(n2oHg);
439         if (gtS(n2oaccum, S1000)) return;
440  Correct_Agent:
441         agentaccum = GAmodPFCorr(agentaccum, co2Hg, n2oHg);
442         agentaccum = GPpgas(AGENTGAS, agentaccum);
443         agentaccum = Gpbcor(agentaccum);
444         agentaccum = GPFmmHg(agentaccum, gOut.Baro, FALSE);
445         if (ltS(agentaccum, gAgentLL)) agentaccum = S0;
446         if (gtS(agentaccum, S1000)) return;
447  #endif
448  Breath_Output:
449         gOut.CO2 = gInsOut.CO2
450                 = pow25
```

```
451                                          addS
452                                          (          addS( gInsOut.CO2, co2accum),
453                                                        pow2S( co2accum, 1);
454                                          ),
455                                          -2
456                                          );
457     #ifdef LATER
458          /* reduce the noise in N2O */
459          n2oaccum = pow2S (ItoS (Stol( pow2S(n2oaccum, -2))), 2);
460          gOut.N2O = gInsOut.N2O
461                   = pow2S
462                          (          addS( gInsOut.N2O, n2oaccum),
463                          addS                pow2S(n2oaccum, 1);
464                          (
465                          ),
466                          -2
467                          );
468          /* agent output averaging: 1/5 new + 4/5 old */
469          gOut.Agent = gInsOut.Agent
470                   = divS
471                          (          agentaccum,
472                          addS       pow2S( gInsOut.Agent, 2)
473                          (
474                          ),
475                          ItoS(5)
476                          );
477     #endif
478          gOut.N2O = S0;
479          gOut.Agent = S0;
480     Display:
481     #ifdef LATER
482          gOut.N2O = GFFpercent(gOut.N2O);
483          gOut.Agent = GFFpercent(gOut.Agent);
484     #endif
485          gOut.CO2 = GFFpercent(gOut.CO2);
486          GupdateINSvalues();
487     }
488
489     void near
490     Gclinmodeinit()
491     {/*      if (initmode) Aagent = PressureGAS; */
492          initclinscr();    */
493     /*   Grstbrth();
494     }
495
496     void near
497     Gclinzero()
498     {    gETout.CO2 = gETout.N2O = gETout.Agent = gETout.br
499               = gInsOut.CO2 = gInsOut.N2O = gInsOut.Agent = S0;
500     }
501
502     void near
503     Gfindminmax()
504     {    short    AX, BX, CX;
505          short    fmnmax, fmnmin, fmndelta;
506          short    quick1, quick2;
507
```

```
508        short        *sptr, *endptr;
509
510                     fmmmin = fmmmax = gco2buf->data[0];
511                     sptr = gco2buf->data;
512                     endptr = gco2buf->data + BUFSIZ - 1;
513  fmmloop:
514        while ((sptr = sptr+3) (= endptr)
515        {
516             if (fmmmax ( *sptr)
517                     fmmmax = *sptr;
518                else if ((fmmmin )= *sptr) && (*sptr != 0))
519                     fmmmin = *sptr;
520        }
521        fmmdelta = fmmmax - fmmmin;
522        if (fmmdelta )= 25) /* 103 = 0.25 volts ???? */
523        { if(gthexp (= 4000) &&             /* check if a good threshhold */
524             (fmmdelta (= (gthexp-gthins)))
525                     fmmdelta = gthexp - gthins;
526        }
527  fmmdeltaok:
528             fmmdelta = fmmdelta/2 + fmmmin;
529  /*          xcli();           */
530             gthresh = gcurr_min = gcurr_max = fmmdelta;
531  /*          xsti();           */
532             quick1 = gcurr_min + (fmmmax - gthresh)/4;
533             quick2 = gcurr_max - (fmmmax - gthresh)/4;
534  /*          xcli();           */
535             gthexp = quick1;
536             gthins = quick2;
537  /*          xsti();           */
538        }
```

```
/*********************************************************************
*
*       pcopp - endtidal co2 project
*
*       module  = agctrans.h
*
*       modification history :
*          date        by        reason(s)
*       07-03-86       laf       converted from alpha's ctrans.h
*
*       This module is an original, unpublished work and is proprietary to
*       NELLCOR INC., and may not be divulged or copied in any form
*       whatsoever without the express written permission of NELLCOR INC.
*
*       purpose :
*
*       data descriptions :
*
**********************************************************************/
```

AGCTRANS.H

```c
20  #define AGENTOFFSET 18
21  #define AGENTMINTICKS 150
22  #define AGENTOKTICKS 170
23  #define SIZETFDIV 9
24
25  struct Out
26  {    SCALED CO2, N2O, Agent, br, Baro;
27  };
28  struct ETout
29  {    SCALED CO2, N2O, Agent, br;
30  };
31  struct InsOut
32  {    SCALED CO2, N2O, Agent;
33  };
34  struct Outvalues
35  {    SCALED etCO2, etN2O, etAgent;
36       SCALED insCO2, insN2O, insAgent;
37       SCALED brate;
38  };
39
40  /* functions */
41  SCALED near  Gtimefilter();
42  void   near  Gstbrth();
43  void   near  GzeroOut();
44  void   near  GzeroOutvalues();
45  void   near  Gexpclinbreath();
46  void   near  Ginsclinbreath();
47  void   near  Grlinmodeinit();
48  void   near  Grlinzero();
49  void   near  Gfindminmax();
50
51  #ifdef INITAGCTRANS
52  short  gbufferticks = 0;
53  short  gtthresh = 0, gtthexp = 0, gtthins = 0;
54  short  gcurr_et = 4095, gcurr_ins = 0; /* for then out of range */
55  short  gfinddelta = 1;
56  SCALED gmodmin = {0x0000, 2, NEG, NOTZERO, 0};
57  SCALED gmodmax = {0xa000, 6, POS, NOTZERO, 0};
58  SCALED gbreathrate = S0m;
59  long   gtfdiv[SIZETFDIV] = {59, 54, 39, 14, -21};
60  SCALED gtfmul[SIZETFDIV] = {0x1bb4, -8, POS, NOTZERO, 0}; /* = 1/231 = 0.004329 */
61  struct Out gOut = {0};
62  struct ETout gETout = {0};
63  struct InsOut ginsOut = {0};
64  struct Outvalues gOutvalues = {S0m, S0m, S0m, S0m, S0m, S0m, S1m};
65  SCALED gN2OLL = {0xf000, 3, POS, NOTZERO, 0}; /* 15mmHg */
66  SCALED gCO2LL = S1m;
67  SCALED gAgentLL = S2m;
68  short  gagentdelay = AGENTOFFSET;
69  short  gagentswticks = AGENTMINTICKS;
70  short  gagentok = AGENTOKTICKS;
71  boolean gAAMsg = FALSE;
72  short  gtt = 0;
73  short  gendt = FALSE;    /* endt is a three state variable:
74                              0 =) that we are looking for an inspired breath.
75                              1 =) that we are looking for an expired breath.
```

```
 77          -1 => that we have detected a breath but are waiting for the
 78                agent delay. Even at high breath rate, when there
 79                is no
                   agent delay endt will be -1 for a short time until
                   the
                   calculation are complete.
                                                                   */
 80   #else
 81   extern short       gbufferticks;
 82   extern short       gtthresh, gtthexp, gtthins;
 83   extern short       gcurr_et; gcurr_ins; /* for them out of range */
 84   extern short       gfinddelta;
 85   extern SCALED      gmodmin;
 86   extern SCALED      gmodmax;
 87   extern SCALED      gbreathrate;
 88   extern long        gtfdiv;          gtfmul[SIZETFDIV];
 89   extern struct Out             gOut;
 90   extern struct ETOut           gETOut;
 91   extern struct InsOut          gInsOut;
 92   extern struct Outvalues       gOutvalues;
 93   extern SCALED      gN2OLL;
 94   extern SCALED      gCO2LL;
 95
 96   extern SCALED      gAgentLL;
 97   extern short       gagentdelay;
 98   extern short       gagentswticks;
 99   extern short       gagentok;
100   extern boolean     gAAMsg;
101   extern short       gtt;
102   extern short       gendt;
103
104   #endif
```

AGTRANS.C

```
  1   /**************************************************************
  2    *
  3    *   project:           nfo
  4    *
  5    *   module:            agtrans.c
  6    *
  7    *   modification history :
  8    *   date         by    reason(s)
  9    *   12-17-85     epr   creation
 10    *   01-30-86     epr   Put the gas correction functions previously in
 11    *                      pressure.c in this module. These functions include
 12    *                      pbcor(), cbcor(), H2OCorr(), PFmmHg(), and
 13    *                      PPpercent().
 14    *   07-16-86     laf   removed halothane option from agentselect()
 15    *   07-17-86     laf   added seperate haloselect() option
 16    *   09-03-86     laf   converted from alpha's gtrans.c
 17    *
 18    *   Copyright (C) 1985, NELLCOR INCORPORATED
 19    *
```

```
20  *  This module is an original, unpublished work and is proprietary to
221 *  NELLCOR INC., and may not be divulged or copied in any form
222 *  whatsoever without the express written permission of NELLCOR INC.
223 *
224 *  purpose :
225 *      This object is responsible for the gas specific transforms.
226 *      The functions in this module are called from either the
227 *      clinical transform object or the engineering transform object,
228 *      and primerily from the functions clinbreath or engupdate (see
229 *      event.c).
230 *
231 *  data descriptions :
232 *      baropressure is the most resent value for barometric pressure.
233 *      pbX, pbY, pbZ are the pressure broadening factors.
234 *      cbK, cbL, cbM are the collision broadening factors.
235 *
236 *  function descriptions :
237 *      gasmod(gastype, gasbuffer) returns % modulation of the
238 *          gas using correction constants determined by gastype.
239 *
240 *      graphCO2(co2val) does the same thing as mod except that it
241 *          scales the final value for graphing.
242 *
243 *      agentselect() -- determines what the current agent is.
244 *
245 *      ppgas(gastype, modgas, range, A, B, C) -- returns the partial
246 *          pressure of gas over range.
247 *
248 *      pbcor(gastype, ppgas, range) -- corrects for pressure broadening
249 *          over range.
250 *
                        Ggasmod
51  *
52  *      cbcor(gastype, pbgas, range) -- corrects for collision broadening
53  *          over range.
54  *
55  *      H2Ocor(etb, press) -- corrects the pressure for H2O if etb is True.
56  *
57  *      PPmmHG(gastype, cwgas, range) -- corrects cell pressure by barometric
58  *          pressure over range.
59  *
60  *      NmodCO2Corr(ppCO2, ppN2O) -- corrects agent modulation form CO2 and N2O
61  *          modulation.
62  *
63  *      AmodPFCorr(ppCO2, ppN2O) -- corrects agent modulation for CO2 and N2O
64  *          partial pressure.
65  *
66  ***********************************************************************/
67
68  #include    "..\bxid.h"
69  #include    "..\xevent.h"
70  #include    "..\itest\aiglue.h"
71  #include    "..\itest\aiglobal.h"
72
```

```
 73   #include      "..\itest\bique.h"
 74   #include      "agacq.h"
 75   #define INITAGTRANS
 76   #include      "agtrans.h"
 77   #include      "agbscan.h"
 78   #include      "agbuffer.h"
 79   #include      "agctrans.h"
 80   #include      "agevent.h"
 81   #include      "agfindie.h"
 82   #include      "agglobal.h"
 83   #include      "agpres.h"
 84   #include      "agstart.h"
 85   #include      "agtemp.h"
 86   #include      "agzcalib.h"
 87
 88   /* modulation = ((1 - ((voltage - ref) / calzero)) * 100%) * calspan */
 89
 90   SCALED near
 91   Ggasmod(gastype, gasvalue)
 92   GAS gastype;
 93   SCALED gasvalue;
 94   {  /* note gasvalue should never be greater than cal. */
 95           return
 96                   mul3         /* calspan * 100% */
 97                   (
 98                           sub5 /* 1 - zero corrected gas */
 99                           (
100                                   div5 /* corrected raw / calzero */
                                        sub5 /* ref - raw */
101
102
103
104
105
106
107                                                       gasvalue,
108                                                       gcalref[(short)gastype]
109                                               ),
110                                               gcalzeros[(short) gastype]
111                                       )
112                               ),
113                               gcalspan[(short) gastype]
114                       );
115   }
116
117   Gagentselect
118
119   void near
120   Gagentselect()
121   { /* outside world needs to select gAagent */
122           gAagent = FORANEGAS;
123           gcalzeros[(short) AGENTGAS] = gcalzeros[(short) gAagent];
          gcalspan[(short) AGENTGAS] = gcalspan[(short) gAagent];
          gtctfA[(short) AGENTGAS] = gtctfA[(short) gAagent];
          gtctfB[(short) AGENTGAS] = gtctfB[(short) gAagent];
          gtctfC[(short) AGENTGAS] = gtctfC[(short) gAagent];
          gtctfD[(short) AGENTGAS] = gtctfD[(short) gAagent];
          return;
   }
```

```
124   /* partial pressure of gas calculation
125    PPgas = B*gcmodZ + C*gcmodZ^2 + D*gcmodZ^3 */
126   SCALED near
127   Gppgas(igas, modgas)
128   register short igas;   /* index into temp. cor. temp factor array */
129   SCALED modgas;
130   {
131       SCALED sqrmod;
132       sqrmod = mulS(modgas, modgas);
133       return
134           addS
135           (
136                              mulS (gtctfB[igas], modgas),
137                              mulS (gtctfC[igas], sqrmod)
138           ),
139           mulS
140           (
141                      gtctfD[igas],
142                      mulS (sqrmod, modgas)
143           )
144       );
145   }
146   /* Pressure broadening correction
147    FCC = X + Y*PPgas + Z*PPgas^2 */
148   SCALED near
149   Gpbcor(ppgas)
150   SCALED ppgas;
151   {
152       return
153           addS
154           (
155                      gpbX,
156                      addS
157                      (
158                                  mulS (gpbY, ppgas),
159                                  mulS
160                                  (
161                                       gpbZ,
162                                       mulS (ppgas, ppgas)
163                                  )
164                      )
165           );
166   }
167   /* collision broadening correction
168    CB = 1 + L*PPN2O + M*PPN2O^2
169    PPCB = PPC * CB */
170   SCALED near
171   Gcbcor(phgas, ppN2O)
172   SCALED pbgas, ppN2O;
173   {
174       return
175           mulS
                   (
                       pbgas,
                       addS
                       (
                           S1,
                           addS
```

```
176                              muls (gcbL, ppN2O),
177                                           gcbM,
178                                  muls (ppN2O, ppN2O)
179                              )
180                          );
181  }
182  /* water vapor correction for expired gases
183  Dry Pressure = Wet Pressure - 42mmHg @ 37degC */
184  /* Coversion to Standard Pressure
185  Standard partial presure =
186          (measured pressure / cell pressure) * dry barometric pressure */
187
188  SCALED near
189  GFPmmHg(gas, cp, etb)
190  SCALED gas;
191  SCALED cp; /* the cell pressure value */
192  boolean etb; /* true if this is an end tidal breath */
193  {
194      return
195          muls
196          (
197              divS
198              (
199                  gas,
200                  GH2OCorr (cp, etb)
201              ),
202              gbaropressure
203          );
204  }
205
206  /* GFPpercent = (FPmmHg/barometric pressure) * 100 */
207  SCALED near
208  GFPpercent(gas)
209  SCALED gas;
210  {
211      return
212          muls
213          (
214              divS (gas, gbaropressure),
215              S100
216          );
217  }
218
219  /* Amod = Imod + (C * modCO2 + N * modN2O) */
220  SCALED near
221  GNmodCO2Corr(Imod, ppCO2)
222  SCALED Imod, ppCO2;
223  {
224      return
225          addS
226          (
227              Imod,
228              muls (gCO2NmodPPCorr, ppCO2)
229          );
230  }
231
232  /* Amod = Imod + (C * modCO2 + N * modN2O) */
```

```
228  SCALED near
229  GAmodPPCorr(Imod, ppCO2, ppN2O)
230  SCALED Imod, ppCO2, ppN2O;
231  {
232      return
233              (           Imod,
234              addS
235                  (
236                          mulS( gCO2AmodPPCorr, ppCO2),
237                          mulS( gN2OAmodPPCorr, ppN2O)
238                  )
239              );
240  }
241
242  /* ???? got lost in the shuffle */
243  /* modulation = 33.3 *.(1 - (voltage / calzero), * 100% */
244  void far
245  GwfCO2(v)
246  Vwf     *v;
247  {
248      short   *rd, i;
249      char    *wr;   *s;
250      Acqwfbuf *d;
251      Vwfbuf   *d;
252      SCALED   accum;
253
254      s = v->srcptr;
255      rd = s->data;
256      d = v->destptr;
257      wr = d->data;
258      d->taskid = PID_WVF;
259      d->dataid = WID_CO2;
260      d->length = s->length;
261      for( i = s->length/2; i ) 0; i--)
262      {
263          accum = Ggasmod(CO2GAS, ItoS(*rd++));
264          accum = GPgas(CO2GAS, accum);
265          accum = GPbcor(accum);
266          /* co2accum = cbcor(accum, n2oHg); */
267          accum = GPFmmHg(accum, GRPtoHg(ItoS(grawpressure)), FALSE);
268          accum = GFPpercent(accum);
269          *wr++ = StoI( mulS(accum, ggraphspan));
270      }
271  }
272
273  void near
274  GenableH2OCorr()
275  {
276      gWP = gWaterPressure;
277      return;
278  }
279
280  SCALED near
281  GVoltstoR(x)
282  SCALED  x;
283  {
284      return ( divS(x, ADCSCALE));
```

GenableH2OCorr

```
281        }
282        SCALED near
283        GRtoVolts(x)
284        SCALED x;
285        {
286           return ( mul5(x, ADCSCALE));
287        }
288
289        SCALED near
290        GH2OCorr(press, etb)
291        SCALED press;
292        boolean etb;  /* true if this is an end tidal breath */
293        {
294           return ( etb ? (sub5(press, gWP)) : press);
295        }
296
```

Wed 10-01-86 18:06:52  AGTRANS.H
Wed 10-15-86 13:02:30

```
 1   /*******************************************************************
 2   **
 3   **       pcopp - endtidal co2 project
 4   **
 5   **       module   = gtrans.h
 6   **
 7   **       modification history:
 8   **         date      by       reason(s)
 9   **       12-17-85.epr         creation
10   **       08-28-86.laf         converted from alpha gtrans.h
11   **
12   **       Copyright (C) 1985, NELLCOR INCORPORATED
13   **
14   **       This module is an original, unpublished work and is proprietary to
15   **       NELLCOR INC., and may not be divulged or copied in any form
16   **       whatsoever without the express written permission of NELLCOR INC.
17   **
18   **       purpose :
19   **          This object is responsible for the gas specific transforms.
20   **
21   **       data descriptions :
22   **          GTRANSIZE -- size of gas transformation arrays.
23   **                       baropressure is the most resent value for barometric pressure.
24   **
25   ********************************************************************/
26
27   #define GTRANSIZE 32
28
29   typedef enum {
30           CO2GAS = 0,
31           N2OGAS = 1,
32           FORANEGAS = 2,
33           HALOTHANEGAS = 3,
34           ETHRANEGAS = 4,
35           AGENTGAS = 5,
36           PRESSUREGAS = 6
```

```
       } GAS; /* any changes must be refected in event.s, temprtr.c,
                                      cal.c, temprtr.h, cal.h*/ define LASTGAS AGENTGAS
define FIRSTGAS CO2GAS

/*      defined in agacq.h here just for reference
        typedef struct
        {       short   taskid;
                short   dataid;
                short   length;
                char    data[1];
        }       Acqwfbuf;
*/ typedef struct
{       short   taskid;
        short   dataid;
        short   length;
        char    data[1];
        Vwfbuf;
} typedef struct
{       Vwfbuf  *destptr;
        short   destlength;
        Acqwfbuf *srcptr;
        short   srclength;
        Vwf;
}

/* functions */
SCALED near Ggasmod();
void   near Gagentselect();
SCALED near GpPgas();
SCALED near Gpbcor();
SCALED near Gcbcor();
SCALED near GPFmmHg();
SCALED near GPFpercent();
SCALED near GNmodCO2Corr();
SCALED near GAmodPPCorr();
void   far  GWFCO2();
void   near GenableH2OCorr();
SCALED near GVoltstoR();
SCALED near GRtoVolts();
SCALED near GH2OCorr();

#ifdef INITAGTRANS
SCALED gbaropressure = {0x6800, 9, POS, NOTZERO, 0}; /* 720 */
GAS    gAagent = PRESSUREGAS;
/* These are emperical constants used the pressure broadening equation. */
SCALED gpbX = SZEROm;
SCALED gpbY = S1m;
SCALED gpbZ = SZEROm;
SCALED gWaterPressure = {0x5000, 5, POS, NOTZERO, 0}; /* 42 mmHg */
SCALED gWP = S0m;
SCALED ggraphspan = { 0x9000, 4, POS, NOTZERO, 0};   /* 250counts/10% = 25 */ else
```

```
 94   extern SCALED gbaropressure;
 95   extern GAS gragent;
 96   /* These are emperical constants used the pressure broadening equation: */
 97   extern SCALED gpbX, gpbY, gpbZ;
 98   extern SCALED gWaterPressure;
 99   extern SCALED gWP;
100   e,tern SCALED ggraphspan;
101
102   #endif
103
104
105
```

```
Wed 09-29-86 08:50:54   AGFINDIE.S                                                    Pg 81
    10-15-86 13:02:30                                                                 of 118
                                                                                      1-50

1   ;186
 2   TITLE  agfindie
 3
 4   ;**********************************************************************
 5
 6        propp - endtidal co2 project
 7
 8        module  = agfindie.s
 9
10        modification history:
11           date      by      reason(s)
12         2-10-85   epr       reduce execution time of putbuf
13         2-24-86   epr       moved findminmax, FindEt, and FindIns here.
14         08-28-86  laf       converted from a, pha to agbufput.s
15         09-10-86  laf       move bGbufput to buffer.c and findminmax to agctrans.c
16                             and changed name to agfindie.s
17
18        This module is an original, unpublished work and is proprietary to
19        NELLCOR INC., and may not be divulged or copied in any form
20        whatsoever without the express written permission of NELLCOR INC.
21
22        purpose :
23             Assembly version of putbuf()
24
25        data descriptions :
26
27        function descriptions :
28
29             GFindET() -- the end tidal point in the expired CO2 buffer.
30
31             GFindIns() -- the inspired point in the expired CO2 buffer.
32
33   ;**********************************************************************
34
35   MT_TEXT   SEGMENT  BYTE PUBLIC 'CODE'
36   MT_TEXT   ENDS
37
38   CONST     SEGMENT  WORD PUBLIC 'CONST'
39   CONST     ENDS
40
```

```
41          BSS     SEGMENT, WORD PUBLIC 'BSS'
42         _BSS    ENDS
43         _DATA    SEGMENT WORD PUBLIC 'DATA'
44
45          extrn   _gco2buf:word,
46          extrn   _gthins:word
47
48          extrn   _gbufroll:word ;     dw 0  ; True if buffer has rolled since last reset.
49          extrn   _gfinddelta:word
50
51         _DATA    ENDS
52
53          DGROUP  GROUP   CONST,  _BSS,   _DATA
54
55          ASSUME  CS: MT_TEXT, DS: DGROUP, SS: DGROUP, ES: DGROUP
56
57          public  _GFindEt, _GFindIns
58
59          MT_TEXT SEGMENT byte public 'code'
60
61                                      GFindEt
62          BUFSIZ equ 2 * 500       ; any change must be reflected in agbuffer.h
63          EXTRASIZ equ 20
64
65         ;*****************************************************************
66         ; Functions:
67         ;     GFindEt(), GFindIns()
68         ;        These functions start from the end of the data and look
69         ;        back for a peak/trough. After finding one they look back
70         ;        a little further to make sure its not at a notch.
71         ;*****************************************************************
72
73
74
75
76
77
78
79         _GFindEt proc near
80                  push    bp
81                  push    di
82                  push    si
83
84                  mov     bx, _gco2buf
85                  mov     bp, [bx]           ; bp = co2buf->ptr
86                  add     bx, 2              ; bx = co2buf->data
87                  xchg    bx, bp
88
89                  add     bp, EXTRASIZ/2
90         FETbackfromend:
91                  sub     bx, 12            ; start only to end minus 5 integers
                    xor     si, si            ; si counts the steps already taken.
```

```
 92             mov     ax, gthins
 93             shl     ax, 1
 94             add     ax, gthins
 95             mov     cx, bx
 96             sub     cx, bp
 97             shl     cx, 1   ; cx = the # of elements to examine in buffer.
 98             mov     dx, bx
 99             jmp     short FindETloop
100
101     NewMin:
102             mov     dx, bx
103             sub     dx, 2   ; return a point just before the min.
104             mov     ax, di
105             mov     cx, 10  ; the good enough number (1/3 sec)
106
107     FindETloop:
108             dec     cx
109             jz      FETGoodenough  ; if good enough in a row then quit.
110             sub     bx, 6   ; step a little extra each time.
111             add     si, 6
112             cmp     bx, bp
113             jbe     FETFinished
114
115     FETLookMore:
116             mov     di, [bx]
117             add     di, [bx - 2]
118             add     di, [bx - 4]
119             sub     ax, gfinddelta ; each time add value needed for new min.
120             cmp     di, ax  ; end tidal point is the minimum!
121             jb      FindETloop
122             jmp     short NewMin
123
124     FETGoodenough:
125             sub     ax, 18h ; look now for .1% inc in modulation!
126             sub     bx, si  ; look back twice as far as we've gone.
127             cmp     bx, bp
128             jbe     FETFinished
129             mov     cx, 2
130             shl     si, 2   ; next time go way back!
131             jmp     FETLookMore
132
133     FETRoll:
134             mov     gbufroll, 0     ; disable roll
135             mov     bx, gco2buf
136             add     bp, [bx]        ; bp = co2buf->ptr
137             add     bp, EXTRASIZ/2  ; new limit is at co2buf->ptr + 5.
138             mov     bx, BUFSIZ + EXTRASIZ/2 ; new bx is middle of extra.
139             jmp     FETLookMore
140
141     FETFinished:
142             cmp     gbufroll, 0
143             jnz     FETRoll
144             mov     ax, dx
145
146             pop     si
147             pop     di
148             pop     bp
```

```
149          nop
150   _GFindIns endp
151          nop
152          nop
153          nop
154   _GFindIns proc near
155          push    bp
156          mov     bp
157          add     bx, gco2buf          ; bp = co2buf->ptr
158          xchg    bx, bp               ; bx = co2buf->data
159          add     bp, 2
160          sub     bp, 20               ; go only to begining plus 10 intergers
161                  bx, 12               ; start at to end minus 5 integers
162
163          mov     ax, [bx]
164          mov     cx, bx
165          sub     cx, bp
166          shr     cx, 2                ; cx = the # of elements to examine in buffer.
167          mov     dx, bx
168          jmp     short FindInsloop
169
170   NewMax:
171          mov     dx, bx               ; return a point just before the max.
172          sub     dx, 8
173          mov     ax, [bx]
174          mov     cx, 20               ; the good enough number
175
176   Findinsloop:
177          dec     cx
178          jz      FIGoodenough         ; if good enough in a row then quit.
179          sub     bx, 4
180          cmp     bx, bp
181          jbe     FIFinished
182          add     ax, [bx]             ; gfinddelta ; each time make it harder.
183          cmp     ax, [bx]             ; inspired point is the maximum!
184          ja      FindInsloop
185          jmp     short NewMax
186
187   FITRoll:
188          mov     gbufroll, 0          ; disable roll
189          mov     bx, gco2buf
190          mov     bp, [bx]             ; bp = co2buf->ptr
191          add     bp, EXTRASIZ/2       ; new limit is at co2buf->ptr + 5.
192          add     bx, BUFSIZ + EXTRASIZ/2 ; new bx is middle of extra.
193          jmp     FindInsloop
194
195   FIFinished:
196          cmp     gbufroll, 0
197          jne     FITRoll
198   FIGoodenough:
199          mov     ax, dx
200          pop     bp
```

```
205         ret
206         _GFindIns endp
207
208     MT_TEXT ENDS
209
210     END
211
```

Wed 09-18-86 08:55:28   AGFINDIE.H
    10-15-86 13:02:30

```
 1  /****************************************************************
 2   *
 3   *      pcapp = endtidal co2 project
 4   *
 5   *      module  = agfindie.h
 6   *
 7   *      modification history :   reason(s)
 8   *           date        by       created
 9   *         08-29-86      laf
10   *
11   *           Copyright (C) 1985, NELLCOR INCORPORATED
12   *
13   *  This module is an original, unpublished work and is proprietary to
14   *  NELLCOR INC., and may not be divulged or copied in any form
15   *  whatsoever without the express written permission of NELLCOR INC.
16   *
17   *      purpose :
18   *
19   *      data descriptions :
20   *
21   *      function descriptions :
22   *
23   ****************************************************************/
24  /* functions */
25  short * near GFindET();
26  short * near GFindIns();
27
```

Wed 10-10-86 17:12:30   AGTIMERS.C    Gautocaltimer
    10-15-86 13:02:30

```
 1  /****************************************************************
 2   *
 3   *      mfo:    project
 4   *
 5   *      module: agtimers.c
 6   *
 7   *      modification history :   reason(s)
 8   *           date        by       creation
 9   *         09-30-86      laf
10   *
11   *           Copyright (C) 1985, NELLCOR INCORPORATED
12   *
```

```
 13    *    This module is an original, unpublished work and is proprietary to
 14    *    NELLCOR INC., and may not be divulged or copied in any form
 15    *    whatsoever without the express written permission of NELLCOR INC.
 16    *
 17         purpose :
 18
 19         data descriptions :
 20
 21   ****************************************************************/
 22
 23   #include     "../xclock.h"
 24   #include     "../itest/aiglue.h"
 25   #include     "../itest/bique.h"
 26   #include     "agstart.h"
 27   #include     "agevent.h"
 28   #define INITAGTIMERS
 29   #include     "agtimers.h"
 30
 31
 32   void    far
 33   Gautocaltimer()
 34   {      lpushinque(>eventQ, AUTOCALTIME);
 35   }
 36
 37   void near
 38   Grstautocaltimer()
 39   {      xSetTimeDelay(>hingstodo.timers[(short)TAUTOCAL],
 40                                            10*60*TIMERSEC, 10*60*TIMERSEC);
 41   }
 42
 43   void    far
 44   Gminmaxtimer()
 45   {      lpushinque(>eventQ, MINMAXTIME);
 46   }
 47
 48
 49   void near
 50   Grstminmaxtimer()
 51   {      xSetTimeDelay(>hingstodo.timers[(short)TMINMAX], 6*TIMERSEC, 6*TIMERSEC);
 52   }
 53
 54   void near
 55   Gsetminmaxtimer(n)
 56   short n;
 57   {      if(n < 1*TIMERSEC)
 58              n = 1*TIMERSEC;
 59          xSetTimeDelay(>hingstodo.timers[(short)TMINMAX], n, n);
 60   }
 61
 62   void    far
 63   Gapneatimer()
 64   {      lpushinque(>eventQ, APNEATIME);
 65   }
 66
 67   void near
```

```
69      Grstapneatimer()
70      {       xSetTimeDelay(>hingstodo.timers[(short)TAPNEA], 20*TIMERSEC, 20*TIMERSEC);
71      }

Wed 10-01-86 15:50:32  AGTIMERS.H      DefineTimers
Wed 10-15-86 13:02:30

1  /*******************************************************************
 2   *
 3   *     mfo:    project
 4   *
 5   *     module: agtimers.h
 6   *
 7   *     modification history :
 8   *           date           by         reason(s)
 9   *        05-30-86          laf        creation
10   *
11   *     Copyright (C) 1985, NELLCOR INCORPORATED
12   *
13   *     This module is an original, unpublished work and is proprietary to
14   *     NELLCOR INC., and may not be divulged or copied in any form
15   *     whatsoever without the express written permission of NELLCOR INC.
16   *
17   *     purpose :
18   *
19   *     data descriptions :
20   *
21   ********************************************************************/
22
23  #define TDISABLE       -1
24
25  typedef enum
26  {    TAUTOCAL = 0,
27       TMINMAX,
28       TAFNEA
29  };
30
31  /* functions */
32  void far  Gautocaltimer();
33  void near Grstautocaltimer();
34  void far  Gminmaxtimer();
35  void near Grstminmaxtimer();
36  void near Gsetminmaxtimer();
37  void far  Gapneatimer();
38  void near Grstapneatimer();
39
40
41  #ifdef INITAGTIMERS
42  /* timers set up */
43  DefineTimers (gthingstodo, 3)
44  DefineTimer  ( TDISABLE, TDISABLE, Gautocaltimer)
45  DefineTimer  ( TDISABLE, TDISABLE, Gminmaxtimer)
46  DefineTimer  ( TDISABLE, TDISABLE, Gapneatimer, gthingstodo)
47  EndTimers    ( TDISABLE, TDISABLE, Gapneatimer, gthingstodo)
48
49  #else
50  extern TIMERS gthingstodo;
```

```
51    #endif
52
53
54
Wed 10-06-86  15:03:06   AGCOMM.H
    10-15-86  13:02:30

1   /**********************************************************************
 2   **
 3   **      info:      project
 4   **
 5   **                 module: agcomm.h
 6   **
 7   **                 modification history :    reason(s)
 8   **                         date      by      creation
 9   **                 10-02-86           laf
10
11   **      Copyright (C) 1985, NELLCOR INCORPORATED
12   **
13   **      This module is an original, unpublished work and is proprietary to
14   **      NELLCOR INC., and may not be divulged or copied in any form
15   **      whatsoever without the express written permission of NELLCOR INC.
16   **
17   **      purpose :
18   **
19   **      data descriptions :
20   **
21   ***********************************************************************/
22
23   #define BYTESPERSCALED 4
24   #define BYTESPERSHORT  2
25
26   /* functions */
27   void near GupdateETvalues();
28   void near GupdateINSvalues();
29   void near Gcommbaro();
30

Wed 10-07-86  06:54:44   AGCOMM.C                    GupdateETvalues
    10-15-86  13:02:30

1   /**********************************************************************
 2   **
 3   **      info:      project
 4   **
 5   **                 module: agcomm.c
 6   **
 7   **                 modification history :    reason(s)
 8   **                         date      by
```

```
 9    *
10    *           10-02-86       laf     creation
11    *
12    *           Copyright (C) 1985, NELLCOR INCORPORATED
13    *
14    *           This module is an original, unpublished work and is proprietary to
15    *           NELLCOR INC., and may not be divulged or copied in any form
16    *           whatsoever without the express written permission of NELLCOR INC.
17    *
18    *           purpose :
19    *
20    *           data descriptions :
21    *
22    ***************************************************************************/
23
24    #include       ":.\bxid.h"
25    #include       "..\itest\aiglue.h"
26    #include       "..\itest\bique.h"
27    #include       "agglobal.h"
28    #define INITAGCOMM
29    #include       "agcomm.h"
30    #include       "agtrans.h"
31    #include       "agacq.h"
32    #include       "agtrans.h"
33    #include       "agevent.h"
34
35    void near
36    GupdateETvalues()
37    {
38         cSendSlow(CO2_ET, &gOut.CO2, BYTESPERSCALED);
39         cSendSlow(N2O_ET, &gOut.N2O, BYTESPERSCALED);
40         cSendSlow(AGT_ET, &gOut.Agent, BYTESPERSCALED);
41         cSendSlow(RESP_RATE, &gOut.br, BYTESPERSCALED);
42    }
43
44    void near
45    GupdateINSvalues()
46    {
47         cSendSlow(CO2_IN, &gOut.CO2, BYTESPERSCALED);
48         cSendSlow(N2O_IN, &gOut.N2O, BYTESPERSCALED);
49         cSendSlow(AGT_IN, &gOut.Agent, BYTESPERSCALED);
50    }
51
52    void near                                Gcommbaro
53    Gcommbaro()
54    {
55         cSendSlow(BAROP_MEAN, &gbaropressure, BYTESPERSCALED);
56    }
57    void near
58    Gcommapnea()
59    {
60         cSendSlow(CO2_APNEA, &gapneaalarmon, BYTESPERSHORT);
61    }
```

```
Wed 10-08-86 17:23:34  DGGLOBAL.H
    10-15-86 13:02:30

1  /*********************************************************************
 2  **    mfo project
 3  **
 4  **    module = dgglobal.h
 5  **
 6  **    modification history :       reason(s)
 7  **         date          by
 8  **        10-02-86       laf       created
 9  **
10  **    Copyright (C) 1985, NELLCOR INCORPORATED
11  **
12  **    This module is an original, unpublished work and is proprietary to
13  **    NELLCOR INC., and may not be divulged or copied in any form
14  **    whatsoever without the express written permission of NELLCOR INC.
15  **
16  **    purpose :
17  **
18  **    function descriptions :
19  **
20  *********************************************************************/
21
22  /* functions */
23  char far CommLink();
24  void far LarmLink();
25  void far HLink();
26  void far DSMRLink();
27  void far DSMRPut();
28
```

```
DGSTART.H

1  /*********************************************************************
 2  **    mfo project
 3  **
 4  **    module = dgstart.h
 5  **
 6  **    modification history :       reason(s)
 7  **         date          by
 8  **        10-02-86       laf       created
 9  **
10  **    Copyright (C) 1985, NELLCOR INCORPORATED
11  **
12  **    This module is an original, unpublished work and is proprietary to
13  **    NELLCOR INC., and may not be divulged or copied in any form
14  **    whatsoever without the express written permission of NELLCOR INC.
15  **
16  **    purpose :
17  **
18  **    function descriptions :
19  **
20  *********************************************************************/
21
```

```
 22   #define GSTACKSIZE 220
 23
 24   /* functions */
 25   void far  GCreateP();
 26   void far  Gmain();
 27   void near GinitCLink();
 28   void near GinitLarmLink();
 29   void near GinitDSMRLink();
 30   void near GinitHistLink();
 31   void far  Gterm();
 32
 33   #ifdef INITAGSTART
 34
 35   #else
 36
 37   #endif
 38
 39

Wed 10-10-86 10:00:36   DGSTART.C        GCreateP
    10-15-86 13:02:30

1  /****************************************************************
  2   *
  3   *   info:    project
  4   *
  5   *   module:  dgstart.c
  6   *
  7   *   modification history :     reason(s)
  8   *            date        by    creation
  9   *          10-02-86      laf
 10   *
 11   *        Copyright (C) 1985, NELLCOR INCORPORATED
 12   *
 13   *   This module is an original, unpublished work and is proprietary to
 14   *   NELLCOR INC., and may not be divulged or copied in any form
 15   *   whatsoever without the express written permission of NELLCOR INC.
 16   *
 17   *   purpose :
 18   *
 19   *   data descriptions :
 20   *
 21   ****************************************************************/
 22  #include "..\itest\aiglobal.h"
 23  #include "..\itest\aiglue.h"
 24  #include "..\display\dwindow.h"
 25  #include "..\display\dresult.h"
 26  #include "..\xevent.h"
 27  #include "..\nsid.h"
 28  #include "dgglobal.h"
 29  #define INITDGSTART
 30  #include "dgstart.h"
 31  #include "dgrcv.h"
```

```
34  #include "dgalarm.h"
35  #include "dgunits.h"
36  #include "dghist.h"
37
38  char *gstackp = NULL;
39
40  void far
41  GCreateF()
42  {
43      gstackp = XALLOC(GSTACKSIZE);
44      XCreateF(PID_GAS, Gmain, (gstackp + GSTACKSIZE - 2), 0 , Gterm);
45  }
46
47  void far
48  Gmain()
49  {   /* not really sure what I should do */
50      GinitCLink();
51      GinitLarmLink();  /* link funct that check if alarm condition exists */
52
                         GinitCLink
53
54      GinitDSMRLink();  /* link funct that convert alarm limits to proper units */
55      GinitHistLink();  /* link funct that return value to be trended */
56      while(1)
57      {   xWait(A_DATA_EV, 0);   /* should never come out */
58      }
59  }
60
61  void near
62  GinitCLink()
63  {
64      CommLink(Grcvslow);
65  }
66
67  void near
68  GinitLarmLink()
69  {  /* time in seconds and whole units */
70  #ifdef KENNEY
71      LarmLink(mCO2ET, GCO2ETLarmck, 1);
72      LarmLink(mN2OET, GN2OETLarmck, 1);
73      LarmLink(mAGAET, GAGTETLarmck, 1);
74      LarmLink(mCO2INS, GCO2INSLarmck, 1);
75      LarmLink(mN2OINS, GN2OINSLarmck, 1);
76      LarmLink(mAGAINS, GAGTINSLarmck, 1);
77      LarmLink(mBR, GBRLarmck, 1);
78      LarmLink(mAPNEA, GApneaLarmck, 1);
79  #endif
80  }
81
82  void near
83  GinitDSMRLink()
84  {   /* time in seconds and whole units */
      DSMRLink(mCO2ET, Sresult, GCO2ETLarmcnvrt, 1);
      DSMRLink(mN2OET, Sresult, GN2OETLarmcnvrt, 1);
```

```
 85             DSMRLink(mAGAET, Sresult, GAGTETLarmcnvrt, 1);
 86             DSMRLink(mCO2INS, Sresult, GCO2INSLarmcnvrt, 1);
 87             DSMRLink(mN2OINS, Sresult, GN2OINSLarmcnvrt, 1);
 88             DSMRLink(mAGAINS, Sresult, GAGTINSLarmcnvrt, 1);
 89             DSMRLink(mBR, Sresult, GBRLarmcnvrt, 1);
 90             return;
 91        }
 92     void near
 93     GinitHistLink()
 94     {   /* time in seconds and whole units */
 95     #ifdef KENNEY
 96             HLink(mCO2ET, GCO2ETHistavg, 5);
 97             HLink(mN2OET, GN2OETHistavg, 5);
 98             HLink(mAGAET, GAGTETHistavg, 5);
 99             HLink(mCO2INS, GCO2INSHistavg, 5);
100
                                    @term
101             HLink(mN2OINS, GN2OINSHistavg, 5);
102             HLink(mAGAINS, GAGTINSHistavg, 5);
103             HLink(mBR, GBRHistavg, 5);
104     #endif
105             return;
106     }
107     void far
108     Gterm()
109     {
110             MFREE(gstackp);
111     }
112
113
Wed 10-08-86 17:30:40    DGRCV.H
    10-15-86 13:02:30
```

```
 1    /***********************************************************
 2    **
 3    **  nfo project
 4    **
 5    **  module = dgrcv.h
 6    **
 7    **  modification history :
 8    **       date            by        reason(s)
 9    **       10-02-86        laf       created
10    **
11    **  Copyright (C) 1985, NELLCOR INCORPORATED
12    **
13    **  This module is an original, unpublished work and is proprietary to
14    **  NELLCOR INC., and may not be divulged or copied in any form
15    **  whatsoever without the express written permission of NELLCOR INC.
16    **
17    **  purpose :
18    **
19    **  function descriptions :
```

```
20  /****************************************************************/
21
22  typedef struct
23  {     short   taskid;
24        short   dataid;
25        short   length;       /* in bytes */
26        SCALED  data[1];
27  }     Commbuf;
28
29  typedef struct
30  {     SCALED  etCO2,  etN2O, etAgent;
31        SCALED  insCO2, insN2O, insAgent;
32        SCALED  brate;
33  }     Outvalues;
34
35  /* functions */
36  void far Grcvslow();
37  char * near GStoa();
38  void near GprintCO2ET();
39  void near GprintCO2INS();
40  void near GprintBR();
41  void near Gprintbaro();
42  void near Gprintapnea();
43
44  #ifdef INITDGRCV
45  Outvalues gOutvalues = { S0m, S0m, S0m, S0m, S0m, S0m};
46  /* .firstXXbreaths gets set to TRUE after the first XX value is sent from the analog side */
47  SCALED  gbaropressure = S0m;
48  short   gapneaalarmon = FALSE;
49  short   gfirstCO2breath = FALSE;
50
                              DGRCV.H 51  short   gfirstN2Obreath = FALSE;
52  short   gfirstAGTbreath = FALSE;
53  short   gfirstBRbreath = FALSE;
54  #else
55  extern  Outvalues gOutvalues;
56  extern  SCALED    gbaropressure;
57  extern  short     gapneaalarmon;
58  extern  short     gfirstCO2breath;
59  extern  short     gfirstN2Obreath;
60  extern  short     gfirstAGTbreath;
61  extern  short     gfirstBRbreath;
62
63  #endif
64

Wed 10-11-86 13:13:36  DGRCV.C         Grcvslow
    10-15-86 13:02:30

1  /****************************************************************
```

```
 2  **
 3  **   mfo project
 4  **
 5  **   module = dgrcv.c
 6  **
 7  **   modification history ;    by         reason(s)
 8  **         date                laf         created
 9  **         10-02-86
10  **
11  **   Copyright (C) 1985, NELLCOR INCORPORATED
12  **
13  **   This module is an original, unpublished work and is proprietary to
14  **   NELLCOR INC., and may not be divulged or copied in any form
15  **   whatsoever without the express written permission of NELLCOR INC.
16  **
17  **   purpose :
18  **
19  **   function descriptions :
20  **
21  *************************************************************************/
22
23  #include "..\itest\aiglue.h"
24  #include "..\itest\aiglobal.h"
25  #include "..\bxid.h"          /* communication id's */
26  #include "..\msid.h"          /* communication id's */
27  #define INITDGRCV
28  #include "dgrcv.h"
29  #include "dgunits.h"
30  #include "dghist.h"
31
32  void far
33  Grcvslow(ptr)
34  Commbuf *ptr;
35  {
36      SCALED Sx;  *sptr;
37      short    x,  *sptr;
38      switch(ptr->dataid)
39      {    case CO2_ET:
40              gfirstCO2breath = TRUE;  /* et values come before ins values */
41              goutvalues.etCO2 = Sx = ptr->data[0];
42              DSMRPut( mCO2ET, Ggasunitcnvrt(Sx, gCO2ETunits));
43              GprintCO2ET();
44              GCO2ETHist(Sx);
45              break;
46          case N2O_ET:
47              gfirstN2Obreath = TRUE;
48              goutvalues.etN2O = Sx = ptr->data[0];
49              DSMRPut( mN2OET, Ggasunitcnvrt(Sx, gN2OETunits));
50              GN2OETHist(Sx);
              break;
                                        GStd&
51          case AGT_ET:
52              gfirstAGTbreath = TRUE;
```

```
53             gOutvalues.etAgent = Sx = ptr->data[0];
54             DSMRput( mAGAET, Ggasunitcnvrt(Sx, gAGTETunits));
55             GAGTEHist(Sx);
56             break;
57       case CO2_IN:
58             gOutvalues.insCO2 = Sx = ptr->data[0];
59             DSMRput( mCO2INS, Ggasunitcnvrt(Sx, gCO2INSunits));
60             GCO2INSHist(Sx);
61             GprintCO2IN();
62             break;
63       case N2O_IN:
64             gOutvalues.insN2O = Sx = ptr->data[0];
65             DSMRput( mN2OINS, Ggasunitcnvrt(Sx, gN2OINSunits));
66             GN2OINSHist(Sx);
67             break;
68       case AGT_IN:
69             gOutvalues.insAgent = Sx = ptr->data[0];
70             DSMRput( mAGAINS, Ggasunitcnvrt(Sx, gAGTINSunits));
71             GAGTINSHist(Sx);
72             break;
73       case RESP_RATE:
74             gFirstBRbreath = TRUE;
75             gOutvalues.brate = Sx = ptr->data[0];
76             DSMRput( mBR, Sx);
77             GBRHist(Sx);
78             GprintBR();
79             break;
80       case BAROF_MEAN:
81             gbaropressure = ptr->data[0];
82             Gprintbaro();
83             break;
84       case CO2_APNEA:
85             sptr = (short *) ptr->data;        /* apnea in not a SCALED its a
                                                      short */
86             gapneaalarmon = *sptr;
87             Gprintapnea();
88             break;
89       default:
90             break;
91    }
92  }
93
94
95  char GCnvtstr[32] = {0}; /* string pointer */
96  #define strstartindex 18
97
98  char near
99  GStoa(inval)                                    GprintCO2ET
100 SCALED inval;
101 {    register int i;
102      register int k = 0;
```

```
103     int  sign = 0;
104     int  factor = 1;
105     /* default value for now. rtdig can later be passed as a parameter */
106     int  rtdig = 1;
107     int  linval;
108
109     if (equS(inval, S0)) return "0";   /* take care of special case. */
110
111     if (ltS(inval, S0)) {
112         inval = absS(inval);           /* force n positive */
113         sign = -1;
114     }
115
116     for(i = 0; i < rtdig; i++)                    factor *= 10;
117
118     linval = StoI( addS ( mulS ( ItoS(factor), inval), S0p5));
119
120     GCnvtstr[strstartindex] = 0;
121     for (i = strstartindex - 1; linval > 0; --i )
122     {
123         /* generate digits in reverse order */
124         GCnvtstr[i] = linval % 10 + '0';
125         linval /= 10;
126         if(++k == rtdig) GCnvtstr[--i] = '.';
127     }
128
129     if (sign < 0) GCnvtstr[i--] = '-';
130     return &GCnvtstr[i+1];
131 }
132 void near
133 GprintCO2ET()
134 {
135     char * top;
136     top = " etCO2=";
137     /* keep trying to send it out until returns 0 */
138     while(cMsgOut(top));
139     top = GStoa(gOutvalues.etCO2);
140     while(cMsgOut(top));
141 }
142 void near
143 GprintCO2INS()
144 {
145     char * top;
146     top = " insCO2=";
147     /* keep trying to send it out until returns 0 */
148     while(cMsgOut(top));
149     top = GStoa(gOutvalues.insCO2);
150     while(cMsgOut(top));
151 }
```

GprintBR

```
152  void near
153  GprintBR()
154  {
155      char * top;
156      top = " BR=";
157      /* keep trying to send it out until returns 0 */
158      while(cMsgOut(top));
159      top = GStoa(gOutvalues.brate);
160      while(cMsgOut(top));
161  }
162
163  void near
164  Gprintbaro()
165  {
166      char * top;
167      top = " Pbaro=";
168      /* keep trying to send it out until returns 0 */
169      while(cMsgOut(top));
170      top = GStoa(gbaropressure);
171      while(cMsgOut(top));
172  }
173
174  void near
175  Gprintapnea()
176  {
177      char * top;
178      top = " AFNEA!!!";
179      /* keep trying to send it out until returns 0 */
180      while(cMsgOut(top));
181  }

Wed 10-08-86 15:08:18  DGUNITS.H
    10-15-86 13:02:30
```

```
/****************************************************************
**
**     mfg:      project
**
**     module: dgunits.h
**
**     modification history :    reason(s)
**             date      by      creation
**          10-04-86    laf
**
**     Copyright (C) 1985, NELLCOR INCORPORATED
**
**     This module is an original, unpublished work and is proprietary to
**     NELLCOR INC., and may not be divulged or copied in any form
**     whatsoever without the express written permission of NELLCOR INC.
**
**     purpose :
**
**     data descriptions :
**
****************************************************************/
```

```
24    /* default units are used in communication values and alarm limits */
25
26    typedef enum
27    {     UPERCENT = 0,    /* default and alarm limits representation */
28          UMMHG = 1,       /* torr is the same as mmHg */
29          UTORR = 1
30    } GasUnits;
31
32    /* functions */
33    SCALED near GmmHgtoPer();
34    SCALED near GPertomnHg();
35    SCALED near Ggasunitcnvrt();
36    void far GCO2ETunitselect();
37    void far GN2OETunitselect();
38    void far GAGTETunitselect();
39    void far GCO2INSunitselect();
40    void far GN2OINSunitselect();
41    void far GAGTINSunitselect();
42
43    #ifdef INITDGUNITS
44    GasUnits gCO2ETunits = UPERCENT;
45    GasUnits gN2OETunits = UPERCENT;
46    GasUnits gAGTETunits = UPERCENT;
47    GasUnits gCO2INSunits = UPERCENT;
48    GasUnits gN2OINSunits = UPERCENT;
49    GasUnits gAGTINSunits = UPERCENT;
50
51    #else
52    extern GasUnits gCO2ETunits;
53    extern GasUnits gN2OETunits;
54    extern GasUnits gAGTETunits;
55    extern GasUnits gCO2INSunits;
56    extern GasUnits gN2OINSunits;
57    extern GasUnits gAGTINSunits;
58
59    #endif
60
61

Wed 10-08-86 17:15:03  DGUNITS.C                        GmmHgtoPer

1    /*****************************************************************
 2     *
 3     *      mfo:    project
 4     *
 5     *      module: dgunits.c
 6     *
 7     *      modification history :
 8     *            date        by           reason(s)
 9     *         10-04-86       laf          creation
10     *
11     *      Copyright (C) 1985, NELLCOR INCORPORATED
```

```
12  *
13  *       This module is an original, unpublished work and is proprietary to
14  *       NELLCOR INC., and may not be divulged or copied in any form
15  *       whatsoever without the express written permission of NELLCOR INC.
16  *
17  *       purpose :
18  *
19  *       data descriptions :
20  *
21  *
22  ********************************************************************/
23  #include "..\msid.h"
24  #include "..\itest\aiglue.h"
25  #include "dgrcv.h"
26  #define INITDGUNITS
27  #include "dgunits.h"
28
29  /* FFprecent = (FFmmHg/barometric pressure) * 100 */
30  /* GFPpercent(gas) conversion name from agtrans.c */
31  SCALED near
32  GmmHgtoFer(gas)
33  SCALED gas;
34  {
35      return
36          muls
37              (       divS (gas, gbaropressure ),
38                      S100
39              );
40  }
41
42  /* mmHg = barometric pressure * percent / 100 */
43  SCALED near
44  GFertommHg(gas)      /* value in percent */
45  SCALED gas;
46  {
47      return
48          muls    (       gbaropressure,
49                          divS ( gas, S100)
50                  );
51  }
52
53  SCALED                          @gasunitcnvrt
54  Ggasunitcnvrt(gas, unit)
55  SCALED gas;     unit;
56  GasUnits        if((short)unit == (short)UPERCENT)
57                      return(gas);
58                  else    /* request in mm Hg */
59                      return( GFertommHg(gas));
60  }
```

```
 63
 64     void far
 65     GCO2ETunitselect(unit)
 66     GasUnits unit;
 67     {
 68         gCO2ETunits = unit;
 69         DSMRPut( mCO2ET, Ggasunitcnvrt(gOutvalues.etCO2, gCO2ETunits));
 70     }
 71
 72     void far
 73     GN2OETunitselect(unit)
 74     GasUnits unit;
 75     {
 76         gN2OETunits = unit;
 77         DSMRPut( mN2OET, Ggasunitcnvrt(gOutvalues.etN2O, gN2OETunits));
 78     }
 79
 80     void far
 81     GAGTETunitselect(unit)
 82     GasUnits unit;
 83     {
 84         gAGTETunits = unit;
 85         DSMRPut( mAGAET, Ggasunitcnvrt(gOutvalues.etAgent, gAGTETunits));
 86     }
 87
 88     void far
 89     GCO2INSunitselect(unit)
 90     GasUnits unit;
 91     {
 92         gCO2INSunits = unit;
 93         DSMRPut( mCO2INS, Ggasunitcnvrt(gOutvalues.insCO2, gCO2INSunits));
 94     }
 95
 96     void far
 97     GN2OINSunitselect(unit)
 98     GasUnits unit;
 99     {
100         gN2OINSunits = unit;

GAGTINSunitselect

DSMRPut( mN2OINS, Ggasunitcnvrt(gOutvalues.insN2O, gN2OINSunits));
    }
101
102     void far
103     GAGTINSunitselect(unit)
104     GasUnits unit;
105     {
106         gAGTINSunits = unit;
107         DSMRPut( mAGAINS, Ggasunitcnvrt(gOutvalues.insAgent, gAGTINSunits));
108     }
109
110
111
112
```

```
Wed 10-08-86 15:20:32  DGALARM.H

1  /****************************************************************
 2   **
 3   **      nfo:     project
 4   **
 5   **      module:  dgalarm.h
 6   **
 7   **      modification history :     reason(s)
 8   **              date         by
 9   **              10-04-86     laf         creation
10   **
11   **      Copyright (C) 1985, NELLCOR INCORPORATED
12   **
13   **      This module is an original, unpublished work and is proprietary to
14   **      NELLCOR INC., and may not be divulged or copied in any form
15   **      whatsoever without the express written permission of NELLCOR INC.
16   **
17   **      purpose :
18   **
19   **      data descriptions :
20   **
21   ****************************************************************/
22
23  /* functions */
24  short   far     GCO2ETLarmck();
25  short   far     GN2OETLarmck();
26  short   far     GAGTETLarmck();
27  short   far     GCO2INSLarmck();
28  short   far     GN2OINSLarmck();
29  short   far     GAGTINSLarmck();
30  short   far     GBRLarmck();
31  short   far     GApneaLarmck();
32  SCALED  far     GCO2ETLarmcnvrt();
33  SCALED  far     GN2OETLarmcnvrt();
34  SCALED  far     GAGTETLarmcnvrt();
35  SCALED  far     GCO2INSLarmcnvrt();
36  SCALED  far     GN2OINSLarmcnvrt();
37  SCALED  far     GAGTINSLarmcnvrt();
38  SCALED  far     GBRLarmcnvrt();

Wed 10-08-86 15:31:46  DGALARM.C                    GCO2ETLarmck

1  /****************************************************************
2   **
3   **      nfo:     project
4   **
5   **      module:  dgalarm.c
6   **
7   **      modification history :
```

```
/***********************************************************
 *      10-04-86    date    by    reason(s)
 *                          laf   creation
 *
 *      Copyright (C) 1985, NELLCOR INCORPORATED.
 *
 *      This module is an original, unpublished work and is proprietary to
 *      NELLCOR INC., and may not be divulged or copied in any form
 *      whatsoever without the express written permission of NELLCOR INC.
 *
 *      purpose :
 *
 *      data descriptions :
 *
 ***********************************************************/
#include "..\itest\alglue.h"
#include "..\msid.h"
#include "..\larmsvr.h"
#define INITOGALARM
#include "dgalarm.h"
#include "dgrcv.h"
#include "dgunits.h"

short   far
GCO2ETLarmck(lo, hi)
short   lo, hi;
{
        if(gfirstCO2breath == FALSE)    /* haven't received first breath data yet */
                return(WAIT);           /* can't start testing yet */
        else if( ltS ( gOutvalues.etCO2, (ItoS(lo))))
                return( BLOLIMIT);
        else if( gtS ( gOutvalues.etCO2, (ItoS(hi))))
                return( ABVLIMIT);
        else
                return(OK);
} short   far
GN2OETLarmck(lo, hi)
short   lo, hi;
{
        if(gfirstN2Obreath == FALSE)    /* haven't received first breath data yet */
                return(WAIT);           /* can't start testing yet */
        else if( ltS ( gOutvalues.etN2O, (ItoS(lo))))
                return( BLOLIMIT);
        else if( gtS ( gOutvalues.etN2O, (ItoS(hi))))
                return( ABVLIMIT);
        else
                return(OK);
} short   far
GAGTETLarmck(lo, hi)
short   lo, hi;
{
        if(gfirstAGTbreath == FALSE)    /* haven't received first breath data yet */
```

```
 64             else if( lts ( gOutvalues.etAgent, (ItoS(lo))))
 65             else if( gts ( gOutvalues.etAgent, (ItoS(hi))))
 66                 return( ABVLIMIT);
 67             else     return(WAIT);    /* can't start testing yet */
 68             else     return( BLOLIMIT);
 69         else     return(OK);
 70     }
 71
 72
 73     short far
 74     GCO2INSLarmck(lo, hi)
 75     short  lo, hi;
 76     {
 77         if(gfirstCO2breath == FALSE)    /* haven't received first breath data yet */
 78             return(WAIT);    /* can't start testing yet */
 79         else if( lts ( gOutvalues.insCO2, (ItoS(lo))))
 80             return( BLOLIMIT);
 81         else if( gts ( gOutvalues.insCO2, (ItoS(hi))))
 82             return( ABVLIMIT);
 83         else     return(OK);
 84     }
 85
 86
 87     short far
 88     GN2OINSLarmck(lo, hi)
 89     short  lo, hi;
 90     {
 91         if(gfirstN2Obreath == FALSE)    /* haven't received first breath data yet */
 92             return(WAIT);    /* can't start testing yet */
 93         else if( lts ( gOutvalues.insN2O, (ItoS(lo))))
 94             return( BLOLIMIT);
 95         else if( gts ( gOutvalues.insN2O, (ItoS(hi))))
 96             return( ABVLIMIT);
 97         else     return(OK);
 98     }
 99
100
101     short far
102     GAGTINSLarmck(lo, hi)
103     short  lo, hi;
104     {
105         if(gfirstAGTbreath == FALSE)    /* haven't received first breath data yet */
106             return(WAIT);    /* can't start testing yet */
107         else if( lts ( gOutvalues.insAgent, (ItoS(lo))))
108             return( BLOLIMIT);
109         else if( gts ( gOutvalues.insAgent, (ItoS(hi))))
110             return( ABVLIMIT);
111         else     return(OK);
112     }
113
114
115     short far
116     GBRLarmck(lo, hi)
117     short  lo, hi;
118     {
119         if(gfirstBRbreath == FALSE)    /* haven't received first breath data yet */
120             return(WAIT);    /* can't start testing yet */
121         else if( lts ( gOutvalues.brate, (ItoS(lo))))
122             return( BLOLIMIT);
```

```
121             else if( gtS ( gOutvalues.brate, (ItoS(hi))))
122                  return( ABVLIMIT);
123             else    return(OK);
124     }
125
126
127     short far
128     GApneaLarmck(lo, hi)
129     short   lo, hi;  /* ignored */
130     {    if(gapneaalarmon)
131               return(ABVLIMIT);
132          else      return(OK);
133     }
134
135
136
137     SCALED far
138     GCO2ETLarmcnvrt(gaslimit)
139     short   gaslimit;
140     {       return ( Ggasunitcnvrt( (ItoS(gaslimit)), gCO2ETunits') );
141     }
142
143
144
145     SCALED far
146     GN2OETLarmcnvrt(gaslimit)
147     short   gaslimit;
148     {       return( Ggasunitcnvrt( (ItoS(gaslimit)), gN2OETunits ) );
149     }
150
151     SCALED far
152     GAGTETLarmcnvrt(gaslimit)
153     short   gaslimit;
154     {       return( Ggasunitcnvrt( (ItoS(gaslimit)), gAGTETunits ) );
155     }
156
157     SCALED far
158     GCO2INSLarmcnvrt(gaslimit)
159     short   gaslimit;
160     {       return( Ggasunitcnvrt( (ItoS(gaslimit)), gCO2INSunits ) );
161     }
162
163     SCALED far
164     GN2OINSLarmcnvrt(gaslimit)
165     short   gaslimit;
166     {       return( Ggasunitcnvrt( (ItoS(gaslimit)), gN2OINSunits ) );
167     }
168
169     SCALED far
170     GAGTINSLarmcnvrt(gaslimit)
171     short   gaslimit;
172     {       return( Ggasunitcnvrt( (ItoS(gaslimit)), gAGTINSunits ) );
173     }
174
175     SCALED far
176     GBRLarmcnvrt(brlimit)
177     short   brlimit;
```

```
178        {        return( ItoS(brlimit));
179        }
180    }

Wed 10-09-86 11:57:44    DGHIST.C          GrstHist
Wed 10-15-86 13:02:30

1    /******************************************************************
2     *
3     *    mfo:    project
4     *
5     *    module: dghist.c
6     *
7     *    modification history -
8     *            date    by / test / reason(s)
9     *            10-07-86        l.f. creation
10    *
11    *    Copyright (C) 1985 NELLCOR INCORPORATED
12    *
13    *    This module is an original unpublished work and is proprietary to
14    *    NELLCOR INC. and may not be divulged or copied in any form
15    *    whatsoever without the express written permission of NELLCOR INC.
16    *
17    *    purpose :
18    *
19    *    data descriptions :
20    *
21    ******************************************************************/
22
23    #include "..\msid.h"
24    #include "..\ltest\asblue.h"
25    #define INITDGHIST    80
26    #include "dghist.h"
27
28    void near
29    GrstHist()
30    {
31        ghistsum.etCO2 = ghistsum.etN2O = ghistsum.etAgent =
32        ghistsum.inCO2 = ghistsum.inN2O = ghistsum.inAgent =
33        ghistsum.brate = 80;
34        ghistcnt.etCO2 = ghistcnt.etN2O = ghistcnt.etAgent =
35        ghistcnt.inCO2 = ghistcnt.inN2O = ghistcnt.inAgent =
36        ghistcnt.brate = 0;
37    }
38
39    void near
40    GCO2ETHist(value)
41    SCALED value;
42    {   ghistsum.etCO2 = addS(ghistsum.etCO2, (value));
43        ghistcnt.etCO2++;
44    }
45
46    void near
47    GN2OETHist(value)
48    SCALED value;
```

```
 49         ghistsum.etN2O = addS(ghistsum.etN2O, value);
 50         ghistcnt.etN2O++;
 51 }
 52 void near
 53 GAGTETHist(value)
 54 SCALED value;
 55 {       ghistsum.etAgent = addS(ghistsum.etAgent, value);
 56         ghistcnt.etAgent++;
 57 }
 58 }
 59 void near
 60 GCO2INSHist(value)
 61 SCALED value;
 62 {       ghistsum.insCO2 = addS(ghistsum.insCO2, value);
 63         ghistcnt.insCO2++;
 64 }
 65 }
 66 void near
 67 GN2OINSHist(value)
 68 SCALED value;
 69 {       ghistsum.insN2O = addS(ghistsum.insN2O, value);
 70         ghistcnt.insN2O++;
 71 }
 72 }
 73 void near
 74 GAGTINSHist(value)
 75 SCALED value;
 76 {       ghistsum.insAgent = addS(ghistsum.insAgent, value);
 77         ghistcnt.insAgent++;
 78 }
 79 }
 80 void near
 81 GBRHist(value)
 82 SCALED value;
 83 {       ghistsum.brate = addS(ghistsum.brate, value);
 84         ghistcnt.brate++;
 85 }
 86 }
 87
 88 char far                /* later to be changed to short */
 89 GCO2ETHistavg()
 90 {       SCALED avg;
 91         avg = divS(ghistsum.etCO2, (itoS(ghistcnt.etCO2)));
 92         ghistsum.etCO2 = S0;
 93         ghistcnt.etCO2 = 0;
 94         /* reduce value to max of MAXCO2HIST but still SCALED format */
 95         avg = mulS( avg, itoS(CO2VAL2HIST));
 96         return( (char)(StoI(avg)));
 97 }
 98
 99 char far
100 GN2OETHistavg()
101 {       SCALED avg;
102         char Cavg;
103         avg = divS(ghistsum.etN2O, (itoS(ghistcnt.etN2O)));
104         ghistsum.etN2O = S0;
105         ghistcnt.etN2O = 0;
```

```
106        /* reduce value to max of MAXN2OHIST, still SCALED format */
107        avg = mul8(avg, itos(N2OVAL2HIST));
108        return( (char) (stoi(avg)));
109  }
110
111  char far
112  GAGTETHistavg()
113  {    SCALED avg;
114       char   Cavg;
115       avg = div5(ghistsum.etAgent, (itos(ghistcnt.insCO2)));
116       ghistsum.etAgent = 50;
117       ghistcnt.etAgent = 0;
118       /* reduce value to max of MAXCO2HIST, still SCALED format */
119       avg = mul8(avg, itos(CO2VAL2HIST));
120       return( (char) (stoi(avg)));
121  }
122
123  char far
124  GCO2INSHistavg()
125  {    SCALED avg;
126       char   Cavg;
127       avg = div5(ghistsum.insCO2, (itos(ghistcnt.insCO2)));
128       ghistsum.insCO2 = 50;
129       ghistcnt.insCO2 = 0;
130       /* reduce value to max of MAXCO2HIST, but still SCALED format */
131       avg = mul8(avg, itos(CO2VAL2HIST));
132       return( (char) (stoi(avg)));
133  }
134
135  char far
136  GN2OINSHistavg()
137  {    SCALED avg;
138       char   Cavg;
139       avg = div5(ghistsum.insN2O, (itos(ghistcnt.insN2O)));
140       ghistsum.insN2O = 60;
141       ghistcnt.insN2O = 0;
142       /* reduce value to max of MAXN2OHIST, but still SCALED format */
143       avg = mul8(avg, itos(N2OVAL2HIST));
144       return( (char) (stoi(avg)));
145  }
146
147  char far
148  GAGTINSHistavg()
149  {    SCALED avg;
150       char   Cavg;
151       avg = div5(ghistsum.insAgent, (itos(ghistcnt.insAgent)));
152       ghistsum.insAgent = 50;
153       ghistcnt.insAgent = 0;
154       /* reduce value to max of MAXAGTHIST, but still SCALED format */
155       avg = mul8(avg, itos(AGTVAL2HIST));
156       return( (char) (stoi(avg)));
157  }
158
159  char far
160  GBRHistavg()
161  {    SCALED avg;
162       char   Cavg;
```

SERVER

SECTION D

```
Thu 10-15-86 17:15:16  AWLINK.C
Thu 10-16-86 15:13:06

1  /* AWLINK.C - Waveform Link program, called by MT */
 2  /** 10/09/86 */
 3  /*****************************************************************
 4  ** MFO Ver 0.0
 5  **
 6  ** module: awlink.c
 7  **
 8  ** modification history :   reason(s)
 9  **       date       by
10  **     10/15/86     jab     Written to mfo.src
11  **
12  ** This module is an original, unpublished work and is proprietary to
13  ** NELLCOR INC., and may not be divulged or copied in any form
14  ** whatsoever without the express written permission of NELLCOR INC.
15  **
16  ** purpose : see spec s wfs.doc
17  **    wfLink function builds a waveform control block in allocated
18  **    memory which contains the waveform function and the buffer
19  **    addresses it needs for the measurement task td process
20  **    waveform data.
21  **
22  ** data descriptions :
23  **
24  ** function descriptions :
25  **
26  **    wfLink (fct_entry, dst_id, #src_ids, src_id);
27  **        See above;
28  **    wfInit (pid,...)
29  **        Creates waveform server process.
30  ******************************************************************/
31
32  #define STACKSIZE    128
33
34  #include "bwdef.h"
35
```

```
 36  #include "bwext.h"
 37  #include "bcSysDef.h"
 38  #include "xEvent.h"
 39
 40  extern struct acb            far  xCreateP ();
 41  extern struct wfcb * far         xALLOC (unsigned);
 42  extern int                   far wfServer ();
 43
 44
 45  extern char        cOutBuf0 [];         /* defined    */
 46  extern char        cOutBuf1 [];         /*            */
 47  extern char        cOutBuf2 [];         /*    in      */
 48  extern char       *cOutTbl [];          /*       bcomm */
 49
 50
 51  /*------------------------------------------------------------*/
 52  far WFLINK (fpFCT, ID, NSrc)
 53        int       *fpFCT) ();
 54        unsigned   ID, NSrc;
 55  {
 56  unsigned         I, J, FOUND;
 57  unsigned far    *fpW;
 58  struct wfcb    **pWFCB;
 59  struct wfrec   **pWRecTbl;
 60  struct acb      **pACB;
 61  struct acb      **pAcbTbl;
 62
 63  pWFCB = xALLOC (30+12*NSrc);            /* allocate block */
 64  if (pWFCB == 0)                          /* if alloc error */
 65       return (E_Alloc);
 66  pWFCB->wLink = wRoot;                    /* link to list */
 67  wRoot = pWFCB;
 68
 69  pWFCB->wActive = 1;                      /* fill wf control block */
 70  pWFCB->wProc = fpFCT;                    /* set active */
 71  pWFCB->wTable0 = &pWFCB->wTable[0];      /* function entry */
 72  pWFCB->wTable1 = &pWFCB->wTable [2+2*NSrc];
 73  pWFCB->wTable2 = &pWFCB->wTable [2+(2+NSrc)];
 74  pwRecTbl = &wRecTbl[0];                  /* find and fill dest acb */
 75  for (I=FOUND=0; pwRecTbl[I] != 0; I++)
 76       if (pwRecTbl[I]->wID == ID)
 77            {FOUND = 1;
 78             break;
 79            }
 80  if (FOUND == 0)                          /* if no dest found, error */
 81       return (E_wfName);
 82
 83  pWFCB->wTable0[0] = (int)pwRecTbl[I]->wBufOff + (int)cOutTbl[0];  /* stuff destination data */
 84  pWFCB->wTable0[1] = (int)pwRecTbl[I]->wBufLgth;
 85  pWFCB->wTable1[0] = (int)pwRecTbl[I]->wBufOff + (int)cOutTbl[1];
 86  pWFCB->wTable1[1] = (int)pwRecTbl[I]->wBufLgth;
 87  pWFCB->wTable2[0] = (int)pwRecTbl[I]->wBufOff + (int)cOutTbl[2];
 88  pWFCB->wTable2[1] = (int)pwRecTbl[I]->wBufLgth;
 89
 90  fpW = &NSrc;                             /* find and fill sources */
 91  fpW++;                                   /* ptr into stack to #sources */
 92                                           /* advance to first srcID */
```

```
 93   for (I=0; I(NSrc; I++)                              /* for each source */
 94     {pAcbTbl = A_ArrayPtr;                             /* Ptr to table of acb addresses */
 95      for (J=FOUND=0; PAcbTbl[J]!=0; J++)               /* find acb */
 96        if (PAcbTbl[J]->A_ID == *fpW)
 97          {FOUND = 1;
 98           break;
 99          }
100      if (FOUND == 0)                                   /* if no such acb, return */
101        return (E_ACB_Name);
102
103      pWFCB->wTable0[2*I+0] = (int)PAcbTbl[J]->A_BUFFER0; /* stuff source data into tables */
104      pWFCB->wTable0[2*I+1] = (int)PAcbTbl[J]->A_LENGTH;
105      pWFCB->wTable1[2*I+0] = (int)PAcbTbl[J]->A_BUFFER1;
106      pWFCB->wTable1[2*I+1] = (int)PAcbTbl[J]->A_LENGTH;
107      pWFCB->wTable2[2*I+0] = (int)PAcbTbl[J]->A_BUFFER2;
108      pWFCB->wTable2[2*I+1] = (int)PAcbTbl[J]->A_LENGTH;
109      fpW++;                                             /* advance to next src name */
110     }
111   return (0);
112  }
113
114  /*----------------------------------------------------------
115   * Creates waveform server task and its stack
116   */
117  far wfinit ()
118  {
119   struct wfcb *SP;
120
121   SP = xALLOC (STACKSIZE);
122   SP += STACKSIZE-2;
123   xCreateP (PID_WVF, wfServer, SP, 0, 0, 0);
124   return;
125  }
126
127  /* vClear dummy for analog unit */
128  vClear ()
129  {}
130
131  /* xWatch dummy for analog unit */
132  xWatch ()
133  {}
```

```
Thu 10-15-86 17:24:02  AWSERVER.S                 reason
    10-16-86 15:13:06

1  |AWSERVER.S - Waveform Server ****************************************
2  |10/03/86
3  |********************************************************************
4  |MFO Ver 0.0
5  |
6  | Module: awServer.s
```

```
 7  ; modification history : reason(s)
 8  ;       date    by      written to mfo.src
 9  ;     10/15/86  jab
10  ;
11  ;       This module is an original, unpublished work and is proprietary to
12  ;  NELLCOR INC., and may not be divulged or copied in any form
13  ;  whatsoever without the express written permission of NELLCOR INC.
14  ;       Copyright 1986.
15  ;
16  ; Purpose:
17  ;  WFS works down list of waveform control blocks, calling each proc.
18  ;  It pushes pointer to address list onto stack as indexed by global
19  ;  A_BufIdx and then far calls the procedure in the measurement task.
20  ;  Upon completion it activates the communication task (posts);
21  ;
22  ; Procedures:
23  ;       wfServer, waveform server function
24  ; Public Data:
25  ;       see bwGlob.s
26  ;*************************************************************
27      .186
28      include SysProl.i
29      include xEvent.i
30  ;
31  ; publics and externals
32  ;
33      public   _wfServer
34      extrn    _xWait    :far
35      extrn    _Comm     :far
36
37  _BSS  segment
38      extrn    _A_BufNum :word
39      extrn    _wRoot    :word
40  _BSS  ends
41
42  wLink    equ  0
43  wActive  equ  2                           ;waveform control block equates
44  wProc    equ  4                           ;active switch
45  wTable0  equ  8
46
47  ; _wfServer
48
49  _wfServer proc far
50      push     0
51      push     xA_Data_EV                   ;wait for post by ??
52      call     _xWait
53      add      sp,4
54  ;hold wfcb address in si, hold index in bx
55      mov      bx, _A_BufNum                ;index into bx
56      shl      bx, 1                        ;gives index adder
57      mov      si, _wRoot                   ;wfcb address into si
58  ;check for end of list
59  WFS10:
60      or       si, si
61      jz       WFS90                        ;finished
62      cmp      word ptr [si+wActive],0      ;skip if zero
```

```
64              ;treat one waveform control block
65                      jz      WFS20
66                      mov     di, [si+wTable0+bx]
67                      push    si
68                      push    bx
69                      push    di
70                      call    dword ptr es:[si+wProc]
71                      add     sp, 2           ;argument for me
72                      pop     bx
73                      pop     si
74              ;advance to next waveform control block
75              WFS20:
76                      mov     si, [si]
77                      jmp     WFS10
78              ;finished, post to communications task and loop
79              WFS90:  call    _Cohm
80                      jmp     _wfServer
81              _wfServer endp
82
83                      include SysEpil.i
84                      end
85
86
87
88

Thu 10-15-86 17:42:08   BWGLOB.C
    10-16-86 15:13:06

1  /* bwGLOB.C - Global data for waveform/analog output Servers */
2  /* 09/25/86 */
3  /*****************************************************************/
4  ** MFO Ver 0.0
5  **
6  ** module: bwGlob.c
7  **
8  ** modification history :
9  **         date    by   reason(s)
10 **      10/15/86  jab   written to mfg-src
11 **
12 **
13 ** This module is an original, unpublished work and is proprietary to
14 ** NELLCOR INC., and may not be divulged or copied in any form
15 ** whatsoever without the express written permission of NELLCOR INC.
16 **
17 ** purpose :
18 **      Data for waveform server (analog unit)
19 **      Data for analog output server (display unit)
20 **
21 ** data descriptions :
22 **      See listing
23 **
24 ** function descriptions :
25 **      none
26 /*****************************************************************/
```

```
27  #include          "bwdef.h"
28  #include          "bxID.h"
29
30  struct wfcb       *wRoot =0;         /* root pointer to wfcb list */
31
32
33  struct wfrec.     wfrIR   = {wID_IR,   1gIR,  /* sat ir waveform record */
34                                                0 };
35  struct wfrec      wfrRED  = {wID_RED,  1gRED, /* sat red waveform record */
36                                                0 };
37  struct wfrec      wfrCO2  = {wID_CO2,  1gCO2, /* Gas CO2 waveform record */
38                                                1gIR+1gRED };
39  struct wfrec      wfrN2O  = {wID_N2O,  1gN2O, /* Gas N2O waveform record */
40                                                1gIR+1gRED+1gCO2, 0 };
41  struct wfrec      wfrAGT  = {wID_AGT,  1gAGT, /* Gas Agent waveform record */
42                                                1gIR+1gRED+1gCO2+1gN2O };
43
44  struct wfrec      *wRecTbl [] =                 /* Table of WF Record addresses */
45                    {&wfrIR, &wfrRED, &wfrCO2, &wfrN2O, &wfrAGT, 0
46                    };
47  struct aocb       *vRoot =0;          /* root of ao ctl blk list */
48
```

```
Thu 10-15-86 17:45:48   BWEXT.H
    10-16-86 15:13:06

1  /* bwEXT.H -- Global data external declaration for waveform server */
 2  /** 09/18/86 */
 3  /*****************************************************************
 4  ** MFO Ver 0.0
 5  **
 6  ** module: bwExt.h
 7  **
 8  ** modification history :
 9  **       date       by:     reason(s)
10  **    10/15/86     jab      written to mfo.src
11  **
12  ** This module is an original, unpublished work and is proprietary to
13  ** NELLCOR INC., and may not be divulged or copied in any form
14  ** whatsoever without the express written permission of NELLCOR INC.
15  **
16  **
17  ** purpose :
18  **     External declaration to accompany bwGlobls.
19  ** data descriptions :
20  **
21  ** function descriptions :
22  **
23  *****************************************************************/
24
25  extern struct wfcb      *wRoot;
26  extern struct wfrec     wfrIR;
27  extern struct wfrec     wfrRED;
28
```

```
                  29   extern struct wfrec      wfrCO2;
                  30   extern struct wfrec      wfrN2O;
                  31   extern struct wfrec      wfrAGT;
                  32
                  33   extern struct wfrec      *wRecTbl [];
                  34
                  35   extern struct aocb       *vRodt;

Thu 10-15-86 17:44:16      BWDEF.H
Thu 10-16-86 15:13:06

1   /* bwDEF.H - Waveform server C definitions */
 2   /* 10/01/86 */
 3   /*******************************************************************/
 4   **   MFO Ver 0.0
 5   **
 6   **   module:  bxDef.h
 7   **
 8   **   modification history :
 9   **       date        by      reason(s)
10   **     10/15/86     jab      written to mfo.src
11   **
12   **
13   **  This module is an original, unpublished work and is proprietary to
14   **  NELLCOR INC. and may not be divulged or copied in any form
15   **  whatsoever without the express written permission of NELLCOR INC.
16   **
17   **   Purpose :
18   **      Definitions of structures for waveform server
19   **                                   analog output server
20   **   data descriptions :
21   **
22   **   function descriptions :
23   **
24   /*******************************************************************/
25
26   #define    lgBuf        80
27
28   #define    lgIR         12
29   #define    lgRED        12
30   #define    lgCO2        12
31   #define    lgN2O        12
32   #define    lgAGT        12
33
34   struct acb
35   {  unsigned   A_ID;           /* acb identifier */
36      unsigned   A_space[10];
37      unsigned   A_PID;          /* id of requesting task */
38      unsigned   A_LENGTH;
39      unsigned  *A_BUFFER0;
40      unsigned  *A_BUFFER1;
41      unsigned  *A_BUFFER2;
42   };
43
44   struct wfrec                  /* waveform record, static in ds */
```

```
45      {unsigned         WID;            /* waveform identifier */
46       unsigned         wBufLgth;       /* length of buffer, bytes */
47       unsigned         wBufOff;        /* index of 1st byte */
48       struct aocb      *wAoPtr;        /* ptr to aocb for aoserv */
49      };
50      struct wfcb                       /* waveform control block, in heap */
51      {struct wfcb      *wLink;         /* far ptr to wfcb */
52       unsigned         wActive;        /* 1=active, 0=disabled */
53       unsigned    (far *wProc)();      /* ptr to far function */
54       unsigned         *wTable0;       /* address of table0 */
55       unsigned         *wTable1;
56       unsigned         *wTable2;
57       unsigned         wTable[1];      /* address tables start here */
58
59      };
60
61      struct aocb                       /* analog output control block */
62      {unsigned         Link;           /* addr of next aocb in list-SD only */
63       unsigned         Active;         /* active=1, inactive=0 */
64       unsigned         DataID;         /* data identifier            -SD only */
65       unsigned         PortID;         /* port identifier, 0-7 */
66       unsigned         Factor;         /* scale multiplier */
67       unsigned         TimeSet;        /* value to be set into counter */
68       unsigned         TimeCount;      /* decremented to zero to activate */
69       unsigned         Index;          /* index of WF data           -WF only */
70       long             Function;       /* entry address of function -SD only */
71      };

Thu 10-03-86 10:47:54      DVLINK.C                          vSlowLink

1      /* dvLINK.C - Link programs for analog output server
 2       * 10/03/86
 3       *
 4       * vSlowLink()  passes function entry to AOB from MT
 5       * vSlowOout()  passes port info to AOB from control server
 6       * vWfOut()     links port to waveform data by control server
 7       * vAoServ      is analog output server in assembler
 8       */
 9      #include "bwdef.h"
10      #include "bwext.h"
11      #include "bcSysDef.h"
12      #include "xEvent.h"
13
14      #define STACKSIZE         128
15
16      extern int far              vAoServ ();
17      extern far                  xCreateP ();
18      extern char * far           xALLOC ();
19
20      /* vSlowLink --------------------------------------------
21       *          Link MT function for slow data
22       */
23      far vSlowLink (ID, FCT)
```

```
24          unsigned        ID;
25          long            FCT;
26   {
27      unsigned            G;
28      struct aocb         *pCB;
29
30      G = FIND_CB (&pCB, ID);
31      if (G == 0)
32          xErrPost (E_NoMem);          /* if no memory avail */
33      else
34      {pCB->Link = vRoot;              /* link it to list */
35       vRoot = pCB;
36       pCB->Function = FCT;            /* insert function */
37       pCB->DataID = ID;               /* insert data identifier */
38       pCB->Active = 0;                /* flag as inactive */
39       if (G == 1)                     /* if aocb already existed */
40          pCB->Active = 1;             /* flag as active */
41      }
42      return;
43   }
44
45   /* vSlowOut ------ Pass port data from control server for slow data
46   */
47   far vSlowOout (ID, PORT, PERIOD, FSCALE)
48       unsigned            ID;
49       unsigned            PORT;
50       unsigned            PERIOD;
51       unsigned            FSCALE;
52   {
53      unsigned             G;
54      struct aocb          *pCB;
55
56      G = FIND_CB (&pCB, ID);
57      if (G == 0)
58          xErrPost (E_NoMem);          /* if no memory avail */
59      else
60      {pCB->Link = vRoot;              /* link it to list */
61       vRoot = pCB;
62       pCB->Active = 0;                /* flag as inactive */
63       if (G == 1)                     /* if aocb already existed */
64          pCB->Active = 1;             /* flag as active */
65       pCB->DataID = ID;               /* insert data identifier */
66       pCB->PortID = PORT;
67       pCB->TimeSet = PERIOD;
68       pCB->TimeCount = PERIOD;
69       pCB->Factor = SCALE (FSCALE);   /* calculate scale factor */
70      }
71      return;
72   }
73
74
75   /* vWFOut ------ Link Waveform data by control server. Attach to wFRecord
76   */
77   far vWFOut (ID, PORT, PERIOD, FSCALE)
78       unsigned            ID;
79       unsigned            PORT;
80
```

```
 81        unsigned        PERIOD;
 82        unsigned        FSCALE;
 83
 84   {
 85        unsigned         G, I, FOUND;
 86        struct aocb      *pCB;                       /* ptr to analog output cb */
 87        struct wfrec     **pwRecTbl;                 /* ptr to waveform record tbl */
 88
 89        G = FIND_CB (&pCB, ID);
 90        if (G == 0)
 91            xErrPost (E_NoMem);                      /* if no memory avail */
 92        else
 93        {pCB->Active = 0;
 94         if (G == 1)
 95            pCB->Active = 1;                         /* flag as inactive */
 96            pCB->PortID = PORT;                      /* if aocb already existed */
 97            pCB->TimeSet = PERIOD;                   /* flag as active */
 98            pCB->TimeCount = PERIOD;
 99            pCB->Factor = SCALE (FSCALE);            /* calculate scale factor */
100            pwRecTbl = &wRecTbl[0];                  /* find waveform record */
101            for (I=FOUND=0; pwRecTbl[I] != 0; I++)
102               if (pwRecTbl[I]->wID == ID)
103               {FOUND = 1;
104                pCB->Index = pwRecTbl[I]->wBufOff;
105                pwRecTbl[I]->wAoPtr = pCB;           /* link to wfRec */
106                break;
107               }
108            if (FOUND == 0)
109               xErrPost (E_wfName);                  /* wfRec not found */
110        }
111   returns
112   }
113
114   /* FIND_CB -----------------------------------
115   **                Stores ptr to aocb in argument addr. 0=if none
116   **                Returns 0=no mem, 1=already existed, 2=new
117   */
118   near FIND_CB (ppCB, ID)
119        unsigned         *ppCB, ID;
120   {
121        unsigned         FLAG;
122        struct aocb      **pCBp;
123
124        pCBp = &vRoot;
125        FLAG = 0;
126        while (*pCBp != 0)                           /* set up the control block */
127        {if ((*pCBp)->PortID == ID)                  /* does one already exist */
128            {FLAG = 1;
129             break;
130            }
131         pCBp = *pCBp;                               /* advance along list */
132        }
133        if (FLAG)                                    /* if it exists */
134            *ppCB = *pCBp;                           /* then use it */
135        else                                         /* if it doesn't exist */
136        {*ppCB = xALLOC (0x18);                      /* then allocate it */
137         if (*ppCB != 0)
138            FLAG = 2;
```

```
138        }
139        return (FLAG);                          /* return flag */
140    }
141    /* SCALE ----- calculates oacb.Factor from full scale millivolts
142    */
143    near SCALE (FS)
144        unsigned    FS;
145    {
146        unsigned long  TLONG;
147        TLONG = FS;
148        TLONG = TLONG * 0x1000;
149        return (unsigned) TLONG;
150    }
151
152    /*
153    *  Creates analog output server task and its stack
154    */
155    far vInit ()
156    {
157        char   *SP;
158
159        SP = xALLOC (STACKSIZE);
160        SP += STACKSIZE-2;
161        xCreateP (PID_AOUT, vAOServ, SP, 0, 0, 0);
162        return;
163    }
```

```
!dvServ.s - Analog Output Server in the display unit
! 10/03/86
        name    dvServer
.186
include sysprol.i
include xEvent.i public  _vAOServ
    public  _vClear
    public  _vOutDac
    public  _A_BufNum
    extrn   _xWait:far _BSS segment
                                       ;analog output server
vWfRecX   dw    ?                      ;clears data indices in oacb's
vBuffer   dw    ?
_BSS ends _DATA segment
    _A_BufNum       dw    0
    extrn   _vRoot  :word
    extrn   _wRoot  :word
    extrn   _cIntTbl:word
```

Thu 10-03-86 10:46:30  DVSERVER.S
    10-16-86 15:13:06

```
        extrn           _wRecTbl:word
_DATA   ends aocb    struc                   ;analog output control block
        Link            dw (?)  ;ptr to next block -SD only
        Active          dw (?)  ;active=1, inactive=0
        DataID          dw (?)  ;data identifier      -SD only
        PortID          dw (?)  ;port identifier
        Factor          dw (?)  ;scale multiplier
        TimeSet         dw (?)  ;value to be set into counter
        TimeCount       dw (?)  ;timer counter         WF only
        Index           dw (?)  ;index of WF data     -SD only
        Function        dd (?)  ;entry address of:fct
aocb    ends
wfrec   struc                   ;waveform record
        wID             dw (?)  ;waveform identifier
        wBufLgth        dw (?)  ;length of buffer in bytes
        wBufOff         dw (?)  ;index of first byte
        wAoPtr          dw (?)  ;addr of aocb if not zero
wfrec   ends ;       vAOServ Analog Output Server
;
_vAOServ proc far
        push    xTime_EV
        push    xWait
        call ;set up pointer to comm input buffer
        mov     bx, A_BufNum            ;index into bx
        shl     bx, 1                   ;gives index adder
        mov     di, offset dgroup:_cInTbl ;table of input buffer addrs
        mov     di, [di][bx]            ;address of input buffer
        mov     si, vBuffer             ;save buffer address ;handle each waveform buffer
        xor     ax, ax
        mov     vWfRecX, ax
AOS10:
        mov     bx, vWfRecX
        or      bx, bx
        jnz     AOS20
        jmp     AOS90
AOS20:
        inc     vWfRecX                 ;inc index for next loop
        mov     bx, offset dgroup:wRop:wRopt[bx];rdr is addr of wf rec
        shl     bx, 1                   ;offset dgroup [bx] is addr of aocb
        mov     si, [di].wAOPtr         ;inactive, proceed if zero ;check active, decr count, proceed if zero
        cmp     [si].Active, 0          ;inactive, go to next
        jz      AOS10
        dec     [si].TimeCount          ;not ready, go to next
        jnz     AOS10
        mov     ax, [si].TimeSet        ;reset count
        mov     [si].TimeCount, ax ;;;pick up data, scale it
        mov     bx, vBuffer             ;in wf record
        add     bx, [di].wBufOff
```

```
 81             add     bx, [si].Index           ;in aocb
 82             mov     ax, [bx]
 83             shl     ax, 4
 84             xor     dx, dx
 85             mov     bx, [si].Factor
 86             mul     bx
 87             call    vOutDac                  ;output dx reg to dac
 88             jmp     AOS10                    ;go to next
 89  ;handle slow data
 90  AOS90:
 91             mov     si, vRoot                ;list root/aocb addr
 92             jmp     AOS110
 93  AOS100:
 94             mov     si, [si]                 ;advance down list
 95  AOS110:
 96             or      si, si                   ;check end of list
 97             jnz     AOS120
 98             jmp     AOS200                   ;finished with slow data
 99  AOS120:                                     ;si = aocb address
100  ;check active, decr counter, proceed if zero
101             cmp     [si].Active, 0
102             jz      AOS100                   ;inactive, go to next
103             dec     [si].TimeCount
104             jnz     AOS100                   ;not ready, go to next
105             mov     ax, [si].TimeSet         ;reset count
106             mov     [si].TimeCount, ax
107  ;call function to get data, scale, output to dac
108             call    dword ptr [si].Function  ;returns data in ax
109             mov     bx, [si].Factor
110             mul     bx
111             call    vOutDac
112             jmp     AOS100                   ;next in list
113  ;finished, so exit
114  AOS200:    jmp     _vAoServ                 ;go to wait for next time
115  _vAoServ   endp
116
117  ;—————————————————————————————————————————
118  ; _vClear   Clears data indices for waveform data
119  ;—————————————————————————————————————————
120  _vClear    proc far
121             push    di
122             push    si
123  ;work down table of pointers to waveform records
124             mov     di, _wRecTbl
125  VC10:
126             cmp     word ptr [di], 0         ;end of table
127             jz      VC30
128             mov     si, [di].wAoPtr
129             cmp     word ptr [si], 0         ;no Aocb, if zero
130             jz      VC20
131             mov     [si].Index, 0            ;next table entry
132  VC20:
133             add     di, 2
134             jmp     VC10
135  ;exit
136  VC30:
137             pop     si
```

```
138             pop      dl
139             ret
140    _vClear  endp
141
142    ; vOutDac ------
143    ;           Output to the dac
144    ;
145    vOutDac  proc near
146             ret
147    vOutDac  endp
148
149    include sysepil.i
150             end
151
152
153
154
```

SECTION E

COMM

```
Wed 10-07-86 18:04:02  BCOMM.S        reason
    10-15-86 13:19:54

1  ;bCOMM.S - System interface procedures for Comm
 2  ;10/07/86
 3  ;******************************************************************
 4          .186
 5          name    bCOMM
 6  ;
 7  MFO Ver 0.0
 8  Module: BCOMM.S
 9
10  modification history :  reason(s)
11          date    by      reason
12  ;
13  ;******************************************************************
14          This module is an original, unpublished work and is proprietary to
15          NELLCOR INC., and may not be divulged or copied in any form
16          whatsoever without the express written permission of NELLCOR INC.
17          Copyright 1986.
18
19  Purpose:     Communication application procedures, called by application
20               users.
21  Procedures:
22       cInit:      Initializes the communications package
23       Comm:       Starts the communication process
24       cSendSlow:  Sends slow data across line
25       CommLink:   Linkd data consumer to the received comm data
```

```
26  ;**************************************************************
27  ; Public  cLinkDummy:Sets ax to 0FFFFh
28  ;   none
29  ;**************************************************************
30          include sysprol.i
31          include bcdef.i
32          include bcext.i
33          include bcSysDef.i
34
35  Arg0        equ     6
36  STACKLGTH   equ     256
37
38  public  _Comm                ;far, c-call, send periodic block
39  public  _cTrigEcg            ;far, c-call, send ecg trigger block
40  public  _CommLink            ;far, c-call, link mt slow data to comm
41  public  _cInit               ;far, c-call, initialize the comm hw/sw
42  public  _cSendSlow           ;far, c-call, send slow data
43  public  _cSendSlow           ;far, asm-call, send slow data
44  public  _cLinkDummy          ;     cMeasTbl/cServTbl initial value
45
46          extrn   _CharPut    :near
47          extrn   _cxInit     :far
48          extrn   _cNitRing   :near
49          extrn   _xLock      :near
50          extrn   _xUnlock    :near
51          extrn   _xPost      :far
52          extrn   _xPID       :near
53          extrn   _xCreateP   :far
54          extrn   _xErrPost   :far
55          extrn   _xRING      :far
56          extrn   _xAlloc     :far
57          extrn   _CommTask   :far
58
59  _BSS    segment
60          extrn   _A_BufNum:word
61  _BSS    ends
62
63  ;_cInit  Initializes the Communications server
64  ;        Argument in 'M'=master, 'S'=slave
65  _cInit  proc far
66          push    bp
67          mov     bp, sp
68          push    di
69          push    si
70  ;initialize cxcomm
71          push    [bp+Arg0+0]         ;first arg, M or S
72          call    _cxInit             ;init cx Package
73          add     sp,2
74  ;initialize slow data ring and general ring
75          call    _cNitRing           ;init slow data ring
76          push    offset dgroup:cRING
77          push    0                   ;init fct code
78          call    _xRING              ;initialize comm/cEcgTrig ring
79          add     sp, 4
80  ;initialize commlink tables to cLinkDummy (returns -1)
81          mov     di, offset dgroup:cMeasTbl
```

```
82              mov     cx, 2*MAX_FID + 2
83      CINIT10:
84              mov     [di], offset Sys_Text:cLinkDummy
85              mov     [di+2], Sys_Text
86              add     di, 4
87              dec     cx
88              jnz     CINIT10
89      ;allocate stack space
90              push    STACKLGTH
91              call    xAlloc                  ;leaves ax=bottom of stack
92              add     sp, 2
93              or      ax, ax
94              jnz     CINIT20
95              push    E_Alloc
96              call    xErrPost
97              add     sp, 2
98      CINIT20:
99              add     ax, STACKLGTH-2         ;to top of stack
100     ;create Commtask
101             push    0                       ;termination address: 0,0
102             push    0
103             push    0                       ;no extra timers
104             push    ax                      ;stack pointer
105             push    Sys_Text                ;Commtask code seg
106             push    offset Sys_Text:CommTask
107             push    PID_COMM                ;process indentifier
108             call    xCreateP
109             add     sp, 14
110     ;exit
111             pop     si
112             pop     di
113             pop     bp
114             ret
115     cInit   endp
116     ;
117     ; _COMM and _cTrigEcg ------------------------------
118     ;
119     _COMM   proc far
120             mov     cCHAR, 'P'              ;send periodic block
121             jmp     COMM10
122     ;
123     _cTrigEcg label word
124             mov     cCHAR, 'E'              ;send ecg trigger block
125     COMM10:
126             inc     cPostCount              ;for debug
127             cmp     cPostCount, 00          ;for debug
128             jge     COMM20                  ;for debug
129             ret                             ;for debug
130     COMM20:                                 ;end for debug
131             mov     cPostCount, 0           ;lock to prevent splitting
132             call    xLock                   ; of ring put and post
133             push    offset dgroup:cCHAR
134             push    offset dgroup:cRING
135             push    3                       ;put character
136             call    xRING
137             add     sp, 6
```

```
138             push    XCOMM_EV
139             push    PID_COMM
140             call    _xPOST
141             add     sp, 4
142             call    _xUnlock
143             ret
144     _COMM   endp
145
146     ; _cSendSlow (id, &data, lgth) -----------------------------------------
147     ;       C- call verson. Sends slow data,into output buffer or ring
148     cSendSlow proc far
149             push    bp
150             mov     bp, sp
151             mov     ax, [bp+Arg0+0]
152             mov     bx, [bp+Arg0+2]
153             mov     cx, [bp+Arg0+4]
154             call    far ptr cSendSlow
155             pop     bp
156             ret
157     _cSendSlow endp
158
159     ; cSendSlow -----------------------------------------------------------
160     ;       asm call, at entry ax=id, bx=data_ptr, cx=lgth-of-data
161     cSendSlow proc far
162             push    bp                      ;bp+0
163             mov     bp, sp
164             push    di                      ;bp-2
165             push    si                      ;bp-4
166             push    ax                      ;bp-6, id
167             mov     si, bx                  ;data ptr to s
168             call    _xLock                  ;lock to keep bytes together in ring
169     ;is there room in output buffer?
170             mov     ax, OUT_LG_SLOW         ;length for slow data
171             sub     ax, cOutSlowX           ;gives length left
172             sub     ax, cx                  ;new data
173             sub     ax, 8                   ;tid, did, lgth, and end-of-buffer
174             jl      SS50                    ;no room, put in ring
175     ;put data in output buffer
176             mov     di, offset dgroup: cOutTbl ;address of buffer addr table
177             mov     ax, _A_BufNum           ;user index
178             inc     ax                      ;advance to fill index
179             cmp     al, 3
180             jne     SS10
181             xor     ax, ax
182     SS10:
183             shl     ax, 1                   ;*2 for words
184             add     di, ax                  ;address of buffer address
185             mov     bx, [di]                ;address of output buffer
186             mov     bx, cOutSlowX           ;slow data index into bx
187             call    xPID                    ;returns current pid in ax
188             mov     [di+bx+OUT_LG_WF+0], ax ;data id
189             mov     ax, [bp-6]
190             mov     [di+bx+OUT_LG_WF+2], ax ;data id
191             mov     [di+bx+OUT_LG_WF+4], cx ;data length
192             add     bx, 6
193     SS20:                                   ;move data into buffer
```

```
194             mov     al, [si]
195             mov     [di+bx+OUT_LG_WF], al
196             inc     si
197             dec     bx
198             jnz     SS20
199             mov     word ptr [di+bx+OUT_LG_WF], 0FFFFh   ;term buf
200             jmp     SS90                                 ;exit
201     ;put data in ring
202     SS50:   call    xPID                                 ;task id in ax
203             mov     bx, ax
204             call    CharPut
205             mov     al, bh
206             call    CharPut
207             mov     bx, [bp-6]                           ;data id
208             mov     al, bl
209             call    CharPut
210             mov     al, bh
211             call    CharPut
212             mov     al, cl                               ;data count
213             call    CharPut
214             mov     al, ch
215             call    CharPut
216     SS60:   mov     al, [si]
217             call    CharPut
218             inc     si
219             dec     cx
220             jnz     SS60
221     ;exit
222     SS90:   call    xUnlock
223             pop     ax
224             pop     si
225             pop     di
226             mov     sp, bp
227             pop     bp
228             ret
229     cSendSlow endp
230     ; _CommLink (fct far_address) --------------------------------
231     ;  Inserts procedure entry address (dword) into table
232     ;  cMeasrTbl if in hibyte, cServTbl if in lobyte
233     _CommLink proc  far
234             push    bp
235             mov     bp, sp
236             push    di
237             push    si
238     ;pick up task id, place in bx as index                ;task id into ax
239             call    xPID
240             mov     bx, ax
241             or      bl, bl
242             jz      CL10
243             mov     di, offset dgroup:cServTbl
244             jmp     CL20
```

```
251            CL10:
252                    mov     bl, bh
253                    xor     bh, bh
254                    mov     di, offset dgroup:cMeasTbl
255            ;write into table
256                    shl     bx, 2           ;*4 for dwords
257                    mov     ax, [bp+Arg0+0] ;offset
258                    mov     [di+bx+0], ax
259                    mov     ax, [bp+Arg0+2] ;segment
260                    mov     [di+bx+2], ax
261            CL20:
262            ;exit
263                    pop     si
264                    pop     di
265                    mov     sp, bp
266                    pop     bp
267                    ret
268            _CommLink endp
269
270            ; cLinkDummy cMeasTbl and cServTbl are initialized to this
271            ;
272            cLinkDummy proc far
273                    mov     ax, 0FFFFh
274                    ret
275            cLinkDummy endp
276
277            include sysepil.i
278                    end
```

Wed 10-03-86 12:12:14  BCDEF.I

```
 1  ;bcDef.i - Comm task and interface definitions
 2  ;10/03/86
 3  ;******************************************************************
 4  ;
 5  ;  MFO Ver 0.0
 6  ;
 7  ;  Module: bcDef.i
 8  ;
 9  ;  modification history :
10  ;     date       by      reason(s)              reason
11  ;
12  ;     This module is an original, unpublished work and is proprietary to
13  ;     NELLCOR INC., and may not be divulged or copied in any form
14  ;     whatsoever without the express written permission of NELLCOR INC.
15  ;     Copyright 1986.
16  ;
17  ;  Purpose:
18  ;     Defines structures and constants for bComm, the application level
19  ;     of communications.
20  ;  Procedures:
21  ;     None
```

```
222  ; Public Data:
223  ;      None
224  ;***********************************************************
225
226  ccb struc
227       Status    dw    (?)         ;status return
228       Bytes     dw    (?)         ;byte count of received data
229       DataPtr   dw    (?)         ;offset address of received data
230       OutBuf    dw    (?)         ;output buffer offset address
231       OutLgth   dw    (?)         ;output buffer length in bytes
232       InBuf     dw    (?)         ;Input buffer offset address
233       InLgth    dw    (?)         ;input buffer length in bytes
234  ccb ends
235
236  LG_ECG     equ    2              ;length of ecg message
237  MAX_PID    equ    10             ;max number of processes
238
239  IN_LG_WF      equ    60          ;length of inbuf for wf data
240  IN_LG_SLOW    equ    20          ;length of inbuf for slow data
241  OUT_LG_WF     equ    60          ;length of outbuf for wf data
242  OUT_LG_SLOW   equ    20          ;length of outbuf for slow data
```

Wed 10-07-86 12:38:40  BCGLOB.S                reason
    10-15-86 13:19:54

```
 1  ;bcGLOB.S - Global data for communications task
 2  ;10/07/86
 3  ;***********************************************************
 4   186       name    bcGlob
 5   MFO Ver 0.0
 6
 7  ; Module: bcGlob.s
 8
 9  ; modification history :  reason(s)
10  ;       date        by       reason
11
12  ;       This module is an original, unpublished work and is proprietary to
13  ;       NELLCOR INC., and may not be divulged or copied in any form
14  ;       whatsoever without the express written permission of NELLCOR INC.
15  ;       Copyright 1986.
16
17  ; Purpose:
18  ;       Data declarations for all variables for the bComm level of comm.
19  ; Procedures:
20  ;       None
21  ; Public Data:
22  ;       All public, see listing below.
23  ;***********************************************************
24
25   include sysprol.i
26   include bcdef.i
27   include bcSysDef.i
```

```
     ;This data is cleared by startup --------------------
     _BSS segment word public 'BSS'
         cMeasTbl     dd    MAX_PID+1 dup (?)
         cServTbl     dd    MAX_PID+1 dup (?)
         _cInBuf0     db    IN_LG_WF + IN_LG_SLOW   10h dup (?)   ;input buffers
         _cInBuf1     db    IN_LG_WF + IN_LG_SLOW   10h dup (?)   ;input buffers
         _cInBuf2     db    IN_LG_WF + IN_LG_SLOW   10h dup (?)   ;input buffers
         _cOutBuf0    db    OUT_LG_WF + OUT_LG_SLOW       dup (?) ;output buffers
         _cOutBuf1    db    OUT_LG_WF + OUT_LG_SLOW       dup (?) ;output buffers
         _cOutBuf2    db    OUT_LG_WF + OUT_LG_SLOW       dup (?) ;output buffers
     _BSS ends ; Initialized data ----------------------------------
     _DATA segment word public 'DATA'
         ;Ecg buffers and comm control blocks
         cEcgIn       dw    3 dup (0)
         cEcgOut      dw    0FFFFh
         CcbEcg       ccb   <0, 0, 0, cEcgOut, LG_ECG, cEcgIn, LG_ECG+6>
         Ccbwf        ccb   <0, 0, 0, OUT_LG_WF+OUT_LG_SLOW, 0, IN_LG_WF+IN_LG_SLOW+6>
         ;buffer tables and sizes
         _cInLg       dw    IN_LG_WF + IN_LG_SLOW
         _cInSlowLg   dw    IN_LG_SLOW
         _cInTbl      dw    offset dgroup:_cInBuf0, offset dgroup:_cInBuf1, offset dgroup:
         _cOutLg      dw    OUT_LG_WF + OUT_LG_SLOW
         _cOutSlowLg  dw    OUT_LG_SLOW
         _cOutTbl     dw    offset dgroup:_cOutBuf0, offset dgroup:_cOutBuf1, offset dgroup:
         cOutBuf2
         cOutSlowX    dw    0
         ;cRING        for comm and cExtTrig
         cCHAR        db    0                           ;character 'P' or 'T'
         cCHAR2       db    0                           ;for commtask
         cWORD        dw    0                           ;for commtask
         cPostCount   dw    10                          ;for debug, call countdown
         cRING        dw    5   dup (0)                 ;ringsize is ten
                      dw    10  dup (0)                 ;6 control words
                      db                                ;10 byte ring
     _DATA ends public    cMeasTbl
         public    cServTbl
         public    _cInBuf0
         public    _cInBuf1
         public    _cInBuf2
         public    _cOutBuf0
         public    _cOutBuf1
         public    _cOutBuf2 public    cEcgIn
         public    cEcgOut
         public    CcbEcg
         public    Ccbwf
         public    _cInLg
         public    _cInSlowLg
```

```
         83            public    _cInTbl
         84            public    _cOutLg
         85            public    _cOutSlowLg
         86            public    _cOutTbl
         87            public    _cOutSlowX
         88            public    cCHAR
         89            public    cCHAR2
         90            public    cWORD
         91            public    cPostCount
         92            public    cRING
         93            include   sysepil.i
         94            end Wed 10-08-86 11:25:38  BCRING.S        reason
    10-15-86 13:19:54

1    ;BCRING.S - Ring Buffer Implementation for Slow Data Input
  2    ;10/07/86
  3    ;**************************************************************
  4            name    bcRing
  5    186
  6    ;**************************************************************
  7    ; MFO Ver 0.0
  8    ;
  9    ; Module: bcRing.s
 10    ;
 11    ; modification history :    reason(s)
 12    ;        date         by        reason
 13    ;
 14    ;       This module is an original, unpublished work and is proprietary to
 15    ;       NELLCOR INC., and may not be divulged or copied in any form
 16    ;       whatsoever without the express written permission of NELLCOR INC.
 17    ;       Copyright 1986.
 18    ;
 19    ; Purpose:
 20    ;       Ring buffer implementation for slow data handling.
 21    ; Procedures:
 22    ;
 23    ; Public Data:
 24    ;
 25    ;**************************************************************
 26            include sysprol.i
 27
 28    RINGSIZE    equ     128
 29    Arg0        equ     6             ;for far call
 30
 31            public    CharPut         ;Puts char from al into ring
 32            public    CharGet         ;Gets char from ring to ax
 33            public    cGetLgth        ;gets the packet length
 34            public    cNitRing        ;initializes the ring
 35            public    cSlowRing       ;ring for slow data
 36
 37            extrn     _xLock:near     ;prevents task switch
 38            extrn     _xUnLock:near   ;enables task switch
```

```
39  ring    struc
40          Size    dw      (?)
41          Count   dw      (?)
42          Getx    dw      (?)
43          Putx    dw      (?)
44          Flag    dw      (?)
45          Buf     db      RINGSIZE dup (?)       ;ring buffer definitions
46  ring    ends
47
48  _BSS    segment word public 'BSS'
49          cSlowRing       ring    (?)            ;ring buffer declaration
50  _BSS    ends
51
52
53  ;----------------------------------------------------------------
54  ; CharPut --- Write character in al to the ring
55  ;             Return ax=0 if buffer full
56  CharPut  proc   near
57          push    bx
58          pushf
59          cli                                    ;disable intpts
60  ;if no buffer space, return -1
61          mov     bx, cSlowRing.Count
62          cmp     bx, cSlowRing.Size
63          jne     COUT10
64          xor     ax, ax                         ;ax=0
65          jmp     COUT90
66  COUT10:
67  ;pick up character from stack
68          xor     ah, ah
69          dec     ah                             ;ah=0FFh (!=0)
70  ;put char in ring, increment index
71          mov     bx, cSlowRing.Putx
72          mov     cSlowRing.Buf[bx], al
73          inc     cSlowRing.Putx
74          inc     cSlowRing.Count
75  ;wrap index if necessary
76          mov     bx, cSlowRing.Putx
77          cmp     bx, cSlowRing.Size
78          jne     COUT30
79          mov     cSlowRing.Putx, 0
80  ;exit
81  COUT30:
82  COUT90:
83          popf                                   ;enable intpts
84          pop     bx
85          ret
86  CharPut  endp
87
88  ;----------------------------------------------------------------
89  ; CharGet --- Return char from ring in al, return ax=0 if none
90  CharGet  proc   near
91          push    bx
92          pushf
93          cli
94
```

```
95          ;if count is zero, exit with ax=0
96                  cmp     cSlowRing.Count, 0
97                  jne     CIN10
98                  xor     ax, ax
99                  jmp     CIN90                   ;ax=0 if no char
100         CIN10:
101         ;get char from ring
102                 mov     bx, cSlowRing.Getx
103                 mov     al, cSlowRing.Buf [bx]
104                 xor     ah, ah                  ;ah=0FFh
105                 dec     cSlowRing.Count
106                 inc     cSlowRing.Getx
107                 dec     ah
108                 mov     bx, cSlowRing.Getx
109                 cmp     bx, cSlowRing.Size
110                 jne     CIN80
111                 xor     bx, bx                  ;wrap getx
112         CIN80:
113                 mov     cSlowRing.Getx, bx
114         CIN90:
115                 popf                            ;enable intpts
116                 pop     bx
117                 ret
118         CharGet endp
119
120         ; RingInit ---- Initialize the ring buffers
121         cNitRing proc    near
122                 mov     ax, RINGSIZE
123                 mov     cSlowRing.Size, ax
124                 xor     ax, ax
125                 mov     cSlowRing.Count, ax
126                 mov     cSlowRing.Getx, ax
127                 mov     cSlowRing.Putx, ax
128                 mov     cSlowRing.Flag, ax
129                 ret
130         cNitRing endp
131
132         ; cGetLgth ---- Returns packet length in ax without changing the ring
133         ;               Length = word2 + 6, returns zero if ring empty
134         cGetLgth proc    near
135                 push    bx
136                 call    xLock
137                 cmp     cSlowRing.Count, 0
138                 jnz     GL10
139                 xor     bx, bx                  ;if count zero, zero bx(ax)
140                 jmp     GL80                    ;and return
141         GL10:
142         ;save ring parameters
143                 push    cx
144                 push    dx
145                 mov     cx, cSlowRing.Count
146                 mov     dx, cSlowRing.Getx
147         ;get length and add 6
148                 call    CharGet                 ;task id word
```

```
151         call    CharGet
152         call    CharGet
153         call    CharGet
154         call    CharGet
155         mov     bl, al
156         call    CharGet           ;data id word
157         mov     bh, al
158         add     bx, 6             ;data lgth lobyte
159 ;restore ring parameters and exit
160         mov     cSlowRing.GetX, dx
161         mov     cSlowRing.Count, cx
162         pop     dx
163         pop     cx
164 GL80:
165         call    xUnlock
166         mov     ax, bx
167         pop     bx
168         ret
169 cGetLgth endp
170 include sysepil.i
171         end
172
```

Wed 10-04-86 17:49:50  BCSYSDEF.I         reason
    10-15-86 13:19:54

```
 1 ;*********************************************************************
 2 ; bcSysDef.I   - System definitions for MFO
 3 ;   10/04/86
 4 ;
 5 ; MFO Ver 0.0
 6 ;
 7 ; Module: bcSysDef.i
 8 ;
 9 ; modification history :
10 ;     date       by       reason(s)
11 ;
12 ;   This module is an original, unpublished work and is proprietary to
13 ;   NELLCOR INC., and may not be divulged or copied in any form
14 ;   whatsoever without the express written permission of NELLCOR INC.
15 ;              Copyright 1986.
16 ;
17 ; Purpose:
18 ;   Defines error numbers for comm, waveform, analog out, servers and
19 ;      allocation routines.
20 ; Procedures:
21 ;   None
22 ; Public Data:
23 ;   None
24 ;*********************************************************************
25
26 include xEvent.i
27
28 ;Error/Status codes
```

```
29  E_Free          equ  1        ;allocate errors
30
31                           ;Comm errors
32  E_Timeout       equ  2
33  E_Sequence      equ  3
34  E_CRC           equ  4
35  E_Serial        equ  5
36  E_CommRing      equ  6
37  E_Overrun       equ  7
38  E_Count         equ  8
39
40
41                           ;General Ring Buffer errors
42  E_Empty         equ  0Ah
43  E_Full          equ  0Bh
44  E_Invalid       equ  0Ch
45  E_Inv_TID       equ  0Eh
46
47                           ;WaveForm Server errors
48  E_wfName        equ  15
49  E_ACB_Name      equ  16
50  E_Alloc         equ  17

Wed 10-07-86 17:47:32  BCTASK.S                 reason
    10-15-86 13:19:54

1  ;bcTASK.S - Main Comm task Program
 2  ;10/04/86      bcTASK
 3
 4  ;**************************************************************
 5  186
 6  MFO Ver 0.0
 7
 8  Module: bcTask.s
 9
10  modification history : reason(s)
11          date       by       reason(s)
12
13          This module is an original, unpublished work and is proprietary to
14          NELLCOR INC., and may not be divulged or copied in any form
15          whatsoever without the express written permission of NELLCOR INC.
16          Copyright 1986.
17
18  Purpose:
19          This is the comm process, created by cInit, posted to by comm.
20  Procedures:
21          None (procedure CommTask is the process entry point)
22  Public Data:
23          None (all in bcglob.s)
24  ;**************************************************************
25
26  include sysprol.i
27  include bcdef.i
28  include bcext.i
```

```
        include bcSysDef.i
Arg0    equ     6 public  _CommTask extrn   _cGetLgth:near
        extrn   _CharGet:near
        extrn   _xRING:far
        extrn   _xErrPost:far
        extrn   _cxCOMM:far
        extrn   _xWait:far
        extrn   _vClear:far _BSS    segment word public 'BSS'
        extrn   _A_BufNum:word
        extrn   _cType:word
extrn _XCP_ID:word
_BSS    ends ;─── _CommTask ── Communications task ─────────────────────────────────
;
_CommTask proc  far
        cmp     _cType, 'M'                     ;if master
        je      BC00                            ;then execute wait
        jmp     BC40                            ;else wait in comm
BC00:
        push    0
        push    XCOMM_EV
        call    _xWait
        add     sp, 4
; get byte from cring, 'E' or 'P', error if other
BC10:
        push    offset dgroup:cCHAR2
        push    offset dgroup:cRING
        push    1
        call    _xRING                          ;get byte
        add     sp, 6
        or      ax, ax
        jz      BC20                            ;success
        push    E_CommRing
        call    _xErrPost
        add     sp, 2
        jmp     BC00
BC20:
; look at character from ring
        cmp     cCHAR2, 'E'
        je      BC30                            ;send ecg block
        cmp     cCHAR2, 'P'
        je      BC40                            ;send periodic blk
        push    E_CommRing
        call    _xErrPost                       ;else error
        jmp     BC90                            ;look for another entry
BC30:
; send trigger packet. ccb and message exists in data
```

```
085         push    offset dgroup:CcbEcg    ;send packet
086         call    far ptr _cxCOMM
087         add     sp, 2
088         jmp     BC90                    ;look for another
089 ;send/receive regular packet ------------
090     BC40:
091         mov     si, offset dgroup:CcbWf ;waveform ccb
092         mov     ax, A_BufNum            ;set buffer
093         cmp     cType, 'S'              ;if slave, use A_BufNum+1
094         jne     BC41                    ; (slave is display end)
095         inc     ax                      ;generate A_BufNum+1
096         cmp     al, 3
097         jne     BC41
098         xor     ax, ax
099     BC41:
100         shl     ax, 1                   ;word array
101         mov     di, offset dgroup:_cOutTbl
102         add     di, ax
103         mov     di, [di]                ;address of buffer
104         mov     [si].Outbuf, di         ;out..if address into ccb
105         mov     di, offset dgroup:_cInTbl
106         add     di, ax
107         mov     di, [di]                ;address of input buffer
108         mov     [si].InBuf, di          ;input address to ccb
109 ;initialize input buffer to -1
110         mov     ax, ds
111         mov     es, ax
112         mov     di, [si].InBuf
113         mov     cx, [si].InLgth
114         mov     ax, 0FFFFh
115         rep     stosb                   ;store bytes
116 ;execute the data transfer ;;;;;;;;;;;;;;;;;;;;;;;;;;;;;;
117         push    si
118         call    _cxCOMM
119         pop     si
120 ;wait for completion ;;;;;;;;;;;;;;;;;;;;;;;;;;;;;;;;;;;;
121 ;if errors, post an error and continue
122         mov     ax, [si].Status         ;check status
123         or      ax, ax
124         jz      BC50                    ;no errors, proceed
125         push    ax
126 ;****   call    xErrPost                ;handle errors
127         add     sp, 2
128     BC50:
129 ;errors or not, proceed
130 ;if slave (display end), incr A_BufNum, clear user indexes
131         cmp     cType, 'S'
132         jne     BC56
133         inc     A_BufNum
134         cmp     byte ptr _A_BufNum, 3
135         jne     BC55
136         mov     _A_BufNum, 0
137     BC55:
138         call    _vClear                 ;clear AOServ indexes
139     BC56:
140 ;activate slow data tasks
```

```
141         mov    di, [si].DataPtr        ;data address from ccb
142         add    di, _cinLg              ;add length of buffer
143         sub    di, _cInSlowLg          ;sub length of slow space
144   BC60:
145         cmp    [di], 0FFFFh            ;loop target
146         jne    BC62                    ;end of buffer?
147         jmp    BC68
148   BC62:
149         mov    ax, [di]                ;finished
150         or     al, al
151         jz     BC64                    ;task id
152         mov    bx, offset dgroup:cServTbl
153         jmp    BC66
154   BC64:
155         xchg   ah, al
156         mov    bx, offset dgroup:cMeasTbl
157   BC66:
158         cmp    ax, MAX_PID             ;check task id valid
159         jle    BC67                    ;looks ok
160         push   E_Inv_TID
161         call   _XErrPost
162         add    sp, 2
163         jmp    BC68
164   BC67:
165         shl    ax, 2                   ;dword array
166         add    bx, ax                  ;bx is address of fct entry
167         push   di                      ;save di, push for function
168         call   dword ptr [bx]          ;call MT function
169         pop    di                      ;restore di
170         add    di, 6                   ;advances to data
171         add    di, [di-2]              ;add lgth, advances to next
172         jmp    BC60
173   BC68:
174   ;put slow data from ring into next outbuffer ------------------
175         mov    ax, _A_BufNum           ;always filling A_BufNum+1
176         inc    ax
177         cmp    al, 3                   ;inc mod 3
178         jne    BC70
179         xor    ax, ax
180   BC70:
181         shl    ax, 1                   ;word array
182         mov    di, offset dgroup:_cOutTbl
183         add    di, ax
184         mov    di, [di]                ;address of buffer
185         mov    cOutSlowX, 0            ;init buffer index
186   BC75:
187         mov    di, [si].OutBuf
188         mov    cx, [si].OutLgth
189         xor    bx, bx
190   BC75:
191         mov    [di+bx], bl
192         inc    bx
193         loop   BC75
194         mov    word ptr [di+OUT_LG_WF], 0FFFFh  ;terminate slow data
195   ;is finished? is there room for the packet?
```

```
196         BC80:
197                 call    cGetLgth        ;length of packet in ring
198                 or      ax, ax
199                 jnz     BC82
200                 jmp     BC88            ;zero, no data in ring
201         BC82:
202                 cmp     ax, 6
203                 jge     BC83            ;check for valid length
204                 push    E_Invalid       ;invalid length
205                 call    xErrPost
206                 add     sp, 2
207                 jmp     BC88            ;exit
208         BC83:
209                 mov     cx, ax          ;byte count into cx
210                 add     ax, 2           ;for end-of-buffer
211                 cmp     ax, cOutSlowX   ;buffer room needed
212                 jg      BC88            ;compare w/room avail
213                 mov     ax, OUT_LG_SLOW ;no more room in ring
214                 mov     bx, _cOutSlowX
215         BC84:
216                 call    CharGet
217                 mov     [di+bx+OUT_LG_WF], al
218                 inc     bx
219                 dec     cx
220                 jnz     BC84
221                 mov     word ptr [di+bx+OUT_LG_WF], 0FFFFh  ;mark end of buffer
222                 mov     cOutSlowX, bx   ;store slow index
223                 jmp     BC80            ;next packet
224         BC88:                           ;finished
225 ;if slave, go directly to comm to receive
226                 cmp     cType, 'S'
227                 jne     BC90            ;if master, proceed to check
228                 jmp     BC40            ;  ring buffer
229 ;if master, look at ring buffer for another
230         BC90:
231                 push    offset dgroup:CWORD
232                 push    offset dgroup:CRING
233                 push    07              ;fct code to get byte count
234                 call    xRING
235                 add     sp, 6
236                 cmp     CWORD, 0
237                 jnz     BC91
238                 jmp     BC00            ;wait for next post
239         BC91:
240                 jmp     BC10            ;get next byte from ring
241 _CommTask endp
242 include sysepil.i
243         end
244
```

```
Wed 10-06-86 09:12:00    BCXCOMM.S              reason
    10-15-86 13:19:54

1  ;BcxCOMM.S - Communication Program, Channel A Asyncronous
 2  ;10/04/86
 3  ;*********************************************************************
 4          name    bcxComm
 5  ;*********************************************************************
 6          186
 7          MFO Ver 0.0
 8
 9  ; Module: bcxComm.s
10
11  ; modification history :
12  ;       date    by      reason(s)
13
14  ;       This module is an original, unpublished work and is proprietary to
15  ;       NELLCOR INC., and may not be divulged or copied in any form
16  ;       whatsoever without the express written permission of NELLCOR INC.
17  ;       Copyright 1986.
18
19  ; Purpose:
20  ;       This is the basic communications procedure. It runs as the callers
21  ;       task. The caller in the mfo system is always _Comm.
22  ; Procedures:
23  ;       _cxComm provides the basic control block interface to the synchronous
24  ;       communications line.
25  ; Public Data:
26  ;       cTxControl, cRxControl, cExtFlag, cError, cType, cPID, cTimeOut
27  ;*********************************************************************
28          include sysprol.i
29          include bcxDEF.i
30
31  Arg0    equ     6               ;for far
32
33          public  _cxCOMM
34
35          public  cTxControl
36          public  cRxControl
37          public  cExtFlag
38          public  cError
39          public  cType
40          public  cPID
41          public  cTimeOut
42
43          extrn   _xWait    :far
44          extrn   _xPost    :far
45          extrn   _xErrPost :far
46          extrn   _xPID     :near
47          extrn   _ERL_Nit  :near
48
49          BSS segment
50  cTxControl      db              ;cleared by cxInit
51  cRxControl      db              ;   ''
52  cExtFlag        dw              ;cleared by cxComm
53  cError          dw
```

```
54              _cType          dw      ?               ;set by cxInit
55              _cPID           dw      ?               ;set by cxComm
56              cTimeOut        dw      ?               ;set by cxInit
57      _BSS    ends
58
59      ;;;;;;;;;;;;;;;;;;;;;;;;;;;;;;;;;;;;;;;;;;;;;;;;;;;;;;;;;;;;;;;;;;;;;
60      ;_cxCOMM transmits and receives a block of data
61      ; All parameters are located in the comm control block
62      ; Enter with address of comm control block in stack
63      ; All buffers and ccb's are in the system data segment
64      ; This program is for both master and slave. Differences are
65      ; in the interrupt service routine and setting cTxSequence
66      ;;;;;;;;;;;;;;;;;;;;;;;;;;;;;;;;;;;;;;;;;;;;;;;;;;;;;;;;;;;;;;;;;;;;;
67      _cxCOMM proc    far
68              push    bp
69              mov     bp, sp
70              push    di
71              push    si
72              mov     si, [bp+Arg0]           ;ccb address
73              mov     di, BaseB274            ;set 8274 segment address
74              mov     es, di
75      ;prepare global variables; set up pid, clear flags
76              call    xPID                    ;get task id
77              mov     CPID, ax
78              xor     ax, ax
79              mov     cExtFlag, ax            ;zero flag, used by slave isr
80              mov     cError, ax              ;zero errors, used by slave isr
81              mov     ax, [si].OutLgth        ;build control byte
82              and     al, 03Fh                ;keep 6 bits
83              and     cTxControl, 0C0h        ;keep high two bits
84              or      cTxControl, al          ;or in length
85      ;prepare dma channel 0 for send, src is memory output buffer
86      ;                                dest is i/o port, set by init
87              mov     ax, [si].OutBuf         ;output buffer offset
88              mov     cx, ds
89              shl     cx, 4                   ;leaves lower 12 bits in cx
90              mov     dx, ds
91              shr     dx, 12                  ;leaves upper 4 bits in dx
92              add     ax, cx                  ;gives 16 bits in ax
93              mov     cx, 0
94              adc     dx, cx                  ;add carry from add
95              mov     cx, dx                  ;hold upper 4 bits in cx
96              out     dx, ax                  ;source ptr, ch0 send
97              mov     dx, CpD0_SP
98              mov     ax, cx
99              out     dx, ax                  ;source ptr, upper 4 bits
100             mov     ax, [si].OutLgth        ;buffer length
101             mov     dx, CpD0_TC
102             out     dx, ax                  ;terminal count
103     ;prepare dma channel 1 for rcv, dest is memory input buffer
104     ;                               src is i/o port, set at init
105             mov     ax, [si].InBuf          ;input buffer offset
106             mov     cx, ds
107             shl     cx, 4                   ;leaves lower 12 bits
108             mov     dx, ds
109
```

```
110         shr     dx, 12                          ;leaves upper 4 bits
111         add     ax, cx
112         mov     cx, 0
113         adc     cx, cx                          ;add carry from add
114         mov     dx, cx
115         out     dx, CpD1_DP
116         mov     dx, ax                          ;dest ptr, ch1 rcv
117         out     dx, CpD1_DP
118         mov     dx, cx
119         mov     dx, CpD1_DF4                    ;dest ptr, upper 4 bits
120         out     ax, [si].InLgth                 ;terminal count
121         mov     dx, CpD1_TC
122         out     dx, ax                          ;terminal count
123 ;unmask interrupts - always unmasked
124 ;prepare 8274 channel A
125         lea     bx, cs:ChA_Strt                 ;address of start table
126         mov     di, ChA_CtI                     ;port address
127         call    cBT_Nit
128         jmp     COMM15
129 ChA_Strt label byte
130         db      028h                            ;reset tx int/dma
131         db      040h                            ;reset rx crc checker
132         db      030h                            ;reset tx crc generator
133         db      ax                              ;error reset
134         db      010h                            ;reset ext/status
135         dw      0FFFFh                          ;end of table
136 COMM15:
137 ;set dma0 (trx) start
138         mov     dx, CpD0_CW
139         in      ax, dx
140         or      ax, 06                          ;or start and change bits
141         out     dx, ax                          ;start Ch0
142 ;set dma1 start (rcv)
143         mov     dx, CpD1_CW
144         in      ax, dx
145         or      ax, 06                          ;or start and change bits
146         out     dx, ax                          ;start Ch1
147 ;if master then output control byte
148         cmp     cType, 'M'
149         jne     COMM18
150         mov     di, ChA_Data
151         mov     al, cTxControl
152         out     es:[di], al                     ;output to 8274
153 ;if master then reset trx underrun latch
154         mov     di, ChA_Ctl
155         mov     al, 0C0h
156         out     es:[di], al
157 COMM18:
158 ;wait for completion of transfer
159 COMM19:
160         mov     dx, cTimeOut                    ;timeout, ticks
161         push    dx
162         mov     ax, XCOMMISR_EV or XTIME_EV
163         push    ax
164         call    xWait                           ;wait for completion
165         add     sp, 4
```

```
166     ;;;;;;;;;;;;;;;;;;;;;;;;;;;;;;;;;;;;;;;;;;;;;;;;;;;;;;;;;
167     ;resumes here after completion of transfer w/event in ax
168     ;
169     ;check for proper post event
170             test    ax, XCOMMISR_EV or XTIME_EV
171             jz      COMM19                  ;wait again if wrong post
172     ;pick up errors from isr, report them
173             mov     bx, cError
174             or      bx, bx
175             jz      COMM20
176             jmp     COMM60
177     COMM20:
178     ;check for timeout
179             test    ax, XTIME_EV
180             jz      COMM25
181             mov     bx, E_Timeout
182             jmp     COMM60
183     COMM25:
184     ;check for sequence error
185             mov     di, [si].InBuf
186             mov     cl, [di]                ;look at first byte of msg
187             and     cl, 0C0h
188             cmp     cl, cRxControl          ;keep sequence #
189             je      COMM30
190             mov     bx, E_Sequence
191             mov     cRxControl, cl          ;correct sequence#
192             jmp     COMM60
193     COMM30:
194     ;check for count error, dropped bytes
195             in      ax, dx                  ;read rcv term count
196             mov     dx, [si].InLgth         ;count was set to buffer lgth-1
197             sub     dx, ax                  ;leaves count
198             sub     dx, 3                   ;remove control, 2 byte crc
199             mov     [si].Rytes, dx          ;to ccb
200             and     dx, 3Fh                 ;keep 6 bits of actual
201             mov     ax, [di]                ;control byte from buffer
202             and     ax, 3Fh                 ;keep six bits
203             cmp     ax, dx
204             jz      COMM40
205             mov     bx, E_Count
206             jmp     COMM60
207     COMM40:
208     ;report errors if any exist
209             mov     [si].Status, bx
210     COMM60: or      bx, bx
211             jz      COMM70
212             push    bx
213             call    xErrPost
214             add     sp, 2
215     COMM70:
216     ;put returns in ccb, note that bx is reported error
217             add     cRxControl, 040h        ;inc rx sequence#
218             add     cTxControl, 040h        ;inc tx sequence#
219             mov     ax, [si].InBuf
```

```
222         add     ax,1            ;allow for control byte
223         mov     [si].DataPtr, ax;address of data
224 ;return
225         mov     ax, [si].Status
226         pop     si
227         pop     di
228         pop     bp
229         ret
230 _cxCOMM  endp
231
232 include sysepil.i
233         end Wed 09-24-86 16:41:00  BCXDEF.I                  reason
Wed 10-15-86 13:19:54

1 ;bcxDEF.I - Definition include file with hardware port addresses
  2 ;09/24/86   For the Analog/Display Unit Common Items
  3 ;*************************************************************************
  4 ;*************************************************************************
  5 ; MFO Ver 0.0
  6 ;
  7 ; Module: bcxDef.i
  8 ;
  9 ; modification history :  reason(s)
 10 ;        date      by    reason
 11 ;
 12 ;       This module is an original, unpublished work and is proprietary to
 13 ;       NELLCOR INC., and may not be divulged or copied in any form
 14 ;       whatsoever without the express written permission of NELLCOR INC.
 15 ;       Copyright 1986.
 16 ;
 17 ; Purpose:
 18 ;       Defines for the cxComm package.
 19 ; Procedures:
 20 ;       None
 21 ; Public Data:
 22 ;       None
 23 ;*************************************************************************
 24
 25 include bcSysDef.i
 26
 27 ccb struc
 28         Status   dw      (?)     ;status return
 29         Bytes    dw      (?)     ;byte count of received data
 30         DataPtr  dw      (?)     ;offset address of received data
 31         OutBuf   dw      (?)     ;output buffer offset address
 32         OutLgth  dw      (?)     ;output buffer length in bytes
 33         InBuf    dw      (?)     ;input buffer offset address
 34         InLgth   dw      (?)     ;input buffer length in bytes
 35 ccb ends
 36
 37 ;Interrupt Vectors
 38 CpD0_Vect   equ    0Ah
 39 CpDi_Vect   equ    0Bh
```

```
40      CPI0_Vect       equ     0Ch
41      CPI1_Vect       equ     0Dh
42      CPI2_Vect       equ     0Eh
43      CPI3_Vect       equ     0Fh
44      CPT0_Vect       equ     08h
45      CPT1_Vect       equ     12h
46      CPT2_Vect       equ     13h
47      ;8274 Memory Port Addresses
48      Base8274        equ     10000h          ;segment address
49      ChA_Data        equ     0000h           ;channel A data
50      ChB_Data        equ     2000h           ;channel B data
51      ChA_Ctl         equ     1000h           ;channel A control
52      ChB_Ctl         equ     3000h           ;channel B control
53      
54      ;Relocation Registers in Cpu, based at 0FF00h
55      ;DMA channel 0
56      CPD0_CW         equ     0FFCAh
57      CPD0_TC         equ     0FFC8h
58      CPD0_DP4        equ     0FFC6h
59      CPD0_DP         equ     0FFC4h
60      CPD0_SP4        equ     0FFC2h
61      CPD0_SP         equ     0FFC0h
62      ;DMA channel 1
63      CPD1_CW         equ     0FFDAh
64      CPD1_TC         equ     0FFD8h
65      CPD1_DP4        equ     0FFD6h
66      CPD1_DP         equ     0FFD4h
67      CPD1_SP4        equ     0FFD2h
68      CPD1_SP         equ     0FFD0h
69      ;Chip Selects
70      CP_MPCS         equ     0FFA8h
71      CP_MMCS         equ     0FFA6h
72      CP_LMCS         equ     0FFA2h
73      CP_UMCS         equ     0FFA0h
74      ;Timer #2
75      CPT2_Ctl        equ     0FF66h
76      ;       CPT2_Amax not present
77      CPT2_Bmax       equ     0FF62h
78      CPT2_Cnt        equ     0FF60h
79      ;Timer #1
80      CPT1_Ctl        equ     0FF5Eh
81      CPT1_Amax       equ     0FF5Ch
82      CPT1_Bmax       equ     0FF5Ah
83      CPT1_Cnt        equ     0FF58h
84      ;Timer #0
85      CPT0_Ctl        equ     0FF56h
86      CPT0_Amax       equ     0FF54h
87      CPT0_Bmax       equ     0FF52h
88      CPT0_Cnt        equ     0FF50h
89      ;Interrupts
90      CPI3_Ctl        equ     0FF3Eh
91      CPI2_Ctl        equ     0FF3Ch
92      CPI1_Ctl        equ     0FF3Ah
93      CPI0_Ctl        equ     0FF38h
94      CPI01_Ctl       equ     0FF36h
95      CPI00_Ctl       equ     0FF34h
```

```
 96   CpIT_Ctl      equ     0FF32h
 97   CPI_Stt       equ     0FF30h
 98   CPI_IReq      equ     0FF2Eh
 99   CPI_InSvc     equ     0FF2Ch
100   CPI_Prio      equ     0FF2Ah
101   CPI_Mask      equ     0FF28h
102   CPI_PStt      equ     0FF26h
103   CPI_Poll      equ     0FF24h
104   CPI_EOI       equ     0FF22h
```

Wed 10-04-86 17:13:00  BCXINIT.S         cxInit
Wed 10-15-86 13:19:54

```
 1   ;bcxINIT.S - initializes comm channel
 2   ;10/04/86    Includes all hardware dependent code except for 8274
 3   ;            Includes cEOI, end of intpt to intpt controller
 4   ;
 5   ;call with 'M' or 'S' on the stack for master/slave
 6   ;     cxInit ('M') or cxInit ('S')
 7   ;
 8          name   bcxINIT
 9   ;***********************************************************************
10          186
11          MFO Ver 0.0
12   ;
13          Module: bcxInit.s
14   ;
15          modification history :  reason(s)
16                  date        by
17   ;
18              This module is an original, unpublished work and is proprietary to
19              NELLCOR INC., and may not be divulged or copied in any form
20              whatsoever without the express written permission of NELLCOR INC.
21              Copyright 1986.
22   ;
23   ;Purpose:
24   ;     Initializer for the cxComm (lower) level of the comm package.
25   ;Procedures:
26   ;     cxInit,       the cxComm initializer.
27   ;     cBT_Nit,      Byte table initializer.
28   ;     WT_Nit,       Word table initializer.
29   ;     cEOI,         generates end of interrupt to cpu
30   ;     cOutChB,      Outputs a character to channel B
31   ;Public Data:
32   ;     None
33   ;***********************************************************************
34
35   include sysprol.i
36   include bcxDef.i
37
38   Arg0           equ     6
39                                                         ;-old-        -new-
40   IntVect8274    equ     CpI2_Vect         ;CpI3_Vect,  CpI2_Vevt
```

```
CpuIntMask    equ    040h      ;;;; also switch timer ---- ;080h    040h
                                                           ;  1, 0  0, 1

;Publics and Externals public   _cxInit                           ;far
       public   _cxEOI                            ;near, end of interrupt
       public   _ChA_NIT                          ;near
       public   ChA_Nit, ChB_Nit                  ;tables, for debug only
       public   conTChB                           ;near extrn    cxISR:far
       extrn    cxNitRing:near                    ;initialize ring buffers _BSS   segment  word public 'BSS'
       extrn    cTxControl:byte
       extrn    cRxControl:byte
       extrn    cType     :word
       extrn    cTimeOut  :word
_BSS   ends ;----- 8274 Channel A initialization table -----
;                                                 ;form is register#, register_value
ChA_Nit  label   byte                             ;reset channel
         db      00h,  18h                        ;reset trx crc
         db      00h,  80h                        ;D1D0=01, chA dma, chB interrupt
         db      02h,  11h                        ;D2=0 for default priority
                                                  ;D4D3=10, for 8086
                                                  ;D5=0, non vectored interrupts
                                                  ;D6=0, 7201 feature not avail on 8274
                                                  ;D7=0, pin 10 is rts- (don't care)
         db      04h,  20h                        ;D0=0, no parity
                                                  ;D1=0, even/odd, don't care
                                                  ;D3D2=00, select synchronous modes
                                                  ;D5D4=10, select synch mode, sdlc
                                                  ;D7D6=00, select clock mult, x1
         db      01h,  0Bh                        ;D0=0, enable external interrupts
                                                  ;D1=1, TxInt/dma enable
                                                  ;D2=0, status affects vect enabled (chB only)
                                                  ;D4D3=01, rx int on 1st char/special conds
                                                  ;D7-D5=000, all wait disabled d
         db      03h,  0C9h                       ;D0=1, receiver enabled
                                                  ;D1=0, sync char load inhibit
                                                  ;D3=1, address search = recv everthing
                                                  ;D4=0, hunt phase
                                                  ;D5=0, auto enable off
                                                  ;D7D6=11, eight bit data
         db      05h,  69h                        ;D0=1, tx crc enable
                                                  ;D1=0, rts inactive
                                                  ;D2=0, select ccitt-crc for sdlc
                                                  ;D3=1, trx enable
                                                  ;D4=0, send break
                                                  ;D6D5=11, trx eight data
```

```
 97             db      06h,    00h             ;D7=0, DTR inactive
 98             db      07h,    7Eh             ;D7-D0=0, address, (insert control byte)
 99             db      10h,    30h             ;D7-D0=7E, sdlc flag byte.
100             dw      0FFFFh                  ;reset ext status & error
101                                             ;end of table
102
103     ;8274 Channel B initialization table ----
104
105     ChB_Nit label   byte
106             db      00h,    10h             ;form is register#, register_value
107             db      02h,    00h             ;reset channel
108             db      04h,    44h             ;D7D0 =
109                                             ;D0=0, no parity
110                                             ;D1=0, even/odd,don't care
111                                             ;D3D2=01, one stop bits
112                                             ;D5D4=00, synch mode, don't care
113             db      01h,    1Eh             ;D7D6=01, x16 clock mult
114                                             ;D0=0, disable external interrupts
115                                             ;D1=1, Txint/dma enable
116                                             ;D2=1, status effects vector enabled
117                                             ;D4D3=11, rcv intpt on all rcv chars
118                                             ;D7-D5=000, all wait disabled
119             db      03h,    0C1h            ;D0=0, receiver begin (dynamic)
120                                             ;D1=0, sync char load inhibit
121                                             ;D2=0, address search = recv everthing
122                                             ;D3=0, Receive crc enable
123                                             ;D4=0, enter hunt phase (no)
124                                             ;D5=0, auto enable off
125                                             ;D7D6=11, eight bit data
126             db      05h,    06Bh            ;D0=0, tx crc enable
127                                             ;D1=0, rts active
128                                             ;D2=0, select ccitt-crc for sdlc
129                                             ;D3=1, trx enable
130                                             ;D4=0, send break
131                                             ;D6D5=11, trx eight data
132                                             ;D7=0, DTR active
133             db      06h,    00h             ;D7-D0=0, address, (insert control byte)
134             db      07h,    7Eh             ;D7-D0=sync flag
135             db      10h,    30h             ;reset ext status & errors
136             dw      0FFFFh                  ;end of table
137
138     ;Cpu Interrupt Initialization Table
139
140     CpuI_Nit label  word
141             dw      CpI00_Ctl,      0Fh     ;format is port address,register_value
142             dw      CpI01_Ctl,      0Fh     ;dma0    default priorities
143             dw      CpI2_Ctl,       0Fh     ;dma1    mask to one, disables
144             dw      0FFFFh                  ;int2
145                                             ;end of table
146     ;Cpu DMA Initialization Table
147
148     CpuD_Nit label  word
149             dw      CpD0_CW,        07680h  ;control word, ch0, sender
150             dw      CpD0_DP,        ChA_Data ;8274 data address
151             dw      CpD0_DP4,       01Fh    ;upper 4 bits
152             dw      CpD1_CW,        0B240h  ;control word, ch1, receiver
```

```
152             dw      CpD1_SP, ChA_Data       ;8274 data address
153             dw      CpD1_SP4, 01Fh          ;upper 4 bits
154             dw      0FFFFh                  ;end of table
155
156 ;Cpu Timer Initialization Tables ------
157
158 CpuTim0_Nit label word
159             dw      CpT0_Ctl, 0C003h        ;ctl, timer0 for ChB
160             dw      CpT0_Amax, 06h          ;for 153.6k, 16*9600 baud
161             dw      CpT0_Bmax, 07h          ;count is 13
162             dw      0FFFFh                  ;end of table 0
163
164 CpuTim1_Nit label word
165             dw      CpT1_Ctl, 0C003h        ;ctl, timer1 for ChA
166             dw      CpT1_Amax, 002h         ;for 500,000Hz, 500K baud.
167             dw      CpT1_Bmax, 002h
168             dw      0FFFFh                  ;end of table
169
170 ;------ cxInit ------
171 ;Initialization of Communications Hardware
172
173 ;       Saves all registers except ax, bx
174
175
176 cxInit  proc    far
177         push    bp
178         mov     bp, sp
179         push    di
180         push    si
181         push    dx
182         push    es
183 ;disable interrupts
184         pushf
185         pushf
186         pop     ax
187         and     ax, not 0200h
188         push    ax
189         popf
190 ;set global variables
191         mov     ax, [bp+Arg0+0]
192         and     ax, not 020h            ;type
193         mov     cType, ax               ;to upper
194         cmp     cType, 'M'              ;set type
195         jne     INIT10
196         mov     cTimeOut, 08h           ;set master timeout
197         jmp     INIT12
198 INIT10:
199 INIT12: mov     cTimeOut, 0             ;set slave timeout
200         mov     dx, CpI_Mask
201 ;mask off 8274 interrupt
202         in      ax, dx
203         or      ax, CpuIntMask
204         out     dx, ax
205 ;reset 8274
206         mov     di, Base8274            ;port address, ChA
207
```

```
2208            mov     es, di
2209            mov     di, ChA_Ctl
2210            mov     al, 1Bh
2211            mov     es:[di], al
2212            mov     es:[di], al
2213  ;initialize 80186 timer 0 for comm channel B
2214            lea     bx, cs:CpuTim0_Nit
2215            call    WT_Nit
2216  ;initialize 80186 timer 1 in slave (display unit) for comm channel A
2217            cmp     cType, 'S'
2218            jne     INIT20
2219            lea     bx, cs:CpuTim1_Nit
2220            call    WT_Nit
2221  INIT20:
2222  ;initialize 80186 dma channels
2223            lea     bx, cs:CpuD_Nit
2224            call    WT_Nit
2225  ;initialize 80186 interrupts
2226            lea     bx, cs:CpuI_Nit
2227            call    WT_Nit
2228  ;initialize 8274
2229            lea     bx, cs:Base8274
2230            mov     di, ChA_Nit              ;table address, ChA
2231            mov     es, di                   ;port address, ChA
2232            mov     di, ChA_Ctl
2233            call    CRT_Nit
2234            lea     bx, cs:ChB_Nit           ;table address, ChB
2235            mov     di, ChB_Ctl              ;port address, ChB
2236            call    CRT_Nit
2237  ;set interrupt vectors, int procs in this code segment
2238            xor     bx, bx
2239            mov     es, bx                   ;clear es
2240            mov     bx, IntVect8274          ;Int vector for 8274
2241            shl     bx, 1
2242            shl     bx, 1
2243            mov     ax, offset cxISR
2244            mov     es:[bx+0], ax
2245            mov     es:[bx+2], cs
2246  ;initialize global locations
2247            mov     cTxControl, 0
2248            mov     cRxControl, 0
2249            call    cxNitRing                ;init ring buffers
2250            mov     ax, [bp+Arg0+0]          ;type
2251            mov     cType, ax                ;store locally
2252  ;reset interrupt in 8274
2253            mov     di, Base8274
2254            mov     es, di
2255            mov     di, ChA_Ctl
2256            mov     al, 02
2257            mov     es:[di], al
2258            mov     al, es:[di]
2259            mov     al, 10h
2260            mov     es:[di], al
2261            mov     al, 38h
2262            mov     es:[di], al
2263
```

```
264         ;unmask interrupt
265             mov     dx, CpI_InSvc
266             in      ax, dx
267             test    al, CpuIntMask
268             jz      INIT30
269             mov     dx, CpI_EOI
270             mov     ax, 8000h
271             out     dx, ax
272     INIT30:
273             mov     dx, CpI_Mask
274             in      ax, dx
275             and     ax, not CpuIntMask
276             out     dx, ax              ;restore interrupts
277     ;restore registers and exit
278             pop     f
279             pop     es
280             pop     dx
281             pop     si
282             pop     di
283             pop     bp
284             ret
285     cxInit  endp
286     ;-------------------------------------------------------------
287     ;BT_Nit Byte Table Initialization Procedure for [reg#, reg_val] table
288     ; Enter with es:di = memory port address
289     ;              bx = table address
290     ; Saves all but ax, bx
291     BT_Nit  proc    near
292     BT_Nit00:
293             mov     ax, cs:[bx]
294             cmp     ax, 0FFFFh          ;end of table?
295             je      BT_Nit10            ;exit
296             mov     al, cs:[bx]
297             mov     es:[di], al         ;output value
298             inc     bx
299             jmp     BT_Nit00
300     BT_Nit10:
301             ret
302     BT_Nit  endp
303     ;-------------------------------------------------------------
304     ;WT_Nit Word Table Initialization Procedure for [port, val] table
305     ; Enter with bx = table address
306     ; Saves all but ax
307     WT_Nit  proc    near
308             push    dx
309             xor     di, di
310     WT_Nit00:
311             mov     dx, cs:[bx]         ;port address
312             cmp     dx, 0FFFFh          ;end of table?
313             je      WT_Nit10            ;finished
314             inc     bx
315             mov     ax, cs:[bx]         ;register value
316             out     dx, ax              ;output value
```

```
320             inc     bx
321             inc     bx
322             jmp     WT_Nit00
323     WT_Nit10:
324             pop     dx
325             ret
326     WT_Nit  endp
327
328     ; _cEOI   End of interrupt, hardware dependent code
329
330     _cEOI   proc near
331             mov     dx, CpI_EOI
332             mov     ax, 8000h
333             out     dx, ax
334             ret
335     _cEOI   endp
336
337     ; cOutChB   Outputs a character to channel B, enter with al=char
338     ;          Saves all registers
339     cOutChB proc near
340             push    di
341             push    es
342             mov     di, Base8274
343             mov     es, di
344             mov     di, ChB_Data
345             mov     es:[di], al
346             pop     es
347             pop     di
348             ret
349     cOutChB endp
350
351     include sysepil.i
352             end
353
354
Wed 09-24-86 17:59:26    BCXISR.S            reason
    10-15-86 13:19:54

1  ;bcxISR.S -- Interrupt routines for Comm, Master and Slave
 2  ;09/24/86
 3  ;******************************************************************
 4            name    bcxISR
 5  ;******************************************************************
 6           .186
 7           MFO Ver 0.0
 8
 9  Module: bcxISR.s
10
11  modification history :  reason(s)
12        date      by      reason(s)
13
14  This module is an original, unpublished work and is proprietary to
15  NELLCOR INC., and may not be divulged or copied in any form
16  whatsoever without the express written permission of NELLCOR INC.
    Copyright 1986.
```

```
17  ;**************************************************************
18  ; Purpose:
19  ;     Interrupt service routine for the communications package (8274).
20  ; Procedures:
21  ;     CxISR, the interrupt service routine.
22  ; Public Data:
23  ;     None.
24  ;**************************************************************
25
26  include sysprol.i
27  include bcxDef.i
28
29  public          CxISR
30
31          extrn   _cEOI           :near   ;end of interrupt
32          extrn   _ciRxPut        :near   ;Put char in rcv ring buffer
33          extrn   _ciTxClear      :near   ;clear ChB Tx Flag
34          extrn   _ciTxGet        :near   ;Get char from trx ring buffer
35          extrn   _cOutChB        :near   ;Output char to ChB line
36          extrn   _xErrPost       :far    ;post an error
37          extrn   _xPost          :far    ;post event to scheduler
38  _BSS    segment
39          extrn   _cError         :word
40          extrn   _cType          :word   ;ccb address
41          extrn   _CTxControl     :byte
42          extrn   _cExtFlag       :word
43          extrn   _cPID           :word
44  _BSS    ends
45
46  ; Master Station Interrupt Service Routine ;;;;;;;;;;;;;;;;;;;;;;;
47
48  CxISR   proc    far
49          pusha
50          push    ds
51          push    es
52          mov     ax, DGROUP
53          mov     ds, ax
54          mov     ax, Base8274
55          mov     es, ax
56  ;read status affect vector
57          mov     di, ChB_Ctl
58          mov     al, 02
59          mov     es:[di], al
60          mov     bl, es:[di]
61          and     bx, 07
62          shl     bx, 1
63          cmp     cType, 'M'      ;master or slave
64          je      COMM05
65          or      bx, 10h
66  COMM05: jmp     cs:TABLE [bx]
67  TABLE   label   word
68          dw      ChB_TxRdy       ;select rr2
69          dw      ChB_Ext         ;input rr2
70          dw      ChB_RxRdy       ;mask
71          dw      ChB_Spec
72
```

```
 73         dw      ChA_TxRdy       ;master
 74         dw      ChA_ExtM        ;master
 75         dw      ChA_RxRdy       ;master
 76         dw      ChA_SpecM       ;master
 77         dw      ChB_TxRdy
 78         dw      ChB_Ext
 79         dw      ChB_RxRdy
 80         dw      ChB_Spec
 81         dw      ChA_TxRdy       ;slave
 82         dw      ChA_ExtS        ;slave
 83         dw      ChA_RxRdy       ;slave
 84         dw      ChA_SpecS       ;slave
 85 ;return to here after special processing
 86 KISR99:
 87         mov     di, ChA_Ctl
 88         mov     al, 038h        ;8274 end of interrupt
 89         mov     es:[di], al
 90         call    _cEOI           ;80186 non specific eoi
 91 ;exit
 92         pop     es
 93         pop     ds
 94         popa
 95         iret
 96
 97 ;;;;;;;;;;;;;;;;;;;;;;;;;;;;;;;;;;;;;;;;;;;;;;;;;;;
 98 ChB_TxRdy:                      ;#0 - ChanB Transmit ready
 99         call    ciTxGet         ;get char from ring buffer
100         or      ax, ax          ;if zero, no char
101         jz      ChB10
102         call    cOutChB         ;output char in al
103         jmp     KISR99
104 ChB10:
105         call    ciTxClear       ;clear trx flag
106         mov     di, ChB_Ctl
107         mov     ax, 28h
108         mov     es:[di], al     ;reset trx int pend
109         jmp     KISR99
110 ;;;;;;;;;;;;;;;;;;;;;;;;;;;;;;;;;;;;;;;;;;;;;;;;;;;
111 ChB_Ext:                        ;#1 - ChanB ext/status interrupt,
112         mov     di, ChB_Ctl
113         mov     al, 10h
114         mov     es:[di], al     ;reset ext status
115         mov     al, es:[di]     ;read rr0
116         mov     ax, 010h
117         mov     es:[di], al     ;reset ext/status intpts, 010h
118         jmp     KISR99
119 ;;;;;;;;;;;;;;;;;;;;;;;;;;;;;;;;;;;;;;;;;;;;;;;;;;;
120 ChB_RxRdy:                      ;#2 - ChanB rcv char rdy
121         mov     di, ChB_Ctl
122         mov     al, 01
123         mov     es:[di], al
124         mov     ah, es:[di]     ;read RR1
125         mov     di, ChB_Data
126         mov     al, es:[di]     ;get char
127         call    ciRxPut         ;write to rxring
128         jmp     KISR99
```

```
129         ChB_Spec:
130                 mov     al, 1                   ;3 - ChanB special receive condition
131                 mov     di, ChB_Ctl
132                 mov     es:[di],al              ;select reg 1
133                 mov     ah, es:[di]             ;get rcv conditions
134                 mov     al, 30h
135                 mov     es:[di], al             ;reset special rcv cond
136                 jmp     KISR99
137         ;;;;;;;;;;;;;;;;;;;;;;;;;;;;;;;;;;;;;;;;;;;;;;;;;;;;;;;;;;;;;
138         ChA_TxRdy:                              ;4 - ChanA Transmit ready,
139                 mov     di, ChA_Ctl
140                 mov     al, 28h                 ;reset trx int pend
141                 mov     es:[di], al
142                 jmp     KISR99
143         ;;;;;;;;;;;;;;;;;;;;;;;;;;;;;;;;;;;;;;;;;;;;;;;;;;;;;;;;;;;;;
144         ChA_ExtM:                               ;5M - ChanA ext/status interrupt
145                 mov     di, ChA_Ctl             ;ignore these
146                 mov     al, 10h
147                 mov     es:[di], al             ;reset ext/status intpts, 010h
148                 mov     ah, es:[di]             ;read status
149                 mov     al, 028h
150                 mov     es:[di], al             ;reset txint/drq pending, 028h
151                 cmp     cExtFlag, 0             ;if flag zero
152                 jne     CHA10M
153                 mov     dx, CpD0_TC             ;and term count zero
154                 in      ax, dx
155                 or      ax, ax
156                 jnz     CHA10M
157                 mov     cExtFlag, 01            ;then set flag
158         CHA10M:
159                 jmp     KISR99                  ;exit
160         ;;;;;;;;;;;;;;;;;;;;;;;;;;;;;;;;;;;;;;;;;;;;;;;;;;;;;;;;;;;;;
161         ChA_ExtS:                               ;5S - ChanA ext/status interrupt
162                 mov     di, ChA_Ctl
163                 mov     al, 10h
164                 mov     es:[di], al             ;reset ext/status intpts, 010h
165                 mov     ah, es:[di]             ;read status
166                 cmp     cExtFlag, 01
167                 jne     CHA10S
168                 mov     dx, CpD0_TC             ;is term count zero
169                 in      ax, dx
170                 or      ax, ax
171                 jnz     CHA10S                  ;no, skip
172                 mov     cExtFlag, 02
173                 push    XCOMMISR_EV             ;post complete to cxComm
174                 push    cPID
175                 call    xPost
176                 add     sp, 4
177         CHA10S:
178                 mov     al, 028h
179                 mov     es:[di], al             ;reset tx int/dma pending (28h)
180                 jmp     KISR99
181         ;;;;;;;;;;;;;;;;;;;;;;;;;;;;;;;;;;;;;;;;;;;;;;;;;;;;;;;;;;;;;
182         ChA_RxRdy:                              ;6 - ChanA receive character ready
183                 mov     di, ChA_Data
184                 mov     al, es:[di]
```

```
185 ;;;;;;;;;;;;;;;;;;;;;;;;;;;;;;;;;;;;;;;;;;;;;;;;;;;;;;;;;;;;;;;;;;;;;;;;;
186                 jmp     KISR99
187 ChA_SpecM:                              ;7M - ChanA special receive conditon
188         mov     di, ChA_Ctl
189         mov     al, 01                  ;select RR1
190         mov     es:[di], al
191         mov     al, es:[di]             ;read RR1
192         mov     bl, 030h                ;error reset
193         mov     es:[di], bl
194         xor     bx, bx                  ;clear error word
195 ;if end of frame, then check for crc error
196         test    al, 80h
197         jz      CHA20M
198         test    al, 40h
199         jz      CHA40M
200         mov     bx, E_CRC
201         jmp     CHA40M
202 CHA20M:
203 ;if not end of frame, check overrun error
204         test    al, 20h
205         jz      CHA25M
206         mov     cError, E_Overrun
207 CHA25M:
208         jmp     CHA90M
209 ;post to Comm task
210 CHA40M:
211         mov     cError, bx
212         cmp     cExtFlag, 01
213         jne     CHA90M
214         mov     cExtFlag, 02
215         push    XCOMMISR_EV             ;event word
216         push    cPID                    ;id of task
217         call    xPost                   ;post completion
218         add     sp, 4
219 CHA90M:
220         jmp     KISR99                  ;exit
221 ;;;;;;;;;;;;;;;;;;;;;;;;;;;;;;;;;;;;;;;;;;;;;;;;;;;;;;;;;;;;;;;;;;;;;;;;;
222 ChA_SpecS:                              ;7S - ChanA special receive conditon
223         mov     di, ChA_Ctl
224         mov     al, 01                  ;select RR1
225         mov     es:[di], al
226         mov     al, es:[di]             ;read RR1
227         mov     bl, 030h                ;reset errors
228         mov     es:[di], bl
229         xor     bx, bx                  ;clear error word
230 ;if end of frame, then check for crc error
231         test    al, 80h                 ;if end of frame
232         jz      CHA30S
233         test    al, 40h                 ;and if crc
234         jz      CHA40S
235         mov     bx, E_CRC               ;then report crc error
236         jmp     CHA40S
237 CHA30S:
238 ;if not end of frame, check overrun error
239         test    al, 20h                 ;if overrun
240         jz      CHA35S
```

```
Wed 10-08-86 11:29:18  BCXRING.S                          reason 241              mov      bx, E_Overrun
 242    CHA35S:   jmp      CHA90S
 243   ;enable ext/status intpts, disable rcv, start transmit process
 244    CHA40S:
 245              mov      cError, bx            ;save errors
 246              cmp      cExtFlag, 0           ;..............;
 247              jnz      CHA90S                ;..............;
 248              mov      cExtFlag, 01          ;..............;
 249              mov      di, ChA_Data          ;now prime with data
 250              mov      al, cTxControl        ;  Control byte, built by cComm
 251              mov      es:[di], al           ;  starts the dma transmission
 252              mov      di, ChA_Ctl
 253              mov      al, 0D0h              ;reset e/s intpts and
 254              mov      es:[di], al           ;  tx underrun/eom latch
 255
 256   ;exit
 257    CHA90S:   jmp      KISR99                ;exit
 258    cxISR     endp
 259
 260    include sysepil.i
 261    end
 262

Wed 10-15-86 13:19:54  BCXRING.S                          reason

1  ;BCXRING.S - Ring Buffer Implementation for Channel B line
   2  ;10/08/86
   3  ;**********************************************************************
   4  ;       name      bcxRing
   5  ;       MFG Ver 0.0
   6  ;
   7  ; Module: bcxRing.s
   8  ;
   9  ; modification history :
  10  ;       date           by          reason(s)
  11  ;
  12  ;       This module is an original, unpublished work and is proprietary to
  13  ;       NELLCOR INC., and may not be divulged or copied in any form
  14  ;       whatsoever without the express written permission of NELLCOR INC.
  15  ;       Copyright 1986.
  16  ;
  17  ; Purpose:
  18  ;       Ring buffer for the 8274 channel B, asynchronous line
  19  ; Procedures:
  20  ;       cMsgOut         Puts a string into the transmit ring buffer.
  21  ;       cStrOut         Prints a string directly from user's line buffer.
  22  ;       cStrIn          Inputs a string to user's line buffer.
  23  ;       CharOut         Writes a character to the transmit ring buffer.
  24  ;       CharIn          Reads a character from the receive ring buffer.
  25  ;       cxRingInit      Initializes the ring buffer.
  26  ;       cxRxPut         Puts a char into the receive ring buffer (by isr).
  27  ;       cxTxGet         Gets a char from the transmit ring buffer (by isr).
```

```
29  ; Public cTxClear:       Clears transmit busy flag (so txRing not public).
30  ;    None (cTxRing and cRxRing are used only in this module).
31  ;*********************************************************************
32
33
34      include sysprol.i
35      include bcSysDef.i
36
37  RINGSIZE    equ     96
38  Arg0        equ     6               ;for far call
39
40      public  cStrIn                  ;input string from kb, term/cr
41      public  cStrOut                 ;writes string to Channel B
42      public  cCharOut                ;Puts char from stk into tx ring
43      public  cCharIn                 ;Gets char from rcv ring to ax
44      public  cMsgOut                 ;outputs msg with no wait
45      public  cxInitRing              ;initializes the ring
46      public  cTxGet                  ;isr gets char from txring to ax
47      public  cTxPut                  ;isr puts char in rxring from ax
48      public  cTxClear                ;clears ring tx busy flag
49      public  cRxRing
50
51      extrn   cOutChB :near           ;primes usart on send
52      extrn   xPost   :far            ;post event to task
53      extrn   xLock   :near           ;prevents task switch
54      extrn   xUnLock :near           ;enables task switch
55      extrn   xPID    :far            ;fetches current pid in ax
56
57
58  ring struc                          ;ring buffer definitions
59      Size    dw      (?)             ;ring size
60      Count   dw      (?)             ;current count of bytes in ring
61      Getx    dw      (?)             ;get index
62      Putx    dw      (?)             ;put index
63      Flag    dw      (?)             ;for transmit priming, 0=needs prime
64      sPid    dw      (?)             ;for string in/out process id
65      sBuf    dw      (?)             ;string buffer
66      sSize   dw      (?)             ;string length
67      sIndex  dw      (?)             ;string index
68      sEvent  dw      (?)             ;string event to post
69      Buf     db      RINGSIZE dup (?)
70  ring ends
71
72  _BSS segment
73  cTxRing ring <>                     ;ring buffer declaration
74  cRxRing ring <>
75  _BSS ends
76
77  ;cMsgOut (&buffer)
78  ;    Prints a string on terminal on Channel B
79  ;    Returns ax=0 successful
80  ;    Returns E_Full if buffer too full
81  ;    Returns E_Invalid if msg larger than buffer
82  cMsgOut proc    far
83      push    bp
84      mov     bp, sp                  ;di, si not used
```

```
 85         push    di
 86         push    bx
 87         call    xLOCK                  ;prevent task switch
 88 ;measure msg length
 89         mov     di, [bp+Arg0]          ;string address
 90         xor     bx, bx
 91 MOUT10:
 92         cmp     byte ptr [di+bx], 0    ;look for null term.
 93         jz      MOUT20                 ;null terminator found
 94         inc     bx
 95         jmp     MOUT10
 96 MOUT20:
 97         inc     bx                     ;is buffer>message
 98         cmp     bx, cTxRing.Size
 99         jle     MOUT30
100         mov     ax, E_Invalid
101         jmp     MOUT90
102 MOUT30:
103         mov     ax, cTxRing.Size       ;is buffer space>message
104         sub     ax, cTxRing.Count
105         cmp     bx, ax
106         jle     MOUT40
107         mov     ax, E_Full
108         jmp     MOUT90
109 ;put characters in ring buffer
110 MOUT40:
111 MOUT50: mov     al, [di]
112         or      al, al
113         jz      MOUT70                 ;zero is end of string
114         push    ax
115         call    far ptr _CharOut
116         add     sp, 2
117         or      ax, ax
118         jz      MOUT60                 ;ax=0 if buffer full
119         inc     di
120         jmp     MOUT50
121 MOUT60:
122         mov     ax, E_Full             ;buffer full error
123         jmp     MOUT90
124 MOUT70:
125         xor     ax, ax                 ;successful completion
126 ;exit
127 MOUT90: push    ax
128         call    xUNLOCK
129         pop     ax
130         pop     bx
131         pop     di
132         pop     bp
133         ret
134 _cMsgOut endp
135
136 _CHARCUT --------------------------------------------------
137 ;
138 ;       Write a character from stack to the transmit ring
139 ;       Return ax=0 if buffer full
140
```

```
141  _CharOut proc  far
142           push  bp
143           mov   bp, sp
144           push  bx
145           pushf
146           cli
147  ;if no buffer space, return -1
148           mov   bx, cTxRing.Count
149           cmp   bx, cTxRing.Size
150           jne   COUT10
151           mov   ax, ax                          ;ax=0
152           jmp   COUT90
153  COUT10:
154  ;pick up character from stack
155           mov   al, [bp+Arg0]
156           xor   ah, ah
157           dec   ah                              ;ah=0FFh (!=0)
158  ;if count zero and flag is zero, start usart and set flag
159           cmp   cTxRing.Count, 0
160           jne   COUT20
161           cmp   cTxRing.Flag, 0
162           jnz   COUT20
163           call  cOutChB                         ;start usart, al=char
164           inc   cTxRing.Flag
165           jmp   COUT90
166  COUT20:
167  ;put char in ring, increment index
168           mov   bx, cTxRing.Putx
169           mov   cTxRing.Buf[bx], al
170           inc   cTxRing.Putx
171           inc   cTxRing.Count
172  ;wrap index if necessary
173           mov   bx, cTxRing.Putx
174           cmp   bx, cTxRING.SIZE
175           jne   COUT30
176           mov   cTxRing.Putx, 0
177  COUT30:
178  ;exit
179  COUT90:
180           popf                                  ;restores intpts
181           pop   bx
182           pop   bp
183           ret
184  _CharOut endp
185  ;
186  ;_CharIn  Get char from rcv ring, return ax=0 if none
187  _CharIn  proc  far
188           push  bp
189           mov   bp, sp
190           push  bx
191           pushf
192           cli
193  ;if count is zero, exit with ax=0
194           cmp   cRxRing.Count, 0
195           jne   CIN10
196           mov   ax, ax                          ;di, si not used
```

```
197              xor     ax,ax              ;ax=0 if no char
198              jmp     CIN90
199      CIN10:
200      ;get char from string
201              mov     bx, cRxRing.Getx
202              mov     al, cRxRing.Buf [bx]
203              dec     ah                 ;ah=0FFh
204              inc     ah
205              mov     cRxRing.Getx
206              dec     cRxRing.Count
207              mov     bx, cRxRing.Getx
208              cmp     bx, cRxRing.Size
209              jne     CIN80
210              xor     bx, bx             ;wrap getx
211      CIN80:
212              mov     cRxRing.Getx, bx
213      CIN90:
214              popf                       ;restores intpts
215              pop     bx
216              pop     bp
217              ret
218      _CharIn endp
219      ;-----------------------------------------------------------
220      ; cxRingInit    Initialize the ring buffers
221      cxNitRing proc  near
222              mov     ax, RINGSIZE
223              mov     cTxRing.Size, ax
224              mov     cRxRing.Size, ax
225              xor     ax, ax
226              mov     cTxRing.Count, ax
227              mov     cTxRing.Getx, ax
228              mov     cTxRing.Putx, ax
229              mov     cTxRing.Flag, ax
230              mov     cTxRing.sPid, ax
231              mov     cRxRing.Count, ax
232              mov     cRxRing.Getx, ax
233              mov     cRxRing.Putx, ax
234              mov     cRxRing.Flag, ax
235              mov     cRxRing.sPid, ax
236              ret
237      cxNitRing endp
238      ;-----------------------------------------------------------
239      ; ciRxPut     Put a char in al into the rxring, return ax=0 if buffer full
240      ;             Runs as part of ISR, therefore intpts are already disabled
241      ciRxPut proc   near
242              push    bx
243      ;branch if string buffer input
244              cmp     cRxRing.sPid, 0
245              jnz     RX100              ;for string buffer input
246      ;continue with ring buffer input
247              mov     bx, cRxRing.Count
248              cmp     bx, cRxRing.Size
249              jne     RX10               ;if no buffer space
250              xor     ax, ax             ;return ax = 0
251                                         ;ax=0
252
```

```
253            jmp     RX90
254 ;put char in rxring
255            mov     bx, cRxRing.Putx
256            mov     cRxRing.Buf[bx], al
257            inc     cRxRing.Putx
258            inc     cRxRing.Count
259 ;wrap index if necessary
260            mov     bx, cRxRing.Putx
261            cmp     bx, cRxRing.Size
262            jne     RX30
263            mov     cRxRing.Putx, 0
264 ;exit
265 RX30:
266 RX90:      pop     bx
267            ret
268 ;to here for input to string buffer
269 RX100:     mov     bx, cRxRing.sBuf
270            add     bx, cRxRing.sIndex
271            mov     [bx], al
272            inc     cRxRing.sIndex
273            mov     bx, cRxRing.sIndex
274            cmp     bx, cRxRing.sSize
275            jge     Rx105
276            push    ax
277            call    _CharOut                ;echo character
278            pop     ax
279            cmp     al, 0Dh                 ;check terminator
280            je      Rx110
281            jmp     Rx90                    ;exit
282 ;post to user
283 Rx105:     add     bx, cRxRing.sBuf        ;already bx=index
284            mov     al, 0Dh                 ;insert carriage return
285            mov     [bx-1], al              ;echo a carriage return
286            push    ax
287            call    _CharOut
288            add     sp, 2
289 Rx110:     push    0Ah                     ;echo line feed
290            call    _CharOut
291            add     sp, 2
292            push    cRxRing.sEvent          ;event word
293            push    cRxRing.sPid            ;process id
294            call    _Post
295            add     sp, 4
296            mov     cRxRing.sPid, 0         ;clear flag
297            jmp     Rx90
298 cIRxPut    endp
299
300 ;cIRxGet    Get character from ring buffer in al, returns ax=0 if no char.
301 ;           Then gets char from string buffer if extant
302 ;           Runs as part of ISR, therefore intpts are already disabled
```

```
3309   ciTxGet proc  near
3310           push  bx
3311   ;proceed with ring buffer
3312           cmp   cTxRing.Count, 0
3313           jne   TX10
3314           xor   ax, ax                      ;ax=0
3315           jmp   TX60                        ;ring '', empty, try str buf
3316   TX10:
3317           mov   bx, cTxRing.Getx
3318           mov   al, cTxRing.Buf[bx]
3319           xor   ah, ah
3320           dec   ah                          ;ah = 0FFh, so ax no zero
3321           dec   cTxRing.Count
3322           inc   cTxRing.Getx
3323           mov   bx, cTxRing.Getx
3324           cmp   bx, cTxRing.Size
3325           jne   TX50
3326           mov   cTxRing.Getx, 0             ;wrap index
3327   TX50:
3328           jmp   TX100                       ;exit
3329   ;check for string buffer active
3330   TX60:
3331           cmp   cTxRing.sPid, 0
3332           je    TX100                       ;if pid zero
3333                                             ;go to exit
3334   ;handle string buffer output
3335           mov   bx, cTxRing.sBuf
3336           add   bx, cTxRing.sIndex
3337           inc   cTxRing.sIndex              ;incr index
3338           mov   al, [bx]                    ;get character
3339           or    al, al
3340           jnz   TX100                       ;not end, skip post
3341           push  cTxRing.sEvent
3342           push  cTxRing.sPid
3343           call  qPost
3344           add   sp, q
3345           xor   ax, ax                      ;ax=0 says no more
3346           mov   cTxRing.sPid, ax            ;clear pid flag
3347   ;exit
3348   TX100:
3349           pop   bx
3350           ret
3351   ciTxGet endp
3352   ;-----------------------------------------------------------------
3353   ;  ciTxClear  Clear the transmit busy flag
3354   ;            Allows string to not be Public
3355   ciTxClear proc  near
3356           mov   cTxRing.Flag, 0
3357           ret
3358   ciTxClear endp
3359   ;-----------------------------------------------------------------
3360   ;  cStrIn (event, &buffer, length)
3361   ;        Input to a string buffer, post to user upon CR
3362   ;-----------------------------------------------------------------
3363   cStrIn  proc  far
3364           push  bp
```

```
365         mov     bp, sp
366         push    di
367         push    si
368 ;check for line already in use
369         cmp     cRxRing.sPid, 0
370         jz      StrIn10
371         mov     ax, E_Serial
372         jmp     StrIn90                 ;already in use
373 ;set up storage
374 StrIn10:
375         call    xPID
376         mov     cRxRing.sPid, ax        ;get, store pid
377         mov     ax, [bp+Arg0+0]
378         mov     cRxRing.sEvent, ax      ;store event
379         mov     ax, [bp+Arg0+2]
380         mov     cRxRing.sBuf, ax        ;store buffer address
381         mov     ax, [bp+Arg0+4]
382         mov     cRxRing.sSize, ax       ;store buffer size
383         mov     cRxRing.sIndex, 0       ;clear index
384         xor     ax, ax                  ;return zero for success
385 ;exit StrIn90:
386         pop     si
387         pop     di
388         mov     sp, bp
389         pop     bp
390         ret
391 cStrIn  endp
392
393
394
395 ;_cStrOut (event, &buffer)
396 ;       Input to a string buffer, post to user upon CR
397
398 cStrOut proc    far
399         push    bp
400         mov     bp, sp
401         push    di
402         push    si
403         pushf
404         cli
405 ;disable interrupts because isr changes these values
406 ;check for line already in use
407         cmp     cTxRing.sPid, 0
408         jz      StrOut10
409         mov     ax, E_Serial
410         jmp     StrOut90                ;already in use
411 ;set up storage
412 StrOut10:
413         call    xPID
414         mov     cTxRing.sPid, ax        ;get, store pid
415         mov     ax, [bp+Arg0+0]
416         mov     cTxRing.sEvent, ax      ;store event
417         mov     ax, [bp+Arg0+2]
418         mov     cTxRing.sBuf, ax        ;store buffer address
419         mov     cTxRing.sIndex, 0       ;clear index
420 ;test, prime if needed
```

```
421             cmp     cTxRing.Flag, 0     ;test for priming
422             jnz     StrOut80
423             mov     di, cTxRing.sBuf    ;get first char
424             add     di, cTxRing.sIndex
425             inc     cTxRing.sIndex
426             mov     al, [di]            ;get the char
427             call    cOutChB             ;output char, primes
428             inc     cTxRing.Flag        ;set flag
429     StrOut80:
430             xor     ax, ax              ;return zero for success
431     ;exit
432     StrOut90:
433             popf                        ;reenable intpts
434             pop     si
435             pop     di
436             mov     sp, bp
437             pop     bp
438             ret
439     _cStrOut endp
440             end
441     include sysppil.i
442     end
```

Wed 10-08-86 11:38:24   BXRING.S
    10-15-86 13:19:54

```
1  ;BXRING.S - Generalized Ring Buffer Implementation
2  ;**********************************************************************
3  ;10/08/86
4  ;       .186
5  ;       name    bxRing
6  ;       MFO Ver 0.0
7  ;
8  ; Module: bxRing.s
9  ;
10 ; modification history :          reason(s)
11 ;      date       by           reason
12 ;
13 ;       This module is an original, unpublished work and is proprietary to
14 ;       NELLCOR INC., and may not be divulged or copied in any form
15 ;       whatsoever without the express written permission of NELLCOR INC.
16 ;       Copyright 1986.
17 ;
18 ; Purpose:
19 ;       General purpose ring buffer that may be used by anyone
20 ; Procedures:
21 ;       _xRing, called with pointer to buffer as argument so that any
22 ;              user can allocate his own buffer and use these routines.
23 ;
24 ; Public Data:
25 ;       Only data is the user's own data area.
26 ;**********************************************************************
27 include sysprol.i
28 include hcSysDef.i
```

```
29      Arg0            equ     6               ;for far call
30                                              ;arg0+0 = function, 1 - 7
31                                              ;arg0+2 = rcb offset address
32                                              ;arg0+4 = word address
33
34      ring    struc                           ;ring buffer definitions
35              Size    dw      (?)
36              Count   dw      (?)
37              Getx    dw      (?)
38              Putx    dw      (?)
39              Flag    dw      (?)
40              Buf     db      (?)
41      ring    ends
42
43      ;       _xRing
44      public  _xRING  ;far
45
46      _xRING  proc    far
47              push    bp
48              mov     bp, sp
49              push    di
50              push    si
51              mov     si, [bp+Arg0+2]
52              mov     bx, [bp+Arg0+0]         ;check validity
53      ;if not initialize, check validity
54              cmp     bx, 0                   ;is i. init?
55              je      XR10
56              mov     ax, [si].Flag           ;yes, skip test
57              cmp     ax, [bp+Arg0+2]
58              je      XR10
59              jmp     XR999                   ;error exit
60      XR10:
61      ;check function range of values
62              cmp     bx,7
63              jg      XR999
64      ;disable interrupts
65              pushf
66              cli
67      ;jmp to function execution
68              shl     bx, 1
69              jmp     cs:TABLE [bx]
70      ;jump table
71              TABLE label word
72              dw      Init                    ;0
73              dw      GetByte                 ;1
74              dw      GetWord                 ;2
75              dw      PutByte                 ;3
76              dw      PutWord                 ;4
77              dw      LookByte                ;5
78              dw      LookWord                ;6
79              dw      GetCount                ;7
80
81      ;to here to exit
82      XR900:  xor     ax, ax                  ;zero status
83      XR999:
```

```
85              popf
86              pop     si
87              pop     di
88              pop     sp, bp
89              mov     bp
90              pop
91              ret
92      ;error exit
93      XR999:  mov     ax, E_Invalid
94              jmp     XR900
95      _xRing  endp
96
97      ; Fct 0, Initialize ─────────────────────────────────────
98      ;
99      Init:
100             mov     ax, ds
101             mov     es, ax
102             xor     ax, ax
103             mov     di, si
104             add     di, 2              ;skips size
105             mov     cx, [si].Size
106             add     cx, 10             ;includes control block
107             rep     stosb              ;clear buffer
108             mov     [si].Flag, si      ;set check
109             jmp     XR900
110
111     ; Fct 1, Get Byte from Ring Buffer, return ax=0 if none ──
112     ;
113     GetByte:
114             call    Get
115             or      ax, ax
116             jnz     XR110
117             mov     ax, E_EMPTY
118             jmp     XR900
119     XR110:
120             mov     di, [bp+Arg0+4]
121             mov     [di], al
122             jmp     XR900
123
124     ; Fct 2, Get a word from ring buffer ─────────────────────  ;check count = 2 or more
125     ;
126     GetWord:
127             mov     ax, [si].Count
128             cmp     ax, 1
129             jg      XR210
130             mov     ax, E_Empty
131             jmp     XR900
132     XR210:
133             call    Get
134             push    ax
135             call    Get
136             mov     ah, al
137             pop     bx
138             mov     al, bl
139             mov     di, [bp+Arg0+4]
140             mov     [di], ax
```

```
141                    jmp     XR900
142
143        ; Get procedure ----------------------------------------
144        Get     proc near
145        ;if count is zero, exit with ax= 0
146                    cmp     [si].Count, 0
147                    jne     XR910                   ; if count is zero
148                    xor     ax, ax                  ;exit with ax=0
149                    jmp     XR990
150        XR910:
151        ;get char from ring
152                    mov     bx, [si].Getx
153                    mov     al, [si].Buf [bx]
154                    xor     ah, ah                  ;ah=0FFh
155                    dec     [si].Count
156                    inc     [si].Getx
157                    mov     bx, [si].Size
158                    cmp     bx, [si].Getx
159                    jne     XR920
160                    xor     bx, bx                  ;wrap getx
161        XR920:
162                    mov     [si].Getx, bx
163        XR990:
164                    ret
165        Get     endp
166
167
168        ; Fct 3. Put a byte in the buffer ----------------------
169        PutByte:
170                    mov     di, [bp+Arg0+4]
171                    mov     al, [di]
172                    call    Put
173                    cmp     ax, ax
174                    jnz     XR310
175                    mov     ax, E_Full
176                    jmp     XR990
177        XR310:
178                    jmp     XR900
179
180        ; Fct 4. Put a word into the buffer --------------------
181        PutWord:
182                    mov     ax, [si].Size
183                    sub     ax, [si].Count
184                    cmp     ax, 1
185                    jg      XR410
186                    mov     ax, E_FULL
187                    jmp     XR990
188        XR410:
189                    mov     di, [bp+Arg0+4]
190                    mov     al, [di]
191                    call    Put
192                    mov     al, [di+1]
193                    call    Put
```

```
197              jmp      XR900
198   ; Put procedure ────────────────────────────────────────────
199   ; Enter with char in al, return ax=0 if buffer full
200   Put proc near
201              mov      bx, [si].Count
202              cmp      bx, [si].Size       ;if no buffer space
203              jl       COUT10
204              xor      ax, ax              ;return ax=0
205              jmp      COUT90
206   COUT10:
207   ;character is in al register
208              xor      ah, ah              ;ah=0FFh (!=0)
209              dec      ah
210   ;put char in ring, increment index
211              mov      bx, [si].Putx
212              mov      [si].Buf[bx], al
213              inc      [si].Putx
214              inc      [si].Count
215   ;wrap index if necessary
216              mov      bx, [si].Putx
217              cmp      bx, [si].SIZE
218              jl       COUT30
219              mov      [si].Putx, 0
220   COUT30:
221   ;exit COUT90:
222              ret
223   Put endp
224
225   ; Get 5. Look at a Byte from Ring Buffer, return ax=0 if none ────
226   LookByte:
227              push     [si].Count
228              push     [si].Getx
229              call     Get
230              or       ax, ax
231              jnz      XR510
232              mov      ax, E_EMPTY
233              jmp      XR990
234   XR510:
235              mov      di, [bp+Arg0+4]
236              mov      [di], al
237   XR520:
238              pop      [si].Getx
239              pop      [si].Count
240              jmp      XR990
241
242   ; Get 6. Look at a word from ring buffer ────────────────────
243   LookWord:
244              push     [si].Count
245              push     [si].Getx
246              mov      ax, 1               ;check count = 2 or more
247              cmp      ax, 1
248              jl       XR610
```

```
253         mov     ax, E_Empty
254         jmp     XR6101
255 XR6101: call    Get
256         push    ax
257         call    Get
258         pop     bx
259         mov     ah, bl
260         mov     di, [bp+Arg0+4]
261         mov     [di], ax
262         jmp     XR6901
263 XR6901: pop     [si].Getx
264         pop     [si].Count
265         jmp     XR9900
266
267 ; Get Count from control block -------------
268 ;
269 GetCount:
270         mov     ax, [si].Count
271         mov     di, [bp+Arg0+4]
272         mov     [di], ax
273         jmp     XR9900
274
275         include sysepil.i
276         end
277
```

```
Wed 08-20-84 12:12:32       SYSPROL.1
    10-15-84 13:19:54

1   DATA    segment word public 'DATA'
  2   DATA    ends
  3   CONST   segment word public 'CONST'
  4   CONST   ends
  5   BSS     segment word public 'BSS'
  6   BSS     ends
  7   SYS_TEXT segment byte public 'CODE'
  8   SYS_TEXT ends
  9   DGROUP  group   CONST, BSS, DATA
 10   assume  cs:SYS_TEXT, ds:DGROUP, ss:DGROUP, es:nothing
 11   SYS_TEXT segment byte public 'code'
 12
```

```
Wed 08-20-84 15:04:03      SYSPIL.1
    10-15-84 13:19:54

1   SYS_TEXT    ends
```

```
Wed 10-06-82, 11:06:03  BCEXT.I                    reason
     10/06/86

;BCEXT.I    External data definitions
;10/06/86
;***************************************************************
; MFO Ver 0.0
;
; Module: bcExt.i
;
; modification history :   reason(s)
;        date       by     reason
;
;         This module is an original, unpublished work and is proprietary to
;         NELLCOR INC., and may not be divulged or copied in any form
;         whatsoever without the express written permission of NELLCOR INC.
;         Copyright 1986.
;
; Purpose:
;         External declaration of bComm application level variables
; Procedures:
;         None
; Public Data:
;         None
;***************************************************************

BSS segment word public 'BSS'
    extrn  cMeasTbl        :word        ;Array of 4-byte fct entries
    extrn  cServTbl        :word        ; one for MTs, one for servers
                                        ; indexed by process id
    extrn  _cInBuf0        :word
    extrn  _cInBuf1        :word
    extrn  _cInBuf2        :word
    extrn  _cOutBuf0       :word
    extrn  _cOutBuf1       :word
    extrn  _cOutBuf1       :word
BSS ends _DATA segment word public 'DATA'
    extrn  cEcgIn          :word        ;CCB for ecg trigger message
    extrn  cEcgOut         :word        ;CCB for normal waveform trx
    extrn  CcbEcg          :word
    extrn  CcbWf           :word extrn  _cInLg          :word        ;Input buffer length
    extrn  _cInSlowLg      :word        ;Length of slow data
    extrn  _cInTbl         :word        ;Array of addresses of InBufs extrn  _cOutLg         :word        ;Output buffer length
    extrn  _cOutSlowLg     :word        ; length for slow data
    extrn  _cOutSlowX      :word        ;Slow data index from top of buf
    extrn  _cOutTbl        :word        ;Array of addresses of OutBufs extrn  _CHAR           :byte        ;for comm/cEcgTrig
```

DISPLAY

SECTION F

```
53          extrn       UCHAR2          :byte       ;for commtask
54          extrn       cWORD           ::word      ;for commtask
55          extrn       cPostCount      ::word
56          extrn       CRING           ::word      ;for comm/cEcgTrig
57  _DATA  ends Wed 10-15-86 13:53:42               DFONT.I                 reason 1  .186
  2
  3  ;*************************************************************
  4
  5  ; MFO Ver 8.0
  6
  7  ; Module: dfont.i
  8
  9  ; Modification history :  reason(s)
 10  ;         date       by
 11  ;       8-9-86       epr       creation -- oh my God will this ever be done on
 12  ;                              time.
 13
 14  ;           COPYRIGHT  (C) 1986 NELLCOR INCORPORATED
 15
 16  ;       This module is an original, unpublished work and is proprietary to
 17  ;       NELLCOR INC., and may not be divulged or copied in any form
 18  ;       whatsoever without the express written permission of NELLCOR INC.
 19
 20  ; Purpose:
 21  ;       To provide a common source of definitions for font constants in the
 22  ;       display server.
 23
 24  ; Procedures:
 25
 26  ; Public Data:
 27
 28  ;*************************************************************
 29
 30
 31  ; structure used in RAM based fonts.
 32  FontStruc   struc
 33  fontwidth   dw ?
 34  fontheight  dw ?
 35  FontBitMaps dw ?
 36  FontStruc   ends
```

```
37              ; Structure used for temporary bit maps residing in char plane
38              FCBitMap struc
39              cwidth db ?
40              cbwidth db ?
41
42              cheight db ?
43              cbsize db ?
44
45              cdeltax db ?
46              cxoffset db ?
47
48              cyoffset db ?
49              cdummy db ?
50
51              cbitmap dw ?
52              FCBitMap ends
53
54              FontInfoWSize equ 4
55
56              ; structure used in ROM based fonts.
57              AFont struc
58              fID dw ?
59              fEND dw ?
60
61              fwidth dw ?
62              fheight dw ?
63              fbitmaps db ?
64              AFont ends
65
66              ; structure used in ROM based font bit maps
67              CFont struc
68              cfID dw ?
69              cfxoffset dw ?
70              cfyoffset dw ?
71              cfwidth dw ?
72              cfheight dw ?
73              cfdeltax dw ?
74              cfbitmap dw ?
75              CFont ends
76
77              LowChar equ ' '
78              HighChar equ 'a'
79              MaxChars equ 96
80              FontIndexSize equ MaxChars * 2
81
82
83              DFonts equ (1280/8) * 256      ; End of display.
84              DoSmallFont equ DFonts
85
86              TSmallFontIndexes equ DFonts + 6
87
88              DStartTFonts equ TSmallFontIndexes + 2 * MaxChars
89
90              .xlist
91
92
```

```
 93  ifdef FONTDEF
 94
 95  FONTNUM macro FONTNAME,FONTID
 96  even
 97  &FONTNAME equ this word
 98  public &FONTNAME
 99  dw FONTID
100  dw &FONTNAME&_END
101  endm
102
103
104
105  CHARCODE macro CHARNAME,CHARNUM
106  &CHARNAME&_&CHARNUM equ this word
107  dw CHARNUM
108  public &CHARNAME&_&CHARNUM
109  endm
110
111  DFont segment word public 'font'
112
113  DSmallFont equ this word
114  include dfont16.f
115  DFont16_End equ this word
116
117  DMediumFont equ this word
118  include dfont24.f
119  DFont24_End equ this word
120
121  DLargeFont equ this word
122  include dfont32.f
123  DFont32_End equ this word
124
125  DFont ends
126
127  endif
128
129  .list
130
131
```

```
Wed 10-11-86 005:26:12  DFONT16.F                                           reason 1
 2
 3
 4   ;*****************************************************************
 5   ;
 6   ; MFO Ver 0.0
 7   ;
 8   ; Module: dfont16.f
 9   ;
10   ; modification history :  reason(s)
11   ;       date        by    reason(s)
12   ;
13   ;         COPYRIGHT (C) 1986 NELLCOR INCORPORATED
14   ;
15   ;    This module is an original, unpublished work and is proprietary to
16   ;    NELLCOR INC., and may not be divulged or copied in any form
17   ;    whatsoever without the express written permission of NELLCOR INC.
18   ;
19   ; Purpose:
20   ;       Font definition for the mfo small font 16 by 9 pixels
21   ;
22   ; Procedures:
23   ;
24   ; Public Data:
25   ;
26   ;*****************************************************************
27
28   ; Font Header from file MFO16.SFP.
29
30   FONTNUM DFont16,1 ; this is a macro
31
32           dw      16   ; cellw
33           dw      13   ; cellh
34
35   ;CHAROFFSETS ; this is a macro time
36
37   ; char code is 33 = "!"
38   ; char bytes is 32
39   CHARCODE DFMF016,33 ; this is a macro
40           dw      1  ; left offset
41           dw      11 ; top offset
42           dw      2  ; char width
43           dw      6  ; char height
44           dw      14 ; delta x
45
46           dw      0001111000000000b
47           dw      0110000110000000b
48           dw      1000000011000000b
```

```
53   dw 0000001111100000000b
54   dw 0001100000111000000b
55   dw 1111111111111000000b
56   
57   ;
58   ; char code is 34 = """
59   ; char bytes is 30
60   CHARCODE DMF016,34 ; this is a macro
61   dw 1 ; left offset
62   dw 4 ; top offset
63   dw 14 ; char width
64   dw 7 ; char height
65   dw 16 ; delta X
66   
67   dw 0000001111111000000b
68   dw 0001111111111000000b
69   dw 0011111111111000000b
70   dw 0011111111111000000b
71   dw 0011111111111000000b
72   dw 0001111111111000000b
73   dw 0000001111111000000b
74   
75   ;
76   ; char code is 35 = "#"
77   ; char bytes is 34
78   CHARCODE DMF016,35 ; this is a macro
79   dw 3 ; left offset
80   dw 14 ; top offset
81   dw 9 ; char width
82   dw 16 ; char height
83   dw 16 ; delta X
84   
85   dw 0000000011000000000b
86   dw 0000000011000000000b
87   dw 0000000110000000000b
88   dw 0001101111111000000b
89   dw 0011011111111000000b
90   dw 0011011000000000000b
91   dw 0011111111110000000b
92   dw 0001111111111000000b
93   dw 0000001111111000000b
94   dw 0001011110110000000b
95   dw 0001101100011000000b
96   dw 0110111111111000000b
97   
98   ;
99   ; char code is 36 = "$"
100  ; char bytes is 36
101  CHARCODE DMF016,36 ; this is a macro
102  dw 0 ; left offset
103  dw 0 ; top offset
104  dw 1 ; char width
105  dw 1 ; char height
106  dw 7 ; delta X
107  
108  dw 0000000000000000000b
```

```
109   ; char code is 37 = "%"
110   ; char bytes is 34
111   CHARCODE LMFO16,37 ; this is a macro
112   dw 1 ; left offset
113   dw 3; top offset
114   dw 14 ; char width
115   dw 9; char height
116   dw 16 ; delta X
117
118   dw 0111100000111000b
119   dw 1100100000111000b
120   dw 1100110001110000b
121   dw 0111110001110000b
122   dw 0000011001110000b
123   dw 0000011001110000b
124   dw 0000011001110000b
125   dw 0111000001110000b
126   dw 1110000001110000b
127
128
129   ; char code is 44 = ","
130   ; char bytes is 12
131   CHARCODE LMFO16,44 ; this is a macro
132   dw 3 ; left offset
133   dw 105 ; top offset
134   dw 3; char width
135   dw 3; char height
136   dw 9 ; delta X
137
138
139   dw 1110000000000000b
140   dw 0110000000000000b
141   dw 1100000000000000b
142
143
144
145   ; char code is 46 = "."
146   ; char bytes is 17
147   CHARCODE LMFO16,46 ; this is a macro
148   dw 1 ; left offset
149   dw 1 ; top offset
150   dw 1 ; char width
151   dw 1 ; char height
152   dw 3 ; delta X
153
154   dw 1000000000000000b
155
156
157   ; char code is 47 = "/"
158   ; char bytes is 34
159   CHARCODE LMFO16,47 ; this is a macro
160   dw 1 ; left offset
161   dw 3; top offset
162   dw 14 ; char width
163   dw 9; char height
164
```

```
165     dw  16 ; delta X
166     dw  0000000000111000b
167     dw  0000000001111100b
168     dw  0000000111000000b
169     dw  0000001110000000b
170     dw  0000011100000000b
171     dw  0000111000000000b
172     dw  0001110000000000b
173     dw  0011100000000000b
174     dw  0111000000000000b
175     dw  1110000000000000b
176     dw  1100000000000000b
177
178     ; char code is 48 = "0"
179     ; char bytes is 34
180     CHARCODE DWFO16,48 ; this is a macro
181     dw  1 ; left offset
182     dw  3 ; top offset
183     dw  14; char width
184     dw  7 ; char height
185     dw  16; delta X
186
187     dw  0011111111100000b
188     dw  0111111111110000b
189     dw  1110000011111000b
190     dw  1110000001111000b
191     dw  1110000001111000b
192     dw  1110000001111000b
193     dw  1110000011111000b
194     dw  1101001111111000b
195     dw  0111111111110000b
196     dw  0011111111100000b
197
198
199
200     ; char code is 49 = "1"
201     ; char bytes is 26
202     CHARCODE DWFO16,49 ; this is a macro
203     dw  1 ; left offset
204     dw  3 ; top offset
205     dw  5 ; char width
206     dw  10; char height
207     dw  7 ; delta X
208
209     dw  0011100000000000b
210     dw  0111100000000000b
211     dw  1111100000000000b
212     dw  0011100000000000b
213     dw  0011100000000000b
214     dw  0011100000000000b
215     dw  0011100000000000b
```

COPYRIGHT

```
216    dw  0011100000000000b
217    dw  0011100000000000b
218    dw  0011100000000000b
219
220
221    ; char code is 50 = "2"
222    ; char bytes is 34
223    CHARCODE THFO16,50  ; this is a macro
224    dw  1 ; left offset
225    dw  3 ; top offset
226    dw  14 ; char width
227    dw  9 ; char height
228    dw  16 ; delta x
229
230    dw  1111111111100000b
231    dw  0000000000110000b
232    dw  0000000000011000b
233    dw  0000000000011000b
234    dw  0000000001110000b
235    dw  0000000011000000b
236    dw  0000001110000000b
237    dw  0000110000000000b
238    dw  0111100000000000b
239    dw  1111111111111000b
240
241
242    ; char code is 51 = "3"
243    ; char bytes is 34
244    CHARCODE THFO16,51  ; this is a macro
245    dw  1 ; left offset
246    dw  3 ; top offset
247    dw  13 ; char width
248    dw  9 ; char height
249    dw  16 ; delta x
250
251    dw  1111111111100000b
252    dw  0000000000110000b
253    dw  0000000000011000b
254    dw  0000000011110000b
255    dw  0000000000011000b
256    dw  0000000000001100b
257    dw  0011111100001100b
258    dw  0000000000011000b
259    dw  0111100000110000b
260    dw  1111111111100000b
261
262
263    ; char code is 52 = "4"
264    ; char bytes is 34
265    CHARCODE THFO16,52  ; this is a macro
266    dw  1 ; left offset
267    dw  3 ; top offset
268    dw  14 ; char width
269    dw  9 ; char height
270    dw  16 ; delta x
271
```

```
272     dw  0000000111110000b
273     dw  0000001111100000b
274     dw  0000011111000000b
275     dw  0000111110000000b
276     dw  0001111100000000b
277     dw  0011111000000000b
278     dw  0111110000000000b
279     dw  1111111111111100b
280     dw  1111111111111100b
281     dw  0000000000000000b
282     dw  0000000000000000b
283     dw  0000000000000000b
284     ; char code is 53 = "5"
285     ; char bytes is 34
286     CHARCODE DHF 016,53 ; this is a macro
287     dw  1 ; left offset
288     dw  3 ; top offset
289     dw  14 ; char width
290     dw  7 ; char height
291     dw  16 ; delta X
292
293     dw  1111111111111100b
294     dw  1111111111111100b
295     dw  1100000000000000b
296     dw  1100000000000000b
297     dw  1100000000000000b
298     dw  1111111111000000b
299     dw  0000000011100000b
300     dw  0000000001110000b
301     dw  0000000000111000b
302     dw  0000000000011100b
303
304     ; char code is 54 = "6"
305     ; char bytes is 34
306     CHARCODE DHF 016,54 ; this is a macro
307     dw  1 ; left offset
308     dw  3 ; top offset
309     dw  14 ; char width
310     dw  7 ; char height
311     dw  16 ; delta X
312
313     dw  0011111111110000b
314     dw  0111111111111000b
315     dw  1110000000011100b
316     dw  1100000000000000b
317     dw  1100000000000000b
318     dw  1111111110000000b
319     dw  1111111111100000b
320     dw  1100000000110000b
321     dw  1100000000011000b
322     dw  1100000000011000b
323     dw  1100000000011000b
324     dw  0111111111110000b
325     dw  0011111111100000b
326
327     ; char code is 55 = "7"
```

```
328         ; char bytes is 34
329         CHARCODE INFO16,55  ; this is a macro
330         dw 1 ; left offset
331         dw 3 ; top offset
332         dw 14 ; char width
333         dw 9 ; char height
334         dw 16 ; delta x
335
336         dw 1111111111111000b
337         dw 1100000000111000b
338         dw 0000000000111000b
339         dw 0000000000111000b
340         dw 0000000111111000b
341         dw 0000011100111000b
342         dw 0000111000111000b
343         dw 0000111111111000b
344         dw 0000011111111000b
345         dw 0000000000111000b
346         dw 0000000000111000b
347         dw 0000011111000000b
348
349         ; char code is 56 = "8"
350         ; char bytes is 34
351         CHARCODE INFO16,56  ; this is a macro
352         dw 1 ; left offset
353         dw 3 ; top offset
354         dw 14 ; char width
355         dw 9 ; char height
356         dw 16 ; delta x
357
358         dw 0111111111100000b
359         dw 0111000000110000b
360         dw 0111000000110000b
361         dw 0111000000110000b
362         dw 0111000000110000b
363         dw 0011100001110000b
364         dw 0111000000110000b
365         dw 0111000000110000b
366         dw 0111000000110000b
367         dw 0111000000110000b
368         dw 0011111111100000b
369
370         ; char code is 57 = "9"
371         ; char bytes is 34
372         CHARCODE INFO16,57  ; this is a macro
373         dw 1 ; left offset
374         dw 3 ; top offset
375         dw 14 ; char width
376         dw 9 ; char height
377         dw 16 ; delta x
378
379         dw 0011111111100000b
380         dw 0111000000111000b
381         dw 1110000000011100b
382         dw 1110000000011100b
383         dw 0111111111111000b
```

```
384        dw    0000000000011100b
385        dw    0100000001110000b
386        dw    0011111111100000b
387
388
389
390        ; char code is 58 = ":"
391        ; char bytes is 19
392        CHARCODE_DW 016,58  ; this is a macro
393        dw    3 ; left offset
394        dw    0 ; top offset
395        dw    3 ; char width
396        dw    5 ; char height
397        dw    9 ; delta x
398
399        dw    1110000000000000b
400        dw    0000000000000000b
401        dw    1110000000000000b
402
403
404
405        ; char code is 59 = ";"
406        ; char bytes is 21
407        CHARFONT_DW 016,59  ; this is a macro
408        dw    3 ; left offset
409        dw    0 ; top offset
410        dw    3 ; char width
411        dw    5 ; char height
412        dw    9 ; delta x
413
414        dw    1110000000000000b
415        dw    1110000000000000b
416        dw    0110000000000000b
417        dw    0110000000000000b
418        dw    1100000000000000b
419
420
421
422        ; char code is 63 = "?"
423        ; char bytes is 34
424        CHARCODE_DW 016,63  ; this is a macro
425        dw    1 ; left offset
426        dw    0 ; top offset
427        dw    14 ; char width
428        dw    9 ; char height
429        dw    16 ; delta x
430
431        dw    0011111111100000b
432        dw    0111111111110000b
433        dw    1110000001111000b
434        dw    0000000001111000b
435        dw    0000000011110000b
436        dw    0000111111100000b
437        dw    0000111100000000b
438        dw    0000000000000000b
439        dw    0000111100000000b
```

```
440         ; char code is 65 = "A"
441         ; char bytes is 34
442         CHARCODE_INFO16,65 ; this is a macro
443             dw 1 ; left offset
444             dw 3; top offset
445             dw 14 ; char width
446             dw 9; char height
447             dw 16 ; delta x
448             dw 0000000111000000b
449             dw 0000001111100000b
450             dw 0000011100110000b
451             dw 0000111000111000b
452             dw 0001110000011100b
453             dw 0011111111111110b
454             dw 0111000000000111b
455             dw 1110000000000011b
456             dw 1100000000000001b
457
458         ; char code is 66 = "B"
459         ; char bytes is 34
460         CHARCODE_INFO16,66 ; this is a macro
461             dw 1 ; left offset
462             dw 3; top offset
463             dw 14 ; char width
464             dw 9; char height
465             dw 16 ; delta x
466             dw 1111111111000000b
467             dw 1110000001110000b
468             dw 1110000000111000b
469             dw 1110000000111000b
470             dw 1110000001110000b
471             dw 1111111111000000b
472             dw 1110000001110000b
473             dw 1110000000111000b
474             dw 1110000000111000b
475             dw 1110000001110000b
476             dw 1111111111000000b
477
478         ; char code is 67 = "C"
479         ; char bytes is 34
480         CHARCODE_INFO16,67 ; this is a macro
481             dw 1 ; left offset
482             dw 3; top offset
483             dw 14 ; char width
484             dw 9; char height
485             dw 16 ; delta x
486             dw 0011111111111000b
```

```
495        dw   0110000001111000b
496        dw   1110000001111000b
497        dw   1110000001111000b
498        dw   1110000001111000b
499        dw   1110000001111000b
500        dw   1110000001111000b
501        dw   0110000001111000b
502        dw   0001111111110000b
503
504
505
506        ; char code is 68 = "D"
507        ; Char bytes is 34
508        CHARCODE [MHF016,68  ; this is a macro
509        dw   1    ; left offset
510        dw   3;   ; top offset
511        dw   14;  ; char width
512        dw   9;   ; char height
513        dw   16;  ; delta x
514
515        dw   1111111111100000b
516        dw   1110000001110000b
517        dw   1110000000111000b
518        dw   1110000000111000b
519        dw   1110000000111000b
520        dw   1110000000111000b
521        dw   1110000000111000b
522        dw   1110000001110000b
523        dw   1111111111100000b
524
525
526        ; char code is 69 = "E"
527        ; Char bytes is 34
528        CHARCODE [MHF016,69  ; this is a macro
529        dw   1;   ; left offset
530        dw   3;   ; top offset
531        dw   14;  ; char width
532        dw   9;   ; char height
533        dw   16;  ; delta x
534
535        dw   1111111111111000b
536        dw   1110000000011000b
537        dw   1110000000011000b
538        dw   1110000001111000b
539        dw   1111111111111000b
540        dw   1110000001111000b
541        dw   1110000000011000b
542        dw   1110000000011000b
543        dw   1111111111111000b
544
545
546
547        ; char code is 70 = "F"
548        ; Char bytes is 34
549        CHARCODE [MHF016,70  ; this is a macro
550
```

```
551         dw    1  ; left offset
552         dw    3; top offset
553         dw    14 ; char width
554         dw    9; char height
555         dw    16 ; delta X
556
557         dw    1111111111111000b
558         dw    1110000000011100b
559         dw    1110000000000000b
560         dw    1110000000000000b
561         dw    1110000000000000b
562         dw    1110000001111100b
563         dw    1110000000011100b
564         dw    1110000000011100b
565         dw    1110000000011100b
566         dw    1110000000011100b
567         dw    1111111111111000b
568
569     ; char code is 71 = "G"
570     ; char bytes is 34
571     CHARCODE DMF-014,71 ; this is a macro
572         dw    1; left offset
573         dw    3; top offset
574         dw    14 ; char width
575         dw    9; char height
576         dw    16 ; delta X
577
578         dw    0011111111111000b
579         dw    0110000000011100b
580         dw    1110000000000000b
581         dw    1110000000000000b
582         dw    1110000000000000b
583         dw    1110000001111100b
584         dw    1110000000011100b
585         dw    0110000000011100b
586         dw    0011111111111000b
587
588
589     ; char code is 72 = "H"
590     ; char bytes is 34
591     CHARCODE DMF-014,72 ; this is a macro
592         dw    1; left offset
593         dw    3; top offset
594         dw    14 ; char width
595         dw    9; char height
596         dw    16 ; delta X
597
598         dw    1110000000011100b
599         dw    1110000000011100b
600         dw    1110000000011100b
601         dw    1110000000011100b
602         dw    1111111111111100b
603         dw    1110000000011100b
604         dw    1110000000011100b
605         dw    1110000000011100b
606         dw    1110000000011100b
```

```
607         dw  1110000000011000b
608
609
610     ; char code is 73 = "I"
611     ; char bytes is 25
612     CHARCODE DMF016,73 ; this is a macro
613         dw  1 ; left offset
614         dw  3 ; top offset
615         dw  7 ; char width
616         dw  9 ; char height
617         dw  9 ; delta x
618
619
620         dw  1111111000000000b
621         dw  0001110000000000b
622         dw  0001110000000000b
623         dw  0001110000000000b
624         dw  0001110000000000b
625         dw  0001110000000000b
626         dw  0001110000000000b
627         dw  0001110000000000b
628         dw  1111111000000000b
629
630
631     ; char code is 74 = "J"
632     ; char bytes is 34
633     CHARCODE DMF016,74 ; this is a macro
634         dw  1 ; left offset
635         dw  3 ; top offset
636         dw  14 ; char width
637         dw  9 ; char height
638         dw  16 ; delta x
639
640
641         dw  0000001111111100b
642         dw  0000000011100000b
643         dw  0000000011100000b
644         dw  0000000011100000b
645         dw  0000000011100000b
646         dw  0000000011100000b
647         dw  1110000011100000b
648         dw  0111000111000000b
649         dw  0011111110000000b
650
651
652     ; char code is 75 = "K"
653     ; char bytes is 34
654     CHARCODE DMF016,75 ; this is a macro
655         dw  1 ; left offset
656         dw  14 ; top offset
657         dw  14 ; char width
658         dw  9 ; char height
659         dw  16 ; delta x
660
661
```

```
662         dw    1110000000111000b
663         dw    1110000000111000b
664         dw    1110000001111000b
665         dw    1110000111111000b
666         dw    1110001111111000b
667         dw    1110111100111000b
668         dw    1111111000111000b
669         dw    1111110000111000b
670         dw    1111100000111000b
671         dw    1110000000111000b
672
673         ; char code is 76 = "L"
674         ; char bytes is 34
675         CHARCODE IMF016,76   ; this is a macro
676         dw    1 ; left offset
677         dw    3 ; top offset
678         dw    14 ; char width
679         dw    9 ; char height
680         dw    16 ; delta X
681
682         dw    1111111000000000b
683         dw    0011100000000000b
684         dw    0011100000000000b
685         dw    0011100000000000b
686         dw    0011100000000000b
687         dw    0011100000000000b
688         dw    0011100000000000b
689         dw    0011100000000000b
690         dw    0011100000000011b
691         dw    0011100000011111b
692         dw    1111111111111111b
693
694         ; char code is 77 = "M"
695         ; char bytes is 34
696         CHARCODE IMF016,77   ; this is a macro
697         dw    1 ; left offset
698         dw    3 ; top offset
699         dw    14 ; char width
700         dw    9 ; char height
701         dw    16 ; delta X
702
703         dw    1110000000111000b
704         dw    1111000001111000b
705         dw    1111100011111000b
706         dw    1110110111011000b
707         dw    1110011110011000b
708         dw    1110001100011000b
709         dw    1110000000011000b
710         dw    1110000000011000b
711         dw    1110000000011000b
712         dw    1110000000011000b
713         dw    1110000000011000b
714
715         ; char code is 78 = "N"
716         ; char bytes is 34
717
```

```
7718           CHARCODE DMF016,78  ; this is a macro
7719           dw  1   ; left offset
7720           dw  3   ; top offset
7721           dw  14  ; char width
7722           dw  9   ; char height
7723           dw  16  ; delta X
7724
7725           dw  1111100000111100b
7726           dw  1111110001111100b
7727           dw  1110110001111100b
7728           dw  1110011001111100b
7729           dw  1110011001111100b
7730           dw  1110001101111100b
7731           dw  1110001101111100b
7732           dw  1110000011111100b
7733           dw  1110000011111100b
7734
7735
7736           ; char code is 79 = "O"
7737           ; char bytes is 34
7738           CHARCODE DMF016,79  ; this is a macro
7739           dw  1   ; left offset
7740           dw  3   ; top offset
7741           dw  14  ; char width
7742           dw  9   ; char height
7743           dw  16  ; delta X
7744
7745           dw  0011111111100000b
7746           dw  1111111111110000b
7747           dw  1110000000111000b
7748           dw  1110000000111000b
7749           dw  1110000000111000b
7750           dw  1110000000111000b
7751           dw  1110000000111000b
7752           dw  1110000000111000b
7753           dw  0111111111110000b
7754           dw  0011111111100000b
7755
7756
7757
7758           ; char code is 80 = "P"
7759           ; char bytes is 34
7760           CHARCODE DMF016,80  ; this is a macro
7761           dw  1   ; left offset
7762           dw  3   ; top offset
7763           dw  14  ; char width
7764           dw  9   ; char height
7765           dw  16  ; delta X
7766
7767           dw  1111111111000000b
7768           dw  1111111111100000b
7769           dw  1110000001110000b
7770           dw  1110000001110000b
7771           dw  1110000001110000b
7772           dw  1111111111100000b
7773           dw  1111111111000000b
```

```
774        dw  111000000000000b
775        dw  111000000000000b
776
777
778        ; char code is 81 = "Q"
779        ; char bytes is 34
780        CHARCODE DMF016,81 ; this is a macro
781        dw  1 ; left offset
782        dw  3; top offset
783        dw  14 ; char width
784        dw  9; char height
785        dw  16 ; delta X
786
787        dw  001111111111100000b
788        dw  011100000001110000b
789        dw  111000000000111000b
790        dw  111000000000111000b
791        dw  111000000000111000b
792        dw  111000000010111000b
793        dw  111000000100111000b
794        dw  111000001000111000b
795        dw  111000010001110000b
796        dw  011111111111101000b
797
798
799
800
801        ; char code is 82 = "R"
802        ; char bytes is 34
803        CHARCODE DMF016,82 ; this is a macro
804        dw  1 ; left offset
805        dw  3; top offset
806        dw  14 ; char width
807        dw  9; char height
808        dw  16 ; delta X
809
810        dw  111111111111000000b
811        dw  111000000011100000b
812        dw  111000000001110000b
813        dw  111000000001110000b
814        dw  111000000011100000b
815        dw  111111111111000000b
816        dw  111000111000000000b
817        dw  111000011100000000b
818        dw  111000001110000000b
819
820
821        ; char code is 83 = "S"
822        ; char bytes is 34
823        CHARCODE DMF016,83 ; this is a macro
824        dw  1 ; left offset
825        dw  3; top offset
826        dw  14 ; char width
827        dw  9; char height
828        dw  16 ; delta X
829
```

```
8830    dw 001111111111110000b
8831    dw 011000000000111000b
8832    dw 111000000000011100b
8833    dw 011000000000111000b
8834    dw 001111111111110000b
8835    dw 000011111111000000b
8836    dw 000000111110000000b
8837    dw 000000011100000000b
8838    dw 000000111110000000b
8839    dw 001111111111110000b
8840    dw 011111111111111000b
8841    
8842    ; char code is 84 = "T"
8843    ; char bytes is 34
8844    CHARCODE DWFO16,84  ; this is a macro
8845    dw 1 ; left offset
8846    dw 3 ; top offset
8847    dw 13 ; char width
8848    dw 9 ; char height
8849    dw 16 ; delta X
8850    
8851    dw 111111111111111000b
8852    dw 100000011000001000b
8853    dw 000000011000000000b
8854    dw 000000011000000000b
8855    dw 000000011000000000b
8856    dw 000000011000000000b
8857    dw 000000011000000000b
8858    dw 000000011000000000b
8859    dw 000000111100000000b
8860    dw 000001111111000000b
8861    
8862    ; char code is 85 = "U"
8863    ; char bytes is 34
8864    CHARCODE DWFO16,85  ; this is a macro
8865    dw 3 ; left offset
8866    dw 3 ; top offset
8867    dw 14 ; char width
8868    dw 7 ; char height
8869    dw 16 ; delta X
8870    
8871    dw 111000000001111000b
8872    dw 111000000011111000b
8873    dw 111000000011111000b
8874    dw 111000000011111000b
8875    dw 111000000011111000b
8876    dw 111000000011111000b
8877    dw 111000000011111000b
8878    dw 011000000011111000b
8879    dw 011100000111111000b
8880    dw 001111111111110000b
8881    
8882    
8883    ; char code is 86 = "V"
8884    ; char bytes is 34
8885    
```

```
886         CHARCODE DMFO16,86 ; this is a macro
887         dw  1 ; left offset
888         dw  3 ; top offset
889         dw 14 ; char width
890         dw  9 ; char height
891         dw 16 ; delta X
892
893         dw 1110000000111100b
894         dw 1110000000111100b
895         dw 1110000000111000b
896         dw 0110000000111000b
897         dw 0110000001110000b
898         dw 0011000011110000b
899         dw 0011000110110000b
900         dw 0001100110110000b
901         dw 0000011011100000b
902
903         dw 0000000110000000b
904
905         ; char code is 87 = "W"
906         ; char bytes is 34
907         CHARCODE DMFO16,87 ; this is a macro
908         dw  1 ; left offset
909         dw  3 ; top offset
910         dw 14 ; char width
911         dw  9 ; char height
912         dw 16 ; delta X
913
914         dw 1110000000111100b
915         dw 1110011000111100b
916         dw 1110011000111100b
917         dw 1110011100111100b
918         dw 1110111101111100b
919         dw 1111111101111100b
920         dw 1111110011111100b
921         dw 0111110011111000b
922         dw 0110000001110000b
923
924
925         ; char code is 88 = "X"
926         ; char bytes is 34
927         CHARCODE DMFO16,88 ; this is a macro
928         dw  1 ; left offset
929         dw  3 ; top offset
930         dw 14 ; char width
931         dw  9 ; char height
932         dw 16 ; delta X
933
934         dw 1110000000111100b
935         dw 0110000001111000b
936         dw 0011100001110000b
937         dw 0000110011100000b
938         dw 0000011110000000b
939         dw 0000011110000000b
940         dw 0000110111000000b
941         dw 0011000011100000b
```

```
942         dw    0110000000001110000b
943         dw    1110000000001110000b
944
945
946
947         ; char code is 89 = "Y"
948         ; char bytes is 34
949         CHARCODE INFO16,89 ; this is a macro
950         dw    1 ; left offset
951         dw    3 ; top offset
952         dw    13 ; char width
953         dw    9 ; char height
954         dw    16 ; delta X
955
956         dw    1100000000011100000b
957         dw    0110000000011100000b
958         dw    0011000000111000000b
959         dw    0001100001110000000b
960         dw    0000111011100000000b
961         dw    0000011111000000000b
962         dw    0000001110000000000b
963         dw    0000001110000000000b
964         dw    0000001110000000000b
965
966
967         ; char code is 90 = "Z"
968         ; char bytes is 34
969         CHARCODE INFO16,90 ; this is a macro
970         dw    1 ; left offset
971         dw    3 ; top offset
972         dw    14 ; char width
973         dw    7 ; char height
974         dw    16 ; delta X
975
976         dw    1111111111111100000b
977         dw    1111111111111100000b
978         dw    0000000011111000000b
979         dw    0000001111100000000b
980         dw    0000111110000000000b
981         dw    0011111000000000000b
982         dw    0111110000000000000b
983         dw    1111111111111100000b
984         dw    1111111111111100000b
985
986
987
988
989         ; char code is 97 = "a"
990         ; char bytes is 30
991         CHARCODE INFO16,97 ; this is a macro
992         dw    1 ; left offset
993         dw    5 ; top offset
994         dw    14 ; char width
995         dw    7 ; char height
996         dw    16 ; delta X
997
```

```
 998  dw  0111111111110000b
 999  dw  0000000000111100b
1000  dw  0000000000111100b 1001  dw  0111111111110000b
1002  dw  0110000000111100b
1003  dw  0110000000111100b
1004  dw  0111111111110000b
1005  dw  0111111111110000b
1006  dw  0111111111110000b
```

```
                                                      reason

1  ;****************************************************************
2  ;
3  ;
4  ;    MFO Ver 3.0
5  ;
6  ;    Module: dfont24.f
7  ;
8  ;    Modification history :   reason(s)
9  ;            date      by     reason
10 ;
11 ;         COPYRIGHT (C) 1986 NELLCOR INCORPORATED
12 ;
13 ;    This module is an original, unpublished work and is proprietary to
14 ;    NELLCOR INC., and may not be divulged or copied in any form
15 ;    whatsoever without the express written permission of NELLCOR INC.
16 ;
17 ;
18 ; Purpose:
19 ;    Font definition for the mfo medium font, 24 by 16 pixels
20 ; Procedures:
21 ;
22 ; Public Data:
23 ;
24 ;
25 ;****************************************************************
26
27 ; Font Header from file MFO24.SFP.
28
29 FONTNUM dfont24,1 ; this is a macro
30
31    dw  24 ; cellw
32    dw  15 ; cellh
33
34 ;CHAROFFSET15 ; this is a macro time
35
36
37
38
39 ; char code is 33 ; '!'
40 ; char bytes is 47
41 CHARCODE DMFO24,33 ; this is a macro
42    dw 1 ; font offset
```

```
44    dw    5  ; top offset
45    dw   21  ; char width
46    dw    9  ; char height
47    dw   24  ; delta X
48
49    dw   1111100111111111b, 1110000000000000b
50    dw   0000001111111111b, 1111000000000000b Wed 10-10-86 00:17:38    LFONT24.F          COPYRIGHT
    10-15-86 14:53:42

51    dw   0000000000000000b, 0111100000000000b
52    dw   0000000000000000b, 1111000000000000b
53    dw   0000011100000000b, 1111000000000000b
54    dw   0000111110000000b, 1111000000000000b
55    dw   0111111111000000b, 1110000000000000b
56    dw   0111111111100000b, 1110000000000000b
57    dw   1111111111110000b, 1110000000000000b
58
59
60    ; char code is 34 = """
61    ; char bytes is 43
62    CHARCODE LFO24,34     ; this is a macro
63    dw    1 ; left offset
64    dw    4 ; top offset
65    dw   21 ; char width
66    dw    9 ; char height
67    dw   24 ; delta X
68
69    dw   0000000000011100b, 1110000000000000b
70    dw   0000000000011100b, 1110000000000000b
71    dw   0000000000111110b, 1111000000000000b
72    dw   0000000000111110b, 1111000000000000b
73    dw   0000000000111111b, 1111000000000000b
74    dw   0000000000111111b, 1111000000000000b
75    dw   0000000000111111b, 1110000000000000b
76    dw   0000000001111111b, 1110000000000000b
77    dw   0000000001111111b, 1110000000000000b
78    dw   0000000001111111b, 1100000000000000b
79
80
81    ; char code is 35 = "#"
82    ; char bytes is 49
83    CHARCODE LFO24,35     ; this is a macro
84    dw    3 ; left offset
85    dw    4 ; top offset
86    dw   21 ; char width
87    dw   11 ; char height
88    dw   24 ; delta X
89
90    dw   0000000011100001b, 1000000000000000b
91    dw   0000000011100001b, 1000000000000000b
92    dw   0000000011100001b, 1100000000000000b
93    dw   0000000011110001b, 1100000000000000b
94    dw   0000000011110001b, 1100000000000000b
```

```
95      dw  0000000111000011011b,  00000000000000000b
96      dw  0000001110000011011b,  10000000000000000b
97      dw  0000011100000011011b,  11000000000000000b
98      dw  0111111111111111111b,  11110000000000000b
99      dw  1111111111111111111b,  11111000000000000b
100     dw  0000001110001100000b,  00000000000000000b
101
102     dw  0000001110000000000b,  00000000000000000b
103
104
105     ; char code is 36 = "$"
106     ; char bytes is 55
107     CHARCODE DMFO24,36  ; this is a macro
108     dw  0 ; left offset
109     dw  1 ; top offset
110     dw  1 ; char width
111     dw  17; char height
112     dw  11; delta X
113
114     dw  0000000111000000000b,  00000000000000000b
115
116
117     ; char code is 37 = "%"
118     ; char bytes is 55
119     CHARCODE DMFO24,37  ; this is a macro
120     dw  3 ; left offset
121     dw  1 ; top offset
122     dw  17; char width
123     dw  13; char height
124     dw  24; delta X
125
126     dw  0111111000000111b,  00000000000000000b
127     dw  1100000110001110b,  00000000000000000b
128     dw  1100000110001110b,  00000000000000000b
129     dw  1100000110011100b,  00000000000000000b
130     dw  1100000110011100b,  00000000000000000b
131     dw  0111111000111000b,  00000000000000000b
132     dw  0000000000111000b,  00000000000000000b
133     dw  0000000001110001b,  11111000000000000b
134     dw  0000000001110011b,  00001100000000000b
135     dw  0000000011100011b,  00001100000000000b
136     dw  0000000011100011b,  00001100000000000b
137     dw  0000000111000011b,  00001100000000000b
138     dw  0111000110000001b,  11111000000000000b
139
140
141     ; char code is 44 = ","
142     ; char bytes is 20
143     CHARCODE DMFO24,44  ; this is a macro
144     dw  5 ; left offset
145     dw  10; top offset
146     dw  4 ; char width
147     dw  4 ; char height
148     dw  15; delta X
149
150
```

```
151         dw  1111000000000000b
152         dw  1111000000000000b
153         dw  0011000000000000b
154         dw  0110000000000000b
155
156
157     ; char code is 46 = "."
158     ; char bytes is 18
159     CHARCODE DMFO24,46  ; this is a macro
160         dw  2 ; left offset
161         dw  12; top offset
162         dw  4 ; char width
163         dw  2 ; char height
164         dw  5 ; delta X
165
166
167         dw  1110000000000000b
168         dw  1110000000000000b
169
170
171     ; char code is 47 = "/"
172     ; char bytes is 42
173     CHARCODE DMFO24,47  ; this is a macro
174         dw  4 ; left offset
175         dw  1 ; top offset
176         dw  15; char width
177         dw  13; char height
178         dw  24; delta X
179
180         dw  0000000000111000b
181         dw  0000000000111000b
182         dw  0000000001110000b
183         dw  0000000001110000b
184         dw  0000000011100000b
185         dw  0000000011100000b
186         dw  0000000111000000b
187         dw  0000000111000000b
188         dw  0000001110000000b
189         dw  0000001110000000b
190         dw  0000011100000000b
191         dw  0000111000000000b
192         dw  0011100000000000b
193         dw  1110000000000000b
194
195
196
197     ; char code is 48 = "0"
198     ; char bytes is 35
199     CHARCODE DMFO24,48  ; this is a macro
200         dw  1 ; left offset
201         dw  1 ; top offset
202         dw  21; char width
203         dw  13; char height
204         dw  24; delta X
205
206         dw  0001111111111110b, 1110000000000000b
```

```
207         dw      0111000000011b, 1111000000000000b
208         dw      1111000000011b, 1111000000000000b
209         dw      1111000000110b, 0111000000000000b
210         dw      1111000000110b, 0111000000000000b
211         dw      1111000000110b, 0111000000000000b
212         dw      1111000000110b, 0111000000000000b
213         dw      1111000000011b, 0111000000000000b
214         dw      1111000000011b, 0111000000000000b
215         dw      1111000000011b, 0111000000000000b
216         dw      1111000110011b, 0111000000000000b
217         dw      1111011011111b, 0111000000000000b
218         dw      1111111111111b, 1111000000000000b
219         dw      0001111111111b, 1111000000000000b
220
221     ; char code is 49 = "1"
222     ; char bytes is 29
223     CHARCODE DMF024,49 ; this is a macro
224         dw      5 ; left offset
225         dw      1 ; top offset
226         dw      7 ; char width
227         dw      13 ; char height
228         dw      16 ; delta X
229
230
231         dw      0000111111000000b
232         dw      0001111111000000b
233         dw      0011111111000000b
234         dw      0111111111000000b
235         dw      1111111111000000b
236         dw      0000111111000000b
237         dw      0000111111000000b
238         dw      0000111111000000b
239         dw      0000111111000000b
240         dw      0000111111000000b
241         dw      0000111111000000b
242         dw      0000111111000000b
243         dw      0000111111000000b
244         dw      0000111111000000b
245         dw      0000111111000000b
246
247     ; char code is 50 = "2"
248     ; char bytes is 55
249     CHARCODE DMF024,50 ; this is a macro
250         dw      1 ; left offset
251         dw      1 ; top offset
252         dw      21 ; char width
253         dw      13 ; char height
254         dw      24 ; delta X
255
256         dw      0011111111111b, 1100000000000000b
257         dw      0111111111111b, 1110000000000000b
258         dw      1110000000000b, 0111000000000000b
259         dw      1110000000000b, 0011000000000000b
260         dw      1110000000000b, 0111000000000000b
261         dw      0000000000000b, 0111000000000000b
262         dw      0000000000001b, 1110000000000000b
```

```
263         dw      0000000001111111b,      0000000000000000b
264         dw      0000001111111000b,      0000000000000000b
265         dw      0011111110000000b,      0000000000000000b
266         dw      0111111000000000b,      0000000000000000b
267         dw      1111111111111111b,      0000000000000000b
268         dw      1111111111111111b,      1111000000000000b
269
270
271     ; char code is 51 = "3"
272     ; char bytes is 55
273     CHARCODE IMFO24,51 ; this is a macro
274         dw      1 ; left offset
275         dw      1 ; top offset
276         dw      21 ; char width
277         dw      13 ; char height
278         dw      24 ; delta X
279
280
281         dw      0001111111111111b,      1110000000000000b
282         dw      0111100000000011b,      0011100000000000b
283         dw      1111000000000000b,      0001110000000000b
284         dw      1110000000000000b,      0001110000000000b
285         dw      0000000000000000b,      0001110000000000b
286         dw      0000000000000000b,      0011100000000000b
287         dw      0000000000001111b,      1111000000000000b
288         dw      0000000000000000b,      0011100000000000b
289         dw      0000000000000000b,      0001110000000000b
290         dw      1110000000000000b,      0001110000000000b
291         dw      1111000000000000b,      0001110000000000b
292         dw      0111100000000011b,      0011100000000000b
293         dw      0001111111111111b,      1110000000000000b
294
295
296
297     ; char code is 52 = "4"
298     ; char bytes is 55
299     CHARCODE IMFO24,52 ; this is a macro
300         dw      1 ; left offset
301         dw      1 ; top offset
302         dw      21 ; char width
303         dw      13 ; char height
304         dw      24 ; delta X
305
306         dw      0000000000000111b,      1100000000000000b
307         dw      0000000000001111b,      1100000000000000b
308         dw      0000000000011110b,      1100000000000000b
309         dw      0000000000111100b,      1100000000000000b
310         dw      0000000001111000b,      1100000000000000b
311         dw      0000000011110000b,      1100000000000000b
312         dw      0000000111100000b,      1100000000000000b
313         dw      0000001111000000b,      1100000000000000b
314         dw      0000011110000000b,      1100000000000000b
315         dw      0000111111111111b,      1111000000000000b
316         dw      0000000000000000b,      1100000000000000b
317         dw      0000000000000000b,      1100000000000000b
318         dw      0000000000000000b,      1100000000000000b
```

```
319         ; char code is 53 = "5"
320         ; char bytes is 55       ; this is a macro
321         CHARCODE DMF024,53
322         dw 1  ; left offset
323         dw 1  ; top offset
324         dw 21 ; char width
325         dw 13 ; char height
326         dw 24 ; delta X
327
328
329         dw 1111111111111b, 1111100000000000b
330         dw 1111111111111b, 0000000000000000b
331         dw 1111111111111b, 0000000000000000b
332         dw 1111111111111b, 0000000000000000b
333         dw 1111000000000b, 0000000000000000b
334         dw 1111000000000b, 0000000000000000b
335         dw 1111000000000b, 1111000000000000b
336         dw 1111111111111b, 1111100000000000b
337         dw 1111111111111b, 1111110000000000b
338         dw 0000000000000b, 0111111000000000b
339         dw 0000000000000b, 0111111000000000b
340         dw 1111000000000b, 0111111000000000b
341         dw 1111111111111b, 1111110000000000b
342         dw 1111111111111b, 1111100000000000b
343         dw 0111111111111b, 1111000000000000b
344         dw 0011111111111b, 1100000000000000b
345
346
347         ; char code is 54 = "6"
348         ; char bytes is 55       ; this is a macro
349         CHARCODE DMF024,54
350         dw 1  ; left offset
351         dw 1  ; top offset
352         dw 21 ; char width
353         dw 13 ; char height
354         dw 24 ; delta X
355
356         dw 0111111111111b, 1110000000000000b
357         dw 0111111111111b, 0111000000000000b
358         dw 1111111111111b, 0111000000000000b
359         dw 1111111111111b, 0111000000000000b
360         dw 1111000000000b, 0000000000000000b
361         dw 1111000000000b, 0000000000000000b
362         dw 1111000000000b, 0111000000000000b
363         dw 1111111111111b, 0111100000000000b
364         dw 1111111111111b, 0111110000000000b
365         dw 1111000000000b, 0111110000000000b
366         dw 1111000000000b, 0111110000000000b
367         dw 1111000000000b, 0111110000000000b
368         dw 1111111111111b, 1111110000000000b
369         dw 1111111111111b, 1111100000000000b
370         dw 0111111111111b, 1111000000000000b
371         dw 0011111111111b, 1100000000000000b
372
373         ; char code is 55 = "7"
374         ; char bytes is 55       ; this is a macro
                CHARCODE DMF024,55
```

```
375         dw   1 ;  left offset
376         dw   1 ;  top offset
377         dw  21 ;  char width
378         dw  13 ;  char height
379         dw  24 ;  delta X
380
381         dw   1111111111111111b, 111110000000000b
382         dw   0000000000000001b, 111100000000000b
383         dw   0000000000000011b, 111000000000000b
384         dw   0000000000000111b, 110000000000000b
385         dw   0000000000001111b, 100000000000000b
386         dw   0000000000011110b, 000000000000000b
387         dw   0000000000111100b, 000000000000000b
388         dw   0000000001111000b, 000000000000000b
389         dw   0000000011110000b, 000000000000000b
390         dw   0000000111100000b, 000000000000000b
391         dw   0000001111000000b, 000000000000000b
392         dw   0000011110000000b, 000000000000000b
393         dw   0000111100000000b, 000000000000000b
394         dw   0001111000000000b, 000000000000000b
395         dw   0011110000000000b, 000000000000000b
396         dw   0111100000000000b, 000000000000000b
397         ; char code is 56 = "8"
398         ; char bytes is 55
399         CHARCODE LMFO24,56 ; this is a macro
400         dw   1 ;  left offset
401         dw   1 ;  top offset
402         dw  21 ;  char width
403         dw  13 ;  char height
404         dw  24 ;  delta X
405
406         dw   0111111111111111b, 111100000000000b
407         dw   0111111111111111b, 111100000000000b
408         dw   0111100000000000b, 011110000000000b
409         dw   0111100000000000b, 011110000000000b
410         dw   0111100000000000b, 011110000000000b
411         dw   0111100000000000b, 011110000000000b
412         dw   0111100000000000b, 011110000000000b
413         dw   0111100000000000b, 011110000000000b
414         dw   0111111111111111b, 111100000000000b
415         dw   0111111111111111b, 111100000000000b
416         dw   0111100000000000b, 011110000000000b
417         dw   0111100000000000b, 011110000000000b
418         dw   0111100000000000b, 011110000000000b
419         dw   0111111111111111b, 111100000000000b
420         dw   0111111111111111b, 111100000000000b
421         ; char code is 57 = "9"
422         ; char bytes is 55
423         CHARCODE LMFO24,57 ; this is a macro
424         dw   1 ;  left offset
425         dw   1 ;  top offset
426         dw  21 ;  char width
427         dw  13 ;  char height
428         dw  24 ;  delta X
429
```

```
430         dw      0011111111111111b,1110000000000000b
431         dw      0111111111111111b,1110000000000000b
432         dw      1111000000000000b,0111000000000000b
433         dw      1111000000000000b,0111000000000000b
434         dw      1111000000000000b,0111000000000000b
435         dw      1111000000000000b,0111000000000000b
436         dw      0000000000000000b,1111000000000000b
437         dw      0111111111111111b,1110000000000000b
438         dw      0011111111111111b,1110000000000000b
439         dw      0000000000000000b,0111000000000000b
440         dw      1111000000000000b,0111000000000000b
441         dw      1111000000000000b,0111000000000000b
442         dw      1111000000000000b,0111000000000000b
443         dw      0111111111111111b,1110000000000000b
444         dw      0011111111111111b,1110000000000000b
445
446
447     ; char code is 58 = ":"
448     ; char bytes is 22
449     CHARCODE DMF024,5A ; this is a macro
450         dw      5 ; left offset
451         dw      6 ; top offset
452         dw      4 ; char width
453         dw      6 ; char height
454         dw      15 ; delta X
455
456         dw      1110000000000000b
457         dw      1110000000000000b
458         dw      0000000000000000b
459         dw      0000000000000000b
460         dw      1110000000000000b
461         dw      1110000000000000b
462
463
464     ; char code is 59 = ";"
465     ; char bytes is 24
466     CHARCODE DMF024,59 ; this is a macro
467         dw      5 ; left offset
468         dw      6 ; top offset
469         dw      4 ; char width
470         dw      8 ; char height
471         dw      15 ; delta X
472
473         dw      1110000000000000b
474         dw      1110000000000000b
475         dw      0000000000000000b
476         dw      0000000000000000b
477         dw      1110000000000000b
478         dw      1110000000000000b
479         dw      0110000000000000b
480         dw      0110000000000000b
481
482
483
484
485     ; char code is 57 = "?"
```

```
486  ; char bytes is 55
487  CHARCODE IMF024,63      ; this is a macro
488    dw  1 ; left offset
489    dw 21 ; top offset
490    dw 13 ; char width
491    dw 24 ; char height
492    dw 24 ; delta X
493
494    dw 0011111111111111b, 1110000000000000b
495    dw 0111111111111111b, 1111000000000000b
496    dw 1111110000001111b, 1111100000000000b
497    dw 1111100000000111b, 1111100000000000b
498    dw 1111000000000011b, 1111100000000000b
499    dw 1111000000000011b, 1111100000000000b
500    dw 0000000000000011b, 1111100000000000b
501    dw 0000000000000111b, 1111000000000000b
502    dw 0000000000001111b, 1110000000000000b
503    dw 0000000011111111b, 1000000000000000b
504    dw 0000001111111110b, 0000000000000000b
505    dw 0000011111111000b, 0000000000000000b
506    dw 0000111111100000b, 0000000000000000b
507    dw 0001111110000000b, 0000000000000000b
508    dw 0011111000000000b, 0000000000000000b
509
510  ; char code is 65 = "A"
511  ; char bytes is 55
512  CHARCODE IMF024,65      ; this is a macro
513    dw  1 ; left offset
514    dw 21 ; top offset
515    dw 13 ; char width
516    dw 24 ; char height
517    dw 24 ; delta X
518
519    dw 0000000000100000b, 0000000000000000b
520    dw 0000000001110000b, 0000000000000000b
521    dw 0000000001110000b, 0000000000000000b
522    dw 0000000011111000b, 0000000000000000b
523    dw 0000000111011100b, 0000000000000000b
524    dw 0000000111011100b, 0000000000000000b
525    dw 0000001110001110b, 0000000000000000b
526    dw 0000011110001111b, 0000000000000000b
527    dw 0000011100000111b, 0000000000000000b
528    dw 0000111111111111b, 1000000000000000b
529    dw 0001111111111111b, 1100000000000000b
530    dw 0001110000000011b, 1100000000000000b
531    dw 0011100000000001b, 1110000000000000b
532    dw 0111100000000001b, 1111000000000000b
533    dw 1111110000001111b, 1111100000000000b
534
535  ; char code is 66 = "B"
536  ; char bytes is 55
537  CHARCODE IMF024,66      ; this is a macro
538    dw  1 ; left offset
539    dw 21 ; top offset
540    dw 13 ; char width
541    dw 24 ; char height
542    dw 24 ; delta X
```

```
543         dw      1111111111111111b,      1110000000000000b
544         dw      1111111111111111b,      0111000000000000b
545         dw      1111100000000000b,      0011100000000000b
546         dw      1111000000000000b,      0001110000000000b
547         dw      1110000000000000b,      0000111000000000b
548         dw      1110000000000000b,      0000111000000000b
549         dw      1111000000000000b,      0001110000000000b
550         dw      1111111111111111b,      1111000000000000b
551,        dw      1111111111111110b,      0111000000000000b
552         dw      1111111111111100b,      0011100000000000b
553         dw      1111000000000000b,      0001110000000000b
554         dw      1110000000000000b,      0000111000000000b
555         dw      1110000000000000b,      0000111000000000b
556         dw      1111000000000000b,      0001110000000000b
557         dw      1111100000000000b,      0011100000000000b
558         dw      1111111111111111b,      0111000000000000b
559         dw      1111111111111111b,      1110000000000000b
560 ; char code is 67 = "C"
561 ; char bytes is 55
562 CHARCODE DMFO24,67 ; this is a macro
563         dw      1 ; left offset
564         dw      21; top offset
565         dw      13; char width
566         dw      13; char height
567         dw      24 ; delta X
568         dw      0011111111111111b,      1110000000000000b
569         dw      0111111111111111b,      0111000000000000b
570         dw      1111100000000000b,      0011100000000000b
571         dw      1111000000000000b,      0001110000000000b
572         dw      1110000000000000b,      0000111000000000b
573         dw      1110000000000000b,      0000000000000000b
574         dw      1110000000000000b,      0000000000000000b
575         dw      1110000000000000b,      0000000000000000b
576         dw      1110000000000000b,      0000000000000000b
577         dw      1110000000000000b,      0000000000000000b
578         dw      1110000000000000b,      0000111000000000b
579         dw      1111000000000000b,      0001110000000000b
580         dw      1111100000000000b,      0011100000000000b
581         dw      0011111111111111b,      0111000000000000b
582         dw      0011111111111111b,      1110000000000000b
583
584
585 ; char code is 68 = "D"
586 ; char bytes is 55
587 CHARCODE DMFO24,68 ; this is a macro
588         dw      1 ; left offset
589         dw      21; top offset
590         dw      13; char width
591         dw      13; char height
592         dw      24 ; delta X
593         dw      1111111111111110b,      1110000000000000b
594         dw      1111111111111111b,      0111000000000000b
595         dw      1110000000000000b,      0011100000000000b
596         dw      1110000000000000b,      0001110000000000b
597         dw      1110000000000000b,      0000111000000000b
```

```
601         dw  1111110000000000b,  0000000000000000b
602         dw  1111110000000000b,  0000000000000000b
603         dw  1111110000000000b,  0000000000000000b
604         dw  1111110000000000b,  0111100000000000b
605         dw  1111110000000000b,  0111100000000000b
606         dw  1111110000000000b,  0111100000000000b
607         dw  1111111111111111b,  0111100000000000b
608         dw  1111111111111111b,  0111100000000000b
609         dw  1111111111111111b,  1111100000000000b
610 ; char code is 69 = "E"
611 ; char bytes is 55
612 CHARCODE DMFO24,69 ; this is a macro
613         dw  1   ; left offset
614         dw  1   ; top offset
615         dw  21  ; char width
616         dw  13  ; char height
617         dw  24  ; delta X
618
619         dw  1111111111111111b,  1111100000000000b
620         dw  1111111111111111b,  0011100000000000b
621         dw  1111111111111111b,  0000000000000000b
622         dw  1111110000000000b,  0000000000000000b
623         dw  1111110000000000b,  0000000000000000b
624         dw  1111110000000000b,  0000000000000000b
625         dw  1111111111111111b,  0000000000000000b
626         dw  1111111111111111b,  0000000000000000b
627         dw  1111111111111111b,  0000000000000000b
628         dw  1111110000000000b,  0000000000000000b
629         dw  1111110000000000b,  0000000000000000b
630         dw  1111110000000000b,  0000000000000000b
631         dw  1111111111111111b,  1111100000000000b
632         dw  1111111111111111b,  0011100000000000b
633         dw  1111111111111111b,  1111100000000000b
634
635 ; char code is 70 = "F"
636 ; char bytes is 55
637 CHARCODE DMFO24,70 ; this is a macro
638         dw  1   ; left offset
639         dw  1   ; top offset
640         dw  21  ; char width
641         dw  13  ; char height
642         dw  24  ; delta X
643
644         dw  1111111111111111b,  1111100000000000b
645         dw  1111111111111111b,  0011100000000000b
646         dw  1111111111111111b,  0000000000000000b
647         dw  1111110000000000b,  0000000000000000b
648         dw  1111110000000000b,  0000000000000000b
649         dw  1111110000000000b,  0000000000000000b
650         dw  1111110000000000b,  0000000000000000b
```

```
651        dw  1111000000000000b,  0000000000000000b
652        dw  1111000000000000b,  0000000000000000b
653        dw  1111000000000000b,  0000000000000000b
654        dw  1111000000000000b,  0000000000000000b
655        dw  1111000000000000b,  0000000000000000b
656        dw  1111000000000000b,  0000000000000000b
657        dw  1111000000000000b,  0000000000000000b
658
659    ; char code is 71 = "G"
660    ; char bytes is 55
661    CHARCODE DMFO24,71 ; this is a macro
662        dw  1;  left offset
663        dw  1;  top offset
664        dw  21; char width
665        dw  13; char height
666        dw  24; delta X
667
668        dw  0011111111111111b,  1110000000000000b
669        dw  1111111111111111b,  1111000000000000b
670        dw  1111000000000000b,  0000000000000000b
671        dw  1111000000000000b,  0000000000000000b
672        dw  1111000000000000b,  0000000000000000b
673        dw  1111000000000111b,  1111000000000000b
674        dw  1111000000000111b,  1111000000000000b
675        dw  1111000000000111b,  1111000000000000b
676        dw  1111000000000111b,  1111000000000000b
677        dw  1111000000000111b,  1111000000000000b
678        dw  1111111111111111b,  1111000000000000b
679        dw  0111111111111111b,  1111000000000000b
680        dw  0011111111111111b,  1111000000000000b
681
682
683
684    ; char code is 72 = "H"
685    ; char bytes is 55
686    CHARCODE DMFO24,72 ; this is a macro
687        dw  1;  left offset
688        dw  1;  top offset
689        dw  21; char width
690        dw  13; char height
691        dw  24; delta X
692
693        dw  1111000000000000b,  0000000000000000b
694        dw  1111000000000000b,  0000000000000000b
695        dw  1111000000000000b,  0000000000000000b
696        dw  1111000000000000b,  0000000000000000b
697        dw  1111000000000000b,  0000000000000000b
698        dw  1111111111111111b,  0111000000000000b
699        dw  1111111111111111b,  0111000000000000b
700        dw  1111111111111111b,  0111000000000000b
701        dw  1111000000000000b,  0111000000000000b
702        dw  1111000000000000b,  0111000000000000b
703        dw  1111000000000000b,  0111000000000000b
704        dw  1111000000000000b,  0111000000000000b
705        dw  1111000000000000b,  0111000000000000b
706        dw  1111000000000000b,  0111000000000000b
```

```
707      ; char code is 73 = "I"
708      ; char bytes is 42 ; this is a macro
709      CHARCODE DMF024,73
710      dw  1 ; left offset
711      dw  1 ; top offset
712      dw 12 ; char width
713      dw 13 ; char height
714      dw 15 ; delta x
715
716      dw 1111111111110000b
717      dw 0000011111100000b
718      dw 0000011111100000b
719      dw 0000011111100000b
720      dw 0000011111100000b
721      dw 0000011111100000b
722      dw 0000011111100000b
723      dw 0000011111100000b
724      dw 0000011111100000b
725      dw 0000011111100000b
726      dw 0000011111100000b
727      dw 0000011111100000b
728      dw 1111111111110000b
729
730      ; char code is 74 = "J"
731      ; char bytes is 55 ; this is a macro
732      CHARCODE DMF024,74
733      dw  1 ; left offset
734      dw  1 ; top offset
735      dw 21 ; char width
736      dw 13 ; char height
737      dw 24 ; delta x
738
739      dw 0000000000111111111b
740      dw 0000000000011111111b
741      dw 0000000000011111111b
742      dw 0000000000011111111b
743      dw 0000000000011111111b
744      dw 0000000000011111111b
745      dw 0000000000011111111b
746      dw 0000000000011111111b
747      dw 0000000000011111111b
748      dw 0000000000011111111b
749      dw 1110000000011111111b
750      dw 1111000000011111111b
751      dw 0111111111111111b
752
753      ; char code is 75 = "K"
754      ; char bytes is 55 ; this is a macro
755      CHARCODE DMF024,75
```

```
763         dw 1   ; left offset
764         dw 1   ; top offset
765         dw 21  ; char width
766         dw 13  ; char height
767         dw 24  ; delta X
768
769         dw 111111110000000000000b,
770         dw 111111110000000000000b,
771         dw 000000110000000000000b,
772         dw 000000110000000000000b,
773         dw 000000110000000000000b,
774         dw 000000110000000000000b,
775         dw 000000110000000000000b,
776         dw 000000110000000000000b,
777         dw 000000110000000000000b,
778         dw 000000110000000000000b,
779         dw 000000110000011111100b,
780         dw 111111111111111111100b,
781         dw 111111111111111111100b,
782
783 ; char code is 76 = "L"
784 ; char bytes is 55
785 CHARCODE DMF024,76 ; this is a macro
786         dw 1   ; left offset
787         dw 1   ; top offset
788         dw 21  ; char width
789         dw 13  ; char height
790         dw 24  ; delta X
791
792         dw 111111110000000000000b,
793         dw 111111110000000000000b,
794         dw 000011110000000000000b,
795         dw 000011110000000000000b,
796         dw 000011110000000000000b,
797         dw 000011110000000000000b,
798         dw 000011110000000000000b,
799         dw 000011110000000000000b,
800         dw 000011110000000000000b,
801         dw 000011110000000000000b,
802         dw 000011110000000000000b,
803         dw 000011110000011111100b,
804         dw 000011110000111111110b,
805         dw 000011110000111111110b,
806         dw 111111111111111111110b,
807
808
809 ; char code is 77 = "M"
810 ; char bytes is 55
811 CHARCODE DMF024,77 ; this is a macro
812         dw 1   ; left offset
813         dw 1   ; top offset
814         dw 21  ; char width
815         dw 13  ; char height
816         dw 24  ; delta X
817
818
```

```
819         dw      1111000000000000b,      0111100000000000b
820         dw      1111000000000000b,      1111100000000000b
821         dw      1111100000000000b,      1111100000000000b
822         dw      1111110000000001b,      1111100000000000b
823         dw      1111011000000001b,      1111100000000000b
824         dw      1111001100000011b,      1111100000000000b
825         dw      1111000110000011b,      1111100000000000b
826         dw      1111000011000110b,      1111100000000000b
827         dw      1111000011000110b,      1111100000000000b
828         dw      1111000001101100b,      1111100000000000b
829         dw      1111000000111000b,      1111100000000000b
830         dw      1111000000111000b,      1111100000000000b
831         dw      1111000000011000b,      1111100000000000b
832         dw      1111000000001000b,      1111100000000000b
833         dw      1111000000000000b,      0111100000000000b
834
835 ; char code is 78 = "N"
836 ; char bytes is 55
837 CHARCODE DMF024,78 ; this is a macro
838         dw      1 ; left offset
839         dw      21 ; top offset
840         dw      13; char width
841         dw      24 ; char height
842         dw      ; delta x
843
844         dw      1111000001110000b,      0111100000000000b
845         dw      1111000111111000b,      0111100000000000b
846         dw      1111001111111100b,      0111100000000000b
847         dw      1111011100011100b,      0111100000000000b
848         dw      1111011000001110b,      0111100000000000b
849         dw      1110000000000110b,      0111100000000000b
850         dw      1110000000000111b,      0111100000000000b
851         dw      1110000000000011b,      0111100000000000b
852         dw      1110000000000011b,      0111100000000000b
853         dw      1110000000000011b,      0111100000000000b
854         dw      1110000000000011b,      0111100000000000b
855         dw      1110000000000011b,      0111100000000000b
856         dw      1110000000000111b,      0111100000000000b
857         dw      1110000000000110b,      0111100000000000b
858         dw      1110000000001110b,      1111100000000000b
859
860 ; char code is 79 = "O"
861 ; char bytes is 55
862 CHARCODE DMF024,79 ; this is a macro
863         dw      1 ; left offset
864         dw      21 ; top offset
865         dw      13; char width
866         dw      24 ; char height
867         dw      ; delta x
868
869         dw      0011111111111111b,      1110000000000000b
870         dw      0111111111111111b,      1111000000000000b
871         dw      0111100000000000b,      0111100000000000b
872         dw      0111100000000000b,      0111100000000000b
873         dw      0111100000000000b,      0111100000000000b
874         dw      1111000000000000b,      0111100000000000b
```

```
875         dw  1110000000000000b,  0111000000000000b
876         dw  1110000000000000b,  0111000000000000b
877         dw  1110000000000000b,  0111000000000000b
878         dw  1110000000000000b,  0111000000000000b
879         dw  0111000000000000b,  1110000000000000b
880         dw  0011111111111111b,  1110000000000000b
881         dw  0001111111111111b,  1100000000000000b
882
883
884     ; char code is 80 = "P"
885     ; char bytes is 55
886     CHARCODE DMF024,80  ; this is a macro
887         dw  1;  left offset
888         dw  1;  top offset
889         dw  21; char width
890         dw  13; char height
891         dw  24; delta X
892
893         dw  1111111111111b,  1110000000000000b
894         dw  1111111111111b,  0111000000000000b
895         dw  1111111111111b,  0011100000000000b
896         dw  1111111111111b,  0001110000000000b
897         dw  1111111111111b,  0000111000000000b
898         dw  1111111111111b,  0000011100000000b
899         dw  1111111111111b,  0000001110000000b
900         dw  1111111111111b,  0000000111000000b
901         dw  1111111111111b,  0000000011100000b
902         dw  1111111111111b,  0000000001110000b
903         dw  1111111111111b,  0000000000111000b
904         dw  1111111111111b,  0000000000011100b
905         dw  1111111111111b,  0000000000001110b
906
907
908
909     ; char code is 81 = "Q"
910     ; char bytes is 55
911     CHARCODE DMF024,81  ; this is a macro
912         dw  1;  left offset
913         dw  1;  top offset
914         dw  21; char width
915         dw  13; char height
916         dw  24; delta X
917
918         dw  0011111111111111b,  1110000000000000b
919         dw  0111111111111111b,  1111000000000000b
920         dw  1111000000000011b,  1111100000000000b
921         dw  1110000000000001b,  1111110000000000b
922         dw  1110000000000000b,  1110111000000000b
923         dw  1110000000000000b,  1110011100000000b
924         dw  1110000000000000b,  1110001110000000b
925         dw  1110000000000000b,  1110000111000000b
926         dw  1110000000000000b,  1110000011100000b
927         dw  1110000000000001b,  1110000001110000b
928         dw  1110000000000010b,  1110000000111000b
929         dw  0111000000000110b,  1110000000011100b
930         dw  0111000000001100b,  1111000000001110b
```

```
931              dw  0001111111111111b, 1110100000000000b
932
933              ; char code is 82 = "R"
934              ; char bytes is 55          ; this is a macro
935     CHARCODE DMF024,82
936              dw  1 ; left offset
937              dw  1 ; top offset
938              dw  21 ; char width
939              dw  13 ; char height
940              dw  24 ; delta X
941
942              dw  1111111111111111b, 1110000000000000b
943              dw  1111111111111111b, 0011100000000000b
944              dw  1111100000001111b, 0001110000000000b
945              dw  1111100000000111b, 0000111000000000b
946              dw  1111100000000111b, 0000111000000000b
947              dw  1111100000000111b, 0001110000000000b
948              dw  1111100000001111b, 0011100000000000b
949              dw  1111111111111111b, 1111000000000000b
950              dw  1111111111111111b, 1110000000000000b
951              dw  1111100001111000b, 0000000000000000b
952              dw  1111100000111100b, 0000000000000000b
953              dw  1111100000011110b, 0000000000000000b
954              dw  1111100000001111b, 0000000000000000b
955              dw  1111100000000111b, 1000000000000000b
956              dw  1111100000000011b, 1100000000000000b
957              dw  1111100000000001b, 1110000000000000b
958              dw  1111100000000000b, 1111000000000000b
959
960              ; char code is 83 = "S"
961              ; char bytes is 55          ; this is a macro
962     CHARCODE DMF024,83
963              dw  1 ; left offset
964              dw  1 ; top offset
965              dw  21 ; char width
966              dw  13 ; char height
967              dw  24 ; delta X
968
969              dw  0011111111111111b, 1110000000000000b
970              dw  0111111111111111b, 0111000000000000b
971              dw  1111100000001111b, 0011100000000000b
972              dw  1111000000000111b, 0001110000000000b
973              dw  0111000000000000b, 0001110000000000b
974              dw  0011100000000000b, 0001110000000000b
975              dw  0001111000000000b, 0001110000000000b
976              dw  0000111110000000b, 0000000000000000b
977              dw  0000011111100000b, 0000000000000000b
978              dw  0000000111111000b, 0000000000000000b
979              dw  0000000001111100b, 0000000000000000b
980              dw  0000000000011110b, 0000000000000000b
981              dw  0111000000001111b, 0000111000000000b
982              dw  0111000000000111b, 0001111000000000b
983              dw  0011100000000111b, 0011110000000000b
984              dw  0011111111111111b, 1111100000000000b
985              dw  0001111111111111b, 1110000000000000b
986
987              ; char code is 84 = "T"
```

```
986   ; char bytes is 55
987   CHARCODE DMF024,84  ; this is a macro
988       dw 1;   left offset
989       dw 1;   top offset
990       dw 21;  char width
991       dw 13;  char height
992       dw 24;  delta X
993
994       dw 1111111111111111b,
995       dw 1100000111111000b,
996       dw 0000000011111000b,
997       dw 0000000011111000b,
998       dw 0000000011111000b,
999       dw 0000000011111000b,
1000      dw 0000000011111000b,
1001      dw 0000000011111000b,
1002      dw 0000000011111000b,
1003      dw 0000000011111000b,
1004      dw 0000000011111000b,
1005      dw 0000000011111000b,
1006      dw 0000000011111000b,
1007
1008  ; char code is 85 = "U"
1009  ; char bytes is 55
1010  CHARCODE DMF024,85  ; this is a macro
1011      dw 1;   left offset
1012      dw 1;   top offset
1013      dw 21;  char width
1014      dw 13;  char height
1015      dw 24;  delta X
1016
1017      dw 1111100000000000b,
1018      dw 1111100000000000b,
1019      dw 1111100000000000b,
1020      dw 1111100000000000b,
1021      dw 1111100000000000b,
1022      dw 1111100000000000b,
1023      dw 1111100000000000b,
1024      dw 1111100000000000b,
1025      dw 1111100000000000b,
1026      dw 1111100000000000b,
1027      dw 1111100000000000b,
1028      dw 0111100000000000b,
1029      dw 0011111111111111b,
1030
1031  ; char code is 86 = "V"
1032  CHARCODE DMF024,86  ; this is a macro
1033      dw 1;   left offset
1034      dw 1;   top offset
1035      dw 21;  char width
1036      dw 13;  char height
```

```
1042        dw   24  ; delta X
1043
1044        dw   1111000000000000b, 01111000000000000b
1045        dw   1111000000000000b, 01111000000000000b
1046        dw   1110000000000000b, 11111000000000000b
1047        dw   0111000000000001b, 11111000000000000b
1048        dw   0111100000000001b, 11011000000000000b
1049        dw   0011100000000011b, 11011000000000000b
1050        dw   0011110000000011b, 10001100000000000b
1051        dw   0001110000000111b, 10001100000000000b
1052        dw   0001111000000111b, 00001100000000000b
1053        dw   0000111000001111b, 00000110000000000b
1054        dw   0000111100001110b, 00000110000000000b
1055        dw   0000011100011110b, 00000011000000000b
1056        dw   0000011110011100b, 00000011000000000b
1057        dw   0000001110111100b, 00000001100000000b
1058        dw   0000001111111000b, 00000001100000000b
1059        dw   0000000111111000b, 00000000110000000b
1060
1061        ; char code is 87 = "W"
1062        ; char bytes is 55
1063        CHARCODE DMF024,87  ; this is a macro
1064        dw   1 ; left offset
1065        dw   21; top offset
1066        dw   13; char width
1067        dw   24 ; delta X
1068
1069        dw   1111000000000000b, 01111000000000000b
1070        dw   1111000000000000b, 01111000000000000b
1071        dw   1110000000000000b, 01111000000000000b
1072        dw   1110000000010000b, 01111000000000000b
1073        dw   0111000000101000b, 00111000000000000b
1074        dw   0111000000101000b, 00111000000000000b
1075        dw   0111000001101100b, 00111000000000000b
1076        dw   0111000001000100b, 00111000000000000b
1077        dw   0011100010000010b, 00011000000000000b
1078        dw   0011100010000010b, 00011000000000000b
1079        dw   0011100110000011b, 00011000000000000b
1080        dw   0011110100000001b, 00011000000000000b
1081        dw   0001110000000001b, 10001000000000000b
1082        dw   0001111000000001b, 11001000000000000b
1083        dw   0001111000000000b, 11001000000000000b
1084
1085        ; char code is 88 = "X"
1086        ; char bytes is 55
1087        CHARCODE DMF024,88  ; this is a macro
1088        dw   1 ; left offset
1089        dw   21; top offset
1090        dw   13; char width
1091        dw   24 ; delta X
1092
1093        dw   1111000000000000b, 01111000000000000b
1094        dw   0111000000000001b, 11110000000000000b
1095        dw   0011100000000011b, 11100000000000000b
1096        dw   0001110000000111b, 11000000000000000b
1097        dw   0000111000001111b, 10000000000000000b
```

```
1096         dw      0000001111000111b, 0000000000000000b
1097         dw      0000000111001110b, 0000000000000000b
1100         dw      0000000011011100b, 0000000000000000b
1101         dw      0000000011111000b, 0000000000000000b
1102         dw      0000000001111000b, 0000000000000000b
1103         dw      0000000001110000b, 0000000000000000b
1104         dw      0000000011100000b, 0000000000000000b
1105         dw      0001111111000000b, 1110000000000000b
1106         dw      0111111110000000b, 1110000000000000b
1107         dw      0111110000000000b, 0111000000000000b
1108
1109         ; char code is 89 = "Y"
1110         ; char bytes is 55
1111         CHARCODE DMF024,89 ; this is a macro
1112         dw      1 ; left offset
1113         dw      20 ; top offset
1114         dw      13 ; char width
1115         dw      23 ; char height
1116         dw      23 ; delta X
1117
1118         dw      1110000000000001b, 1110000000000000b
1119         dw      0111000000000011b, 1100000000000000b
1120         dw      0011100000000111b, 1000000000000000b
1121         dw      0001110000001111b, 0000000000000000b
1122         dw      0000111000011110b, 0000000000000000b
1123         dw      0000011100111100b, 0000000000000000b
1124         dw      0000001111111000b, 0000000000000000b
1125         dw      0000000111110000b, 0000000000000000b
1126         dw      0000000011100000b, 0000000000000000b
1127         dw      0000000011100000b, 0000000000000000b
1128         dw      0000000011100000b, 0000000000000000b
1129         dw      0000000011100000b, 0000000000000000b
1130         dw      0000000011100000b, 0000000000000000b
1131         dw      0000000011100000b, 0000000000000000b
1132         dw      0000000011100000b, 0000000000000000b
1133
1134         ; char code is 90 = "Z"
1135         ; char bytes is 55
1136         CHARCODE DMF024,90 ; this is a macro
1137         dw      1 ; left offset
1138         dw      21 ; top offset
1139         dw      13 ; char width
1140         dw      13 ; char height
1141         dw      24 ; delta X
1142
1143         dw      1111111111111111b, 1111000000000000b
1144         dw      1111111111111111b, 1111000000000000b
1145         dw      1100000000000111b, 1110000000000000b
1146         dw      1000000000001111b, 1100000000000000b
1147         dw      0000000000011111b, 1000000000000000b
1148         dw      0000000000111111b, 0000000000000000b
1149         dw      0000000001111110b, 0000000000000000b
1150         dw      0000000011111100b, 0000000000000000b
1151         dw      0000000111111000b, 0000000000000000b
1152         dw      0000001111110000b, 0000000000000000b
1153         dw      0000011111100000b, 0000000000000000b
```

```
1154        dw  0011111100000000b, 0000000000000000b
1155        dw  0011111100000000b, 0000000000000000b
1156        dw  0011111111111111b, 1111110000000000b
1157        dw
1158

Wed 10-06-86 15:25:22    DHWDEF.I            reason
    10-15-86 14:53:42

1          .186
 2          ;*********************************************************************
 3          ;
 4          ; MFO Ver 0.0
 5          ;
 6          ; Module: dhwdef.i
 7          ;
 8          ; modification history :   reason(s)
 9          ;            date    by    creation
10          ;          8-25-86  epr
11          ;
12          ;           COPYRIGHT (C) 1986 NELLCOR INCORPORATED
13          ;
14          ;   This module is an original, unpublished work and is proprietary to
15          ;   NELLCOR INC., and may not be divulged or copied in any form
16          ;   whatsoever without the express written permission of NELLCOR INC.
17          ;
18          ;
19          ; Purpose:
20          ;     Display Hardware Definitions.
21          ;
22          ; Procedures:
23          ;
24          ; Public Data:
25          ;
26          ;*********************************************************************
27
28          GraphicPlaneSelectPort equ 90h
29          GPlane0Val         equ 0
30          GPlane1Val         equ 1
31
32          NormalVideoPort    equ 94h
33          NormalVidVal       equ 1
34          ReverseVidVal      equ 0
35
36          BlinkLatchPort     equ 92h
37          BlinkCharVal       equ 1
38          NoBlinkVal         equ 0
39
40          BlankLatchPort     equ 96h
41          BlankVal           equ 1
42          VideoOnVal         equ 0
43
44          ; Video Scroll Ports.
45
```

```
46  VerticalStartPort      equ 200h
47  VerticalEndPort        equ 202h
48  HorizontalStartPort    equ 204h
49  HorizontalEndPort      equ 206h
50  FirstPixelLSBPort      equ 208h
51  FirstPixelMSBPort      equ 20Ah
52
53  ScrollWrapEnable       equ 80h
54
55  SampleHoldPort         equ 314h
56  DACPort                equ 320h
57
58  NoScrollVal            equ 0ffh
59
60  ; Scroll Detect Enable
61  DetectorEnablePort     equ 20eh
62  DetectEnableVal        equ 1
63  DetectDisableVal       equ 0
64
65  DISABLEVIDEO  macro
66          mov     dx, BlankLatchPort
67          mov     al, BlankVal
68          out     dx, al
69          mov     dx, NormalVideoPort
70          mov     al, NormalVidVal
71          out     dx, al
72          mov     al, NoScrollVal
73          mov     dx, VerticalStartPort
74          out     dx, al
75          mov     dx, VerticalEndPort
76          out     dx, al
77          mov     dx, HorizontalStartPort
78          out     dx, al
79          mov     dx, HorizontalEndPort
80          out     dx, al
81          mov     dx, FirstPixelLSBPort
82          out     dx, al
83          mov     dx, FirstPixelMSBPort
84          out     dx, al
85          mov     dx, SampleHoldPort
86          mov     al, 1
87          out     dx, al
88          mov     dx, DACPort
89          mov     ax, 300h
90          out     dx, ax
91          mov     al, GPlane0Val
92          out     GraphicPlaneSelectPort, al
93  endm
94
95  DONVIDEO macro
96          mov     dx, BlankLatchPort
97          mov     al, VideoOnVal
98          out     dx, al
99  endm
100
```

```
Wed 10-15-86 11:30:42  DISPMAIN.C       PutTimer
     10-15-86 14:53:42

1  /******************************************************************
 2   *
 3   * MFO Ver 0.0
 4   *
 5   * module: dispmain.c
 6   *
 7   * modification history :  reason(s)
 8   *         date    by     creation
 9   *      8-24-86  epr      creation
10   *
11   *
12   *
13   * This module is an original, unpublished work and is proprietary to
14   * NELLCOR INC., and may not be divulged or copied in any form
15   * whatsoever without the express written permission of NELLCOR INC.
16   *
17   * purpose :
18   *     This module provides the main loop of the display server.
19   *
20   * data descriptions :
21   *
22   * function descriptions :
23   *     dispmain() -- the dispaly server entry point.
24   *     dcreatep() -- funtion to create the display server as a process.
25   *
26   ******************************************************************/
27
28  #include ".\xevent.h"
29  #include ".\xclock.h"
30  #include "..\xscaled.h"
31
32  #include "dwindow.h"
33  #include "dstring.h"
34  #include "dwutil.h"
35  #include "dresult.h"
36  #include "dwvform.h"
37  #include "daudio.h"
38
39  int far displtimeout();
40  int far DBlinkToggle();
41
42  extern int far DPutWFData();
43
44  #define BlinkTimer 6
45  #define PutTimer  (BlinkTimer + 1)
46
47  DefineTimers(dtimers, 9)
48  DefineTimer(TDISABLE,TDISABLE,DBeepon)          /* DAudioTimer[0] */
49  DefineTimer(TDISABLE,TDISABLE,DBeepoff)         /* DAudioTimer[1] */
```

```
51   DefineTimer(TDISABLE,TDISABLE,TDISABLE,DSilentAudio)    /* DAudioTimer[2] */
52   DefineTimer(TDISABLE,TDISABLE,TDISABLE,DOutAudioPort)   /* DAudioTimer[3] */
53   DefineTimer(TDISABLE,TDISABLE,TDISABLE,DUpdateAlarm)    /* DAudioTimer[4] */
54   DefineTimer(TDISABLE,TDISABLE,TDISABLE,DOutputAudio)    /* DAudioTimer[5] */
55
56   DefineTimer(100, 30, DBlinkToggle)
57   /*DefineTimer(-100, 2, DPutWFData)*/
58   EndTimers(-1, -1, disptimeout, dtimers)
59
60   int x = 0, y = 0, pat = 0, L = 0;
61   int lx = 0, ly = 0;
62   int tx = 0, ty = 0;
63
64   WinPlane plane = Gr0Plane;
65
66
67   dispmain()
68   {
69       register i;
70       DMakeDefaultWins();
71       DMRInit();
72       DInitTChars();
73       DAudioInit();
74
75       ShowDefaultScreen();
76       /*XSetTimeDelay(&dtimers.timers[PutTimer], 2, 2);*/
77
78
79       for (;;)
80       {
81           i = XWait((int) DISP_EV : (int) COMM_EV);
82           switch (i)
83           {
84               case DISP_EV:
85                   DispResults();
86                   break;
87               case COMM_EV:
88                   DWFUpdate();
89                   break;
90           }
91       }
92   }
93
94   DispUnlink()
95   {
96   }
97
98   disptimeout()
99   {
100  }
101
```

```
Wed  10-07-86  11:46:08   DOUTPORT.S                                     reason
     10-15-86  14:53:42

1         .186
  2  ;*********************************************************************
  3
  4         MFO Ver 0.0   9-5-86 11:00am kht
  5
  6         Module: doutport.s
  7
  8         modification history :
  9              date         by          reason(s)
 10
 11                 COPYRIGHT (C) 1986 NELLCOR INCORPORATED
 12
 13         This module is an original, unpublished work and is proprietary to
 14         NELLCOR INC., and may not be divulged or copied in any form
 15         whatsoever without the express written permission of NELLCOR INC.
 16
 17  ; Purpose: Output audio frequency volume to beeper addresses.
 18
 19  ; Procedures:
 20
 21  ; Public Data:
 22
 23  ;*********************************************************************
 24
 25    NAME     DOUTPORT
 26
 27    PUBLIC   _DOUTAUDIOPORT
 28
 29    FREQPORT      EQU     310H         ;BEEPER FREQUENCY PORT ADDRESS
 30    VOLPORT       EQU     314H         ;BEEPER VOLUME PORT ADDRESS
 31    DAPORT        EQU     320H         ;D/A PORT ADDRESS
 32
 33    extrn    _outfreq:word
 34    extrn    _outvol:word
 35
 36    SYS_TEXT segment byte public 'CODE'
 37
 38    ASSUME CS:SYS_TEXT
 39
 40    _DOUTAUDIOPORT  PROC    FAR
 41
 42         PUSH    BP
 43         MOV     BP,SP
 44
 45         PUSH    DX
 46         MOV     AX,_outfreq          ;GET FREQUENCY
 47         CMP     AX,0
 48         JE      NEXT
 49         MOV     DX,DAPORT            ;DECODE FREQUENCY
```

```
54          OUT     DX,AX
55          MOV     DX,FREQPORT     ;CLOSE AUDIO FREQUENCY PORT
56          mov     ax,1
57          OUT     DX,AL
58          MOV     CX,80           ;wait loop
59          LOOP    $
60          mov     ax,0
61          OUT     DX,al           ;OPEN AUDIO FREQUENCY PORT
62
63  NEXT:
64          MOV     AX,outvol
65          MOV     DX,DAPORT       ;DECODE VOLUME
66          OUT     DX,AX
67          MOV     DX,VOLPORT      ;CLOSE VOLUME PORT
68          mov     ax,1
69          OUT     DX,al
70          MOV     CX,80
71          LOOP    $
72          mov     ax,0
73          OUT     DX,al           ;WAIT LOOP
74                                  ;OPEN AUDIO FREQUENCY PORT
75          POP     DX
76          POP     BP
77          RET
78
79  _DOUTAUDIOPORT  ENDP
80  SYS_TEXT ENDS
81  END
82
83
84
85
86
Wed 10-13-86  23:29:30   DRESULT.C
    10-15-86  14:53:42
```

```
 1  /****************************************************
 2   *
 3   * MFO Ver 0.0
 4   *
 5   * module: dresult.c
 6   *
 7   * modification history :    reason(s)
 8   *         date         by      creation
 9   *      9-30-86        epr
10   *
11   *
12   *
13   * This module is an original, unpublished work and is proprietary to
14   * NELLCOR INC., and may not be divulged or copied in any form
15   * whatsoever without the express written permission of NELLCOR INC.
16   *
17   *
```

```
18  * purpose :
19  *      Contains code for result window managment.
20  *
21  * data descriptions :
22  *      DMRLinkTab[MaxMRs] -- The Measurement Result Link Table, data
23  *              in this table controls the MR output.
24  *
25  * function descriptions :
26  *      DMRInit() -- initializes DMRLinkTab.
27  *      DStartMR(wp) -- routine to initialize Measurement Result linkage
28  *              for dynamic operation.
29  *      DSMRPut(mid, val) -- routine for measurement tasks to call to place
30  *              results on screen.
31  *      DispResults() -- called to display all current measurement results.
32  *      DSMRLink(mid, ntype, afc) -- routine for measurement tasks to link
33  *              with display server.
34  *      DSMRDeleteMR(mid) -- routine called by DMRWDelete to get rid of a
35  *              result winodows dynamic connection.
36  *      DSMRUnlinkP(pid) -- routine to unlink all mid associated with this
37  *              process I.D.
38  *      DSMRClear(mid) -- routine for clearing results from an MT in its window.
39  *      DSMRSlash(mid) -- routine for slashing results from an MT in its window.
40  *
41  **************************************************************************/
42
43  #include "..\xscaled.h"
44  #include "..\xevent.h"
45  #include "dwindow.h"
46  #include "dresult.h"
47  #include "dwutil.h"
48  #include "dstring.h"
49
50
51  MRCt1B DMRLinkTab[MaxMRs] = {-1};
52
53  void near
54  DMRInit()
55  {
56      register MRCt1B *mrtp;
57
58      for (mrtp = DMRLinkTab; mrtp < &DMRLinkTab[MaxMRs]; mrtp++)
59      {
60          mrtp->mrwp = NULLW;
61          mrtp->state = NotActive;
62      }
63  }
64
65  void near
66  DStartMR(mid, wp)
67  int mid;
68  DWindow *wp;
69  {
70      register MRCt1B *mrtp;
71
72      if (mid <= MaxMRs)
```

```
 74              {
 75                  mrtp = &DMRLinkTab[mid];
 76                  mrtp->mrwp = wp;
 77              }
 78          }
 79      
 80      void far
 81      DSMRLink(mid, ntype, acf, minticks)
 82      int mid;
 83      MRType ntype;
 84      long (far *acf) ();  /* Alarm Conversion Function */
 85      int minticks;
 86      {
 87          register MRCtlB *mrtp;
 88      
 89          if (mid < MaxMRs)
 90          {
 91              mrtp = &DMRLinkTab[mid];
 92              mrtp->ntype = ntype;
 93              mrtp->acf = acf;
 94              mrtp->state++;
 95              mrtp->ticks = minticks;
 96              mrtp->pid = XPID();
 97          }
 98      }
 99      
100      void near
101      DSMRDelateMR(mid)
102      {
103          register MRCtlB *mrtp;
104      
105          if (mid <= MaxMRs)
106          {
107              mrtp = &DMRLinkTab[mid];
108              mrtp->state = NotActive;
109              mrtp->mrwp = NULLW;
110          }
111      }
112      
113      void far
114      DSMRUnlinkP(pid)
115      register int pid;
116      {
117          register MRCtlB *mrtp;
118      
119          for (mrtp = DMRLinkTab; mrtp < &DMRLinkTab[MaxMRs]; mrtp++)
120              if ((mrtp)->pid == pid)
121              {
122                  mrtp->mrwp = NULLW;
123                  mrtp->state = -1;
124              }
125      }
126      
127      void far
```

```
130  DSMRUnlinkW(wp)
131  register DWindow *wp;
132  {
133      register MRCt1B *mrtp;
134
135      for (mrtp = DMRLinkTab; mrtp < &DMRLinkTab[MaxMRs]; mrtp++)
136          if (mrtp->mrwp == wp)
137          {
138              mrtp->mrwp = NULLW;
139          }
140  }
141
142  void far
143  DSMRClear(mid)
144  {
145      register DWindow *wp;
146
147      if (mid <= MaxMRs)
148      {
149          wp = DMRLinkTab[mid].mrwp;
150          DRasterFill(wp->wplane, CORNERS(wp->sw.rw.mesval), wp->background);
151      }
152  }
153
154  void far
155  DSMRSlash(mid)
156  {
157      register DWindow *wp;
158
159      if (mid <= MaxMRs)
160      {
161          wp = DMRLinkTab[mid].mrwp;
162          DrawLine(wp->wplane, CORNERS(wp->sw.rw.mesval), 0);
163      }
164  }
165
166  char far dimr[] = "%F%s";
167  char far dimr[] = "%F%s";
168  char far dSmr[] = "%F%s";
169
170  void near
171  DispResults()
172  {
173      register DWindow *wp;
174      register MRCt1B *mrtp;
175      char far *cp;
176      int dx;
177
178      for (mrtp = DMRLinkTab; mrtp < &DMRLinkTab[MaxMRs]; mrtp++)
179          if ((mrtp->mrwp) != NULLW)
180          {
181              if ((wp = mrtp->mrwp) != NULLW)
182              {
183                  if ((wp->state >= 1)
184                  {
185                      DBlank(wp->wnum, CORNERS(wp->sw.rw.mesval), 0);
```

```
186        switch ((int) mrtp->ntype)
187        {
188            case (int) iresult:
189                cp = Dadjitoa(mrtp->lval.i, 3, 0);
190                dx = DstrPixln(wp->wCharInfo.cFontno, cp);
191                dprintf(wp->wnum, dlmr,
192                    wp->sw.rw.mesval.brhcx - dx,
193                    wp->sw.rw.mesval.tlhcy,
194                    cp
195                    );
196                break;
197            case (int) lresult:
198                cp = Dadjltoa(mrtp->lval.l, 3, 0);
199                dx = DstrPixln(wp->wCharInfo.cFontno, cp);
200                dprintf(wp->wnum, dlmr,
201                    wp->sw.rw.mesval.brhcx - dx,
202                    wp->sw.rw.mesval.tlhcy,
203                    cp
204                    );
205                break;
206            case (int) Sresult:
207                cp = DadjStoa(mrtp->lval.S, 3, 0);
208                dx = DstrPixln(wp->wCharInfo.cFontno, cp);
209                dprintf(wp->wnum, dSmr,
210                    wp->sw.rw.mesval.brhcx - dx,
211                    wp->sw.rw.mesval.tlhcy,
212                    cp
213                    );
214                break;
215            default: break;
216        }
217        mrtp->state = 0;
218    }
219 }
220
221 void far
222 DSMRPut(mid, val)
223 int mid;
224 MRESULT val;  /* Note val may be one for several types (int, long, SCALED) */
225 {
226    register MRCtlB *mrtp;
227
228    XLock();
229    mrtp = &DMRLinkTab[mid];
230    mrtp->lval = val;
231    if (++mrtp->state > 0)
232    {
233        XPost(PID_DISPLAY, DISP_EV);
234    }
235    XUnLock();
236 }
```

```
Wed 10-13-86 15:00:26   DRESULT.H
    10-15-86 14:53:42

1  /*******************************************************************************
 2   *
 3   * MFO Ver 0.0
 4   *
 5   * module: dresult.h
 6   *
 7   * modification history : reason(s)
 8   *      date       by
 9   *    9-30-86     epr        creation
10   *
11   * This module is an original, unpublished work and is proprietary to
12   * NELLCOR INC., and may not be divulged or copied in any form
13   * whatsoever without the express written permission of NELLCOR INC.
14   *
15   * purpose :
16   *    To act as the common source of C language definitions of the result
17   *    window interface.
18   *
19   * data descriptions :
20   *
21   *
22   *******************************************************************************/
23
24  typedef enum {
25      noresult = 0,
26      iresult = 1,
27      lresult = 2,
28      sresult = 3,
29      Sresult = 3,
30      topresult
31      } MRType;
32
33  typedef struct scaled {int i1, i2} Scaled;
34
35  typedef union {
36      struct scaled S; /* Scaled result */
37      int i; /* integer result */
38      long l; /* long result */
39      } MRESULT;
40
41  #define NotActive -1
42
43  typedef struct {
44      int state; /* The link state ((0) => not linked, 0 => linked with
45                    no result pending, 1=> linked with result pending. */
46      MRType mtype;
47      MRESULT lval;
48      LWindow *mrwp;
49      long (far *acf) (); /* Alarm Conversion Function */
50      int pid; /* linking Processes Process I. D. */
51      int ticks; /* if expires put slash on number */
52
```

```
53           ) MRCtlB; /* Measure Result Control Block */
54
55    #define MaxMRs 13
56
57    void near DMRInit();
58    void near DStartMR();
59    void far  DSMRPut();
60    void far  DSMRLink();
61    void far  DSMRUnlink();
62    void far  DSMRClear();
63    void far  DSMRSlash();
64    void far  DSMRUnlinkF();
65    void far  DSMRDelateMR();
66    void near DispResults();
67
```

```
Wed 09-26-86 11:49:30  DRASTER.F               reason
    10-15-86 14:53:42
```

```
 1    .xlist
 2    .186
 3
 4    ;******************************************************************
 5
 6    MFQ Ver 0.0
 7
 8    Module: raster.f
 9
10    modification history :   reason(s)
11                  date   by   creation
12              8-23-86 epr
13
14              COPYRIGHT (C) 1986 NELLCOR INCORPORATED
15
16              This module is an original, unpublished work and is proprietary to
17              NELLCOR INC.; and may not be divulged or copied in any form
18              whatsoever without the express written permission of NELLCOR INC.
19
20    Purpose:
21              Definition of background rasters and line patterns.
22
23    Public Data:
24              DRasters[16]
25
26    ;******************************************************************
27
28
29    DFont segment word public 'font'
30
31    even
32    DRasters equ this word
33    dw DRaster0
34    dw DRaster1
```

```
36  dw  DRaster2
37  dw  DRaster3
38  dw  DRaster4
39  dw  DRaster5
40  dw  DRaster6
41  dw  DRaster7
42  dw  DRaster8
43  dw  DRaster9
44  dw  DRasterA
45  dw  DRasterB
46  dw  DRasterC
47  dw  DRasterD
48  dw  DRasterE
49  dw  DRasterF
50  dw  DRaster0
51
52  DRaster7 equ this word
53  DRaster8 equ this word
54  DRaster9 equ this word
55  DRasterA equ this word
56  DRasterB equ this word
57  DRasterC equ this word
58  DRasterD equ this word
59  DRasterE equ this word
60  DRasterF equ this word
61  DRaster0 equ this word
62
63  dw  0000000000000000b, 0000000000000000b
64  dw  0000000000000000b, 0000000000000000b
65  dw  0000000000000000b, 0000000000000000b
66  dw  0000000000000000b, 0000000000000000b
67  dw  0000000000000000b, 0000000000000000b
68  dw  0000000000000000b, 0000000000000000b
69  dw  0000000000000000b, 0000000000000000b
70  dw  0000000000000000b, 0000000000000000b
71  dw  0000000000000000b, 0000000000000000b
72  dw  0000000000000000b, 0000000000000000b
73  dw  0000000000000000b, 0000000000000000b
74  dw  0000000000000000b, 0000000000000000b
75  dw  0000000000000000b, 0000000000000000b
76  dw  0000000000000000b, 0000000000000000b
77  dw  0000000000000000b, 0000000000000000b
78  dw  0000000000000000b, 0000000000000000b
79
80  DRaster1 equ this word
81  dw  1111111111111111b, 1111111111111111b
82  dw  1111111111111111b, 1111111111111111b
83  dw  1111111111111111b, 1111111111111111b
84  dw  1111111111111111b, 1111111111111111b
85  dw  1111111111111111b, 1111111111111111b
86  dw  1111111111111111b, 1111111111111111b
87  dw  1111111111111111b, 1111111111111111b
88  dw  1111111111111111b, 1111111111111111b
89  dw  1111111111111111b, 1111111111111111b
90  dw  1111111111111111b, 1111111111111111b
91  dw  1111111111111111b, 1111111111111111b
```

```
92          dw      1111111111111111b, 1111111111111111b
93          dw      1111111111111111b, 1111111111111111b
94          dw      1111111111111111b, 1111111111111111b
95          dw      1111111111111111b, 1111111111111111b
96          dw      1111111111111111b, 1111111111111111b
97          dw      1111111111111111b, 1111111111111111b
98          dw      1111111111111111b, 1111111111111111b
99          dw      1111111111111111b, 1111111111111111b
100     DRaster2 equ this word
101         dw      1010101010101010b, 1010101010101010b
102         dw      0101010101010101b, 0101010101010101b
103         dw      1010101010101010b, 1010101010101010b
104         dw      0101010101010101b, 0101010101010101b
105         dw      1010101010101010b, 1010101010101010b
106         dw      0101010101010101b, 0101010101010101b
107         dw      1010101010101010b, 1010101010101010b
108         dw      0101010101010101b, 0101010101010101b
109         dw      1010101010101010b, 1010101010101010b
110         dw      0101010101010101b, 0101010101010101b
111         dw      1010101010101010b, 1010101010101010b
112         dw      0101010101010101b, 0101010101010101b
113         dw      1010101010101010b, 1010101010101010b
114         dw      0101010101010101b, 0101010101010101b
115         dw      1010101010101010b, 1010101010101010b
116         dw      0101010101010101b, 0101010101010101b
117         dw      1010101010101010b, 1010101010101010b
118         dw      0101010101010101b, 0101010101010101b
119         dw      1010101010101010b, 1010101010101010b
120         dw      0101010101010101b, 0101010101010101b
121         dw      1010101010101010b, 1010101010101010b
122     DRaster3 equ this word
123         dw      1100110011001100b, 1100110011001100b
124         dw      0011001100110011b, 0011001100110011b
125         dw      1100110011001100b, 1100110011001100b
126         dw      0011001100110011b, 0011001100110011b
127         dw      1100110011001100b, 1100110011001100b
128         dw      0011001100110011b, 0011001100110011b
129         dw      1100110011001100b, 1100110011001100b
130         dw      0011001100110011b, 0011001100110011b
131         dw      1100110011001100b, 1100110011001100b
132         dw      0011001100110011b, 0011001100110011b
133         dw      1100110011001100b, 1100110011001100b
134         dw      0011001100110011b, 0011001100110011b
135         dw      1100110011001100b, 1100110011001100b
136         dw      0011001100110011b, 0011001100110011b
137         dw      1100110011001100b, 1100110011001100b
138         dw      0011001100110011b, 0011001100110011b
139         dw      1100110011001100b, 1100110011001100b
140     DRaster4 equ this word
141         dw      1010010010010010b, 1010010010010010b
142         dw      0101001001001001b, 0101001001001001b
143         dw      1010100100100100b, 1010100100100100b
144         dw      0101010010010010b, 0101010010010010b
145         dw      1010101001001001b, 1010101001001001b
146         dw      0101010100100100b, 0101010100100100b
147         dw      1010101010010010b, 1010101010010010b
```

```
148     dw      0101001001001001b,      0101001001001001b
149     dw      0101010101010101b,      1001001001001001b
150     dw      0101010010010010b,      0101001001001001b
151     dw      1010010010010010b,      1010010100100100b
152     dw      0101001001001001b,      1010010100100100b
153     dw      1010010010010010b,      1010010100100100b
154     dw      0101001001001001b,      1010010100100100b
155     dw      0101010010010010b,      1010010100100100b
156     dw      0101010101010010b,      1010010100100100b
157     dw      0101010101010101b,      1010010100100100b
158     dw      0101010010010010b,      0101010100100100b
159     dw      0101010010010010b,      0101010100100100b
160
161 DRaster5 equ this word
162     dw      1010101010101010b,      1010101010101010b
163     dw      0101010101010101b,      0000000000000000b
164     dw      1010101010101010b,      1010101010101010b
165     dw      0101010101010101b,      0000000000000000b
166     dw      1010101010101010b,      1010101010101010b
167     dw      0101010101010101b,      0000000000000000b
168     dw      1010101010101010b,      1010101010101010b
169     dw      0101010101010101b,      0000000000000000b
170     dw      1010101010101010b,      1010101010101010b
171     dw      0101010101010101b,      0000000000000000b
172     dw      1010101010101010b,      1010101010101010b
173     dw      0101010101010101b,      0000000000000000b
174     dw      1010101010101010b,      1010101010101010b
175     dw      0101010101010101b,      0000000000000000b
176     dw      1010101010101010b,      1010101010101010b
177     dw      0101010101010101b,      0000000000000000b
178
179
180 DRaster6 equ this word
181     dw      0011001100110011b,      0011001100110011b
182     dw      1100110011001100b,      1100110011001100b
183     dw      1100110011001100b,      1100110011001100b
184     dw      0011001100110011b,      0011001100110011b
185     dw      0011001100110011b,      0011001100110011b
186     dw      1100110011001100b,      1100110011001100b
187     dw      1100110011001100b,      1100110011001100b
188     dw      0011001111110011b,      0011001111110011b
189     dw      0011001100110011b,      0011001100110011b
190     dw      1100110011001100b,      1100110011001100b
191     dw      1100110011001100b,      1100110011001100b
192     dw      0011001100110011b,      0011001100110011b
193     dw      0011001100110011b,      0011001100110011b
194     dw      1100110011001100b,      1100110011001100b
195     dw      1100110011001100b,      1100110011001100b
196     dw      0011001100110011b,      0011001100110011b
197
198 DFont ends
199
```

```
Wed  09-04-86 15:16:10  DRASTER.1                           reason
     10-15-86 14:53:42

1          .186
 2          .xlist
 3
 4   ;*************************************************************
 5   ;
 6       MFQ Ver 0.0
 7
 8       Module: draster.i
 9
10       modification history :     reason(s)
11            date       by
12            8-24-86   epr          creation -- oh my God will this ever be done on
13                                              time.
14
15            COPYRIGHT (C) 1986 NELLCOR INCORPORATED.
16
17            This module is an original, unpublished work and is proprietary to
18            NELLCOR INC., and may not be divulged or copied in any form
19            whatsoever without the express written permission of NELLCOR INC.
20
21       Purpose:
22            To provide a common source of definitions for raster constants
23            in the display server.
24
25       Procedures:
26
27       Public Data:
28
29   ;*************************************************************
30
31   TRaster   equ 0ffffh - (2 * 2 * 16) + 1
32   RWColLength equ 200h  ; 512 bytes
33
34
35

Wed  10-10-86 09:30:00  DRASTER.5                           reason
     10-15-86 14:53:42

1          .186
 2          .xlist
 3
 4   ;*************************************************************
 5   ;
 6       MFQ Ver 0.0
 7
 8       Module: draster.s
 9
10       modification history :     reason(s)
11            date       by
```

```
12        7-15-86 epr       creation -- this is happing all too late.
13
14        COPYRIGHT (C) 1986 NELLCOR INCORPORATED
15
16        This module is an original, unpublished work and is proprietary to
17        NELLCOR INC., and may not be divulged or copied in any form
18        whatsoever without the express written permission of NELLCOR INC.
19
20   Purpose:
21        This module will hold all the raster related operations for
22        the display server, except for those specificly related to text.
23        (Text raster operations are in dtext.s)
24
25   Procedures:
26        Public _DRasterCopy
27        (SrcPlane, SrcFirstCorner, SrcSecondCorner, DstPlane, DstFirstCorner)
28             This procedure copies, within one display plane, an arbitrary
29             bit block to another location with that plane.
30
31        Public _DWColCopy
32        (bit shift at destination, height of column, source address,
33        destination address, display plane segment,
34        source mask, SrcPlane, DstPlane)
35
36        Public _DRasterFill
37        (Plane, DstFirstCorner, DstSecondCorner, Pattern) -- This
38             procedure fills an arbitrary area within a display plane, with one
39             of 32 by 16 bit patterns.
40        Public _DCopyRasterPatch, DLoadRaster
41        -- Local procs to _DRasterFill
42
43        Public _DrawVertLine
44        (Plane, StartPoint, Length, Pattern) -- Draws a vertitcal line.
45
46        Public _DrawHortLine
47        (Plane, StartPoint, Length, Pattern) -- Draws a Horizontal line.
48
49        Public _DrawLine
50        (Plane, StartPoint, EndPoint, Pattern) -- Draws a Horizontal line.
51
52        Public _Dot
53        (Plane, X, Y, Val) -- plots a zero or one value at (Plane, X, Y)
54        if val == 0 it plots a zero, otherwise it plots a one.
55
56   Public Data:
57        Public DLinePatterns
58        Public DEndMasks, DShiftMasks, DStartMasks
59
60   ;*****************************************************************
61
62   include draster.i
63   include draster.f
64   include dwindow.i
65
66
67   CONST segment word public 'CONST'
```

```
 68          even
 69          DLinePatterns equ this word
 70          dw      1111111111111111b
 71          dw      1010101010101010b
 72          dw      1100110011001100b
 73          dw      1001100110011001b
 74          dw      1111000011110000b
 75          dw      1110000111000011b
 76          dw      1100001111000011b
 77          dw      1000011110000111b
 78          dw      1111111100000000b
 79          dw      0001111111100000b
 80          dw      0101010110101010b
 81          dw      1010100101010101b
 82          dw      1110000111100111b
 83          dw      0111000011110001b
 84          dw      0111100011100111b
 85          dw      1011000111100111b
 86          dw      1010101010101010b
 87          dw      0000000000000000b
 88          DEndMasks equ this word
 89          dw      00000h, 0c000h, 0e000h
 90          dw      0f000h, 0f800h, 0fc00h
 91          dw      0fe00h, 0ff00h, 0ff80h
 92          dw      0ffc0h, 0ffe0h, 0fff0h
 93          dw      0fff8h, 0fffch, 0fffeh
 94
 95          DShiftMasks equ this word    ; index both foward and bacwards
 96          dw      0ffffh, 07fffh, 03fffh, 01fffh
 97          dw      00fffh, 007ffh, 003ffh, 001ffh
 98          dw      000ffh, 0007fh, 0003fh, 0001fh
 99          dw      0000fh, 00007h, 00003h, 00001h
100
101          dw      0ffffh, 0fffeh, 0fffch, 0fff8h
102          dw      0fff0h, 0ffe0h, 0ffc0h, 0ff80h
103          dw      0ff00h, 0fe00h, 0fc00h, 0f800h
104          dw      0f000h, 0e000h, 0c000h, 08000h
105
106          dw      00000h, 00001h, 00003h, 00007h
107          dw      0000fh, 0001fh, 0003fh, 007fh
108          dw      000ffh, 001ffh, 003ffh, 007ffh
109          dw      00fffh, 01fffh, 03fffh, 07fffh
110
111          CONST ends
112
113          _DATA segment word public 'DATA'
114          _DATA ends
115
116          _BSS  segment word public 'BSS'
117          even
118
119          DSrcMask dw ? ; temoprary location for a source mask
```

```
124         _BSS ends
125
126         DGROUP Group CONST, _DATA, _BSS
127
128         SYS_TEXT segment byte public 'Code'
129
130         assume CS:SYS_TEXT, DS:nothing, SS:DGROUP, ES:nothing
131
132 ;******************************************************************
133 ; Function:  DRasterCopy -- C callable.
134 ;            (Plane, SrcFirstCorner, SrcSecondCorner, DstFirstCorner) -
135 ;            This procedure copies, within one display plane, an arbitrary
136 ;            bit block to another location with that plane.
137 ;
138 ; Algorithm -
139 ;     Givens: each display plane is 64K bytes of which the first 40K is
140 ;             displayed.  Word address progress vertically down the screen from
141 ;             0 to 1ffh, and then go to the top of the screen, but 16 pixels over
142 ;             to the right.  Therefor the Nth column of 16th pixel wide columns goes
143 ;             from 2N100h to 2N1ffh + 1ffh.
144 ;
145 ;     Determine the first hort. word boundry (FHWB)
146 ;     sFHWB = ((SFCx / 16) * 200h) + SFCy * 2 = ((SFCx >> 4) << 9) + (SFCy << 1)
147 ;     Determine the Start Bits Width (SBW)
148 ;     SBW = SFCx and 0fh
149 ;     Determine Start Bit Mask (SBM)
150 ;     SBM = DStartMask[SBW]
151 ;
152 ;     Determine the last hort. word boundry (LHWB)
153 ;     LHWB = ((SSCx / 16) * 200h) + SFCy * 2 = ((SSCx >> 4) << 9) + (SFCy << 1)
154 ;     Determine the End Bits Width (EBW)
155 ;     EBW = SSCx and 0fh
156 ;     Determine Start Bit Mask (EBM)
157 ;     EBM = EndMasks[EBW]
158 ;
159 ;     Determine Delta Y (DY)
160 ;     DY = SFCy - SSCy + 1
161 ;     Determine Delta X (DelX)
162 ;     DelX = SFCx - SSCx + 1
163 ;
164 ;     Determine the Destination Hort. Word Boundry (DHWB)
165 ;     dFHWB = = ((DFCx / 16) * 200h) + DFCy * 2 = ((DFCx >> 4) << 9) + (DFCy << 1)
166 ;
167 ;     Copy Stuff before sFHWB (horizontally)
168 ;     This involves DY Reads, Masks, Rotations, Read Modifies, and Writes.
169 ;
170 ;     Copy Stuff between sFHWB and sLHWB
171 ;     This Involves (sLHWB - sFHWB (8mh)) * DY Reads, Rotations, Read Modifies, and
172 ;     Writes.
173 ;
174 ;     Copy Stuff after LHWB (horizontally)
```

```
;----
; This involves DY Reads, Masks, Rotations, Read Modifies, and Writes.
;----
; Parameter Loctions on Entry:
;       x equ 0 ; offset for x element of structures
;       y equ 2 ; offset for y element of structures
        DRCSrcPlane equ bp + 4
        SFC equ bp + 6             ; source First Corner
        SFCx equ SFC + x
        SFCy equ SFC + y
        SSC equ bp + 10            ; Source Second Corner
        SSCx equ SSC + x
        SSCy equ SSC + y
        DRCDstPlane equ bp + 14
        DFC equ bp + 16            ; Destination First Corner
        DFCx equ DFC + x
        DFCy equ DFC + y ;Local Variables sFHWB equ bp -2              ; src First Hort Word Boundry
sLHWB equ bp -4              ; src Last Hort Word Boundry
dFHWB equ bp -6              ; dst First Hort Word Boundry
dLHWB equ bp -8              ; dst Last Hort Word Boundry
DelY equ bp -12              ; Delta Y
DelX equ bp -14              ; Delta X
sSBW equ bp -16              ; src Start Bit Width
sEBW equ bp -18              ; src End Bit Width
dSBW equ bp -22              ; dst Start Bit Width
dEBW equ bp -24              ; dst End Bit Width
sStartMask equ bp -26        ; src Start Mask
sEndMask equ bp -28          ; src End Mask
dStartMask equ bp -30        ; dst Start Mask
dEndMask equ bp -32          ; dst End Mask
DRCStackAlloc equ 34

;*************************************************************

_DRasterCopy proc near
        enter   DRCStackAlloc, 0
        push    ds
        push    es
        push    di
        push    si mov     ds, ss:[DRCSrcPlane]
        mov     es, ss:[DRCDstPlane]

mov     bx, ss:[SFCx]     ; get start x
        mov     cx, ss:[SSCx]     ; get end x
        sub     cx, bx
        inc     cx                ; calc DelX
        mov     ss:[DelX], cx ExtractSrcStartBitMask:
```

```
236         mov     al, bl
237         and     ax, 0fh
238         mov     ss:[sSBW], ax          ; # of bits that before word boundry
239         shl     si, 1
240         mov     ax, ss:DStartMasks[si]
241         mov     ss:[sStartMask], si
242 SaveStartMask:  ; # bits to right of word.
243 ; Calc the Source First Hort Word Boundry.  See Above.
244         xor     bl, al
245         shl     bx, 5
246         add     bx, dx
247         add     bx, dx
248         mov     ss:[sFHWB], bx
249
250         mov     bx, ss:[SSCx]          ; get end x
251         mov     al, bl
252         and     ax, 0fh                ; extract start bit mask
253         mov     di, ax
254         shl     di, 1
255         mov     di, ss:DEndMasks[di]
256 DRCSaveEndMask:
257 Public DRCSaveEndMask
258         mov     ss:[sEndMask], di
259
260 ; Calc Delta Y, see equation above.
261         mov     cx, ss:[SSCy]          ; cx = DY = (SSCy - SFCy + 1)
262         sub     cx, dx
263         inc     cx
264         mov     ss:[DelY], cx
265         and     bx, 0fff0h
266         shl     bx, 5
267         add     bx, dx
268         add     bx, dx
269         mov     [sLHWB], bx
270
271         mov     bx, ss:[DFCx]          ; get dst start mask
272         mov     al, bl
273         and     ax, 0fh
274         mov     ss:[dpSBB], ax
275         mov     di, 1
276         mov     di, ss:DStartMasks[di]
277 ExtractDstStartBitMask:
278         mov     ss:[dEndMask], di      ; extract start bit mask
279         xor     bl, al
280         shl     bx, 5
281         mov     dx, ss:[DFCy]
282         add     bx, dx
283         add     bx, dx
284         mov     ss:[dFHWB], bx
285         cmp     bx, ss:[sLHWB]
286 SaveDstStartMask:
```

```
2292            ja      DRCFirstPart
2293            add     bx,2                    ; one word over is ok for start
2294            cmp     bx,ss:[sFHWB]
2295            jbe     DRCFirstPart
2296
2297            mov     cx,ss:[DelX]
2298            add     cx,ax
2299            mov     ax,cx
2300            add     cx,0fff0h
2301            xor     ax,cx
2302            mov     ss:[dEBW],ax
2303            mov     ax,cx
2304            mov     di,1
2305            shl     di,1
2306            mov     ax,ss:DEndMasks[di]
2307            mov     ss:[dEndMask],ax
2308            mov     cx,5
2309            add     bx,cx
2310            mov     ss:[dLHWB],bx
2311            jmp     DRCReverse
2312
2313  DRCOneWord:
2314            and     dx,ss:[sEndMask]
2315            call    DWColCopy
2316            jmp     DRCExit
2317
2318  DRCFirstPart:
2319  Public DRCFirstPart
2320            mov     si,ss:[sFHWB]
2321            mov     di,ss:[dFHWB]
2322            mov     cx,ss:[DelY]
2323            mov     ax,ss:[dSBW]
2324            mov     ax,ss:[sSBW]   ; first bit shift = src start bit width - dSBW
2325            sub     ax,ss:[sStartMask]
2326            mov     dx,ss:[DelX],16
2327            cmp     word ptr ss:[DelX],16
2328            jle     DRCOneWord
2329
2330  ; Parameters for DWColCopy
2331  ;         ax = bit shift at destination
2332  ;         cx = height of column
2333  ;         ds:si = source address
2334  ;         es:di = destination address
2335  ;         ds = src display plane segment
2336  ;         es = dst display plane segment
2337  ;         dx = source mask
2338            call    DWColCopy
2339
2340  DRCMidLoopSetup: ; Set loop count = DelX in words.
2341  Public DRCMidLoopSetup
2342            mov     cx,ss:[DelX]            ; To get word count get delta x
2343            add     cx,16                   ; add one word width then
2344            sub     cx,ss:[sSBW]            ; subtract src start bit width
2345            js      DRCExit
2346            mov     cx,4                    ; cx = (DelX - left bits - right bits)/16
2347            shr     DRCEndPart
```

```
348  DRCMidLoop:
349         push    cx
350         ; see DWColCopy parameters above.
351         add     ss:[sFHWB], DColBytes
352         add     ss:[dFHWB], DColBytes
353         mov     si, ss:[sFHWB]
354         mov     di, ss:[dFHWB]
355         mov     cx, ss:[DelY]
356         mov     ax, ss:[dSBW]
357         mov     ax, ss:[sSBW]
358         sub     ax, ss:[sSBW]
359         mov     dx, 0ffffh
360
361         call    DWColCopy
362
363         pop     cx
364         loop    DRCMidLoop
365
366 DRCEndPart:
367 Public DRCEndPart
368         mov     si, ss:[sFHWB]
369         add     si, DColBytes
370         mov     di, ss:[dFHWB]
371         add     di, DColBytes
372         mov     cx, ss:[DelY]
373         mov     ax, ss:[dSBW]
374         mov     ax, ss:[sSBW]
375         sub     ax, ss:[sSBW]
376         mov     dx, ss:[sEndMask]
377
378         call    DWColCopy
379
380 DRCExit:
381         pop     si
382         pop     di
383         pop     es
384         pop     ds
385         leave
386         ret
387
388 DRCReverse:
389 DRCRightPart:
390 Public DRCRightPart
391         mov     si, ss:[sLHWB]
392         mov     di, ss:[dLHWB]
393         mov     cx, ss:[DelY]
394         mov     ax, ss:[dSBW]
395         mov     ax, ss:[sSBW]
396         sub     ax, ss:[sSBW]
397         mov     dx, ss:[sEndMask]
398
399
400         ; Parameters for DWColCopy
401         ;       ax = bit shift at destination    ; first bit shift at destination
402         ;       cx = height of column
403                                                  ; first bit shift = src start bit width - dSBW
```

```
404                    ;         si = source address
405                    ;         di = destination address
406                    ;         ds = src plane segment
407                    ;         es = dst plane segment
408                    ;         dx = source mask
409                            call    DWColCopy
410
411
412     DRCRMidLoopSetup:  ; Set loop count = Delx in words.
413     Public DRCRMidLoopSetup
414                            mov     cx, ss:[Delx]     ; To get word count get delta x
415                            sub     cx, ss:[sEBW]     ; subtract end start bit width
416                            js      DRCExit
417                            shr     cx, 4             ; cx = (Delx - left bits - right bits)/16
418                            jz      DRCREndPart
419
420     DRCRMidLoop:
421                            push    cx
422                            ; see DWColCopy parameters above.
423                            sub     ss:[sLHWB], DColBytes
424                            sub     ss:[dLHWB], DColBytes
425                            mov     si, ss:[sLHWB]
426                            mov     di, ss:[dLHWB]
427                            mov     cx, ss:[DelY]
428                            mov     ax, ss:[dSBM]
429                            mov     ax, ss:[sSBM]
430                            sub     dx, 0ffffh
431                            mov
432
433                            call    DWColCopy
434
435                            pop     cx
436                            loop    DRCRMidLoop
437
438     DRCREndPart:
439     Public DRCREndPart
440                            mov     si, ss:[sLHWB]
441                            mov     si, DColBytes
442                            mov     di, ss:[dLHWB]
443                            sub     di, DColBytes
444                            mov     cx, ss:[DelY]
445                            mov     ax, ss:[dSBM]
446                            mov     ax, ss:[sSBM]
447                            mov     dx, ss:[sStartMask]
448
449                            call    DWColCopy
450                            jmp     DRCExit
451     _DRasterCopy endp
452
453     ;***********************************************************
454     ;
455     ;   Procedure:
456     ;       DRasterFill(Plane, tlhc, brhc, Pat)  - takes a video plane a
457
458
459
```

```
460  ;
461  ;   Top and bottom corners and a raster pattern.  It fills the
462  ;   square with the specified pattern.
463  ;
464  ; Agorithm:
465  ;   Raster patterns are 32 bits wide by 16 bits high.  The approch
466  ;   is to break the area to be filled into patchs that are 32 bits
467  ;   wide and 16 bits high.  The to fill each one of these using
468  ;   DWColCopy.  The raster of interest is always copied to the
469  ;   last 32 word of the display plane.
470  ;
471  ; Entry:
472  ;   x    equ  0
473  ;   y    equ  2
474  ;   DRFPlane equ bp + 4
475  ;   tlhc  equ bp + 6
476  ;   tlhcx equ tlhc + x           ; Top Left Hand Corner
477  ;   tlhcy equ tlhc + y
478  ;   brhc  equ bp + 10
479  ;   brhcx equ brhc + x           ; Bottom Right Hand Corner
480  ;   brhcy equ brhc + y
481  ;   pat   equ bp + 14
482  ;
483  ; Local:
484  ;   lx   equ bp - 2              ; local x
485  ;   ly   equ bp - 4              ; local y
486  ;   xend equ bp - 6
487  ;   yend equ bp - 8
488  ;
489  ; Constants:
490  ;   DRFStackAlloc equ 12
491  ;   rwidth  equ 32              ; raster width
492  ;   rwmask  equ 31              ; raster width mask
493  ;   rheight equ 16              ; raster height
494  ;   rhmask  equ 15              ; raster height mask
495  ;
496  ;**********************************************************************
497
498  DRasterFill proc near
499    enter DRFStackAlloc, 0
500    push  ds
501    push  es
502    push  di
503    push  si
504    call  DLoadRaster             ; local -- uses this bp.
505
506  DRFLoop0Setup: ; for (lx = tlhc.x; lx (<= brhc.x;) {
507    mov   ax, ss:[tlhc.x]
508    mov   ss:[lx], ax
509  DRFLoop0:
510    cmp   ax, ss:[brhc.x]
511    jg    DRFExit
512                                  ; move x from right to left
513                                  ; check for end of loop
514  ; xend = x - rsx + rwidth - 1   ; fill width upto 32 pixels
515    or    ax, rwmask              ; allow only properly specd. fills.
```

```
5516            ; if (xend > brhc.x) xend = brhc.x;
5517                    cmp     ax, ss:[brhc.x]
5518                    jbe     DRFNotXend
5519                    mov     ax, ss:[brhc.x]
5520    DRFNotXend:
5521                    mov     ss:[xend], ax
5522
5523            ; rex = xend & rwmask;
5524
5525    DRFLoop1Setup:  ; for (ly = tlhc.y; ly <(= brhc.y; ) {
5526                    mov     ax, ss:[tlhc.y]         ; move y from top to bottom
5527                    mov     ss:[ly], ax
5528    DRFLoop1:
5529                    mov     ax, ss:[brhc.y + y]
5530                    cmp     ax, rwmask              ; check for end of inner loop
5531                    jg      DRFLoop1Exit            ; allow only properly speced. fills
5532
5533            ; yend = y - rsy + rheight - 1;
5534                    or      ax, rwmask
5535
5536            ; if (yend > brhc.y) yend = brhc.y
5537                    cmp     ax, ss:[brhc.y]
5538                    jle     DRFNotYend
5539                    mov     ax, ss:[brhc.y + y]
5540    DRFNotYend:
5541                    mov     ss:[yend], ax
5542
5543                    call    LCopyRasterPatch        ; local -- uses current bp
5544
5545                    mov     ax, ss:[yend]
5546                    inc     ax
5547                    mov     ss:[lx], ax
5548                    jmp     DRFLoop0
5549    DRFLoop1Exit:
5550                    mov     ax, ss:[xend]
5551                    inc     ax
5552                    mov     ss:[lx], ax
5553                    jmp     DRFLoop1
5554    DRFLexit:
5555                    pop     si
5556                    pop     di
5557                    pop     es
5558                    pop     ds
5559                    leave
5560                    ret
5561
5562    ; Entry: ss:bp is base of vars of interest
5563    ; Exit: es == Plane, Pat in temp Raster
5564
5565    DLoadRaster     proc near   ;   -- local to DRasterFill
5566                    mov     es, ss:[DRFPlane]
5567                    mov     bx, ss:[Pat]
5568                    shl     bx, 1
```

```
572             mov     ax, DFont
573             mov     ds, ax
574     assume ds:DFont
575             mov     si, DRasters[bx]
576
577             mov     di, TRaster
578             cmp     bx, word ptr es:[di - 2]
579             je      DLRexit
580
581             mov     word ptr es:[di - 2], 4x
582
583             mov     dx, si                  ; save for Right raster loop
584             mov     cx, 16
585
586     LeftRasterLoop:
587             movsw
588             add     si, 2                   ; get next word in left raster
589             loop    LeftRasterLoop
590
591             mov     si, dx                  ; get start of raster
592             mov     cx, 16
593
594     RightRasterLoop:
595             movsw
596             add     si, 2                   ; get next word in right side of raster
597             loop    RightRasterLoop
598
599
600     DLRexit:
601             mov     ds, ss:[DRFPlane]
602             ret
603     DLoadRaster     endp
604
605     assume ds:nothing
606
607     ;****************************************************************
608     ; Function: DCopyRasterPatch -- copies rasters that are 32 by 16
609     ;   bit wide copies of the current raster pattern. This routine is
610     ;   local to DRasterFill, and uses its local variables.
611     ; Algorithm: Determine which part of raster to copy and copy it
612     ;   using DoColCopy.
613     ; Entry: ss:bp is base of vars of interest
614     ;        es, ss = Plane, Pattern copied to patch
615     ; Exit:  nothing
616     ;****************************************************************
617
618     assume CS:SYS_TEXT, DS:nothing, SS:DGROUP, ES:nothing
619
620     DCopyRasterPatch proc near      ; -- local to DRasterFill
621             mov     cx, ss:[ix]
622             mov     dx, ss:[xend]
623             mov     di, cx
624             and     cx, rwmask      ; source mask index
625             mov     ax, cx          ; save start bit offset
626             sub     di, cx          ; get source x word
```

```
6628         sub     dx, di          ; dx = (lx % 16) + delta x
6629         inc     dx
6630         shl     di, 5           ; di = ((wordof x) << 5)==((x %16) * 512) == (x >> 4) << 9
6631         and     cx, 0fh         ; reduce cx to word mask
6632         mov     bx, cx
6633         shl     bx, 1
6634         mov     cx, ss:DStartMasks[bx]
6635         mov     ss:DSrcMask, cx
6636
6637         mov     si, TRaster;    get source offset
6638         mov     bx, ss:[ly]
6639         mov     cx, bx
6640         and     cx, rhmask
6641         add     si, cx          ; si = source word offset
6642         and     si, 0ffffeh     ; make it a word offset!
6643         mov     cx, ss:[yend]
6644         sub     cx, bx          ; height = yend - y + 1
6645         mov     bx, 1
6646         shl     di, bx          ; each y is one word
6647                                 ; dst addr = (x & 0ff00h) + (y & 0feh)

6649         sub     dx, 16          ; dx = remaining width after Col Copy
6650         cmp     ax, 16
6651         jl      DCRFOneCol
6652         mov     ax, DCRFFullCopy ; if width < 16 get a different mask
6653         mov     bx, dx          ; get end mask index
6654         shl     bx, 1
6655         mov     dx, ss:DEndMasks[bx]
6656         and     dx, ss:DSrcMask
6657         jmp     short DCRP2ndCol
6658 DCRPOneCol:
6659         mov     bx, dx
6660         add     bx, 16
6661         shl     bx, 1
6662         mov     ax, ss:DEndMasks[bx]
6663         and     ss:DSrcMask, ax
6664 DCRPFullCopy:
6665         xor     ax, ax          ; bit shift always zero!
6666
6667 ; Parameters for DWColCopy
6668 ;       ax = bit shift at destination
6669 ;       cx = height of column
6670 ;       si = source address
6671 ;       di = destination address
6672 ;       es = dst display plane segment
6673 ;       ds = src display plane segment
6674 ;       dx = source mask
6675
6676         push    cx              ; save height
6677         push    di              ; save dst address
6678         push    dx              ; save remaining width
6679         push    si              ; save src address
6680         mov     dx, ss:DSrcMask
6681
6682         call    DWColCopy
```

```
684             pop     si
685             pop     dx
686             pop     di
687             pop     cx
688
689             or      dx, dx
690             jle     DCRFExit
691             mov     bx, dx
692             shl     bx, 1
693             mov     dx, ss:DEndMasks[bx]
694 DCRP2ndCol:
695             add     di, RWColLength
696             add     si, 32   ; a raster is 32 words or 64 bytes so move 1/2
697             mov     ax, ax
698
699             call    RWColCopy
700
701 DCRFExit:
702             ret
703
704 DCopyRasterPatch endp
705
706
707 _DRasterFill endp
708
709
710 ;*******************************************************************************
711 ;*******************************************************************************
712 ;
713 ; Procedure:
714 ;       RWColCopy --- Copy a word column with source mask and bit
715 ;       boundry in destination word. The screen is organized in
716 ;       columns of words. This routine serves as the foundation
717 ;       for other bit block moves in the dispaly server.
718 ;
719 ; Alogrithm:
720 ;       The source is always on a word boundry with a source
721 ;       mask (dx) specifing which of these bits are of interest.
722 ;       These SIXTEEN bits are going to some arbitarty SIXTEEN
723 ;       bits somewhere in the image plane. The destination 16
724 ;       bits are specified by es:di and the bit shift in reg ax.
725 ;       The source 16 bits are specified by es:si. Reg cx specifies
726 ;       the number of 16 bit moves (max. is 256). To move one 16 bit
727 ;       chunk do the folowing:
728 ;               S16 = *(es:si)
729 ;               S16 = S16 & Source Mask
730 ;               if (bit_shift ( 0) D16 = *(es:di) with stuff for non-word
731 ;                       boundry destinations.
732 ;               D16 = D16 % not Source Mask
733 ;               D16 := D16 ¦ S16
734 ;               *(es:di++) = D16 with that magic.
735 ;
736 ; Entry:
737 ;       ax = bit shift at destination
738 ;       cx = height of column
739 ;       si = source address
740 ;       di = destination address
```

```
                ds = src display plane segment
                es = dst display plane segment
                dx = source mask
;***********************************************************
assume ds:nothing, es:nothing, ss:DGROUP DWColCopy proc near
        push    bp
        mov     ch,-cl
        mov     cl, al
        mov     bx, ax
        shl     bx, 1
        jz      DstWidth_eq_SrcWidth
        mov     bp, ss:DShiftMasks[bx]
        or      ax, ax
        js      DstWidth_gt_SrcWidth    ; requires left rotation SrcWidth_gte_DstWidth:
        cmp     dx, 0ffffh
        je      DWCC_gtLoop
        jmp     DWCC_gtMasked
DWCC_gtLoop:
        lodsw
        mov     ax, cl
        and     ax, bx
        not     ax
        and     bp
                                ; first word
        and     bx, bp
        mov     dx, es:[di]
        and     ax, bp
        or      bx, dx
        stosw
        mov     dx, es:[di + DColBytes - 2] ; 200h - 2 after auto increment
        and     dx, bp
        or      bx, dx
        mov     es:[di + DColBytes - 2], bx
        dec     ch
        jnz     DWCC_gtLoop
        jmp     short DWCCExit DstWidth_eq_SrcWidth:    ; easy case need worry only about source mask
        mov     bp, dx
        not     dx
        xchg    cl, ch DWCC_eqLoop:
        lodsw
        and     ax, bp  ; mask off source
        mov     bx, es:[di]
        and     bx, dx  ; mask off dst
```

```
795             or      ax, bx          ; put src and dst together
796             stosw                   ; store them
797             loop    DWCC_eqLoop
798             jmp     short DWCCExit
799
800 DstWidth_gt_SrcWidth:                ; like above except go left rather than right.
801             neg     cl
802             cmp     dx, 0ffffh
803             je      DWCC_ltLoop
804             jmp     DWCC_ltMasked
805
806 DWCC_ltLoop:
807             lodsw
808             rol     ax, cl
809             mov     bx, ax
810             and     ax, bp
811             not     bp
812             mov     dx, es:[di]
813             and     dx, bp
814             and     bx, bp
815             or      ax, dx
816             not     bp
817             stosw
818             mov     dx, es:[di - (DColBytes + 2)]  ; on back shift we want same mask
819             and     dx, bp
820             and     bx, dx
821             mov     es:[di - (DColBytes + 2)], bx
822             dec     ch
823             jnz     DWCC_ltLoop
824
825 DWCCExit:
826             pop     bp
827   ;         pop     ds
828             ret
829
830 DWCC_ltMasked:
831   ;         pop     dx, cl
832 DWCC_gtMaskedLoop:
833             mov     ax, dx
834             and     bx, dx
835             not     ax
836             mov     ax, bp
837             not     bp
838             mov     bx, bp
839             and     bx, bp
840             or      es:[di], ax
841             mov     es:[di + DColBytes], bx
842
843             rol     ax, cl                         ; align ax for destination
844             and     dx, ax          ; mask off source ; need two copies for two dst words
845             not     bx, ax                           ; do the opposite of second word.
846             and     bx, bp                           ; mask of second word is opposite
847             lodsw
848   ; first word
             and     ax, bp                             ; mask off bits not in this word
```

```
849              or    es:[di], ax
850              or    es:[di + DColBytes], bx   ; store them
851              add   di, 2
852              dec   ch
853              jg    DWCC_gtMaskedLoop
854              jmp   DWCCExit
855
856    DWCC_ltMasked:
857              rol   dx, cl
858    DWCC_ltMaskedLoop:
859              mov   ax, dx
860              mov   bx, dx
861              and   ax, bp
862              not   ax
863              not   bp
864              and   bx, bp
865              not   bp
866              and   es:[di], ax
867              and   es:[di - DColBytes], bx
868              lodsw
869              rol   ax, cl          ; allow only mask bits
870              and   ax, dx
871              mov   bx, ax
872              and   bx, bp
873              not   bp
874              and   ax, bp
875              not   bp
876              or    es:[di], ax
877              or    es:[di - DColBytes], bx
878              add   di, 2
879              dec   ch
880              jg    DWCC_ltMaskedLoop
881              jmp   DWCCExit
882
883    DWColCopy endp
884
885    assume ds:DGroup
886
887    ;*********************************************************************
888    ;*********************************************************************
889    ; Procedure:
890    ;    DrawHorLine(Plane, StP, length, pattern) --
891    ;       draws a line from StP of length with pattern.
892    ;
893    ; Algorithm:
894    ;    Break problem into three parts:
895    ;    1) Partial start word = #DFW & (not StartMask) ; pat & StartMask
896    ;    2) fill middle words with pat
897    ;    3) Partial end word with pattern etc. (as above)
898    ;
899    ; Entry: x equ 0 ; offset of x in point strcture
900    ;        y equ 2 ; offset of y in point strcture
901    ;        LblPlane equ bp + 4
```

```
;******************************************************************
;
;   _DrawHLine proc near                    ; Start Point
        StP     equ bp + 6
        StPx    equ StP + x
        StPy    equ StP + y
        length  equ bp + 10
        Pat     equ bp + 12
;******************************************************************
;
_DrawHLine proc near
        enter   0, 0
        push    es
        push    di
        push    si mov     ax, ss:[DHLPlane]
        mov     es, ax
        mov     ax, ss:[StP + x]
        mov     di, ss:[StP + y]
        shl     di, 1                   ; y word offset
        mov     si, ss:[length]
        mov     dx, ax
        and     dx, 0fffh
        shl     dx, 5                   ; dx = (x % 16) * 512
        add     di, dx                  ; di = addr (r dst start word
        mov     bx, ss:[Pat]
        shl     bx, 1
        mov     dx, DLinePatterns[bx]
        and     ax, 0fh
        jz      DHLStartOnWord mov     bx, ax
        shl     bx, 1
        mov     cx, DStartMasks[bx]
        sub     ax, 16
        add     si, ax                  ; si = remaining length after we do start word
        jl      DHLLineInOneWord DHLStartNotEndOfWord:
        mov     bx, cx
        not     bx
        mov     ax, es:[di]
        and     ax, bx
        or      ax, dx
        mov     ax, cx                  ; mask off unwanted bits
        and     ax, dx                  ; trun on selected bits in dst word
        or      es:[di], cx
        mov     di, DColBytes DHLStartOnWord:
        mov     cx, si
        and     si, 0fh
        shr     cx, 4
        jz      DHLEndWord DHLWordStoreLoop:
        mov     es:[di], dx
        add     di, DColBytes
```

```
961             loop    DHLWordStoreLoop
962                     or      si, si
963                     jle     DHLExit
964                     shl     si, 1
965                     mov     cx, DEndMasks[si]
966
967
968     DHLEndStore:
969                     mov     bx, cx
970                     not     bx
971                     mov     ax, es:[di]
972                     and     ax, bx
973                     and     cx, dx
974                     or      ax, cx          ; trun on ; mask off unwanted bits
975                     mov     es:[di], cx     ; trun on selected bits in dst word
976                                             ; trun on selected bits in dst word
977     DHLExit:
978                     pop     si
979                     pop     di
980                     pop     es
981                     leave
982                     ret
983
984     DHLLineInOneWord:
985                     add     si, 16          ; line fits in one word!
986                     shl     si, 1
987                     and     cx, DEndMasks[si]
988                     jmp     short DHLEndStore
989
990     DHLEndWord:
991                     shl     si, 1
992                     mov     cx, DEndMasks[si]
993                     jmp     short DHLEndStore
994
995     DrawHorzLine endp
996
997     ;************************************************************************
998     ;
999     ; Procedure:
1000    ;       DrawVertLine(Plane, StP, length, Pattern) --
1001    ;       draws a line from StP of length with pattern, and width
1002    ;
1003    ; Entry:
1004    ;       DVLPlane equ bp + 4
1005    ;       StP equ bp + 6
1006    ;       length equ bp + 10
1007    ;       Pat equ bp + 12
1008    ;       x equ 0
1009    ;       y equ 2
1010    ;
1011    ;************************************************************************
1012
1013    DrawVertLine proc near
1014                    enter   0, 0
1015                    push    es
1016
```

```
1017            push    di
1018            push    si
1019
1020            mov     es, ss:[DVLPlane]
1021            mov     ax, ss:[StP + x]
1022            mov     cx, ax
1023            and     ax, 0fff0h
1024            shl     ax, 5   ; ax = (x % 16) * 512
1025            mov     di, ss:[StP + y]
1026            shl     di, 1
1027            shl     di, 1
1028            add     di, ax          ; es:di = dst word
1029
1030            and     cx, 0fh
1031            mov     dx, 8000h
1032            ror     dx, cl          ; dx contains word(x) bit position of interest.
1033
1034            mov     cx, si
1035            and     cx, 0fh
1036            mov     bx, ss:[Pat]
1037            shl     bx, 1
1038            mov     bx, ss:DLinePatterns[bx]
1039            ror     bx, cl          ; position pattern
1040
1041            mov     cx, ss:[length] ; do length of them
1042
1043    DVLLoop:
1044            mov     ax, bx  ; mov pat into ax
1045            mov     si, es:[di]
1046            and     ax, dx  ; select bit of interest
1047            not     dx
1048            and     si, dx  ; zero bit of interest
1049            not     dx
1050            or      ax, si
1051            mov     es:[di], ax     ; set bit in dst if on
1052            add     di, 2   ; go to next word
1053
1054            rol     bx, 1   ; mov pat to next bit
1055            loop    DVLLoop
1056
1057            pop     si
1058            pop     di
1059            pop     es
1060            leave
1061            ret
1062    DrawVertLine endp
1063
1064    ;****************************************************************
1065    ;
1066    ; Procedure: Dot
1067    ;    (DotPlane, X, Y, [Val])  --  plots a zero or one value at (Plane, X, Y)
1068    ;
1069    ;****************************************************************
1070
1071    Entry:  DotPlane equ bp + 4
1072            DotP equ bp + 6
```

```
1073                x  equ  4
1074                y  equ  6
1075                DVal equ bp + 10
1076 ;*********************************************************
1077
1078        Dot proc near
1079            enter 0, 0
1080            push  es
1081            push  di
1082            push  si
1083
1084            mov   es, ss:[DotPlane]
1085            mov   ax, ss:[DotP + x]
1086            mov   cx, ax
1087            and   ax, 0fff0h
1088            shr   ax, 5        ; ax = (x % 16) * 512
1089            add   di, ss:[DotP + y]
1090            mov   si, di
1091            shl   di, 1
1092            mov   di, ax       ; es:di = dst word
1093
1094            and   cx, 0fh
1095            mov   dx, 8000h
1096            shr   dx, cl       ; dx contains word(x) bit position of interest.
1097
1098            mov   cx, si
1099            and   cx, 0fh
1100            mov   ax, ss:[DVAL]
1101            or    ax, ax
1102            jz    DotIt
1103            mov   ax, 0ffffh
1104 DotIt:
1105            mov   si, es:[di]
1106            and   ax, dx       ; select bit of interest
1107            not   dx
1108            and   si, dx       ; zero bit of interest
1109            or    ax, si
1110            mov   es:[di], si 1112            pop   si
1113            pop   di
1114            pop   es
1115            leave
1116            ret
1117        Dot endp
1118
1119 ;*********************************************************
1120
1121 ; Procedure:
1122 ;   Drawline(Plane, StP, EndP, pattern) -
1123 ;     draws a line from StP of length with pattern, and width
1124
1125 ; Entry: nLPlane equ bp + 4
```

```
1129            Str equ bp + 6
1130            EndP equ bp + 10
1131            Pat equ bp + 14
1132            x equ 0
1133            y equ 2
1134        ;
1135        ;*********************************************
1136            _DrawLine proc near
1137                ret
1138            _DrawLine endp
1139
1140
1141        SYS_TEXT ends
1142        End
1143
1144
1145
```

Wed 10-02-86 20:31:36  DS:SRVIN.S          reason
    10-15-86 14:53:42

```
 1    .186
 2   ;*********************************************************
 3   MFO Ver 0.0
 4   ;
 5   Module: dspsrvint.s -- display server initialization.
 6   ;
 7   modification history :   reason(s)
 8        date         by          creation
 9        6 04-86 err
10
11   COPYRIGHT (C) 1986 NELLCOR INCORPORATED
12
13        This module is an original, unpublished work and is proprietary to
14        NELLCOR INC., and may not be divulged or copied in any form
15        whatsoever without the express written permission of NELLCOR INC.
16
17   Purpose:
18        This module initializes the display servers data structures,
19        as well as the video controller hardware.
20
21   Procedures:
22
23        Public DVideoInit
24        Public _DispCreateP
25
26   Public Data:
27        Public DStackBeg, DStackEnd
28
29   ;*********************************************************
```

```
  34         include dbgdef.i
  35         include ..\xdef.i
  36         include ..\yevent.i
  37
  38         CONST   segment word public 'CONST'
  39         CONST   ends
  40
  41         _DATA   segment word public 'DATA'
  42         _DATA   ends
  43
  44         _BSS    segment word public 'BSS'
  45  0000                ; this word
  46
  47         even
  48  0000   DStackBeg    db this word
  49  0000     0100 [     db 100 dup (?)
  50                ??
  51                ]
  52
  53  0100   DStackEnd    db ?
  54         _BSS    ends
  55
  56         DGROUP  Group CONST, _DATA, _BSS
  57         Sys_text segment byte public 'code'
  58
  59         extrn   _XCrystal:far
  60         extrn   _DisqMain:near
  61         extrn   _DisqDbLink:far
  62
  63         ;**********************************************************
  64         assume cs:Sys_text, ds:DGROUP, ss:DGROUP
  65         ;**********************************************************
  66         ; Function:
  67         ;   DVideoInit -- Does the CRT controller setup.
  68         ;
  69         ;   All addresses are left shifted one relative to the 8057 address.
  70         ;   This is because the low order bit is not decoded.
  71         ;**********************************************************
  72
  73  0000   DVideoInit proc near
  74  0000       xor   ax, ax
  75  0002       mov   dx, 0eh shl 1   ; start 8057 timing chain.
  76  0005       out   dx, al
  77
  78  0006       mov   dx, 0014H       ; reset 8057
  79  0009       out   dx, AL
  80
  81  000A       mov   dx, 0000H       ; 8057 reg 0 -- Horizontal line count register.
  82  000D       mov   AL, 70          ; 80 (= 1280/16) + 18 for padding.
  83  000F       out   dx, AL
  84
  85  0010       add   AL, 27H         ; 8057 reg 1 -- (Non)Interlace, HSYNC width/delay
  86  0012       out   dx, 2           ; Non-interlaces, Hsync width= 5, hsync delay = 1
```

```
 90            out     dx,al
 91
 92            add     al,7DH
 93            mov     dx,2            ; 8057 reg 2 -- (scans, chars)/data row
 94            out     dx,al           ; (16 scans, "@ characters) / data row (see table)
 95
 96            add     al,0FH
 97            mov     dx,2            ; 8057 reg 3 -- skew bits, data row/frame
 98            out     dx,al           ; 0 skew bits, 16 data rows/frame
 99
100            add     al,06H
101            mov     dx,2            ; 8057 reg 4 -- extra scan lines/frame
102            out     dx,al           ; 6 extra scan lines/frame for vert. retrace
103
104            add     al,11
105            mov     dx,2            ; 8057 reg 5 -- vertical data start delay in lines.
106            out     dx,al           ; 11 line delay.
107
108            add     al,0FH
109            mov     dx,2            ; 8057 reg 6 -- last displayed data row.
110            out     dx,al           ; 15 is the 16th row displayed.
111
112            mov     dx,001CH
113            mov     al,00H
114            out     dx,al           ; start timing chain!
115
116            ret
117    DVideoInit endp
118
119
120    ;*******************************************************************
121    ;*******************************************************************
122    ; DispCreateP -- Creates the display server process
123    ;*******************************************************************
124    ;*******************************************************************
125
126
127    _DispCreateP proc near
128            push    offset _DispUnlink
129            push    Sys_Text
130            push    offset DGROUP:dtimers
131            push    offset DGROUP:DStackEnd
132            push    SYS_TEXT
133            push    offset DispMain
134            push    PID_DISPLAY
135            call    XCreateP
136            add     sp,14
137            call    DVideoInit
138            ret
139    _DispCreateP endp
140
141    Sys_text ends
142
143            end
```

```
Wed 10-14-86 14:47:48 DSTRING.C

1  /********************************************************
  2  *
  3  *   MFO Ver 0.0
  4  *
  5  *   module: dstring.c
  6  *
  7  *   modification history :
  8  *       date       by      reason(s)
  9  *     7-28-86     epr       Creation
 10  *
 11  *
 12  *   This module is an original, unpublished work and is proprietary to
 13  *   NELLCOR INC., and may not be divulged or copied in any form
 14  *   whatsoever without the express written permission of NELLCOR INC.
 15  *
 16  *   purpose:
 17  *       This module will handle the c language string functions for the mfo
 18  *       display.  It relies heavily on dtext.s.
 19  *
 20  *
 21  *   data descriptions :
 22  *       dcir - is a pointer to a display character information (DCI)
 23  *              structure.
 24  *
 25  *   function descriptions :
 26  *       dprintf(winno, string, string identified optional parameters) --
 27  *           this function work's very much like the C library fprintf(), but
 28  *           writes to windows on the MFO display. dprintf assumes the windows
 29  *           current text position, but dprintf supports some window positioning.
 30  *           Special sequences supported by dprintf:
 31  *               %d  --  prints an integer as an ASCII decimal string,
 32  *               %l  --  prints a long integer as an ASCII decimal string,
 33  *               %s  --  prints a SCALED as an ASCII decimal string,
 34  *               %s  --  prints a string,
 35  *               %%  --  prints the character '%,'
 36  *
 37  *               %A  -- Accepts a new character attribute and font.
 38  *               %P  -- Accepts a new (X,Y) positon.
 39  *               %L  -- Left Justify string at (X,Y). Same as %P
 40  *           (not implemented) %R -- Right Justify string at (X, Y).
 41  *               %X  -- Accepts a new X positon.
 42  *               %Y  -- Accepts a new Y positon.
 43  *               %B  -- Selects a background different than the default.
 44  *
 45  *
 46  *       dprint(winno, string) -- like dprintf, but it does not take optional
 47  *            parameters.  It is used primarily by dprintf.
 48  *
 49  *       itoascii -- returns the ASCII equivalent of short interger val.
 50  *            (sign,justify) -- takes an integer value and returns a
```

```
 51         left or right justified string of slen characters.  If slen is zero
 52         the string returned is the unjustified conversion of val.  Otherwise
 53         if the string length to be returned is greater than slen a NULL (0)
 54         pointer is returned.
 55
 56    ltoa(val)  -- returns the ASCII equivalent of long interger val.
 57    ladjitoa(val, slen, justify) -- takes an long value and returns a
 58         left or right justified string of slen characters.  If slen is zero
 59         the string returned is the unjustified conversion of val.  Otherwise
 60         if the string length to be returned is greater than slen a NULL (0)
 61         pointer is returned.
 62
 63    LGtoa(val)  -- returns the ASCII equivalent of float (SCALED) val.
 64    Ladjftoa(val, slen, justify) -- takes an float (SCALED) value and
 65         returns a left or right justified string of slen characters.
 66         If slen is zero the string returned is the unjustified conversion
 67         of val.  Otherwise, if the string length to be returned is greater
 68         than slen a NULL (0) pointer is returned.
 69
 70 * External Functions used:
 71    DispChar(winp, lchar) -- takes a pointer the window, and the
 72         long character (with attributes) and displays it on the screen.
 73
 74 *************************************************************/
 75
 76 #include "..\scaled.h"
 77 #include "dwindow.h"
 78 #include "dputil.h"
 79 #include "dstring.h"
 80
 81
 82 void near
 83 dprintf(winno, dstring, params)
 84 int winno;
 85 char far *dstring;
 86 int params;  /* these are optional */
 87 {
 88     char far *cp;
 89     register int *pp;
 90     unsigned int attrib;
 91     unsigned int background;
 92     int number;
 93
 94     attrib = dwindows[winno]->cattribute | dwindows[winno]->wCharInfo.cFontno;
 95     background = dwindows[winno]->background;
 96
 97     for (cp = dstring, pp = ¶ms; *cp != 0; cp++) {
 98         if (*cp == '%') {
 99             switch (*(++cp)) {
100                 dpswitch:;
101
102                 case '0':
103                 case '1':
104                 case '2':
105
```

```
107     case '3':
108     case '4':
109     case '5':
110     case '6':
111     case '7':
112     case '8':
113     case '9':
114             for (number = (*(cp++) - '0');
115                      (*cp) >= '0' & (*cp) <= '9'); cp++)
116                     number += 10 * (*cp - '0');
117             cp--;
118             goto dpswitch;
119             break;
120     /* %d -- prints an integer as an ASCII decimal string. */
121     case 'd': dprint(winno,
122                     Dadjitoa(*((int *)pp++), number, 0),
123                     attrib,
124                     background);
125             goto dprinfloopend;
126             break;
127     /* %f -- prints a SCALED as an ASCII decimal string. */
128     case 'f': dprint(winno,
129                     DadjStoa(*((SCALED *)pp)++), number, 0),
130                     attrib,
131                     background);
132             goto dprinfloopend;
133             break;
134     /* %s -- prints a string. */
135     case 's': dprint(winno, *((long *)pp)++, attrib, background);
136             goto dprinfloopend;
137             break;
138     /* %% -- prints the character '%' */
139     case '%': break;
140     /* %l -- prints a long integer as an ASCII decimal string. */
141     case 'l': dprint(winno,
142                     Dadjitoa(*((int *)pp++), number, 0),
143                     attrib, background);
144             goto dprinfloopend;
145             break;
146     case 'A': if (*((unsigned int *)pp) & FontMask) {
147                     attrib = *((unsigned int *)pp++);
148             }
149             else {
150                     attrib = (attrib & FontMask) | *((unsigned int
151     *)pp++);
152             }
153             goto dprinfloopend;
154             break;
155     case 'B': background = *((unsigned int *)pp++);
156             goto dprinfloopend;
157             break;
```

```
163         case 'H': /* Move to a new hort position */
164             DSetWinCharLoc (winno,
165                 *((int *)pp++),
166                             dwindows[winno]->wCharInfo.charrow -
167                             dwindows[winno]->WA.tlhcy
168                 );
169             goto dprinfloopend;
170             break;
171         case 'P':
172         case 'L':
173             DSetWinCharLoc (winno,
174                 dwindows[winno]->wCharInfo.charcol -
175                 *((int *)pp), *((int *)(pp+1))
176                 );
177             pp += 2; /* pp already (int *) so this ok */
178             goto dprinfloopend;
179             break;
180         case 'V':
181             DSetWinCharLoc (winno,
182                 dwindows[winno]->wCharInfo.charcol -
183                             dwindows[winno]->WA.tlhcx,
184                 *((int *)pp++)
185                 );
186             pp += 2; /* pp already (int *) so this ok */
187             goto dprinfloopend;
188             break;
189         }
190         DispChar(dwindows[winno], attrib : *cp, background);
191 dprinfloopend:;
192     }
193 }
194
195
196
197 void near
198 dprint(winno, dstring, attrib, background)
199 int winno;
200 char far *dstring;
201 {
202     char far *cp;
203
204     if (dstring == (char *) 0) return;
205     for (cp = dstring; *cp != 0; cp++)
206         DispChar(dwindows[winno], attrib : *cp, background);
207 }
208
209
210
211 char DCnvtstr[32] = {0}; /* string pointer */
212 #define strstartindex 18
213 #define strstartloc (&DCnvtstr[strstartindex])
214
```

```
215  char far ZeroStr[] = "0";
216  char far FZeroStr[] = "0.0";
217
218  char far * near
219  DItoa(inval)
220  register int inval;    /* input integer */
221  {
222      register int i;
223      int sign;
224
225      if (inval == 0) return ZeroStr;  /* take care of special case. */
226
227      if ((sign = inval) < 0) inval = -inval;   /* force n positive */
228
229      DCnvtstr[strstartindex] = 0;
230      for (i = strstartindex - 1; inval > 0; i--) {
231          /* generate digits in reverse order */
232          DCnvtstr[i] = inval % 10 + '0';
233          inval /= 10;
234      }
235
236      if (sign < 0) DCnvtstr[i--] = '-';
237      return &DCnvtstr[i+1];
238  }
239
240  char far * near
241  DItoa(inval)
242  long inval;    /* input integer */
243  {
244      register int i;
245      int sign;
246
247      if (inval == 0) return ZeroStr;  /* take care of special case. */
248
249      if ((sign = inval) < 0) inval = -inval;   /* force n positive */

DStoa

250      DCnvtstr[strstartindex] = 0;
251      for (i = strstartindex - 1; inval > 0; i--) {
252          /* generate digits in reverse order */
253          DCnvtstr[i] = inval % 10 + '0';
254          inval /= 10;
255      }
256
257      if (sign < 0) DCnvtstr[i--] = '-';
258      return &DCnvtstr[i+1];
259  }
260
261  char far * near
262  DStoa(inval)
263  SCALED inval;
264  {
265      register int i;
266      register int k = 0;
```

```
int sign = 0;
int factor = 1;
/* default value for now. rtdig can later be passed as a parameter */
int rtdig = 1;
int linval;

if (equF(inval, S0)) return FZeroStr; /* take care of special case. */ if (ltF(inval, S0))
{
    inval = absF(inval);    /* force n positive */
    sign = -1;
} for (i = 0; i < rtdig; i++)         factor *= 10;

linval = FtoI ( addF ( mulF ( ItoF(factor), inval), S0p5));

DCnvtstr[strstartindex] = 0;
for (i = strstartindex - 1; linval > 0; --i )
{
    /* generate digits in reverse order */
    DCnvtstr[i] = linval % 10 + '0';
    linval /= 10;
    if(++k == rtdig) DCnvtstr[--i] = '.';
} if (sign < 0) DCnvtstr[--i] = '-';
return &DCnvtstr[i+1];
}

/* adjusted character string */
/* if string length (slen) do not justify -- simply return string */

Dadjitoa char far * near
Dadjitoa(inval, slen, justify)
int inval;    /* input integer */
int slen;     /* string length */
int justify;  /* left (True) or right (False) alignment */
{
    register char *cp;
    register int i;
    char *cpt;
    long tt;

/* Take care of special cases */
    if (slen <= 0) return Ditoa(inval);

if ((cp = (char near *) Ditoa(inval)) == NULL) return NULL;

return DStrAdjust(cp, slen, justify);
```

```
3319    char far * near
3320    Dadjltoa(inval, slen, justify)
3321    long inval;   /* input integer */
3322    int slen;     /* string length */
3323    int justify;  /* left (True) or right (False) alignment */
3324    {
3325        register char *cp;
3326        register int i;
3327        char *cpt;
3328
3329        /* Take care of special cases */
3330        if (slen == 0) return Dltoa(inval);
3331
3332        if ((cp = (char near *) Dltoa(inval)) == NULL) return NULL;
3333
3334        return DStrAdjust(cp, slen, justify)
3335    }
3336
3337                            DStrAdjust
3338
3339    char far * near
3340    DadjStoa(inval, slen, justify)
3341    SCALED inval;  /* input SCALED private floating point */
3342    int slen;      /* string length */
3343    int justify;   /* left (True) or right (False) alignment */
3344    {
3345        register char *cp;
3346        register int i;
3347        char *cpt;
3348
3349        /* Take care of special cases */
3350        if (slen == 0) return (char far *) DStoa(inval);
3351
3352        if ((cp = (char near *) DStoa(inval)) == NULL) return (char far *) NULL;
3353
3354        return DStrAdjust(cp, slen + 1, justify);
3355    }
3356
3357    char far * near
3358    DStrAdjust(cp, slen, justify)
3359    register char *cp;
3360    int slen;      /* string length */
3361    int justify;   /* left (True) or right (False) alignment */
3362    {
3363        register int i;
```

```
        char *cpt;

if ((i = Dstrln((char far *)cp)) >= slen) {
                if (i == slen) return cp;   /* String is a perfect fit! */
                /* else */
                return NULL;
        };

/* Need to adjust string */
        if (justify) {
                cpt = cp;
                cp += i;
                for (; i < slen; i++) *(cp++) = ' ';
                *cp = 0;
                return cpt;
        }
        else {
                for (; i < slen; i++) *(--cp) = ' ';
                return cp;
        }
        return NULL;
}
```

```
Wed 10-13-86 11:35:38 DSTRING.H       NULL
    10-15-86 14:53:42
```

```
/*****************************************************************
**  MFO Ver 0.0
**
**  module:
**      dstring.h -- contains definitions for strings in the display
**      server.
**
**  modification history :
**      date        by      reason(s)
**
**  This module is an original, unpublished work and is proprietary to
**  NELLCOR INC., and may not be divulged or copied in any form
**  whatsoever without the express written permission of NELLCOR INC.
**
**  purpose :
**      To provide a common source of definitions for strings in the
**      display server.
**
**  data descriptions :
**
*****************************************************************/
```

```
27  /* Attribute definitions */
28
29  #define AttrNone    0x0000
30  #define AttrNormal  None
31  #define AttrReverse 0x0100
32  #define AttrBlink   0x0200
33
34  /*
35   Font Definitions
36   Note font definitions are exclusive, i.e. one and only one font
37   can be selected.
38  */
39  #define FontSmall  0x4000
40  #define FontMedium 0x8000
41  #define FontLarge  0xc000
42  #define FontMask   0xe000
43
44  #define NULL ((char *) 0)
45
46  void near dprintf();
47  void near dprint();
48
49  char far * near DStrAdjust();  /* (char far * str, slen, justify) */
50  char far * near DItoa();       /* (inval) */
51  char far * near DadjItoa();    /* (inval, slen, justify) */
52  char far * near DLtoa();       /* (inval) */
53  char far * near DadjLtoa();    /* (inval, slen, justify) */
54  char far * near DStoa();       /* (inval) */
55  char far * near DadjStoa();    /* (inval, slen, justify) */
56
57  /* Functions from dtext.i */
58  void near DInitTChars();       /* () */
59  void near DispChar();          /* (Attrib ; char) */
60  int  near DstrIn();            /* (far string) */
61  int  near DStrPixIn();         /* (FontNo, far string) */
62
63
64
    07-17-86  13:36:06   DSTRING.I
Wed 10-15-86  14:53:42                           reason 1  .186
 2  .xlist
 3  ;**********************************************************
 4  ;*
 5  ;*  MFO Ver 1.0
 6  ;*
 7  ;*  Module: dstring.i
 8  ;*
 9  ;*  modification history :
10  ;*      date        by       reason(s)
11  ;*      6-4-86      epr      creation -- oh my God will this ever be done on
```

```
              COPYRIGHT (C) 1986 NELLCOR INCORPORATED

This module is an original, unpublished work and is proprietary to
        NELLCOR INC., and may not be divulged or copied in any form
        whatsoever without the express written permission of NELLCOR INC.

Purpose:
        To provide a common source of definitions for strings in the
        display server.

Procedures:

Public Data:
;*************************************************************

;/* Attribute definitions */

AttrNone       equ 0000h
AttrNormal     equ 0100h
AttrReverse    equ 0100h
AttrBlink      equ 0200h ; byte versions of attributes
AttrBNone      equ 00h
AttrBNormal    equ AttrBNone
AttrBReverse   equ 01h
AttrBBlink     equ 02h ; Font Definitions
; Note font definitions are exclusive, i.e. one and only one font
; can be selected.
FontSmall      equ 0400h
FontMedium     equ 0800h

LISTRING.I                COPYRIGHT

FontLarge      equ 0C00h

; byte versions of fonts
FontBSmall     equ 04h
FontBMedium    equ 08h
FontBLarge     equ 0Ch .list
```

```
   .xlist
   ****************************************************************
 3 MFO Ver 0.0
 4
 5 Module: dtext.i
 6
 7 Modification history :
 8      date       by       reason(s)
 9    8-7-86      epr      creation -- oh my God will this ever be done on
10                                     time.
11
12        COPYRIGHT (C) 1986 NELLCOR INCORPORATED
13
14        This module is an original, unpublished work and is proprietary to
15        NELLCOR INC., and may not be divulged or copied in any form
16        whatsoever without the express written permission of NELLCOR INC.
17
18 Purpose:
19        To provide a common source of definitions for text constants in the
20        display server.
21
22 Procedures:
23
24 Public Data:
25 ****************************************************************
26    .list Wed 10-10-86 14:00:56  DTEXT.S                          reason
     10-15-86 14:53:42

.186
   ****************************************************************
 3 MFO Ver 0.0
 4
 5 Module: dtext.s
 6
 7 Modification history :
 8      date       by       reason(s)
 9    7-28-86     epr      creation -- this is happing all too late.
10
11        COPYRIGHT (C) 1986 NELLCOR INCORPORATED
12
13        This module is an original, unpublished work and is proprietary to
14        NELLCOR INC., and may not be divulged or copied in any form
15        whatsoever without the express written permission of NELLCOR INC.
16
17
18 Purpose:
19
20
```

```
     Procedures:
21       Public _DispChar
22           (winpz, lchar) -- Dispchar takes a pointer to a window
23           structure and a lchar (a long character containing both the
24           ASCII code and character attributes) and rasters the character
25           to the windows current character position. It also modifies the
26           windows character position. It uses DBltChar to copy the char to
27           a temporary char bit map, and DCopyCharBitMap to copy the temporary
28           bit map to the screen.
29
30       Public DGetBitMap
31           (lchar, charinfo) -- allocates a temp y character bit
32           map in the extra area of the graphics plane in question.
33
34       Public DCopyCharBitMap
35           (charinfo) -- copies a temporary char bitmap to
36           to the location defined by charinfo.
37
38       Public DClearCharSpace
39       (pattern, charinfo)
40       Public _WriteChars, _LoadFont;
41           () -- Loads all fonts into the character
42           pl  nes extra memory.
43
44       Public DSetAttributes ; -- proc local to _DispChar
45       Public _lstrln ; (far string) -- returns string length in chars
46       Public _lstrPixln; (fontno, far string) -- returns string length
47           in pixels.
48       (str, char *str; -- returns in ax the string length of zero DispChar ;  terminated strings;
   Public _DBlinkToggle ;  -- toggles blink state, called by timer
;************************************************************************

FONTDEF equ 1  ; enable font definition
include dfont.j include dwindow.j
include dstring.j
include dtext.j
include dhwdef.j CONST segment word public 'CONST'
CONST ends DATA segment word public 'DATA'
```

```
 71         extrn DEndTasks:word
 72
 73         _DATA ends
 74
 75         BSS segment word public 'BSS'
 76   DFlipState dw ?
 77         _BSS ends
 78
 79
 80   DGROUP Group _DATA, CONST, _BSS
 81
 82   SYS_TEXT segment byte public 'code'
 83
 84   assume CS:SYS_TEXT, DS:DGROUP, SS:DGROUP, ES:DGROUP
 85
 86         extrn DWColCopy:near
 87         extrn DRasterFill:near
 88
 89
 90   ;**************************************************************
 91   ;
 92   ; Function:
 93   ;    DispChar(winp, lchar, bground)
 94   ;
 95   ; Entry:
 96   ;    winp equ bp + 4 ; pointer to window at bp + 4
 97   ;    lchar equ bp + 6 ; at bp + 6
 98   ;    bground equ bp + 8 ; background pattern
 99
100   ;
101   ; Exit:
102   ;    window char position: winp.charx += winp->font[lchar]->deltax
103   ;    winp->font[lchar] on screen
104   ;
105   ;**************************************************************
106
107
108   DispChar proc near
109
110         push    bp
111         mov     bp, sp
112         push    di
113         push    si
114
115         mov     si, [winp]
116         mov     es, [si].wplane
117
118         mov     ax, [lchar]
119         mov     dx, ax    ; save for attribute processing
120         mov     ax, FontSmall
121         sub     DCDoCntrl1
122         jb      bx, [si].wcharinfo
123         lea
124
125         sub     al, ' '
126         jbe     DCDoSpace     ; see if it is a control char
```

```
127         call    USetBitMap
128         jz      DCNoCharExit
129
130         jc      DC_NeedtoSetAttr
131
132         mov     ax, [bground]
133         call    DClearCharSpace
134         call    DCopyCharBitMap ; copy tBitMap to char position.
135
136 DCNoCharExit:
137         pop     si
138         pop     di
139         pop     bp
140         ret
141
142 DCDoCntr11:
143         add     ax, FontSmall
144         jmp     DCDoCntr12
145
146 DCCheckSpaceBlink:
147         and     dh, AttrBBlink
148         jz      DCFillSpace
149         mov     di, [bx].ctbitmap
150         call    USetAttributes
151         jmp     DCFillSpace
152
153 DCDoSpace:
154         jb      DCDoCntrl
155         call    USetBitMap
156         jz      DCNoCharExit
157         jc      DCCheckSpaceBlink
158 DCFillSpace:
159         mov     ax, [bground]
160         call    DClearCharSpace
161         mov     ax, [bx].charcol
162         mov     di, [bx].ctfont
163         add     ax, es:[di].fontwidth       ; ax = X
164         mov     [bx].charcol, ax
165         cmp     ax, [si].wincol
166         jbe     DCNoSpcaeWrap
167         cmp     [si].wtype, TextWin
168         jne     DCNoSpcaeWrap
169 DCWrap:
170         mov     ax, [si].winlcol
171         mov     [bx].charcol, ax
172         mov     dx, [bx].charrow
173         add     dx, es:[di].fontheight      ; dx = Y
174         mov     [bx].charrow, dx
175 DCNoSpcaeWrap:
176         pop     si
177         pop     di
178         pop     bp
179         ret
180
181 DC_NeedtoSetAttr:
182
```

```
183                     ; lchar in dx
184             mov      di, [bx].ctbitmap
185             call     DSetAttributes
186             mov      ax, [bground]
187             call     DClearCharSpace
188             call     DCopyCharBitMap  ; copy tBitMap to char position.
189     DCDCExit:
190             pop      si
191             pop      di
192             pop      bp
193             ret
194
195     DCDoCntrl:
196             add      al, ' '  ; restore ax to positive
197             js       DCDCExit
198     DCDoCntrl2:
199             cmp      al, 10   ; Line Feed
200             jnz      DCDCExit
201             call     DGetBitMap
202             mov      di, [bx].ctfont
203             jmp      DCWrap
204
205     _DispChar endp
206
207     ;*********************************************************************
208     ;*********************************************************************
209     ; Procedure: DSetAttributes [lchar, tcfont]
210     ;
211     ; Entry: ds = es = plane of interest
212     ;        di = tcbitmap offset
213     ;        dh = attributes
214     ;
215     ;*********************************************************************
216     ;*********************************************************************
217     DSetAttributes proc near
218             push     si
219
220             xor      cx, cx
221             mov      cl, es:[di].cbsize
222             shl      cl, 1        ; convert it to words
223             mov      dl, cl       ; save height
224             lea      di, [di].cBitMap
225
226     DSA_IsItAttrReverse:
227             test     dh, AttrBReverse
228             jz       DSA_IsItAttrBlink
229     DSA_AReverseLoop:
230             mov      ax, es:[di]
231             not      ax
232             stosw
233             loop     DSA_AReverseLoop
```

```
239         DSA_IsItAttrBlink:
240                 test    dh, AttrBBlink
241                 jz              DSA_Exit
242
243                 push    bx              ; protect bx
244
245                 ; calc brh corner
246                 push    1               ; solid fill pattern
247                 mov     ax, [bx].charcol
248                 mov     dx, [bx].charrow
249                 mov     di, [bx].ctfont
250                 mov     cx, es:[di].fontheight
251
252                                         _DRasterFill
253
254                 dec     cx
255                 add     cx, dx          ; adjust to end pixel
256                 push    cx
257                 mov     cx, es:[di].fontwidth
258                 dec     cx              ; brhc.y
259                 add     cx, ax          ; adjust to end pixel
260                 push    cx              ; brhc.x
261                 push    dx              ; tlhc.y
262                 push    ax              ; tlhc.x
263                 push    EnhPlane
264                 call    _DRasterFill
265                 ;       _DRasterFill(Plane, tlhc, brhc, Pat)
266                 add     sp, 12
267
268                 pop     bx
269         DSA_Exit:
270                 pop     si
271                 ret
272
273         DSetAttributes endp
274
275         ;*********************************************************************
276         ; Procedure:
277         ;       DGetBitMap[lchar, charinfo]
278         ;
279         ; Entry:
280         ;       ax = lchar with font
281         ;       ds:si = window in question
282         ;       ds:bx = character info block
283         ;       es = is diplay segment in question.
284         ;
285         ; Exit:
286         ;       cinfo->ctbitmap = offset of temporary char bit map in display segment
287         ;       cinfo->ctfont = offset of font in display segment
288         ;       if (attr) carry set and ax = space
289         ;       else carry clear
290         ;       zero flag set if no character.
```

```
;*******************************************************************
;
        DGetBitMap proc near
                mov     di, ax   ; get font
                shr     di, 14
                shl     di, 1 cmp     al, MaxChars
                jae     DGTBMErrorExit mov     di, es:[di + DFonts]      ; get offset of this font
                lea     cx, es:[di + FontIndexSize] ; get offset of font size
                mov     [bxj.ctfont, cx           ; save address of font size test    ah, AttrBReverse
                jnz     DGTMPlaceAtSpace mov     cx, ax cbw shl     ax, 1 add     di, ax
                mov     ax, es:[di]               ; Get offset of Temp bit map.
                mov     [bxj.ctbitmap, ax         ; es:ax contains addr of BitMap test    ch, AttrBBlink
                jnz     DGTBMBlink or      ax, ax   ; set zero flag if no character map for this char.
                                 ; indicate no attributes clc
                ret DGTBMBlink:
                or      ax, ax   ; set zero flag if no character map for this char.
                                 ; indicate attributes stc
                ret DGTBMErrorExit:
                xor     ax, ax   ; get a zero flag
                clc              ; no attributes so clear carry
                ret DGTMPlaceAtSpace:
        Public DGTMPlaceAtSpace
                push    ds
                push    si
                mov     si, di
                mov     di, es
                mov     ds, di
```

```
347         mov     di, cx
348         add     di, 4          ; space follows fontheight and fontwidth
349         mov     ss:[bx].ctbitmap, di
350         cld charinfo.

351         shl     ax, 1
352         add     si, ax         ; [points to source font]
353         mov     si, [si]       ; Get offset of char bit map.
354         xor     cx, cx
355         mov     cl, [si].cbsize
356         shr     cx, 1
357         add     cx, FontInfoWSize
358                                ; move header info and bit map to space
359         rep     movsw
360
361         pop     si
362         pop     ds
363
364         stc                    ; indicate attributes
365         ret
366
367 DGetBitMap endp
368
369 ;****************************************************************
370 ; Procedure:
371 ;   DCopyCharBitMap [charinfo] -- Takes the charinfo stuff
372 ;   and calls DWColCopy to get the character pointed to by
373 ;   charinfo.ctbitmap to the current screen location defined
374 ;   by charinfo.(row,col).
375 ;
376 ; Entry: ds:bx = pointer to charinfo structure.
377 ;        ds:si = points to window
378 ;        es    points to segment
379 ;
380 ; Exit:  Character is displayed.
381 ;        Char Position moved to next char position.
382 ;
383 ;****************************************************************
384
385 DCopyCharBitMap proc near
386         push    bp
387         push    bx
388
389 ; get start (x, y)
390         mov     bp, [bx].charrow   ; bp = Y
391         mov     dx, [bx].charcol   ; dx = X
392         mov     cx, dx             ; calc next (x, y)
393         mov     di, [bx].ctbitmap
```

```
399              or      di, di
400              mov     al, es:[di].cdeltax 401              cbw
402              add     cx, ax
403              cmp     cx, [si].winrcol
404              jbe     DCCBMGetSrcAddress
405              cmp     [si].wtype, TextWin
406              je      DCCBMWrap
407              pop     bx              ; temporary measure until font out of bit map
408              pop     bp
409              ret
410
411      ; if text window wrap
412      DCCBMWrap:
413              jne     next
414              mov     dx, [si].winlcol
415              mov     di, [bx].ctfont
416              mov     bp, es:[di].fontheight
417              add     [bx].charrow, bp        ; bp = Y
418              mov     cx, dx ; dx = X
419
420
421      DCCBMGetSrcAddress:
422              mov     [bx].charcol, cx
423              mov     si, [bx].ctbitmap
424
425      DCCBMLoopSetup: ; get loop parameters
426              push    ds
427              mov     cx, es
428              mov     ds, cx
429              mov     ax, [si].cyoffset
430              xor     al, al
431              mov     bp, 1           ; bp = Y with offset
432              add     al, [si].cxoffset
433              shl     dx, ax
434              mov     dx, dx
435              add     di, dx
436              and     ax, 0fff0h
437              mov     di, 5           ; di = (x % 16) * 512
438              shl     di, bp          ; di = dst word!   ; save bit shift
439              add
440
441              xor     cx, [si].cheight
442              mov     cl, dx
443              xor     dx, [si].ltpimc
444              mov     lp,
445
446      DCCBMLoopSetup1:
447              lea     si, es:[si].cbitmap
448
449
450
```

```
451         DCCBMLoop:
452                 mov     bp, dx          ; save width in bp
453                 sub     dx, 16
454                 jbe     DCCBM_OneColMore
455                 mov     bp, 16          ; bp == 0 unless this is last column
456         DCCBM_OneColMore:
457                 shl     bp, 1
458                 mov     bp, ss:DEndMasks[bp]
459                 xchg    dx, bp          ; mov mask into dx and save value of dx
460
461         ; Parameters needed by DWColCopy!:
462         ;       ax = bit shift at destination
463         ;       cx = height of column
464         ;       si = source address
465         ;       di = destination address
466         ;       ds = src display plane segment
467         ;       es = dst display plane segment
468         ;       dx = source mask
469
470                 pusha
471                 call    DWColCopy
472                 popa
473
474                 mov     dx, bp
475                 add     di, DColBytes
476                 add     si, cx
477                 add     si, cx
478                 or      dx, dx
479                 jg      DCCBMLoop
480
481         DCCBMClipedExit:
482                 pop     ds
483
484                 pop     bx
485                 pop     bp
486                 ret
487
488         DCopyCharBitMap endp
489
490 ;*************************************************************************
491
492 ; Function: DClearCharSpace
493
494 ; Entry:    ds:bx = pointer to charinfo structure.
495 ;           ds:si points to window
496 ;           ax = background to be used.
497
498
499
500 ;*************************************************************************
501                                                                 _DRasterFill
```

```
502  DClearCharSpace proc near
503         push    bx
504         mov     ax,         ; push pattern
505         mov     dx, [bx].charcol
506         mov     di, [bx].charrow
507         mov     cx, es:[di].ctfont
508         dec     cx          ; adjust to end pixel
509         add     cx, es:[di].fontheight
510         or      cx, dx
511         add     dx, dx
512         jns     DCCSNoTopClip
513         xor     dx, dx
514  DCCSNoTopClip:
515         cmp     cx, 255
516         jbe     DCCSNoBotClip
517         mov     cx, 255
518  DCCSNoBotClip:
519         push    cx
520         mov     di, [bx].ctbitmap
521         xor     cx, cx
522         mov     cl, es:[di].cdeltax
523         mov     cx, ax
524         add     cx
525         push    dx
526         push    ax
527         push    es
528         push    bx
529         call    DRasterFill(Plane, tlhc, brhc, Pat)
530         add     sp, 12
531
532         pop     bx
533         ret
534  DClearCharSpace endp
535
536  ;*************************************************************
537  ;*
538  ;* Function: DInitTChars() -- Loads all fonts into the character
539  ;*           planes extra memory.
540  ;*
541  ;* Entry: Memory in char plane from a000 to ffff = 0
542  ;*
543  ;* Exit:
544  ;*   a000 = a006  -- offset of font 1 indexes
545  ;*   a002 = offset of font 2 indexes
546  ;*   a004 = offset of font 3 indexes
547  ;*   a006 to a0c6 = offsets of char maps for font 0
548  ;*
549  ;*                   _DInitTChars
550  ;*
551  ;*   a0c8 to ???? = font 1 char maps
552  ;*              followed by font 2 offsets and charmaps
553  ;*              followed by font 3 offsets and charmaps
```

```
554  ; Local Variables:
555  ;     currentchar is cc
556      ccpp     equ bp - 2    ; offset of the current char pointer
557      ccwidth  equ bp - 4    ; cc target width
558      ccbwidth equ bp - 6    ; cc target byte width
559      ccwwidth equ bp - 8    ; cc target word width
560      ccsrc    equ bp - 10   ; cc tmp source word
561      endfont  equ bp - 12   ; marks end of font
562      DITCAlloc equ 12
563
564  ;*********************************************************************
565
566  _DInitTChars proc near
567      enter  DITCAlloc, 0
568      push   di
569      push   si
570      push   ds
571      push   es
572
573      mov    ax, CharPlane
574      mov    es, ax
575
576      mov    ax, DFont
577      mov    ds, ax
578
579      mov    word ptr [ccpp], TSmallFontIndexes
580
581      mov    di, DFonts
582      mov    word ptr es:[di], TSmallFonts
583      mov    di, DStartTFonts
584      mov    si, offset DSmallFont
585      call   DLoadFont
586
587      add    di, 2
588      and    di, 0ffffh
589      mov    si, DFonts + 2
590      mov    es:[si], di
591      mov    [ccpp], di
592      add    di, FontIndexSize
593
594      mov    si, offset DMediumFont
595      call   DLoadFont
596
597      add    di, 2
598      and    di, 0ffffh
599      mov    si, DFonts + 4
600      mov    es:[si], di
601      mov    [ccpp], di
602      add    di, FontIndexSize
603
604      mov    si, offset DLargeFont
```

```
610             call    DLoadFont
611
612             pop     es
613             pop     ds
614             pop     si
615             pop     di
616             leave
617             ret
618
619
620 ;*********************************************************
621 ; Function:
622 ; DLoadFont --- Local to _DInitTChars
623 ;
624 ; Entry:
625 ;   ds:si = pointer to font
626 ;   es:di = pointer to dst of font info
627 ;   ccpp  = array of offset to the fonts char maps
628 ;
629 ; Exit:
630 ;   es:di points past end of T Font just loaded
631 ;
632 ;*********************************************************
633
634 DLoadFont proc near
635         mov     cx, [si].fwidth
636         mov     es:[di].fontwidth, cx    ; save space width
637         mov     cx, [di + 4].cwidth, cl
638         add     cx, 15                   ; add 15 to get word.
639         shr     cx, 4                    ; divide width by 16 for word size
640         mov     ax, [si].fheight
641         mov     es:[di].fontheight, ax
642         mov     es:[di + 4].cheight, ax
643         mov     di, 4
644         mov     bx, [ccpp]
645         mov     es:[bx], di
646         lea     di, es:[di].cbitmap      ; save offset of space
647         mul     cl
648         mov     cx, ax
649
650         xor     ax, ax
651         rep     stosw                    ; store zeros where the space goes.
652
653         mov     cx, [si].fEND
654         mov     [endfont], cx
655         lea     si, [si].fbitmaps
656
657 DITCLoadLoop:
658         mov     bx, [ccpp]
659         mov     ax, [si]
660         sub     ax, 7
661         jle     DLFExit
662         add     bx, ax
663         add     bx, ax                   ; characaters start with space
```

```
6666        mov     es:[bx], di
6667
6668        mov     ax, [si].cfwidth          ; convert char bit width to words
6669        mov     es:[di].cwidth, al
6670        mov     [ccwidth], ax
6671        add     ax, 15
6672        shr     ax, 4                     ; convert to words
6673        shl     ax, 1                     ; convert back to bytes
6674        mov     [ccbwidth], ax            ; save this for move later
6675        mov     es:[di].cbwidth, al
6676
6677        mov     cx, [si].cfheight
6678        mov     es:[di].cheight, cl       ; save this
6679
6680        mul     cl
6681        mov     es:[di].cbsize, al
6682        mov     dx, ax                    ; save
6683
6684        mov     ax, [si].cfxoffset
6685        mov     es:[di].cxoffset, al
6686
6687        mov     ax, [si].cfyoffset
6688        mov     es:[di].cyoffset, al
6689
6690        mov     ax, [si].cfdeltax
6691        mov     es:[di].cdeltax, al
6692
6693        lea     si, [si].cfbitmap
6694        lea     di, [di].cbitmap
6695
6696        mov     bx, [ccbwidth]            ; bx = src font row length - 1 word
6697        mov     bx, 2
6698
6699        sub     si, 2                     ; back load si for loop
6700        mov     [cctsrc], si DNEXT.S    Dstrln 6701  DLFStoBits:
6702  ; this outer loop selects the column of char bit map
6703        mov     si, [cctsrc]
6704        add     si, 2
6705        mov     ch, cl
6706        mov     [cctsrc], si
6707  DLFStoBitsLoop:
6708  ; this loop moves one column
6709        mov     si, bx                    ; wrap to next row of source font
6710        mov     ch
6711        add     DLFStoBitsLoop
6712        dec
6713        jg
6714        sub     dl, cl
6715        sub     dl, cl                    ; sub height byte twice
6716        jg      DLFStoBits
6717
```

```
7718            sub     si, bx    ; mov back to previous loc
7719            cmp     si, [endfont]
7720            jl      DlTCLoadLoop
7721    DLFExit:
7722            ret
7723    DLoadFont endp
7724
7725    _DInitChars    endp
7726
7727    ;****************************************************************
7728    ; Function:
7729    ;   DstrIn(str) char *str -- returns the length of a zero terminated
7730    ;   string in ax.
7731    ;
7732    ; Entry:  str equ bp + 4
7733    ;
7734    ; Exit:   ax = string length
7735    ;
7736    ;****************************************************************
7737
7738    DstrIn  proc    near
7739            push    bp
7740            mov     bp, sp
7741            les     bx, [str]
7742            xor     ax, ax
7743    DslLoop:
7744            cmp     byte ptr es:[bx], 0
7745            je      DslExit
7746            inc     ax
7747            inc     bx
7748            jmp     DslLoop
7749    DslExit:
7750            pop     bp
7751            ret
7752    _DstrIn endp
7753
7754    ;****************************************************************
7755    ; Function:
7756    ;   DstrPixLn(FontNo, far str) -- returns the pixel length of a zero
7757    ;   terminated string in ax.
7758    ;
7759    ; Entry: FontNo equ bp + 4
7760    ;        fstr   equ bp + 6
7761    ;
7762    ; Exit:
```

```
;   ax = string length
;************************************************************

DstrFixln   proc near
            push    bp
            mov     bp, sp
            push    ds
            push    di
            push    si mov     ax, CharPlane
            mov     ds, ax mov     si, [FontNo]
            sub     si, FontSmall
            shl     si, 1
            shl     si, 1
            mov     si, [si + DFonts]       ; get offset of this font les     di, [fstr]
            xor     ax, ax
            xor     cx, cx
            dec     di DsPlLoop:
            inc     di
            mov     cl, es:[di]
            sub     cl, ' '
            je      DsPlSpace
            cmp     cl, MaxChars
            jae     DsPlLoop mov     bx, cx
            shl     bx, 1
            mov     bx, [si][bx]
            add     bx, [bx].cdeltax
            adc     ah, 0
            jmp     DsPlLoop DsPlSpace:
            add     ax, [si + FontIndexSize].fontwidth
            jmp     DsPlLoop DsPlExit:
            pop     si
            pop     di
            pop     ds
            pop     bp
            ret
DstrFixln   endp ;************************************************************
; Procedure: DBlinkToggle
; -- Called by a timer to cause blinking to toggle
;************************************************************
```

```
826  ;*********************************************************
827  ;
828          _BSS    segment word public 'BSS'
829  DBlinkState    dw ?    ; guaranteed to start as 0
830          _BSS    ends
831
832  _DBlinkToggle   proc    far
833          mov     ax, DBlinkState
834          out     BlinkLatchPort, al
835          xor     al, 1
836          mov     DBlinkState, ax
837          ret
838
839  _DBlinkToggle   endp
840
841          Public  _DFlip
842  _DFlip  proc    near    ; for demo
843          mov     ax, DFlipState
844          out     94h, al
845          not     ax
846          mov     DFlipState, ax
847          ret
848  _DFlip  endp
849
850  SYS_TEXT ends
851
852          end
853

Wed  10-13-86  11:05:44   DTREND.C
     10-15-86  14:53:42
```

```
 1  /*********************************************************
 2   *
 3   *  MFO Ver 0.0
 4   *
 5   *  module: dtrend.c
 6   *
 7   *  modification history :   reason(s)
 8   *       date     by
 9   *      0-25-86   epr     creation
10   *
11   *
12   *
13   *  This module is an original, unpublished work and is proprietary to
14   *  NELLCOR INC., and may not be divulged or copied in any form
15   *  whatsoever without the express written permission of NELLCOR INC.
16   *
17   *
18   *  purpose :
19   *      Contains code for trend window management.
20   *
21   *  data descriptions :
22   *
23   *  function descriptions :
24   *      IIStartTR(mid_num, wp)  -- intializes dynamic display of trending.
```

```
25  /*****************************************************************/
26  #include "..\xscaled.h"
27  #include "..\xclock.h"
28  #include "..\xevent.h"
29  #include "..\hissvr.h"
30  #include "dwindow.h"
31  #include "dwutil.h"
32  #include "dstring.h"
33  #include "dtrend.h"
34
35
36
37  extern TIMERS dtimers;
38
39  int DTrendEvents = 0;
40
41  #define maxtrends 6
42
43  TSPs DTrends[maxtrends] = {0};
44
45  DefineTimer0(dtrendtimers, 7)
46  DefineTimer1( -1, -1, DTrendTimer0)
47  DefineTimer1( -1, -1, DTrendTimer1)
48  DefineTimer1( -1, -1, DTrendTimer2)
49  DefineTimer1( -1, -1, DTrendTimer3)
50  DefineTimer1( -1, -1, DTrendTimer4)
51  DefineTimer1( -1, -1, DTrendTimer5)
52  EndTimers(1000, 50, DTrendEvent, dtrendtimers)
53
54
55  void near
56  DStartTR(wp)
57  register DWindow *wp;
58  {
59      register TSPs *tspp;
60      int trnum;
61      long deltax;
62
63      tspp = &DTrends[trnum = DTRAlloc()];
64      deltax = wp->sw.wfw.wave.brhcx - wp->sw.wfw.wave.tlhcx + 1;
65      tspp->period = 3600; /* 1hr. for now, it is fixed (until show) */
66      tspp->updaterate = ((tspp->period * TOCS) / deltax) * 2;
67      tspp->updateperiod = tspp->period / tspp->updaterate;
68      XSetTimeDelay(
69          &(dtrendtimers.timers[trnum]),
70          tspp->updaterate, tspp->updaterate
71      );
72  }
73
74
75  void near
76  DTRInit()
77  {
78      register TSPs *tspp;
79
80      for (tspp = DTrends; tspp <= &DTrends[maxtrends]; tspp++)
```

```
 81         {
 82             tspp->enabled = 0;
 83         }
 84         XLinkTimer(&dtrendtimers);
 85     }
 86
 87  int near
 88  DTRAlloc()
 89  {
 90      register TSF's *tspp;
 91      register int i;
 92
 93      for (i = 0, tspp = DTrends; tspp (= &DTrends[maxtrends]; i++, tspp++)
 94      {
 95          if (tspp->enabled == 0) return i;
 96      }
 97      return -1;
 98  }
 99
100                    DTREND.C              DTrendTimer0

101
102  int far DTrendTimer0()
103  {
104      ++(DTrends[0].updates);
105  }
106
107  int far DTrendTimer1()
108  {
109      ++(DTrends[1].updates);
110  }
111
112  int far DTrendTimer2()
113  {
114      ++(DTrends[2].updates);
115  }
116
117  int far DTrendTimer3()
118  {
119      ++(DTrends[3].updates);
120  }
121
122  int far DTrendTimer4()
123  {
124      ++(DTrends[4].updates);
125  }
126
127  int far DTrendTimer5()
128  {
129      ++(DTrends[5].updates);
130  }
```

```
131      }
132      int far DTrendEvent()
133      {
134          DTrendEvents++;
135          XPOST(PID_DISPLAY, DISP_EV);
136
137      }
138
139      DTrendUpdate()
140      {
141          register TSPs *tspp;
142          register DWindow *wp;
143          TDATAS far *ndp;
144          int i, n, delay;
145
146          if (DTrendEvents)
147          {
148              DTrendEvents = 0;
149              for (tspp = DTrends; tspp (= &DTrends[maxtrends]; tspp++)
150              {

151                  DTrendUpdate
152
153                  if (tspp->updates)
154                  {
155                      wp = tspp->trwp;
156                      n = 2 * tspp->updates;
157                      DrasterCopy
158                      (
159                          wp->wplane,
160                          FCORNER(wp->sw.tw.trend),
161                          wp->sw.tw.trend.brhcx - n,
162                          wp->sw.tw.trend.brhcy,
163                          wp->wplane,
164                          wp->sw.tw.trend.brhcx - n,
165                          wp->sw.tw.trend.brhcy,
166                          SCORNER(wp->sw.tw.trend)
167                      );
168                      if (wp->sw.tw.trtype == 1)
169                      {
170                          ndp = HSDData
171                          (
172                              wp->sw.tw.id,
173                              (long) 0, (long) n * tspp->updateperi
174                              od,
175                              n
176                          );
177                          delay = wp->sw.tw.trend.brhcy -
178                                  wp->sw.tw.trend.tlhcy + 1;
179                          if (ndp->numpoint)
                             {
                                 for (i = 0; i < ndp->numpoint; i++)
                                 {
                                     DrawVertLine
```

```
180                    (
181                        wp->wplane,
182                        wp->sw.tw.trend.brhcx - i,
183                        wp->sw.tw.trend.brhcy + ndp->
     fdisdata[i],
184                        wp->sw.tw.trend.brhcx - i,
185                        wp->sw.tw.trend.brhcy,
186                        1
187                    );
188                }
189                tspp->updates = 0;
190            }
191            else
192            {
193                ndp = HDDData
194                    (
195                        wp->sw.tw.tw.id,
196                        (long) 0, (long) n * tspp->updateperi
     od,
197                        n
198                    );
199                if (ndp->numpoint)
200                {
201                    deltay = wp->sw.tw.trend.tlhcy -
     wp->sw.tw.trend.brhcy + 1;
202                    for (i = 0; i < ndp->numpoint; i++)
203                    {
204                        DrawVertLine
205                        (
206                            wp->wplane,
207                            wp->sw.tw.trend.brhcx - i,
208                            wp->sw.tw.trend.brhcy -
     ((ndp->fdisdata[i] * deltay) >>
209                            8),
210                            wp->sw.tw.trend.brhcx - i,
211                            wp->sw.tw.trend.brhcy -
     ((ndp->sdisdata[i] * deltay) >>
212                            8),
213                            1
214                        );
215                    }
216                    tspp->updates = 0;
217                }
```

```
 1  /*****************************************************************
 2   * MFO Ver 0.0
 3   *
 4   * module: dtrend.h
 5   *
 6   * modification history :   reason(s)
 7   *       date      by
 8   *     9-30-86    epr       creation
 9   *
10   * This module is an original, unpublished work and is proprietary to
11   * NELLCOR INC., and may not be divulged or copied in any form
12   * whatsoever without the express written permission of NELLCOR INC.
13   *
14   * purpose :
15   *     To act as the common source of C language definitions of the trend
16   *     window interface.
17   *
18   * data descriptions :
19   *
20   *****************************************************************/
21
22  typedef struct
23  {
24      int enabled;
25      Window *trwp;      /* pointer to window struct associated with this trend */
26      long period;       /* period in seconds */
27      int updateperiod;  /* update rate for this trend. */
28      int updaterate;    /* number of updates that have not been processed */
29      int updates;       /* the time of the left side of displayed trend. */
30      long trleft;       /* the time of the right side of displayed trend. */
31      long trright;
32  } TSPs;  /* Trend Scroll Parameters. */
33
34  void near DStartTR();
35  int  near DTRAlloc();
36  void near DTRInit();
37
38  int far DTRendTimer0();
39  int far DTRendTimer1();
40  int far DTRendTimer2();
41  int far DTRendTimer3();
42  int far DTRendTimer4();
43  int far DTRendTimer5();
44  int far DTRendEvent();
```

```
/*****************************************************************
 * MFO Ver 0.0
 *
 * module: dwindow.c
 *
 * modification history :    reason(s)
 *          date    by
 *          8-25-86 epr      creation
 *
 * This module is an original, unpublished work and is proprietary to
 * NELLCOR INC., and may not be divulged or copied in any form
 * whatsoever without the express written permission of NELLCOR INC.
 *
 * purpose :
 *      Contains code for window managment.
 *
 * data descriptions :
 *
 * function descriptions :
 *      DCreateTXW(wtemplate)    -- creates a text window
 *      DCreateMRW(wtemplate)    -- creates a Result Window window
 *      DCreateWFW(wtemplate)    -- creates a Wave Form window
 *      DCreateTRW(wtemplate)    -- creates a Trend window
 *      DMakeDefaultWins()       -- creates default windows 0 thru 4
 *
 *      WindowNum DWAlloc()      -- allocate a window from the avalible windows.
 *      DWFree(winno)            -- frees (deallocates) a window.
 *
 *****************************************************************/
#define WINDOWINIT
#include "../xscaled.h"
#include "dwindow.h"
#include "dutil.h"
#include "dstring.h"
#include "dresult.h"
#include "dtrend.h"
#include "dwvform.h"
#include "../menu/instrgptr.h"
#include "../menu/mwdwdblk.h"

/* Allocate five Predefined window */
DWindow WIN0 = {TextW};
DWindow WIN1 = {TextW};

DCreateTXW

DWindow WIN2 = {TextW};
DWindow WIN3 = {TextW};
DWindow WIN4 = {TextW};
```

```
54  /* Allocate Space for up to 20 more windows */
55  #define LowWindowNum 5
56  DWindow WINDOWSL20] = (OtherW);
57
58  WinNumber near
59  DCreateTxW(WT)
60  register wtemplate *WT;
61  {
62      register DWindow *wp;
63      WinNumber wn;
64
65      if ((int)(wn = DWAlloc()) < (int)LowWindowNum) return (BadWindow);
66      wp = dwindowsl(int) wn];
67
68      wp->wtype = TextW;
69      wp->wnum = wn;
70      wp->header.headtype = NoHeader;
71      wp->wCharInfo.charcol = WT->xtlc;
72      wp->wCharInfo.charrow = WT->ytlc;
73      wp->wCharInfo.cFontno = WT->name_font;
74      wp->wCharInfo.cwindowp = wp;
75      wp->wplane = CharPlane;
76      wp->cattribute = 0;
77      wp->WA.tlhcx = WT->xtlc;
78      wp->WA.tlhcy = WT->ytlc;
79      wp->WA.brhcx = WT->xbrc;
80      wp->WA.brhcy = WT->ybrc;
81      wp->background = 0;
82      return wn;
83  }
84
85  WinNumber near
86  DCreateMRW(WT)
87  register dwtemplate *WT;
88  {
89      register DWindow *wp;
90      WinNumber wn;
91
92      if ((int)(wn = DWAlloc()) < LowWindowNum) return (BadWindow);
93      wp = dwindowsl(int) wn];
94
95      wp->sw.rw.id = WT->mid_num;
96      wp->sw.rw.unitstr = WT->units_nptr;
97      wp->wtype = ResultW;
98      wp->wnum = wn;
99      wp->header.headtype = Headerstring;
100
```

```
Wed 10-15-86 00:36:10    UWINDOW.C                    DCreateMRW
    10-15-86 14:53:42

101         wp->header.hinfo.Hstring = WT->name_ptr;
102         wp->header.hloc.tlhcx = WT->nxtlc;
103         wp->header.hloc.tlhcy = WT->nytlc;
104         wp->header.hloc.brhcx = WT->nxbrc;
105         wp->header.hloc.brhcy = WT->nybrc;
106         wp->wCharInfo.charcol = WT->xtlc;
107         wp->wCharInfo.charrow = WT->ytlc;
108         wp->wCharInfo.cFontno = WT->name_font;
109         wp->wCharInfo.cwindowp = wp;
110         wp->wplane = CharPlane;
111         wp->cattribute = 0;
112         wp->WA.tlhcx = WT->xtlc;
113         wp->WA.tlhcy = WT->ytlc;
114         wp->WA.brhcx = WT->xbrc;
115         wp->WA.brhcy = WT->ybrc;
116         wp->sw.rw.limitfont = WT->lmtfont;
117         wp->sw.rw.mesval.tlhcx = WT->rxtlc;
118         wp->sw.rw.mesval.tlhcy = WT->rytlc;
119         wp->sw.rw.mesval.brhcx = WT->rxbrc;
120         wp->sw.rw.mesval.brhcy = WT->rybrc;
121         wp->sw.rw.lolimit.tlhcx = WT->llxtlc;
122         wp->sw.rw.lolimit.tlhcy = WT->llytlc;
123         wp->sw.rw.lolimit.brhcx = WT->llxtlc;
124         wp->sw.rw.lolimit.brhcy = WT->llytlc;
125         wp->sw.rw.hilimit.tlhcx = WT->ulxtlc;
126         wp->sw.rw.hilimit.tlhcy = WT->ulytlc;
127         wp->sw.rw.hilimit.brhcx = WT->ulxtlc;
128         wp->sw.rw.hilimit.brhcy = WT->ulytlc;
129         wp->background = 0;
130         wp->sw.rw.unit.tlhcx = WT->xutlc;
131         wp->sw.rw.unit.tlhcy = WT->yutlc;
132         wp->sw.rw.unit.brhcx = WT->xubrc;
133         wp->sw.rw.unit.brhcy = WT->yubrc;
134         wp->sw.rw.agentstr = WT->agent_ptr;
135         wp->sw.rw.agentloc.tlhcx = WT->agxtlc;
136         wp->sw.rw.agentloc.tlhcy = WT->agytlc;
137         wp->sw.rw.agentloc.brhcx = WT->agxtlc;
138         wp->sw.rw.agentloc.brhcy = WT->agytlc;
139         wp->sw.rw.bell.tlhcx = WT->offxtlc;
140         wp->sw.rw.bell.tlhcy = WT->offytlc;
141         wp->sw.rw.bell.brhcx = WT->offxtlc;
142         wp->sw.rw.bell.brhcy = WT->offytlc;
143     
144         InitMRW(wp);
145     
146         InstallMRW(WT->mid_num, wp);
147     
148         return wp;
149     }
150     
151     WinNumber near
152     DCreateWFW(WT)
153     register wtemplate *WT;
```

```
154     {
155         register DWindow *wp;
156         WinNumber wn;
157
158         if ((int)(wn = DWAlloc()) < LowWindowNum) return (BadWindow);
159         wp = dwindows[(int)wn];
160
161         wp->sw.wfw.id = WT->wfid;
162         wp->wtype = WaveFormW;
163         wp->wnum = wn;
164         wp->header.headtype = Headerstring;
165         wp->header.hinfo.Hstring = WT->name_ptr;
166         wp->header.hloc.tlhcx = WT->nxtlc;
167         wp->header.hloc.tlhcy = WT->nytlc;
168         wp->header.hloc.brhcx = WT->nxbrc;
169         wp->header.hloc.brhcy = WT->nybrc;
170         wp->wCharInfo.charcol = WT->xtlc;
171         wp->wCharInfo.charrow = WT->ytlc;
172         wp->wCharInfo.cFontno = WT->name_font;
173         wp->wCharInfo.cwindowp = wp;
174         wp->wplane = CharPlane;
175         wp->cattribute = 0;
176         wp->WA.tlhcx = WT->xtlc;
177         wp->WA.tlhcy = WT->ytlc;
178         wp->WA.brhcx = WT->xbrc;
179         wp->WA.brhcy = WT->ybrc;
180
181         wp->boarder = 0;
182         wp->background = 0;
183
184         wp->sw.wfw.wave.tlhcx = WT->xtlc + 1;
185         wp->sw.wfw.wave.tlhcy = WT->ytlc;
186         wp->sw.wfw.wave.brhcx = WT->xbrc - 1;
187         wp->sw.wfw.wave.brhcy = WT->ybrc;
188
189         wp->sw.wfw.wave.ScrollRate = WT->scrollrate;
190         wp->sw.wfw.wave.SampleRate = ItoF(WT->samplerate);
191
192         DPaintWFW(wp);
193
194         DStartWF(wp);
195
196         return wn;
197     }
198     WinNumber
199     DCreateWaveWin()
200     register wtemplate *WT;
201     {
202         register DWindow *wp;
203         WinNumber wn;
204
205         if ((int)(wn = DWAlloc()) < LowWindowNum) return (BadWindow);
206         wp = dwindows[(int)wn];
```

```
210     wp->wtype = OtherW;
211     wp->wnum = wn;
212     wp->sw.tw.id = WT->mid_num;
213     /* wp->sw.tw.trtype = WT->trend_type; */
214     wp->header.headtype = Headerstring;
215     wp->header.hinfo.Hstring = WT->name_ptr;
216     wp->header.hloc.tlhcx = WT->nxtlc;
217     wp->header.hloc.tlhcy = WT->nytlc;
218     wp->header.hloc.brhcx = WT->nxbrc;
219     wp->header.hloc.brhcy = WT->nybrc;
220     wp->wCharInfo.charcol = WT->xtlc;
221     wp->wCharInfo.charrow = WT->ytlc;
222     wp->wCharInfo.cFontno = WT->name_font;
223     wp->wCharInfo.cWindowp = wp;
224     wp->wplane = CharPlane;
225     wp->cattribute = 0;
226     wp->WA.tlhcx = WT->xtlc;
227     wp->WA.tlhcy = WT->ytlc;
228     wp->WA.brhcx = WT->xbrc;
229     wp->WA.brhcy = WT->ybrc;
230     wp->boarder = 0;
231     wp->background = 0;
232
233     sw->tw.tperiod = WT->period_nameptr;
234     sw->tw.tparea.tlhcx = WT->pxtlc;
235     sw->tw.tparea.tlhcy = WT->pytlc;
236     sw->tw.tparea.brhcx = WT->pxbrc;
237     sw->tw.tparea.brhcy = WT->pybrc;
238
239     sw->tw.trend.tlhcx = WT->xtlc + 1;
240     sw->tw.trend.tlhcy = WT->ytlc + 1;
241     sw->tw.trend.brhcx = WT->xbrc - 1;
242     sw->tw.trend.brhcy = WT->ybrc - 1;
243
244     DPaintTRW(wp);
245 /*  DStartTR(WT->mid_num, wp); */
246
247     return wn;
248 }
249
250                                 DMakeDefaultWins
251 void near
252 DMakeDefaultWins()
253 {
254     register int i;
255     for (i = 0; i < MaxWindows; i++) dWindows[i] = (DWindow *) 0;
256     /* Make background window */
257     dWindows[0] = &WIN0; /* set window index */
258
259     WIN0.wtype = TextW;
260     WIN0.wnum = Win0;
261     WIN0.wCharInfo.charcol = W0TLHCX;
262     WIN0.wCharInfo.charrow = W0TLHCY;
```

```
263    WIN0.wCharInfo.cFontno = FontSmall;
264    WIN0.wCharInfo.cwindowp = &WIN0;
265    WIN0.cattribute = 0;
266    WIN0.wplane = CharPlane;
267    WIN0.WA.tlhcx = W0TLHCX;
268    WIN0.WA.tlhcy = W0TLHCY;
269    WIN0.WA.brhcx = W0BRHCX;
270    WIN0.WA.brhcy = W0BRHCY;
271    WIN0.background = 0;
272
273    /* Make Message Line Window */
274    dwindows[1] = &WIN1; /* set window index */
275
276    WIN1.wtype = OtherW;
277    WIN1.wnum = Win1;
278    WIN1.wCharInfo.charcol = W1TLHCX;
279    WIN1.wCharInfo.charrow = W1TLHCY;
280    WIN1.wCharInfo.cFontno = FontSmall;
281    WIN1.wCharInfo.cwindowp = &WIN1;
282    WIN1.cattribute = AttrReverse;
283    WIN1.wplane = CharPlane;
284    WIN1.WA.tlhcx = W1TLHCX;
285    WIN1.WA.tlhcy = W1TLHCY;
286    WIN1.WA.brhcx = W1BRHCX;
287    WIN1.WA.brhcy = W1BRHCY;
288    WIN1.background = 1;
289    DRasterFill(CharPlane, CORNERS(WIN1.WA), WIN1.background);
290
291    /* Make Bottom Line Window */
292    dwindows[2] = &WIN2; /* set window index */
293
294    WIN2.wtype = OtherW;
295    WIN2.wnum = Win2;
296    WIN2.wCharInfo.charcol = W2TLHCX;
297    WIN2.wCharInfo.charrow = W2TLHCY;
298    WIN2.wCharInfo.cFontno = FontSmall;
299    WIN2.wCharInfo.cwindowp = &WIN2;
300    WIN2.cattribute = 0;

DWAlloc

301    WIN2.wplane = CharPlane;
302    WIN2.WA.tlhcx = W2TLHCX;
303    WIN2.WA.tlhcy = W2TLHCY;
304    WIN2.WA.brhcx = W2BRHCX;
305    WIN2.WA.brhcy = W2BRHCY;
306    WIN2.background = 0;
307
308    /* Make Wave Form Format and Help Window */
309    dwindows[3] = &WIN3; /* set window index */
310
311    WIN3.wtype = TextW;
312    WIN3.wnum = Win3;
313    WIN3.wCharInfo.charcol = W3TLHCX;
314    WIN3.wCharInfo.charrow = W3TLHCY;
315    WIN3.wCharInfo.cFontno = FontSmall;
```

```
316        WIN3.wCharInfo.cwindowp = &WIN3;
317        WIN3.cattribute = 0;
318        WIN3.wplane = CharPlane;
319        WIN3.WA.tlhcx = W3TLHCX;
320        WIN3.WA.tlhcy = W3TLHCY;
321        WIN3.WA.brhcx = W3BRHCX;
322        WIN3.WA.brhcy = W3BRHCY;
323        WIN3.background = 0;
324
325        /* Make Result Format Window */
326        dwindows[4] = &WIN4; /* set window index */
327
328        WIN4.wtype = OtherW;
329        WIN4.wnum = Win4;
330        WIN4.wCharInfo.charcol = W4TLHCX;
331        WIN4.wCharInfo.charrow = W4TLHCY;
332        WIN4.wCharInfo.cFontno = FontSmall;
333        WIN4.wCharInfo.cwindowp = &WIN4;
334        WIN4.cattribute = 0;
335        WIN4.wplane = CharPlane;
336        WIN4.WA.tlhcx = W4TLHCX;
337        WIN4.WA.tlhcy = W4TLHCY;
338        WIN4.WA.brhcx = W4BRHCX;
339        WIN4.WA.brhcy = W4BRHCY;
340        WIN4.background = 0;
341        WIN4.boarder = 0;
342    }
343
344    WinNumber near
345    DWalloc()
346    {
347        register DWindow **dwp;
348        register int i;
349
350
351        for (dwp = dwindows, i = 0; i < MaxWindows; i++, dwp++)
352            if (*dwp == ((DWindow *) 0)) break;
353        if (i == MaxWindows) return (WinNumber) -1;
354        *dwp = &WINDOWS[i - LowWindowNum];
355        return (WinNumber) i;
356    }
357
358    void near
359    DWFree(winno)
360    WinNumber winno;
361    {
362        register DWindow *wp;
363
364        wp = dwindows[(int) winno];
365
366        switch (wp->wtype)
```

```
368              case WaveFormW:
369                  DeleteWF(wp);
370                  DBlank(wp->wnum, CORNERS(wp->sw.wfw.wave), 0);
371              case ResultW:
372                  DBlank(wp->wnum, CORNERS(wp->sw.rw.mesval), 0);
373                  DSMRUnlinkW(wp);
374                  break;
375              case TextW:
376                  break;
377              case TrendW:
378                  break;
379              case OtherW:
380                  break;
381          }
382
383
384
385      dwindows[(int) winnol = NULLW;
386  }
387
```

Wed 10-12-86 17:00:00    DWINDOW.H
Wed 10-15-86 14:53:42

```
 1  /****************************************************************
 2  **
 3  ** MFO Ver 0.0
 4  **
 5  ** module: dwindow.h
 6  **
 7  ** modification history :
 8  **     date    by     reason(s)
 9  **   8-04-86  epr    creation
10  **   9-17-86  kht    added sub-windows in union to struct AWindow
11  **   9-22-86  epr             integrated kht's with mine.
12  **
13  ** This module is an original, unpublished work and is proprietary to
14  ** NELLCOR INC., and may not be divulged or copied in any form
15  ** whatsoever without the express written permission of NELLCOR INC.
16  **
17  ** purpose :
18  **     To act as the common source of C language definitions of window
19  **     stucture in the display server.
20  **
21  ** data descriptions :
22  **
23  **     dwindows[] -- the display servers primary window organization
24  **         structure. It is an array of pointers to structures of the
25  **         type DWindow.
26  **     DBItCharInfo structure describes the information necessary
27  **         to put a character on a screen, one of these is included in the
28  **         DWindow structure.
29  **     WinRegion provides the top left hand corner and bottom right hand
30  **         corners of a window region.
```

```
33  *
34  *
35  ****************************************************************/
36
37  #define FONT int /* see dstring.h for fonts */
38
39  typedef struct APoint {int x, y;} Point;
40
41  typedef struct WinArea { /*                    (tlhcx, tlhcy)    */
42      int tlhcx;  /* first corner x position       |             */
43      int tlhcy;  /* first corner y position       |             */
44      int brhcx;  /* second corner x position      ---------     */
45      int brhcy;  /* second corner y position             (brhcx, brhcy)*/
46  } WinRegion;
47
48  typedef struct ACharInfo {
49      int charcol, charrow; /* the current (x,y) char position in the window. */
50      int cFontno; /* this contains the font number of interest */
51      struct AWindow *cWindowp; /* pointer to back to window */
52      int *ct(bitmap); /* pointer to temp bit map. */
53      int *ctfont; /* offset of the font used right now */
54  } DBlitCharInfo;
55
56  typedef enum {
57      WaveFormW, /* a window to display waveforms */
58      ResultW,   /* a window to display Results */
59      TextW,     /* a window for text (e.g help window) */
60      TrendW,    /* a window to display trends */
61      OtherW     /* a window for ??? */
62  } WinType;
63
64  typedef enum {NoHeader, Headerstring, Iconstring} HType;
65
66  typedef struct AHeader {
67      HType headtype;
68      union {
69          char far *Hstring; /* points to window header string */
70          int far *Istring;  /* points to window ICON */
71      } hinfo;
72      struct WinArea hloc;
73  } WHeader;
74
75  #define RasterPattern int
76  #define LinePattern int
77
78  typedef enum {
79      CharPlane = 0x40000,
80      EnhPlane  = 0x50000,
81      GrdPlane  = 0x60000,
82      GrfPlane  = 0x70000
83  } WinPlane;
```

```
088  struct SubWindow {
089      struct WinArea sa;              /* sub-region x,y coordinates */
090      WinPlane sp;                    /* plane of subwindow */
091      int sf;                         /* sub-region character size */
092      char far **str;                 /* sub-region string pointer */
093  };
094
095
096
097  struct resultwindow {
098      int id;
099      FONT limitfont;
100      struct WinArea mesval;          /* measured value */
101      struct WinArea lolimit;         /* low limit value */
102      struct WinArea hilimit;         /* high limit value */
103      struct WinArea unit;            /* unit type */
104      char far *unitstr;
105      struct WinArea agentloc;        /* location of sub-string for agent */
106      char far * agentstr;            /* sub-string for agent */
107      struct WinArea bell;            /* bell condition */
108  };
109
110
111
112  struct waveformwindow {
113      int id;
114      int *wfnum;    /* stores the value used by the scroll module */
115      FONT labelfont;
116      struct WinArea wave;            /* wave area */
117      struct WinArea ylabel1;         /* 1st label on y axis (left edge)*/
118      struct WinArea ylabel2;         /* 2nd label on y axis (right edge)*/
119      struct WinArea xlabel1;         /* 1st label on x axis (top)*/
120      struct WinArea xlabel2;         /* 2nd label on x axis (bottom)*/
121      struct ASCALED ScrollRate;      /* real type is SCALED */
122      struct ASCALED SampleRate;      /* real type is SCALED */
123  };
124
125
126  struct trendwindow {
127      int id;
128      int *trnum;    /* stores the value used by the scroll module */
129      FONT labelfont;
130      struct WinArea trend;           /* trending area */
131      struct WinArea tparea;          /* 1st label on y axis (left edge)*/
132      char far * tperiod;             /* sub-string for trend period */
133      struct WinArea ylabel2;         /* 2nd label on y axis (right edge)*/
134      struct WinArea xlabel1;         /* 1st label on x axis (top)*/
135      struct WinArea xlabel2;         /* 2nd label on x axis (bottom)*/
136      int trtype;
137  };
138
139
140  struct subtextwindow {
141      FONT labelfont;
142      struct APoint label1;           /* 1st label */
143      struct APoint label2;           /* 2nd label */
```

```
144         struct APoint label3;           /* 3rd label */
145         struct APoint label4;           /* 4th label */
146     };
147
148     typedef enum {
149         BackgroundWin = -1,
150         Win0 = BackgroundWin,
151         MsgWin = 1,
152         Win1 = MsgWin,
153         ButtonWin = 2,
154         Win2 = ButtonWin,
155         WFWin = 3,
156         Win3 = WFWin,
157         ResultWin = 4,
158         Win4 = ResultWin,
159         Win5, Win6, Win7, Win8, Win9,
160         Win10, Win11, Win12, Win13, Win14, Win15, Win16, Win17, Win18, Win19,
161         Win20, Win21, Win22, Win23, Win24, Win25, Win26, Win27, Win28, Win29,
162         Win30, Win31, Win32, Win33, Win34, Win35, Win36, Win37, Win38, Win39,
163         Win40, Win41, Win42, Win43, Win44, Win45, Win46, Win47, Win48, Win49,
164         Win50, Win51, Win52, Win53, Win54, Win55, Win56, Win57, Win58, Win59
165     } WinNumber;
166
167
168     union swindows {    /* sub-windows */
169         struct resultwindow     rw;     /* result window info */
170         struct waveformwindow   wfw;    /* waveform window info */
171         struct trendwindow      tw;     /* trend window info */
172         struct subtextwindow    stw;    /* sub-text window info */
173     };
174
175
176     typedef struct AWindow {
177         WinType wtype;
178         WinNumber wnum;
179         struct AHeader header;
180         struct ACharInfo wCharInfo;
181         WinPlane wplane;
182         unsigned int cattribute;
183         struct WinArea WA;
184         RasterPattern background;
185         LinePattern *boarder;
186         char *message;
187         union swindows sw;
188     } DWindow;
189
190     /* win0  corners = ((0, 0), (1279, 255)) */
191     #define W0TLHCX 0
192     #define W0TLHCY 0
193     #define W0BRHCX 1279
194     #define W0BRHCY 255
195     /* win1  corners = ((0, 224), (1279, 240)) */
196     #define W1TLHCX 0
197     #define W1TLHCY 224
198     #define W1BRHCX 1279
199     #define W1BRHCY 240
```

```
201  /* win2 corners = ((0, 241), (1279, 255)) */
202  #define W2TLHCX    0
203  #define W2TLHCY    241
204  #define W2BRHCX    1279
205  #define W2BRHCY    255
206  /* win3 corners = ((0, 0), (779, 223)) */
207  #define W3TLHCX    0
208  #define W3TLHCY    0
209  #define W3BRHCX    779
210  #define W3BRHCY    223
211  /* win4 corners = ((812, 0), (1279, 223)) */
212  #define W4TLHCX    812
213  #define W4TLHCY    0
214  #define W4BRHCX    1279
215  #define W4BRHCY    223
216
217  #define MaxWindows   30
218  #define LowWindowNum 5
219  #define NULLW        (* DWindow) 0
220
221  #ifdef WINDOWINIT
222
223  DWindow *dwindows[MaxWindows] = {0};
224
225  #else
226
227  extern DWindow *dwindows[MaxWindows];
228
229  #endif
230
231
232
233
234  WinNumber near DCreateTXW();
235  WinNumber near DCreateMRW();
236  WinNumber near DCreateWFW();
237  WinNumber near DCreateTRW();
238  WinNumber near DWAlloc();
239  void      near DWFree();
240  void      near MakeDefaultWins();
241
242
243  void near DStartWF();                        reason
244  void near DStartMR();
245  void near DStartTR();
246

Wed 09-26-86 16:45:30  DWINDOW.I
    10-15-86 14:54:42

1  .186
2
3  .xlist
4
5
```

```
; *******************************************************************
; MFO Ver 0.0
;
; module: dwindow.i
;
; modification history :   reason(s)
;       date      by
;       8-04-86   epr           creation
;
;               COPYRIGHT (C) 1986 NELLCOR INCORPORATED
;
;       This module is an original, unpublished work and is proprietary to
;       NELLCOR INC., and may not be divulged or copied in any form
;       whatsoever without the express written permission of NELLCOR INC.
;
; Purpose:
;       To act as the common source of asm86 language definitions of window
;       structure in the display server.
;
; Procedures:
;
; Public Data:
; *******************************************************************

DCharInfo struc
        charcol  dw  ?  ; /* the current (x,y) char position in the window. */
        charrow  dw  ?  ; /* this contains the font number of interest */
        cfontno  dw  ?  ; /* pointer to window structure. */
        cwindowp dw  ?  ; /* offset of the font used right now */
        cfont    dw  ?  ; /* pointer to temp bit map. */
        ctbitmap dw  ?  ; *ctbitmap;
DCharInfo ends ;typedef struct APoint {int x, y;}
APoint struc
        px  dw ?
        py  dw ?
APoint ends ;typedef union AWinArea {
;       struct {int fcx, fcy, scx, scy;};
;       struct {
;                       struct APoint fc;
;                       struct APoint sc;
;              };
;       } WinRegion;
AWinArea struc
        tlx dw ?
        tly dw ?
```

COPYRIGHT

```
 58              brx dw ?
 59              bry dw ?
 60      AWinArea ends
 61      WinRegion struc
 62
 63              fc dw (size APoint)/2 dup (?)
 64              sc dw (size APoint)/2 dup (?)
 65      WinRegion ends
 66
 67      ; typedef enum {
 68              WaveFormWin equ 0 ;   /* a window to display waveforms */
 69              ResultWin equ 1 + WaveFormWin ; /* a window to display Results */
 70              TextWin equ 1 + ResultWin ;  /* a window for text (e.g help window) */
 71              TrendWin equ 1 + TextWin ;   /* a window to display trends */
 72              OtherWin equ 1 + TrendWin ;  /* a window for ??? */
 73      } WinType;
 74
 75      ; typedef enum {Headerstring, Iconstring} HType;
 76              Headerstring equ 0
 77              Iconstring equ Headerstring + 1
 78
 79      WHeader struc ;
 80              hHType headtype;
 81              union {
 82                      char far *Hstring; /* points to window header string */
 83                      void far *Istring;  /* points to window ICON */
 84              struct AWinArea HeadLoc;
 85              } headinfo;
 86              headtype dw ? ; HType headtype;
 87              headinfo dd ?
 88              headloc dw 4 dup (?)
 89      WHeader ends ;
 90
 91      ;#define RasterPattern void /* will not be known to C */
 92      ;#define LinePattern void /* will not be known to C */
 93
 94      ; typedef enum {
 95              CharPlane equ 4000h ;
 96              EnhPlane equ 5000h ;
 97              GrphPlane equ 6000h ;
 98              GrlPlane equ 7000h ;
 99      } WinPlane;
100
101      ;typedef struc {
102      DWindow struc
103              wtype dw ? ; WinType wtype;
104              wn dw ? ; window number
105              header dw (size WHeader)/2 dup (?) ;WHeader header;
106              wCharInfo dw (size DCharInfo)/2 dup (?) {,,,,};
107              wplane dw ? ;WinPlane wplane;
108              cattribute dw ? ; unsigned int cattribute;
109              winlcol dw ? ;int winlcol,  /* the windows left column in absolute pixels */
110              wintrow dw ? ;winrow,  /* the windows top row in absolute pixels */
111              winrcol dw ? ;winrcol, /* the windows right column in absolute pixels */
112              winbrow dw ? ;winbrow; /* the windows bottom row in absolute pixels */
113              background dw ? ;RasterPattern background;
114              boarder dw ? ;LinePattern boarder;
```

```
114         DWindow  message dd ?  ;char *message;
115         DWindow  message ends;
116
117         DColBytes equ 512
118         .list
119
120
Wed 10-15-86 12:52:24    NWUTIL.C
Wed 10-15-86 14:53:42

1    /******************************************************
 2    ** MFO Ver 0.0
 3    **
 4    ** module: dwutil.c
 5    **
 6    ** modification history :
 7    **       date     by        reason(s)
 8    **     8-25-86   epr        creation
 9    **
10    **
11    **
12    **
13    **
14    ** This module is an original, unpublished work and is proprietary to
15    ** NELLCOR INC., and may not be divulged or copied in any form
16    ** whatsoever without the express written permission of NELLCOR INC.
17    **
18    ** purpose :
19    **       Contains code window utility code, i.e. funtions the provide
20    **       utility but do not provide management of the window structures.
21    **
22    ** data descriptions :
23    **
24    ** function descriptions :
25    **
26    **    DHome(Wonno)   -- moves char position to (0, 0) in window.
27    **
28    **    DBlink(winno, tlhc, brhc) -- causes the sub-region of window
29    **        number to be set to blink attribute.
30    **
31    **    WUnBlink(winno, tlhc, brhc) -- causes the sub-region of window
32    **        number to be set to unblink attribute.
33    **
34    **    DBlinkWin(winno)  -- causes region of window
35    **        number to be set to blink attribute.
36    **
37    **    WUnBlinkWin(winno) -- causes region of window
38    **        number to be set to unblink attribute.
39    **
40    **    DBlank(winno, area) -- Blanks a window sub area.
41    **    WBlankWin(winno)    -- Blanks an entire window.
42    **
43    **    DSaveWFWin()   -- saves the Waveform window bit map.
44    **    DRestoreWFWin() -- restores the Waveform window bit map.
45    **    DHelp((char * far) hstring)  -- Puts up help text. Acomplishes
```

```
46          all screen manipuation required in the process.
47
48          DSetWinCharLoc(winno, X, Y) -- all in the name.
49
50    Point near DGetWinCharLoc(winno) -- all in the name.

DSetWinCharLoc

51    /***************************************************************
52
53       DPaintMRW(wp)     -- paints a reult window.
54
55       DPaintTRW(wp),    -- paints a trend window.
56       DShowTRW(area, strloc, str1, str2loc, str2) -- paints a trend
57       window like area.
58
59       DPaintWFW(wp)     -- paints a wave form window.
60       DShowWFW(area, strloc, str) -- paints a wave form window like area.
61
62       DHighLW(wnum)     -- Highlights the area define by wnum.
63       DHighLW(wnum)     -- Highlights the area define by wnum.
64       DUnHighLA(area)   -- Highlights area like DHighLW.
65       DUnHighLA(area)   -- Highlights area like DHighLW.
66
67       DrawBox(plane, tlc, brc, lpat) -- draws a box on the screen
68       in the line pattern lpat with corners at tlc and brc.
69
70    ****************************************************************/
71
72    #include "..\xscaled.h"
73    #include "dwindow.h"
74    #include "dstring.h"
75    #include "dwutil.h"
76
77    char far uformat[] = "%A%5";
78
79    void near
80    DSetWinCharLoc(winno, X, Y)
81    WinNumber winno;
82    int X, Y;
83    {
84        register DWindow *wp;
85
86        wp = dwindows[(int) winno];
87        wp->wCharInfo.charcol = wp->WA.tlhcx + X;
88        wp->wCharInfo.charrow = wp->WA.tlhcy + Y;
89    }
90
91    Point near
92    DGetWinCharLoc(winno)
93    WinNumber winno;
94    {
95        register DWindow *wp;
96        register Point p;
97
98        wp = dwindows[(int) winno];
```

```
  99            p.y = wp->wCharInfo.charcol - wp->WA.tlhcx;
 100            if (p.x > 1023) p.x = 1023;
 101            return p;
 102        }
 103
 104        DHome
 105
 106        void near
 107        DHome(winno)
 108        WinNumber winno;
 109        {
 110            DSetWinCharLoc(winno, 0, 0);
 111        }
 112
 113
 114        void near
 115        DBlink(winno, tlc, brc)
 116        WinNumber winno;
 117        Point tlc, brc;
 118        {
 119            register DWindow *wp;
 120
 121            wp = dwindows[(int) winno];
 122
 123            DRasterFill(EnhPlane,
 124                                    wp->WA.tlhcx + tlc.x,  wp->WA.tlhcy + tlc.y,
 125                                    wp->WA.tlhcx + brc.x,  wp->WA.tlhcy + brc.y,
 126                                    1);
 127        }
 128
 129        void near
 130        DUnBlink(winno, tlc, brc)
 131        WinNumber winno;
 132        Point tlc, brc;
 133        {
 134            register DWindow *wp;
 135
 136            wp = dwindows[(int) winno];
 137
 138            DRasterFill(EnhPlane,
 139                                    wp->WA.tlhcx + tlc.x,  wp->WA.tlhcy + tlc.y,
 140                                    wp->WA.tlhcx + brc.x,  wp->WA.tlhcy + brc.y,
 141                                    0);
 142        }
 143
 144        void near
 145        DBlinkWin(winno)
 146        WinNumber winno;
 147        {
 148            register DWindow *wp;
 149
 150            wp = dwindows[(int) winno];
```

```
151                 DUnBlinkWin
152
153             DRasterFill(EnhPlane, CORNERS(wp->WA), 1);
154     }
155     void near
156     DUnBlinkWin(winno)
157     WinNumber winno;
158     {
159             register DWindow *wp;
160
161             wp = dwindows[(int) winno];
162             DRasterFill(EnhPlane, CORNERS(wp->WA), 0);
163     }
164     void near DSaveWFWin()
165     {
166             register DWindow *wp;
167
168             wp = dwindows[(int) WFWin];
169             DRasterCopy(CharPlane, CORNERS(wp->WA),
170                         GrlPlane, CORNERS(wp->WA));
171     }
172
173     void near DRestoreWFWin()
174     {
175             register DWindow *wp;
176
177             wp = dwindows[(int) WFWin];
178             DRasterCopy(GrlPlane, CORNERS(wp->WA),
179                         CharPlane, CORNERS(wp->WA));
180     }
181
182
183     void near DHelp(hstring)
184     char far *hstring;
185     {
186             register DWindow *wp;
187
188             wp = dwindows[(int) WFWin];
189
190             DInhibitWF();
191             DSaveWFWin();
192             DRasterFill(CharPlane, CORNERS(wp->WA), 0);
193             dprintf(WFWin, hstring);
194     }
195
196
197     void near DHelpEnd()
198     {
199             register DWindow *wp;
200
```

DBlank

```
201         DRestoreWFWin();
202         DWinInhibitWF();
203     }
204
205     void near
206     DBlank(winno, area)
207     WinNumber winno;
208     WinRegion area;
209     {
210         register DWindow *wp;
211         WinRegion la;
212
213         wp = dwindows[(int) winno];
214         la.tlhcx = area.tlhcx + wp->WA.tlhcx;
215         la.tlhcy = area.tlhcy + wp->WA.tlhcy;
216         la.brhcx = area.brhcx + wp->WA.tlhcx;
217         la.brhcy = area.brhcy + wp->WA.tlhcy;
218
219         DRasterFill(wp->wplane, CORNERS(la), wp->background);
220     }
221
222     void near
223     DBlankWin(winno)
224     WinNumber winno;
225     {
226         register DWindow *wp;
227
228         wp = dwindows[(int) winno];
229         DRasterFill(wp->wplane, CORNERS(wp->WA), wp->background);
230     }
231
232     #define notchlen 8
233
234     void near
235     DPaintTRW(wp)
236     register DWindow *wp;
237     {
238         register int midy;
239
240         DRasterFill(wp->wplane, CORNERS(wp->WA), 0); /* Blank window */
241         DrawBox(wp->wplane, CORNERS(wp->WA), wp->boarder);
242
243         midy = wp->WA.tlhcy + ((wp->WA.brhcy - wp->WA.tlhcy) >> 1);
244         DrawHorLine(wp->wplane, wp->WA.tlhcx, midy, notchlen, 0);
245         wp->WA.tlhcx += notchlen;
246         DrawHorLine(wp->wplane, wp->WA.brhcx - notchlen, midy, notchlen, 0);
```

```
                        DShowTRW

251             DSetWinCharLoc(wp->wnum, wp->header.hloc.tlhcx, wp->header.hloc.tlhcy);
252             dprintf(wp->wnum, wp->header.hinfo.Hstring);
253             DSetWinCharLoc(wp->wnum, wp->sw.tw.tparea.tlhcx, wp->sw.tw.tparea.tlhcy);
254             dprintf(wp->wnum, wp->sw.tw.tperiod);
255     }
256
257     void near
258     DShowTRW(area, strloc, str1, str1loc, str2loc, str2)
259     WinRegion area;
260     Point strloc, str2loc;
261     char far *str1, *str2;
262     {
263             register int midy;
264
265             DRasterFill(CharPlane, CORNERS(area), 0);  /* Blank window */
266             DrawBox(CharPlane, CORNERS(area), 0);
267
268             midy = area.tlhcy + ((area.brhcy - area.tlhcy) >> 1);
269             DrawHortLine(CharPlane, area.tlhcx, midy, notchlen, 0);
270             DrawHortLine(CharPlane, area.brhcx - notchlen, midy, notchlen, 0);
271
272             DSetWinCharLoc(Win0, str1loc);
273             dprintf(Win0, str1);
274             DSetWinCharLoc(Win0, str2loc);
275             dprintf(Win0, str2);
276     }
277
278     void near
279     DPaintWFW(wp)
280     register DWindow *wp;
281     {
282             register int midy;
283
284             DRasterFill(wp->wplane, CORNERS(wp->WA), 0);  /* Blank window */
285             DrawBox(wp->wplane, CORNERS(wp->WA), wp->boarder);
286
287             midy = wp->WA.tlhcy + ((wp->WA.brhcy - wp->WA.tlhcy) >> 1);
288             DrawHortLine(wp->wplane, notchlen, midy, notchlen, /* line pattern */ 0);
289                      wp->WA.tlhcx, midy, notchlen,       0);
290             DrawHortLine(wp->wplane, wp->WA.brhcx - notchlen, midy, notchlen, 0);
291
292             DSetWinCharLoc(wp->wnum, wp->header.hloc.tlhcx, wp->header.hloc.tlhcy);
293             dprintf(wp->wnum, wp->header.hinfo.Hstring);
294     }
295
296     void near
297     DShowWFW(area, strloc, str)
298     WinRegion area;
299     Point strloc;
300     char *str;
```

```c
301   char far *str;
302   {
303       register int midy;
304
305       DRasterFill(CharPlane, CORNERS(area), 7); /* Blank window */
306       DrawBox(CharPlane, CORNERS(area), 0);
307
308       midy = area.tlhcy + ((area.brhcy - area.tlhcy) >> 1);
309       DrawHortLine(CharPlane, area.tlhcx, midy, 6, 0);
310       DrawHortLine(CharPlane, area.brhcx - 4, midy, 6, 0);
311
312       DSetWinCharLoc(Win0, strloc);
313       dprintf(Win0, str);
314   }
315
316   void near
317   DPaintMRW(wp)
318   register LWindow *wp;
319   {
320       DRasterFill(wp->wplane, CORNERS(wp->WA), 0); /* Blank window */
321       DSetWinCharLoc(wp->wnum, wp->header.hloc.tlhcx, wp->header.hloc.tlhcy);
322       dprintf(wp->wnum, wp->header.hinfo.Hstring);
323       DSetWinCharLoc(wp->wnum, wp->sw.rw.unit.tlhcx, wp->sw.rw.unit.tlhcy);
324       dprintf(wp->wnum, uformat, FontSmall, wp->sw.rw.unitstr);
325   }
326
327   void near
328   DrawBox(plane, tlc, brc, lpat)
329   WinPlane plane;
330   Point tlc, brc;
331   LinePattern lpat;
332   {
333       register int len;
334
335       /* Top line of box */
336       DrawHortLine(plane, tlc.x, tlc.y, len = (brc.x - tlc.x + 1), lpat);
337       /* Bottom line of box */
338       DrawHortLine(plane, tlc.x, brc.y, len, lpat);
339       /* Left side of box */
340       DrawVertLine(plane, tlc.x, tlc.y, len = (brc.y - tlc.y + 1), lpat);
341       DrawVertLine(plane, tlc.x + 1, tlc.y, len, lpat);
342       /* Right side of box */
343       DrawVertLine(plane, brc.x, tlc.y, len, lpat);
344       DrawVertLine(plane, brc.x - 1, tlc.y, len, lpat);
345   }
346
347   void near DHighLW(area)
348   WinRegion area;
349   {
350                                       DHighLW
351
352       DRasterFill(Gr0Plane, CORNERS(area), 3);
```

```
353    }
354    void near UHighLW(wnum)
355    {
356        UHighLA(CORNERS(dwindows[wnum]->WA));
357    }
358    void near UUnHighLA(area)
359    WinRegion area;
360    {
361        PRasterFill(Gr0Plane, CORNERS(area), 0);
362    }
363    void near UUnHighLW(wnum)
364    {
365        UUnHighLA(CORNERS(dwindows[wnum]->WA));
366    }
367
368
369
370
```

IWUTIL.H          CORNERS

```
1   /**********************************************************************
2   *  MFO Ver 1.0
3   *
4   *  module: dwutil.h
5   *
6   *  modification history :
7   *      date       by       reason(s)
8   *      8-04-86    epr      creation
9   *      9-17-86    kht      added sub-windows in union to struct AWindow
10  *      9-22-86    epr      integrated kht's with mine.
11  *
12  *
13  *
14  *  This module is an original, unpublished work and is proprietary to
15  *  NELLCOR INC., and may not be divulged or copied in any form
16  *  whatsoever without the express written permission of NELLCOR INC.
17  *
18  *  purpose :
19  *      To act as the common source of C language definitions of window
20  *      utility functions and structures
21  *
22  *  data descriptions :
23  *
24  *
25  ***********************************************************************/
26
27  #define CORNERS(c)   (c).tlhcx, (c).tlhcy, (c).brhcx, (c).brhcy
28  #define FCORNER(c)   (c).tlhcx, (c).tlhcy
29  #define SCORNER(c)   (c).brhcx, (c).brhcy
30
31  /* C language definitions for assembly functions */
32  void near URasterFill();
33
```

```
34    void near  DRasterCopy();
35    void near  DispChar();
36    void near  DrawHortLine();
37    void near  DrawVertLine();
38    void near  DrawLine();
39    void near  Dot();
40
41    /* Definitions of functions in dwutil.c */
42    void near  DHome();
43    void near  DSetWinCharLoc();
44    void near  DBlank();
45    void near  DBlankWin();
46    void near  DRlink();
47    void near  DUnblink();
48    void near  DBlinkWin();
49    void near  DUnblinkWin();
50
                                SCORNER 51    void near  DSaveWFWin();
52    void near  DRestoreWFWin();
53    void near  DInhibitWF();
54    void near  DUninhibitWF();
55    void near  DHelp();
56
57    void near  DPaintTRW();
58    void near  DPaintWFW();
59    void near  DPaintMRW();
60
61    /* DShowTRW(area, str1loc, str1, str2loc, s r.)
62    --  paints a trend window like area. */
63    void near  DShowTRW();
64    /* DShowWFW(area, strloc, string) -- paints a wave form window like area. */
65    void near  DShowWFW();
66    /* DHighLA(area)  -- Highlights area like DHighLW. */
67    void near  DHighLA();
68    /* DHighLW(wnum) -- Highlights the area define by wnum. */
69    void near  DHighLW();
70    void near  DUnHighLA();  /* DUnHighLA(area)  -- Highlights area like DHighLW. */
71    void near  DUnHighLW();  /* DUnHighLA(area)  -- Highlights area like DHighLW. */
72
73    void near  DrawBox();
74
75
76                  DWVF.S              waveform
77

.186
1    ;*************************************************************
2
3
4
```

```
  5  MFQ Ver 0.0
  6
  7  Module: dwvf.s -- display server waveform (assembly) processing.
  8
  9  modification history :
 10        date        by      reason(s)
 11     10-01-86       epr     creation
 12
 13               COPYRIGHT (C) 1986 NELLCOR INCORPORATED
 14
 15     This module is an original, unpublished work and is proprietary to
 16     NELLCOR INC., and may not be divulged or copied in any form
 17     whatsoever without the express written permission of NELLCOR INC.
 18
 19  Purpose:
 20     This module contains that code (which is in assembly language)
 21     that controls the display of wave form data.
 22
 23  Procedures:
 24     Public DVertWindowInt
 25     Public DVertSyncInt
 26     Public DStopWF ;() -- Stops waveform scrolling.
 27     Public DGoWF ;() -- Allows waveform scrolling.
 28     Public DWFPutStart ; (wnum, CORNERS);
 29     Public DWFPutStep ; (wnum, pos, inc);
 30     Public DWFFreeze1 ; (WVFData.* wvdata) freezes a single w.f.
 31     Public DWFUnfreeze ; (WVFData.* wvdata) unfreezes a single w.f.
 32     Public DRemoveWF ; (WVFData *wvdata) removes the scroll winodow.
 33     Public DWFUpdate ;() -- Updates all current wave forms.
 34     Public DGetWFData ;-- Get the current available WF data and stores in CData
 35     Public DEraseOldPoints ;-- Erases the points between current point and next.
 36     Public DrawNewPoints ;-- Generates and draws points new points
 37     Public DEraseOldVertWFLine ;-- Erases the old hort line between win and max.
 38     Public DrawNewVertWFLine ;-- Draws New VertWF line between min max
 39     Public DrawVertWFLine ; -- routine that does the drawing
 40     Public DEraseVertWFLine ; -- routine that does the erasing
 41     Public DWFMinMax ;-- Finds Min Max in current Data
 42
 43  Public _DPutWFData ; routine for genrating phoney wave form data.
 44
 45  Public Data:
 46
 47                              WVFWin
 48
 51  include dhwdef.i
 52  include dwvf.i
 53  include ..\xdef.i
 54  include ..\xevent.i
 55
 57  CommBlockSize equ 12
```

```
 58  ; the items in the WVFWin (wave form window) structure are in the
 59  ; order of the ports the control waveform scrolling.
 60  WVFWin struc
 61      Enable   db ?
 62      VStart   db ?   ; first y pixel address from top of display
 63      VEnd     db ?   ; last y pixel address from top of display
 64      HStart   db ?   ; first hort word boundry (or 16bit character)
 65      HEnd     db ?   ; last hort word boundry (or 16bit character)
 66      FPixLSB  db ?   ; 8 LSBs of the offset of fisrt pixel to display
 67      FPixMSB  db ?   ; 4 MSBs of the offset of fisrt pixel to display and
 68              ; wrap enable bit (bit 8).
 69      fill    db ?   ; make even number
 70      WVFDp   dw ?   ; pointer to WVFData struc
 71  WVFWin ends
 72
 73  SizeWVFW equ (size WVFWin)
 74
 75  ;****************************************************************
 76  ; The WVFData structure holds the real time wave form information.
 77  ; CurrenD is a pointer into Dinfo. Dinfo tells the DWFUpdate to
 78  ; either gather N data samples for this data point or to use N pixels
 79  ; since the last sample.
 80  ;****************************************************************
 81
 82  SizeDeltaPoints equ 256
 83  SizeDataPoints  equ 1024
 84  WVFData struc
 85      Freeze    dw ?   ; if not 0 do not scroll this wave form.
 86      DataLoc   dw ?   ; offset comm buffer block of interest
 87      DataNum   dw ?   ; used to compare with last buffer used.
 88      ScrollDelta dw ? ; Amount to scroll next interrupt for this window
 89      SlopeX    dw ?
 90      Lowy      dw ?
 91      Highy     dw ?
 92      Loby      dw ?
 93      Delay     dw ?
 94      CurrentD  dw ?
 95      either_Pixels_per_point_or_point_per_pixels
 96      Dinfo   dw SizeDeltaPoints dup (?)
 97      CurrentP dw ?
 98
 99
100                                  of
101      StartPtr dw ?   ; index into Pinfo
102      EndPtr   dw ?   ; index into Pinfo
103      Pinfo    dw SizeDeltaPoints dup (?) ; either y of (low y, high y)
104  WVFData ends
105
106  DeltaInfoPixpp struc ; struc for pixels per point
107      PixPerPoint db ? ; these are represented by negative numbers
108      PixRemaining db ?
109  DeltaInfoPixpp ends
110
111  PointInfoPixpp struc ; struc for pixels per point
```

```
112             PMax db ?
113             PMin db ?
114     PointInfopixpp ends
115
116     DeltaInfopppix struc  ; struc for points per pixel
117             PointPerPix dw ?  ; these are represented by negative numbers
118     DeltaInfopppix ends
119
120     PointInfopppix struc  ; struc for pixels per point
121             Point db ?
122     PointInfopppix ends
123
124
125     GraphicsPlane segment word public 'grplane'
126
127             org 0A000h       ; move past displayed part of video
128
129             ScrollEnable dw ? ; if zero no scroll advance
130     Public ScrollEnable
131             SFSelect dw ? ; this is the offset of the next scroll window.
132     Public SFSelect
133             ScrollParams WVFWin 3 dup ((?))
134     Public ScrollParams
135             even
136             SFStop dw ? ; this must always be zero to form stop in scroll win
137     Public SFStop
138
139             even
140     Public WVFData;
141             WVFDatap dw 3 dup (?) ; pointers to WVFData structures, these
142     ; the window sequence.   These data structures therefore support a
143     ; maximum of three active window.
144
145             even
146             WVFData0 WVFData (?)
147     Public WVFData0
148             even
149             WVFData1 WVFData (?)
150     Public WVFData1
151
152             even
153             WVFData2 WVFData (?)
154     Public WVFData2
155
156     GraphicsPlane ends
157     CONST segment word public 'CONST'
158     CONST ends
159
160     _DATA segment word public 'DATA'
161
162     extrn _BufNum:word, _cIntbl:word
163     extrn _DWFTrouble:word dup
164
```

```
165         _DATA ends
166
167         _BSS segment word public 'BSS'
168         even
169
170         _BSS ends
171
172
173         DGROUP Group CONST, _DATA, _BSS
174
175
176         Sys_Text segment byte public 'code'
177
178         extrn XFrost:far
179         extrn XWait:far
180
181
182 ;*************************************************************
183 ;
184 ; Procedure: DVertWindowInt -- From INT1 pin on processor.
185 ;               This function is called by the vertical window interrupt. This
186 ;               interrupt is generated by the gate array hardware to indicate the
187 ;               window lower window boundry has been crossed. This function must
188 ;               initialize the window boundries to the next window. Where next has
189 ;               a circular definition, i.e. the top window follows the bottom window.
190 ;               After moving to next window boundry it updates the scroll pameters
191 ;               of the next next window.
192 ;
193 ;*************************************************************
194
195         assume cs:SYS_TEXT, ds:GraphicsPlane, ss:DGROUP
196
197         DVWIDataOnlyScroll:
198                 add     bx, size WVFWin
199                 jmp     DVWIExit
200
201         DVertWindowInt proc far
202                 push    ds
203                 push    ax
204                 push    bx
205                 push    cx
206                 push    dx
207                 push    si
208                 mov     ax, GraphicsPlane
209                 mov     ds, ax
210
211         ; Disable boundry detection while changing boundry.
212                 mov     dx, DetectorEnablePort
213                 mov     al, DetectDisableVal
214                 out     dx, al
215
216                 cmp     ScrollEnable, 1
217                 jne     DVWIDataOnlyScroll
218                 mov     bx, SPSelect
219                 mov     ax, bx
220                 add     ax, SizeWVFM
```

```
221                 cmp     ax, offset ScrollParams + 2 * SizeWVFW
222                 jbe     DWVWINext
223                 mov     ax, offset ScrollParams
224                 mov     bx, ax
225     
226     DWVWINext:
227                 mov     SFSelect, ax
228                 mov     [bx].Enable, 1   ; make it be one to allow scroll
229                 cmp     DVWINoPhysicalScroll
230                 jne     DVWINoPhysicalScroll
231                 mov     dx, VerticalStartPort  ; note other vid ports follow this one
232                 mov     bx              ; first info starts at WVFWin + 1
233     
234                 ; And force this for max speed!
235                 ; Vertical start
236                 mov     al, [bx]
237                 out     dx, al
238                 add     dl, 2
239                 inc     bx
240     
241                 ; Vertical end
242                 mov     al, [bx]
243                 out     dx, al
244                 add     dl, 2
245                 inc     bx
246     
247                 ; Horizontal start
248                 mov     al, [bx]
249                 out     dx, al
250                 add     dl, 2
251                 inc     bx
252     
253                 ; Horizontal end
254                 mov     al, [bx]
255                 out     dx, al
256                 add     dl, 2
257                 inc     bx
258     
259                 ; First Pixel LSB
260                 mov     al, [bx]
261                 out     dx, al
262                 add     dl, 2
263                 inc     bx
264     
265                 ; First Pixel MSB
266                 mov     al, [bx]
267                 out     dx, al
268     
269     DVWINoPhysicalScroll:
270                 ; Reenable Detection before at exit
271                 mov     dx, DetectorEnablePort
272                 mov     al, DetectEnableVal
273                 out     dx, al
274     
275                 mov     bx, SFSelect
276     
277     DVWIExit:
                    Public DVWIExit
```

```
278             mov     si, [bx].WVFDp
279             or      si, si
280             jz      DVWIRewindWFMS
281
282     ; What we really want to do here is scroll 1/3 of Scroll Delta.
283     ; But we are going to approximate it with 1/2.
284     ; But we do not want to scroll only one pixel in order to avoid a word offset of 15 pixels.
285
286             mov     dx, [si].ScrollDelta
287             shr     cx, 1
288             sub     cx, dx
289             mov     cx, dx  ; dx = 1/2 ScrollDelta, cx = 1/2 ScrollDelta + rem
290             mov     ax, word ptr [bx].FPixLSB
291             and     ah, 7fh ; get rid of wrap bit
292             add     ax, dx
293             mov     dx, ax
294             sub     ax, 1
295             add     cx, dx
296             mov     [si].Scrolldelta, cx
297
298
299
300     DVWIPlaceScroll:                        DRemoveWF
301             mov     dx, ax
302             sub     dx, [si].EndX
303             jae     DVWIWrap
304             or      ah, 80h ; put in auto wrap.
305             mov     word ptr [bx].FPixLSB, ax
306
307     DVWIleave:      ; Acknowledge interrupt.
308             VWIACK
309             pop     si
310             pop     dx
311             pop     cx
312             pop     bx
313             pop     ax
314             pop     ds
315             iret
316
317
318     DVWIRewindWFMS:
319             mov     bx, offset ScrollParams
320             mov     SPSelect, bx
321             jmp     DVWIExit
322
323     DVWIWrap:
324             add     dx, [si].StartX
325             mov     ax, dx
326             jmp     DVWIPlaceScroll
327
328     DVertWindowInt  endp
329
330     ;****************************************************************
```

```
331    ;*******************************************************************
332    ; Procedure: DRemoveWF (WVFData) -- Remove the active state of the waveform.
333    ; Entry:
334    ;     wvdata equ bp + 4
335    ;
336    ;*******************************************************************
337
338    DRemoveWF proc near
339         push    bp
340         mov     bp, sp
341         push    ds
342         mov     ax, GraphicsPlane
343         mov     ds, ax
344
345         pop     ds
346         pop     bp
347         ret
348    DRemoveWF endp
349
350
351    ;*******************************************************************
352    ; Procedure: DStopWF() -- Stops waveform scrolling.
353    ;
354    ;*******************************************************************
355
356    DStopWF proc near
357         push    ds
358         mov     ax, GraphicsPlane
359         mov     ds, ax
360
361         mov     ScrollEnable, 0
362         pop     ds
363         ret
364    DStopWF endp
365
366
367    ;*******************************************************************
368    ; Procedure: DGoWF() -- Allows waveform scrolling.
369    ;           Resets scroll parameters based on WVFDatap.
370    ;*******************************************************************
371
372    DGoWF proc near
373         push    ds
374         push    di
375         push    si
376         mov     ax, GraphicsPlane
377         mov     ds, ax
```

```
383            mov     ScrollEnable, 0
384            mov     bx, offset WVFDatap
385            mov     di, offset ScrollParams
386            mov     SPSelect, di    ; restart scrolling from the top.
387
388   DGWFLoop:
389            mov     si, [bx]
390            or      si, si
391            jz      DGWFExit
392            mov     [di].WVFDp, si
393            mov     [di].Enable, 1
394            mov     ax, [si].HighY
395            mov     [di].VStart, al
396            mov     ax, [si].LowY
397            mov     [di].VEnd, al
398            mov     ax, [si].EndX
399            mov     al, 4
400            jmp     DGWF 401            mov     [di].HEnd, al
402            mov     ax, [si].StartX
403            mov     dx, 4
404            shl     ax, 4
405            mov     [di].HStart, al
406            mov     [di].FPixLSB, dl
407            mov     dh, ScrollWrapEnable
408            mov     [di].FPixMSB, dh
409
410            add     di, SizeWVFW
411            add     bx, 2
412            loop    DGWFLoop
413
414   DGWFExit:
415            mov     ScrollEnable, 1
416            mov     dx, DetectorEnablePort
417            mov     al, DetectEnableVal
418            out     dx, al
419            mov     dx, VerticalEndPort
420            mov     al, 0feh
421            out     dx, al      ; get it to interrupt at the end of the window.
422            pop     si
423            pop     di
424            pop     ds
425            pop
426            ret
427   DGWF     endp
428   ;*****************************************************************
429   ; Function: wfwd *DWFPutStart(wfid, CORNERS);
430   ;
431   ; Entry:    wfid equ bp + 4
432            ttx equ bp + 6
433            tly equ bp + 8
```

```
                 bp5 equ bp + 10
                 bp7 equ bp + 12

; Exit:          ax = Pointer to WFData selected
;****************************************************************

DWFPutStart proc near
                 enter 0, 0
                 push ds
                 push es
                 push di
                 push si mov  ax, GraphicsPlane
                 mov  ds, ax
                 mov  es, ax mov  bx, offset WVFDataP
                 xor  ax, ax
                 mov  cx, 3

DWFPSLookW:
                 mov  dx, offset WVFData0
                 cmp  ax, [bx]
                 je   DWFPSFoundWP
                 add  bx, 2
                 loop DWFPSLookW
                 jmp  DWFPSErrorExit DWFPSFoundWP: ; See if it is in the right order
                 cmp  cl, 3
                 je   DWFPSWInOrder
                 cmp  cl, 2
                 je   DWFPSWCheckLast ; Solve this part later!

DWFPSWCheckLast:
                 mov  dx, offset WVFData1
                 mov  si, [bx - 2]
                 mov  ax, [si].HighY
                 jb   DWFPSWInOrder   ; x starts from top so we want below
                 sub  ax, [tly]
                 mov  [bx], si
                 mov  bx, 2
                 mov  dx, offset WVFData0
                 cmp  si, dx          ; if si does not point to Data0 use Data0
                 jne  DWFPSWInOrder
                 add  bx, 2
                 mov  dx, offset WVFData1

DWFPSWInOrder:
                 mov  [bx], dx
                 mov  si, dx
                 mov  ax, [tlx]
                 mov  [si].StartX, ax
                 shl  ax, 1
```

```
493         add    ax, si
494         mov    [si].StartPtr, ax
495         mov    ax, [tly]
496         mov    [si].HighY, ax
497         mov    cx, ax
498         mov    ax, [brx]
499         mov    [si].EndX, ax
500         dec    ax
501         shl    ax, 1
502         mov    dx, ax
503         sub    dx, 8
504         add    ax, dx
505         mov    [si].CurrentP, dx
506         mov    ax, si
507         mov    [si].EndPtr, ax
508         mov    ax, [bry]
509         mov    [si].LowY, ax
510         sub    ax, cx
511         inc    ax
512         mov    [si].DeltaY, ax
513         mov    ax, [wfid]
514         dec    ax
515         mov    bx, CommBlockSize
516         mul    bx
517         inc    ax         ; offset of 1 for comm control byte.
518         mov    [si].DataLoc, ax
519
520         lea    di, [si].PInfo
521         mov    cx, SizeDataPoints
522         mov    ax, si     ; return pointer to data structure.
523         pop    si
524         pop    di
525         pop    es
526         pop    ds
527         leave
528         ret
529
530 DWFPutStep: ; ax already zero if jump here!
531         rep stosw
532
533 DWFPutStart endp
534
535 ;********************************************************************
536 ;
537 ; Procedure: DWFPutStep(wfwp, pos, dpos, points, pppix, LT);
538 ;
539 ; Entry:   wfwp  equ bp + 4
540          pos   equ bp + 6
541          dpos  equ bp + 8
542          points equ bp + 10
543          pppix equ bp + 12
544          LT    equ bp + 14
545 ;
546 ;********************************************************************
```

```
        DWFPutStep proc near
                DWVF.S
                            DWFFreeze1 pub    0, 0
                push   ds
                mov    si
                mov    ax, GraphicsPlane
                       ds, ax xor    ax, ax
                mov    bx, [points]
                mov    bx, SizeDeltaPoints
                cmp    DWFPutExit
                jae    si, [wfwp]
                mov    bx, 1          ; index into 2 byte Dinfo struc
                cmp    word ptr [LT], 0
                jne    DWFPutLT
                mov    ax, [pppix]
                neg    al
                mov    ah, al
                mov    word ptr [si][bx].Dinfo.PixPerPoint, ax
        DWFPutExit:
                pop    si
                pop    ds
                leave
                ret
        DWFPutLT:
                mov    ax, [dpos]
                mov    [si][bx].Dinfo, ax
                jmp    DWFPutExit DWFPutStep endp ;**************************************************************
; Procedure: DWFFreeze1(*wvdata) -----
;
; Entry:  wvdata equ bp + 4
;
; Exit:   Wave form data structure pointed at by wvdata frozen
;**************************************************************

DWFFreeze1 proc near
                push   bp
                mov    bp, sp
                mov    bx, [wvdata]
```

```
                            DWFUnfreeze1

6601                    mov         [bx].Freeze, 1
6602                    pop         bp
6603                    ret
6604    DWFFreeze1 endp
6605
6606    ;*******************************************************************
6607    ;
6608    ; Procedure: DWFUnfreeze1(*wvdata) --
6609    ;
6610    ; Entry:
6611    ;   wvdata equ bp + 4
6612    ;
6613    ; Exit: Wave form data structure pointed at by wvdata unfrozen
6614    ;
6615    ;*******************************************************************
6616
6617    DWFUnfreeze1 proc near
6618                    push        bp
6619                    mov         bp, sp
6620                    mov         bx, [wvdata]
6621                    mov         [bx].Freeze, 0
6622                    pop         bp
6623                    ret
6624    DWFUnfreeze1 endp
6625
6626    ;*******************************************************************
6627    ;
6628    ; Procedure: DWFUpdate();
6629    ;
6630    ; Locals:
6631    ;   DataPtr  equ bp -  2  ; Pointer to data pointer
6632    ;   DataCnt  equ bp -  4  ; Count of data available
6633    ;   CData    equ bp - 12  ; Current Data gotton by local proc DGetWFData
6634    ;   DataVal  equ bp - 14  ; val to be used by plot routines
6635    ;   DataPtr  equ bp - 16  ; ptr to current val
6636    ;   DWFUpdloc equ 16
6637    ;
6638    ; DGetWFData -- Get the current available WF data and stores in CData
6639    ; DErasePoints -- Erases the points between current point and next.
6640    ; DGenPoints -- Generates and draws points new points
6641    ; DEraseVertLine -- Erases the old hort line between min and max
6642    ; DDrawNewVertLine -- Draws New VertWF line between min max
6643    ; DMinMax -- Finds Min Max in current Data
6644    ;
6645    ;*******************************************************************
```

```
654     DWFUpdate proc near
655         enter DWFUAlloc, 0
656         push ds
657         push di
658         push si
659
660         mov    ax, GraphicsPlane
661         mov    ds, ax
662
663         mov    [datapp], offset WVFDatap - 2
664
665 DWFULoop:
666         add    word ptr [datapp], 2
667         mov    bx, [datapp]
668         mov    si, [bx]
669         cmp    si, si
670         jz     DWFUDoIt
671         jmp    DWFUExit
672
673 DWFUDoIt:
674         call   LGetWFData ; palaces results in CDataCnt and Cdata uses si
675         jc     DWFULoop
676
677         mov    bx, [si].CurrentD
678         mov    ax, [si][bx].DInfo
679         or     ax, ax
680         js     DWFU_GT ; if DInfo < 0 then greater than one sample pixel
681
682         lea    di, [CData]
683         mov    [CDataPtr], di
684     ; Less than one sample per pixel
685         mov    cx, [CDataCnt]
686 DWFULoop:
687         mov    cx
688         mov    di, [CDataPtr], cx ; loc + size of buffer
689         mov    cl, ss:[di]
690         mov    byte ptr [CDataVal], cl
691         inc    di
692         mov    [CDataPtr], di
693
694         mov    ax, [si][bx].DInfo
695         add    bx, 2 * SizeDeltaPoints
696         cmp    bx
697         jb     DWFULTNoDeltaWrap
698         mov    bx, bx
699
700 DWFULTNoDeltaWrap:
701         mov    [si].CurrentD, bx
702         mov    [si].ScrollDelta, ax
703         mov    DWFEnable, 1
704         mov    DWFU_LT
705         cmp    [si].Freeze, 0
706         jne    DWFU_LT
707         push   bx
708         call   DEraseOldPoints
709         push   ax
```

```
7710            mov     ax, XALWAYS_EV
7711            call    XWait
7712            pop     ax
7713            call    DrawNewPoints
7714            pop     bx
7715            jmp     DWFU_LT
7716
7717    DWFU_GT:  ; greater than one sample per pixel
7718            mov     di, [CData]
7719    DWFU_GTLoop:
7720            mov     cl, al
7721            mov     ch, byte ptr [CDataCnt]
7722            add     cl, ch
7723            jnc     DWFUGTDraw
7724            mov     al, cl
7725            mov     [si][bx].DInfo, ax
7726            add     bx, cl
7727            cmp     bx, 2 * SizeDeltaPoints
7728            jb      DWFUGTNoDWrap
7729            mov     bx, bx
7730
7731    DWFUGTDrawDWrap:
7732            mov     [si].CurrentD, bx
7733            call    DWFMinMax
7734            jmp     DWFULoop
7735
7736    DWFUGTDraw:
7737            sub     ch, cl ; ch = cnt for MinMax
7738            inc     [si].ScrollDelta
7739            mov     al, ah
7740            mov     [si][bx].DInfo, ax
7741            add     bx, cl
7742            cmp     bx, 2 * SizeDeltaPoints
7743            jb      DWFUGTNoDWrap
7744            sub     bx, bx
7745    DWFUGTNoDWrap:
7746            mov     [si].CurrentD, bx
7747            mov     byte ptr [CDataCnt], cl
7748            push    bx
7749            call    DWFMinMax
7750            pop     bx
                                        dup 7751            cmp     DWFEnable, 1
7752            jne     DWFU_GTLoop
7753            cmp     [si].Freeze, 0
7754            je      DWFU_GTLoop
7755            push    di
7756            call    tErase0ldVertWFLine
7757            pop     ax
7758            call    XWait
7759            pop     ax
7760            call    DrawNewVertWFLine
7761            pop     di
```

```
                    jmp     bx
                    mov     ax,[si][bx].DInfo
                    jmp     LWFU_GTLoop LWFU_Exit:
                    pop     si
                    pop     di
                    pop     ds
                    leave
                    ret ;DGetWFData -- Get the current available WF data and stores in CData
;              It converts the data to the plotable range in the process.
;
; Entry: si points WVFData
;        [CData] and [CDataCnt] available
;
; Exit:  cx = count of data
;        data in CData and count in CDataCnt Commblock struc
taskid     dw ?
Dataid     dw ?
clength    dw ?
wfdata     db 6 dup (?)
Commblock ends DGetWFData proc near
           mov    bx, A_BufNum
           shl    bx, 1
           cmp    bx, [si].DataNum
           je     DGWFDNoData
           mov    [si].DataNum, bx
           mov    bx, cInTbl[bx]
           add    bx, [si].DataLoc
           mov    cx, ss:[bx].clength
           jcxz   DGWFDNoData
           cmp    cx, 6
           ja     DGWFDNoData
           mov    [CDataCnt], cx
           lea    di, [bx].cwfdata
           lea    di, [CData]
           mov    dx, [si].DeltaY
           sub    dl, 2

DGWFDLoop:
           mov    al, ss:[bx]
           ; Plot conversion Y, = Y * (Dy/256)
           mul    dl                      ; ax = Y * Dy, ah = Y * Dy / 256
           cmp    ah, dl
           ja     DGWFDClip
           inc    ah
           mov    ss:[di], ah
           inc    di
           inc    bx
```

```
B18              loop    DGWFDLoop
B19              stc
B20              ret
B21     DGWFDClip:
B22              mov     ss:[di], dl
B23              inc     di
B24              inc     bx
B25              loop    DGWFDLoop
B26              stc
B27              ret
B28     DGWFDNoData:
B29              clc
B30              ret
B31     DGWFData endp
B32
B33     ; DEraseOld -- Erases the points between current point and next.
B34     ;
B35     ; Entry:
B36     ;   ax = delta X
B37     ;   si = WFWData
B38     ;   new Y in [CDataVal]
B39     ;   old Y in
B40
B41     DEraseOld Proc near
B42              push    ax
B43              mov     cx, ax
B44              mov     di, [si].CurrentP
B45              add     di, si
B46              add     di, 2
B47              cmp     di, [si].EndPtr
B48              jbe     DEOFStartWraped
B49              mov     di, [si].StartPtr
B50     DEOFStartWraped:
B51              mov     dx, [di].PInfo ; Y2 in dx
B52     DEOFLoop:
B53              mov     bx, di        ; put X in bx
B54              sub     bx, si
B55              shr     bx, 1
B56              mov     ax, [di].PInfo ; Y1 in ax
B57              add     di, 2
B58              cmp     di, [si].EndPtr
B59              jbe     DEOPWraped
B60              mov     di, [si].StartPtr
B61     DEOPWraped:
B62              mov     dx, [di].PInfo ; Y2 in dx
```

```
                sub     dx,ax ; Dy in ax
                jge     DEOPDirOK
                neg     dx
DEOPDirOK:      mov     ax, [di].PInfo ; Y2 in dx
                int     dx
                sub     ax, [si].LowY
                neg     ax    ; ax = Y in screen coordinates push    di
                push    cx
                call    DEraseVertWFLine
                pop     cx
                pop     di loop    DEOPLoop pop     ax
                ret
DrawOldPoints   endp LNFLoop:        mov     dl, cl
                jmp     short LNFSaveY ;  addOldPoints proc near
                mov     cx, ax
                mov     dh, cl  ; use dh for looping mov     di, [si].CurrentP
                add     si, si
                mov     di, byte ptr [di].PInfo
                mov     al, [CDataVal]
                sub     al, dl
                cbw idiv    cl ; al = integer part of ddy, ah = fractional part of ddy
                mov     bx, ax
                mov     ch, byte ptr [si].DeltaY LNFLoop:        add     di, 2
                cmp     di, [si].EndPtr
                jbe     LNFLWraped
                mov     di, [si].StartPtr
LNFLWraped:     cmp     dl, ch
                ja      LNFClip
LNFSaveY:       mov     byte ptr [di].PInfo, dl
                add     bl, al
                adc     bh, ah
                js      LNFPDown
                cmp     bh, cl
                jae     LNFUpAddF
LNFUpAddI:
```

```
9930         add    dl, bl
9931         xor    bl, bl
9932         dec    dh
9933         jnz    DNFLoop
9934         jmp    short DNFDraw
9935 DNFDownAdd:
9936         sub    bh, cl
9937         inc    bl
9938         jmp    DNFUpAddI
9939         sub    bh, cl
9940         neg    bh
9941         dec    bl
9942         jmp    short DNFDownAddI
9943 DNFDown:
9944         neg    bh, cl
9945         cmp    bh, cl
9946         jae    DNFDownAddF
9947 DNFDownAdd1:
9948         neg    bh
9949         add    dl, bl
9950         xor    bl, bl
9951         dec    dh
9952         jnz    DNFLoop
9953
9954 DNFDraw:
9955         mov    di, [si].CurrentP
9956         add    di, si
9957         xor    ch, ch
9958
9959 DNFClip:
9960         mov    bx, di   ; put X in bx
9961         sub    bx, si
9962         shr    bx, 1    ; make X coordinate
9963
9964         mov    ax, [di].PInfo ; Y1 in ax
9965         add    di, 2
9966         cmp    di, [si].EndPtr
9967         jbe    DDNFWraped
9968         mov    di, [si].StartPtr
9969
9970 DNFWraped:
9971         mov    dx, [di].PInfo ; Y2 in dx
9972         sub    dx, ax ; Dy n ax
9973         jge    DDNPDirOK
9974         neg    dx
9975         mov    ax, [di].PInfo ; Y2 in dx
9976
9977 DNFDirOK:
9978         inc    dx
9979         sub    ax, [si].LowY
9980         neg    ax     ; ax = Y in screen coordinates
9981         push   di
9982         push   cx
9983         ; cx = Y
9984         ; dx = del Y
9985
```

```
986              ; bx = X
987                       call    DrawVertWFLine
988                       pop     cx
989                       pop     di
990
991                       loop    DDNFLoop
992
993                       sub     di, si
994                       mov     [si].CurrentP, di
995                       ret
996
997
998      DrawNFPoints endp
999
1000     ; DEraseOldVertWFLine -- Erases the old hort line between min and max.
1001     DEraseOldVertWFLine proc near
1002                       mov     di, [si].CurrentP
1003                       add     di, 2    ; Erases point Line we are drawing.
1004                       add     di, si
1005                       cmp     di, [si].EndPtr
1006                       jbe     DEOVWFLWraped
1007                       mov     di, [si].StartPtr
1008     DEOVWFLWraped:
1009                       mov     ax, [di].PInfo
1010                       xor     dx, dx
1011                       mov     [di].PInfo, dx  ; zero in for next min max
1012                       clw
1013                       sub     dl, ah
1014                       jge     DEOVWFLDirOK
1015                       add     ax, dx
1016                       xchg    ax, dx
1017                       sub     dx, ax
1018                       neg     ax
1019     DEOVWFLDirOK:
1020                       inc     dx
1021                       mov     bx, di
1022                       sub     bx, si
1023                       shr     bx, 1
1024                       sub     ax, [si].LowY
1025                       neg     ax
1026                       jmp     DEraseVertWFLine
1027                       ret
1028     DEraseOldVertWFLine endp
1029
1030     ; DrawNewVertWFLine -- Draws New VertWF line between min max
1031     DrawNewVertWFLine proc near
1032                       mov     di, [si].CurrentP
1033                       add     di, si
1034                       mov     ax, [di].PInfo
1035                       xor     dx, dx
1036                       mov     dx, dx
1037                       clw
1038                       sub     dl, ah
1039                       jge     DNWVWFLDirOK
1040                       add     ax, dx
1041                       xchg    ax, dx
```

```
1042            sub     dx, ax
1043    DNVWFLDirOK:
1044            inc     dx
1045            mov     bx, di
1046            sub     bx, si
1047            shr     bx, 1
1048            add     di, [si].EndPtr
1049            cmp     di, DNVWFLWrapped
1050            jle     word 1051            mov                     di, [si].StartPtr
1052    DNVWFLWrapped:
1053            sub     di, si
1054            mov     [si].CurrentP, di
1055            sub     ax, [si].LowY
1056            neg     ax
1057            jmp     DrawVertWFLine
1058            ret
1059    DrawNewVertWFLine endp
1060    ; DrawVertWFLine -- Draws New VertWF line between min max
1061    ; ax = Y
1062    ; dx = del Y
1063    ; bx = X
1064    DrawVertWFLine proc near
1065
1066
1067            mov     cx, bx
1068            and     bx, 0fff0h    ; bx = (x % 16) * 512
1069            shl     bx, 5
1070
1071            and     cx, 0fh
1072            mov     di, 8000h
1073            ror     di, cl        ; di contains word(x) bit position of interest.
1074
1075            mov     cx, dx
1076            sub     bx, ax        ; add in Y offset
1077            add     bx, ax
1078
1079    DVLLoop:
1080            add     [bx], di      ; set bit in dst
1081            loop    DVLLoop
1082            bx, 2         ; go to next word
1083
1084                    [si].ScrollDelta
1085
1086            ret
1087    DrawVertWFLine endp
1088
1089    ; DrawVertWFLine -- Draws New VertWF line between min max
1090    ;         bottom and work up!
1091
1092    ;       = Y
1093    ;       = del Y
1094    ;       = X
```

```
                                                             ; di contains word(x) bit position of interest.
1075      ;EraseVertWFLine proc near
1096
1097            mov     cx, bx
1098            and     bx, 0fff0h
1099            mov     bx, 5       ; bx = (x % 16) * 512
1100            ror     di, cl
1101            and     cx, 0ffh
1102            mov     di, 7fffh
1103            ror     di, cl
1104
1105            mov     cx, dx
1106            add     bx, ax      ; add in Y offset
1107            add     bx, ax
1108
1109      EVLLoop:
1110            and     [bx], di    ; set bit in dst
1111            sub     bx, 2       ; go to next word
1112            loop    EVLLoop
1113
1114            ret
1115
1116      ;EraseVertWFLine endp
1117
1118      ;DWFMinMax -- Finds Min Max in current Data
1119      ; Start from bottom and work up!
1120      ; Entry: ch = count to examine
1121      ;        di = pointer to data
1122
1123      DWFMinMax proc near
1124            mov     bx, [si].CurrentP
1125            mov     ax, [si][bx].PInfo     ; ax contains current min max
1126            or      ax, ax
1127            jz      DWFMMNew
1128
1129      DWFMMNormal:
1130            mov     cl, ch
1131            xor     ch, ch
1132            jcxz    DWFMMExit0
1133
1134      DWFMMLoop:
1135            mov     dl, ss:[di]
1136            inc     di
1137            cmp     dl, al
1138            jb      DWFMMPlaceMin
1139            cmp     dl, ah
1140            ja      DWFMMPlaceMax
1141            loop    DWFMMLoop
1142
1143      DWFMMExit:
1144      DWFMMExit0:
1145            mov     [si][bx].PInfo, ax
1146            ret
1147
1148      DWFMMPlaceMin:
1149            mov     al, dl
1150            loop    DWFMMLoop
                      jmp     DWFMMExit
```

```
1151                DWFMMPlaceMax:
1152                        mov     ah, dl
1153                        loop    DWFMMLoop
1154                        jmp     DWFMMExit
1155
1156                DWFMMNew:
1157                        mov     al, ss:[di]
1158                        mov     ah, al
1159                        jmp     DWFMMNormal
1160
1161                DWFMinMax       endp
1162
1163                DWFUpdate       endp
1164
1165
1166  ;*********************************************************************
1167  ;*********************************************************************
1168  ; Procedure DVertSyncInt -- From INT1 pin of processor.
1169  ;       This function is called by the Vertical Sync interrupt. This
1170  ;       interrupt is generated by the CRT controller chip. Window scroll
1171  ;       parameters may be updated during this interrupt.
1172  ;*********************************************************************
1173  ;*********************************************************************
1174
1175                DVertSyncInt    proc    far
1176                        push    ax
1177                        push    dx
1178                        STI/POLL
1179                        VSTACK
1180                        pop     dx
1181                        pop     ax
1182                        iret
1183                DVertSyncInt    endp
1184
1185
1186                DFVal   db      ?
1187                DFVal1  db      ?50
1188
1189                DFutWFData      proc far
1190        Public  DFutWFData
1191                        push    ?
1192                        cli
1193                        mov     bx, _A_BufNum
1194                        dec     bx
1195                        jns     DFWFDABNOK
1196                        mov     bx, 2
1197                DFWFDABNOK:
1198                        mov     _A_BufNum, bx
1199                        shl     bx, 1
1200                        mov     bx, cIntTbl[bx]
1201                        mov     cx, 3
1202                        mov     [bx + 1].clength, 3
1203                        mov     [bx + 25].clength, 5
1204
1205
```

```
1206            mov     al, DPVal
1207            sub     al, 3
1208            mov     [bx + 1].cwfdata, al
1209            sub     al, 4
1210            mov     [bx + 2].cwfdata, al
1211            sub     al, 2
1212            mov     [bx + 3].cwfdata, al
1213            mov     DPVal, al
1214            mov     al, DPVal1
1215            sub     al, 3
1216            mov     [bx + 25].cwfdata, al
1217            sub     al, 1
1218            mov     [bx + 25 + 1].cwfdata, al
1219            mov     al, 1
1220            sub     [bx + 25 + 2].cwfdata, al
1221            mov     al, 1
1222            sub     [bx + 25 + 3].cwfdata, al
1223            mov     al, 2
1224            mov     [bx + 25 + 4].cwfdata, al
1225            mov     DPVal1, al
1226
1227            mov     bx, PID_DISPLAY
1228            mov     ax, XCOMM_EV
1229            call    Xfrost
1230            popf
1231            ret
1232    _DPutWFData endp
1233
1234    Sys_Text ends
1235            end
1236
```

LWVF.I                          reason

/*************************************************************************
 MPo Ver 0.0
 Module: dswf.i
 Modification history :
      date          by        reason(s)
   10/01/86        epr        creation

COPYRIGHT (C) 1986 NELLCOR INCORPORATED

This module is an original, unpublished work and is proprietary to
 NELLCOR INC., and may not be divulged or copied in any form
 whatsoever without the express written permission of NELLCOR INC.
**************************************************************************/

Purpose:
    Display wave form processing data structure definitions.

```
222     Procedures:
223     Public Data:
224  /***************************************************
225
226
227
228
229
230
231

1  /***************************************************
 2  *
 3  *                    WAVEFORM.C           DStartWF
 4  *
 5  ****************************************************
 6  *
 7  * MFO Ver. 0.0
 8  *
 9  * module: dwvform.c
10  *
11  * modification history :      reason(s)
12  *          date      by
13  *        8-25-86    epr       creation
14  *
15  *
16  * This module is an original, unpublished work and is proprietary to
17  * NELLCOR INC., and may not be divulged or copied in any form
18  * whatsoever without the express written permission of NELLCOR INC.
19  *
20  * purpose :
21  *   Contains code for wave form window managment.
22  *
23  * data descriptions :
24  *
25  * function descriptions :  deleteWF(wp) -- deletes here and in dwvf.s the scroll window.
26  *                          InhibitWF()  -- Stops waveform display and clears waveform
27  *                                          dsiplay.
28  *                          UnInhibitWF() -- Allows waveform display and restores waveform
29  *                                           display.
30  *                          DFreeze()    -- freezes all wave forms.
31  *                          UnFreeze()   -- unfreezes all wave forms.
32  *                          DWFStepsInit(SRate, SampRate) -- Calculates each scroll step for
33  *                                          a waveform at a given Sample Rate and a give Scroll Rate.
34  *
35  ****************************************************/
36
37  #include "..\\xscaled.h"
38  #include "window.h"
39  #include "dwutil.h"
40  #include "dstring.h"
41  #include "dwvform.h"
42
43  #define MAXWFS 3
```

```
44      DWindow *DActiveWF[MaxWFS];
45
46      void near
47      DStartWF(wp)
48      DWindow *wp;
49      {
50

LWVFORM.C               DeleteWF 51
52          for (DAWF = DActiveWF; DAWF <= &DActiveWF[MaxWFS]; DAWF++)
53          {
54              if (*DAWF == wp) break;
55          }
56          if (*DAWF != wp)
57          {
58              if (*DAWF == NULLW) *DAWF = wp;
59              else
60              {
61                  if (*(++DAWF) == NULLW) *DAWF = wp;
62                  else
63                  {
64                      if (*(++DAWF) == NULLW) *DAWF = wp;
65                      else return;
66                  }
67              }
68          }
69          DWFStepsInit(wp);
70          DGoWF();
71      }
72
73      void near
74      DeleteWF(wp)
75      register DWindow *wp;
76      {
77          register DWindow **DAWF;
78
79          for (DAWF = DActiveWF; DAWF <= &DActiveWF[MaxWFS]; DAWF++)
80          {
81              if (*DAWF == wp) *DAWF = NULLW;
82          }
83          DRemoveWF(wp->sw.wfw.wfnum);
84      }
85
86      int DWFEnable = 1;
87
88      void near
89      DInhibitWF()
90      {
91          DWFEnable = 0;
92          DStopWF();
93      }
94
95      void near
96      DUninhibitWF()
```

```
 97            MultEnable = 1;
 98            DDrawWF();
 99        }
100    }
101
102    /* FCon gives (mm/pixel)/(update freq.) == (190.5/1280) */
103    SCALED FCon = (0x30cc, -3, POS, NOTZERO, 0);  /* 0.148827 */
104
105    void near
106    DWFStepsInit(wp)
107    DWindow *wp;
108    {
109        SCALED pstep, p;
110        register int i, x;
111        int dx, pppix;
112        int *wfwp;  /* holds the wave form window data pointer */
113        int pgteone; /* true if more than one sample per pixel */
114
115        pstep = divF(wp->sw.wfw.ScrollRate, FCon), wp->sw.wfw.SampleRate);
116        pgteone = gteF(pstep, S1);
117
118        x = wp->sw.wfw.wave.tlhcx;
119        p = ItoF(x);
120
121        wfwp = DWFPutStart(wp->sw.wfw.id, CORNERS(wp->sw.wfw.wave));
122        wp->sw.wfw.wfnum = wfwp;
123
124        for (i = 0; ; i++)
125        {
126            for (pppix = 0, dx = 0; dx == 0;)
127            {
128                p = addF(p, pstep);
129                dx = FtoI(subF(p, ItoF(x)));
130                pppix++;
131            }
132            if (!DWFPutStep(wfwp, x, dx, i, pppix, pgteone)) break;
133            x += dx;
134        }
135    }
136
137    void near
138    DFreeze()
139    {
140        register DWindow **DAWF;
141
142        for (DAWF = DActiveWF; DAWF <= &DActiveWF[MaxWFS]; DAWF++)
143        {
144            if (*DAWF != NULLW) DWFFreeze((*DAWF)->sw.wfw.wfnum);
145        }
146    }
```

DWFStepsInit

DUnfreeze

```
151      void near
152      DUnfreeze()
153      {
154          register DWindow **DAWF;
155
156          for (DAWF = DActiveWF[MaxWFS]; DAWF
157          {
158              if (*DAWF != NULLW) DWFUnfreeze1((*DAWF)->sw.wfw.wfnum);
159          }
160      }
161
```

DWVFORM.H

```
 1   /*******************************************************************************
 2   ** MFO Ver 0.0
 3   **
 4   ** module: dwvform.h
 5   **
 6   ** modification history :     reason(s)
 7   **         date      by
 8   **       9-30-86    epr       creation
 9   **
10
11   ** This module is an original, unpublished work and is proprietary to
12   ** NELLCOR INC., and may not be divulged or copied in any form
13   ** whatsoever without the express written permission of NELLCOR INC.
14   **
15   ** purpose :
16   **         to act as the common source of C language definitions of the wave form
17   **         window interface.
18   **
19   ** data descriptions :
20   **
21   *******************************************************************************/
22
23
24
25   void near DStartWF();       /* (DWindow *wp) */
26   void near DWFStepsInit();   /* (DWindow *wp) */
27
28   void near DInhibitWF();     /* (void) */
29   void near DUninhibitWF();   /* (void) */
30
31   void near DFreeze();        /* (void) */
32   void near DUnfreeze();      /* (void) */
33
34   void near DeleteWF();       /* (DWindow *wp) */
35
36   /* Functions in dwf.s */
37   void near DRemoveWF();      /* (WVFData *wvdata) */
38   void near DStopWF();        /* (void) */
39   void near DGoWF();          /* (void) */
40   int  near DWFPutStep();     /* () */
41
```

```
42  int  * near  DWFOutStart();   /* ()   */
43  void near  DWFUpdate();       /* (void) */
44
45  void near  DWFFreeze1();      /* (WVFData * wvdata)  freezes one wave form */
46  void near  DWFUnfreeze1();    /* (WVFData * wvdata)  unfreezes one wave form */
47
48
49
```

MENU

SECTION G

Thu 10-15-86 02:00:56  MCLUDE.H
    10-16-86 14:52:38

```
 1  /***************************************************************************
 2   *
 3   * MFO Ver 0.0
 4   *
 5   * module:mclude.h
 6   *
 7   * modification history :                                  reason(s)
 8   *         date           by
 9   *
10   *
11   * This module is an original, unpublished work and is proprietary to
12   * NELLCOR INC., and may not be divulged or copied in any form
13   * whatsoever without the express written permission of NELLCOR INC.
14   *
15   *
16   * purpose :     include file for entire control server
17   *
18   * data descriptions :
19   *
20   * function descriptions :
21   *
22   ***************************************************************************/
23
24  extern char far *xAlloc();
25  extern far xWait();
26  extern far xCreateP();
27  extern far xPost();
28
29  #include "\mfo\display\daudio.h"
30  #include "\mfo\xscaled.h"
31  #include "msysdefs.h"
32  #include "\mfo\xclock.h"
33  #include "\mfo\larmsvr.h"
```

Thu 10-15-86 01:47:14   MCTRLSRV.C        mCreateP
Thu 10-16-86 14:52:38

```
1  /*
2  ** MFO Ver 0.0
3  **
4  ** module: mctrlsrvr.c
5  **
6  ** modification history :
7  **     date                by          reason(s)
8  **     19 sept 86          rlp         creation
9  **
10 ** This module is an original, unpublished work and is proprietary to
11 ** NELLCOR INC. and may not be divulged or copied in any form
12 ** whatsoever without the express written permission of NELLCOR INC.
13 **
14 ** purpose :
15 **
16 ** data descriptions :
17 **
18 ** function descriptions :
19 **
20 *****************************************************************/
21
22 #define MESSAGES
23 #include "mclude.h"
24 #include ".\mfo\itest\mbique.h"
25 #include ".\mfo\xevent.h"
26 #include "mEnglish.h"
27 #include "mSpanish.h"
28 #include "mFrench.h"
29 #include "mGerman.h"
30
31 #define NEW_CASE  -1
32 #define OLD_CASE   0
33 #define MSTACKSIZE 250
34
35 char *mstackp = 0;
36
34 #include "mkybd.h"
35 #include "mknobkybd.h"
36 #include "mkybdtmrs.h"
37 #include "mwdows.h"
38 #include "mstrgptr.h"
39 #include ".\mfo\display\dstring.h"
40 #include ".\mfo\display\dwindow.h"
41 #include ".\mfo\display\dwutil.h"
42 #include "mwdwdblks.h"
43 #include "mwdowram.h"
44 #include "mwdowrom.h"
45 #include "menusrvr.h"
46 #include "mrommnus.h"
47 #include "mctrlsrvr.h"
48
```

```
37  char *far xALLOC();
38
39  /******************************************************
40   *
41   * THIS ROUTINE IS CALLED AT SYSTEM INITIALIZATION
42   *
43   *
44   ******************************************************/
45  mCreateP()
46  {
47      mstackp = xALLOC( MSTACKSIZE );
48      xCreateP( PID_CONTROL,mControlServer, ( mstackp + MSTACKSIZE - 2 ), &kybd_timers, mOff );
49
50  }
51  /******************************************************
52   *
53   * CONTROL SERVER MAIN ENTRY POINT
54   *
55   *
56   ******************************************************/
57  far
58  mControlServer()
59  {
60      short patient;
61      short kybd_input;
62
63      mKybdInit();             /* initialize kybd timers and queues */
64      Language = DetermineLanguge();/**/
65      Language = English;
66      patient = NewCaseOrOld();
67      XWait(ALWAYS_EV);
68      if ( patient == NEW_CASE )
69          ShowDefaultScreen();
70
71      else RebuildOldScreen();
72
73      /* start keyboard timer */
74
75      xSetTimeDelay( &kybd_timers.timers[ PROC_KYBD_TIMER ], KYBD_TICKS, NO_RESTART );
76
77      FOREVER
78      {
79          XWait( FP_INPUT_EV );     /* wait for keyboard/knob input */
80          kybd_input = mIgetfromque( &kybdque );
81          if ((( kybd_input & KEY_CODE ) == POWER_BUTTON ) && (!(kybd_input & RELEASED)))
82              SystematicPowerDown();
83
84          else
85              MenuServer( kybd_input );
86      }
87  }
88  /******************************************************
```

```
 93   * NOTIFY EVERYONE THAT POWER IS GOING OFF
 94   ******************************************************/
 95   SystematicPowerDown()
 96   {}
 97
 98   /******************************************************
 99   *
100   * CONTROL SERVER TERMINATION
101   *
102   ******************************************************/
103   mOff()
104   {}
105
106   /******************************************************
107   * This routine sets the language that the system will display its messages in.
108   ******************************************************/
109   LanguagePtr
110   DetermineLanguage()
111   {
112        return ( English );
113   }
114   */
115
116   /******************************************************
117   * If the unit has been off for less than a given amount of time, this routine
118   * finds out from the operator if this is a new patient ( which means use default
119   * screen and variables) or an old patient ( use screen and variables saved at
120   * power down ).
121   * If it is determined that the unit has been off longer than this given time,
122   * the patient is defaulted to new.
123   ******************************************************/
124   short
125   NewCaseOrOld()
126   {
127   short patient;
128        return ( NEW_CASE );
129   }
```

```
Thu 10-16-86 14:11:38  MENGLISH.C
    10-16-86 14:52:38

1   /********************************************************
 2    *
 3    * MFO Ver 0.0
 4    *
 5    * module: mEnglish.h
 6    *
 7    * modification history :
 8    *       date    by      reason(s)
 9    *    9 SEPT    RLP     CREATION
10    *
11    * This module is an original, unpublished work and is proprietary to
12    * NELLCOR INC., and may not be divulged or copied in any form
13    * whatsoever without the express written permission of NELLCOR INC.
14    *
15    *
16    * Purpose : English strings for menu server
17    *
18    * data descriptions :
19    *
20    * function descriptions :
21    *
22    ********************************************************/
23
24   /********************************************************
25    *
26    * MID NAMES
27    *
28    ********************************************************/
29
30
31   char far *English [] =
32   {
33       "NELLCOR",
34       "SaO!",
35       "PLETH",
36       "ET$CO!",
37       "INS CO!",
38       "INS N!O",
39       "ET$N!O",
40       "ET$AGT",
41       "INS AGT",
42       "RESP",
```

```
54        "PULSE",
55
56        "CO!",
57
58        "N!O",
59
60        "AGENT",
61
62        "SaO! TREND",
63
64        "CO! TREND",
65
66        "N!O TREND",
67
68        "AGENT TREND",
69
70        "RESP TREND",
71
72        "PULSE TREND",
73
74        "HAL",
75
76        "ETH",
77
78        "FOR",
79
80        "1 HR",
81
82        "8 HRS",
83
84        "20MINS",
85
86        " %",
87
88        "mmHg",
89
90        " KPa",
91
92        " BFM",
93
94        " /MIN",
95
96
97 /*****************************************************
98  **                                                 **
99  **        DEFAULT ALARM LIMIT SETS                 **
100 *****************************************************/
101       "NEONATAL LIMIT SET",
102       "ADULT LIMITS SET",
103
104
105 /*****************************************************
106  **                                                 **
107  **        AGENT FULL NAMES                         **
108 *****************************************************/
```

```
111         "NO AGENT",
112         "HALOTHANE",
113         "ENFLURANE",
114         "ISOFLURANE",
115
116    /***********************************************************
117    **
118    **    PROMPT MESSAGES
119    **
120    ************************************************************/
121
122         "PRESS HELP FOR ASSISTANCE",
123         "INSTRUMENT TEST IN PROGRESS",
124         "PRESS KEY FOR ITEM TO BE CONFIGURED.",
125         "SELECT DESIRED AGENT.",
126         "PRESS SELECT LIMIT UNTIL DESIRED LIMIT IS HIGHLIGHTED, THEN TURN KNOB",
127         "YOU MAY PRESS CONFIGURE TO SELECT AN AGENT",
128         "AGENT DETECTED WHILE NO AGENT SELECTED. USE CONFIGURE TO SELECT AN AGENT",
129         "SELECT ITEM WHOSE UNITS ARE TO BE CHANGED, THEN SELECT UNITS",
130         "SELECT WINDOW, THEN SELECT ITEM TO BE SHOWN IN THAT WINDOW",
131         "SELECT WINDOW,DUAL OR SINGLE TREND FOR THAT WINDOW,THEN SELECT ITEM",
132         "PRESS HELP AGAIN TO RESUME",
133         "SaO2 AT OR ABOVE UPPER LIMIT. RESPIRATORY RATE AT OR BELOW LOWER LIMIT",
134         "SCREEN FORMAT =",
135         "SELECT LOCATION, THEN SELECT ITEM TO APPEAR AT THAT LOCATION",
136         "SELECT ITEM, THEN SELECT DESIRED SWEEP SPEED.",
137         "YOU ARE NOW AT A LEVEL THAT REQUIRES TECHNICAL KNOWLEDGE OF THE SYSTEM",
138         "SELECT THE LIMIT SET THAT YOU WOULD LIKE LOADED.",
139         "SELECT CHANNEL, THEN SIGNAL TO BE ON THAT CHANNEL,AND FINALLY THE SCALE",
140         "SELECT WINDOW, THEN SELECT TREND FOR THAT WINDOW,THEN SELECT ITEM",
141         "SELECT PARAMETER THEN THE VALUE FOR THAT PARAMETER",
142         "SELECT INITIALS WITH LETTER AND KNOB ROTATION, THEN NAME THE SET",
143         "SELECT CALIBRATION GAS, THEN PRESS CALIBRATE",
```

```
167         "VOLTAGES CHANGE IN REAL TIME",
168         "SELECT THE NAME YOU WOULD LIKE LIMITS SAVED UNDER.",
169         "SELECT INITIALS WITH SELECT LETTER AND KNOB ROTATION, THEN EXECUTE",
170         "SELECT PARAMETER (LINE), THEN SELECT POSITION IN THAT LINE,THEN ROTATE KNOB",
171         "SELECT THE LIMIT SET THAT YOU WOULD LIKE LOADED.",
172         "TO CLEAR ALL TREND MEMORY, PRESS CLEAR AGAIN, OTHERWISE PRESS EXIT",
173         "THE WAVEFORM SCREEN IS NOW FROZEN.  UNFREEZE OR EXIT RESUMES NORMAL OPERATION.",
174         " YOU MUST FIRST SELECT A WINDOW.",
175    /**************************************************************
176     **     MENU OPTIONS/BUTTON NAMES
177     **************************************************************/
178         " ",
179         "EXIT",
180         "SCREEN",
181         "TECHNICAL",
182         "CALIBRATION",
183         "AGENT",
184         "SELECT",
185         "PRINT",
186         "USE LIMIT",
187         "SELECT LIMIT",
188         "SAVE SETUP",
189         "SELECT ITEM",
190         "SELECT UNITS",
191         "SELECT WINDOW",
192         "TREND PERIOD",
193         "DUAL TREND",
194         "SELECT PERIOD",
```

```
224     "CLEAR TRENDS",
225     "DEFINE WINDOW",
226     "SWEEP SPEED",
227     "ITEM LOCATION",
228     "CHANGE UNITS",
229     "FREEZE",
230     "TREND",
231     "LIMITS",
232     "CONFIGURE",
233     "ENTIRE SCREEN",
234     "ON ALARM ON",
235     "ALL TRENDS",
236     "AUTO ON ",
237     "SELECT FORMAT",
238     "SELECT WINDOW",
239     "SELECT ITEM",
240     "SAVE/RECALL",
241     "SELECT LOCATION",   /*    too long   */
242     "SELECT SPEED",
243     "OUTPUTS",
244     "SYS PARAMETERS",    /*    too long   */
245     "ANALOG",
246     "DIGITAL",
247     "UNFREEZE",
248     "SPLIT SCREEN",
249     "SELECT SETUP",
250     "EXECUTE",
251     "SELECT CHANNEL",    /*    too long   */
252     "SELECT SIGNAL",
```

```
281        "SELECT SCALE",
282        "TREND PERIOD",
283        "SELECT PARAMETER",    /* too long */
284        "SELECT VALUE",
285        "USE LIMIT SET",
286        "RECALL",
287        "SAVE",
288        "NAME SET",
289        "SELECT LETTER",
290        "SELECT GAS",
291        "SET TO ZERO",
292        "CALIBRATE",
293        "ANALOG OUTPUT",
294        "DIGITAL OUTPUT",      /* too long */
295        "SELECT NAME",
296        "SELECT POSITION",     /* too long */
297        "SELECT SETUP",
298        "CLEAR BUFFER",
299        "GAS CALIBRATION",     /* too long */
300        "TEST MODE",
301        "PRINT TREND",
302        "ON ALARM OFF",
303        "AUTO OFF", /*******************************************************
 **    HELP MESSAGES
 *******************************************************/

"HELP MESSAGE 0",
```

```
337         "HELP MESSAGE 1",
338         "HELP MESSAGE 2",
339         "HELP MESSAGE 3",
340         "HELP MESSAGE 4",
341         "HELP MESSAGE 5",
342         "HELP MESSAGE 6",
343         "HELP MESSAGE 7",
344         "HELP MESSAGE 8",
345         "HELP MESSAGE 9",
...
357      };
```

Thu 10-11-86 19:26:54    MENGLISH.H
    10-16-86 14:52:38

```
 1  /****************************************************************
 2  ** MFO Ver 0.0
 3  **
 4  ** module: menglish.h
 5  **
 6  ** modification history :   reason(s)
 7  **       date       by
 8  **
 9  **
10  **
11  **
12  ** This module is an original, unpublished work and is proprietary to
13  ** NELLCOR INC., and may not be divulged or copied in any form
14  ** whatsoever without the express written permission of NELLCOR INC.
15  **
16  ** purpose :external include
17  **
18  ** data descriptions :
19  **
20  ** function descriptions :
21  **
22  *****************************************************************/
23
24  extern char far * far English[];
```

```
Thu 10-16-86 14:20:52    MENUSRVR.C
    10-16-86 14:52:38

1   /**************************************************************
 2   **
 3   **  MFO Ver 0.0
 4   **
 5   **  module: menusrvr.c
 6   **
 7   **  modification history :
 8   **       date                  by                    reason(s)
 9   **    12 aug 86              ron parks              creation
10   **
11   **
12   **  This module is an original, unpublished work and is proprietary to
13   **  NELLCOR INC., and may not be divulged or copied in any form
14   **  whatsoever without the express written permission of NELLCOR INC.
15   **
16   **  purpose : test menu implementation software
17   **
18   **  data descriptions :
19   **
20   **  function descriptions :
21   **
22   **
23   **  THE FOLLOWING IS THE DEFINITION OF THE BUTTON TABLES.
24   **  USED TO DETERMINE WHICH MENU IS TO BE DISPLAYED FOLLOWING THE PRESSING OF
25   **  ANY GIVEN BUTTON.  A 'BUTTON', AS FAR AS THESE TABLES ARE CONCERENED, ARE THE
26   **  LOWER 5 FUNCTION BUTTONS, THE 'HELP BUTTON, AND THE KNOB, THE 'ALARM SILENCE
27   **  BUTTON AND THE POWER ON/STANBY ARE NOT HANDLED IN THESE TABLES.
28   **
29   **
30   **  THE PRESSED IS USED TO INDEX INTO THE CURRENT BUTTON TABLE (MENU). WHEN A
31   **  NEW MENU IS CALLED FOR, THE BUTTON TABLE PTR IS CHANGED BY THE FUNCTION THAT
32   **  PROCESSED THE PRESSED BUTTON.
33   **
34   **  THE BUTTONS ARE NUMBERED (FOR INTERNAL USE) FROM RIGHT TO LEFT AS ONE FACES
35   **  THE MFO UNIT AS FOLLOWS:
36   **
37   **         HELP       = 0
38   **         KNOB       = 1
39   **         1ST BUTTON = 2
40   **         2ND BUTTON = 3
41   **         3RD BUTTON = 4
42   **         4TH BUTTON = 5
43   **         5TH BUTTON = 6       EXIT KEY
44   **
45   ***************************************************************/
46   #define MENU
47   #define BLENGTH
48
49   #include "mclude.h"
50   extern int near DstrPixln();
51
52
```

```
 53    char far *StringAddress = {0};
 54    short absxtlc = {0};
 55    short absytlc = {0};
 56    short absxbrc = {0};
 57    short absybrc = {0};
 58    WinNumber win_num = ((WinNumber) 0);
 59    short xcorner = {0};
 60    short ycorner = {0};
 61
 62    /****************************************************************
 63     *
 64     *
 65     *                    MAIN ENTRY POINT IS HERE
 66     *
 67     *           NOW PROCESS THE NEW BUTTON/KNOB ACCORDING TO THE ACTIVE MENU AND
 68     *           RETURN A NEW ACTIVE MENU IF NECESSARY OTHERWISE RETURN THE SAME
 69     *           MENU ADDRESS
 70     *
 71     *
 72     ****************************************************************/
 73
 74    void
 75    MenuServer(keyknob)
 76    short keyknob;
 77    {
 78    short results;
 79    short results1;
 80    short index;
 81
 82
 83
 84
 85    /* start-restart menu timeout ( 2 mins of no operator intervention will
 86       execute current menu exit and return to top level menu */
 87
 88    results = CheckForSilence( keyknob );
 89    if ( results == FALSE )
 90      {
 91        results1 = WhoOwnsKnob( keyknob );   /* if this is a knob, see if alarm silence
 92                    owns it */
 93        if ( results1 == FALSE )
 94          {
 95            screen.kybd_input = keyknob;
 96            index = keyknob & KEY_CODE;
 97            /* this is just in case they don't press help again before preceding */
 98            if ((screen.hlp_dflag) && (index != HELP_BUTTON) && (!(screen.kybd_input
 99                & RELEASED)))
100              {
101                DRestoreWFWin();
102                screen.nonwf_dflag = FALSE;
103              }
104
105    if (( screen.kybd_input & PRESSED ) || ( index & KEY_CODE == KNOB_CODE ))
106        DHome(PROMPT_BUFFER);
107    screen.actv_btn_menu = (*screen.actv_btn_menu->menu_hdlr[ index ])();
```

```
108  }
109  }
110  }
111  
112  /****************************************************
113  *
114  *
115  *
116  ****************************************************/
117  short
118  WhoOwnsKnob( input_code )
119  short input_code;
120  {
121  short results;
122  short save_direction;
123  
124  
125  
126  
127      if ((( input_code & KEY_CODE ) == KNOB_CODE ) && ( screen.silence_btnflg ))
128      {
129          save_direction = ( input_code & KNOB_CLOCKWISE );
130          input_code &= KNOB_DELTA ;
131          input_code >>= 8 ;
132          if ( !save_direction )
133              input_code = -input_code;
134          LKnobInput( CHNG_SILENT_PERIOD, *(digwdw_tbl[ screen.digwdw_selctd].curr_mid),
135                      screen.limit_selctd,input_code);
136          results = TRUE;
137          return ( results );
138      }
139  
140      if ((( input_code & KEY_CODE ) == ALARM_BUTTON )
141      {
142          if ( input_code & PRESSED )
143          {
144              screen.silence_btnflg = TRUE;
145              LKeyInput( SILENT_KEY,0,0 );
146              results = TRUE;
147              return ( results );
148          }
149          else
150              screen.silence_btnflg = FALSE;
151      }
152  
153      results = FALSE;
154  
155      return ( results );
156  }
157  /****************************************************
158  *
159  * See if the alarm silence function is to be called
160  *
161  *
162  ****************************************************/
163  
```

```
164  short CheckForSilence( input_code )
165  short input_code;
166  {
167    short results;
168
169    if (( input_code & KEY_CODE ) == ALARM_BUTTON )
170    {
171       if ( input_code & RELEASED )
172          screen.silence_btnflg = FALSE;   /* reset silence btn depressed flag */
173       else screen.silence_btnflg = TRUE;
174          results = TRUE;
175    }
176
177    else results = FALSE;
178
179    return (results);
180
181  }
182  /************************************************************************
183  ** COMPUTE ABSOULTE TOP LEFT CORNER AND BOTTOM RIGHT CORNER
184  **
185  *************************************************************************/
186
187  void
188  mDoAbsCorners()
189  {
190
191     absxtlc = coord_ptr->xtlc + wcoord_ptr->xtlc;
192     absytlc = coord_ptr->ytlc + wcoord_ptr->ytlc;
193     absxbrc = coord_ptr->xbrc + wcoord_ptr->xbrc;
194     absybrc = coord_ptr->ybrc + wcoord_ptr->ybrc;
195
196  }
197  /************************************************************************
198  ** THESE ROUTINES RETURN THE X POSITION FOR CENTERING THE GIVEN STRING IN A MENU BUTTON
199  ** POSITION
200  *************************************************************************/
201
202  short
203  BPos1(string_ptr)
204  char far *string_ptr;
205  {
206     return ( BtnlCntr - ( DstrPixln(FontSmall,string_ptr ) / 2 ));
207  }
208
209  short
210  BPos2(string_ptr)
211  char far *string_ptr;
212  {
213     return (Btn2Cntr - ( DstrPixln(FontSmall,string_ptr ) / 2));
214  }
```

```
220    short
221    BPos3(string_ptr)
222    char far *string_ptr;
223    { return (Btn3Cntr - ( DstrPixln(FontSmall,string_ptr) / 2 ));
224    }
225
226    short
227    BPos4(string_ptr)
228    char far *string_ptr;
229    { return (Btn4Cntr - ( DstrPixln(FontSmall,string_ptr) / 2 ));
230    }
231
232
233    short
234    BPos5(string_ptr)
235    char far *string_ptr;
236    { return (Btn5Cntr - ( DstrPixln(FontSmall,string_ptr) / 2 ));
237    }
238
239    /*****************************************************************
240    **
241    ** BEEP AND GIVE NO WINDOW SELECTED ERROR MESSAGE
242    **
243    *****************************************************************/
244    void
245    NoWinSelected()
246    {
247        BEEP;
248        first*/              /* operator tried to change units without selecting a window
249        DBlankWin( PROMPT_BUFFER );
250        dprintf( PROMPT_BUFFER, PMSG28 );
251    }
252
253    /*****************************************************************
254    ** DISPALY HELP- THIS ROUTINE FLIP FLOPS THE HELP DISPLAYED FLAG IN THE SCREEN
255    **              DESCRIPTION BLOCK. IF THE RESULT IS TRUE THEN THE HELPSCREEN
256    **              IS DISPLAYED.  FALSE MEANS THE HELPSCREEN IS ALREADY UP, SO
257    **              IT BRINGS BACK THE SCREEN THAT WAS DISPLAYED WHEN HELPWAS
258    **              PRESSED.
259    **
260    *****************************************************************/
261    void
262    display_hlp(help_msgptr)
263    msgx help_msgptr;
264    {
265        screen.hlp_dflag = ~screen.hlp_dflag;      /*flip flop help disp flag */
266        if ( screen.hlp_dflag == TRUE )
267        {
268            screen.nonwf_dflag = TRUE;
269            DHelp( Language[(short) help_msgptr ]);
270            dprintf( PROMPT_BUFFER, PMSG10 );
```

```
276    else    /* bring back previous screen */
277        {
278         DRestoreWFWin();        /* display waveform/trend again */
279         screen.nonwf_dflag = FALSE;
280         DBlankWin( PROMPT_BUFFER );
281        }
282        }
283
284
285  /*****************************************************************/
286  **  DISPLAY TOP LEVEL HELPTEXT
287  /*****************************************************************/
288
289  struct btn_menu far *
290  top_lv_hlp()
291  {
292   display_hlp( HELP0 );
293   return (screen.actv_btn_menu);   /* no menu change */
294  };
295
296
297  /*****************************************************************/
298  **  ROUTINE TO HANDLE KNOB WHEN IT IS TO BE USED FOR VOLUME ADJUSTMENT
299  /*****************************************************************/
300
301  struct btn_menu far *
302  volume_adj()
303  {
304   short save_direction;
305   short knobstatus;
306
307   /*give knob information to display server */
308   save_direction = ( screen.kybd_input & KNOB_CLOCKWISE );
309   knobstatus = screen.kybd_input & KNOB_DELTA_;
310   if (! (save_direction & KNOB_CLOCKWISE ))
311       knobstatus = -knobstatus;
312   LKnobInput( CHNG_PULSE_VOL, 0,  0, knobstatus );
313   return (screen.actv_btn_menu);   /* no menu change */
314  };
315
316
317  /*****************************************************************/
318  **  DISPLAY LEVEL 0 CONFIGURE MENU.
319  **  NEW MENU = 'cfig_mnu' = EXIT SCREEN TECHNICAL (BLANK) AGENT
320  /*****************************************************************/
321
322  struct btn_menu far *
323  cfig_lv0()
```

```
332     {
333     DBlankWin( PROMPT BUFFER );     /* clear prompt buffer */
334     dprintf( PROMPT BUFFER, PMSG2 );
335     DBlankWin( MENU BUFFER );
336     dprintf( MENU BUFFER, MENU PARAMETERS,
337             BPos5(OPT1),0,OPT1,BPos4(OPT2),0,OPT2,BPos2(BPos2(BLANK),0,OPT3,BPos2(BLANK),0,BLANK,
338             BPos1(OPT5),0,OPT5);
339     return (&cfig_mnu);
340     }
341     /*********************************************************************
342     ** ROUTINE TO HANDLE 1ST LEVEL OF LIMITS (CONFIGURE)
343     ** NEW MENU = 'lmts_mnu' = EXIT PRINT LIMIT SELECT  SAVE SETUP  SELECT SET
344     *********************************************************************/
345     struct btn_menu far *
346     lmts_lv0()
347     {
348     DBlankWin(MENU BUFFER);       /* clear previous menu */
349     dprintf( MENU BUFFER, MENU PARAMETERS,
350             BPos5(OPT1),0,OPT1,BPos4(OPT7),0,OPT7,BPos3(OPT9),0,OPT9,BPos2(OPT10),0,OPT10,
351             BPos1(OPT41),0,OPT42);
352     return (&lmts_mnu);
353     }
354     /*********************************************************************
355     ** HANDLER FOR TREND (CONFIGURE)
356     ** NEW MENU = 'trnd_mnu' =   EXIT    WINDOW SELECT  SELECT PERIOD  CLEAR TRENDS  SELECT ITEM
357     *********************************************************************/
358     struct btn_menu far *
359     trend_lv0()
360     {
361     DBlankWin( PROMPT BUFFER );
362     DBlankWin( MENU BUFFER );
363     dprintf( MENU BUFFER, MENU PARAMETERS,
364             BPos5(OPT1),0,OPT1,BPos4(OPT13),0,OPT13,BPos3(OPT16),0,OPT16,BPos2(OPT17),0,OPT17,
365             BPos1(OPT11),0,OPT11);
366     return (&trnd_mnu);
367     }
368     /*********************************************************************
369     ** HANDLER FOR THE FREEZE (CONFIGURE) BUTTON
370     ** frz_mnu =   EXIT   PRINT   UNFREEZE   SAVE/RECALL   SPLIT SCREEN
371     *********************************************************************/
372     struct btn_menu far *
```

```
385  *frz_lv0()
386  {
387     /* tell display server to freeze the screen */
388     screen.freez_stat = FROZEN;
389     /* DFreeze(); */
390     DBlankWin( MENU_BUFFER );
391     dprintf(MENU_BUFFER, MENU_PARAMETERS,
392           BPos5(OPT1),0,OPT1,BPos4(OPT7),0,OPT7,BPos3(OPT40),0,OPT40,BPos2(OPT33),0,OPT33,
393           BPos1(OPT41),0,OPT41) );
394     DBlankWin(PROMPT_BUFFER);
395     dprintf(PROMPT_BUFFER, PMSG28 );
396     return (&frz_mnu);
397  };
398
399  /****************************************************************
400  **
401  ** HANDLER FOR THE PRINT (CONFIGURE) BUTTON
402  **         EXIT  ON ALARM =   PRINT TREND      AUTO =    SCREEN
403  ****************************************************************/
404
405
406  struct btn_menu far *
407  prt_lv0()
408  {
409     short autop;
410     short onalarm;
411
412     DBlankWin( MENU_BUFFER );
413     if ( screen.auto_prtflg )
414        autop = (short) BTN29;      /* AUTO =ON  */
415     else autop = (short) BTN68;    /* AUTO =OFF */
416
417     if (screen.prt_onalrm_flg)
418        onalarm = (short) BTN27;
419     else onalarm = (short) BTN67;
420
421     dprintf( MENU_BUFFER, MENU_PARAMETERS,
422           BPos5(OPT1),0,OPT1,BPos4(Language[ onalarm ],0,Language[ onalarm ],BPos3(OPT66),
423           0,OPT66,BPos2(Language[ autop ],0,Language[ autop ],BPos1(OPT2),0,OPT2) );
424
425     /* now put 'ON' or 'OFF' for auto and on alarm */
426     return (&prnt_mnu);
427  };
428
429  /****************************************************************
430  **
431  ** HANDLER FOR CONFIGURE LEVEL 0 HELP
432  ****************************************************************/
433
434
435  struct btn_menu far *
436  *cfig0_hlp()
437  {
438     dprintf(HELP0);
```

```
439        return (screen.actv_btn_menu);    /* no menu change */
440    };
441    /*******************************************************************
442    ** HANDLER FOR AGENT SELECTION (CONFIGURE)                        **
443    **       agt_mnu =    EXIT      BLANK       HALOTHANE   ENFLURANE   ISOFLURANE
444    *******************************************************************/
445    struct btn_menu far *
446    agt_lv0()
447    {
448
449      DBlankWin( PROMPT_BUFFER );
450      DBlankWin( MENU_BUFFER );
451      dprintf( PROMPT_BUFFER, PMSG3 );
452      dprintf( MENU_BUFFER, MENU_PARAMETERS,
453             BPos5(OPT1),0,OPT1,BPos4(BLANK),0,BLANK,BPos3(Language[(short) HALO]),
454             0,Language[(short) HALO],BPos2(Language[(short) ENFLUR]),0,Language[(short)
455             ENFLUR],
456             BPos1(Language[(short) ISOFLUR]),0,Language[(short) ISOFLUR] );
457      return (&agt_mnu);
458    }
459    /*******************************************************************
460    ** HANDLER FOR TECHNICAL (CONFIGURE) BUTTON LEVEL 0               **
461    **       EXIT        OUTPUTS      CALIBRATION      SYS PARAMETER
462    *******************************************************************/
463    struct btn_menu far *
464    tech_lv0()
465    {
466
467      DBlankWin( PROMPT_BUFFER );
468      DBlankWin( MENU_BUFFER );
469      dprintf( MENU_BUFFER, MENU_PARAMETERS,
470             BPos5(OPT1),0,OPT1,BPos4(BLANK),0,BLANK,BPos3(OPT36),0,OPT36,BPos2(OPT4),0,OPT4,
471             BPos1(OPT37),0,OPT37);
472      dprintf(PROMPT_BUFFER, PMSG15);
473      return (&all_exits);
474    };
475    /*******************************************************************
476    ** HANDLER FOR SCREEN (CONFIGURE) BUTTON                          **
477    ** EXIT    DEFINE WINDOW   SWEEP SPEED   ITEM LOCATION   CHANGE UNITS
478    *******************************************************************/
479    struct btn_menu far *
480    scrn_lv0()
481    {
482      DBlankWin(MENU_BUFFER);
```

```
492         DBlankWin(PROMPT_BUFFER);
493         dprintf(PROMPT_BUFFER,PMSG0 );
494         dprintf( MENU_BUFFER, MENU_PARAMETERS,
495              BPos5(OPT1),0,OPT1,BPos4(OPT18),0,OPT18,BPos3(OPT19),0,OPT19,BPos2(OPT20),0,OPT20,
                 BPos1(OPT21),0,OPT21 );
496         return (&scrn_mnu);
497    }
498
499    /*********************************************************************
500    **    RESTORE TOP LEVEL MENU AND NORMAL RUN SCREEN
501    **         PRINT       FREEZE       TREND       LIMITS       CONFIGURE
502    *********************************************************************/
503    struct btn_menu far *
504    show_top()
505    {    /* build normal run screen */
506
507         DBlankWin( MENU_BUFFER );
508         DBlankWin(PROMPT_BUFFER );
509         dprintf( MENU_BUFFER, MENU_PARAMETERS,
510              BPos5(OPT7),0,OPT7,BPos4(OPT22),0,
                 OPT22,BPos3(OPT23),0,OPT23,BPos2(OPT24),0,OPT24,BPos1(OPT25),0,OPT25 );
511         return (&top_lv_mnu);
512    }
513
514    /*********************************************************************
515    **    BLANK BUTTON HANDLER (FOR THE IDIOT THAT PUSHES A BLANK BUTTON)
516    *********************************************************************/
517    struct btn_menu far *
518    blank_btn()
519    {    /* sound operator error tone (BEEP?) */
520         BEEP;
521         return (screen.actv_btn_menu);    /* no menu change */
522    }
523
524    struct btn_menu far *
525    save_fmt()
526    {
527         return (screen.actv_btn_menu);
528    }
529
530    struct btn_menu far *
531    oputs_lv0()
532    {
533         return (screen.actv_btn_menu);
534    }
```

```
547    struct btn_menu far *
548    prat_int_sav()
549    {
550    return (screen.actv_btn_menu);
551    }
552
553    struct btn_menu far *
554    recall_fmt()
555    {
556    return (screen.actv_btn_menu);
557    }
558
559    struct btn_menu far *
560    fmtsr_execut()
561    {
562    return (screen.actv_btn_menu);
563    }
564
565    struct btn_menu far *
566    fmsvrcal_exit()
567    {
568    return (screen.actv_btn_menu);
569    }
570
571    struct btn_menu far *
572    fmtsvrcal()
573    {
574    return (screen.actv_btn_menu);
575    }
576
577    struct btn_menu far *
578    wfmt_svrcall()
579    {
580    return (screen.actv_btn_menu);
581    }
582
583    struct btn_menu far *
584    sys_params()
585    {
586    return (screen.actv_btn_menu);
587    }
588
589    struct btn_menu far *
590    fmtsvrcal_exit()
591    {
592    return (screen.actv_btn_menu);
593    }
594
595    struct btn_menu far *
596    fmtsvrcal_hlp()
597    {
598    return (screen.actv_btn_menu);
599    }
600
```

```
Thu 10-11-86 13:38:32   MFRENCH.C
    10-16-86 14:52:38

1  /*****************************************************************
 2  **
 3  **  MFO Ver 0.0
 4  **
 5  **  module: mFrench.h
 6  **
 7  **  modification history :  reason(s)
 8  **          date        by
 9  **
10  **
11  **  This module is an original, unpublished work and is proprietary to
12  **  NELLCOR INC., and may not be divulged or copied in any form
13  **  whatsoever without the express written permission of NELLCOR INC.
14  **
15  **  purpose : Messages for French Language version
16  **
17  **  data descriptions : Data layed out exactly as English.
18  **
19  **  function descriptions :
20  **
21  ******************************************************************/
22
23
24  char far *French [] =
25          {
26                  { "Le SaO2" }
27          };
28
29
```

```
Thu 10-11-86 13:38:26   MFRENCH.H
    10-16-86 14:52:38

1  /*****************************************************************
 2  **
 3  **  MFO Ver 0.0
 4  **
 5  **  module:
 6  **
 7  **  modification history :  reason(s)
 8  **          date        by
 9  **
10  **
11  **  This module is an original, unpublished work and is proprietary to
12  **  NELLCOR INC., and may not be divulged or copied in any form
13  **  whatsoever without the express written permission of NELLCOR INC.
14  **
15  **  purpose :
16  **
17  **  data descriptions :
18
```

```
19   *  function descriptions :
20   *
21   **********************************************************/
22
23   extern far *French[];
24
25

Thu 10-11-86 13:44:02   MGERMAN.C
    10-16-86 14:52:38

1   /**********************************************************
2    *
3    *  MFO Ver 0.0
4    *
5    *  module: mGerman.h
6    *
7    *  modification history :  reason(s)
8    *          date       by
9    *
10   *
11   *  This module is an original, unpublished work and is proprietary to
12   *  NELLCOR INC., and may not be divulged or copied in any form
13   *  whatsoever without the express written permission of NELLCOR INC.
14   *
15   *  purpose : Messages for German Language version
16   *
17   *  data descriptions : Data layed out exactly as English.
18   *
19   *  function descriptions :
20   *
21   **********************************************************/
22
23   char far *German [] =
24        {          { "Der SaO2" }
25
26        };
27

Thu 10-11-86 13:43:46   MGERMAN.H
    10-16-86 14:52:38

1   /**********************************************************
2    *
3    *  MFO Ver 0.0
4    *
5    *  module: mgerman.h
6    *
7    *  modification history :  reason(s)
8    *          date       by
9    *
10   *
11   *
```

```
12   * This module is an original, unpublished work and is proprietary to
13   * NELLCOR INC., and may not be divulged or copied in any form
14   * whatsoever without the express written permission of NELLCOR INC.
15   *
16   * purpose :
17   *
18   * data descriptions :
19   *
20   * function descriptions :
21   *
22   *
23   ******************************************************************/
24
25   extern char far *German[];

Thu 10-14-86 21:47:50   MKNOBKYB.C
    10-16-86 14:52:38

1  /*****************************************************************
 2   *
 3   * MFO Ver 0.0
 4   *
 5   * module:  mknobkybd.c
 6   *
 7   * modification history :
 8   *       date     by   rlp   reason(s)
 9   *    16 sept          rlp   creation
10   *
11   *
12   * This module is an original, unpublished work and is proprietary to
13   * NELLCOR INC., and may not be divulged or copied in any form
14   * whatsoever without the express written permission of NELLCOR INC.
15   *
16   * purpose :Knob processing - Process the NELLCOR Knob at interrupt time, called by a
17   *                            video sync interrupt handler.
18   *
19   *          Keyboard processing - The keyboard is processed once every 40ms
20   *                                until                   a change is status is
21   *                                detected, then a 80ms to   debounce the key. The keycode is placed in the
22   *                                                           keyboard queue with it's direction bit (bit 15 =
23   *                                                           1 = key released after being depressed).
24   *
25   * data descriptions :
26   *
27   * function descriptions : If a change in the knob is detected, the knob code (9)
28   *                         along with the direction bit (bit 15) and cnt is placed in the
29   *                         Keyboard Queue.
30   *
31   ******************************************************************/
32   #define KYBD_STUFF
33   mProcKybd();
```

```
34  short DetermineDirection();
35  void PutInKybdQ();
36  void near mProcKnob();
37  void mKybdInit();
38  far mDebounce();
39
40
41  #include "mclude.h"
42  #include ":\mfo\xevent.h"
43  #include "\mfo\itest\mbique.h"
44
45
46
47  short prev_image = {-1};       /* last valid kybd image */
48  short new_image = {0};          /* present kybd image */
49  short interim_image = {0};     /* last undebounced image */
50  short button = {0};
51  short knob = {0};
52  short direction = {0};
53
54
55  /***********************************************************
56  *  THIS ROUTINE PROCESSES THE KEYBOARD BUTTONS AND STARTS DEBOUNCE TIMER IF
57  *  A CHANGE IN STATUS IS DETECTED. IT IS REQUEUED BY THE DEBOUNCE ROUTINE.
58  *
59  ***********************************************************/
60
61  mProcKybd()
62  {
63    short knob_value;
64
65    interim_image = ( prev_image ^ mInputKybd() );   /* look for a change in status */
66    interim_image &= CLEAR_KNOB;                      /* clear all knob bits */
67    if ( interim_image )
68       xSetTimeDelay( &kybd_timers.timers[ DEBOUNCE_TIMER ], DEBOUNCE_TICKS, NO_RESTART );
69
70  /* no change in status so this routine requeues itself */
71
72    else xSetTimeDelay( &kybd_timers.timers[ PROC_KYBD_TIMER ], KYBD_TICKS, NO_RESTART );
73
74    if ( knob & KNOB_CNT )
75    {
76        knob_value = mGetKnob( &knob );        /* gets knob value and zeros previous value */
77        PutInKybdQ( knob_value | KNOB_CODE );  /* put knob in queue and post it */
78    }
79  }
80
81  /***********************************************************
82  *  THIS ROUTINE INITITALIZES THE KEYBOARD VARIABLES AND TIMERS. CALLED AT POWER
83  *  UP TIME. TIMERS ARE CREATED BUT NOT STARTED.
84  *
85  ***********************************************************/
86
87  void
```

```
 90  mKybdInit()
 91  {
 92      prev_image = -1;
 93      knob = 0;
 94  }
 95
 96
 97
 98  /************************************************************************
 99  ** THIS ROUTINE DETERMINES WHETHER THE KEY WAS DEPRESSED OR RELEASED.
100  **
101  ************************************************************************/
102  short DetermineDirection( bit )
103  short bit;
104  {
105      short temp;
106      short action;
107
108      temp = prev_image ^ bit;
109      if( temp > prev_image )
110          action = RELEASED;
111
112      else action = PRESSED;
113
114      return ( action );
115  }
116
117
118
119  /************************************************************************
120  ** THIS ROUTINE PUTS THE KEY/KNOB AND ITS DIRECTION IN THE KEYBOARD QUEUE AND
121  ** POSTS THE FACT TO THE MENU SERVER
122  ************************************************************************/
123  void PutInKybdQ( front_panel_input )
124  short front_panel_input;
125  {
126      short que_status;
127
128      que_status = mIputinque( &kybdque, front_panel_input );
129      XPost( PID_CONTROL, FP_INPUT_EV );
130  }
131
132
133
134  /************************************************************************
135  ** THIS ROUTINE PROCESSES THE KNOB ON THE FRONT PANEL AT EVERY VERTICAL SYNC
136  ** INTERRUPT.
137  **
138  ************************************************************************/
139  void near
140  mProcKnob()
```

```
146    {
147     short new_knob;
148     short old_knob;
149
150     new_knob = mInputKybd();          /* read knob/kybd port */
151     if ( new_knob & KNOB_MOVED )      /* see if knob has moved */
152     {
153         if ((new_knob & KDIRECTION_BIT ) != ( old_knob & KDIRECTION_BIT ))
154             knob = 0;  /* clear count if direction has changed */
155
156         else {
157             if ( new_knob & KNOB_CLOCKWISE )
158                 knob |= KNOB_UP;
159
160             else knob &= KNOB_DOWN;
161
162             knob += 0x100;             /* increment count half of knob word */
163             old_knob = new_knob;
164         }
165     }
166    }
167
168
169
170
171   /********************************************************************
172   * THIS ROUTINE IS CALLED AFTER 2 TICKS TO SEE IF THE KYBD INTERIM STATUS IS
173   * VALID. IF THE NEW STATUS = INTERIM STATUS THEN THE KEY CODE CORRESPONDING TO
174   * ANY BIT THAT HAS CHANGED STATUS ( AS COMPARED TO THE PREVIOUS STATUS )
175   * IS PLACED IN THE KYBD QUEUE.
176   *
177   ********************************************************************/
178
179   mDebounce()
180   {
181    short knob_value;
182
183    new_image = ( prev_image ^ mInputKybd());
184    new_image &= CLEAR_KNOB;
185    if ( new_image == interim_image )
186    {
187        if ( new_image & ALARM_BUTTON_BIT )
188        {
189            direction = DetermineDirection( ALARM_BUTTON_BIT );
190            button = ALARM_BUTTON | direction;
191            PutInKybdQ( button );
192            prev_image ^= ALARM_BUTTON_BIT;     /* update kybd status */
193        }
194
195        if ( new_image & POWER_BUTTON_BIT )
196        {
197            direction = DetermineDirection( POWER_BUTTON_BIT );
198            button = POWER_BUTTON | direction;
199            PutInKybdQ( button );
200            prev_image ^= POWER_BUTTON_BIT;
201        }
202    }
```

```
203         if ( new_image & HELP_BUTTON_BIT )
204         {
205             direction = DetermineDirection( HELP_BUTTON_BIT );
206             button = HELP_BUTTON | direction;
207             PutInKybdQ( button );
208             prev_image ^= HELP_BUTTON_BIT;
209         }
210
211         if ( new_image & BUTTON1_BIT )
212         {
213             direction = DetermineDirection( BUTTON1_BIT );
214             button = BUTTON1 | direction;
215             PutInKybdQ( button );
216             prev_image ^= BUTTON1_BIT;
217         }
218
219         if ( new_image & BUTTON2_BIT )
220         {
221             direction = DetermineDirection( BUTTON2_BIT );
222             button = BUTTON2 | direction;
223             PutInKybdQ( button );
224             prev_image ^= BUTTON2_BIT;
225         }
226
227         if ( new_image & BUTTON3_BIT )
228         {
229             direction = DetermineDirection( BUTTON3_BIT );
230             button = BUTTON3 | direction;
231             PutInKybdQ( button );
232             prev_image ^= BUTTON3_BIT;
233         }
234
235         if ( new_image & BUTTON4_BIT )
236         {
237             direction = DetermineDirection( BUTTON4_BIT );
238             button = BUTTON4 | direction;
239             PutInKybdQ( button );
240             prev_image ^= BUTTON4_BIT;
241         }
242
243         if ( new_image & BUTTON5_BIT )
244         {
245             direction = DetermineDirection( BUTTON5_BIT );
246             button = BUTTON5 | direction;
247             PutInKybdQ( button );
248             prev_image ^= BUTTON5_BIT;
249         }
250
251     }
252
253     /* restart keyboard scan timer */
254     xSetTimeDelay( &kybd_timers.timers[ PROC_KYBD_TIMER ], KYBD_TICKS, NO_RESTART );
255
256     if ( knob & KNOB_CNT )
```

```
259              {       knob_value = mGetKnob( &knob );  /* gets knob value and zeros previous value */
260                      PutInKybdQ( knob_value | KNOB_CODE );
261              }
262
263
264
265
266
267
```

Thu 10-14-86 21:47:32   MKYBD.S
    10-16-86 14:52:38                       reason

```
 1  ;******************************************************************
 2  ;
 3  ;       MFO Ver 0.0
 4  ;
 5  ;       Module: mkybd.s
 6  ;
 7  ;       modification history :
 8  ;               date            by              reason(s)
 9  ;               18 sept         rlp             creation
10  ;
11  ;            COPYRIGHT (C) 1986 NELLCOR INCORPORATED
12  ;
13  ;       This module is an original, unpublished work and is proprietary to
14  ;       NELLCOR INC.; and may not be divulged or copied in any form
15  ;       whatsoever without the express written permission of NELLCOR INC.
16  ;
17  ;       Purpose: read kybd and knob
18  ;
19  ;       Procedures: Read keyboard and knob
20  ;               Public  _mInputKybd
21  ;               Public  _mGetKnob
22  ;
23  ; Public Data:
24  ;
25  ;******************************************************************
26  ;
27
28  SYS_TEXT segment byte public 'code'
29  ASSUME CS:SYS_TEXT
30
31  KEYBOARD_PORT equ 280h
32  _mInputKybd proc near
33          mov     dx,KEYBOARD_PORT
34          in      ax,dx
35          ret
36  _mInputKybd endp
37
38
39  knobptr equ bp+4
40  _mGetKnob proc near
41
```

```
42              push    bp
43              mov     bp, sp
44              mov     bx,[knobptr]
45              xor     ax, ax
46              xchg    ax,[bx]
47              pop     bp
48              ret
49      _mGetKnob endp
50
51      SYS_TEXT ends
52
53              end
54
Thu 10-16-86 10:21:24    MROMMNUS.C
Thu 10-16-86 14:52:38

1       /****************************************************
2       **
3       **      MFO Ver 0.0
4       **
5       **      module: mrommnus.c
6       **
7       **      modification history :
8       **          date              by              reason(s)
9       **       12 aug 86        ron parks          creation
10      **
11      **      This module is an original, unpublished work and is proprietary to
12      **      NELLCOR INC., and may not be divulged or copied in any form
13      **      whatsoever without the express written permission of NELLCOR INC.
14      **
15      **      purpose : test menu implementation software
16      **
17      **      data descriptions :
18      **
19      **      function descriptions :
20      **
21      **
22      **
23      **      THE FOLLOWING IS THE DEFINITION OF THE BUTTON TABLES.  THE BUTTON TABLES ARE
24      **      USED TO DETERMINE WHICH MENU IS TO BE DISPLAYED FOLLOWING THE PRESSING OF
25      **      ANY GIVEN BUTTON.  A 'BUTTON', AS FAR AS THESE TABLES ARE CONCERENED, ARE THE
26      **      LOWER 5 FUNCTION BUTTONS, THE 'HELP' BUTTON, AND THE KNOB.  THE 'ALARM SILENCE
27      **      BUTTON AND THE POWER ON/STANBY ARE NOT HANDLED IN THESE TABLES.
28      **
29      **      THE PRESSED IS USED TO INDEX INTO THE CURRENT BUTTON TABLE (MENU).  WHEN A
30      **      NEW MENU IS CALLED FOR, THE BUTTON TABLE PTR IS CHANGED BY THE FUNCTION THAT
31      **      PROCESSED THE PRESSED BUTTON.
32      **
33      **      THE BUTTONS ARE NUMBERED (FOR INTERNAL USE) FROM RIGHT TO LEFT AS ONE FACES
34      **      THE MFO UNIT AS FOLLOWS:
35      **
36      **              HELP     =    0
37      **
```

```
**                     KNOB        = 1
**                     1ST BUTTON  = 2
**                     2ND BUTTON  = 3
**                     3RD BUTTON  = 4
**                     4TH BUTTON  = 5
**                     5TH BUTTON  = 6           EXIT KEY
***********************************************************************/ define WROM include "mclude.h"

struct btn_menu far top_lv_mnu =          /* normal top level run menu */
{
    top_lv_hlp,
    volume_adj,
    cfig_lv0,                /* configure level 0 */
    lmts_lv0,                /* limits level 0 */
    trend_lv0,               /* trend level 0 */
    frz_lv0,                 /* freeze level 0 */
    prt_lv0                  /* print level 0 */
};

/***********************************************************************
** CONFIGURE TOP LEVEL MENU
***********************************************************************/ struct btn_menu far cfig_mnu =
{
    cfig0_hlp,
    volume_adj,              /* volume adjust */
    agt_lv0,                 /* agent select level 0 */
    blank_btn,               /* button not used in this menu */
    tech_lv0,                /* technical level 0 */
    scrn_lv0,                /* screen configure level 0 */
    show_top                 /* configure exit from level 0 */
};

/***********************************************************************
** MENU FOR FIRST LEVEL OF LIMITS CONFIGURATI
***********************************************************************/ struct btn_menu far lmts_mnu =
{
    lmts_hlp,                /* limits level 0 help */
    chg_alrm_lmts,           /* change alarm limit selected */
    use_prst_lmts,           /* use preset limits */
    prst_lmt_sav,            /* save limits in as a preset */
    sel_next_dwltm,          /* select first/next digital window */
```

```
 94          prt_lmts,            /* print limits */
 95          lmts_exit            /* limits menu exit  */
 96       };
 97  /************************************************************************
 98   *
 99   ************************************************************************/
100  /*
101   * FIRST LEVEL OF TREND MENU
102   */
103  struct btn_menu far trnd_mnu =
104     {
105         trnd_hlp,           /* level 0 trend help */
106         volume_adj,         /* volume adjust */
107         titm_sel,           /* trend item select */
108         clr_tbfr,           /* clear trend buffers */
109         tdisp_prd,          /* select trend display period */
110         twdow_sel,          /* select trend window */
111         trnd_exit           /* trend exit */
112     };
113  /************************************************************************
114   *
115   ************************************************************************/
116  /*
117   * FIRST LEVEL FREEZE MENU
118   */
119  struct btn_menu far frz_mnu =
120     {
121         frz_hlp,            /* freeze help */
122         volume_adj,         /* volume adjust */
123         split_scrn;         /* split the screen */
124         fsav_rcall,         /* save/recall split screen */
125         unfrz,              /* unfreeze screen */
126         frz_prt,            /* print screen */
127         show_top            /* freeze exit */
128     };
129  /************************************************************************
130   *
131   ************************************************************************/
132  /*
133   * FIRST LEVEL PRINT MENU
134   */
135  struct btn_menu far prnt_mnu =
136     {
137         prnt_hlp,           /* print help menu */
138         volume_adj,         /* */
139         prt_scrn,           /* print screen */
140         auto_prt;           /* auto print toggle */
141         prt_alltrn,         /* print all trend buffers */
142         prt_onalrm,         /* print on alarm toggle */
143         show_top
144     };
145  /************************************************************************
146   *
```

```
151  /****************************************************************
152   * AGENT SELECT MENU
153   ****************************************************************/
154  struct btn_menu far agt_mnu =
155  {
156       agt_hlp,
157       volume_adj,
158       select_iso,              /* agent select */
159       select_eth,
160       select_hal,
161       blank_btn,
162       agtcfg_exit
163  };
164
165  /****************************************************************
166   * TECHNICAL MENU
167   ****************************************************************/
168  struct btn_menu far tech_mnu =
169  {
170       tech_hlp,
171       volume_adj,
172       sys_params,              /* setup system parameters */
173       cal_lv0,                 /* calibration level 0 */
174       oputs_lv0,               /* output ports setup level 0 */
175       blank_btn,
176       show_top
177  };
178
179  /****************************************************************
180   * SCREEN CONFIGURATION MENU
181   ****************************************************************/
182  struct btn_menu far scrn_mnu =
183  {
184       scrn_cfig_hlp,
185       volume_adj,
186       chg_unts,                /* change units for MID */
187       sel_next_dwitm,          /* select first/next digital window */
188       swp_spd,                 /* setup sweep speed */
189       def_wdows,               /* define windows */
190       show_top
191  };
192
193  /****************************************************************
194   * CHANGE UNITS FOR SELECTED MID         (SCREEN CONFIGURATION)
195   ****************************************************************/
196  struct btn_menu far chg_unts_mnu =
```

```
207         {
208             chg_unts_hlp,
209             volume_adj,
210             chgu_sel,            /* select next units for MID selected */
211             sel_next_dwitm,      /* select next MID */
212             blank_btn,
213             blank_btn,
214             chgu_exit            /* exit to screen configure levl 0 */
215         };
216
217     /******************************************************************
218     ** MENU FOR PRESET ALARM LIMITS
219     **
220     ******************************************************************/
221
222
223     struct btn_menu far prst_lmts_mnu =
224         {
225             prst_lmts_hlp,
226             volume_adj,
227             sel_prst_lmts,       /* display preset (ADULT,NEONATE) */
228             excut_lmtsel,        /* use preset displayed */
229             blank_btn,
230             blank_btn,
231             prstlmts_exit        /* restores previous limits if execute was not pressed*/
232         };
233
234     /******************************************************************
235     ** DEFINE WINDOWS MENU
236     **
237     ******************************************************************/
238
239
240     struct btn_menu far defwdow_mnu =
241         {
242             defwdow_hlp,
243             volume_adj,
244             wfmt_savrcall,       /* save/recall window format */
245             fmtitm_sel,          /* select MID to be displayed in window selected */
246             fmtwdw_sel,          /* select a window to be formatted */
247             frmt_num_sel,        /* select format number (layout) */
248             defw_exit
249         };
250
251     /******************************************************************
252     ** SAVE/RECALL SCREEN FORMAT MENU (SCREEN CONFIGURE)
253     **
254     ******************************************************************/
255
256
257     struct btn_menu far fmtsavrcall_mnu =
258         {
```

```
263         fmtsvrcal_hlp,
264         volume_adj,
265         save_fmt,           /* save present format (windows and limits) */
266         recall_fmt,         /* recall format (windows and limits) */
267         blank_btn,
268         blank_btn,
269         fmtsvrcal_exit
270     };
271
272 /***********************************************************************
273  ** SAVE/RECALL SCREEN FORMAT MENU (SCREEN CONFIGURE)
274  **      (NOTE CHANGE IN KNOB OWNER)
275  ***********************************************************************/
276
277 struct btn_menu far fmtknob_mnu =
278     {
279         fmtsvrcal_hlp,
280         chg_initials,       /* knob changes the char in the selected field */
281         save_fmt,
282         recall_fmt,
283         fmtsr_execut,       /* save/recall format under initials entered */
284         blank_btn,
285         fmtsvrcal_exit
286     };
287
288 /***********************************************************************
289  ** DUMMY TABLE FOR TEST PURPOSES ONLY
290  ***********************************************************************/
291
292 struct btn_menu far all_exits =
293     {
294         show_top,
295         show_top,
296         show_top,
297         show_top,
298         show_top,
299         show_top,
300         show_top
301     };
302
303 struct btn_menu far fsv_rcall_mnu =
304     {
305         show_top,
306         volume_adj,
307         show_top,
308         show_top,
309         show_top,
310         show_top,
311         show_top
```

```
318   };
319
320   struct btn_menu far swp_spdmnu =
321      {
322         show_top,
323         volume_adj,
324         show_top,
325         show_top,
326         show_top,
327         show_top,
328         show_top,
329         show_top
330      };
```

```
 1   /****************************************************************
 2   * MFO Ver 0.0
 3   *
 4   * module: mctrlsrvr.h
 5   *
 6   * modification history :
 7   *      date             by          reason(s)
 8   *      19 sept 86       rlp         creation
 9   *
10   *
11   * This module is an original, unpublished work and is proprietary to
12   * NELLCOR INC., and may not be divulged or copied in any form
13   * whatsoever without the express written permission of NELLCOR INC.
14   *
15   * purpose :
16   *
17   * data descriptions :
18   *
19   * function descriptions :
20   *
21   ****************************************************************/
22
23   #define NEW_CASE  -1
24   #define OLD_CASE   0
25
26   #ifdef MSTACKSIZE
27
28   mControlServer();
29   short NewCaseOrOld();
30   far mOff();
31   SystematicPowerDown();
32
33   #else
34
35   extern SystematicPowerDown();
36   extern mControlServer();
37   extern short NewCaseOrOld();
38   extern far mOff();
```

MCTRLSRV.H

```
40  extern void MenuServer();
41  #endif
42
43

1   /****************************************************************
2   *   MFO Ver 0.0
3   *
4   *   module: mwdows.c                    MWDOWS.H
5   *
6   *   modification history :
7   *       date        by          reason(s)
8   *       20 aug 86   rlp         creation
9   *
10  *
11  *   This module is an original, unpublished work and is proprietary to
12  *   NELLCOR INC., and may not be divulged or copied in any form
13  *   whatsoever without the express written permission of NELLCOR INC.
14  *
15  *
16  *   purpose : Build and display the initial screen after self test.
17  *
18  *   data descriptions :
19  *
20  *   function descriptions :
21  *
22  ****************************************************************/
23
24  #ifdef MWDW
25
26  void  ShowDefaultScreen();
27  void  InitScreen_Dblk();
28  void  InitMidUnits();
29  void  Bluprint_Wfw();
30  void  Bluprint_Trndw();
31  void  Build_DfIt_WfWindows();
32  void  Bluprint_DigWindow();
33  void  BuildWfScreen();
34  void  Display_DfltDScreen();
35  short DWSsearch();
36  void  SelectNextDW();
37  void  FindDW_UpdateAGT();
38  void  FindTW_UpdateAGT();
39  void  RebuildOldScreen();
40  void  Blank_EntireScreen();
41
42  #else
43
44
45  extern void ShowDefaultScreen();
46  extern void InitScreen_Dblk();
47  extern void InitMidUnits();
```

```
48  extern void Bluprint_Wfw();
49  extern void Bluprint_Trndw();
50  extern void Build_Dflt_WfWindows();
51  extern void Bluprint_DigWindow();
52  extern void BuildWfScreen();
53  extern void Display_DfltDScreen();
54  extern void DWsearch();
55  extern void SelectNextDW();
56  extern void FindDW_UpdateAGT();
57  extern void FindTW_UpdateAGT();
58  extern void RebuildOldScreen();
59  extern void Blank_EntireScreen();
60  #endif
61
62
63                  MWDOWROM.C        s0endx
64
```

```
 1  /*****************************************************************
 2  **
 3  **    MFO Ver 0.0
 4  **
 5  **    module:mwdwrom.h
 6  **
 7  **    modification history :         by              reason(s)
 8  **         date                                       creation
 9  **         12 aug 86              ron parks
10  **
11  **    This module is an original, unpublished work and is proprietary to
12  **    NELLCOR INC., and may not be divulged or copied in any form
13  **    whatsoever without the express written permission of NELLCOR INC.
14  **
15  **    purpose :
16  **
17  **    data descriptions : romable window discription block initialization
18  **
19  **    function descriptions :
20  **
21  **
22  **
23  **    THE FOLLOWING IS THE DEFINITION OF THE BUTTON TABLES.  THE BUTTON TABLES ARE
24  **    USED TO DETERMINE WHICH MENU IS TO BE DISPLAYED FOLLOWING THE PRESSING OF
25  **    ANY GIVEN BUTTON.  A 'BUTTON', AS FAR AS THESE TABLES ARE CONCERENED, ARE THE
26  **    LOWER 5 FUNCTION BUTTONS, THE 'HELP' BUTTON, AND THE KNOB.  THE 'ALARM SILENCE
27  **    BUTTON AND THE POWER ON/STANBY ARE NOT HANDLED IN THESE TABLES.
28  **
29  **
30  **    THE PRESSED IS USED TO INDEX INTO THE CURRENT BUTTON TABLE (MENU).  WHEN A
31  **    NEW MENU IS CALLED FOR, THE BUTTON TABLE PTR IS CHANGED BY THE FUNCTION THAT
32  **    PROCESSED THE PRESSED BUTTON.
33  **
34  **
35  **
36  ***********************************************************************************/
```

```
37      #define COORDINATES
38      #include "mclude.h"
39
40
41      #define lwstartx 63
42      #define lwendx 801
43      #define swlen 19 * 16
44      #define s0startx lwstartx
45      #define s0endx (s0startx + swlen )
46      #define swmargin 96
47      #define sistartx (lwstartx + swmargin)
48      #define slendx (sistartx + swlen )
49      #define ScrlSpeed6_25mm { 0x9000, 2, POS, NOTZERO, 0 }
50      #define ScrlSpeed12_25mm { 0x9000, 3, POS, NOTZERO, 0 }
51      #define ScrlSpeed25mm  { 0x9000, 4, POS, NOTZERO, 0 }
52      #define ScrlSpeed50mm  { 0x9000, 5, POS, NOTZERO, 0 }
53
54      coord_tbl dummy =
55         { 0,0,0,0,0 };
56
57
58      /*******************************************************************
59      ** COORDINATE TABLE FOR MID NAME IN WAVEFORM/TREND WINDOW
60      *******************************************************************/
61      coord_tbl wfname_coord =
62         { -16,-3,137,T1,FontSmall };       /* relative pixel address in defined wf window */
63
64      /*******************************************************************
65      ** COORDINATE TABLE FOR LONG WAVEFORM/TREND WINDOW
66      *******************************************************************/
67      coord_tbl lngw1_coord =
68         { lwstartx,0,lwendx,67,0 };                /* absoulte pixel address */
69      coord_tbl lngw3_coord =
70         { lwstartx,74,lwendx,141,0 };
71      coord_tbl lngw5_coord =
72         { lwstartx,149,lwendx,216,0 };
73
74      /*******************************************************************
75      ** COORDINATE TABLES FOR SHORT WAVEFORM/TREND WINDOWS
76      *******************************************************************/
77      coord_tbl shrtw1_coord =                      /* absoulte pixel address */
```

```
 93          { s0startx,0,s0endx,67,0 };
 94
 95     coord_tbl shrtw2_coord =
 96          { s1startx,0,s1endx,67,0 };
 97
 98     coord_tbl shrtw3_coord =
 99          { s0startx,74,s0endx,141,0 };
100
101     coord_tbl shrtw4_coord =
102          { s1startx,74,s1endx,141,0 };
103
104     coord_tbl shrtw5_coord =
105          { s0startx,149,s0endx,216,0 };
106
107     coord_tbl shrtw6_coord =
108          { s1startx,149,s1endx,216,0 };
109
110     /***********************************************************************
111     *
112     * COORDINATES FOR MID NAME IN DIGITAL RESULT WINDOW
113     *
114     ***********************************************************************/
115
116
117     coord_tbl digw_lncoord =
118          { 0,0,224,20,FontLarge };           /* large font rel pixel addresses */
119
120     coord_tbl digw_mncoord =
121          { 0,0,168,15,FontMedium };          /* medium font rel pixel addresses */
122
123
124     /***********************************************************************
125     *
126     * COORDINATES FOR PERIOD IN TREND WINDOWS
127     *
128     ***********************************************************************/
129
130     coord_tbl lwprd_coord =
131          { 596,-3,708,11,FontSmall };        /* long window period */
132
133     coord_tbl swprd_coord =                  /* short window period */
134          { 201,-3,313,11,FontSmall };
135
136
137     /***********************************************************************
138     *
139     * COORDINATES FOR DIGITAL RESULT WINDOWS
140     *
141     ***********************************************************************/
```

```
150  ***************************************************************/
Thu 10-16-86 10:21:30    MWDOWROM.C         slendx
    10-16-86 14:52:38

151
152
153     coord_tbl digw1_coord =
154        { 855,0,1279,20,0 };
155
156     coord_tbl digw2_coord =
157        { 855,31,1279,51,0 };
158
159     coord_tbl digw3_coord =                  /* absoulte pixel addresses */
160        { 855,61,1279,81,0 };
161
162     coord_tbl digw4_coord =
163        { 855,91,1279,111,0 };
164
165     coord_tbl digw5_coord =
166        { 855,115,1279,130,0 };
167
168     coord_tbl digw6_coord =
169        { 855,140,1279,155,0 };
170
171     coord_tbl digw7_coord =
172        { 855,159,1279,174,0 };
173
174     coord_tbl digw8_coord =
175        { 855,184,1279,199,0 };
176
177     coord_tbl digw9_coord =
178        { 855,203,1279,218,0 };
179
180  /***************************************************************
181   **
182   ** COORDINATES FOR UNITS DISPLAYED IN LARGE DIGITAL RESULT WINDOWS
183   **
184   ***************************************************************/
185
186
187     coord_tbl lrgdwu_coord =
188        { 320,3,384,20,FontSmall };            /* window relative values */
189
190
191  /***************************************************************
192   **
193   ** COORDINATES FOR UNITS DISPLAYED IN SMALL DIGITAL RESULT WINDOWS
194   **
195   ***************************************************************/
196
197
198
199     coord_tbl smldwu_coord =
200        { 320,1,384,15,FontSmall };            /* window relative values */
```

```
201 /*****************************************************************
202 ** AXIS COORDINATES
203 ******************************************************************/
204
205
206 coord_tbl longax =
207     { 0,0,780,67,0 };
208
209 coord_tbl shortax =
210     { 0,0,368,67,0 };
211
212
213 /*****************************************************************
214 ** COORDINATES FOR LOW ALARM LIMIT DISPLAYED N DIGITAL RESULT WINDOWS
215 ******************************************************************/
216
217 coord_tbl slwlmt_coord =
218     { 328,4,392,15,FontSmall };
219
220 coord_tbl llwlmt_coord =
221     { 416,9,464,20,FontSmall };
222
223
224 /*****************************************************************
225 ** COORDINATES FOR UPPER ALARM LIMIT DISPLAYED IN DIGITAL RESULT WINDOWS
226 ******************************************************************/
227
228 coord_tbl suplmt_coord =
229     { 262,4,312,15,FontSmall };
230
231 coord_tbl luplnt_coord =
232     { 352,9,400,20,FontSmall };
233
234
235 /*****************************************************************
236 ** COORDINATES FOR SMALL RESULT DIGITS IN A SMALL DIGITAL RESULTS WINDOW
237 ******************************************************************/
238
239 coord_tbl smlrsult_coord =
240     { 240,0,320,15,FontMedium };
241
242 /*****************************************************************
```

```
                /**************************************************************
                 * CORRDINATES FOR LARGE DIGITS IN A LARGE DIGITAL RESULT WINDOW
                 **************************************************************/
                coord_tbl lrsult_coord =               /* window relative values */
                    {-214,0,320,20,FontLarge };

/**************************************************************
                 * CORRDINATES FOR LARGE AGENT INITIALS IN A LARGE DIGITAL RESULT WINDOW
                 **************************************************************/
                coord_tbl lagnt_coord =                /* window relative values */
                    {-1,2,3,4,5 };

/**************************************************************
                 * COORDINATES FOR SMALL AGENT INITIALS IN A SMALL DIGITAL RESULT WINDOW
                 **************************************************************/
                coord_tbl smlagnt_coord =
                    {-1,2,3,4,5 };

/**************************************************************
                 * COORDINATES FOR THE SLASHED BELL ( ALARM OFF INDICATION )
                 **************************************************************/
                coord_tbl bell1_coord =
                    {-32,0,0,32,FontLarge };
                coord_tbl bell2_coord =
                    {-32,0,0,32,FontLarge };
                coord_tbl bell3_coord =
                    {-32,0,0,32,FontLarge };
                coord_tbl bell4_coord =
                    {-32,0,0,32,FontLarge };
                coord_tbl bell5_coord =
                    {-24,0,0,24,FontMedium };
                coord_tbl bell6_coord =
                    {-24,0,0,24,FontMedium };
```

```
313    coord_tbl_bel17_coord =
314        { -24,0,0,24,FontMedium };
315
316    coord_tbl_bel18_coord =
317        { -24,0,0,24,FontMedium };
318
319    coord_tbl_bel19_coord =
320        { -24,0,0,24,FontMedium };
321
322    /********************************************************
323     * COORDINATE TABLE FOR SCREEN ( WAVEFORM AND DIGITAL RESULTS)
324     *
325     ********************************************************/
326
327
328    coord_tbl_screen_coords =
329        { 1,2,3,4,5 };
330
331    /********************************************************
332     * COORDINATE TABLE FOR PROMPT BUFFER
333     *
334     ********************************************************/
335
336    coord_tbl_prompt_coords =
337        { 1,2,3,4,5 };
338
339
340    /********************************************************
341     * COORDINATE TABLE FOR THE MENU BUFFER
342     *
343     ********************************************************/
344
345
346    coord_tbl_menu_coords =
347        { 1,2,3,4,5 };
348
349    /********************************************************
350     * RECALL/SAVE INITIALS COORDINATES
351     *
352     ********************************************************/
353
354    coord_tbl_initial1_coords =
355        { 1,2,3,4,5 };
356
357    coord_tbl_initial2_coords =
358        { 1,2,3,4,5 };
359
360    coord_tbl_initial3_coords =
361        { 1,2,3,4,5 };
```

```
370  /******************************************************************
371   *
372   *  DESCRIPTION OF FORMAT 1
373   *
374   *     waveform
375   *     waveform
376   *     trend
377   *
378   ******************************************************************/
379
380  wndow_dblk format_tbl[NUM_FORMATS][NUM_WFWINDOWS] =
381  {
382
383   {
384    {TRUE,FALSE,&lngw1_coord,&wndw1_mid,&wfname_coord,&dummy,&w1_prd,&w1_dswnum,&longax },
385    {FALSE,FALSE,&dummy,&wndw2_mid,&dummy,&wfname_coord,&dummy,&w2_prd,&w2_dswnum,&shortax },
386    {TRUE,FALSE,&lngw3_coord,&wndw3_mid,&wfname_coord,&dummy,&w3_prd,&w3_dswnum,&longax },
387    {FALSE,FALSE,&dummy,&wndw4_mid,&wfname_coord,&dummy,&w4_prd,&w4_dswnum,&shortax },
388    {TRUE,TRUE,&lngw5_coord,&wndw5_mid,&wfname_coord,&lwprd_coord,&w5_prd,&w5_dswnum,&longax },
389    {FALSE,FALSE,&dummy,&wndw6_mid,&dummy,&w6_prd,&w6_dswnum,&shortax },
390   },
391  /******************************************************************
392   *
393   *  DESCRIPTION OF FORMAT 2
394   *
395   *     waveform
396   *     waveform
397   *     trend          trend
398   *
399  ******************************************************************/
400   {
401    {TRUE,FALSE,&lngw1_coord,&wndw1_mid,&wfname_coord,&dummy,&w1_prd,&w1_dswnum,&longax },
402    {FALSE,FALSE,&dummy,&wndw2_mid,&wfname_coord,&dummy,&w2_prd,&w2_dswnum,&shortax },
403    {TRUE,FALSE,&lngw3_coord,&wndw3_mid,&wfname_coord,&dummy,&w3_prd,&w3_dswnum,&longax },
404    {FALSE,FALSE,&dummy,&wndw4_mid,&wfname_coord,&dummy,&w4_prd,&w4_dswnum,&shortax },
405    {TRUE,TRUE,&shrtw5_coord,&wndw5_mid,&dummy,&swprd_coord,&w5_prd,&w5_dswnum,&shortax },
406    {TRUE,TRUE,&shrtw6_coord,&wndw6_mid,&dummy,&swprd_coord,&w6_prd,&w6_dswnum,&shortax },
407   },
408  /******************************************************************
```

```
427   /****************************************************************
428   *
429   *   DESCRIPTION OF FORMAT 3
430   *
431   *       waveform
432   *       waveform
433   *       waveform
434   *
435   ****************************************************************/
436   {
437     {TRUE,FALSE,&lngw1_coord,&wndw1_mid,&dummy,&wfname_coord,&dummy,&w1_prd,&w1_dswnum,&longax },
438     {FALSE,FALSE,&dummy,&wndw2_mid,&dummy,&wfname_coord,&dummy,&w2_prd,&w2_dswnum,&shortax },
439     {TRUE,FALSE,&lngw3_coord,&wndw3_mid,&dummy,&wfname_coord,&dummy,&w3_prd,&w3_dswnum,&longax },
440     {FALSE,FALSE,&dummy,&wndw4_mid,&dummy,&wfname_coord,&dummy,&w4_prd,&w4_dswnum,&shortax },
441     {TRUE,FALSE,&lngw5_coord,&wndw5_mid,&dummy,&wfname_coord,&dummy,&w5_prd,&w5_dswnum,&longax },
442     {FALSE,FALSE,&dummy,&wndw6_mid,&dummy,&wfname_coord,&dummy,&w6_prd,&w6_dswnum,&shortax },
443   };
444
445
446
447
448
449
450
451   /****************************************************************
452   *
453   *   DESCRIPTION OF FORMAT 4
454   *
455   *       waveform        trend
456   *       waveform        trend
457   *       waveform        trend
458   *
459   ****************************************************************/
460   {
461     {TRUE,FALSE,&shrtw1_coord,&wndw1_mid,&wfname_coord,&dummy,&w1_prd,&w1_dswnum,&shortax },
462     {TRUE,TRUE,&shrtw2_coord,&wndw2_mid,&wfname_coord,&dummy,&swprd_coord,&dummy,&w2_prd,&w2_dswnum,&shortax },
463     {TRUE,TRUE,&shrtw3_coord,&wndw3_mid,&wfname_coord,&dummy,&dummy,&w3_prd,&w3_dswnum,&shortax },
464     {TRUE,TRUE,&shrtw4_coord,&wndw4_mid,&wfname_coord,&dummy,&swprd_coord,&dummy,&w4_prd,&w4_dswnum,&shortax },
465     {TRUE,TRUE,&shrtw5_coord,&wndw5_mid,&wfname_coord,&dummy,&dummy,&w5_prd,&w5_dswnum,&shortax },
466     {TRUE,TRUE,&shrtw6_coord,&wndw6_mid,&wfname_coord,&dummy,&swprd_coord,&dummy,&w6_prd,&w6_dswnum,&shortax },
467   };
```

```
482  /******************************************************************
483   **
484   ** DIGITAL (RESULT) WINDOW DESCRIPTION BLOCKS
485   **
486   ******************************************************************/
487
488  digwdw_dblk digwdw_tbl [ENDIGWDOWS] =
489  {
490    { &dw1_mid,&dw1_bflg,&dw1_dswnum,&dw1_units,&digw1_coord,&lrgdwu_coord,
491      &luplmt_coord, &llwlmt_coord, &lagnt_coord, &lrsult_coord,&bell1_coord,&digw_lncoo
492      rd },
493    { &dw2_mid,&dw2_bflg,&dw2_dswnum,&dw2_units,&digw2_coord, &lrgdwu_coord,
494      &luplmt_coord, &llwlmt_coord, &lagnt_coord, &lrsult_coord,&bell2_coord,&digw_lncoor
495      d },
496    { &dw3_mid,&dw3_bflg,&dw3_dswnum,&dw3_units, &digw3_coord, &lrgdwu_coord,
497      &luplmt_coord, &llwlmt_coord, &lagnt_coord, &lrsult_coord,&bell3_coord,&digw_lncoor
498      d },
499    { &dw4_mid,&dw4_bflg,&dw4_dswnum,&dw4_units, &digw4_coord, &lrgdwu_coord,
500      &luplmt_coord, &llwlmt_coord, &lagnt_coord, &lrsult_coord,&bell4_coord,&digw_lncoor
501      d },
502    { &dw5_mid,&dw5_bflg,&dw5_dswnum,&dw5_units, &digw5_coord, &smldwu_coord,
503      &suplmt_coord, &slwlmt_coord, &smlagnt_coord, &smlrsult_coord,&bell5_coord,&
504      digw_mncoord},
505    { &dw6_mid,&dw6_bflg,&dw6_dswnum,&dw6_units, &digw6_coord, &smldwu_coord,
506      &suplmt_coord, &slwlmt_coord, &smlagnt_coord, &smlrsult_coord,&bell6_coord,&
507      digw_mncoord},
508    { &dw7_mid,&dw7_bflg,&dw7_dswnum,&dw7_units, &digw7_coord, &smldwu_coord,
509      &suplmt_coord, &slwlmt_coord, &smlagnt_coord, &smlrsult_coord,&bell7_coord,&
510      digw_mncoord},
511    { &dw8_mid,&dw8_bflg,&dw8_dswnum,&dw8_units, &digw8_coord, &smldwu_coord,
512      &suplmt_coord, &slwlmt_coord, &smlagnt_coord, &smlrsult_coord,&bell8_coord,&
513      digw_mncoord},
514    { &dw9_mid,&dw9_bflg,&dw9_dswnum,&dw9_units, &digw9_coord, &smldwu_coord,
515      &suplmt_coord,&slwlmt_coord, &smlagnt_coord, &smlrsult_coord,&bell9_coord,&
516      digw_mncoord }
517  };
518  /******************************************************************
519   **
520   ** MID ALTERNATE UNITS
521   **
522   ******************************************************************/
523
524  msgx sao2_altu [] =
525    { PER_CENT,PER_CENT,PER_CENT,PER_CENT };
```

```
528  msgx pleth_altu [] =
529       { PER_CENT, PER_CENT,PER_CENT };
530
531  msgx three_altus [] =
532       { PER_CENT, MMHg, PASCALS };
533
534  msgx breath_altus [] =
535       { BPER_MINUTE, BPER_MINUTE };
536
537  msgx Pulse_altus [] =
538       { PER_MINUTE,PER_MINUTE,PER_MINUTE };
539  /*****************************************************
540   *
541   * DEFAULT MID NUMBERS FOR DEFAULT WAVEFORM FORMAT
542   *
543   *****************************************************/
544
545
546  msgx dflt_wfmidtbl [3] =
547       { PLETH, CO2, CO2 };
548
549  /*****************************************************
550   *
551   * DEFAULT MID NUMBERS FOR DEFAULT DIGITAL FORMAT
552   *
553   *****************************************************/
554
555
556  msgx dflt_dmid_list [ NDIGWDOWS ] =
557       { SaO2, PULSE, BREATH, EtCO2, INSCO2, EtAGT, INSAGT, EtN2O, INSN2O };
558
559
560  /*****************************************************
561   *
562   * MID DESCRIPTION BLOCKS
563   *
564   *****************************************************/
565
566
567  mid_dblk mid_dblktbl[] =
568  {
569       {SaO2,&sao2_stat,SaO2_TNAME,&sao2_units,PER_CENT,1,sao2_altu,50m,57,0,1 },
570       {PLETH,&pleth_stat,PULSE_TNAME,&pleth_units,BPER_MINUTE,0,pleth_altu,ScrlSpeed25mm,57,1,
571        1 },
572       {EtCO2,&etco2_stat,CO2_TNAME,&co2_units,PER_CENT,3,three_altus,50m,100,0,2 },
573       {INSCO2,&insco2_stat,CO2_TNAME,&co2_units,PER_CENT,3,three_altus,50m,100,0,2 },
574       {INSN2O, &insn2o_stat, N2O_TNAME, &n2o_units, PER_CENT,3,three_altus,50m,100,0,2 },
575       {EtN2O,&etn2o_stat,N2O_TNAME,&n2o_units,PER_CENT,3,three_altus,50m,100,0,2 },
```

```
583         {EtAGT,&etagent_stat, AGENT_TNAME, &agent_units, PER_CENT ,3,three_altus,60m,100,0,2 },
584         {INSAGT,&insagent_stat, AGENT_TNAME, &agent_units, PER_CENT ,3,three_altus,60m,100,0,2 },
585
586         {BREATH, &breath_stat, BREATH_TNAME, &breath_units, PER_MINUTE,1,breath_altus,60m,100,0,
587         1 },
588                                         NUM_IMIDS
589         {PULSE, &pulse_stat, PULSE_TNAME, &pulse_units, BPER_MINUTE,1,pulse_altus,60m,57,0,1 },
590
591         {CO2, &insco2_stat, CO2_TNAME, &co2_units, PER_CENT ,3,three_altus,ScrlSpeed12_25mm,100,
592         3,2 },
593         {N2O, &insn2o_stat, N2O_TNAME, &n2o_units, PER_CENT ,3,three_altus,60m,100,4,2 },
594
595         {AGENT,&insagent_stat, AGENT_TNAME, &agent_units, PER_CENT ,3,three_altus,60m,100,5,2 }
596         };
597
598  #define NUM_IMIDS (sizeof(mid_dblktbl)/sizeof(mid_dblk))
599  /******************************************************************************
600  ** TABLE OF PERIOD NAME INDEXES ( INDEXED BY PERIOD NUMBER)
601  ******************************************************************************/
602  msgx period_nametbl [ NUM_PERIODS ] =
603         { MIN20, HOUR1, HOUR8 };
604
605  /******************************************************************************
606  ** DEFAULT DIGITAL RESULT WINDOW MID TABLE( used to build initial result windows
607  ******************************************************************************/
608  msgx dflt_digw_tbl [] =
609         { SaO2,PULSE,BREATH,EtCO2,INSCO2,EtAGT,INSAGT,EtN2O,INSN2O };
610
611  /******************************************************************************
612  ** TABLE OF UNITS
613  ******************************************************************************/
614  msgx units_tbl [NUM_UNITS ] =
615         { PER_CENT, MMHg, PASCALS, BPER_MINUTE, PER_MINUTE };
```

```
634  /******************************************************
635   * TABLE OF MIDS THAT CAN BE TRENDED
636   *
637   ******************************************************/
638
639
640  msgx trendable_mids [] =
641      { SaO2, PULSE, CO2, N2O, AGENT         };
642
643
644
Thu 10-08-86 21:17:34    MKYBDTMR.H    DefineTimers
    10-16-86 14:52:38

1   /******************************************************
 2    * MFO Ver 0.0
 3    *
 4    * module:
 5    *
 6    * modification history : reason(s)
 7    *        date      by         creation
 8    * 10-6-86         rlp         creation
 9    *
10    * This module is an original, unpublished work and is proprietary to
11    * NELLCOR INC., and may not be divulged or copied in any form
12    * whatsoever without the express written permission of NELLCOR INC.
13    *
14    *
15    * purpose :
16    *
17    * data descriptions :
18    *
19    * function descriptions :
20    *
21    ******************************************************/
22
23
24
25
26   #ifdef KYBD_STUFF
27   DefineTimers( kybd_timers, NUM_KYBD_TIMERS )
28   DefineTimer( NO_RESTART, NO_RESTART, mProckybd )
29   DefineTimer( NO_RESTART, NO_RESTART, mDebounce, kybd_timers )
30   EndTimers( NO_RESTART, NO_RESTART, mDebounce, kybd_timers )
31
32   #else
33
34   extern TIMERS kybd_timers;
35
36   #endif              MKNOBKYB.H
```

```
/*****************************************************************
** MFO Ver 0.0
**
** module:   mknobkybd.h
**
** modification history :
**          date       by     rlp      reason(s)
**      16 sept        rlp            creation
**
** This module is an original, unpublished work and is proprietary to
** NELLCOR INC., and may not be divulged or copied in any form
** whatsoever without the express written permission of NELLCOR INC.
**
** Purpose :Knob processing - Process the NELLCOR Knob at interrupt time, called by a
**                            video sync interrupt handler.
**
**   until                Keyboard processing - The keyboard is processed once every 40ms
**                                              a change is status is
**  detected, then a 80ms to       debounce the key. The keycode is placed in the
**                                 keyboard queue with it's direction bit (bit 15 =
**                                 1 = key released after being depressed).
** data descriptions :
**
** function descriptions : If a change in the knob is detected, the knob code (9)
**                         along with the direction bit (bit 15) and cnt is placed in the
**                         Keyboard Queue.
**
*****************************************************************/ extern short near mInputKybd();
extern short near mGetKnob();
extern        xPost();
extern        xSetTimeDelay();

#define KNOB_CNT          0x7F00     /* mask to look at knob count */
#define KNOB_MOVED        0x200      /* bit 9 = 1 */
#define KNOB_CLOCKWISE    0x100      /* bit 8 = 1 */
#define KNOB_UP           0x8000     /* KNOB CODE & bit 15 */
#define KNOB_DOWN         0x7FFF     /* bit 15 = 0 = down */
#define CLEAR_KNOB        0x0FF      /* clears knob change and direction bits */
define BIT15             0x8000 define ALARM_BUTTON_BIT  0x1
define POWER_BUTTON_BIT  0x4
#define HELP_BUTTON_BIT   0x2
#define BUTTON1_BIT       0x10
#define BUTTON2_BIT       0x20
#define BUTTON3_BIT       0x80
```

```
55  #define BUTTON4_BIT        0x40
56  #define BUTTON5_BIT        0x8
57  #define KDIRECTION_BIT     0x100     /* knob direction bit */
58
59  #define ALARM_BUTTON       7
60  #define POWER_BUTTON       8
61  #define HELP_BUTTON        6
62  #define BUTTON1            5
63  #define BUTTON2            4
64  #define BUTTON3            3
65  #define BUTTON4            2
66  #define BUTTON5
67  #define KNOB_CODE          1
68
69  #define PRESSED            0x8000
70  #define RELEASED           0
71
72  #define KYBD_TICKS         1         /* number of ticks on 50hz timer */
73  #define DEBOUNCE_TICKS     2         /* number of ticks on 50hz timer */
74
75  #define PROC_KYBD_TIMER    0
76  #define DEBOUNCE_TIMER     1         /* keyboard timer numbers */
77  #define NUM_KYBD_TIMERS    2
78
```

MENUSRVR.H

```
1   /****************************************************************
2   ** MFO Ver 0.0
3   **
4   ** module:menusrvr.h
5   **
6   ** modification history : reason(s)
7   **        date  by
8   ** 10 sept 86  rlp
9   **
10  ** This module is an original, unpublished work and is proprietary to
11  ** NELLCOR INC., and may not be divulged or copied in any form
12  ** whatsoever without the express written permission of NELLCOR INC.
13  **
14  ** purpose :
15  **
16  ** data descriptions :
17  **
18  ** function descriptions :
19  **
20  *****************************************************************/
21
22  /* THESE ARE THE TABLES THAT PROCESS THE BUTTONS AND BUILD MENUS */
23
24  /* BUTTON TABLE STRUCTURE */
```

```
29  struct btn_menu
30  {
31
32      struct btn_menu far *( far *menu_hdlr[7])();
33  };
34
35
36
37
38  void display_hlp();
39  struct btn_menu far *fmtwdw_sel();
40  struct btn_menu far *fmtitm_sel();
41  struct btn_menu far *frmt_num_sel();
42  struct btn_menu far *prst_lmts_hlp();
43  struct btn_menu far *prt_onalrm();
44  struct btn_menu far *fsav_rcall();
45  struct btn_menu far *trnd_exit();
46  struct btn_menu far *prstlmts_exit();
47  struct btn_menu far *excut_lmtsel();
48  struct btn_menu far *sel_prst_lmts();
49  struct btn_menu far *lmts_exit();
50  struct btn_menu far *chgu_exit();
51  struct btn_menu far *defwdow_hlp();
52  struct btn_menu far *sel_next_dwitm();
53  struct btn_menu far *agtcfig_exit();
54  struct btn_menu far *top_lv_hlp();
55  struct btn_menu far *cfig_lv0();
56  struct btn_menu far *lmts_lv0();
57  struct btn_menu far *trend_lv0();
58  struct btn_menu far *frz_lv0();
59  struct btn_menu far *prt_lv0();
60  struct btn_menu far *cfig0_hlp();
61  struct btn_menu far *volume_adj();
62  struct btn_menu far *agt_lv0();
63  struct btn_menu far *blank_btn();
64  struct btn_menu far *tech_lv0();
65  struct btn_menu far *scrn_lv0();
66  struct btn_menu far *cfig_exit();
67  struct btn_menu far *show_top();
68  struct btn_menu far *prt_lmts();
69  struct btn_menu far *lmt_sel();
70  struct btn_menu far *prst_lmt_sav();
71  struct btn_menu far *use_prst_lmts();
72  struct btn_menu far *chg_alrm_lmts();
73  struct btn_menu far *lmts_hlp();
74  struct btn_menu far *trnd_hlp();
75  struct btn_menu far *titm_sel();
76  struct btn_menu far *clr_tbfr();
77  struct btn_menu far *disp_prd();
78  struct btn_menu far *twdow_sel();
79  struct btn_menu far *trend_sel();
80  struct btn_menu far *trend_sel();
81  struct btn_menu far *frz_hlp();
82  struct btn_menu far *split_scrn();
83  struct btn_menu far *fsavrcall();
84  struct btn_menu far *unfrz();
```

```
85   struct btn_menu far *frz_exit();
86   struct btn_menu far *prnt_hlp();
87   struct btn_menu far *frz_prt();
88   struct btn_menu far *prt_scrn();
89   struct btn_menu far *auto_prt();
90   struct btn_menu far *prt_all_trn();
91   struct btn_menu far *prt_onaIrm();
92   struct btn_menu far *agt_hlp();
93   struct btn_menu far *agt_sel();
94   struct btn_menu far *tech_hlp();
95   struct btn_menu far *sys_params();
96   struct btn_menu far *cal_lv0();
97   struct btn_menu far *oputs_lv0();
98   struct btn_menu far *scrn_cfig_hlp();
99   struct btn_menu far *chg_unts();
100  struct btn_menu far *sitm_loc();
101  struct btn_menu far *swp_spd();
102  struct btn_menu far *def_wdows();
103  struct btn_menu far *chg_unts_hlp();
104  struct btn_menu far *chgu_sel();
105  struct btn_menu far *chgu_itm_sel();
106  struct btn_menu far *select_iso();
107  struct btn_menu far *select_hal();
108  struct btn_menu far *select_eth();
109  struct btn_menu far *wfmt_savrcall();
110  struct btn_menu far *defw_exit();
111  struct btn_menu far *chg_initials();
112  struct btn_menu far *save_fmt();
113  struct btn_menu far *recall_fmt();
114  struct btn_menu far *fmtsr_execut();
115  struct btn_menu far *fmtsvrcall();
116  struct btn_menu far *fmtsvrcal_hlp();
117  struct btn_menu far *fmtsvrcal_exit();
118  short WhoOwnsKnob();
119  short CheckForSilence();
120  void mDoAbsCorners();
121  void NoWinselected();
122  void SelectNewAgent();
123  struct btn_menu far *select_HAL();
124  struct btn_menu far *select_ISO();
125  struct btn_menu far *select_ETH();
126
127  #ifdef MENU
128
129  short BPos1();
130  short BPos2();
131  short BPos3();
132  short BPos4();
133  short BPos5();
134  #else
135  extern short BPos1();
136  extern short BPos2();
137  extern short BPos3();
138  extern short BPos4();
139  extern short BPos5();
```

```
141  #endif
142
Thu 10-15-86 02:10:44  MROMMNUS.H
    10-16-86 14:52:38

1  /*****************************************************************
 2  *
 3  ** MFO Ver 0.0
 4  *
 5  ** module: mrommnus.h
 6  *
 7  ** modification history :
 8  **     date              by              reason(s)
 9  **     12 aug 86         ron parks       creation
10  *
11  ** This module is an original, unpublished work and is proprietary to
12  ** NELLCOR INC., and may not be divulged or copied in any form
13  ** whatsoever without the express written permission of NELLCOR INC.
14  *
15  *
16  ** Purpose : test menu implementation software
17  *
18  ** data descriptions :
19  *
20  ** function descriptions :
21  *
22  *
23  ** THE FOLLOWING IS THE DEFINITION OF THE BUTTON TABLES.  THE BUTTON TABLES ARE
24  ** USED TO DETERMINE WHICH MENU IS TO BE DISPLAYED FOLLOWING THE PRESSING OF
25  ** ANY GIVEN BUTTON.  A 'BUTTON', AS FAR AS THESE TABLES ARE CONCERENED, ARE THE
26  ** LOWER 5 FUNCTION BUTTONS, THE 'HELP' BUTTON, AND THE KNOB.  THE 'ALARM SILENCE
27  ** BUTTON AND THE POWER ON/STANBY ARE NOT HANDLED IN THESE TABLES.
28  *
29  ** THE PRESSED IS USED TO INDEX INTO THE CURRENT BUTTON TABLE (MENU).  WHEN A
30  ** NEW MENU IS CALLED FOR, THE BUTTON TABLE PTR IS CHANGED BY THE FUNCTION THAT
31  ** PROCESSED THE PRESSED BUTTON.
32  *
33  ** THE BUTTONS ARE NUMBERED (FOR INTERNAL USE) FROM RIGHT TO LEFT AS ONE FACES
34  ** THE MFO UNIT AS FOLLOWS:
35  *
36  **          HELP        =  0
37  **          KNOB        =  1
38  **          1ST BUTTON  =  2
39  **          2ND BUTTON  =  3
40  **          3RD BUTTON  =  4
41  **          4TH BUTTON  =  5
42  **          5TH BUTTON  =  6       EXIT KEY
43  *
44  *
45  ******************************************************************/
46
47
48  #ifdef WROM
49
50
```

```
Thu 10-15-86 02:10:44    MROMMNUS.H
    10-16-86 14:52:38

51
52    #else
53
54    extern struct btn_menu far top_lv_mnu ;    /* normal top level run menu far */
55    extern struct btn_menu far cfig_mnu ;
56    extern struct btn_menu far lmts_mnu ;
57    extern struct btn_menu far trnd_mnu ;
58    extern struct btn_menu far freez_mnu ;
59    extern struct btn_menu far prnt_mnu ;
60    extern struct btn_menu far agt_mnu ;
61    extern struct btn_menu far tech_mnu ;
62    extern struct btn_menu far scrn_mnu ;
63    extern struct btn_menu far chg_unts_mnu ;
64    extern struct btn_menu far prst_lmts_mnu ;
65    extern struct btn_menu far defwdow_mnu ;
66    extern struct btn_menu far fmtsavrcall_mnu ;
67    extern struct btn_menu far fmtknob_mnu ;
68    extern struct btn_menu far all_exits ;
69    extern struct btn_menu far swp_spdmnu;
70    extern struct btn_menu far fsv_rcall_mnu;
71    extern struct btn_menu far frz_mnu;
72
73    #endif
74

Thu 10-11-86 13:43:58    MSPANISH.C
    10-16-86 14:52:38

1    /********************************************************************
 2    **
 3    ** MFO Ver 0.0
 4    **
 5    ** module: mSpanish.h
 6    **
 7    ** modification history :
 8    **          date        by        reason(s)
 9    **
10    **
11    **
12    ** This module is an original, unpublished work and is proprietary to
13    ** NELLCOR INC., and may not be divulged or copied in any form
14    ** whatsoever without the express written permission of NELLCOR INC.
15    **
16    ** Purpose : Messages for Spanish Language version
17    **
18    ** data descriptions : Data layed out exactly as English.
19    **
20    ** function descriptions :
21    **
22    *********************************************************************/
23    char far *Spanish [] =
24    {
```

```
25              }              { "El Sao2" }
26        };
27
                     MSPANISH.H

1 /*********************************************************************
 2 *
 3 *  MFO Ver 0.0
 4 *
 5 *  module: mspanish.h
 6 *
 7 *  modification history :
 8 *       date      by      reason(s)
 9 *
10 *
11 *  This module is an original, unpublished work and is proprietary to
12 *  NELLCOR INC., and may not be divulged or copied in any form
13 *  whatsoever without the express written permission of NELLCOR INC.
14 *
15 *  purpose :
16 *
17 *  data descriptions :
18 *
19 *  function descriptions :
20 *
21 *********************************************************************/
22
23 extern char far *Spanish[];
24
25                     MSTRGPTR.H 1 /*********************************************************************
 2 *
 3 *  MFO Ver 0.0
 4 *
 5 *  module: mstrgptr.h
 6 *
 7 *  modification history :
 8 *       date      by      reason(s)
 9 *    5 sept      rlp
10 *
11 *  This module is an original, unpublished work and is proprietary to
12 *  NELLCOR INC., and may not be divulged or copied in any form
13 *  whatsoever without the express written permission of NELLCOR INC.
14 *
15 *  purpose :
16 *
17 *  data descriptions : This data is used to index into the ASCII string
18 *                      buffer.
19 *  !!!!!!!!!!!!!!!!!!! IMPTORTANT NOTE:    !!!!!!!!!!!!!!!!!!!!!!!!!!!
20 *
```

```
        *       THESE ENUMS ARE GROUPED TOGETHER ACCORDING TO FUNCTION. THE ORDER
        *       WITHIN THE GROUPINGS IS VERY STRICT. ADDITIONS TO A PARTICULAR GROUP IS
        *       MADE AT THE END OF THAT GROUPING. THIS IS IMPORTANT BECAUSE THE RELATIONAL
        *       POSITION OF AN ITEM IN A GROUP IS DETERMINED BY:
        *                       ITEM NUMBER = FIRST GROUP ITEM - ITEM
        *       THIS ITEM NUMBER IS USED TO INDEX INTO OTHER STRUCTURES.
        *
        *  function descriptions :
        *
        **************************************************************************/ define FIRST_UNITS_NAME        PER_CENT
define FIRST_MID_Sa02 ifdef MESSAGES char far *(far *Language) = {0};

else extern char far *(far *Language);

endif define BLANK   Language[ (short) SPACE  ]
define OPT1    Language[ (short) BTN1   ]
#define OPT2    Language[ (short) BTN2   ]
#define OPT3    Language[ (short) BTN3   ]
#define OPT4    Language[ (short) BTN4   ]
#define OPT5    Language[ (short) BTN5   ]
#define OPT6    Language[ (short) BTN6   ]
#define OPT7    Language[ (short) BTN7   ]
#define OPT8    Language[ (short) BTN8   ]
#define OPT9    Language[ (short) BTN9   ]
#define OPT10   Language[ (short) BTN10  ]
#define OPT11   Language[ (short) BTN11  ]
#define OPT12   Language[ (short) BTN12  ]
#define OPT13   Language[ (short) BTN13  ]
#define OPT14   Language[ (short) BTN14  ]
#define OPT15   Language[ (short) BTN15  ]
#define OPT16   Language[ (short) BTN16  ]
#define OPT17   Language[ (short) BTN17  ]
#define OPT18   Language[ (short) BTN18  ]
#define OPT19   Language[ (short) BTN19  ]
#define OPT20   Language[ (short) BTN20  ]
#define OPT21   Language[ (short) BTN21  ]
#define OPT22   Language[ (short) BTN22  ]
#define OPT23   Language[ (short) BTN23  ]
#define OPT24   Language[ (short) BTN24  ]
#define OPT25   Language[ (short) BTN25  ]
#define OPT26   Language[ (short) BTN26  ]
#define OPT27   Language[ (short) BTN27  ]
#define OPT28   Language[ (short) BTN28  ]
#define OPT29   Language[ (short) BTN29  ]
#define OPT30   Language[ (short) BTN30  ]
```

```
78   #define OPT31   Language[ (short) BTN31 ]
79   #define OPT32   Language[ (short) BTN32 ]
80   #define OPT33   Language[ (short) BTN33 ]
81   #define OPT34   Language[ (short) BTN34 ]
82   #define OPT35   Language[ (short) BTN35 ]
83   #define OPT36   Language[ (short) BTN36 ]
84   #define OPT37   Language[ (short) BTN37 ]
85   #define OPT38   Language[ (short) BTN38 ]
86   #define OPT39   Language[ (short) BTN39 ]
87   #define OPT40   Language[ (short) BTN40 ]
88   #define OPT41   Language[ (short) BTN41 ]
89   #define OPT42   Language[ (short) BTN42 ]
90   #define OPT43   Language[ (short) BTN43 ]
91   #define OPT44   Language[ (short) BTN44 ]
92   #define OPT45   Language[ (short) BTN45 ]
93   #define OPT46   Language[ (short) BTN46 ]
94   #define OPT47   Language[ (short) BTN47 ]
95   #define OPT48   Language[ (short) BTN48 ]
96   #define OPT49   Language[ (short) BTN49 ]
97   #define OPT50   Language[ (short) BTN50 ]
98   #define OPT51   Language[ (short) BTN51 ]
99   #define OPT52   Language[ (short) BTN52 ]
100  #define OPT53   Language[ (short) BTN53 ]
101  #define OPT54   Language[ (short) BTN54 ]
102  #define OPT55   Language[ (short) BTN55 ]
103  #define OPT56   Language[ (short) BTN56 ]
104  #define OPT57   Language[ (short) BTN57 ]
105  #define OPT58   Language[ (short) BTN58 ]
106  #define OPT59   Language[ (short) BTN59 ]
107  #define OPT60   Language[ (short) BTN60 ]
108  #define OPT61   Language[ (short) BTN61 ]
109  #define OPT62   Language[ (short) BTN62 ]
110  #define OPT63   Language[ (short) BTN63 ]
111  #define OPT64   Language[ (short) BTN64 ]
112  #define OPT65   Language[ (short) BTN65 ]
113  #define OPT66   Language[ (short) BTN66 ]
114  #define OPT67   Language[ (short) BTN67 ]
115  #define OPT68   Language[ (short) BTN68 ]
116
117
118  #define PMSG0   Language[ (short) PROMPT0 ]
119  #define PMSG1   Language[ (short) PROMPT1 ]
120  #define PMSG2   Language[ (short) PROMPT2 ]
121  #define PMSG3   Language[ (short) PROMPT3 ]
122  #define PMSG4   Language[ (short) PROMPT4 ]
123  #define PMSG5   Language[ (short) PROMPT5 ]
124  #define PMSG6   Language[ (short) PROMPT6 ]
125  #define PMSG7   Language[ (short) PROMPT7 ]
126  #define PMSG8   Language[ (short) PROMPT8 ]
127  #define PMSG9   Language[ (short) PROMPT9 ]
128  #define PMSG10  Language[ (short) PROMPT10 ]
129  #define PMSG11  Language[ (short) PROMPT11 ]
130  #define PMSG12  Language[ (short) PROMPT12 ]
131  #define PMSG13  Language[ (short) PROMPT13 ]
132  #define PMSG14  Language[ (short) PROMPT14 ]
133  #define PMSG15  Language[ (short) PROMPT15 ]
134  #define PMSG16  Language[ (short) PROMPT16 ]
```

```
135  #define PMSG17 Language[ (short) PROMPT17 ]
136  #define PMSG18 Language[ (short) PROMPT18 ]
137  #define PMSG19 Language[ (short) PROMPT19 ]
138  #define PMSG20 Language[ (short) PROMPT20 ]
139  #define PMSG21 Language[ (short) PROMPT21 ]
140  #define PMSG22 Language[ (short) PROMPT22 ]
141  #define PMSG23 Language[ (short) PROMPT23 ]
142  #define PMSG24 Language[ (short) PROMPT24 ]
143  #define PMSG25 Language[ (short) PROMPT25 ]
144  #define PMSG26 Language[ (short) PROMPT26 ]
145  #define PMSG27 Language[ (short) PROMPT27 ]
146  #define PMSG28 Language[ (short) PROMPT28 ]
147
148
149
150
151  typedef enum
152  {
153  /******************************************************************
154  ** MIDS
155  *******************************************************************/
156       COMPANY_NAME = 0,
157       SaO2 = 1,
158       PLETH,
159       EtCO2,
160       INSCO2,
161       INSN2O,
162       EtN2O,
163       EtAGT,
164       INSAGT,
165       BREATH,
166       PULSE,
167       CO2,
168       N2O, AGENT,
169
170  /******************************************************************
171  ** MID FOR TREND
172  *******************************************************************/
173       SaO2_TNAME,
174       CO2_TNAME,
175       N2O_TNAME,
176       AGENT_TNAME,
177       BREATH_TNAME,
178       PULSE_TNAME,
179
180  /******************************************************************
181  ** AGENT INITIALS
```

```
191   *                                                                           */
192   *           HAL,
193   *           ETH,
194   *           FOR,
195   *
196   *****************************************************************************
197   /****************************************************************************/
198   *  PERIODS
199   *
200   *****************************************************************************
201   *
202   *           HOUR1,
203   *           HOUR8,
204   *           MIN20,
205   *
206   *****************************************************************************
207   /****************************************************************************/
208   *  UNIT OF MEASUREMENT
209   *
210   *****************************************************************************
211   *
212   *           PER_CENT,
213   *           MMHG,
214   *           PASCALS,
215   *           BPER_MINUTE,
216   *           PER_MINUTE,
217   *
218   *****************************************************************************
219   /****************************************************************************/
220   *  DEFAULT ALARM LIMIT SET NAMES
221   *
222   *****************************************************************************
223   *
224   *           NEONATE,
225   *           ADULT,
226   *
227   *****************************************************************************
228   /****************************************************************************/
229   *  AGENT FULL NAMES
230   *
231   *****************************************************************************
232   *
233   *           NO_AGENT_SELECTED,
234   *           HALO,
235   *           ENFLUR,
236   *           ISOFLUR,
237   *
238   *****************************************************************************
239   /****************************************************************************/
240   *  PROMPT MESSAGES
241   *
242   *****************************************************************************
```

```
247             PROMPT0,
248             PROMPT1,
249             PROMPT2,
250             PROMPT3,
251             PROMPT4,
252             PROMPT5,
253             PROMPT6,
254             PROMPT7,
255             PROMPT8,
256             PROMPT9,
257             PROMPT10,
258             PROMPT11,
259             PROMPT12,
260             PROMPT13,
261             PROMPT14,
262             PROMPT15,
263             PROMPT16,
264             PROMPT17,
265             PROMPT18,
266             PROMPT19,
267             PROMPT20,
268             PROMPT21,
269             PROMPT22,
270             PROMPT23,
271             PROMPT24,
272             PROMPT25,
273             PROMPT26,
274             PROMPT27,
275             PROMPT28,
276             PROMPT29,
277     /***********************************************
278     ** MENU OPTIONS/BUTTON NAMES
279     ***********************************************/
280
281
282
283             SPACE,
284             BTN1,
285             BTN2,
286             BTN3,
287             BTN4,
288             BTN5,
289             BTN6,
290             BTN7,
291             BTN8,
292             BTN9,
293             BTN10,
294             BTN11,
295             BTN12,
296             BTN13,
297             BTN14,
298             BTN15,
299             BTN16,
300
```

| | |
|---|---|
| 301 | BTN17, |
| 302 | BTN18, |
| 303 | BTN19, |
| 304 | BTN20, |
| 305 | BTN21, |
| 306 | BTN22, |
| 307 | BTN23, |
| 308 | BTN24, |
| 309 | BTN25, |
| 310 | BTN26, |
| 311 | BTN27, |
| 312 | BTN28, |
| 313 | BTN29, |
| 314 | BTN30, |
| 315 | BTN31, |
| 316 | BTN32, |
| 317 | BTN33, |
| 318 | BTN34, |
| 319 | BTN35, |
| 320 | BTN36, |
| 321 | BTN37, |
| 322 | BTN38, |
| 323 | BTN39, |
| 324 | BTN40, |
| 325 | BTN41, |
| 326 | BTN42, |
| 327 | BTN43, |
| 328 | BTN44, |
| 329 | BTN45, |
| 330 | BTN46, |
| 331 | BTN47, |
| 332 | BTN48, |
| 333 | BTN49, |
| 334 | BTN50, |
| 335 | BTN51, |
| 336 | BTN52, |
| 337 | BTN53, |
| 338 | BTN54, |
| 339 | BTN55, |
| 340 | BTN56, |
| 341 | BTN57, |
| 342 | BTN58, |
| 343 | BTN59, |
| 344 | BTN60, |
| 345 | BTN61, |
| 346 | BTN62, |
| 347 | BTN63, |
| 348 | BTN64, |
| 349 | BTN65, |
| 350 | BTN66, |
| 351 | BTN67, |
| 352 | BTN68, |
| 353 | |

```
354   /****************************************
355   * HELP MESSAGES
356   *****************************************/
357
358           HELP0,
359           HELP1,
360           HELP2,
361           HELP3,
362           HELP4,
363           HELP5,
364           HELP6,
365           HELP7,
366           HELP8,
367           HELP9,
368           HELP10,
369
370   }       msgx;
371
```

Thu 10-16-86 10:21:54   MSYSDEFS.H      MENU_PARAMETERS
Thu 10-16-86 14:52:38

```
 1    /*****************************************************************
 2    *
 3    * MFO Ver 0.0
 4    *
 5    * module:
 6    *
 7    * modification history :           reason(s)
 8    *       date        by
 9    *
10    *
11    * This module is an original, unpublished work and is proprietary to
12    * NELLCOR INC., and may not be divulged or copied in any form
13    * whatsoever without the express written permission of NELLCOR INC.
14    *
15    * purpose :
16    *
17    * data descriptions :
18    *
19    * function descriptions :
20    *
21    *****************************************************************/
22
23    #define TRUE -1
24    #define FALSE 0
25    #define NONE 0
```

```
28  #define DFLT_FORMAT_NUM  0
29  #define NOT_USED         -1
30  #define DEFAULT_FONT     0
31  #define NO_RESTART       -1
32  #define FOREVER          for (;;)
33  #define KEY_CODE         0x00FF         /* used for timer\ */
34  #define KNOB_CODE        1              /* mask out all but key code from kybd input */
35  #define KNOB_DELTA       0xFF00         /* get knob delta and direction */
36  #define SILENCE_CODE     5              /* key event code for alarm server */
37  #define FROZEN           1
38  #define UNFREEZE         0
39  #define ENTIRE_SCREEN    0              /* default fixed window numbers */
40  #define PROMPT_BUFFER    Win1
41  #define NONE_SELECTED    -1
42  #define MENU_BUFFER      Win2
43  #define WF_SIDE          Win0
44  #define RESULT_SIDE      ResultWin
45  #define SELECTED_WFMID   *(format_tbl[ screen.frmt_num ][ screen.wfwindow_selctd ].mid_dspd)
46  #define SELECTED_WFWINDOW format_tbl[ screen.frmt_num ][ screen.wfwindow_selctd ]
47  #define MENUZ            1
48  #define MENU_PARAMETERS  (char far *) "%P%s%P%s%P%s%P%s%P%s\n"
49  #define ABSOLUTE_CORNERS absxtlc,absytlc,absxbrc,absybrc
50  #define CLICK            DAudio( CLICK_LEVEL,THIRDPR,0,BUTTON_CLICK_ID )
51  #define BEEP             DAudio( LEVEL0,THIRDPR,0,0 )
52  #define BtnGap           58
53  #define BtnWidth         208
54  #define BtnP1            4
55  #define BtnP2            BtnP1 + BtnWidth + BtnGap
56  #define BtnP3            BtnP2 + BtnWidth + BtnGap
57  #define BtnP4            BtnP3 + BtnWidth + BtnGap
58  #define BtnP5            BtnP4 + BtnWidth + BtnGap
59  #define Btn1Cntr         ( BtnP1 + ( BtnWidth / 2 ))
60  #define Btn2Cntr         ( BtnP2 + ( BtnWidth / 2 ))
61  #define Btn3Cntr         ( BtnP3 + ( BtnWidth / 2 ))
62  #define Btn4Cntr         ( BtnP4 + ( BtnWidth / 2 ))
63  #define Btn5Cntr         ( BtnP5 + ( BtnWidth / 2 ))
64
65  /*typedef char far * far LanguagePtr[];
66  */
67
68  /* positon in button window to center menu option ( used in dprintf ) */
69
70  typedef struct
71  {
72      short xvalue;
73      short yvalue;
74
75  } topleftcorner;
76
```

```
Thu 10-10-86 18:08:48    MWDOWRAM.H
    10-16-86 14:52:38

1   /*****************************************************************
2   **  MFO Ver 0.0
3   **
4   **  module:mwdowram.h
5   **
6   **  modification history :
7   **       date                  by              reason(s)
8   **     12 aug 86           ron parks          creation
9   **
10  **
11  **  This module is an original, unpublished work and is proprietary to
12  **  NELLCOR INC., and may not be divulged or copied in any form
13  **  whatsoever without the express written permission of NELLCOR INC.
14  **
15  **  purpose :
16  **
17  **  data descriptions : contains variable data ptrs for windows and
18  **                      romable window discription block initialization
19  **
20  **  function descriptions :
21  **
22  **
23  *******************************************************************
24  **  THE FOLLOWING IS THE DEFINITION OF THE BUTTON TABLES.  THE BUTTON TABLES ARE
25  **  USED TO DETERMINE WHICH MENU IS TO BE DISPLAYED FOLLOWING THE PRESSING OF
26  **  ANY GIVEN BUTTON.  A 'BUTTON' AS FAR AS THESE TABLES ARE CONCERENED, ARE THE
27  **  LOWER 5 FUNCTION BUTTONS, THE 'HELP' BUTTON, AND THE KNOB.  THE 'ALARM SILENCE'
28  **  BUTTON AND THE POWER ON/STANBY ARE NOT HANDLED IN THESE TABLES.
29  **
30  **  THE PRESSED IS USED TO INDEX INTO THE CURRENT BUTTON TABLE (MENU).  WHEN A
31  **  NEW MENU IS CALLED FOR, THE BUTTON TABLE PTR IS CHANGED BY THE FUNCTION THAT
32  **  PROCESSED THE PRESSED BUTTON.
33  **
34  *******************************************************************/
35
36
37
38  #ifdef COORDINATES
39  /*****************************************************************
40  **
41  **  CURRENT MID NUMBER DISPLAYED IN WAVEFORM/TREND WINDOWS
42  **
43  *****************************************************************/
44
45
46
47  msgx wndw1_mid = { (msgx) 0 };
48  msgx wndw2_mid = { (msgx) 0 };
49  msgx wndw3_mid = { (msgx) 0 };
50  msgx wndw4_mid = { (msgx) 0 };
```

```
 51      msgx wndw5_mid = { (msgx) 0 };
 52      msgx wndw6_mid = { (msgx) 0 };
 53
 54      /****************************************************************
 55       ** CURRENT MID NUMBER DISPLAYED IN DIGITAL RESULTS WINDOWS
 56       **
 57       ****************************************************************/
 58
 59
 60
 61      msgx  dw1_mid = { (msgx) 0 };
 62      msgx  dw2_mid = { (msgx) 0 };
 63      msgx  dw3_mid = { (msgx) 0 };
 64      msgx  dw4_mid = { (msgx) 0 };
 65      msgx  dw5_mid = { (msgx) 0 };
 66      msgx  dw6_mid = { (msgx) 0 };
 67      msgx  dw7_mid = { (msgx) 0 };
 68      msgx  dw8_mid = { (msgx) 0 };
 69      msgx  dw9_mid = { (msgx) 0 };
 70
 71
 72      /****************************************************************
 73       ** DIGITAL RESULT WINDOW IS BLANK FLAGS
 74       **
 75       ****************************************************************/
 76
 77
 78
 79      short  dw1_bflg = {0};
 80      short  dw2_bflg = {0};
 81      short  dw3_bflg = {0};
 82      short  dw4_bflg = {0};
 83      short  dw5_bflg = {0};
 84      short  dw6_bflg = {0};
 85      short  dw7_bflg = {0};
 86      short  dw8_bflg = {0};
 87      short  dw9_bflg = {0};
 88
 89
 90      /****************************************************************
 91       ** TREND PERIOD ID NUMBER
 92       **
 93       ****************************************************************/
 94
 95
 96
 97      short  w1_prd = {0};
 98      short  w2_prd = {0};
 99      short  w3_prd = {0};
100      short  w4_prd = {0};
101      short  w5_prd = {0};
102      short  w6_prd = {0};
103
104
105
106      /****************************************************************
```

```
/*******************************************************************/
/* WAVEFORM/TREND WINDOW NUMBER ASSIGNED BY THE DISPLAY SERVER     */
/*******************************************************************/

WinNumber  w1_dswnum = { (WinNumber) 0 };
WinNumber  w2_dswnum = { (WinNumber) 0 };
WinNumber  w3_dswnum = { (WinNumber) 0 };
WinNumber  w4_dswnum = { (WinNumber) 0 };
WinNumber  w5_dswnum = { (WinNumber) 0 };
WinNumber  w6_dswnum = { (WinNumber) 0 };

/*******************************************************************/
/* DIGITAL RESULT WINDOW NUMBER ASSIGNED BY THE DISPLAY SERVER     */
/*******************************************************************/

WinNumber  dw1_dswnum = { (WinNumber) 0 };
WinNumber  dw2_dswnum = { (WinNumber) 0 };
WinNumber  dw3_dswnum = { (WinNumber) 0 };
WinNumber  dw4_dswnum = { (WinNumber) 0 };
WinNumber  dw5_dswnum = { (WinNumber) 0 };
WinNumber  dw6_dswnum = { (WinNumber) 0 };
WinNumber  dw7_dswnum = { (WinNumber) 0 };
WinNumber  dw8_dswnum = { (WinNumber) 0 };
WinNumber  dw9_dswnum = { (WinNumber) 0 };

/*******************************************************************/
/* UNITS FOR EACH DIGITAL RESULT WINDOW                            */
/*******************************************************************/ short  dw1_units = {0};
short  dw2_units = {0};
short  dw3_units = {0};
short  dw4_units = {0};
short  dw5_units = {0};
short  dw6_units = {0};
short  dw7_units = {0};
short  dw8_units = {0};

short  dw9_units = {0};

/*******************************************************************/
/* MID STATUS FLAGS ( TRUE = CONNECTED )                           */
/*******************************************************************/ short  sao2_stat  = {0};
short  pulse_stat = {0};
short  etco2_stat = {0};
```

```
163   short   insco2_stat = {0};
164   short   etn2o_stat = {0};
165   short   insn2o_stat = {0};
166   short   etagent_stat = {0};
167   short   insagent_stat = {0};
168   short   pleth_stat = {0};
169   short   breath_stat = {0};
170   short   n2o_stat = {0};
171
172   /****************************************************
173   ** MID UNITS
174   **
175   *****************************************************/
176
177
178   msgx   sao2_units = { { (msgx) 0 } };
179   msgx   pleth_units = { { (msgx) 0 } };
180   msgx   co2_units = { { (msgx) 0 } };
181   msgx   n2o_units = { { (msgx) 0 } };
182   msgx   agent_units = { { (msgx) 0 } };
183   msgx   breath_units = { { (msgx) 0 } };
184   msgx   pulse_units = { { (msgx) 0 } };
185
186   #else
187
188
189   extern msgx   wndw1_mid;
190   extern msgx   wndw2_mid;
191   extern msgx   wndw3_mid;
192   extern msgx   wndw4_mid;
193   extern msgx   wndw5_mid;
194   extern msgx   wndw6_mid;
195
196   extern msgx   dw1_mid;
197   extern msgx   dw2_mid;
198   extern msgx   dw3_mid;
199   extern msgx   dw4_mid;
200   extern msgx   dw5_mid;
201   extern msgx   dw6_mid;
202   extern msgx   dw7_mid;
203   extern msgx   dw8_mid;
204   extern msgx   dw9_mid;
205
206   extern short  dw1_bflg;
207   extern short  dw2_bflg;
208   extern short  dw3_bflg;
209   extern short  dw4_bflg;
210   extern short  dw5_bflg;
211   extern short  dw6_bflg;
212   extern short  dw7_bflg;
213   extern short  dw8_bflg;
214   extern short  dw9_bflg;
215
216   extern short  w1_prd;
217   extern short  w2_prd;
218   extern short  w3_prd;
219   extern short  w4_prd;
```

```
220  extern short w5_prd;
221  extern short w6_prd;
222
223  extern WinNumber w1_dswnum;
224  extern WinNumber w2_dswnum;
225  extern WinNumber w3_dswnum;
226  extern WinNumber w4_dswnum;
227  extern WinNumber w5_dswnum;
228  extern WinNumber w6_dswnum;
229
230  extern WinNumber dw1_dswnum;
231  extern WinNumber dw2_dswnum;
232  extern WinNumber dw3_dswnum;
233  extern WinNumber dw4_dswnum;
234  extern WinNumber dw5_dswnum;
235  extern WinNumber dw6_dswnum;
236  extern WinNumber dw7_dswnum;
237  extern WinNumber dw8_dswnum;
238  extern WinNumber dw9_dswnum;
239
240  extern short dw1_units;
241  extern short dw2_units;
242  extern short dw3_units;
243  extern short dw4_units;
244  extern short dw5_units;
245  extern short dw6_units;
246  extern short dw7_units;
247  extern short dw8_units;
248  extern short dw9_units;
249
250  extern short sao2_stat;
251  extern short pulse_stat;
252  extern short etco2_stat;
253  extern short insco2_stat;
254  extern short etn2o_stat;
255  extern short insn2o_stat;
256  extern short etagent_stat;
257  extern short insagent_stat;
258  extern short pleth_stat;
259  extern short breath_stat;
260  extern short n2o_stat;
261
262  extern msgx sao2_units;
263  extern msgx pleth_units;
264  extern msgx co2_units;
265  extern msgx n2o_units;
266  extern msgx agent_units;
267  extern msgx breath_units;
268  extern msgx pulse_units;
269  extern msgx breath_units;
270
271  extern short sao2_stat;
272  extern short pulse_stat;
273  extern short etco2_stat;
274  extern short insco2_stat;
275  extern short etn2o_stat;
```

```
276     extern short insn20_stat;
277     extern short etagent_stat;
278     extern short insagent_stat;
279     extern short pleth_stat;
280     #endif
281
282

Thu 10-13-86 14:12:50   MWDOWROM.H
    10-16-86 14:52:38

1   /****************************************************************
 2   **
 3   **   MFO Ver 0.0
 4   **
 5   **   module:mwdwrom.h
 6   **
 7   **   modification history :                              reason(s)
 8   **       date                by                          creation
 9   **       12 aug 86           ron parks
10   **
11   **   This module is an original, unpublished work and is proprietary to
12   **   NELLCOR INC., and may not be divulged or copied in any form
13   **   whatsoever without the express written permission of NELLCOR INC.
14   **
15   **
16   **   purpose :
17   **
18   **   data descriptions : romable window discription block initialization
19   **
20   **   function descriptions :
21   **
22   **
23   **   THE FOLLOWING IS THE DEFINITION OF THE BUTTON TABLES.  THE BUTTON TABLES ARE
24   **   USED TO DETERMINE WHICH MENU IS TO BE DISPLAYED FOLLOWING THE PRESSING OF
25   **   ANY GIVEN BUTTON.  A 'BUTTON', AS FAR AS THESE TABLES ARE CONCERENED, ARE THE
26   **   LOWER 5 FUNCTION BUTTONS, THE 'HELP' BUTTON, AND THE KNOB.  THE 'ALARM SILENCE
27   **   BUTTON AND THE POWER ON/STANBY ARE NOT HANDLED IN THESE TABLES.
28   **
29   **
30   **   THE PRESSED IS USED TO INDEX INTO THE CURRENT BUTTON TABLE (MENU).  WHEN A
31   **   NEW MENU IS CALLED FOR, THE BUTTON TABLE PTR IS CHANGED BY THE FUNCTION THAT
32   **   PROCESSED THE PRESSED BUTTON.
33   **
34   **
35   *****************************************************************/
36
37   #ifdef COORDINATES
38
39   #else
40
41
42   extern mid_dblk mid_dblktblc NUM_MIDS ];
43   extern digwdw_dblk digwdw_tblc NDIGWDOWS ];
44   extern coord_tbl dummy [];
45   extern coord_tbl wfname_coord [];
```

```
46  extern coord_tbl ingw1_coord [];
47  extern coord_tbl ingw3_coord [];
48  extern coord_tbl ingw5_coord [];
49  extern coord_tbl shrtw1_coord [];
50  extern coord_tbl shrtw2_coord [];
51  extern coord_tbl shrtw3_coord [];
52  extern coord_tbl shrtw4_coord [];
53  extern coord_tbl shrtw5_coord [];
54  extern coord_tbl shrtw6_coord [];
55  extern coord_tbl digw_incoord [];
56  extern coord_tbl digw_mncoord [];
57  extern coord_tbl lwprd_coord [];
58  extern coord_tbl swprd_coord [];
59  extern coord_tbl digw1_coord [];
60  extern coord_tbl digw2_coord [];
61  extern coord_tbl digw3_coord [];
62  extern coord_tbl digw4_coord [];
63  extern coord_tbl digw5_coord [];
64  extern coord_tbl digw6_coord [];
65  extern coord_tbl digw7_coord [];
66  extern coord_tbl digw8_coord [];
67  extern coord_tbl digw9_coord [];
68  extern coord_tbl lrgdwu_coord [];
69  extern coord_tbl smldwu_coord [];
70  extern coord_tbl longax [];
71  extern coord_tbl shortax [];
72  extern coord_tbl slwlmt_coord [];
73  extern coord_tbl llwlmt_coord [];
74  extern coord_tbl suplmt_coord [];
75  extern coord_tbl luplmt_coord [];
76  extern coord_tbl smlrsult_coord [];
77  extern coord_tbl lrsult_coord [];
78  extern coord_tbl lagnt_coord [];
79  extern coord_tbl smlagnt_coord [];
80  extern coord_tbl bell1_coord [];
81  extern coord_tbl bell2_coord [];
82  extern coord_tbl bell3_coord [];
83  extern coord_tbl bell4_coord [];
84  extern coord_tbl bell5_coord [];
85  extern coord_tbl bell6_coord [];
86  extern coord_tbl bell7_coord [];
87  extern coord_tbl bell8_coord [];
88  extern coord_tbl bell9_coord [];
89  extern coord_tbl screen_coords [];
90  extern coord_tbl prompt_coords [];
91  extern coord_tbl menu_coords [];
92  extern coord_tbl initial1_coords [];
93  extern coord_tbl initial2_coords [];
94  extern coord_tbl initial3_coords [];
95  extern wndow_dblk format_tbl[]
96  extern msgx dflt_dmid_list [];
97  extern msgx sao2_altu [];
98  extern msgx pleth_altu [];
99  extern msgx three_altus [];
100 extern msgx breath_altus [] [NUM_WFWINDOWS];
```

```
101    extern msgx pulse_altus [];
102    extern mid_dblk mid_dblk[];
103    #define NUM_IMIDS (sizeof(mid_dblktbl)/sizeof(mid_dblk))
104    extern msgx period_nametbl [];
105    extern msgx dflt_pigw_tbl [];
106    extern msgx units_tbl [];
107    extern msgx trendable_mids [];
108    extern msgx dflt_wfmidtbl [];
109    #endif

MWDOWS.C

1   /***********************************************************************
2   ** MFO Ver 0.0
3   **
4   ** module: mwdows.c
5   **
6   ** modification history :
7   **      date         by           reason(s)
8   **      20 aug 86    rip          creation
9   **
10  **
11  ** This module is an original, unpublished work and is proprietary to
12  ** NELLCOR INC., and may not be divulged or copied in any form
13  ** whatsoever without the express written permission of NELLCOR INC.
14  **
15  ** purpose : Build and display the initial screen after self test.
16  **
17  ** data descriptions :
18  **
19  ** function descriptions :
20  **
21  ***********************************************************************/
22  
23  #define MWDW
24  #define WINDOW_STUFF
25  #include "mclude.h"
26  #include "\info\msid.h"
27  extern char far * far English[];
28  
29  /*extern struct btn_menu top_lv_mnu;*/
30  short xcorner;
31  short ycorner;
32  
33  
34  
35  MSID mid_conversion_tbl [] =
36  {
37      mSAO2,
38      mSAO2,
39      mPLETH,
40  
```

```
41          mCO2ET,
42          mCO2INS,
43          mN2OINS,
44          mN2OET,
45          mAGAET,
46          mAGAINS,
47          mBR,
48          mPULSE
49    };
50

MWDOWS.C         ShowDefaultScreen

51    /*****************************************************************
52    ** BUILD INITIAL SCREEN AND INITIAL DESCRIPTION BLOCKS ACCORDING TO NELLCOR
53    ** DEFAULT TABLES.
54    *****************************************************************/
55
56
57    void
58    ShowDefaultScreen()
59    {
60        Language = English;
61        InitMidUnits();                     /* load default limits */
62        InitScreen_Dblk();                  /* initialize the screen description block */
63        Build_Dflt_WfWindows();             /* put default mids in waveform/trend windows */
64        BuildWfScreen();                    /* display waveform/trend side of screen */
65        Display_DfltDScreen();              /* display default digital screen */
66    }
67
68    /*****************************************************************
69    ** SET THE WAVEFORM SCREEN DESCRIPTION TO IT'S INITIAL VALUES
70    *****************************************************************/
71
72
73    void
74    InitScreen_Dblk()
75    {
76        screen.frmt_num = 0;                      /* screen format 1 */
77        screen.actv_btn_menu = show_top();        /* unlock keyboard */
78        screen.kybd_flag = FALSE;
79        screen.clr_trnd = FALSE;
80        screen.silence_btnflg;
81        screen.freez_stat = FALSE;                /* screen not frozen */
82        screen.wfwndow_selctd = NONE_SELECTED;
83        screen.digwdw_selctd = NONE_SELECTED;     /* waveforms are being displayed */
84        screen.nonwf_dflag = FALSE;
85        screen.agt_seltd = FALSE;
86        screen.hlp_dflag = FALSE;                 /* help not being displayed */
87        screen.auto_prtflg = FALSE;               /* turn off auto print */
88        screen.prt_onalrm_flg = FALSE;            /* turn off print on alarm */
89        screen.scrn_coord = screen_coords;        /* coordinates for waveform and digital
90                                                     results windows combine */
91        screen.prmpt_coord = prompt_coords;
92        screen.mnubtr_coord = menu_coords;
```

```
 95        screen.first_initial = initial1_coords;  /* coords for 1st initial in recall
 96                                                    and save type functions */
 97        screen.secnd_initial = initial2_coords;
 98        screen.third_initial = initial3_coords;
 99
100                              Blank_EntireScreen
101   }
102   /********************************************************/
103   *
104   * CLEAR ENTIRE SCREEN
105   *
106   ********************************************************/
107   void
108   Blank_EntireScreen()
109   {
110        DBlankWin(Win0);
111
112   }
113
114   /********************************************************/
115   *
116   * MOVE DEFAULT UNITS INTO MID DISCRIPTION BLOCKS
117   *
118   ********************************************************/
119   void
120   InitMidUnits()
121   {
122   short mid;
123        for ( mid = 0; mid < NUM_IMIDS; mid++)
124           *( mid_dblktbl mid ].units_nptr ) = mid_dblktbl mid ].dflt_units;
125
126   }
127
128   /********************************************************/
129   *
130   * BUILD A BLUE PRINT FOR THE DISPLAY SERVER TO CREATE A WINDOW
131   *
132   ********************************************************/
133   void
134   Bluprint_Wfw(window)
135   short window;
136   {
137   msgx index;
138
139        blueprint.wndow_num = window;
140        blueprint.wndow_num++ ;
141        blueprint.mid_num = (short) *( format_tblscreen.frmt_num][window].mid_dspd);
142        coord_ptr = format_tblscreen.frmt_num ][window].name_coord;
143
144        blueprint.nxtlc = coord_ptr->xtlc;
```

```
148        blueprint.nytlc = coord_ptr->ytlc;
149        blueprint.nxbrc = coord_ptr->xbrc;
150        blueprint.nybrc = coord_ptr->ybrc;

151                              Blueprint_Trndw
152        blueprint.name_font = coord_ptr->dflt_font;
153        index = mid_dblktbl[(((short)blueprint.mid_num) - 1 )].name_index ;
154        blueprint.name_ptr = Language[ (short)index ];
155
156        coord_ptr = format_tbl[screen.frmt_num][window].wndow_size;
157        blueprint.xtlc = coord_ptr->xtlc;
158        blueprint.ytlc = coord_ptr->ytlc;
159        blueprint.xbrc = coord_ptr->xbrc;
160        blueprint.ybrc = coord_ptr->ybrc;
161
162        coord_ptr = format_tbl[ screen.frmt_num[window].axis_coord;
163        blueprint.axxtlc = coord_ptr->xtlc;
164        blueprint.axytlc = coord_ptr->ytlc;
165        blueprint.axxbrc = coord_ptr->xbrc;
166        blueprint.axybrc = coord_ptr->ybrc;
167
168        blueprint.scrollrate =
169                mid_dblktbl[(((short)blueprint.mid_num) - 1 )].scrollrate ;
170        blueprint.samplerate =
171                mid_dblktbl[(((short)blueprint.mid_num) - 1 )].samplerate ;
172        blueprint.wfid =
173                mid_dblktbl[(((short)blueprint.mid_num) - 1 )].wfid ;
174
175        return ;
176   }
177
178   /*******************************************************************
179   **
180   ** BUILD TREND WINDOW
181   **
182   ********************************************************************/
183
184   void
185   Bluprint_Trndw(trndw)
186   short trndw;
187   {
188   mid_dblk *mid_ptr;
189
190        Bluprint_Wfw(trndw);              /* wf and trends are the same to a point */
191        coord_ptr = format_tbl[ screen.frmt_num ][ trndw ].period_coord;   /* ptr to period
192        coords */
193        blueprint.pxtlc = coord_ptr->xtlc;
194        blueprint.pytlc = coord_ptr->ytlc;
195        blueprint.pxbrc = coord_ptr->xbrc;
196        blueprint.pybrc = coord_ptr->ybrc;
197
198        blueprint.period_num = (short) MIN20 - (short) *(format_tbl[ screen.frmt_num][ trndw
199
```

```
250  void
251  Blueprint_DigWindow(window,mid)
252  short window;
253  short mid;                    /* digital window number */
254  {
255  msgx index;
256
257     dwblueprint.window_num = window + 1;
258     (short) *(digwdw_tbl window ].curr_mid) = mid - 1;
259     dwblueprint.mid_num = mid - 1;
260     index = *( mid_dblktbl (short)mid ].units_nptr) ;
261     dwblueprint.units_nptr = LanguageL (short)index ];
262     dwblueprint.units_num = (short) FIRST_UNITS_NAME ;
263
264     index = mid_dblktbl mid ].name_index ;
265     dwblueprint.name_ptr = Language [ (short)index ];
266     dwblueprint.name_font = coord_ptr->dflt_font;
267
268     coord_ptr = digwdw_tbl[ window ].dw_coord;       /* window coordinates */
269     dwblueprint.xtlc = coord_ptr->xtlc;
270     dwblueprint.ytlc = coord_ptr->ytlc;
271     dwblueprint.xbrc = coord_ptr->xbrc;
272     dwblueprint.ybrc = coord_ptr->ybrc;
273
274     coord_ptr = digwdw_tbl[ window ].du_coord;       /* relative coord for units */
275     dwblueprint.xutlc = coord_ptr->xtlc;
276     dwblueprint.yutlc = coord_ptr->ytlc;
277     dwblueprint.xubrc = coord_ptr->xbrc;
278     dwblueprint.yubrc = coord_ptr->ybrc;
279     dwblueprint.ufont = coord_ptr->dflt_font;
280
281     dwblueprint.units_num = (short) *(digwdw_tbl[window].units_num);
282
283     coord_ptr = digwdw_tbl[ window ].hilm_coord;     /* coordinates for upper limit*/
284     dwblueprint.ulxtlc = coord_ptr->xtlc;
285     dwblueprint.ulytlc = coord_ptr->ytlc;
286     dwblueprint.ulxbrc = coord_ptr->xbrc;
287     dwblueprint.ulybrc = coord_ptr->ybrc;
288
289     coord_ptr = digwdw_tbl[ window ].lwlm_coord;     /* coordinates for low limit*/
290     dwblueprint.llxtlc = coord_ptr->xtlc;
291     dwblueprint.llytlc = coord_ptr->ytlc;
292     dwblueprint.llxbrc = coord_ptr->xbrc;
293     dwblueprint.llybrc = coord_ptr->ybrc;
294
295     dwblueprint.lmtfont = coord_ptr->dflt_font;
296
                                         BuildW+Screen
297     coord_ptr = digwdw_tbl[ window ].agt_coord;      /* coords for agent initials */
298     dwblueprint.agxtlc = coord_ptr->xtlc;
299     dwblueprint.agytlc = coord_ptr->ytlc;
300     dwblueprint.agxbrc = coord_ptr->xbrc;
301     dwblueprint.agybrc = coord_ptr->ybrc;
302
303     dwblueprint.agent_font = coord_ptr->dflt_font;
```

```
                                 Build_Dflt_WfWindows

200        ].period_num);
201        blueprint.period_nameptr = Language[(short)period_nametbl[(short)blueprint.period_num]];
           /* ascii ptr*/
202        blueprint.name_ptr = Language[(short)mid_dblktbl[blueprint.mid_num].trend_namex]];
203        if (blueprint.mid_num == (short) AGENT)
204            blueprint.agent_initials = Language[(short)screen.curr_agent];
205
206        blueprint.trend_type = mid_dblktbl[((short)blueprint.mid_num) - 1 )].trend_type ;
207
208        blueprint.mid_num = (short) mid_conversion_tbl[ blueprint.mid_num ];
209        return ;
210    }
211
212    /*****************************************************************
213    ** BUILD NELLCOR DEFAULT WINDOW DESCRIPTION BLOCKS
214    **
215    *****************************************************************/
216    void
217    Build_Dflt_WfWindows()
218    {
219    short window;
220
221        /* put mid numbers (from default tbl) into each window used in format 1*/
222        for ( window = 0; window ( 6; window++ )
223        {
224        if (format_tbl[DFLT_FORMAT_NUM][ window ].wstat == TRUE)
225            *(format_tbl[DFLT_FORMAT_NUM][window].mid_dspd) = dflt_wfmidtbl[window];
226            if (format_tbl[DFLT_FORMAT_NUM][window].trend_flag == TRUE)
227                *(format_tbl[DFLT_FORMAT_NUM][window].period_num ) = (short)
228                    MIN20;   /* 20min */
229        }
230    }
231
232    /*****************************************************************
233    * BUILD A BLUE PRINT TO CREATE A DIGITAL WINDOW
234    *                                      Blueprint DigWindow
235    *
236    *****************************************************************/
```

```
248         coord_ptr = digwdw_tbl[ window ].results_coord;    /* coords for results */
249         dwblueprint.rxtlc = coord_ptr->xtlc;
304         dwblueprint.rytlc = coord_ptr->ytlc;
305         dwblueprint.rxbrc = coord_ptr->xbrc;
306         dwblueprint.rybrc = coord_ptr->ybrc;
307         dwblueprint.rfont = coord_ptr->dflt_font;
308
309         coord_ptr = digwdw_tbl[ window ].alrm_off_coord;   /* slashed bell coords */
310         dwblueprint.offxtlc = coord_ptr->xtlc;
311         dwblueprint.offytlc = coord_ptr->ytlc;
312         dwblueprint.offxbrc = coord_ptr->xbrc;
313         dwblueprint.offybrc = coord_ptr->ybrc;
314         dwblueprint.offont = coord_ptr->dflt_font;
315
316         coord_ptr = digwdw_tbl[ window ].mid_namecoord;    /* mid name coordinates */
317         dwblueprint.nxtlc = coord_ptr->xtlc;
318         dwblueprint.nytlc = coord_ptr->ytlc;
319         dwblueprint.nxbrc = coord_ptr->xbrc;
320         dwblueprint.nybrc = coord_ptr->ybrc;
321         dwblueprint.name_font = coord_ptr->dflt_font;
322         dwblueprint.mid_num = (short) mid_conversion_tbl[ dwblueprint.mid_num ];
323
324         return ;
325     }
326
327     /****************************************************************
328      * BUILD WAVEFORM SCREEN FROM FORMAT
329      *
330      ****************************************************************/
331     void
332     BuildWfScreen()
333     {
334     short window;
335
336         for (window = 0; window < 6; window++ )
337         {
338             /* if window is used in this format, create it*/
339             MWDOWS.C     Display_DfltDScreen
340
341             if (format_tbl[screen.frmt_num][window].wstat == TRUE )
342             {
343                 Bluprint_Wfw(window);
344                 if (format_tbl[screen.frmt_num][window].trend_flag == TRUE )
345                 {
346                     Bluprint_Trndw(window);
347                     *(format_tbl[screen.frmt_num][window].ds_wnum) = DCreateTRW(
348                         &blueprint);
349                 }
```

```
356                 else *(format_tbl[screen.frmt_num][window].ds_wnum) = DCreateWFW(
                         &blueprint);
357         }
358     }
359
360  /*******************************************************************/
361  /* BUILD BLUE PRINTS FOR ALL DEFAULT DIGITAL WINDOWS THEN CREATE THEM
362  /*******************************************************************/
363
364  void
365  Display_DfltDScreen()
366  {
367      short window;
368      short mid_num;
369
370      for ( window = 0; window < NDIGWDOWS; window++)
371      {
372          mid_num = (short) dflt_dmid_list[ window ];  /* default digital mid list */
373          --mid_num;
374          *(digwdw_tbl[ (short)window ].units_num ) =
375              ((short) *(mid_dblktbl[(short)mid_num].units_nptr) - (short)FIRST_UNITS_NAM
376              .E) + 1;
377          Blueprint_DigWindow( window,mid_num);
378          *(digwdw_tbl[ window ].ds_wnum) = DCreateMRW(&dwblueprint);
379      }
380  }
381
382  /*******************************************************************/
383  /* SEARCH THE DIGITAL RESULTS WINDOWS FOR TARGET, STARTING AT THE SPECFIED WINDOW #
384  /* RETURN A PTR TO THE DIGITAL WINDOW DESCRIPTION BLOCK IF TARGET IS FOUND ELSE
385  /* RETURN FALSE.
386  /*******************************************************************/
387
388                   MWDOWS.C              DWSearch
389
390  short
391  DWSearch( target, window )
392  short window;
393  msgx target;
394  {
395      short flag;
396
397      for ( flag = FALSE; ( window < NDIGWDOWS ) && ( flag = FALSE ); window++ )
398          if ( *( digwdw_tbl[ window ].curr_mid ) == target )
399              flag = TRUE;
400  }
```

```
406        if ( flag = FALSE )
407            window = FALSE ;
408
409        return ( window );
410    }
411
412    /*************************************************
413     * SELECT NEXT DIGITAL WINDOW AND DESELECT ANY OTHER WINDOW THAT MAY BE SELECTED
414     *
415     *************************************************/
416
417
418
419    void
420    SelectNextDW()
421    {
422        if ( screen.digwdw_selctd != NONE_SELECTED )
423            DUnHighLW( *(digwdw_tbl[ screen.digwdw_selctd ].ds_wnum )); /* make sure its not
424                highlighted */
425        if ( screen.wfwindow_selctd != NONE_SELECTED )
426        {
427            DUnHighLW( *(format_tbl [ screen.frmt_num ][ screen.wfwindow_selctd ].ds_wnum ));
428            screen.wfwindow_selctd = NONE_SELECTED;
429        }
430
431        screen.digwdw_selctd++;
432        if ( screen.digwdw_selctd == NDIGWDOWS)
433            screen.digwdw_selctd = 0;
434    }
435
436    /*************************************************
437     * FIND AND UPDATE INS/ET AGENT IN DIGITAL RESULTS WINDOW
438     *
439     *************************************************/
440
441    void
442                                    FindDW_UpdateAGT
443    FindDW_UpdateAGT(agent)
444    msgx agent;                     /* INS or ET AGT */
445    {
446        digwdw_dblk *dblk;          /* ptr to a digital result description block */
447        short found;
448        short window;
449        WinNumber win_num;
450
451        window = DWSearch(agent, 0);   /* find which DIGITAL RESULTS window agent is in */
452        if ( window != FALSE ) /* means agent IS displayed in a DIGITAL RESULTS */
453        {
454            win_num = *( digwdw_tbl [ window ].ds_wnum ); /* get # assigned by the Display
                Server */
455            coord_ptr = digwdw_tbl [ window ].mid_namecoord;
456            xcorner = coord_ptr->xtlc;
```

```
457         ,  ycorner = coord_ptr->ytlc;
458            /* dprintf(win_num,"%P %s\n",xcorner,ycorner,Language[ (short) agent ] ) ;*/
459         }
460    }
461
462    /*****************************************************************
463    ** FIND AND UPDATE AGENT IN TREND WINDOW
464    **
465    *****************************************************************/
466
467    void
468    FindTW_UpdateAGT()
469    {
470    short flag;
471    short window;
472
473       for ( window = 0, flag = FALSE ; ( window < NUM_WFWINDOWS ) && ( flag == FALSE );
474             window++ )
475       {
476          if (( format_tbl[ screen.frmt_num ][ window ].wstat == TRUE ) &&
477              ( format_tbl[ screen.frmt_num ][ window ].trend_flag == TRUE))
478          {
479             if ( *(format_tbl[ screen.frmt_num ][ window ].mid_dspd ) == AGENT )
480             {
481                flag = TRUE;
482                                              /* create new agent window
483                                                 DONNA */
484             }
485          }
486       }
487    }
488
489
490    /*****************************************************************
491    ** POWER HAS BEEN TURNED ON AND THE OPERATOR SAYS THIS IS THE SAME CASE, SO RESTORE
492    ** THE SAME SCREEN THAT WAS DISPLAYED AT POWER DOWN
493    **
494    *****************************************************************/
495
496    void
497    RebuildOldScreen()
498    {
499    ;/* notify display server to display old screen; */
500    }
501

Thu 10-13-86 20:59:00   MWDWDBLK.H
    10-16-86 14:52:38
```

RebuildOldScreen

```
/*****************************************************************
**  MFQ Ver 0.0
**
**  module: mwdwdblks.h
**
**  modification history :
**     date            by                      reason(s)
**     12 aug 86       ron parks               creation
**
**  This module is an original, unpublished work and is proprietary to
**  NELLCOR INC., and may not be divulged or copied in any form
**  whatsoever without the express written permission of NELLCOR INC.
**
**  purpose : describes all there is to know about how a window looks
**
**  data descriptions :
**
**  function descriptions :
**
*****************************************************************/

/*****************************************************************
THE FOLLOWING IS THE DEFINITION OF THE BUTTON TABLES. THE BUTTON TABLES ARE
USED TO DETERMINE WHICH MENU IS TO BE DISPLAYED FOLLOWING THE PRESSING OF
ANY GIVEN BUTTON. A 'BUTTON', AS FAR AS THESE TABLES ARE CONCERENED, ARE THE
LOWER 5 FUNCTION BUTTONS, THE 'HELP' BUTTON, AND THE KNOB. THE 'ALARM SILENCE
BUTTON AND THE POWER ON/STANBY ARE NOT HANDLED IN THESE TABLES.
*****************************************************************/ define NDIGWDOWS       9       /* number of digital (resuslt) windows */
define NUM_WFWINDOWS   4       /* number of waveform/trend windows */
#define NUM_FORMATS     4       /* 4 formats for now */
#define NUM_MIDS        13      /* number of MIDs */
#define NUM_PERIODS     3       /* 20 min, 1 hr, 8 hrs */
#define NUM_UNITS       5       /* number of possible units of measurement */
#define NUM_TRENDABLE_MIDS 5    /* number of mids that may have a trend graph */

/*****************************************************************
   DESCRIPTION BLOCK FOR SCREEN CO-ORDINATES TABLE x/y top left corner  ----
                       |    |
                        ---- x/y bottom right corner
*****************************************************************/
```

```c
typedef struct
{
    short xtlc;                 /* x top left corner literal/relative pixel addr */
    short ytlc;                 /* y top left corner literal/relative pixel addr */
    short xbrc;                 /* x bottom right corner literal/relative pixel addr */
    short ybrc;                 /* y bottom right corner literal/relative pixel addr */
    short dflt_font;            /* default attribute */
} COORD_TBL;

#define coord_tbl COORD_TBL far
/*****************************************************************
** AGENT DESCRIPTION BLOCK
******************************************************************/
typedef struct
{
    msgx far *initials_index;   /* pointer to the agents initials */
    msgx far *full_namex;
} AGENT_BLK;

#define agent_blk AGENT_BLK far
/*****************************************************************
** THIS IS THE CURRENT SCREEN DESCRIPTION BLOCK
******************************************************************/
typedef struct
{
    struct btn_menu far *actv_btn_menu;  /* active menu table for the buttons */
    coord_tbl * scrn_coord;     /* screen coordinates */
    coord_tbl *prmpt_coord;     /* prompt coordinates */
    coord_tbl *mnubtr_coord;    /* menu (btn names) coordinates */
    short kybd_input;           /* unprocessed code from kybd */
    short frmt_num;             /* screen format number */
    short kybd_flag;            /* true if keyboard is locked out */
    short freez_stat;           /* true if screen is frozen */
    short wfwndow_selctd;       /* number of the wf window selected */
    short digwdw_selctd;        /* number of the digital loc selected */
    short nonwf_dflag;          /* true when no waveforms are displayed */ short agt_seltd;            /* eg help,screen format sel,technical etc*/
                                /* agent selected (0 = no agent) */
    short silence_btnflg;       /* whether on not the alarm silence button is depressed */ coord_tbl *agtnm_coord;     /* screen addr of unabreviated agent name*/
    agent_blk *curr_agent;      /* ptr to agent description block */
    short hlp_dflag;            /* help displayed flag */
    short auto_prtflg;          /* auto print flag. true = enabled */
    short prt_onalrm_flg;       /* print on all alarms. true = enabled */
    coord_tbl *first_initial;   /* coordinates of 1st initial (scrn fmt) */
    coord_tbl *secnd_initial;   /* coordinates of 2nd initial */
```

```
110        coord_tbl *third_initial;      /* coordinates of 3rd initial */
111        short    limit_selctd;         /* FALSE = no limit selected, 1= upper, 0 low */
112        short    clr_trnd;             /* TRUE = clear trend buffer */
113
114    }   screen_config;
115
116  /************************************************************************
117   *
118   *   MEASUREMENT ID DESCRIPTION BLOCK
119   *
120   ************************************************************************/
121
122  typedef struct
123  {
124        msgx    name_index;            /* index to ASCII name */
125        short   far *mstat;            /* true = mid hooked up */
126        msgx    trend_namex;           /* index to ASCII trend name */
127        msgx    far *units_nptr;       /* ptr to current units name */
128        msgx    dflt_units;            /* default units */
129        short   num_of_units;          /* number of different units that a valid for this mid */
130        msgx    far *alt_units;        /* list of alternative units */
131        struct  ASCALED scrollrate;    /* floating point scroll rate */
132        short   samplerate;            /* sample rate of waveform data */
133        short   wfid;                  /* waveform I.D. */
134        short   trend_type;            /* 1 = one wave 2 = two waves */
135
136   } mid_dblk;
137
138  /************************************************************************
139   *
140   *  WAVEFORM/TREND WINDOW DESCRIPTION BLOCK
141   *
142   ************************************************************************/
143
144  typedef struct
145  {
146        short   wstat;                 /* true = window not used */
147        short   trend_flag;            /* true = it is a trend window */
148
149        coord_tbl *wndow_size;         /* coordinates of entire window */
150        msgx    far *mid_dspd;         /* mid # displayed in this window */
151        coord_tbl *name_coord;         /* relative cordinates for mid name */
152        coord_tbl *period_coord;       /* rel coords period in trend window */
153        short   far *period_num;       /* period index if trend window */
154        WinNumber *ds_wnum;            /* window # assigned by DisplayServer */
155        coord_tbl *axis_coord;
156        short   trendable_num;         /* number of the trendable mid */
157
158   } wndow_dblk;
159
160  /************************************************************************
161   *
162   *  DIGITAL WINDOW DESCRIPTION BLOCK
163   *
164   ************************************************************************/
165
```

```
typedef struct
{
    msgx *curr_mid;              /* current MID # displayed in this window */
    short *blnk_flag;            /* true if window is blanked */
    WinNumber *ds_wnum;          /* Display Server window number */
    short *units_num;            /* units index */
    coord_tbl *dw_coord;         /* dig window screen coordinates*/
    coord_tbl *du_coord;         /* digital units screen coordinates*/
    coord_tbl *hiIm_coord;       /* high limit address coordinates*/
    coord_tbl *lwlm_coord;       /* low limit screen coordinates */
    coord_tbl *agt_coord;        /* agent screen coordinates*/
    coord_tbl *results_coord;    /* digital results for MID */
    coord_tbl *alrm_off_coord;   /* slashed bell coordinates */
    coord_tbl *mid_nameCoord;    /* coordinates for mid name */

} digwdw_dblk;

/***************************************************************
** BLUE PRINT FOR DISPLAY SERVER WAVEFORM/TREND WINDOW CREATION
**
***************************************************************/ typedef struct
{
    short window_num;            /* menu server window number */
    short mid_num;               /* MID number */
    char far *name_ptr;          /* ptr to ascii name */ short nxtlc;                 /* rel x top left corner addr for mid name*/
    short nytlc;                 /* rel y top left corner*/
    short nxbrc;                 /* rel x bottom right corner */ short nybrc;                 /* rel y bottom right corner */
    short name_font;

short xtlc;                  /* window x top left corner */
    short ytlc;                  /* window y top left corner */
    short xbrc;                  /* window x bottom right corner */
    short ybrc;                  /* window y bottom right corner */ short axxtlc;                /* axis x top left corner rel pixel addr */
    short axytlc;                /* axis y top left corner rel pixel addr */
    short axxbrc;                /* axis x bottom right corner rel pixel addr */
    short axybrc;                /* axis y bottom right corner rel pixel addr */ short period_num;            /* number used for period index */ char far *period_nameptr;    /* ptr to ascii name */
    short pxtlc;                 /* period x top left rel pixel addr */
    short pytlc;                 /* period y top left rel pixel addr */
    short pxbrc;                 /* period x bottom right rel pixel addr */
    short pybrc;                 /* period y bottom right rel pixel addr */
    short pfont;                 /* period font */ char far *agent_initials;    /* ptr to agent initials */
```

```
223              struct ASCALED scrollrate;
224              short samplerate;
225              short wfid;
226
227              short trend_type;
228
229         } wtemplate;
230
231  /*******************************************************************
232   **
233   ** BLUE PRINT FOR DISPLAY SERVER RESULT WINDOW CREATION
234   **
235   *******************************************************************/
236
237
238
239  typedef struct
240  {
241       short   wndow_num;          /* menu server window number */
242       short   mid_num;            /* MID number */
243       char far *name_ptr;         /* ptr to ascii string */
244
245       short   nxtlc;              /* rel x top left corner addr for mid name*/
246       short   nytlc;              /* rel y top left corner */
247       short   nxbrc;              /* rel x bottom right corner */
248       short   nybrc;              /* rel y bottom right corner */
249       short   name_font;
250
251       short   xtlc;               /* window x top left corner */
252       short   ytlc;               /* window y top left corner */
253       short   xbrc;               /* window x bottom right corner */
254       short   ybrc;               /* window y bottom right corner */
255
256       short   xutlc;              /* units coordinates */
257       short   yutlc;
258       short   xubrc;
259       short   yubrc;
260       short   ufont;
261
262       char far *units_nptr;       /* ptr to ascii units */
263
264       short   units_num;          /* units number */
265
266       short   ulxtlc;             /* upper alarm limit coordinates */
267       short   ulytlc;
268       short   ulxbrc;
269       short   ulybrc;
270
271       short   llxtlc;             /* low alarm limit coordinates */
272       short   llytlc;
273       short   llxbrc;
274       short   llybrc;
275       short   lmtfont;
276
277       short   agxtlc;             /* agent coordinates */
278       short   agytlc;
279       short   agxbrc;
```

```
280         short agybrc;
281
282         short agent_font;                   /* agent intitials ptr */
283         char far *agent_ptr;
284                                             /* result coordinates.*/
285         short rxtlc;
286         short rytlc;
287         short rxbrc;
288         short rybrc;
289         short rfont;
290
291         short offxtlc;                      /* alarm off (slashed bell) coordinates */
292         short offytlc;
293         short offxbrc;
294         short offybrc;
295         short offfont;                      /* large or small bell */
296
297
298     } dwtemplate;
299
300 #ifdef WINDOW_STUFF
301 /*
302 digwdw_dblk digwdw_tbl[ NDIGWDOWS ] = {0};
303 */
304 screen_config screen = {0};
305 wtemplate blueprint = {0};
306 dwtemplate dwblueprint = {0};
307 coord_tbl *coord_ptr = {0};
308 coord_tbl *wcoord_ptr = {0};
309 /*wndow_dblk format_tbl[ NUM_FORMATS ][ NUM_WFWINDOWS ];
310 */
311 #else
312 extern screen_config screen;
313 extern wtemplate blueprint;
314 extern dwtemplate dwblueprint;
315 extern coord_tbl *coord_ptr;
316 extern coord_tbl *wcoord_ptr;
317 extern wndow_dblk format_tbl[ NUM_FORMATS ][ NUM_WFWINDOWS ];
318 */
319
320 #endif
```

MBIQUE.C

```
/***************************************************************
 *                                                              *
 *    project :    mfo                                          *
 *    file :      aixfer.c                                      *
 *                                                              *
 *    history :                                                 *
 *    date        by    reason                                  *
 *    07-18-86    laf   creation                                *
 *    08-07-86    laf   individualized for each slw channel     *
 *    08-28-86    laf   write in the same place for each buffer, only keep the last
 *                      value for each slow channel
 *
 *    Copyright (C) 1985, NELLCOR INCORPORATED
 *    This module is an original, unpublished work and is proprietary to
 *    NELLCOR INC., and may not be divulged or copied in any form
 *    whatsoever without the express written permission of NELLCOR INC.
 *
 *    purpose :     establish mta data transfer routines
 *
 *    data descriptions :
 *
 *    function descriptions :
 *    void far lacqCO2S(value); function the acquisition server calls to xfer
 *    slow CO2 "value" to the measurement task.  same function types for N2OS,
 *    AgtS, PreS, TmpS and FloS
 *
 *    short near lacqslw( id, value); function called by mtacqXXXS to xfer slow
 *    data to the mta, where "id" is the local slow data id and "value" is the
 *    actual data point.  returns ERROR if all slow data buffers are full or
 *    being used for other puposes. otherwise returns OK.
 *
 *    lBufinfo * near lfndslwbuf(topslwbuf, mode); searches all of the slow
 *    buffers from 0 through NUMSLWBUF, for the first one who's present use is
 *    equivalent
 *
 *    void near lwrslw( slwbuf, value); writes the parameter value into the slow
 *    buffer pointed to by slwbuf.  if writing to the first available location
 *    adjusts status from EMPTY to NOTFULL.  if writing in the last available
 *    location adjust status from NOTFULL to FULL and change mode to reflect
 *    XXFILL as opposed to XXWR.
 *
 *    short near lrdslw(slwbuf); reads the next slow data in buffer pointed to
 *    by slwbuf. if the status was FULL changes to NOTFULL.  if reading the last
 *    available data point change status to EMPTY and mode to NOTUSED so it can
 *    be picked up by the next guy that needs a slow data buffer. it returns the
 *    data unless no data is available in which case ERROR is returned
 *
 *    void near lgetsnglslw(topslwbuf, rawparam); process all the data in all of
 *    the ACQFILLED buffers as well as the data in the ACQWR buffer. buffer
 *    modes are changed to MTRD before data is taken out. last value is stored
 *
 ***************************************************************/
```

IacqCO2S

```
 * 		void near Icksmpmode(); test if in a onme shot mode and if all data is in.
 * 		if so sets appropriate flags and makes appropriate requests.
 *************************************************************************/ include     "../xevent.h"
include     "aiglobal.h"
#include     "aiglue.h"
#define      INITAIXFER
#include     "aixfer.h"
#include     "bique.h"
#include     "aievnt.h"
#include     "aisrl.h"

void far
IacqCO2S(value)
register short   value;
{    Iacqslw(ICHNLCO2, value);
} void far
IacqN2OS(value)
register short   value;
{    Iacqslw(ICHNLN2O, value);
} void far
IacqAgtS(value)
register short   value;
{    Iacqslw(ICHNLAGT, value);
} void far
IacqFloS(value)
register short   value;
{    Iacqslw(ICHNLFLO, value);
} void far
IacqPreS(value)
register short   value;
{    Iacqslw(ICHNLPRE, value);
} void far
IacqTmpS(value)
register short   value;
{    Iacqslw(ICHNLTMP, value);
}
```

MBIQUE.C          Iacqslw

```
100  short near
101  Iacqslw(id, value)
102  register short id;
103  short     value;
104  {
105      register IBufinfo *slwbuf;
106
107      if( (ismpmode != SYNCSNGLE) && (ismpmode != FLYSNGLE))
108          return(OK);                    /* not interested */
109
110      if( (slwbuf = Ifndslwbuf(ichnlinfo[id].topbuf,NOTUSED)) == NULL)
111          return(ERROR);  /* can't find a buffer in which to write data */
112  /* may have to change this to get rid of oldest data a store the new stuff */
113
114      slwbuf->mode = ACQWR;       /* found a good one in which to write */
115      Iwrslw(slwbuf, value);      /* store the data */
116      if( ismpmode == SYNCSNGLE)
117      {
118          ismpchnlmap=ismpchnlmap& ~(ichnlinfo[id].mask);  /* is this one shot?? */
119          A_Util (DeAct_acq, ichnlinfo[id].pacb);  /* turn off this acq channel */
120      }
121      else if( ismpmode == FLYSNGLE)   /* is this an one the fly one shot?? */
122      {
123          ismpchnlmap=ismpchnlmap& ~(ichnlinfo[id].mask);  /* mask value just in */
124      }
125      Icksmpmode();       /* check smple mode conditions and react */
126      return (OK);        /* data xfer went ok */
127  }
128
129  IBufinfo * near
130  Ifndslwbuf(topslwbuf, mode)
131  IBufinfo   *topslwbuf;
132  IBufmode   mode;
133  {
134      register short i;
135      register IBufinfo *slwbuf;
136      slwbuf = topslwbuf;            /* init pointer to first in set of slw buffers */
137      for(i = 0; i < NUMSLWBUF; i++,slwbuf++)
138      {
139          if ((slwbuf->mode == mode)      /* is this the type we want */
140              return(slwbuf);
141      }
142      return (NULL);
143  }
144
145  void near
146  Iwrslw( slwbuf, value)
147  register IBufinfo *slwbuf;
148  short     value;
149  {
150      register short *wr;
151
152      wr = slwbuf->wrptr;
153      if(slwbuf->status == EMPTY)  /* first thing written to this buffer */
154          slwbuf->status = NOTFULL;
```

```
Thu 10-08-86 20:28:00    MBIQUE.C         lrdslw
    10-16-86 14:52:38

150        else   /* don't need buffers for now, only want the single last value */
151        {
152            slwbuf->wrptr = slwbuf->data;
153            wr = slwbuf->wrptr;
154        }
155        *wr = value;
156        if((++wr == (slwbuf->data + slwbuf->size + 1)) /* end of buf test */
157        {
158            slwbuf->wrptr = slwbuf->data;   /* reset write ptr */
159            slwbuf->mode = ACQFILL;          /* it is filled */
160            slwbuf->status = FULL;
161        }
162        else
163        {
164            slwbuf->wrptr++;                 /* inc wr pointer */
165        }
166        return;
167    }
168    short near
169    lrdslw(slwbuf)
170    register lBufinfo  *slwbuf;
171    {
172        register short  *rd;
173        short    *send;
174        send = rd = slwbuf->rdptr;
175        if(slwbuf->status == EMPTY)              /* nothing to read */
176            return(ERROR);
177        if(slwbuf->status == FULL)    /* if full before, not now */
178            slwbuf->status = NOTFULL;
179        /* test if we have emptied the buf now */
180        if((++rd == slwbuf->wrptr)
181        {
182            slwbuf->rdptr = slwbuf->data + slwbuf->size + 1))
183            slwbuf->wrptr = slwbuf->data; /* reset pointers */
184            slwbuf->status = EMPTY;        /* clear status */
185            slwbuf->mode = NOTUSED;
186        }
187        else  /* increment read pointer */
188            slwbuf->rdptr++;
189        return(*send);  /* return the read va u */
190    }
191    void near
192    lgetsnglslw(topslwbuf, rawparam)
193    lBufinfo   *topslwbuf;
194    short      *rawparam;
195    register lBufinfo *slwbuf;
196    short    value;
197    {
198        while((slwbuf = lfndslwbuf(topslwbuf,ACQWR)) != NULL)
199            slwbuf->mode = MTRD;
            while((value = lrdslw(slwbuf)) != ERROR) /* read it until its empty */
                *rawparam = value; /* this stores the last value */
```

```
200             }
201             return;
202     }
203
204     void near
205     Icksmpmode()
206     {
207             if((ismpmode == SYNCSNGLE) && (ismpchnlmap == 0))   /* all off */
208             {
209                     Iputingue(&Icmdque, PSTSNDSYN);
210                     xPost(PID_ITEST, A_DATA_EV);
211             }
212             else if((ismpmode == FLYSNGLE) && (ismpchnlmap == 0))  /* all off */
213             {
214                     Iputingue(&Icmdque, PSTSNDFLY);
                        xPost(PID_ITEST, A_DATA_EV);
                }
    }
```

```
                                    mIQUEUE

1  /***********************************************************/ /**********************************
2
3       project :       mfo
4       file :          mbique.h
5
6       history :
7       date            by      reason
8       07-23-86        laf     creation            copied from epr's queue.h
9       10-6-86         rlp     copied laf's copy of epr's queue.h
10
11      Copyright (C) 1985, NELLCOR INCORPORATED
12      This module is an original, unpublished work and is proprietary to
13      NELLCOR INC., and may not be divulged or copied in any form
14      whatsoever without the express written permission of NELLCOR INC.
15
16      purpose :       establish queues variables
17
18      data descriptions :
19              struct queue contains read/write pointer, size, status and an array
20              defining a particular queue. size is the actual size-1 to compensate
21              for the fact tha array indeces begin at "0". status consists of
22              QUENOTFULL or QUEFULL
23
24      macro descriptions :
25              QUEUE(name,quesize)           creates a que of name "name" and size "quesize"
26
27   ***********************************************************/ /**********************************
28
29
30   #define NOQUEDATA 0x8000
31   #define QUENOTFULL 0 /* any change should be refected in pevent.s */
32   #define QUEFULL 1
33
```

```
34  typedef struct
35          {
36                  short   *put;
37                  short   *get;
38                  short   *sget;
39                  short   size;
40                  short   status;
41                  short   data[1];
42          } mIqueue;
43  #define mIQUEUE(name,quesize) \
44  struct \
45          { \
46                  short   *put; \
47                  short   *get; \
48                  short   *sget; \
49                  short   size; \
50                  short   status; \
         short   data[quesize]; \
         } name = {name.data, name.data, name.data - 1, quesize - 1, QUENOTFULL, 0};

mIEXTQUEUE

51  #define mIEXTQUEUE(name,quesize) \
52  extern struct \
53          { \
54                  short   *put; \
55                  short   *get; \
56                  short   *sget; \
57                  short   size; \
58                  short   status; \
59                  short   data[quesize]; \
60          } name;
61
62  #ifdef mINITBIQUE
63
64  mIQUEUE(kybdque, 100)                          /* commands being sent to the mta are queued here */
65
66  #else
67
68  mIEXTQUEUE(kybdque, 100)
69
70  #endif
71
72  /* functions */
73  short   near    mIputinque();
74  short   near    mIpushinque();
75  short   near    mIforceinque();
76  short   near    mIgetfromque();
77  void    near    mIflushque();
78
                                         MKYBD.H 1  /*********************************************************************
2  *
```

```
/**********************************************************************
* MFO Ver 0.0
* module: mkybd.h
* modification history :
*       date        by              reason(s)
*
* This module is an original, unpublished work and is proprietary to
* NELLCOR INC., and may not be divulged or copied in any form
* whatsoever without the express written permission of NELLCOR INC.
*
* Purpose :
*
* data descriptions :
*
* function descriptions :
**********************************************************************/
short near mInputKybd();
short near mGetKnob();
```

We claim:

1. A gas analyzer system, comprising:
   (a) an optical bench, further comprising,
       (1) a gas pathway through the optical bench,
       (2) a flow shaper at gas inlet to the gas pathway for changing the cross-sectional shape of the entering gas flow from a first to a second cross-sectional shape,
       (3) at least one gas detector channel assembly disposed along the gas pathway,
       (4) modulating means for modulating the signals detected by the detector channel assembly,
       (5) circuit means associated with the detector channel assembly for separating the AC and DC components of a detected signal to correct the AC component of the signal based on changes in the DC components of the signal,
       (6) pressure sensing means disposed in the gas pathway for measuring the barometric pressure within the gas pathway,
       (7) temperature sensing means for measuring an internal temperature of the optical bench,
       (8) flow rate sensing means disposed in the gas pathway for measuring the flow rate of the gas stream through the gas pathway,
       (9) means for drawing the gas stream through the gas pathway and backflushing the pathway,

(10) first circuit means for generating signals indicative of the detected gas levels of the predetermined gases by detector channel assembly, the pressure and gas flow rate within the gas pathway and the temperature within the optical bench,

(11) second circuit means connected to the first circuit means for providing from memory circuit means signals representative of characterization of components of the optical bench, and

(12) output circuit means connected to the first and second circuit means for providing an output signal indicative of the barometric pressure and gas flow rate within the gas pathway, the temperature within the optical bench, the gas level of the predetermined gas detected by the detector channel assembly, and signal representative of the characterization of the components of the optical bench;

(b) analog signal processing circuitry further comprising, (1) an input circuit for receiving signals output from the optical bench, processing these signals and converting them from analog to digital signals, (2) a digital signal processing circuit, further including a microprocessor and memory circuits for receiving the digital outputs from the input circuit and correcting the signals indicative of the partial gas pressure for temperature, changes in detector sensitivity, collision broadening, cross correction, barometric pressure and characterization of the optical bench components, and (3) output circuit for outputting at least the corrected signals for the partial gas pressure to display processing circuitry;

(c) a display processing circuitry further including at least a microprocessor and memory circuits for receiving the digital signals output from the analog signal processing circuitry and processing the signals to provide outputs for controlling display screen processing circuitry, for digital and analog output means and for alarm means;

(d) the display screen processing circuitry with means connected to display processing circuitry for generating signals for driving a display means; and (e) power supply means for powering the system.

2. The system as recited in claim 1, wherein the pressure sensing means includes an absolute type pressure sensor.

3. The system as recited in claim 1, wherein the flow rate sensing means includes a differential type pressure sensor.

4. The system as recited in claim 1, wherein the flow rate of the gas stream through the gas pathway is preferably of 50 cc/min.

5. The system as recited in claim 1, wherein the display screen processing circuitry further comprises;

a display control gate array circuit for receiving and processing control and data signals from the display processing circuitry and generating signals for controlling the display means;

a scroll/pixel gate array circuitry for receiving and processing control signals and data signals from the display processing circuitry and generating signals for use in controlling the representations on the display means; and a memory circuit with means connected to the display control gate array circuit and the scroll pixel gate array circuit for storing predetermined information for use in displaying representations on the display means.

6. The system as recited in claim 1, where the gas pathway has a first gas passageway, a second gas passageway and a third gas passageway.

7. The system as recited in claim 6, wherein the system further comprises first, second and third gas detector channel assemblies, with the first gas detector channel assembly including a first window mounted as a first portion of a sidewall of the first gas passageway, a first light source mounted behind the first window to provide light through the first window into the first gas passageway, a first filter means mounted as a portion of an opposing sidewall of the first gas passageway from the first window for passing light of a predetermined wavelength range from the first light source in the first gas passageway through it and a first detector means spaced away and behind the first filter means for detecting the light within a predetermined wavelength range passing through the first filter, the second gas detector channel assembly including a second window mounted as a second portion of the sidewall of the first gas passageway, a second light source mounted behind the second window to provide light through the second window into the first gas passageway, a second filter means mounted as a portion of the opposing sidewall of the first gas passageway from the second window for passing light of a predetermined wavelength range from the second light source in the first gas passageway through it, and a second detector means spaced away and behind the the second filter means for detecting the light within a predetermined wavelength range passing through the second filter means, and the third gas detection channel assembly including a third light source disposed with the second gas passageway, third filter means associated with the portion of the second gas passageway opposing the third light source for passing light from the third light source of a predetermined wavelength range through it, and third detector means spaced away and behind the third filter means for detecting the light within a predetermined wavelength range passing through the third filter means with the optical path of the third detector channel assembly being parallel to the longitudinal axis of the second passageway.

8. The system as recited in claim 1, wherein the flow shaping gas inlet means shapes the gas flow from a circular cross-section to a rectangular cross-section.

9. The system as recited in claim 8, wherein the flow shaper further includes a filter disposed across the gas flow which assists in flow shaping.

10. The system as recited in claim 7, wherein when the first, second and third windows are lead selenide detectors.

11. The system as recited in claim 7, wherein the first filter means passes light having wavelengths in an absorption band of gases $CO_2$.

12. The system as recited in claim 7, wherein the second filter means passes light having a wavelength in an absorption band of $N_2O$.

13. The system as recited in claim 7, wherein the third filter means passes light having wavelength in an absorption band of an anesthetic agent.

14. The system as recited in claim 7, wherein the first, second and third light sources are infrared sources.

15. The system as recited in claim 7, wherein the first gas passageway has a rectangular cross sectional shape.

16. The system as recited in claim 7, wherein the second gas passageway has a circular cross sectional shape.

17. The system as recited in claim 7, wherein the length of the optical path between the first and second windows and the first and second filters, respectively, is a first optical path length and the length of the optical path between the third light source and the third filter means is a second greater optical path length.

18. A gas analyzer apparatus, comprising:
  (a) a gas pathway through an optical bench;
  (b) a flow shaper at a gas inlet to the gas pathway for changing the cross-sectional shape of an entering gas flow from a first to a second cross-sectional shape;
  (c) at least one gas detector channel assembly disposed along the gas pathway;
  (d) modulating means for modulating the signal detected by the detector channel assembly;
  (e) means associated with the detector channel assembly for separating the AC and DC components of a detected signal to correct the AC component of the signal based on changes in the DC component of the signal;
  (f) pressure sensing means disposed in the gas pathway for measuring barometric pressure within the gas pathway;
  (g) temperature sensing means for measuring an internal temperature of the apparatus;
  (h) flow rate sensing means disposed in the gas pathway for the measuring flow rate of the gas stream through the gas pathway;
  (i) means for drawing the gas stream through the gas pathway and backflushing the pathway;
  (j) first circuit means for generating signals indicative of the detected gas levels of the predetermined gases by detector channel assembly, the pressure and flow rate within the gas pathway, and the temperature within the optical bench;
  (k) second circuit means connected to the first circuit means for providing from memory circuit means signals representative of characterization of components of the apparatus;
  (l) output circuit means connected to the first and second circuit means for providing output signals indicative of the barometric pressure and gas flow rate within the gas pathway, the temperature within the apparatus, the gas levels of the predetermined gases detected by the first, the second and the third detector channel assemblies, and signals representative of the characterization of the components of the apparatus; and
  (m) power supply means for supplying power to the apparatus.

19. A gas detector apparatus analyzing a multicomponent gas stream comprising:
  (a) an optical bench, further comprising:
    (1) a gas pathway through the optical bench;
    (2) a flow shaper at gas inlet to the gas pathway for changing the cross-sectional shape of the entering gas flow from a first to a second cross-sectional shape;
    (3) first, second and third gas detector channel assemblies disposed along the gas pathway, with at least an optical path of one detector channel assembly being parallel to the longitudinal axis at a portion of the pathway;
    (4) modulating means for modulating the signal detected by the detector channel assembly;
    (5) means associated with the detector channel assembly for separating the AC and DC components of a detected signal to correct the AC component of the signal based on changes in the DC component of the signal;
    (6) pressure sensing means disposed in the gas pathway for measuring the barometric pressure within the gas pathway;
    (7) temperature sensing means for measuring an internal temperature of the optical bench;
    (8) flow rate sensing means disposed in the gas pathway for measuring the flow rate of the gas stream through the gas pathway;
    (9) means for drawing the gas stream through the gas pathway and backflushing the pathway;
    (10) first circuit means for generating signals indicative of the detected gas levels of the predetermined gases by the first, the second and the third detector channel assemblies, the pressure and flow rate within the gas pathway and the temperature within the optical bench;
    (11) second circuit means connected to the first circuit means for providing from memory means signals representative of characterization of components of the optical bench; and
    (12) output circuit means connected to the first and second circuit means for providing an output signal indicative of the barometric pressure and gas flow rate within the gas pathway, the temperature within the optical bench, the gas level of the predetermined gas detected by the detector channel assembly, and signal representative of the characterization of the components of the optical bench;
  (b) analog signal processing circuitry further comprising,
    (1) an input circuit for receiving signals output from the optical bench, processing these signals and converting them from analog to digital signals,
    (2) digital signal processing circuit, further including a microprocessor and memory circuits for receiving the digital outputs from the input circuit and correcting the signals indicative of the partial gas pressure for temperature, changes in detector sensitivity, collision broadening, cross-correction, barometric pressure, and characterization of the optical bench components, and
    (3) output circuitry for outputting at least the corrected signals for the partial gas pressures from the analog processing circuitry; and
  (c) power supply means for powering the apparatus.

20. A method for measuring a partial pressure of a plurality of constituent gases of a gas stream with a gas analyzer apparatus comprising the steps of:
  (a) detecting and generating signals indicative of the amount of each of a plurality of predetermined constituent gases of the gas stream with an infrared detectors assembly for each of the plurality of constituent gases, including correcting a detected signal by separating the AC and DC components of the detected signal and correcting the AC component of the signal based on changes in the DC component of the signal;

(b) detecting and generating a signal indicative of barometric pressure within the apparatus with a pressure sensing means;
(c) storing and generating signals indicative of the characterization of the components of the apparatus;
(d) detecting and generating a signal indicative of a temperature in the apparatus; and
(e) calculating the partial pressure of each constituent gas and correcting the calculated value for barometric pressure within the apparatus, the temperature within the apparatus, cross correction collision broadening, changes in the detector sensitivity of each infrared detector and characterization of the components of the apparatus.

21. A circuit for use in a gas analyzer for separating AC and DC components of a signal from an infrared detector to correct the AC components of the signal based on changes in the DC component of the signal, comprising:

means for biasing the signal;
a first amplifier means for buffering the biased signal;
means for passing the AC component and blocking the DC component for the buffered signal;
a second amplifier which receives the AC component and outputs an amplified AC signal;
means for filtering the DC component of the buffered signal and outputting the DC component of the signal and
means for connecting to the AC component and DC component for modifying the amplitude of the AC component in response to the magnitude of the DC component.

* * * * *

UNITED STATES PATENT AND TRADEMARK OFFICE
CERTIFICATE OF CORRECTION

PATENT NO. : 4,817,013
DATED : October 17, 1986
INVENTOR(S) : James E. Corenman et al.

It is certified that error appears in the above-identified patent and that said Letters Patent is hereby corrected as shown below:

Col. 5, ln. 51 "thru" should be -- and --

Col. 7, ln. 25 "having" should be -- have --

Col. 13, ln. 16 "wth" should be -- with --

Col. 20, ln. 14 "V[Vdc]" should be -- V[Xdc] --

Col. 27, ln. 10 "EL" should be -- SEL --

Col. 28, ln. 11 "is" should be -- in --

Col. 29, ln. 15 "1963" should be -- 1936 --

Col. 29, ln. 29 "advnce" should be -- advance --

Col. 30, ln. 56 "GR-7" should be -- GR0-7 --

Col. 31, ln. 12 "DRMs" should be -- DRAMs --

Col. 32, ln. 34 "lcocked" should be -- clocked --

Col. 36, ln. 66 "thw" should be -- the --

Col. 40, ln. 9 "DRT" should be -- DTR --

Col. 40, ln. 24 "48" should be -- 148 --

Col. 41, ln. 24 After "MAIN" delete "." and insert -- pp. 29-40. --

UNITED STATES PATENT AND TRADEMARK OFFICE
CERTIFICATE OF CORRECTION

PATENT NO. : 4,817,013

DATED : October 17, 1986

INVENTOR(S) : James E. Corenman et al.

It is certified that error appears in the above-identified patent and that said Letters Patent is hereby corrected as shown below:

Col. 41, ln. 29 After "MAIN" delete "." and insert -- pp. 1-11. --

Col. 41, ln. 30 After "MAIN" delete "." and insert -- pp. 18-28. --

Col. 41, ln. 41 After "MAIN" delete "." and insert -- p. 8. --

Col. 41, ln. 42 After "MENU" delete "." and insert -- pp. 1-117. --

Col. 41, ln. 47 After "MAIN" delete "." and insert -- pp. 29-40. --

Col. 41, ln. 48 After "MAIN" delete "." and insert -- pp. 41-67. --

Col. 41, ln. 53 After "MAIN" delete "." and insert -- pp. 29-40. --

Col. 41, ln. 54 After "MAIN" delete "." and insert -- pp. 29 -40. --

Col. 41, ln. 61 After "ACQ" delete "." and insert -- pp. 1-58. --

Col. 41, ln. 68 After "SERVER" delete "." and insert -- pp. 1-9. --

Col. 42, ln. 3 After "GAS" delete "." and insert -- pp. 3-93. --

Col. 42, ln. 9 After "GAS" delete "." and insert -- pp. 1-2, 94-118. --

UNITED STATES PATENT AND TRADEMARK OFFICE
CERTIFICATE OF CORRECTION

PATENT NO. : 4,817,013
DATED : October 17, 1986
INVENTOR(S) : James E. Corenman et al.

Page 3 of 5

It is certified that error appears in the above-identified patent and that said Letters Patent is hereby corrected as shown below:

Col. 42, ln. 13 After "COMM" delete "." and insert -- pp. 8-9. --

Col. 42, ln. 14 After "COMM" delete "." and insert -- pp. 8-9. --

Col. 42, ln. 17 After "COMM" delete "." and insert -- pp. 1-7, 10-41, 51-60. --

Col. 42, ln. 23 After "DISPLAY" delete "." and insert -- pp. 1-188. --

Col. 42, ln. 30 After "MAIN" delete "." and insert -- pp. 92-100. --

Col. 42, ln. 36 After "MAIN" delete "." and insert -- pp. 77-91. --

Col. 42, ln. 40 After "COMM" delete "." and insert -- pp. 42-50. --

Col. 42, ln. 45 After "SERVER" delete "." and insert -- pp. 11-17. --

Col. 1128, ln. 34 Delete "the" (second occurence)

UNITED STATES PATENT AND TRADEMARK OFFICE
CERTIFICATE OF CORRECTION

PATENT NO. : 4,817,013
DATED : October 17, 1986
INVENTOR(S) : James E. Corenman et al.

It is certified that error appears in the above-identified patent and that said Letters Patent is hereby corrected as shown below:

| Col. | ln. | IN THE APPENDIX |
|------|-----|-----------------|
| 420  | 175 | Insert -- ( mu!$ (gcbL. ppN20). -- |
| 421  | 176 | Delete " ( mu!$ (gcbL. ppN20). " |
| 673  | 598 – 601 | [illegible binary data block] |
|      |     | SHOULD BE |
|      |     | 598 dw 1111000000000000b, 01111000000000000b<br>599 dw 1111000000000000b, 01111000000000000b<br>600 dw 1111000000000000b, 01111000000000000b<br>601 dw 1111000000000000b, 01111000000000000b |
| 1091 & 1092 |  | Delete entirely |

UNITED STATES PATENT AND TRADEMARK OFFICE
CERTIFICATE OF CORRECTION

PATENT NO. : 4,817,013

DATED : October 17, 1986

INVENTOR(S) : James E. Corenman et al.

It is certified that error appears in the above-identified patent and that said Letters Patent is hereby corrected as shown below:

Cols. 1103, 1104, ln. entire page     Insert line numbers -- 56 -- thru -- 109 --

Cols. 1107, 1108, ln. entire page     Insert line numbers -- 166 -- thru -- 221 --

Cols. 1119, 1120, ln. entire page     Insert entire page (see attachment)

Col. 1121, lns. 200-214     Insert numbers -- 200 -- thru -- 214 --

Signed and Sealed this

First Day of September, 1992

Attest:

DOUGLAS B. COMER

Attesting Officer     Acting Commissioner of Patents and Trademarks